US009096565B2

(12) United States Patent
Tessier et al.

(10) Patent No.: US 9,096,565 B2
(45) Date of Patent: Aug. 4, 2015

(54) INHIBITORS OF HISTONE DEACETYLASE

(75) Inventors: Pierre Tessier, Hawkesbury (CA); Silvana Leit, Kirkland (CA); David Smil, Montreal (CA); Robert Deziel, Mount-Royal (CA); Alain Ajamian, Montreal (CA); Yves Andre Chantigny, Pincourt (CA); Celia Dominguez, Los Angeles, CA (US)

(73) Assignee: MethylGene Inc., Montreal, Quebec (CA)

( * ) Notice: Subject to any disclaimer, the term of this patent is extended or adjusted under 35 U.S.C. 154(b) by 937 days.

(21) Appl. No.: 12/100,200

(22) Filed: Apr. 9, 2008

(65) Prior Publication Data
US 2009/0181943 A1     Jul. 16, 2009

Related U.S. Application Data

(60) Provisional application No. 60/922,505, filed on Apr. 9, 2007.

(51) Int. Cl.
| | |
|---|---|
| *C07D 295/088* | (2006.01) |
| *A61K 31/5375* | (2006.01) |
| *C07D 307/79* | (2006.01) |
| *C07C 259/06* | (2006.01) |
| *C07C 275/42* | (2006.01) |
| *C07C 311/08* | (2006.01) |
| *C07C 311/21* | (2006.01) |
| *C07C 323/52* | (2006.01) |
| *C07D 205/04* | (2006.01) |
| *C07D 207/263* | (2006.01) |
| *C07D 207/337* | (2006.01) |
| *C07D 209/08* | (2006.01) |

(Continued)

(52) U.S. Cl.
CPC ............ *C07D 307/79* (2013.01); *C07C 259/06* (2013.01); *C07C 275/42* (2013.01); *C07C 311/08* (2013.01); *C07C 311/21* (2013.01); *C07C 323/52* (2013.01); *C07D 205/04* (2013.01); *C07D 207/263* (2013.01); *C07D 207/337* (2013.01); *C07D 209/08* (2013.01); *C07D 209/44* (2013.01); *C07D 211/34* (2013.01); *C07D 211/46* (2013.01); *C07D 211/52* (2013.01); *C07D 211/64* (2013.01); *C07D 211/76* (2013.01); *C07D 213/56* (2013.01); *C07D 213/64* (2013.01); *C07D 213/70* (2013.01); *C07D 213/74* (2013.01); *C07D 215/26* (2013.01); *C07D 219/04* (2013.01); *C07D 231/14* (2013.01); *C07D 233/84* (2013.01); *C07D 235/16* (2013.01); *C07D 235/28* (2013.01); *C07D 239/26* (2013.01); *C07D 239/34* (2013.01); *C07D 239/38* (2013.01); *C07D 239/42* (2013.01); *C07D 249/06* (2013.01); *C07D 267/20* (2013.01); *C07D 277/36* (2013.01); *C07D 277/74* (2013.01); *C07D 285/12* (2013.01); *C07D 295/088* (2013.01); *C07D 295/155* (2013.01); *C07D 295/192* (2013.01); *C07D 295/205* (2013.01); *C07D 295/26* (2013.01); *C07D 311/84* (2013.01); *C07D 317/50* (2013.01); *C07D 333/24* (2013.01); *C07D 401/04* (2013.01); *C07D 401/06* (2013.01); *C07D 409/04* (2013.01); *C07D 413/04* (2013.01); *C07D 413/14* (2013.01); *C07D 417/04* (2013.01); *C07D 417/06* (2013.01); *C07D 471/04* (2013.01); *C07D 491/08* (2013.01); *C07D 491/10* (2013.01); *C07D 513/04* (2013.01)

(58) Field of Classification Search
CPC ........................ C07D 295/088; A61K 31/5375
USPC ................. 548/570; 514/428, 238.2; 544/168
See application file for complete search history.

(56) References Cited

U.S. PATENT DOCUMENTS

| | | | |
|---|---|---|---|
| 4,670,469 A | 6/1987 | Schewe et al. | |
| 5,274,104 A | 12/1993 | Arnaud et al. | |

(Continued)

FOREIGN PATENT DOCUMENTS

| | | | |
|---|---|---|---|
| WO | WO 99/18074 A1 | 4/1999 | |
| WO | 00/59285 A2 | 10/2000 | |

(Continued)

OTHER PUBLICATIONS

Sealy et al., Cell. vol. 14, 115-121, May 1978.*
Byrn et al., Solid-State Chemistry of Drugs, Second Edition, 1999, pp. 233-247.*
Jones et al., Journal of the American Chemical Society (1921), 43, 2422-48.*
Staudinger et al., Berichte der Deutschen Chemischen Gesellschaft (1911), 44, 365-74 (abstract only).*

(Continued)

*Primary Examiner* — Yong Chu
*Assistant Examiner* — Sonya Wright
(74) *Attorney, Agent, or Firm* — McDonnell Boehnen Hulbert & Berghoff LLP

(57) ABSTRACT

This invention relates to compounds for the inhibition of histone deacetylase. More particularly, the invention provides for compounds of the Formula (I)

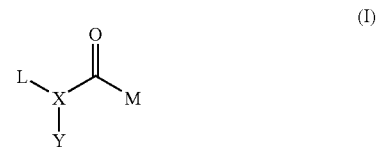

and N-oxides, hydrates, solvates, pharmaceutically acceptable salts, prodrugs and complexes thereof, and racemic and scalemic mixtures, diastereomers and enantiomers thereof, wherein groups L, M, X and Y are as defined herein.

5 Claims, No Drawings

(51) Int. Cl.

| | |
|---|---|
| *C07D 209/44* | (2006.01) |
| *C07D 211/34* | (2006.01) |
| *C07D 211/46* | (2006.01) |
| *C07D 211/52* | (2006.01) |
| *C07D 211/64* | (2006.01) |
| *C07D 211/76* | (2006.01) |
| *C07D 213/56* | (2006.01) |
| *C07D 213/64* | (2006.01) |
| *C07D 213/70* | (2006.01) |
| *C07D 213/74* | (2006.01) |
| *C07D 215/26* | (2006.01) |
| *C07D 219/04* | (2006.01) |
| *C07D 231/14* | (2006.01) |
| *C07D 233/84* | (2006.01) |
| *C07D 235/16* | (2006.01) |
| *C07D 235/28* | (2006.01) |
| *C07D 239/26* | (2006.01) |
| *C07D 239/34* | (2006.01) |
| *C07D 239/38* | (2006.01) |
| *C07D 239/42* | (2006.01) |
| *C07D 249/06* | (2006.01) |
| *C07D 267/20* | (2006.01) |
| *C07D 277/36* | (2006.01) |
| *C07D 277/74* | (2006.01) |
| *C07D 285/12* | (2006.01) |
| *C07D 295/155* | (2006.01) |
| *C07D 295/192* | (2006.01) |
| *C07D 295/205* | (2006.01) |
| *C07D 295/26* | (2006.01) |
| *C07D 311/84* | (2006.01) |
| *C07D 317/50* | (2006.01) |
| *C07D 333/24* | (2006.01) |
| *C07D 401/04* | (2006.01) |
| *C07D 401/06* | (2006.01) |
| *C07D 409/04* | (2006.01) |
| *C07D 413/04* | (2006.01) |
| *C07D 413/14* | (2006.01) |
| *C07D 417/04* | (2006.01) |
| *C07D 417/06* | (2006.01) |
| *C07D 471/04* | (2006.01) |
| *C07D 491/08* | (2006.01) |
| *C07D 491/10* | (2006.01) |
| *C07D 513/04* | (2006.01) |

(56) References Cited

U.S. PATENT DOCUMENTS

| | | |
|---|---|---|
| 6,197,791 B1 | 3/2001 | Venkatesan et al. |
| 6,376,506 B1 | 4/2002 | Broka |
| 6,403,632 B1 | 6/2002 | Duan et al. |
| 6,541,661 B1 | 4/2003 | Delorme |
| 2003/0225054 A1 | 12/2003 | Duan |
| 2008/0207590 A1 | 8/2008 | Deziel et al. |

FOREIGN PATENT DOCUMENTS

| | | |
|---|---|---|
| WO | WO 00/63197 A1 | 10/2000 |
| WO | 01/47874 A1 | 7/2001 |
| WO | 02/22577 A2 | 3/2002 |
| WO | WO 03/041715 A1 | 5/2003 |
| WO | 2007/068474 A1 | 6/2007 |
| WO | WO 2008/074132 A1 | 6/2008 |

OTHER PUBLICATIONS

KrennHrubec, K. et al.: "Design and evaluation of 'Linkerless' hydroxamic acids as selective HDAC8 inhibitors," Bioorganic & Medicinal Chemistry Letters, 2007, vol. 17, pp. 2874-2878.

Venkatesan, A.M. et al.: "Synthesis and Structure-Activity Relationships of 4-alkynyloxy Phenyl Sulfanyl, Sulfinyl, and Sulfonyl Alkyl Hydroxamates as Tumor Necrosis Factor-Converting Enzyme and Matrix Metalloproteinase Inhibitors," Journal of Medicinal Chemistry, 2004, vol. 47, p. 6255-6269.

Matjevic-Sosa, J. et al.: "Antimicrobial activity of N-phtaloylamino acid hydroxamates," Acta Pharm, 2005, vol. 55, pp. 387-399.

Eckstein et al., "Possibilities of synthesis and use of diarylacetohydroximyl chlorides", Przemysl chemiczny, 58(5), 1979, 235-238.

Buraczewski et al., "On the properties and the fungicidal activity of some aryl derivatives of hydroxamic acid", Przemysl chemiczny, 43(11), 1964, 626-629.

Eckstein et al., "On the systemic activity of some hydroxamic acid derivatives", Polytechnic School, Warsaw Agronomic University, 2007-2020.

Elford et al., "New Ribonucleotide Reductase Inhibitors with Antineoplastic Activity", Cancer Research, 39, 1979, 844-851.

Tanaka et al., "Syntheses and Anti-Inflammatory and Analgesic Activities of Hydroxamic Acids and Acid Hydrazides", Chem. Pharm. Bull., 31(8), 1983, 2810-2819.

Byrdy, S. et al., Biological Activity of β-Nitrovinylbenzene Derivatives, Tetra-hedron, Institute of Technology, Warszawa, Poland, 20, Suppl.1, 1964, 509-518.

CAS Registry No. 53648-05-8.

CAS Registry No. 15560-24-4.

Buraczewski, K. et al., "Properties and fungicidal activity of some aryl derivatives of hydroxamic acid", Bulletin De L'Academie Polonaise de Sciences, 1964, vol. 12, 773-779.

Grebenyuk, A. D. et al., "4',4"(5')-Dibenzo-18-Crown-6-Diaryl-Acetohydroxamic Acids", Chemistry of Heterocyclic Compounds, 2006, 42(6), 732-734.

Geffenken, D. et al., "Herstellung von 3-Hydroxyprpiohydroxamsauren mit Hilfe von Dicyclohexylcarbodiimid", Synthesis, 1975, 176-177.

Ruhland, B. et al., "Synthesis of 1-hydroxy-2H,5H-dihydroisoxazolo[5,4-c]qui noline. A novel heterocyclic ring system", Journal of Heterocyclic Chemistry, 1989, vol. 26, 469-471.

KrennHrubec et al., "Design and evaluation of 'Linkerless' hydroxamic acids as selective HDAC8 inhibitors", Bioorganic and Medicinal Chemistry Letters, 2007, 17(10), 2874-2878.

* cited by examiner

INHIBITORS OF HISTONE DEACETYLASE

This application claims the benefit of U.S. provisional application No. 60/922,505 filed Apr. 9, 2007.

BACKGROUND OF THE INVENTION

1. Field of the Invention

This invention relates to compounds for the inhibition of histone deacetylase.

2. Description of Related Art

In eukaryotic cells, nuclear DNA associates with histones to form a compact complex called chromatin. The histones constitute a family of basic proteins which are generally highly conserved across eukaryotic species. The core histones, termed H2A, H2B, H3, and H4, associate to form a protein core. DNA winds around this protein core, with the basic amino acids of the histones interacting with the negatively charged phosphate groups of the DNA. Approximately 146 base pairs of DNA wrap around a histone core to make up a nucleosome particle, the repeating structural motif of chromatin.

Csordas, *Biochem. J.*, 286: 23-38 (1990) teaches that histones are subject to posttranslational acetylation of the N-terminal lysine residues, a reaction that is catalyzed by histone acetyl transferase (HAT 1). Acetylation neutralizes the positive charge of the lysine side chain, and is thought to impact chromatin structure. Indeed, Taunton et al., *Science*, 272: 408-411 (1996), teaches that access of transcription factors to chromatin templates is enhanced by histone hyperacetylation. Taunton et al. further teaches that an enrichment in underacetylated histone H4 has been found in transcriptionally silent regions of the genome.

Histone acetylation is a reversible modification, with deacetylation being catalyzed by a family of enzymes termed histone deacetylases (HDACs). The molecular cloning of gene sequences encoding proteins with HDAC activity has established the existence of a set of discrete HDAC enzyme isoforms. Grozinger et al., *Proc. Natl. Acad. Sci. USA*, 96:4868-4873 (1999), teaches that HDACs may be divided into two classes, the first represented by yeast Rpd3-like proteins, and the second represented by yeast Hd1-like proteins. Grozinger et al. also teaches that the human HDAC-1, HDAC-2, and HDAC-3 proteins are members of the first class of HDACs, and discloses new proteins, named HDAC-4, HDAC-5, and HDAC-6, which are members of the second class of HDACs. Kao et al., *Gene & Development* 14:55-66 (2000), discloses an additional member of this second class, called HDAC-7. More recently, Hu, E. et al. *J. Bio. Chem.* 275: 15254-13264 (2000) disclosed another member of the first class of histone deacetylases, HDAC-8. Zhou et al., *Proc. Natl. Acad. Sci. U.S.A.*, 98: 10572-10577 (2001) teaches the cloning and characterization of a new histone deacetylase, HDAC-9. Kao et al., *J. Biol. Chem.*, 277:187-93 (2002) teaches the isolation and characterization of mammalian HDAC 10, a novel histone deacetylase. Gao et al, *J. Biol. Chem.* (In press) teaches the cloning and functional characterization of HDAC11, a novel member of the human histone deacetylase family. Shore, *Proc. Natl. Acad. Sci. U.S.A.* 97: 14030-2 (2000) discloses another class of deacetylase activity, the Sir2 protein family. It has been unclear what roles these individual HDAC enzymes play.

Studies utilizing known HDAC inhibitors have established a link between acetylation and gene expression. Numerous studies have examined the relationship between HDAC and gene expression. Taunton et al., *Science* 272:408-411 (1996), discloses a human HDAC that is related to a yeast transcriptional regulator. Cress et al., *J. Cell. Phys.* 184: 1-16 (2000), discloses that, in the context of human cancer, the role of HDAC is as a corepressor of transcription. Ng et al., *TIBS* 25: March (2000), discloses HDAC as a pervasive feature of transcriptional repressor systems. Magnaghi-Jaulin et al., *Prog. Cell Cycle Res.* 4:41-47 (2000), discloses HDAC as a transcriptional co-regulator important for cell cycle progression.

Richon et al., *Proc. Natl. Acad. Sci. USA*, 95: 3003-3007 (1998), discloses that HDAC activity is inhibited by trichostatin A (TSA), a natural product isolated from *Streptomyces hygroscopicus*, which has been shown to inhibit histone deacetylase activity and arrest cell cycle progression in cells in the G1 and G2 phases (Yoshida et al., *J. Biol. Chem.* 265: 17174-17179, 1990; Yoshida et al., *Exp. Cell Res.* 177: 122-131, 1988), and by a synthetic compound, suberoylanilide hydroxamic acid (SAHA). Yoshida and Beppu, *Exper. Cell Res.*, 177: 122-131 (1988), teaches that TSA causes arrest of rat fibroblasts at the $G_1$ and $G_2$ phases of the cell cycle, implicating HDAC in cell cycle regulation. Indeed, Finnin et al., *Nature*, 401: 188-193 (1999), teaches that TSA and SAHA inhibit cell growth, induce terminal differentiation, and prevent the formation of tumors in mice. Suzuki et al., U.S. Pat. No. 6,174,905, EP 0847992 and JP 258863/96, disclose benzamide derivatives that induce cell differentiation and inhibit HDAC. Delorme et al., WO 01/38322 and WO 2001/070675, disclose additional compounds that serve as HDAC inhibitors. Other inhibitors of histone deacetylase activity, including trapoxin, depudecin, FR901228 (Fujisawa Pharmaceuticals), and butyrate, have been found to similarly inhibit cell cycle progression in cells (Taunton et al., *Science* 272: 408-411, 1996; Kijima et al., *J. Biol. Chem.* 268(30): 22429-22435, 1993; Kwon et al., *Proc. Natl. Acad. Sci. USA* 95(7):3356-61, 1998).

These and other findings suggest that inhibition of HDAC activity represents a novel approach for intervening in cell cycle regulation and that HDAC inhibitors have great therapeutic potential in the study and/or treatment of diseases or conditions ameliorated by modulating HDAC activity (in particular, cell proliferative diseases (such as cancer), diabetes, inflammation, cardiac disease, stroke, epilepsy, depression, immunological disease or viral or fungal infection). Many HDAC inhibitors, however, inhibit all HDAC isoforms. There is a need to identify selective HDAC inhibitors (i.e., inhibitors that inhibited one or more but not all HDAC isoforms) and to identify the structural features required for potent HDAC inhibitory activity.

SUMMARY OF THE INVENTION

The present invention provides compounds useful in the inhibition of histone deacetylase, and methods for inhibiting histone deacetylase.

In a first aspect, the present invention provides compounds having the Formula (I),

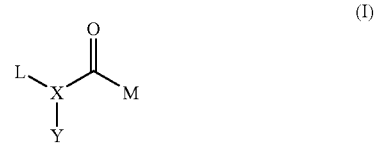

and N-oxides, hydrates, solvates, pharmaceutically acceptable salts, prodrugs and complexes thereof, and racemic and scalemic mixtures, diastereomers and enantiomers thereof, in which groups L, M, X and Y are as defined below.

In a second aspect, the invention provides a composition comprising a pharmaceutically acceptable carrier, diluent or excipient and a compound having the formula (VI)

(VI)

or an N-oxide, hydrate, solvate, pharmaceutically acceptable salt, prodrug or complex thereof or a racemic or scalemic mixture, diastereomer or enantiomer thereof, in which groups L, M, X and Y are as defined below.

In a third aspect, the invention provides a method of inhibiting a histone deacetylase selected from the group consisting of HDAC-4, HDAC-5, HDAC-6, HDAC-7, HDAC-8, HDAC-9, HDAC-10 and HDAC-11 the method comprising contacting the histone deacetylase or a cell containing histone deacetylase, with a histone deacetylase inhibiting amount of a compound having the formula (XII)

(XII)

or an N-oxide, hydrate, solvate, pharmaceutically acceptable salt, prodrug or complex thereof, or a racemic or scalemic mixture, diastereomer or enantiomer thereof, in which groups L, M, X and Y are as defined below.

The present invention provides novel compounds for use in the study and/or treatment of diseases or conditions effected by modulation of HDAC activity.

In some preferred embodiments a patient is administered an effective amount of a compound having a formula as described herein, preferably having any of Formulae (XII)-(XVII), or a composition thereof, in combination (simultaneously or sequentially) with at least one other anti-disease agent.

The present invention provides for the use of compounds having a Formula as described herein, preferably any of Formulae (XII)-(XVII), or a composition thereof, for inhibiting histone deacetylase-4, -5, -6, -7, -8, -9, -10 and/or -11 activity. The present invention also provides for the use of compounds having a Formula has described herein, preferably having any of Formulae (XII)-(XVII), or a composition thereof, for the treatment of diseases or conditions effected by modulation of HDAC activity, such as cell proliferative diseases (such as cancer), diabetes, inflammation, cardiac disease, stroke, epilepsy, depression, immunological disease or viral or fungal infection.

The present invention provides compounds for use in the manufacture of a medicament for the treatment of diseases or conditions effected by modulation of HDAC activity, such as cell proliferative diseases (such as cancer), diabetes, inflammation, cardiac disease, stroke, epilepsy, depression, immunological disease or viral or fungal infection.

The present invention also relates to methods of using a compound having a Formula as described herein, preferably any of Formulae (XII)-(XVII), or a composition thereof, in the treatment of diseases or conditions effected by modulation of HDAC activity, such as cell proliferative diseases (such as cancer), diabetes, inflammation, cardiac disease, stroke, epilepsy, depression, immunological disease or viral or fungal infection.

The foregoing merely summarizes various aspects of the invention and is not intended to be limiting in nature. These aspects and other aspects and embodiments are described more fully below. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

DETAILED DESCRIPTION OF THE INVENTION

The present invention provides compounds that are useful as inhibitors of histone deacetylase.

In one aspect, the invention provides certain compounds of the Formula (I)

(I)

and N-oxides, hydrates, solvates, pharmaceutically acceptable salts, prodrugs and complexes thereof, and racemic and scalemic mixtures, diastereomers and enantiomers thereof, wherein groups L, M, X and Y are as defined herein.

In the second aspect, the invention provides a composition comprising a pharmaceutically acceptable carrier, diluent or excipient and a compound having the Formula (VI)

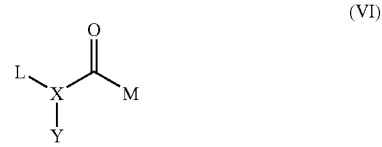

(VI)

or an N-oxide, hydrate, solvate, pharmaceutically acceptable salt, prodrug or complex thereof, or a racemic or scalemic mixture, diastereomer or enantiomer thereof, in which groups L, M, X and Y are as defined below.

In the third aspect, the invention provides a method of inhibiting a histone deacetylase selected from the group consisting of HDAC-4, HDAC-5, HDAC-6, HDAC-7, HDAC-8, HDAC-9, HDAC-10 and HDAC-11. In one embodiment, the method comprises contacting the histone deacetylase with a histone deacetylase inhibiting amount of a compound having the Formula (XII)

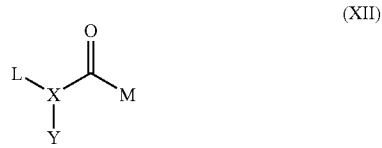

(XII)

or an N-oxide, hydrate, solvate, pharmaceutically-acceptable salt, prodrug or complex thereof, or a racemic or scalemic mixture, diasteromer or enantiomer thereof, or a preferred embodiment thereof.

In a further embodiment of the third aspect, the method comprises contacting the histone deacetylase with a histone deacetylase inhibiting amount of a composition comprising the above-described compound, or an N-oxide, hydrate, solvate, pharmaceutically-acceptable salt, prodrug or complex thereof, or a racemic or scalemic mixture, diasteromer or enantiomer thereof, or a preferred embodiment thereof, and a pharmaceutically-acceptable carrier. In yet another embodiment, the method comprises inhibiting a histone deacetylase selected from the group consisting of HDAC-4, HDAC-5, HDAC-6, HDAC-7, HDAC-8, HDAC-9, HDAC-10 and HDAC-11 in a cell comprising contacting the cell with a histone deacetylase inhibiting amount of the above-described compound, or an N-oxide, hydrate, solvate, pharmaceutically-acceptable salt, prodrug or complex thereof, or a racemic or scalemic mixture, diasteromer or enantiomer thereof, or a preferred embodiment thereof. In still another embodiment, the method comprises inhibiting a histone deacetylase selected from the group consisting of HDAC-4, HDAC-5, HDAC-6, HDAC-7, HDAC-8, HDAC-9, HDAC-10 and HDAC-11 in a cell comprising contacting the cell with a histone deacetylase inhibiting amount of a composition comprising the above-described compound, or an N-oxide, hydrate, solvate, pharmaceutically-acceptable salt, prodrug or complex thereof, or a racemic or scalemic mixture, diasteromer or enantiomer thereof, or a preferred embodiment thereof, and a pharmaceutically-acceptable carrier. According to this aspect, the compounds and compositions according to the invention are useful as tools for exploring the role of histone deacetylases in various disease conditions.

In a preferred method of the present invention, the cell in which inhibition of histone deacetylase is desired is a mammalian cell, preferably a primate cell, more preferably a human cell.

In some preferred embodiments, the contacted cell is in an animal. Thus, the invention provides a method for treating diseases or conditions effected by modulation of HDAC activity, such as cell proliferative diseases (such as cancer), diabetes, inflammation, cardiac disease, stroke, epilepsy, depression, immunological disease or viral or fungal infection in an animal, comprising administering to an animal in need of such treatment a therapeutically effective amount of a compound having a Formula as described herein, preferably having a Formula according to any of Formulae (XII)-(XVII), or a pharmaceutical composition thereof. Preferably, the animal is a mammal, more preferably a domesticated mammal or a primate. Most preferably, the animal is a human.

In some preferred embodiments the animal is administered an effective amount of a compound having a Formula as described herein, preferably a Formula according to any of Formulae (XII)-(XVII), or a pharmaceutical composition thereof, in combination (simultaneously or sequentially) with at least one other anti-disease agent, or a composition thereof. The term "anti-disease agent" includes any agent that is useful for the treatment of the particular disease for which treatment is desired.

Reference to "a compound of the formula (I)" and the like, (or equivalently, "a compound according to the first aspect", or "a compound of the present invention", and the like), herein is understood to include reference to N-oxides, hydrates, solvates, pharmaceutically acceptable salts, prodrugs and complexes thereof, and racemic and scalemic mixtures, diastereomers, enantiomers and tautomers thereof and unless otherwise indicated.

In preferred embodiments, the individual is a mammal, preferably a primate, more preferably a human.

For purposes of the present invention, the following definitions will be used (unless expressly stated otherwise).

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for 0, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—. Also, a number of moietes disclosed here may exist in multiple tautomeric forms, all of which are intended to be encompassed by any given tautomeric structure.

For simplicity, reference to a "$C_n$-$C_m$" heterocyclyl or "$C_n$-$C_m$" heteroaryl means a heterocyclyl or heteroaryl having from "n" to "m" annular atoms, where "n" and "m" are integers. Thus, for example, a $C_5$-$C_6$-heterocyclyl is a 5- or 6-membered ring having at least one heteroatom, and includes pyrrolidinyl ($C_5$) and piperidinyl ($C_6$); $C_6$-heteroaryl includes, for example, pyridyl and pyrimidyl.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$-hydrocarbyl" includes a covalent bond, methyl, ethyl, ethenyl, ethynyl, propyl, propenyl, propynyl, and cyclopropyl.

The term "alkyl" is intended to mean a straight or branched chain aliphatic group having from 1 to 12 carbon atoms, preferably 1-8 carbon atoms, and more preferably 1-6 carbon atoms. Other preferred alkyl groups have from 2 to 12 carbon atoms, preferably 2-8 carbon atoms and more preferably 2-6 carbon atoms. Preferred alkyl groups include, without limitation, methyl, ethyl, propyl, isopropyl, butyl, isobutyl, sec-butyl, tert-butyl, pentyl, and hexyl. A "$C_0$" alkyl (as in "$C_0$-$C_3$-alkyl") is a covalent bond.

The term "alkenyl" is intended to mean an unsaturated straight or branched chain aliphatic group with one or more carbon-carbon double bonds, having from 2 to 12 carbon atoms, preferably 2-8 carbon atoms, and more preferably 2-6 carbon atoms. Preferred alkenyl groups include, without limitation, ethenyl, propenyl, butenyl, pentenyl, and hexenyl.

The term "alkynyl" is intended to mean an unsaturated straight or branched chain aliphatic group with one or more carbon-carbon triple bonds, having from 2 to 12 carbon atoms, preferably 2-8 carbon atoms, and more preferably 2-6 carbon atoms. Preferred alkynyl groups include, without limitation, ethynyl, propynyl, butynyl, pentynyl, and hexynyl.

The terms "alkylene," "alkenylene," or "alkynylene" as used herein are intended to mean an alkyl, alkenyl, or alkynyl group, respectively, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "cycloalkyl" is intended to mean a saturated or unsaturated mono-, bi, tri- or poly-cyclic hydrocarbon group having about 3 to 15 carbons, preferably having 3 to 12 carbons, preferably 3 to 8 carbons, and more preferably 3 to 6 carbons. In certain preferred embodiments, the cycloalkyl group is fused to an aryl, heteroaryl or heterocyclic group. Preferred cycloalkyl groups include, without limitation, cyclopenten-2-enone, cyclopenten-2-enol, cyclohex-2-enone, cyclohex-2-enol, cyclopropyl, cyclobutyl, cyclopentyl, cyclopentenyl, cyclohexyl, cyclohexenyl, cycloheptyl, and cyclooctyl.

In certain preferred embodiments, the cycloalkyl group is a bridged cycloalkyl group, preferably a $C_5$-$C_{10}$ bridged bicyclic group. In certain preferred embodiments, the bridged cycloalkyl group is a $C_5$ bridged bicyclic group. In certain preferred embodiments, the bridged cycloalkyl group is a $C_6$ bridged bicyclic group. In certain preferred embodiments, the bridged cycloalkyl group is a $C_7$ bridged bicyclic group. In certain preferred embodiments, the bridged cycloalkyl group is a $C_8$ bridged bicyclic group. In certain preferred embodiments, the bridged cycloalkyl group is a $C_9$ bridged bicyclic. In certain preferred embodiments, the bridged cycloalkyl group has a bridge of 0, 1, 2 or 3 carbon atoms. A bridge of 0 carbon atoms is a bond, and equates to a cycloalkyl group fused to another ring structure. In certain preferred embodiments, the bridged cycloalkyl group has a bridge of 0, 1 or 3 carbon atoms. In certain preferred embodiments, the bridged cycloalkyl group has a bridge of 1 or 3 carbon atoms. In certain preferred embodiments, the bridged cycloalkyl group has a bridge of 1 carbon atom. In certain preferred embodiments, the bridged cycloalkyl group has a bridge of 2 carbon atoms. In certain preferred embodiments, the bridged cycloalkyl group has a bridge of 3 carbon atoms. If a bridged cycloalkyl group is described as "optionally substituted", it is intended to be optionally substituted on any position, including the bridge. The bridged cycloalkyl group is not limited to any particular stereochemistry.

The term "heteroalkyl" is intended to mean a saturated or unsaturated, straight or branched chain aliphatic group, wherein one or more carbon atoms in the chain are independently replaced by a heteroatom selected from the group consisting of O, S, and N.

The term "aliphatic" is intended to mean both saturated and unsaturated, straight chain or branched aliphatic hydrocarbons. As will be appreciated by one of ordinary skill in the art, "aliphatic" is intended herein to include, but is not limited to, alkyl, alkenyl or alkynyl moieties.

The term "aryl" is intended to mean a mono-, bi-, tri- or polycyclic $C_6$-$C_{14}$ aromatic moiety, preferably comprising one to three aromatic rings. Preferably, the aryl group is a $C_6$-$C_{10}$ aryl group, more preferably a $C_6$ aryl group. Preferred aryl groups include, without limitation, phenyl, naphthyl, anthracenyl, and fluorenyl.

The terms "aralkyl" or "arylalkyl" is intended to mean a group comprising an aryl group covalently linked to an alkyl group. If an aralkyl group is described as "optionally substituted", it is intended that either or both of the aryl and alkyl moieties may independently be optionally substituted or unsubstituted. Preferably, the aralkyl group is $(C_1$-$C_6)$alk$(C_6$-$C_{10})$aryl, including, without limitation, benzyl, phenethyl, and naphthylmethyl. For simplicity, when written as "aralkyl" this term, and terms related thereto, is intended to indicate the order of groups in a compound as "aryl-alkyl". Similarly, "alkyl-aryl" is intended to indicate the order of the groups in a compound as "alkyl-aryl".

The terms "heterocyclyl", "heterocyclic" or "heterocycle" are intended to mean a group which is a mono-, bi-, or polycyclic structure having from about 3 to about 14 atoms, wherein one or more atoms are independently selected from the group consisting of N, O, and S. The ring structure may be saturated, unsaturated or partially unsaturated. In certain preferred embodiments, the heterocyclic group is non-aromatic. In a bicyclic or polycyclic structure, one or more rings may be aromatic; for example one ring of a bicyclic heterocycle or one or two rings of a tricyclic heterocycle may be aromatic, as in indan and 9,10-dihydro anthracene. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In certain preferred embodiments, the heterocyclic group is a bridged heterocyclic group, preferably a $C_6$-$C_{10}$ bridged bicyclic group, wherein one or more carbon atoms are independently replaced by a heteroatom selected from the group consisting of N, O and S. In certain preferred embodiments, the bridged heterocyclic group is a $C_6$ bridged bicyclic group. In certain preferred embodiments, the bridged heterocyclic group is a $C_7$ bridged bicyclic group. In certain preferred embodiments, the bridged heterocyclic group is a $C_8$ bridged bicyclic group. In certain preferred embodiments, the bridged heterocyclic group is a $C_9$ bridged bicyclic. In certain preferred embodiments, the bridged heterocyclic group has a bridge of 0, 1, 2 or 3 carbon atoms. In certain preferred embodiments, the bridged heterocyclic group has a bridge of 0, 1 or 3 carbon atoms. A bridge of 0 carbon atoms is a bond, and equates to a heterocyclic group fused to another ring structure. In certain preferred embodiments, the bridged heterocyclic group has a bridge of 1 or 3 carbon atoms. In certain preferred embodiments, the bridged heterocyclic group has a bridge of 1 carbon atom. In certain preferred embodiments, the bridged heterocyclic group has a bridge of 2 carbon atoms. In certain preferred embodiments, the bridged heterocyclic group has a bridge of 3 carbon atoms. If a bridged heterocyclic group is described as "optionally substituted", it is intended to be optionally substituted on any position, including the bridge. The bridged heterocyclic group is not limited to any particular stereochemistry.

In certain preferred embodiments, the heterocyclic group is a heteroaryl group. As used herein, the term "heteroaryl" is intended to mean a mono-, bi-, tri- or polycyclic group having 5 to 14 ring atoms, preferably 5, 6, 9, or 10 ring atoms; having 6, 10, or 14 pi electrons shared in a cyclic array; and having, in addition to carbon atoms, between one or more heteroatoms independently selected from the group consisting of N, O, and S. For example, a heteroaryl group may be pyrimidinyl, pyridinyl, benzimidazolyl, thienyl, benzothiazolyl, benzofuranyl and indolinyl. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl. The term "heteroaryl" is also intended to encompass the N-oxide derivative (or N-oxide derivatives, if the heteroaryl group contains more than one nitrogen such that more than one N-oxide derivative may be formed) of a nitrogen-containing heteroaryl group. Illustrative examples of N-oxide derivatives of heteroaryl groups include, but are not limited to, pyridyl N-oxide, pyrazinyl N-opxide, pyrimidinyl N-oxide, pyridazinyl N-oxide, triazinyl N-oxide, isoquinolyl N-oxide and quinolyl N-oxide.

The terms "arylene," "heteroarylene," or "heterocyclylene" are intended to mean an aryl, heteroaryl, or heterocyclyl group, respectively, as defined hereinabove, that is positioned between and serves to connect two other chemical groups.

Preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, thiadiazolyl (e.g., 1,2,3-thiadiazolyl, 1,2,4-thiadiazolyl, 1,2,5-thiadiazolyl, 1,3,4-thiadiazolyl), thianthrenyl, thiazolyl, thienyl, thienothiazolyl, thienooxazolyl, thienoimidazolyl, thiophenyl, triazinyl, triazolyl (e.g., 1,2,3-triazolyl, 1,2,4-triazolyl, 1,2,5-triazolyl, 1,3,4-triazolyl), and xanthenyl.

Aromatic polycycles include, but are not limited to, bicyclic and tricyclic fused ring systems, including for example naphthyl.

Non-aromatic polycycles include, but are not limited to, bicyclic and tricyclic fused ring systems where each ring can be 4-9 membered and each ring can containing zero, 1 or more double and/or triple bonds. Suitable examples of non-aromatic polycycles include, but are not limited to, decalin, octahydroindene, perhydrobenzocycloheptene and perhydrobenzo-[f]-azulene.

Polyheteroaryl groups include bicyclic and tricyclic fused rings systems where each ring can independently be 5 or 6 membered and contain one or more heteroatom, for example, 1, 2, 3 or 4 heteroatoms, independently chosen from O, N and S such that the fused ring system is aromatic. Suitable examples of polyheteroaryl ring systems include quinoline, isoquinoline, pyridopyrazine, pyrrolopyridine, furopyridine, indole, benzofuran, benzothiofuran, benzindole, benzoxazole, pyrroloquinoline, and the like.

Non-aromatic polyheterocyclic groups include but are not limited to bicyclic and tricyclic ring systems where each ring can be 4-9 membered, contain one or more heteratom, for example 1, 2, 3 or 4 heteratoms, independently chosen from O, N and S, and contain zero, or one or more C=C double or triple bonds. Suitable examples of non-aromatic polyheterocycles include but are not limited to, hexitol, cis-perhydrocyclohepta[b]pyridinyl, decahydro-benzo[f][1,4]oxazepinyl, 2,8-dioxabicyclo[3.3.0]octane, hexahydro-thieno[3,2-b] thiophene, perhydropyrrolo[3,2-b]pyrrole, perhydronaphthyridine, perhydro-1H-dicyclopenta[b,e]pyran.

Mixed aryl and non-aryl polyheterocycle groups include but are not limited to bicyclic and tricyclic fused ring systems where each ring can be 4-9 membered, contain one or more heteroatom independently chosen from O, N and S and at least one of the rings must be aromatic. Suitable examples of mixed aryl and non-aryl polyheteorcycles include 2,3-dihydroindole, 1,2,3,4-tetrahydroquinoline, 5,11-dihydro-10H-dibenz[b,e][1,4]diazepine, 5H-dibenzo[b,e][1,4]diazepine, 1,2-dihydropyrrolo[3,4-b][1,5]benzodiazepine, 1,5-dihydropyrido[2,3-b][1,4]diazepin-4-one, 1,2,3,4,6,11-hexhydrobenzo[b]pyrido[2,3-e][1,4]diazepine-5-one, methylenedioxyphenyl, bis-methylenedioxyphenyl, 1,2,3,4-tetrahydronaphthalene, dibenzosuberane dihydroanthracene and 9H-fluorene.

As employed herein, and unless stated otherwise, when a moiety (e.g., alkyl, heteroalkyl, cycloalkyl, aryl, heteroaryl, heterocyclyl, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, alkyl, cycloalkyl, heterocyclyl, aryl, heteroaryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, $C_5$-$C_{15}$ heteroaryl or any of these rings fused or spiro-fused to a cycloalkyl, heterocyclyl, or aryl, wherein each of the foregoing is further optionally substituted with one more moieties listed in (a), above; and (c) —$(CR^{32}R^{33})_s$—$NR^{30}R^{31}$, wherein
s is from 0 (in which case the nitrogen is directly bonded to the moiety that is substituted) to 6,
$R^{32}$ and $R^{33}$ are each independently hydrogen, halo, hydroxyl or $C_1$-$C_4$alkyl, and
$R^{30}$ and $R^{31}$ are each independently hydrogen, cyano, oxo, hydroxyl, $C_1$-$C_8$ alkyl, $C_1$-$C_8$heteroalkyl, $C_1$-$C_8$alkenyl, carboxamido-, $C_1$-$C_3$alkyl-carboxamido-, carboxamido-$C_1$-$C_3$alkyl-, amidino-, $C_2$-$C_8$hydroxyalkyl-, $C_1$-$C_3$alkyl-aryl-, aryl-$C_1$-$C_3$ alkyl-, $C_1$-$C_3$alkyl-heteroaryl-, heteroaryl-$C_1$-$C_3$alkyl-, $C_1$-$C_3$alkyl-heterocyclyl-, heterocyclyl-$C_1$-$C_3$alkyl-, $C_1$-$C_3$alkyl-cycloalkyl-, cycloalkyl-$C_1$-$C_3$alkyl-, $C_2$-$C_8$alkoxy-, $C_2$-$C_8$alkoxy-$C_1$-$C_4$alkyl-, $C_1$-$C_8$alkoxy-carbonyl-, aryloxy-carbonyl-, aryl-$C_1$-$C_3$alkoxy-carbonyl-, heteroaryloxy-carbonyl-, heteroaryl-$C_1$-$C_3$alkoxy-carbonyl-, $C_1$-$C_8$acyl, $C_0$-$C_8$alkyl-carbonyl-, aryl-$C_0$-$C_8$alkyl-carbonyl-, heteroaryl-$C_0$-$C_8$alkyl-carbonyl-, cycloalkyl-$C_0$-$C_8$alkyl-carbonyl-, $C_0$-$C_8$alkyl-NH-carbonyl-, aryl-$C_0$-$C_8$alkyl-NH-carbonyl-, heteroaryl-$C_0$-$C_8$alkyl-NH-carbonyl-, cycloalkyl-$C_0$-$C_8$alkyl-NH-carbonyl-, $C_0$-$C_8$alkyl-O-carbonyl-, aryl-$C_0$-$C_8$alkyl-O-carbonyl-, heteroaryl-$C_0$-$C_8$alkyl-O-carbonyl-, cycloalkyl-$C_0$-$C_8$alkyl-O-carbonyl-, $C_1$-$C_8$alkylsulfonyl-, aryl-alkyl-sulfonyl-, aryl-sulfonyl-, heteroaryl-alkyl-sulfonyl-, heteroaryl-sulfonyl-, $C_1$-$C_8$alkyl-NH-sulfonyl-, aryl-alkyl-NH-sulfonyl-, aryl-NH-sulfonyl-, heteroaryl-alkyl-NH-sulfonyl-, heteroaryl-NH-sulfonyl, aroyl-, aryl-, cycloalkyl-, heterocyclyl-, heteroaryl-, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, or protecting group, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents selected from the group consisting of (a) above, a protecting group, and ($X^{30}$—$Y^{31}$—), wherein said heterocyclyl may also be bridged (forming a bicyclic moiety with a methylene, ethylene or propylene bridge); wherein $X^{30}$ is selected from the group consisting of $C_1$-$C_8$alkyl, $C_2$-$C_8$alkenyl-, $C_2$-$C_8$alkynyl-, —$C_0$-$C_3$alkyl-$C_2$-$C_8$alkenyl-$C_0$-$C_3$alkyl, $C_0$-$C_3$alkyl-$C_2$-$C_8$alkynyl-$C_0$-$C_3$alkyl, $C_0$-$C_3$alkyl-O—$C_0$-$C_3$alkyl-, HO—$C_0$-$C_3$alkyl-, CO—$C_4$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkenyl-, N($R^{30}$)($R^{31}$)—$C_0$-$C_3$alkynyl-, (N($R^{30}$)($R^{31}$))$_2$—C═N—, $C_0$-$C_3$alkyl-S(O)$_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with from 1 to 3 substituents from (a); and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C(N$R^{30}$)—N($R^{31}$)—, —N($R^{30}$)—C(N$R^{31}$)—, —C(N$R^{31}$)—N($R^{30}$), —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —S(O)$_{0-2}$—, —SO$_2$N($R^{31}$)—, —N($R^{31}$)—SO$_2$— and —N($R^{30}$)—SO$_2$N($R^{31}$)—.

As a non-limiting example, substituted phenyls include 2-fluorophenyl, 3,4-dichlorophenyl, 3-chloro-4-fluoro-phenyl, 2-fluoro-3-propylphenyl. As another non-limiting example, substituted n-octyls include 2,4-dimethyl-5-ethyl-octyl and 3-cyclopentyl-octyl. Included within this definition are methylenes (—CH$_2$—) substituted with oxygen to form carbonyl —CO—.

When there are two optional substituents bonded to adjacent atoms of a ring structure, such as for example phenyl, thiophenyl, or pyridinyl, the substituents, together with the atoms to which they are bonded, optionally form a 5- or 6-membered cycloalkyl or heterocycle having 1, 2, or 3 annular heteroatoms.

In a preferred embodiment, hydrocarbyl, alkyl, alkenyl, alkynyl, heteroalkyl, cycloalkyl, heterocyclic, aryl, heteroaryl, aromatic polycycle, non-aromatic polycycle, polyheteroaryl, non-aromatic polyheterocyclic and mixed aryl and non-aryl polyheterocycle groups are unsubstituted.

In other preferred embodiments, hydrocarbyl, alkyl, alkenyl, alkynyl, heteroalkyl, cycloalkyl, heterocyclic, aryl, heteroaryl, aromatic polycycle, non-aromatic polycycle, polyheteroaryl, non-aromatic polyheterocyclic and mixed aryl and non-aryl polyheterocycle groups are substituted with from 1 to 3 independently selected substituents more preferably one or two independently selected substituents.

Preferred substituents on alkyl groups include, but are not limited to, hydroxyl, halogen (e.g., a single halogen substituent or multiple halo substituents; in the latter case, groups such as $CF_3$ or an alkyl group bearing $Cl_3$), cyano, nitro, alkyl, cycloalkyl, alkenyl, cycloalkenyl, alkynyl, heterocycle, aryl, —$OR^u$, —$SR^u$, —S(═O)$R^y$, —S(═O)$_2R^y$, —P(═O)$_2R^y$, —S(═O)$_2OR^y$, —P(═O)$_2OR^y$, —NR'R$^w$, —NR'S(═O)$_2R^y$, —NR'P(═O)$_2R^y$, —S(═O)$_2$NR'R$^w$, —P(═O)$_2$NR'R$^w$, —C(═O)$OR^y$, —C(═O)$R^k$, —C(═O)NR'R$^w$, —OC(═O)$R^u$, —OC(═O)NR'R$^w$, —NR'C(═O)$OR^y$, —$NR^x$C(═O)NR'R$^w$, —$NR^x$S(═O)$_2$NR'R$^w$, —$NR^x$P(═O)$_2$NR'R$^w$, —NR'C(═O)$R^u$ or —NR'P(═O)$_2R^y$, wherein $R^u$ is hydrogen, alkyl, cycloalkyl, alkenyl, cycloalkenyl, alkynyl, heterocycle or aryl; R$^v$, R$^w$ and R$^x$ are independently hydrogen, alkyl, cycloalkyl, heterocycle or aryl, or said R$^v$ and R$^w$ together with the N to which they are bonded optionally form a heterocycle; and R$^y$ is alkyl, cycloalkyl, alkenyl, cycloalkenyl, alkynyl, heterocycle or aryl. In the aforementioned exemplary substituents, groups such as alkyl, cycloalkyl, alkenyl, alkynyl, cycloalkenyl, heterocycle and aryl can themselves be optionally substituted.

Preferred substituents on alkenyl and alkynyl groups include, but are not limited to, alkyl or substituted alkyl, as well as those groups recited as preferred alkyl substituents.

Preferred substituents on cycloalkyl groups include, but are not limited to, nitro, cyano, alkyl or substituted alkyl, as well as those groups recited about as preferred alkyl substituents. Other preferred substituents include, but are not limited to, spiro-attached or fused cyclic substituents, preferably spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

In a preferred embodiment, when a cycloalkyl is substituted by two $C_{1-6}$ alkyl groups, the two alkyl groups may combine together to form an alkylene chain, preferably a $C_{1-3}$ alkylene chain. Cycloalkyl groups having this crosslinked structure include bicyclo[2.2.2]octanyl and norbornanyl.

Preferred substituents on cycloalkenyl groups include, but are not limited to, nitro, cyano, alkyl or substituted alkyl, as well as those groups recited as preferred alkyl substituents. Other preferred substituents include, but are not limited to, spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Preferred substituents on aryl groups include, but are not limited to, nitro, cycloalkyl or substituted cycloalkyl, cycloalkenyl or substituted cycloalkenyl, cyano, alkyl or substituted alkyl, as well as those groups recited above as preferred alkyl substituents. Other preferred substituents include, but are not limited to, fused cyclic groups, especially fused cycloalkyl, fused cycloalkenyl, fused heterocycle, or fused aryl, where the aforementioned cycloalkyl, cylcoalkenyl, heterocycle and aryl substituents can themselves be optionally substituted. Still other preferred substituents on aryl groups (phenyl, as a non-limiting example) include, but are not limited to, haloalkyl and those groups recited as preferred alkyl substituents.

Preferred substituents on heterocylic groups include, but are not limited to, cycloalkyl, substituted cycloalkyl, cycloalkenyl, substituted cycloalkenyl, nitro, oxo (i.e., =O), cyano, alkyl, substituted alkyl, as well as those groups recited as preferred alkyl substituents. Other preferred substituents on heterocyclic groups include, but are not limited to, spiro-attached or fused cylic substituents at any available point or points of attachment, more preferably spiro-attached cycloalkyl, spiro-attached cycloalkenyl, spiro-attached heterocycle (excluding heteroaryl), fused cycloalkyl, fused cycloakenyl, fused heterocycle and fused aryl, where the aforementioned cycloalkyl, cycloalkenyl, heterocycle and aryl substituents can themselves be optionally substituted. In a preferred embodiment, when a heterocyclic is substituted by two $C_{1-6}$ alkyl groups, the two alkyl groups may combine together to form an alkylene chain, preferably a $C_{1-3}$ alkylene chain.

In a preferred embodiment, a heterocyclic group is substituted on carbon, nitrogen and/or sulfur at one or more positions. Preferred substituents on nitrogen include, but are not limited to alkyl, aryl, aralkyl, alkylcarbonyl, alkylsulfonyl, arylcarbonyl, arylsulfonyl, alkoxycarbonyl, or aralkoxycarbonyl. Preferred substituents on sulfur include, but are not limited to, oxo and $C_{1-6}$alkyl. In certain preferred embodiments, nitrogen and sulfur heteroatoms may independently be optionally oxidized and nitrogen heteroatoms may independently be optionally quaternized.

Especially preferred substituents on alkyl groups include halogen and hydroxy.

Especially preferred substituents on ring groups, such as aryl, heteroaryl, cycloalkyl and heterocyclyl, include halogen, alkoxy and alkyl.

Preferred substituents on aromatic polycycles include, but are not limited to, oxo, $C_1$-$C_6$alkyl, cycloalkylalkyl (e.g., cyclopropylmethyl), oxyalkyl, halo, nitro, amino, alkylamino, aminoalkyl, alkyl ketones, nitrile, carboxyalkyl, alkylsulfonyl, arylsulfonyl, aminosulfonyl and $OR^{aa}$, such as alkoxy, wherein $R^{aa}$ is selected from the group consisting of H, $C_1$-$C_6$alkyl, $C_4$-$C_9$cycloalkyl, $C_4$-$C_9$heterocycloalkyl, aryl, heteroaryl, arylalkyl, heteroarylalkyl and $(CH_2)_{0-6}Z^aR^{bb}$, wherein $Z^a$ is selected from the group consisting of O, $NR^{cc}$, S and S(O), and $R^{bb}$ is selected from the group consisting of H, $C_1$-$C_6$alkyl, $C_4$-$C_9$cycloalkyl, $C_4$-$C_9$heterocycloalkyl, $C_4$-$C_9$heterocycloalkylalkyl, aryl, mixed aryl and non-aryl polycycle, heteroaryl, arylalkyl, (e.g. benzyl), and heteroarylalkyl (e.g. pyridylmethyl); and $R^{cc}$ is selected from the group consisting of H, $C_1$-$C_6$alkyl, $C_4$-$C_9$cycloalkyl, $C_4$-$C_9$heterocycloalkyl, aryl, heteroaryl, arylalkyl (e.g. benzyl), heteroarylalkyl (e.g. pyridylmethyl) and amino acyl.

Preferred substituents on non-aromatic polycycles include, but are not limited to, oxo, $C_3$-$C_9$cycloalkyl, such as cyclopropyl, cyclobutyl, cyclopentyl, cyclohexyl and the like. Unless otherwise noted, non-aromatic polycycle substituents include both unsubstituted cycloalkyl groups and cycloalkyl groups that are substituted by one or more suitable substituents, including but not limited to, $C_1$-$C_6$alkyl, oxo, halo, hydroxy, aminoalkyl, oxyalkyl, alkylamino and $OR^{aa}$, such as alkoxy. Preferred substituents for such cycloalkyl groups include halo, hydroxy, alkoxy, oxyalkyl, alkylamino and aminoalkyl.

Preferred substituents on carbon atoms of polyheteroaryl groups include but are not limited to, straight and branched optionally substituted $C_1$-$C_6$alkyl, unsaturation (i.e., there are one or more double or triple C—C bonds), acyl, oxo, cycloalkyl, halo, oxyalkyl, alkylamino, aminoalkyl, acylamino, $OR^1$ (for example alkoxy), and a substituent of the formula —O—$(CH_2CH=CH(CH_3)(CH_2))_{1-3}H$. Examples of suitable straight and branched $C_1$-$C_6$alkyl substituents include but are not limited to methyl, ethyl, n-propyl, 2-propyl, n-butyl, sec-butyl, t-butyl and the like. Preferred substituents include halo, hydroxy, alkoxy, oxyalkyl, alkylamino and aminoalkyl. Preferably substitutions on nitrogen atoms include, for example by N-oxide or $R^{cc}$. Preferred substituents on nitrogen atoms include H, $C_1$-$C_4$alkyl, acyl, aminoacyl and sulfonyl. Preferably sulfur atoms are unsubstituted. Preferred substituents on sulfur atoms include but are not limited to oxo and lower alkyl.

Preferred substituents on carbon atoms of non-aromatic polyheterocyclic groups include but are not limited to straight and branched optionally substituted $C_1$-$C_6$alkyl, unsaturation (i.e., there are one or more double or triple C—C bonds), acyl, oxo, cycloalkyl, halo, oxyalkyl, alkylamino, aminoalkyl, acylamino and $OR^{aa}$, for example alkoxy. Examples of suitable straight and branched $C_1$-$C_6$alkyl substituents include but are not limited to methyl, ethyl, n-propyl, 2-propyl, n-butyl, sec-butyl, t-butyl and the like. Preferred substituents include halo, hydroxy, alkoxy, oxyalkyl, alkylamino and aminoalkyl. Preferably substitutions on nitrogen atoms include, for example, N-oxide or $R^{cc}$. Preferred N substituents include H, $C_1$-$C_4$ alkyl, acyl, aminoacyl and sulfonyl. Preferably, sulfur atoms are unsubstituted. Preferred S substituents include oxo and lower alkyl.

Preferred substituents on mixed aryl and non-aryl polyheterocycle groups include, but are not limited to, nitro or as described above for non-aromatic polycycle groups. Preferred substituents on carbon atoms include, but are not limited to, —N—OH, =N—OH, optionally substituted alkyl, unsaturation (i.e., there are one or more double or triple C—C bonds), oxo, acyl, cycloalkyl, halo, oxyalkyl, alkylamino, aminoalkyl, acylamino and $OR^{aa}$, for example alkoxy. Preferably substitutions on nitrogen atoms include, for example, N-oxide or $R^{cc}$. Preferred N substituents include H, $C_{1-4}$alkyl, acyl aminoacyl and sulfonyl. Preferably sulfur atoms are unsubstituted. Preferred S substituents include oxo and lower alkyl.

A "halohydrocarbyl" is a hydrocarbyl moiety in which from one to all hydrogens have been replaced with one or more halo.

The term "halogen" or "halo" is intended to mean chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally optionally substituted. The term "sulfonamido" refers to a sulfonamide substituent attached by either the sulfur or the nitrogen atom. The term "amino" is meant to include $NH_2$, alkylamino, di-alkylamino, arylamino, and cyclic amino groups. The term "ureido" as employed herein refers to a substituted or unsubstituted urea moiety.

The term "radical" is intended to mean a chemical moiety comprising one or more unpaired electrons.

Where optional substituents are chosen from "one or more" groups it is to be understood that this definition includes all substituents being chosen from one of the specified groups or the substituents being chosen from two or more of the specified groups.

In addition, substituents on cyclic moieties (i.e., cycloalkyl, heterocyclyl, aryl, heteroaryl) include 5-6 membered mono- and 9-14 membered bi-cyclic moieties fused to the parent cyclic moiety to form a bi- or tri-cyclic fused ring system. Substituents on cyclic moieties also include 5-6 membered mono- and 9-14 membered bi-cyclic moieties attached to the parent cyclic moiety by a covalent bond to form a bi- or tri-cyclic bi-ring system. For example, an optionally substituted phenyl includes, but is not limited to, the following:

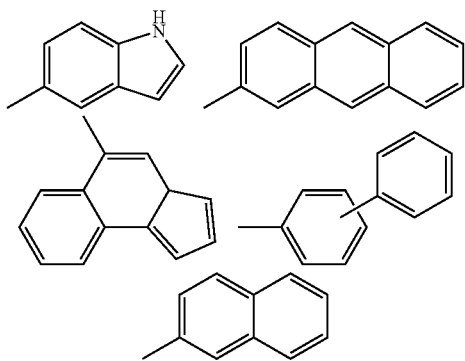

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while a "substituted aryl" includes phenyl substituted with a halo, "unsubstituted aryl" does not include phenyl substituted with a halo.

The terms "inhibition effective amount" or "histone deacetylase inhibiting amount" are meant to denote a dosage or amount sufficient to cause inhibition of histone deacetylase activity in vitro or in vivo. The histone deacetylase may be in a cell, which cell can be in a multicellular organism. The multicellular organism can be a plant or fungus, or an animal, preferably a mammal, more preferably a human. The fungus may be infecting a plant or a mammal, preferably a human, and could therefore be located in and/or on the plant or mammal. If the histone deacetylase is in a multicellular organism, the method according to this aspect of the invention comprises administering to the organism a compound or composition according to the present invention. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

The term "therapeutically effective amount" as employed herein is an amount of a compound of the invention, that when administered to a patient, elicits the desired therapeutic effect. The desired therapeutic effect is dependent upon the disease being treated and the results desired. As such, the therapeutic effect can be treatment of a disease-state. Further, the therapeutic effect can be inhibition of HDAC activity. The amount of a compound of the invention which constitutes a "therapeutically effective amount" will vary depending on the compound, the disease, the disease state and its severity, the age, sex, health, size of the patient to be treated, the results desired, and the like. The therapeutically effective amount can be determined routinely by one of ordinary skill in the art. Optimal amounts can be determined based on monitoring of the patient's response to treatment.

The term "patient" as employed herein for the purposes of the present invention includes humans and other animals, particularly mammals, and other organisms. Thus the compounds, compositions and methods of the present invention are applicable to both human therapy and veterinary applications. In a preferred embodiment the patient is a mammal, and in a most preferred embodiment the patient is human.

The terms "treating", "treatment", or the like, as used herein covers the treatment of a disease-state in an animal and includes at least one of: (i) preventing the disease-state from occurring, in particular, when such animal is predisposed to the disease-state but has not yet been diagnosed as having it; (ii) inhibiting the disease-state, i.e., partially or completely arresting its development; (iii) relieving the disease-state, i.e., causing regression of symptoms of the disease-state, or ameliorating a symptom of the disease; and (iv) reversal or regression of the disease-state, preferably eliminating or curing of the disease. In a preferred embodiment the terms "treating", treatment", or the like, covers the treatment of a disease-state in an animal and includes at least one of (ii), (iii) and (iv) above. In a preferred embodiment of the present invention the animal is a mammal, preferably a primate, more preferably a human. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

As used herein, the terms "histone deacetylase" and "HDAC" are intended to refer to any one of a family of enzymes that remove acetyl groups from the ε-amino groups of lysine residues at the N-terminus of a protein (for example, a histone, or tubulin). Unless otherwise indicated by context, the term "histone" is meant to refer to any histone protein, including H1, H2A, H2B, H3, H4, and H5, from any species. Preferred histone deacetylases include class II enzymes. Preferably the histone deacetylase is a human HDAC, including, but not limited to, HDAC-4, HDAC-5, HDAC-6, HDAC-7, HDAC-8, HDAC-9, HDAC-10 and HDAC-1. In some other preferred embodiments, the histone deacetylase is derived from a protozoal or fungal source.

The terms "histone deacetylase inhibitor" and "inhibitor of histone deacetylase" are intended to mean a compound having a structure as defined herein, which is capable of interacting with a histone deacetylase and inhibiting its enzymatic activity.

The term "inhibiting histone deacetylase enzymatic activity" is intended to mean reducing the ability of a histone deacetylase to remove an acetyl group from a protein, such as but not limited to a histone or tubulin. The concentration of inhibitor which reduces the activity of a histone deacetylase to 50% of that of the uninhibited enzyme is determined as the $IC_{50}$ value. In some preferred embodiments, such reduction of histone deacetylase activity is at least 50%, more preferably at least about 75%, and still more preferably at least about 90%. In other preferred embodiments, histone deacetylase activity is reduced by at least 95% and more preferably by at least 99%.

Preferably, such inhibition is specific, i.e., the histone deacetylase inhibitor reduces the ability of a histone deacetylase to remove an acetyl group from a protein at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect.

The compounds of the present invention form salts which are also within the scope of this invention. Reference to a compound of the invention herein is understood to include reference to salts thereof, unless otherwise indicated.

The term "salt(s)", as employed herein, denotes acidic and/or basic salts formed with inorganic and/or organic acids and bases. In addition, when a compound of the invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic (exhibiting minimal or no undesired toxicological effects), physiologically acceptable) salts are preferred, although other salts are also useful, e.g., in isolation or purification steps which may be employed during preparation. Salts of the compounds of the invention may be formed, for example, by reacting a compound of the present invention with an amount of acid or base, such as an equivalent amount, in a medium such as one in which the salts precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfanotes (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl and butyl chlorides, bromides and iodides), dialkyl sulfates (e.g. dimethyl, diethyl, dibutyl and diamyl sulfates), long chain halides (e.g. decyl, lauryl, myristyl and stearyl chlorides, bromides and iodides), aralkyl halides (e.g. benzyl and phenethyl bromides), and others.

As used herein, the term "pharmaceutically acceptable salts" is intended to mean salts that retain the desired biological activity of the above-identified compounds and exhibit minimal or no undesired toxicological effects.

The present invention also includes prodrugs of compounds of the invention. The term "prodrug" is intended to mean a derivative of a compound of the present invention that requires a transformation, for example, within the body, to release the active compound. Prodrugs are frequently, although not necessarily, pharmacologically inactive until converted to the parent compound. A hydroxyl containing compound may be converted to, for example, a sulfonate, ester or carbonate prodrug, which may be hydrolyzed in vivo to provide the hydroxyl compound. An amino containing compound may be converted, for example, to a carbamate, amide, enamine, imine, N-phosphonyl, N-phosphoryl or N-sulfenyl prodrug, which may be hydrolyzed in vivo to provide the amino compound. A carboxylic acid compound may be converted to an ester (including silyl esters and thioesters), amide or hydrazide prodrug, which be hydrolyzed in vivo to provide the carboxylic acid compound. Prodrugs for drugs which have functional groups different than those listed above are well known to the skilled artisan. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Typically, in a prodrug, a polar functional group (e.g., a carboxylic acid, an amino group, a hydroxyl group, etc.) is masked by a promoiety, which is labile under physiological conditions. "Promoiety" refers to a form of protecting group that when used to mask a functional group within a compound molecule converts the drug into a prodrug. Typically, the promoiety will be attached to the compound via bond(s) that are cleaved by enzymatic or non-enzymatic means in vivo.

Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like.

The term "protecting group" is typically intended to mean a group used in synthesis to temporarily mask the characteristic chemistry of a functional group because it interferes with another reaction. A good protecting group should be easy to put on, easy to remove and in high yielding reactions, and inert to the conditions of the reaction required. A protecting group or protective group is introduced into a molecule by chemical modification of a functional group in order to obtain chemoselectivity in a subsequent chemical reaction. One skilled in the art will recognize that during any of the processes for preparation of the compounds in the present invention, it may be necessary and/or desirable to protect sensitive or reactive groups on any of the molecules concerned. This may be achieved by means of conventional protecting groups, such as but not limited to Bn— (or —$CH_2Ph$), —$CHPh_2$, alloc (or $CH_2$=CH—$CH_2$—O—C(O)—), BOC-, -Cbz (or Z—), —F-moc, —C(O)—$CF_3$, N-Phthalimide, 1-Adoc-, TBDMS-, TBDPS-, TMS-, TIPS-, IPDMS-, —$SiR_3$, SEM-, t-Bu-, Tr-, THP- and Allyl- and those described in standard textbooks, such as Greene, T. W. et al., *Protective Groups in*

*Organic Synthesis*, Wiley, N.Y. (1999). These protecting groups may be removed at a convenient stage using methods known from the art.

When a functional group is termed "protected", this means that the group is in modified form to mitigate, especially preclude, undesired side reactions at the protected site.

The compounds of the invention may be administered as is or as a prodrug, for example in the form of an in vivo hydrolyzable ester or in vivo hydrolyzable amide. An in vivo hydrolyzable ester of a compound of the invention containing carboxy or hydroxy group is, for example, a pharmaceutically acceptable ester which is hydrolyzed in the human or animal body to produce the parent acid or alcohol. Suitable pharmaceutically acceptable esters for carboxy include $C_{1-6}$-alkoxymethyl esters (e.g., methoxymethyl), $C_{1-6}$-alkanoyloxymethyl esters (e.g., for example pivaloyloxymethyl), phthalidyl esters, $C_{3-8}$-cycloalkoxycarbonyloxy$C_{1-6}$-alkyl esters (e.g., 1-cyclohexylcarbonyloxyethyl); 1,3-dioxolen-2-onylmethyl esters (e.g., 5-methyl-1,3-dioxolen-2-onylmethyl; and $C_{1-6}$-alkoxycarbonyloxyethyl esters (e.g., 1-methoxycarbonyloxyethyl) and may be formed at any appropriate carboxy group in the compounds of this invention.

An in vivo hydrolyzable ester of a compound of the invention containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substituents on benzoyl include morpholino and piperazino linked from a ring nitrogen atom via a methylene group to the 3- or 4-position of the benzoyl ring. A suitable value for an in vivo hydrolyzable amide of a compound of the invention containing a carboxy group is, for example, a N—$C_{1-6}$-alkyl or N,N-di-$C_{1-6}$-alkyl amide such as N-methyl, N-ethyl, N-propyl, N,N-dimethyl, N-ethyl-N-methyl or N,N-diethyl amide.

Upon administration to a subject, the prodrug undergoes chemical conversion by metabolic or chemical processes to yield a compound of the present invention, or a salt and/or solvate thereof. Solvates of the compounds of the present invention include, for example, hydrates.

Some compounds of the invention may have chiral centers and/or geometric isomeric centers (E- and Z-isomers), and it is to be understood that the invention encompasses all such optical, enantiomeric, diastereoisomeric and geometric isomers. The invention also comprises all tautomeric forms of the compounds disclosed herein. Where compounds of the invention include chiral centers, the invention encompasses the enantiomerically and/or diasteromerically pure isomers of such compounds, the enantiomerically and/or diastereomerically enriched mixtures of such compounds, and the racemic and scalemic mixtures of such compounds. For example, a composition may include a mixture of enantiomers or diastereomers of a compound of the invention in at least about 30% diastereomeric or enantiomeric excess. In certain embodiments of the invention, the compound is present in at least about 50% enantiomeric or diastereomeric excess, in at least about 80% enantiomeric or diastereomeric excess, or even in at least about 90% enantiomeric or diastereomeric excess. In certain more preferred embodiments of the invention, the compound is present in at least about 95%, even more preferably in at least about 98% enantiomeric or diastereomeric excess, and most preferably in at least about 99% enantiomeric or diastereomeric excess.

The chiral centers of the present invention may have the S or R configuration. The racemic forms can be resolved by physical methods, such as, for example, fractional crystallization, separation or crystallization of diastereomeric derivates or separation by chiral column chromatography. The individual optical isomers can be obtained either starting from chiral precursors/intermediates or from the racemates by any suitable method, including without limitation, conventional methods, such as, for example, salt formation with an optically active acid followed by crystallization.

Another aspect of the invention provides compositions including a compound, N-oxide, hydrate, solvate, pharmaceutically acceptable salt, complex or prodrug of a compound according to the present invention as described herein, or a racemic or scalemic mixture, diastereomer, enantiomer or tautomer thereof. For example, in one embodiment of the invention, a composition comprises a compound, N-oxide, hydrate, solvate, pharmaceutically acceptable salt, complex or prodrug of a compound according to the present invention as described herein present in at least about 30% enantiomeric or diastereomeric excess. In certain desirable embodiments of the invention, the compound, N-oxide, hydrates, solvate, pharmaceutically acceptable salt, complex or prodrug is present in at least about 50%, at least about 80%, or even at least about 90% enantiomeric or diastereomeric excess. In certain other desirable embodiments of the invention, the compound, N-oxide, hydrate, solvate, pharmaceutically acceptable salt, complex or prodrug is present in at least about 95%, more preferably at least about 98% and even more preferably at least about 99% enantiomeric or diastereomeric excess. In other embodiments of the invention, a compound, N-oxide, hydrate, solvate, pharmaceutically acceptable salt, complex or prodrug is present as a substantially racemic mixture.

Throughout the specification, preferred embodiments of one or more chemical substituents are identified. Also preferred are combinations of preferred embodiments. For example, the invention describes preferred embodiments of L in the compounds and describes preferred embodiments of group X. Thus, as an example, also contemplated as within the scope of the invention are compounds in which preferred examples of L are as described and in which preferred examples of group X are as described.

The foregoing merely summarizes some aspects and preferred embodiments thereof and is not intended to be limiting in nature. These aspects and preferred embodiments thereof are described more fully below.

Compounds

In a first aspect, the invention provides novel inhibitors of histone deacetylase. In one embodiment, the novel inhibitors of histone deacetylase are represented by Formula (I):

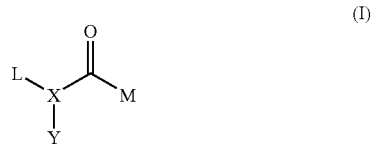

and N-oxides, hydrates, solvates, pharmaceutically acceptable salts, prodrugs and complexes thereof, and racemic and scalemic mixtures, diastereomers and enantiomers thereof wherein M is selected from the group consisting of alkyl, —N($R^e$)O$R^s$, —CF$_3$, —C(O)N($R^e$)($R^f$), -heteroaryl, —H, —OH, —C(O)O$R^e$, —CH$_2$—S(acetyl), —CH$_2$—S$R^e$ and -heterocycloalkyl;

X is selected from the group consisting of CH, C(OH), C(C$_1$-C$_4$alkyl), C(halo), C(aryl), C(heteroaryl), C($R^c$),

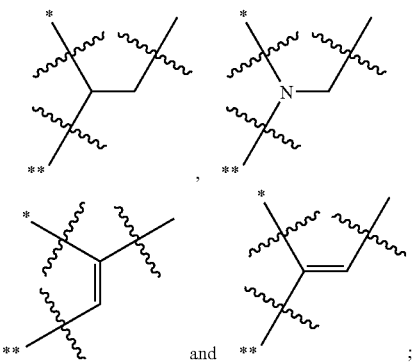

wherein * represents the point of attachment to group L and ** represents the point of attachment to group Y;

L and Y are independently selected from the group consisting of C$_1$-C$_4$alkyl, heteroalkyl, alkenyl, alkynyl, —N$R^a R^b$, —N$R^c R^d$, —O$R^e$, —C$_0$-C$_3$alkyl-aryl, —C$_0$-C$_3$alkyl-heteroaryl, —C$_0$-C$_3$alkyl-heterocyclyl, —C$_0$-C$_3$alkyl-cycloalkyl, —C$_2$-C$_4$alkenyl-aryl, —C$_2$-C$_4$alkenyl-heteroaryl, —C$_2$-C$_4$alkenyl-heterocyclyl, —C$_2$-C$_4$alkenyl-cycloalkyl, —C$_2$-C$_4$alkynyl-aryl, —C$_2$-C$_4$alkynyl-heteroaryl, —C$_2$-C$_4$alkynyl-heterocyclyl, —C$_2$-C$_4$alkynyl-cycloalkyl, —O—C$_0$-C$_3$alkyl-aryl, —O—C$_0$-C$_3$alkyl-heteroaryl, —O—C$_0$-C$_3$alkyl-cycloalkyl, —O—C$_0$-C$_3$alkyl-heterocycloalkyl, —C(O)NH—C$_0$-C$_3$alkyl-aryl, —C(O)NH—C$_0$-C$_3$alkyl-heteroaryl, —O—C$_0$-C$_3$alkyl-aryl-aryl, —O—C$_0$-C$_3$alkyl-heteroaryl-aryl, —O—C$_0$-C$_3$alkyl-aryl-heteroaryl, —O—C$_0$-C$_3$alkyl-heteroaryl-heteroaryl, —S(O)$_{0-2}$—C$_0$-C$_3$alkyl-aryl, —S(O)$_{0-2}$—C$_0$-C$_3$alkyl-heteroaryl-aryl, —S(O)$_{0-2}$—C$_0$-C$_3$alkyl-aryl-aryl, —S(O)$_{0-2}$—C$_0$-C$_3$alkyl-heteroaryl, —S(O)$_{0-2}$—C$_0$-C$_3$alkyl-aryl-heteroaryl, —S(O)$_{0-2}$—C$_0$-C$_3$alkyl-heteroaryl-heteroaryl, -aryl-C$_0$-C$_3$alkyl-aryl, -heteroaryl-C$_0$-C$_3$alkyl-aryl, —C$_0$-C$_3$alkyl-aryl-C$_0$-C$_2$alkyl-N($R^e$)—C$_0$-C$_2$alkyl-aryl, —C$_0$-C$_3$alkyl-aryl-C$_0$-C$_2$alkyl-N($R^e$)—C$_0$-C$_2$alkyl-heteroaryl, —C$_0$-C$_3$alkyl-heteroaryl-C$_0$-C$_2$alkyl-N($R^e$)—C$_0$-C$_2$alkyl-aryl, —C$_0$-C$_3$alkyl-heteroaryl-C$_0$-C$_2$alkyl-N($R^e$)—C$_0$-C$_2$alkyl-heteroaryl, —C$_0$-C$_3$alkyl-aryl-C$_0$-C$_2$alkyl-N($R^e$)—S(O)$_2$—C$_0$-C$_2$alkyl-aryl, —C$_0$-C$_3$alkyl-aryl-C$_0$-C$_2$alkyl-N($R^e$)S(O)$_2$—C$_0$-C$_2$alkyl-heteroaryl, —C$_0$-C$_3$alkyl-heteroaryl-C$_0$-C$_2$alkyl-N($R^e$)S(O)$_2$—C$_0$-C$_2$alkyl-aryl, —C$_0$-C$_3$alkyl-heteroaryl-C$_0$-C$_2$alkyl-N($R^e$)—S(O)$_2$—C$_0$-C$_2$alkyl-heteroaryl, —N($R^e$)—S(O)$_2$—N($R^f$)—, —N($R^e$)—C(O)—, —C(O)—N($R^e$)—, —N($R^e$)C(O)—N($R^f$)—, —N($R^e$)—C(O)—O—, —O—C(O)—N($R^e$)—, —O—, —N($R^e$)—C(O)—C$_2$-C$_4$alkyl-O—, —O—C$_2$-C$_4$alkyl-N($R^e$)—, -heterocyclyl-C$_0$-C$_3$alkyl-aryl, -cycloalkyl-C$_0$-C$_3$alkyl-aryl, -aryl-C$_0$-C$_3$alkyl-heteroaryl, -heteroaryl-C$_0$-C$_3$alkyl-heteroaryl, -heterocyclyl-C$_0$-C$_3$alkyl-heteroaryl, -cycloalkyl-C$_0$-C$_3$alkyl-heteroaryl, -aryl-C$_0$-C$_3$alkyl-heterocyclyl, -heteroaryl-C$_0$-C$_3$alkyl-heterocyclyl, -heterocyclyl-C$_0$-C$_3$alkyl-heterocyclyl, -cycloalkyl-C$_0$-C$_3$alkyl-heterocyclyl, -heterocyclyl-C$_0$-C$_3$alkyl-O—C$_0$-C$_3$alkyl-aryl, -heterocyclyl-C$_0$-C$_3$alkyl-O—C$_0$-C$_3$alkyl-heteroaryl, -heterocyclyl-C$_0$-C$_3$alkyl-O—C(O)NH—C$_0$-C$_3$alkyl-aryl, -heterocyclyl-C$_0$-C$_3$alkyl-O—C(O)NH—C$_0$-C$_3$alkyl-heteroaryl, -heterocyclyl-C$_0$-C$_3$alkyl-heteroaryl-aryl, -heterocyclyl-C$_0$-C$_3$alkyl-heteroaryl-heteroaryl, -heterocyclyl-C$_0$-C$_3$alkyl-aryl-aryl, -heterocyclyl-C$_0$-C$_3$alkyl-aryl-heteroaryl, -heterocyclyl-C$_0$-C$_3$alkyl-heteroaryl-C$_0$-C$_3$alkyl-aryl, -heterocyclyl-C$_0$-C$_3$alkyl-heteroaryl-C$_0$-C$_3$alkyl-heteroaryl, -heterocyclyl-C$_0$-C$_3$alkyl-aryl-C$_0$-C$_3$alkyl-aryl, -heterocyclyl-C$_0$-C$_3$alkyl-aryl-C$_0$-C$_3$alkyl-heteroaryl, -heterocyclyl-S(O)$_2$—C$_0$-C$_3$alkyl-aryl, -heterocyclyl-S(O)$_2$—C$_0$-C$_3$alkyl-heteroaryl, -heterocyclyl-S(O)$_2$—C$_0$-C$_3$alkyl-alkyl, -heterocyclyl-S(O)$_2$—C$_0$-C$_3$alkyl-cycloalkyl, -heterocyclyl-S(O)$_2$—C$_0$-C$_3$alkyl-heterocyclyl, -heterocyclyl-C(O)—C$_0$-C$_3$alkyl-aryl, -heterocyclyl-C(O)—C$_0$-C$_3$alkyl-heteroaryl, -heterocyclyl-C(O)—C$_0$-C$_3$alkyl-alkyl, -heterocyclyl-C(O)—C$_0$-C$_3$alkyl-cycloalkyl, -heterocyclyl-C(O)—C$_0$-C$_3$alkyl-heterocyclyl, -heterocyclyl-C(O)NH—C$_0$-C$_3$alkyl-aryl, -heterocyclyl-C(O)NH—C$_0$-C$_3$alkyl-heteroaryl, -heterocyclyl-C(O)NH—C$_0$-C$_3$alkyl-alkyl, -heterocyclyl-C(O)NH—C$_0$-C$_3$alkyl-cycloalkyl, -heterocyclyl-C(O)NH—C$_0$-C$_3$alkyl-heterocyclyl, -heterocyclyl-C(O)O—C$_0$-C$_3$alkyl-aryl, -heterocyclyl-C(O)O—C$_0$-C$_3$alkyl-heteroaryl, -heterocyclyl-C(O)O—C$_0$-C$_3$alkyl-alkyl, -heterocyclyl-C(O)O—C$_0$-C$_3$alkyl-cycloalkyl, -heterocyclyl-C(O)O—C$_0$-C$_3$alkyl-heterocyclyl, -heterocyclyl-S(O)$_2$—NH—C$_0$-C$_3$alkyl-aryl, -heterocyclyl-S(O)$_2$—NH—C$_0$-C$_3$alkyl-heteroaryl, -heterocyclyl-S(O)$_2$—NH—C$_0$-C$_3$alkyl-alkyl, -heterocyclyl-S(O)$_2$—NH—C$_0$-C$_3$alkyl-cycloalkyl, -heterocyclyl-S(O)$_2$—NH—C$_0$-C$_3$alkyl-heterocyclyl, —C$_0$-C$_3$alkyl-heterocyclyl-C$_2$-C$_4$alkenyl-aryl, —C$_0$-C$_3$alkyl-heterocyclyl-CH(aryl)$_2$, —C$_0$-C$_3$alkyl-heterocyclyl-CH(heteroaryl)$_2$, —C$_0$-C$_3$alkyl-heterocyclyl-CH(aryl)(heteroaryl), —C$_0$-C$_3$alkyl-aryl-C$_0$-C$_3$alkyl-heterocyclyl-C$_0$-C$_3$alkyl-aryl, —C$_0$-C$_3$alkyl-heteroaryl-C$_0$-C$_3$alkyl-heterocyclyl-C$_0$-C$_3$alkyl-aryl, —C$_0$-C$_3$alkyl-aryl-C$_0$-C$_3$alkyl-heterocyclyl-C$_0$-C$_3$alkyl-heteroaryl, —C$_0$-C$_3$alkyl-heteroaryl-C$_0$-C$_3$alkyl-heterocyclyl-C$_0$-C$_3$alkyl-heteroaryl, —C$_0$-C$_3$alkyl-aryl-heterocyclyl-S(O)$_2$-aryl, —C$_0$-C$_3$alkyl-heteroaryl-heterocyclyl-S(O)$_2$-aryl, —C$_0$-C$_3$alkyl-aryl-heterocyclyl-S(O)$_2$-heteroaryl, —C$_0$-C$_3$alkyl-heteroaryl-heterocyclyl-S(O)$_2$-heteroaryl, —C$_0$-C$_3$alkyl-aryl-S(O)$_2$-heterocyclyl-aryl, —C$_0$-C$_3$alkyl-heteroaryl-S(O)$_2$-heterocyclyl-aryl, —C$_0$-C$_3$alkyl-aryl-S(O)$_2$-heterocyclyl-heteroaryl, —C$_0$-C$_3$alkyl-heteroaryl-S(O)$_2$-heterocyclyl-heteroaryl, —C$_0$-C$_3$alkyl-aryl-heterocyclyl-C(O)-aryl, —C$_0$-C$_3$alkyl-heteroaryl-heterocyclyl-C(O)-aryl, —C$_0$-C$_3$alkyl-aryl-heterocyclyl-C(O)-heteroaryl, —C$_0$-C$_3$alkyl-heteroaryl-heterocyclyl-C(O)-heteroaryl, —C$_0$-C$_3$alkyl-aryl-C(O)-heterocyclyl-aryl, —C$_0$-C$_3$alkyl-heteroaryl-C(O)-heterocyclyl-aryl, —C$_0$-C$_3$alkyl-aryl-C(O)-heterocyclyl-heteroaryl, —C$_0$-C$_3$alkyl-heteroaryl-C(O)-heterocyclyl-heteroaryl, —C$_0$-C$_3$alkyl-aryl-heterocyclyl-C(O)N$R^e$-aryl, —C$_0$-C$_3$alkyl-heteroaryl-heterocyclyl-C(O)N$R^e$-aryl, —C$_0$-C$_3$alkyl-aryl-heterocyclyl-C(O)N$R^e$-heteroaryl, —C$_0$-C$_3$alkyl-heteroaryl-heterocyclyl-C(O)N$R^e$-heteroaryl, —C$_0$-C$_3$alkyl-aryl-N$R^e$C(O)-heterocyclyl-aryl, —C$_0$-C$_3$alkyl-heteroaryl-N$R^e$C(O)-heterocyclyl-aryl, —C$_0$-C$_3$alkyl-aryl-N$R^e$C(O)-heterocyclyl-heteroaryl, —C$_0$-C$_3$alkyl-heteroaryl-N$R^e$C(O)-heterocyclyl-heteroaryl, —C$_0$-C$_3$alkyl-aryl-heterocyclyl-C(O)O-aryl, —C$_0$-C$_3$alkyl-heteroaryl-heterocyclyl-C(O)O-aryl, —C$_0$-C$_3$alkyl-aryl-heterocyclyl-C(O)O-heteroaryl, —C$_0$-C$_3$alkyl-heteroaryl-heterocyclyl-C(O)O-heteroaryl, —C$_0$-C$_3$alkyl-aryl-OC(O)-heterocyclyl-aryl, —C$_0$-C$_3$alkyl-heteroaryl-OC(O)-heterocyclyl-aryl, —C$_0$-C$_3$alkyl-aryl-OC(O)-heterocyclyl-heteroaryl, and —C$_0$-C$_3$alkyl-heteroaryl-OC(O)-heterocyclyl-heteroaryl, provided that if an L or a Y is bound directly to a nitrogen of X, then the L or Y is not —N$R^a R^b$, —N$R^c R^d$, —O$R^e$, —S(O)$_{0-1}$—C$_0$-C$_3$alkyl-aryl, —S(O)$_{0-1}$—C$_0$-C$_3$alkyl-heteroaryl, —S(O)$_{0-1}$—C$_0$-C$_3$alkyl-aryl-aryl, —S(O)$_{0-1}$—C$_0$-C$_3$alkyl-heteroaryl-aryl, —S(O)$_{0-1}$—C$_0$-C$_3$alkyl-aryl-heteroaryl or —S(O)$_{0-1}$—C$_0$-C$_3$alkyl-heteroaryl-heteroaryl, in which each R$^a$ and R$^b$ together with the nitrogen to which they are bound form a 4 to 7 membered heterocyclyl having 1 or 2 annular heteroatoms, or a 5 to 8 membered bridged heterocyclyl having 1 or 2 annular heteroatoms, the heterocyclyl being optionally substituted with 1-3 substituents independently selected from the group consisting of H, OH, oxo (i.e., =O), —N(R$^c$)(R$^d$), C$_1$-C$_6$alkyl, aryl, heteroaryl, —C$_1$-C$_6$alkyl-aryl, —C$_1$-C$_6$alkyl-heteroaryl, —C$_1$-C$_3$alkoxy-C$_1$-C$_3$alkyl, —C$_2$-C$_3$alkyl-OH, —C$_2$-C$_3$alkyl-O—C$_1$-C$_4$alkyl, —C$_5$-C$_6$cycloalkyl, —C$_0$-C$_3$alkyl-N(H)—C(O)—C$_1$-C$_3$alkyl, —C$_{0-3}$alkyl-N(H)—C(O)-haloalkyl, —C$_0$-C$_3$alkyl-NHC(O)O—C$_1$-C$_3$alkyl-aryl, —C$_0$-C$_3$alkyl-CF$_3$, —C$_0$-C$_3$alkyl-NHC(O)O—C$_1$-C$_3$alkyl-heteroaryl and —C$_0$-C$_3$alkyl-NH$_2$, wherein said heterocyclyl is optionally fused to an aryl or heteroaryl;

each R$^c$ and R$^d$ is independently selected from the group consisting of H, —C$_1$-C$_6$alkyl, —C$_2$-C$_3$alkyl-OR$^e$, aryl, heteroaryl, -heteroaryl-heteroaryl, -heteroaryl-aryl, -aryl-heteroaryl, —C(O)-aryl, —C$_1$-C$_3$-alkoxy-C$_1$-C$_3$-alkyl, —C$_2$-C$_3$alkyl-O—C$_1$-C$_3$alkyl, —C$_2$-C$_3$alkyl-NR$^e$R$^f$, —CH$_2$—C(CH$_3$)$_2$—NR$^e$R$^f$, in which each aryl and heteroaryl is optionally substituted with one, two or three substituents independently selected from amino, OCH$_3$ and OH; or R$^c$ and Y together with the carbon to which they are bound form an optionally substituted 4 to 7 membered ring system having 0-2 annular heteroatoms, each R$^e$ and R$^f$ is independently selected from the group consisting of —H, -alkyl, -aryl, -aryl-aryl, -hetetoaryl, heteroaryl-aryl, heteroaryl-heteroaryl, C(O)-alkyl and —C(O)CF$_3$; and each R$^s$ is independently selected from the group consisting of —H, C$_1$-C$_6$alkyl, aryl, heteroaryl, heterocyclyl, cycloalkyl and a protecting group, wherein each cycloalkyl, heterocyclyl, aryl, alkyl and heteroaryl moiety is optionally substituted, and wherein a cycloalkyl, heterocyclyl, aryl, alkyl or heteroaryl moiety in L is optionally connected to a cycloalkyl, heterocyclyl, aryl, alkyl or heteroaryl in Y by a bond or by a bridging substituent, provided that the compound does not have the formula (A)

(A)

in which each R$^{10}$ is selected from the group consisting of H, OH, —CH$_2$OH, NH$_2$, COOH and C$_1$-C$_4$alkyl; and each R$^{11}$ is selected from the group consisting of H, halo, C$_1$-C$_6$alkyl, C$_1$-C$_4$alkoxy, —OC(O)C$_1$-C$_4$alkyl, —NH$_2$, —NH(C$_1$-C$_4$alkyl), —N(C$_1$-C$_4$alkyl)$_2$, —SH, —S—C$_1$-C$_4$alkyl, —COOH and —C(O)O—C$_1$-C$_4$alkyl;

the compound does not have the formula (B)

(B)

in which

R$^{12}$ is H, alkyl, halo or alkoxy;

R$^{13}$ is hydrogen or C$_1$-C$_5$alkyl; and

R$^{14}$ is H or OH;

the compound does not have the formula (B) wherein R$^{14}$ is H, R$^{12}$ is NO$_2$ and R$^{13}$ is H; and the compound is not 10,11-dihydro-5H-dibenzo[a,d]cycloheptene-5-hydroxamic acid.

In a preferred embodiment of the first aspect of the invention, M is NHOH.

In a preferred embodiment of the first aspect of the invention, M is

In another preferred embodiment of the first aspect of the invention, M is —H.

In another preferred embodiment of the first aspect of the invention, X is CH.

In another preferred embodiment of the first aspect of the invention, X is C(OH) or C(halo).

In another preferred embodiment of the first aspect of the invention, X is

In another preferred embodiment of the first aspect of the invention, X is

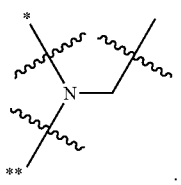

In another preferred embodiment of the first aspect of the invention, L and Y are independently selected from aryl, heteroaryl, O-aryl, heterocyclyl, cycloalkyl, —S-aryl, —S-heteroaryl, —C(O)NH-aryl, —S-heteroaryl-aryl, -aryl-heterocyclyl, -heteroaryl-heterocyclyl, —$C_1$-$C_3$alkyl-aryl, —$S(O)_2$-aryl, —$S(O)_2$-heteroaryl, -heterocyclyl-$C_0$-$C_3$alkyl-aryl, -heteroaryl-$C_0$-$C_3$alkyl-heteroaryl, heteroaryl-$C_0$-$C_3$alkyl-aryl, -aryl-aryl and -heterocyclyl-O-aryl, each of which is optionally substituted.

In another preferred embodiment of the first aspect of the invention L and Y are independently selected from the group consisting of aryl, heteroaryl, alkyl, —O-aryl, —O-cycloalkyl, heterocyclyl, cycloalkyl, —S-aryl, —S-heteroaryl, —C(O)NH-aryl, —S-heteroaryl-aryl, —S-aryl-aryl, -aryl-heterocyclyl, -heteroaryl-heterocyclyl, —$C_1$-$C_3$alkyl-aryl, —$S(O)_2$-aryl, —$S(O)_2$-heteroaryl, —$NHS(O)_2$-aryl, -heterocyclyl-$C_0$-$C_3$alkyl-aryl, -heterocyclyl-$C_0$-$C_3$alkyl-heteroaryl, -heteroaryl-$C_0$-$C_3$alkyl-heteroaryl, heteroaryl-$C_0$-$C_3$alkyl-aryl, -aryl-aryl, -aryl-heteroaryl, -heterocyclyl-O-aryl, -heterocyclyl-O—$C_0$-$C_3$alkyl-aryl, -heterocyclyl-O—$C_0$-$C_3$alkyl-heterocyclyl, -heterocyclyl-$S(O)_2$—$C_0$-$C_3$alkyl-aryl and -heterocyclyl-$S(O)_2$—$C_0$-$C_3$alkyl-heteroaryl, wherein each said cycloalkyl, heterocyclyl, aryl, alkyl and heteroaryl moiety of the forgoing L and Y is optionally substituted with a substituent selected from the group consisting of —$N(R^e)C(O)$—$C_0$-$C_3$alkyl-aryl, —$N(R^e)C(O)$—$C_0$-$C_3$alkyl-heteroaryl, —$N(R^e)C(O)$—$C_0$-$C_3$alkyl-heterocyclyl, —$N(R^e)C(O)$—$C_0$-$C_3$alkyl-cycloalkyl, —$N(R^e)C(O)$—$C_0$-$C_8$alkyl, —$N(R^a)(R^b)$, —$N(R^c)(R^d)$, —$CF_3$, aryl, heteroaryl, cycloalkyl, heterocyclyl, —$C_1$-$C_3$alkyl-aryl, —$C_1$-$C_3$alkyl-heteroaryl, —$C_1$-$C_3$alkyl-cycloalkyl, —$C_1$-$C_3$alkyl-heterocyclyl, and wherein each cycloalkyl, heterocyclyl, aryl, alkyl and heteroaryl moiety in L is further optionally substituted with halo or —O—$C_1$-$C_3$alkyl.

In another preferred embodiment of the first aspect of the invention each cycloalkyl and heterocyclyl moiety is optionally gem or spiro substituted with —OH, —CN or -alkyl.

In another preferred embodiment of the first aspect of the invention, L and Y are independently selected from the group consisting of aromatic polycycle, non-aromatic polycycle, polyheteroaryl, non-aromatic polyheterocyclic and mixed aryl and non-aryl polyheterocycle.

Another preferred embodiment of the first aspect of the invention provides a compound having the Formula (II):

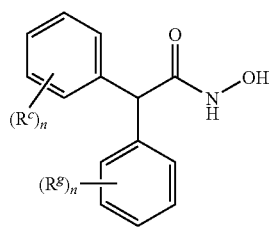

(II)

wherein
$R^c$ is as described above with respect to Formula (I);
each n is independently 0-3; and
$R^g$ is selected from the group consisting of —$C_0$-$C_3$alkyl-aryl, —$C_0$-$C_3$alkyl-heteroaryl, —$C_0$-$C_3$alkyl-cycloalkyl, —$C_0$-$C_3$alkyl-heterocylyl, —$NR^aR^b$, —$NR^cR^d$, —$OR^e$, and N-oxides, hydrates, solvates, pharmaceutically acceptable salts, prodrugs and complexes thereof and racemic or scalemic mixtures, diastereomers and enantiomers thereof.

As described above, a cycloalkyl, heterocyclyl, aryl, alkyl or heteroaryl moiety in L is optionally connected to a cycloalkyl, heterocyclyl, aryl, alkyl or heteroaryl in Y by a bond or by a bridging substituent. Such a bridging substituent preferably has 1-6 atoms along the shortest path between the cycloalkyl, heterocyclyl, aryl, alkyl or heteroaryl moiety in L and the cycloalkyl, heterocyclyl, aryl, alkyl or heteroaryl moiety in Y. For example, another preferred embodiment of the first aspect of the invention provides a compound having the Formula (III):

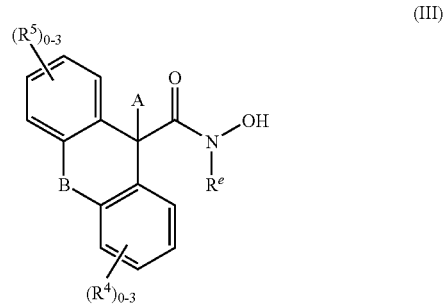

(III)

wherein
$R^4$ and $R^5$ are independently selected from the group consisting of H, halo, —$NH_2$, —$NO_2$, —$C_0$-$C_4$alkyl-aryl, —$C_0$-$C_4$alkyl-heteroaryl, —$C_0$-$C_4$alkyl-heterocyclyl, —$C_0$-$C_4$alkyl-cycloalkyl, —OMe, alkyl, CN and $CF_3$;

A is H, phenyl or OH; and

B is a bond, —O—, —$N(R^6)$—, $S(O)_{0-2}$, —$CH(R^4)$—, —$C(R^5)(R^4)$—, —$C(R^4)$—$N(R^c)$—, —$N(R^c)$—$C(R^4)$—, —$C(R^4)$—O—, —O—$C(R^4)$—, —$S(O)_{0-2}$—$C(R^4)$—, —$C(R^4)$—$S(O)_{0-2}$—, —$C(R^4)$=$C(R^5)$—, —$CH(R^4)$—$CH(R^5)$—, —$C(R^4)$=$N(R^6)$—, —$C(O)N(R^6)$—, —$S(O)_2N(R^6)$—, —$C(R^5)(R^4)$—$C(R^5)(R^4)$—, —$C(R^5)(H)$—$C(H)(R^4)$—, —$N(CH_2Ph)$-, or

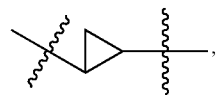

in which $R^6$ is alkyl, cycloalkyl or heterocyclyl, and racemic or scalemic mixtures, diastereomers and enantiomers thereof and N-oxides, hydrates, solvates, pharmaceutically acceptable salts, prodrugs and complexes thereof.

Another preferred embodiment of the first aspect of the invention provides a compound having the Formula (IV):

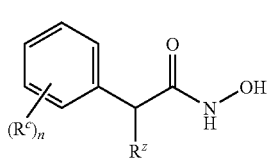

(IV)

wherein
n is 0-3;

$R^z$ is selected from the group consisting of

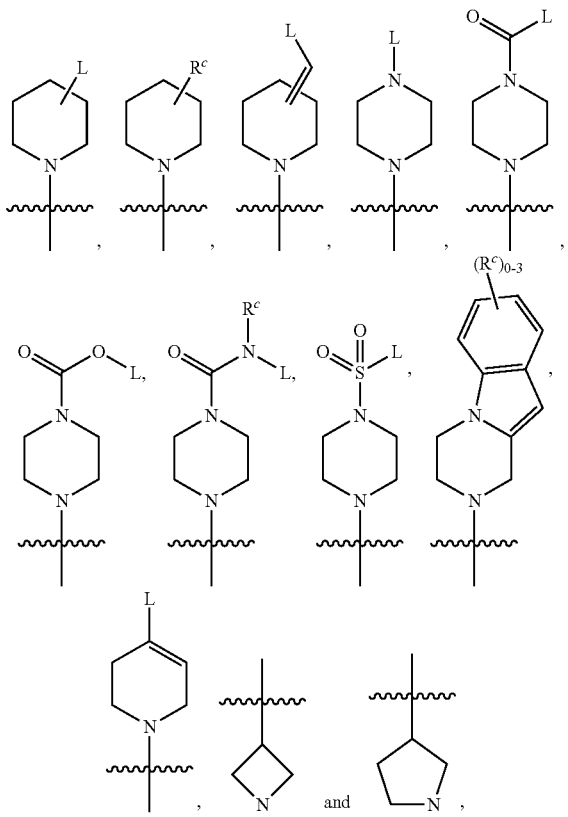

$R^c$ and L are as described above with respect to Formula (I), wherein when L is bound directly to N or O, it is not —NR$^a$R$^b$, —NR$^c$R$^d$, —OR$^e$, —S(O)$_{0\text{-}1}$—C$_0$-C$_3$alkyl-aryl, —S(O)$_{0\text{-}1}$—C$_0$-C$_3$alkyl-heteroaryl, —S(O)$_{0\text{-}1}$—C$_0$-C$_3$alkyl-aryl-aryl, —S(O)$_{0\text{-}1}$—C$_0$-C$_3$alkyl-heteroaryl-aryl, —S(O)$_{0\text{-}1}$—C$_0$-C$_3$alkyl-aryl-heteroaryl or —S(O)$_{0\text{-}1}$—C$_0$-C$_3$alkyl-heteroaryl-heteroaryl.

Another preferred embodiment of the first aspect of the invention provides a compound having the Formula (V)

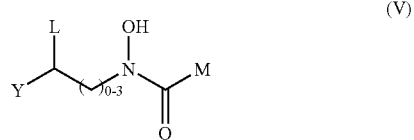

(V)

and N-oxides, hydrates, solvates, pharmaceutically acceptable salts, prodrugs and complexes thereof, and racemic or scalemic mixtures, diastereomers and enantiomers thereof, wherein M is H or alkyl; and L and Y are as defined in Formula (I).

In a preferred embodiment of the first aspect of the invention Y is further selected from the group consisting of —Z$^1$—Z—Z$^2$-D, -D, —Z$^1$—Z$^3$—Z-D, —Z$^1$—Z$^3$—Z$^2$-Z-D, —Z$^1$—Z$^2$-D, —Z$^1$—Z—Z$^3$—Z$^2$-D, —Z—Z$^3$—Z$^2$-Z-D, —Z$^1$—Z—Z$^2$, —Z—Z$^3$-D and —Z$^2$—Z$^1$—Z$^2$-D, wherein Z$^1$ is selected from the group consisting of chemical bond, alkyl, aryl, heterocyclyl, bridged heterocyclyl, spiro heterocyclyl, cycloalkyl, heteroaryl, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;

Z is selected from the group consisting of chemical bond, —O—, —S(O)$_{0\text{-}2}$—, —N(R$^c$)C(O)—, —C(O)N(R$^c$)—C(O)—, —C(O)N(R$^c$)—, —N(R$^c$)S(O)$_2$—, —N(R$^c$)—, —N(R$^c$)(C$_2$-C$_4$alkyl-OR$^d$)—, —C(O)—, —C(NOR$^{21}$)—, —CH[C(O)N(R$^{21}$)(R$^{22}$)]—C(O)N(R$^{22}$)—, —CH(N(R$^{21}$)(R$^{22}$))—C(O)N(R$^{22}$)—, —CH[C(O)N(R$^e$)(R$^f$)]—C(O)N(R$^{22}$)—, —S(O)$_2$N(R$^{21}$)—, —N(R$^{21}$)S(O)$_2$N(R$^{22}$)—, —OC(O)—, —C(O)O—, —N(R$^{21}$)C(NR$^{22}$)—, —C(NR$^{22}$)N(R$^{21}$)—, —N(R$^{21}$)C(O)N(R$^{22}$), —N(R$^{21}$)C(O), —OC(O)N(R$^{21}$)—, —N(R$^{21}$)C(S)—, —C(S)N(R$^{21}$)—, —N(R$^{21}$)C(S)N(R$^{22}$)—, —N(R$^{21}$)C(S)O—, —OC(S)N(R$^{21}$)—, —O—C$_2$-C$_4$alkyl-N(R$^{21}$)—, —N(R$^{21}$)—C$_2$-C$_4$alkyl-O—, —N(R$^1$)—C$_2$-C$_4$alkyl-S(O)$_{0\text{-}2}$—, —N[C$_2$-C$_4$alkyl-N(R$^1$)(R$^2$)]—, —N(C$_2$-C$_4$alkyl-O-alkyl)-C$_2$-C$_4$alkyl-O—, —O—C$_2$-C$_4$alkyl-N(R$^c$)—, —N(R$^c$)—C$_2$-C$_4$alkyl-O—, —N(R$^c$)—C$_2$-C$_4$alkyl-N(R$^d$)—, —O—C$_1$-C$_4$alkyl-S(O)$_2$N(R$^{21}$)—, —O—C$_1$-C$_4$alkyl-O—, —O—C$_1$-C$_4$alkyl-O—C$_1$-C$_4$alkyl-O—, —S(O)$_2$N(R$^{21}$)—C$_2$-C$_4$alkyl-O—, —O—C$_2$-C$_4$alkyl-N(R$^{21}$)S(O)$_2$—, —N(R$^{21}$)S(O)$_2$—C$_1$-C$_4$alkyl-O—, —C(O)—C$_1$-C$_4$alkyl-N(R$^{21}$)—, —N(C(O)—C$_1$-C$_4$alkyl)-, —N(R$^{21}$)—C$_1$-C$_4$alkyl-C(O)—, —O—C$_1$-C$_4$alkyl-C(O)N(R$^{21}$)—, —C(O)N(R$^{21}$)—C$_2$-C$_4$alkyl-O—, —C(O)—C$_1$-C$_4$alkyl-O—, —C(O)—C$_1$-C$_4$alkyl-S(O)$_{0\text{-}2}$—, —O—C$_2$-C$_4$alkyl-N(R$^{21}$)C(O)—, —N(R$^{21}$)C(O)—C$_1$-C$_4$alkyl-O—, —N(R$^{21}$)C(O)—C$_1$-C$_4$alkyl-S(O)$_{0\text{-}2}$—, —O—C$_1$-C$_4$alkyl-C(O)—, —C(O)—C$_1$-C$_4$alkyl-O—, —N(R$^{21}$)—C$_1$-C$_4$alkyl-C(O), —C(O)—C$_1$-C$_4$alkyl-N(R$^{21}$)—, —O—C$_1$-C$_4$alkyl-C(S)—, —C(S)—C$_1$-C$_4$alkyl-O—, —N(R$^{21}$)—C$_1$-C$_4$alkyl-C(S), —C(S)—C$_1$-C$_4$alkyl-N(R$^{21}$)—, —N(R$^{21}$)—C$_1$-C$_4$alkyl-C(S)—, —O—C$_1$-C$_4$alkyl-C(S)N(R$^{21}$)—, —C(S)N(R$^{21}$)—C$_2$-C$_4$alkyl-O—, —O—C$_2$-C$_4$alkyl-N(R$^{21}$)C(S)—, —N(R$^{21}$)C(O)—C$_1$-C$_4$alkyl-O—, —N(R$^{21}$)C(S)—C$_1$-C$_4$alkyl-O—, —N(R$^{21}$)—C$_1$-C$_4$alkyl-S(O)$_2$—, —O—C$_1$-C$_4$alkyl-S(O)$_2$N(R$^{21}$)—, —S(O)$_2$N(R$^{21}$)—C$_2$-C$_4$alkyl-O—, —O—C$_2$-C$_4$alkyl-N(R$^{21}$)S(O)$_2$—, —N(R$^{21}$)S(O)$_2$—C$_1$-C$_4$alkyl-O—, —O—C$_2$-C$_4$alkyl-OC(O)N(R$^{21}$)—, —O—C$_2$-C$_4$alkyl-OC(S)N(R$^{21}$)—, wherein each alkyl moiety is optionally substituted;

Z$^2$ is selected from the group consisting of a chemical bond, alkyl, alkenyl, alkynyl, alkyl-alkenyl, alkynyl-alkyl and alkyl-alkynyl, wherein each alkyl, alkenyl and alkynyl moiety is optionally substituted;

Z$^3$ is selected from the group consisting of a chemical bond, —C$_1$-C$_5$alkyl-, —C$_0$-C$_5$alkyl-aryl-, —C$_0$-C$_5$alkyl-heterocyclyl-, —C$_0$-C$_5$alkyl-bridged heterocyclyl-, -spiro heterocyclyl-, —C$_0$-C$_5$alkyl-cycloalkyl- and —C$_0$-C$_5$alkyl-heteroaryl-, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;

D is selected from the group consisting of H, aryl, heteroaryl, alkyl, alkenyl, alkynyl, heteroalkyl, cycloalyl, heterocyclyl, bridged heterocyclyl, spiro heterocyclyl, aromatic polycycles, non-aromatic polycycles, polyheteroaryl groups, non-aromatic polyheterocyclic, mixed aryl and non-aryl polyheterocycle, each of which is optionally substituted and each of which is optionally fused to one or more aryl or heteroaryl rings, or one or more saturated or partially unsaturated cycloalkyl or heterocyclyl rings, each of which ring is optionally substituted, wherein each $R^{21}$ and $R^{22}$ is independently selected from the group consisting of —H, -alkyl, -aryl and heteroaryl, wherein each said aryl and heteroaryl moiety is optionally substituted; and L is selected from the group consisting of cycloalkyl, heterocyclyl, aryl and heteroaryl (preferably aryl and heteroaryl), wherein each aryl, heteroaryl, heterocyclyl, cycloalkyl and aryl group is optionally fused to a heterocyclyl, or is optionally substituted with a substituent selected from the group consisting of halo, —O-alkyl, —S-alkyl, —NO$_2$, —N(R$^e$)C(O)—C$_0$-C$_3$alkyl-aryl, —N(R$^e$)C(O)—C$_0$-C$_3$alkyl-heteroaryl, —N(R$^a$)(R$^b$), —N(R$^c$)(R$^d$), —OH, -alkyl, aryl, heteroaryl, —OCF$_3$ and —CF$_3$.

In another preferred embodiment of the first aspect of the invention each cycloalkyl, heterocyclyl, aryl, alkyl, alkenyl and heteroaryl moiety in Z, Z$_1$, Z$_2$, Z$_3$ and D is optionally substituted with a substituent selected from the group consisting of —N(R$^e$)C(O)—C$_1$-C$_6$alkyl, —N(R$^e$)C(O)—C$_0$-C$_3$alkyl-aryl, —N(R$^e$)C(O)—C$_0$-C$_3$alkyl-heteroaryl, —N(R$^e$)C(O)—C$_0$-C$_3$alkyl-heterocyclyl, —N(R$^e$)C(O)—C$_0$-C$_3$alkyl-cycloalkyl, —N(R$^e$)C(O)—C$_0$-C$_8$alkyl, —N(R$^a$)(R$^b$), —N(R$^c$)(R$^d$), —CF$_3$, —O—CF$_3$, —S—CF$_3$, aryl, heteroaryl, cycloalkyl, heterocyclyl, —C$_1$-C$_3$alkyl-aryl, —C$_1$-C$_3$alkyl-heteroaryl, —C$_1$-C$_3$alkyl-cycloalkyl, —C$_1$-C$_3$alkyl-heterocyclyl, halo, alkyl, —O-alkyl, —S(O)$_{0-2}$-alkyl, —C$_0$-C$_3$alkyl-CN, NO$_2$, —C(O)-alkyl and —OH.

In a preferred embodiment of the first aspect of the present invention the compound has Formula XX:

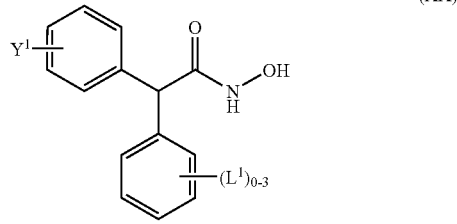

(XX)

wherein each L$^1$ is independently selected from the group consisting of H, halo, —O-alkyl, —S-alkyl, —NO$_2$, —N(R$^e$)C(O)—C$_0$-C$_3$alkyl-aryl, —N(R$^e$)C(O)—C$_0$-C$_3$alkyl-heteroaryl, —N(R$^a$)(R$^b$), —N(R$^c$)(R$^d$), —OH, -alkyl, —OCF$_3$, and —CF$_3$; and Y$^1$ is selected from the group consisting of —Z—Z$^2$-D, —Z$^1$—Z$^2$-D, —CH$_2$-D and D.

In another preferred embodiment of the first aspect of the present invention the compound has Formula XX-A:

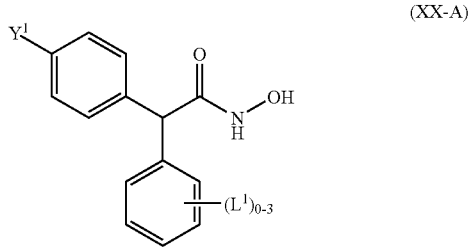

(XX-A)

wherein each L$^1$ is independently selected from the group consisting of H, halo, —O—CH$_3$, —CH$_3$ and —OH; and Y$^1$ is selected from the group consisting of —Z—Z$^2$-D, —Z$^1$—Z$^2$-D, —CH$_2$-D and D;

wherein

Z is selected from the group consisting of —O—, —S(O)$_{0-2}$—, —N(R$^c$)C(O)—, —C(O)N(R$^c$)—, —N(R$^c$)S(O)$_2$—, —N(R$^c$)—, —S(O)$_2$N(R$^{21}$)—, —O—C$_2$-C$_4$alkyl-N(R$^{21}$)—, —N(R$^{21}$)—C$_2$-C$_4$alkyl-O—, —N(R$^c$)—C$_2$-C$_4$alkyl-N(R$^d$)—, and —O—C$_1$-C$_4$alkyl-O—;

Z$^1$ is selected from the group consisting of aryl, heterocyclyl, bridged heterocyclyl, spiro heterocyclyl, cycloalkyl and heteroaryl, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;

Z$^2$ is a chemical bond or an optionally substituted alkyl; and

D is selected from the group consisting of H, aryl, heteroaryl, alkyl, cycloalkyl and heterocyclyl, each of which is optionally substituted and each of which is optionally fused to one or more aryl or heteroaryl rings, or one or more saturated or partially unsaturated cycloalkyl or heterocyclyl rings, each of which ring is optionally substituted.

In another preferred embodiment of the first aspect of the present invention, the compound has the Formula XXI:

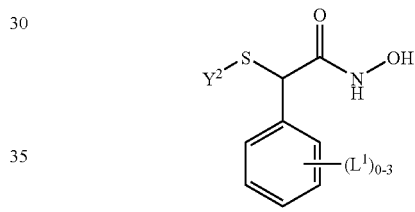

(XXI)

wherein each L$^1$ is independently selected from the group consisting of H, halo, —O-alkyl, —S-alkyl, —NO$_2$, —N(R$^e$)C(O)—C$_0$-C$_3$alkyl-aryl, —N(R$^e$)C(O)—C$_0$-C$_3$alkyl-heteroaryl, —N(R$^a$)(R$^b$), —N(R$^c$)(R$^d$), —OH, -alkyl, —OCF$_3$ and —CF$_3$; and Y$^2$ is —Z$^2$—Z$^1$—Z$^2$-D, —CH$_2$-D or D;

wherein

Z$^1$ is selected from the group consisting of aryl, heterocyclyl, cycloalkyl and heteroaryl, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;

Z$^2$ is a chemical bond or an optionally substituted alkyl; and

D is selected from the group consisting of H, aryl, heteroaryl, alkyl, cycloalyl and heterocyclyl, each of which is optionally substituted and each of which is optionally fused to one or more aryl or heteroaryl rings, or one or more saturated or partially unsaturated cycloalkyl or heterocyclyl rings, each of which ring is optionally substituted.

Another preferred embodiment of the first aspect of the invention provides a compound, an N-oxide, hydrate, solvate, pharmaceutically acceptable salt, prodrug or complex thereof, or racemic or scalemic mixture, diastereomer or enantiomer thereof, as described above with respect to any of Formulae (I)-(V), in which each aryl, heterocyclyl, cycloalkyl and heteroaryl is independently optionally substituted with one, two or three substituents independently selected from the group consisting of H, halo, =O, OH, $C_1$-$C_3$-hydrocarbyl, —OCH$_3$, —CN, —S(O)$_{0-2}$—$C_1$-$C_4$alkyl, —CF$_3$, —OCF$_3$, alkyl, —NH$_2$, —N(alkyl)$_2$, —NH(alkyl), —N(aryl)(alkyl), —N(-alkyl-aryl)(alkyl), —N(heteroaryl)(alkyl), —N(-alkyl-heteroalkylaryl)(alkyl), —NH(aryl), —NH(-alkyl-aryl), —NH(heteroaryl), —NH(-alkyl-heteroalkylaryl), —N(—$C_2$-$C_4$alkyl-O-alkyl)(alkyl), —NH(—$C_2$-$C_4$alkyl-O-alkyl), —NO$_2$, —O—$C_1$-$C_4$alkyl, —$C_0$-$C_4$alkyl-aryl, —$C_0$-$C_4$alkyl-heteroaryl, —$C_0$-$C_4$alkyl-heterocyclyl, —$C_0$-$C_4$alkyl-cycloalkyl, —NHS(O)$_2$-alkyl, —S(O)$_2$NH-alkyl, —NR$^a$R$^b$, —NR$^c$R$^d$, —OR$^e$, —$C_2$-$C_4$alkyl-NR$^a$R$^b$, $C_2$-$C_4$alkyl-NR$^c$R$^d$, —S(O)$_{0-1}$R$^e$, —(CR$^{32}$R$^{33}$)$_s$—NR$^{30}$R$^{31}$, and (X$^{30}$—Y$^{31}$—), in which R$^{30}$ and R$^{31}$ are each independently hydrogen, cyano, oxo, hydroxyl, $C_1$-$C_8$alkyl, $C_1$-$C_8$heteroalkyl, $C_1$-$C_8$alkenyl, carboxamido-, $C_1$-$C_3$alkyl-carboxamido-, carboxamido-$C_1$-$C_3$alkyl-, amidino-, $C_2$-$C_8$hydroxyalkyl-, $C_1$-$C_3$alkyl-aryl-, aryl-$C_1$-$C_3$alkyl-, $C_1$-$C_3$alkyl-heteroaryl-, heteroaryl-$C_1$-$C_3$alkyl-, $C_1$-$C_3$alkyl-heterocyclyl-, heterocyclyl-$C_1$-$C_3$alkyl-, $C_1$-$C_3$alkyl-cycloalkyl-, cycloalkyl-$C_1$-$C_3$alkyl-, $C_2$-$C_8$alkoxy-, $C_2$-$C_8$alkoxy-$C_1$-$C_4$alkyl-, $C_1$-$C_8$alkoxy-carbonyl-, aryloxy-carbonyl-, aryl-$C_1$-$C_3$alkoxy-carbonyl-, heteroaryloxy-carbonyl-, heteroaryl-$C_1$-$C_3$alkoxy-carbonyl-, $C_1$-$C_8$acyl, $C_0$-$C_8$alkyl-carbonyl-, aryl-$C_0$-$C_8$alkyl-carbonyl-, heteroaryl-$C_0$-$C_8$alkyl-carbonyl-, cycloalkyl-$C_0$-$C_8$alkyl-carbonyl-, $C_0$-$C_8$alkyl-NH-carbonyl-, aryl-$C_0$-$C_8$alkyl-NH-carbonyl-, heteroaryl-$C_0$-$C_8$alkyl-NH-carbonyl-, cycloalkyl-$C_0$-$C_8$alkyl-NH-carbonyl-, $C_0$-$C_8$alkyl-O-carbonyl-, aryl-$C_0$-$C_8$alkyl-O-carbonyl-, heteroaryl-$C_0$-$C_8$alkyl-O-carbonyl-, cycloalkyl-$C_0$-$C_8$alkyl-O-carbonyl-, $C_1$-$C_8$alkylsulfonyl-, aryl-alkyl-sulfonyl-, arylsulfonyl-, heteroaryl-alkyl-sulfonyl-, heteroaryl-sulfonyl-, $C_1$-$C_8$alkyl-NH-sulfonyl-, aryl-alkyl-NH-sulfonyl-, aryl-NH-sulfonyl-, heteroaryl-alkyl-NH-sulfonyl-, heteroaryl-NH-sulfonyl, aroyl-, aryl-, cycloalkyl-, heterocyclyl-, heteroaryl-, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, or protecting group, each of which is optionally substituted with one or more substituents selected from halo, cyano, oxo, carboxy, formyl, nitro, amino, amidino and guanidino, or R$^{30}$ and R$^{31}$ taken together with the N to which they are attached form a heterocyclyl or heteroaryl, each of which is optionally substituted with from 1 to 3 substituents selected from the group consisting of halo, cyano, oxo, carboxy, formyl, nitro, amino, amidino, guanidino, a protecting group, and (X$^{30}$—Y$^{31}$—), in which X$^{30}$ is selected from the group consisting of $C_1$-$C_8$alkyl-, $C_2$-$C_8$alkenyl-, $C_2$-$C_8$alkynyl-, $C_0$-$C_3$alkyl-$C_2$-$C_8$alkenyl-$C_0$-$C_3$alkyl-, $C_0$-$C_3$alkyl-$C_2$-$C_8$alkynyl-$C_0$-$C_3$alkyl-, $C_0$-$C_3$alkyl-O—$C_0$-$C_3$alkyl-, HO—$C_0$-$C_3$alkyl-, $C_0$-$C_4$alkyl-N(R$^{30}$)—$C_0$-$C_3$alkyl-, N(R$^{30}$)(R$^{31}$)—$C_0$-$C_3$alkyl-, N(R$^{30}$)(R$^{31}$)—$C_0$-$C_3$alkenyl-, N(R$^{30}$)(R$^{31}$)—$C_0$-$C_3$alkynyl-, (N(R$^{30}$)(R$^{31}$))$_2$—C=N—, $C_0$-$C_3$alkyl-S(O)$_{0-2}$—$C_0$-$C_3$alkyl-, CF$_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N(R$^{30}$)(R$^{31}$)-heterocyclyl-$C_1$-$C_3$alkyl-, wherein the aryl, cycloalkyl, heteroaryl and heterocycyl are optionally substituted with from 1 to 3 substituents selected from halo, cyano, oxo, carboxy, formyl, nitro, amino, amidino and guanidino; and Y$^{31}$ is selected from the group consisting of a direct bond, —O—, —N(R$^{30}$)—, —C(O)—, —O—C(O)—, —C(O)—O—, —N(R$^{30}$)—C(O)—, —C(O)—N(R$^{30}$)—, —N(R$^{30}$)—C(S)—, —C(S)—N(R$^{30}$)—, —N(R$^{30}$)—C(O)—N(R$^{31}$)—, —N(R$^{30}$)—C(NR$^{30}$)—N(R$^{31}$)—, —N(R$^{30}$)—C(NR$^{31}$)—, —C(N$^{31}$)—N(R$^{30}$), —N(R$^{30}$)—C(S)—N(R$^{31}$), —N(R$^{30}$)—C(O)—O—, —O—C(O)—N(R$^{31}$)—, —N(R$^{30}$)—C(S)—O—, —O—C(S)—N(R$^{31}$)—, —S(O)$_{0-2}$—, —SO$_2$N(R$^{31}$)—, —N(R$^{31}$)—SO$_2$— and —N(R$^{30}$)—SO$_2$N(R$^{31}$)—; and R$^{32}$ and R$^{33}$ are independently selected from hydrogen, halo and hydroxyl.

Another preferred embodiment of the first aspect of the invention provides the compounds 2-(4-(diethylamino)phenyl)-N-hydroxy-2-phenylacetamide;
2-(4-(dimethylamino)phenyl)-N-hydroxy-2-phenylacetamide;
2-(biphenyl-4-yl)-N-hydroxy-2-phenylacetamide;
N-hydroxy-2-phenyl-2-(4-(pyrrolidin-1-yl)phenyl)acetamide and
2-(4'-fluorobiphenyl-4-yl)-N-hydroxy-2-phenylacetamide,
and N-oxides, hydrates, solvates, pharmaceutically acceptable salts, prodrugs and complexes thereof, and racemic or scalemic mixtures, diastereomers and enantiomers thereof.

Another preferred embodiment of the first aspect of the invention provides the compounds N-hydroxy-2-phenylbutanamide;
N-hydroxy-2-phenoxy-2-phenylacetamide;
N-hydroxy-2-phenyl-2-(4-(piperidin-1-yl)phenyl)acetamide;
2-(4-benzylpiperidin-1-yl)-N-hydroxy-2-phenylacetamide;
2-cyclohexyl-N-hydroxy-2-phenylacetamide;
2-benzyl-N-hydroxy-2-phenylacetamide;
N-hydroxy-2-phenyl-2-(phenylthio)acetamide;
N-hydroxy-2-phenyl-2-(1H-pyrrol-1-yl)acetamide;
N-hydroxy-2-phenyl-2-(4-phenylpiperazin-1-yl)acetamide;
2-(4-benzylpiperazin-1-yl)-N-hydroxy-2-phenylacetamide;
N-hydroxy-2-phenyl-2-(5-(thiophen-2-yl)-1H-benzo[d]imidazol-2-yl)acetamide;
N-hydroxy-2-(isoindolin-2-yl)-2-phenylacetamide;
2-(benzo[d]thiazol-2-yl)-N-hydroxy-2-phenylacetamide;
2-(5-chloro-6-fluoro-1H-benzo[d]imidazol-2-yl)-N-hydroxy-2-phenylacetamide;
N-hydroxy-2-phenyl-2-(4-phenyl-1H-1,2,3-triazol-1-yl)acetamide;
N-hydroxy-2-(4-phenethyl-1H-1,2,3-triazol-1-yl)-2-phenylacetamide;
2-(4-(4-fluorobenzyl)piperidin-1-yl)-N-hydroxy-2-phenylacetamide;
N$^1$-hydroxy-2-phenyl-N$^3$-(3-(trifluoromethyl)phenyl)malonamide;
2-(4-(1H-indol-3-yl)piperidin-1-yl)-N-hydroxy-2-phenylacetamide;
2-(4-benzyl-1H-1,2,3-triazol-1-yl)-N-hydroxy-2-phenylacetamide;
N-hydroxy-2-phenyl-2-(4-(pyrimidin-2-yl)piperazin-1-yl)acetamide;
2-(4-(4-chlorophenyl)pyrimidin-2-ylthio)-N-hydroxy-2-phenylacetamide;
N-hydroxy-2-(5-(2-methoxyphenyl)-1,3,4-thiadiazol-2-yl)-2-phenylacetamide;
2-(4,5-diphenyl-1H-imidazol-2-ylthio)-N-hydroxy-2-phenylacetamide;
N-hydroxy-2-(4-phenoxypiperidin-1-yl)-2-phenylacetamide;
N-hydroxy-2-phenyl-2-(4-phenylpiperidin-1-yl)acetamide and
2-(biphenyl-4-ylthio)-N-hydroxy-2-phenylacetamide, and N-oxides, hydrates, solvates, pharmaceutically acceptable salts, prodrugs and complexes thereof and racemic or scalemic mixtures, diastereomers and enantiomers thereof.

Another preferred embodiment of the first aspect of the invention provides the compounds
2-(N-benzylphenylsulfonamido)-N-hydroxyacetamide;
N-hydroxy-3,3-diphenylpropanamide;
2,2-bis(2,3-dihydrobenzofuran-5-yl)-N-hydroxyacetamide;
N-hydroxy-2,2-diphenylpropanamide;
(E)-N-hydroxy-2,3-diphenylacrylamide;
N-hydroxy-2,2-di(thiophen-2-yl)acetamide and
N-hydroxy-9H-xanthene-9-carboxamide, and N-oxides, hydrates, solvates, pharmaceutically acceptable salts, prodrugs and complexes thereof, and racemic or scalemic mixtures, diastereomers and enantiomers thereof.

Some examples of the compounds according to the first aspect of the invention are given in Table 1 below. These examples merely serve to exemplify some of the compounds of the first aspect of the invention and do not limit the scope of the invention.

TABLE 1

| Name |
| --- |
| N-hydroxy-2,2-diphenylacetamide |
| N-hydroxy-2-phenoxy-2-phenylacetamide |
| N-hydroxy-2,2-bis(4-nitrophenyl)acetamide |
| N-hydroxy-2-phenyl-2-(piperidin-1-yl)acetamide |
| 2-(N-benzylphenylsulfonamido)-N-hydroxyacetamide |
| N-hydroxy-3,3-diphenylpropanamide |
| N-hydroxy-9H-xanthene-9-carboxamide |
| 2,2-bis(2,3-dihydrobenzofuran-5-yl)-N-hydroxyacetamide |
| 2-(4-benzylpiperidin-1-yl)-N-hydroxy-2-phenylacetamide |
| 2-cyclohexyl-N-hydroxy-2-phenylacetamide |
| N-hydroxy-2,3-diphenylpropanamide |
| N-hydroxy-2-phenyl-2-(phenylthio)acetamide |
| N-hydroxy-2-phenyl-2-(1H-pyrrol-1-yl)acetamide |
| N-hydroxy-2,2-diphenylpropanamide |
| 2,2-bis(4-chlorophenyl)-N-hydroxyacetamide |
| N-hydroxy-2-phenyl-2-(4-phenylpiperazin-1-yl)acetamide |
| 2-(4-benzylpiperazin-1-yl)-N-hydroxy-2-phenylacetamide |
| 2,2-bis(4-fluorophenyl)-N-hydroxyacetamide |
| 2-(4-(diethylamino)phenyl)-N-hydroxy-2-phenylacetamide |
| N-hydroxy-2-phenyl-2-(6-(thiophen-2-yl)-1H-benzo[d]imidazol-2-yl)acetamide |
| (E)—N-hydroxy-2,3-diphenylacrylamide |
| N-hydroxy-2-(isoindolin-2-yl)-2-phenylacetamide |
| N-hydroxy-2,2-di(thiophen-2-yl)acetamide |
| 2-(benzo[d]thiazol-2-ylthio)-N-hydroxy-2-phenylacetamide |
| 2-(5-chloro-6-fluoro-1H-benzo[d]imidazol-2-yl)-N-hydroxy-2-phenylacetamide |
| N-hydroxy-2-phenyl-2-(4-phenyl-1H-1,2,3-triazol-1-yl)acetamide |
| N-hydroxy-2-(4-phenethyl-1H-1,2,3-triazol-1-yl)-2-phenylacetamide |
| N,2-dihydroxy-2,2-diphenylacetamide |
| 2-(4-(dimethylamino)phenyl)-N-hydroxy-2-phenylacetamide |
| 2-(4-(4-fluorobenzyl)piperidin-1-yl)-N-hydroxy-2-phenylacetamide |
| N-hydroxy-2-(4-phenethylpiperidin-1-yl)-2-phenylacetamide |
| 2-(biphenyl-4-yl)-N-hydroxy-2-phenylacetamide |
| $N^1$-hydroxy-2-phenyl-$N^3$-(3-(trifluoromethyl)phenyl)malonamide |
| 2-(4-(1H-indol-3-yl)piperidin-1-yl)-N-hydroxy-2-phenylacetamide |
| 2-(4-benzyl-1H-1,2,3-triazol-1-yl)-N-hydroxy-2-phenylacetamide |
| N-hydroxy-2-phenyl-2-(4-(pyrimidin-2-yl)piperazin-1-yl)acetamide |
| 2-(4-(4-chlorophenyl)pyrimidin-2-ylthio)-N-hydroxy-2-phenylacetamide |
| N-hydroxy-2-(5-(2-methoxyphenyl)-1,3,4-thiadiazol-2-yl)-2-phenylacetamide |
| 2-(5-(4-bromophenyl)-1,3,4-thiadiazol-2-yl)-N-hydroxy-2-phenylacetamide |
| 2-(biphenyl-4-yl)-2-(4-(dimethylamino)phenyl)-N-hydroxyacetamide |
| N-hydroxy-2-phenyl-2-(4-(pyrrolidin-1-yl)phenyl)acetamide |
| 2-(4,5-diphenyl-1H-imidazol-2-ylthio)-N-hydroxy-2-phenylacetamide |
| N-hydroxy-2-(4-phenoxypiperidin-1-yl)-2-phenylacetamide |
| N-hydroxy-2-phenyl-2-(4-phenylpiperidin-1-yl)acetamide |
| 2-(4'-fluorobiphenyl-4-yl)-N-hydroxy-2-phenylacetamide |
| 2-(biphenyl-4-ylthio)-N-hydroxy-2-phenylacetamide |

Preferred compounds according to the invention include those described in the examples below. Compounds were named using Chemdraw Ultra version 10.0 or version 8.0.3, which are available through Cambridgesoft.com, or were derived therefrom.

Synthetic Schemes and Experimental Procedures

The compounds of the invention can be prepared according to the reaction schemes for the examples illustrated below utilizing methods known to one of ordinary skill in the art. These schemes serve to exemplify some procedures that can be used to make the compounds of the invention. One skilled in the art will recognize that other general synthetic procedures may be used. The compounds of the invention can be prepared from starting components that are commercially available. Any kind of substitutions can be made to the starting components to obtain the compounds of the invention according to procedures that are well known to those skilled in the art.

EXAMPLE 1

2,2-bis(2,3-dihydrobenzofuran-5-yl)-N-hydroxyacetamide (3)

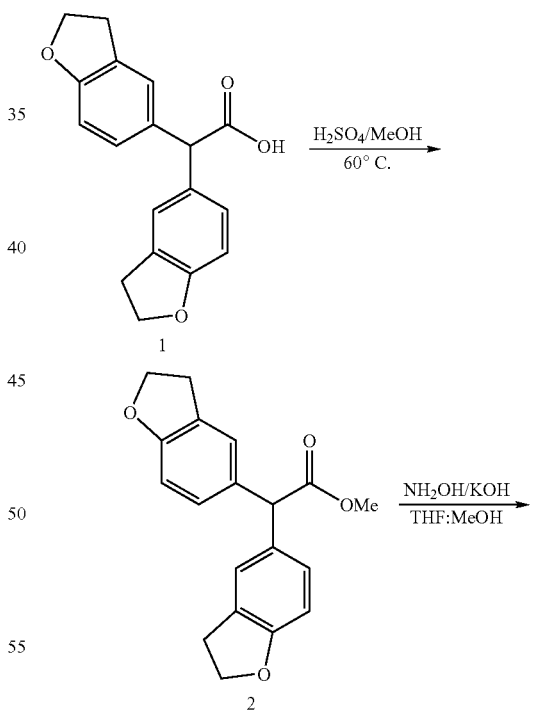

Scheme 1

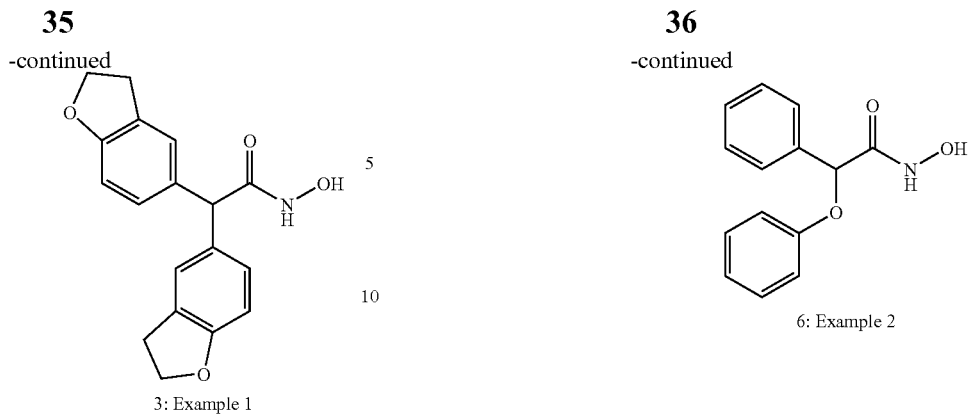

3: Example 1

Step 1: Methyl 2,2-bis(2,3-dihydrobenzofuran-5-yl)acetate (2)

To a solution of 1 (992 mg, 3.35 mmol) in methanol (20 mL) was added concentrated sulfuric acid (2 mL) and stirred for 15 h at 60° C. The solvent was removed under vacuum. The crude was dissolved in ethyl acetate and washed with water. The organic layer was separated, dried over $Na_2SO_4$, filtered and concentrated to afford compound 2 as a white solid (2.25 g, 94%). $^1$H NMR (DMSO-$d_6$) δ (ppm): 7.13 (d, J=1.3 Hz, 2H), 6.99 (dd, J=8.2, 1.8 Hz, 2H), 6.68 (d, J=8.2 Hz, 2H), 5.00 (s, 1H), 4.48 (t, J=8.8 Hz, 4H), 3.63 (s, 3H), 3.12 (t, J=8.8 Hz, 4H).

Step 2: 2,2-bis(2,3-dihydrobenzofuran-5-yl)-N-hydroxyacetamide (3)

To a solution of 2 (380 mg, 1.22 mmol) and hydroxylamine (50% in water, 1.25 mL) in a 1:1 THF:methanol (10 mL) was added base (KOH (275 mg, 4.9 mmol) or NaOH). The mixture was stirred at room temperature for 2 h, acidified to pH 7 with 1M HCl solution, diluted with ethyl acetate and washed with water. The organic layer was separated, dried over $Na_2SO_4$, filtered and concentrated. The residue was triturated with 50% ethyl acetate:hexanes, filtered, and rinsed with hexanes to afford compound 3 as a white solid (170 mg, 45%). $^1$H NMR (DMSO-d6) δ (ppm): 10.81 (br s, 1H), 8.88 (br s, 1H), 7.16 (d, J=1.0 Hz, 2H), 6.99 (dd, J=8.4, 1.8 Hz, 2H), 6.67 (d, J=8.1 Hz, 2H), 4.53-4.45 (m, 5H), 3.12 (t, J=8.6 Hz, 4H). LRMS (ESI): (calc) 311.1 (found) 310.3 (M)⁻.

EXAMPLE 2

N-hydroxy-2-phenoxy-2-phenylacetamide (6)

Scheme 2

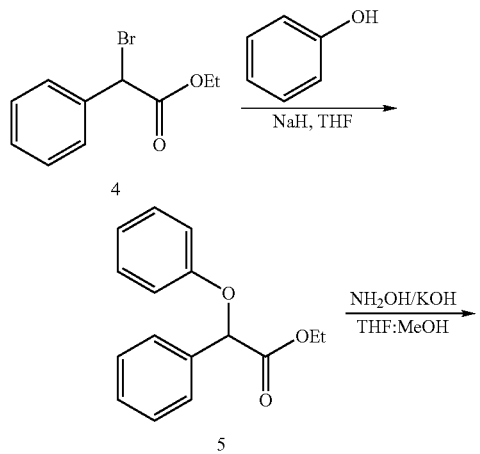

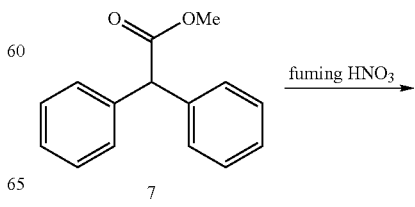

6: Example 2

Step 1: Ethyl 2-phenoxy-2-phenylacetate (5)

To a solution of 4 (0.5 g, 2.06 mmol) and phenol (194 mg, 2.06 mmol) in THF (15 mL) was added base (NaH (60% dispersion, 90 mg, 2.27 mmol) or triethylamine) and stirred at room temperature for 2 h. The reaction mixture was quenched with water, diluted with ethyl acetate and washed with water. The organic layer was separated, dried over $Na_2SO_4$, filtered and concentrated. The crude material was purified by silica gel column chromatography with gradient of ethyl acetate (0-25%) in hexane to afford 5 as a colourless oil (140 mg, 27%). $^1$H NMR (DMSO-$d_6$) δ (ppm): 7.55-7.52 (m, 2H), 7.44-7.34 (m, 3H), 7.30-7.25 (m, 2H), 6.96-6.92 (m, 3H), 5.96 (s, 1H), 4.13-4.05 (m, 2H), 1.09 (t, J=7.0 Hz, 3H).

Alternate Reaction Conditions:

Compound 4 (1 eq), ROH (1 eq), $K_2CO_3$ (1.5 eq), acetone, 50° C., 18 h.

Compound 4 (1 eq), ROH (1 eq), $CsCO_3$ or DIPEA (1.5 eq), THF or DCE, room temperature, 24 h.

Compound 4 (1 eq), RSH (1 eq), $K_2CO_3$ (1.5 eq), acetone, 50° C., 18 h.

Step 2: N-hydroxy-2-phenoxy-2-phenylacetamide (6)

Following the same procedure as described in Example 1, step 2, but substituting compound 2 for compound 5, the title compound 6 was obtained in 15% yield (20 mg). $^1$H NMR (CD$_3$OD-$d_4$) δ (ppm): 5.57-7.54 (m, 2H), 7.39-7.32 (m, 3H), 7.27-7.22 (m, 2H), 7.00-6.92 (m, 3H), 5.60 (s, 1H). LRMS (ESI): (calc) 243.1 (found) 242.0 (M-H)⁻.

EXAMPLE 3

N-hydroxy-2,2-bis(4-nitrophenyl)acetamide (9)

Scheme 3

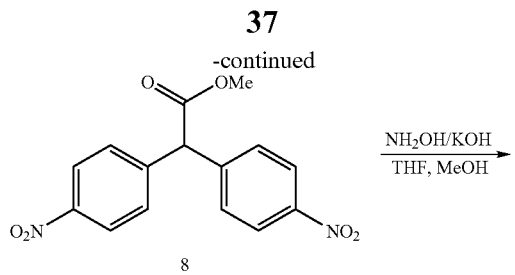

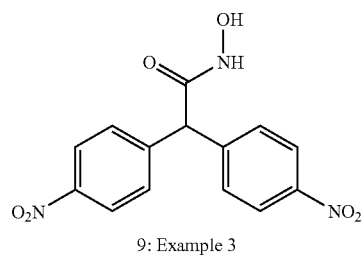

9: Example 3

Step 1: Methyl 2,2-bis(4-nitrophenyl)acetate (8)

Compound 7 (6 g, 26.5 mmol) was dissolved in fuming nitric acid (60 mL) and stirred at room temperature for 16 h. The reaction mixture was poured onto ice, the resulting light yellow sludge was separated out then dissolved in ether to provide a solid. Filtration afforded title compound 8 as a white solid (1.15 g, 14%). $^1$H NMR (DMSO-$d_6$) δ (ppm): 8.22 (d, J=9.0 Hz, 4H), 7.65 (d, J=8.6 Hz, 4H), 5.76 (s, 1H), 3.72 (s, 3H).

Step 2: N-hydroxy-2,2-bis(4-nitrophenyl)acetamide (9)

Following the same procedure as described in Example 1, step 2, but substituting compound 2 for compound 8, the title compound 9 was obtained in 25% yield (50 mg). $^1$H NMR (CD$_3$OD-$d_4$) δ (ppm): 8.21 (d, J=8.8 Hz, 4H), 7.61 (d, J=8.6 Hz, 4H), 5.07 (s, 1H). LRMS (ESI): calc. 317.1, found 316.3 (M-H)$^-$.

EXAMPLE 4

2-(4'-fluorobiphenyl-4-yl)-N-hydroxy-2-phenylacetamide (14)

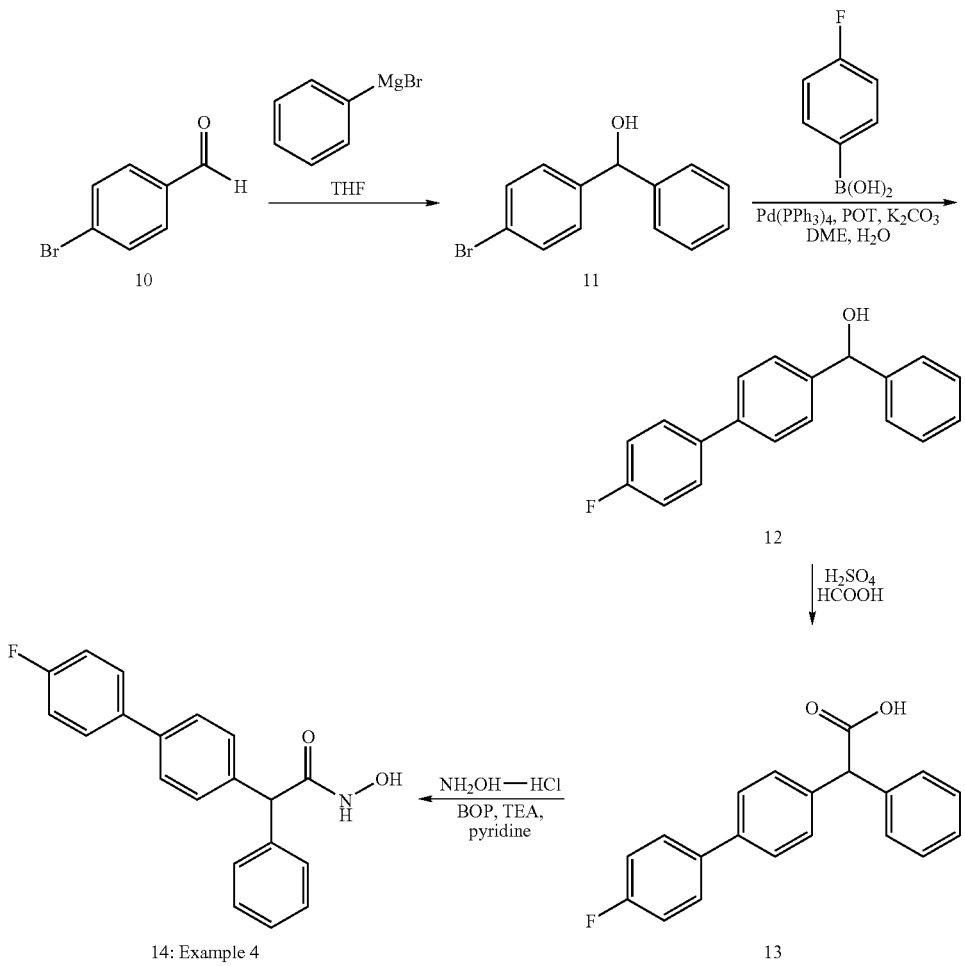

Step 1: (4-bromophenyl)(phenyl)methanol (11)

To a solution of p-bromobenzaldehyde 10 (4 g, 21.6 mmol) in THF (20 mL) was added phenyl magnesium bromide (22.7 mL, 22.7 mmol) and the reaction mixture was stirred at room temperature for 30 minutes, quenched with water and partially concentrated under vacuum. The crude material was dissolved in ethyl acetate and washed with water. The organic layer was separated, dried over $Na_2SO_4$, filtered and concentrated. The residue was purified via prep-HPLC (ISCO) in silica gel column with a gradient of ethyl acetate (5-45%) in hexanes to afford title compound 11 as a colorless oil (3.7 g, 65%). $^1$H NMR (DMSO-$d_6$) δ (ppm): 7.49-7.45 (m, 2H), 7.36-7.17 (m, 7H), 5.98 (d, J=4.1 Hz, 1H), 5.68 (d, J=3.9 Hz, 1H).

Step 2: (4'-fluorobiphenyl-4-yl)(phenyl)methanol (12)

To a solution of 11 (1 g, 3.80 mmol) and 4-fluorophenyl boronic acid (585 mg, 4.18 mmol) in a 2:1 mixture of DME:water (30 mL), was added Pd(PPh$_3$)$_4$ (307 mg, 0.27 mmol), tri-o-toly phosphine (81 mg, 0.27 mmol) and potassium carbonate (2.63 g, 19.0 mmol). The solution was heated to 80° C. and stirred for 16 hours. Then water (50 mL) was added and the organic residue was extracted with ethyl acetate (2×40 mL). The organic layer was dried over $Na_2SO_4$, filtered and concentrated. The residue was purified via prep-HPLC (ISCO) in silica gel column with a gradient of ethyl acetate (2-50%) in hexane to afford compound 12 as a white solid (600 mg, 57%). $^1$H NMR (DMSO-$d_6$) δ (ppm): 7.67-7.63 (m, 2H), 7.56 (d, J=8.4 Hz, 2H), 7.45-7.38 (m, 4H), 7.32-7.17 (m, 5H), 5.93 (d, J=3.9 Hz, 1H), 5.73 (d, J=3.8 Hz, 1H).

Step 3: 2-(4'-fluorobiphenyl-4-yl)-2-phenylacetic acid (13)

Compound 12 (600 mg, 2.16 mmol) was dissolved in a 25:1 mixture of concentrated sulfuric acid:formic acid (19.76 mL) and left without stirring for 2 hours. The reaction mixture was quenched with water and extracted with ethyl acetate. The organic layer was washed with water, dried over $Na_2SO_4$, filtered and concentrated. The residue was purified via prep-HPLC (ISCO) in silica gel column with a gradient of ethyl acetate (20-80%) in hexanes to afford compound 13 as an orange oil (40 mg, 6%). $^1$H NMR (DMSO-$d_6$) δ (ppm): 7.68-7.64 (m, 2H), 7.58 (d, J=8.4 Hz, 2H), 7.40-7.21 (m, 9H), 5.09 (s, 1H).

Step 4: 2-(4'-fluorobiphenyl-4-yl)-N-hydroxy-2-phenylacetamide (14)

To a solution of 13 (40 mg, 0.14 mmol), BOP (58 mg, 0.13 mmol), and hydroxylamine hydrochloride (9 mg, 0.13 mmol) in pyridine (5 mL) was added triethylamine (0.055 mL, 0.39 mmol) and the reaction mixture was stirred at room temperature for 2 h. The solvents were removed under vacuum and the crude was dissolved in ethyl acetate. The organic layer was washed with water, dried over $Na_2SO_4$, filtered and concentrated. The residue was purified via HPLC (Gilson) reverse-phase column with a gradient of methanol (20-75%) in water to afford compound 14 as a white solid (20 mg, 48%). $^1$H NMR (CD3OD-$d_4$) δ (ppm): 7.62-7.57 (m, 2H), 7.53 (d, J=8.2 Hz, 2H), 7.40-7.22 (m, 7H), 7.14 (t, J=8.8 Hz, 2H), 4.82 (s, 1H). LRMS (ESI): (calc.) 321.1 (found) 320.4 (MH)$^-$.

EXAMPLE 5

2-(4-(dimethylamino)phenyl)-N-hydroxy-2-phenylacetamide (17)

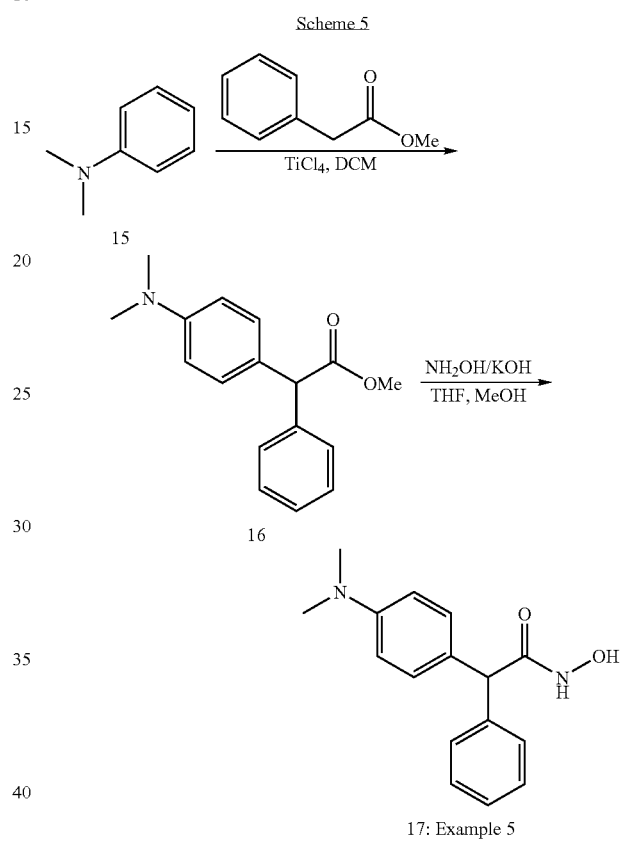

Step 1: methyl 2-(4-(dimethylamino)phenyl)-2-phenylacetate (16)

To a solution of methyl phenyl acetate (0.43 mL, 3 mmol) and 15 (1.36 mL, 10.71 mmol) in dichloromethane (28 mL) at 0° C. was added TiCl$_4$ (14.28 mL, 14.28 mmol). The reaction mixture was warmed to room temperature with stirring for 4 h. The reaction mixture was quenched with a saturated solution of NaHCO$_3$ (aq) and extracted with ethyl acetate. The organic layer was washed with water, saturated solution NaOH (aq), then with 1M HCl, dried over Na$_2$SO$_4$, filtered and concentrated. The residue was purified via prep-HPLC (ISCO) in silica gel column with a gradient of ethyl acetate (2-40%) in hexane to afford compound 16 as a yellow solid (270 mg, 33%). $^1$H NMR (DMSO-$d_6$) δ (ppm): 7.32-7.19 (m, 5H), 7.09 (d, J=8.6 Hz, 2H), 6.65 (d, J=8.8 Hz, 2H), 5.02 (s, 1H), 3.63 (s, 3H), 2.84 (s, 6H).

Step 2: 2-(4-(dimethylamino)phenyl)-N-hydroxy-2-phenylacetamide (17)

Following the same procedure as described in Example 1, step 2, but substituting compound 2 for compound 16, the title compound 17 was obtained in 28% yield. $^1$H NMR (CD$_3$OD-d$_4$) δ (ppm): 7.28-7.19 (m, 5H), 7.15 (d, J=8.4 Hz, 2H), 6.72 (d, J=8.8 Hz, 2H), 4.67 (s, 1H), 2.88 (s, 6H). LRMS (ESI): (calc) 270.3 (found) 271.4 (MH)+.

EXAMPLE 6

2-(biphenyl-4-yl)-N-hydroxy-2-phenylacetamide (20)

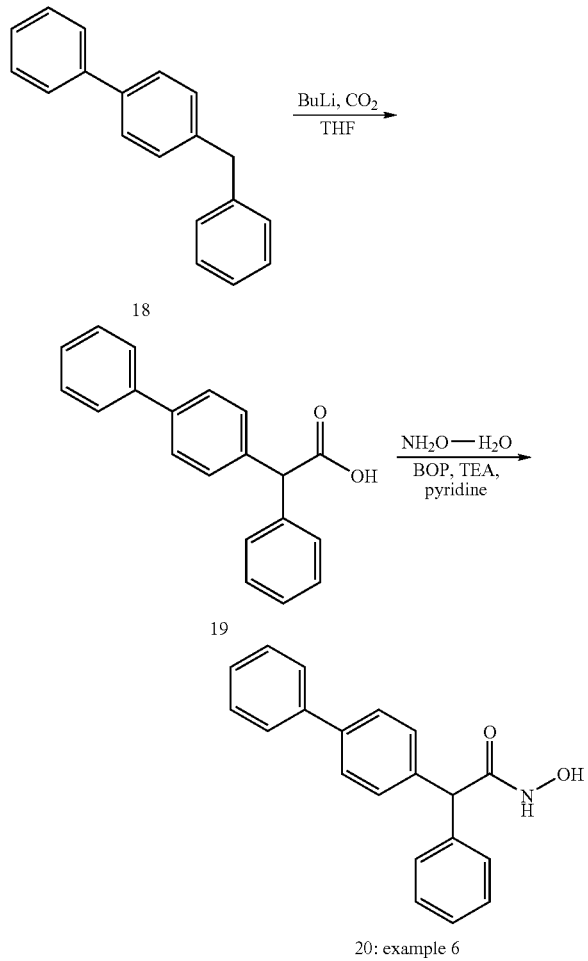

20: example 6

Step 1: 2-(biphenyl-4-yl)-2-phenylacetic acid (19)

To a solution of 18 (2 g, 8.19 mmol) in THF (20 mL) at 0° C. was added butyl lithium in hexanes (4.26 mL, 10.64 mmol). The reaction mixture was warmed to room temperature, stirred for 1 h and then CO$_2$ was bubbled through the stirring solution for 30 minutes. The solution was quenched with H$_2$O and 1M HCl until pH 6 and extracted with ethyl acetate. The organic layer was washed with water, dried over Na$_2$SO$_4$, filtered and concentrated. The residue was purified via prep-HPLC (ISCO) in silica gel column with a gradient of ethyl acetate (2-50%) in hexane to afford compound 19 as a white solid (670 mg, 28%). $^1$H NMR (DMSO-d$_6$) δ (ppm): 12.80 (br s, 1H), 7.62 (t, J=8.2 Hz, 4H), 7.39-7.22 (m, 10H), 5.11 (s, 1H).

Step 2: 2-(biphenyl-4-yl)-N-hydroxy-2-phenylacetamide (20)

Following the same procedure as described in Example 4, step 4, but substituting compound 13 for compound 19, the title compound 20 was obtained in 51% yield (360 mg). $^1$H NMR (CD$_3$OD-d$_4$) δ(ppm): 7.61-7.55 (m, 4H), 7.43-7.23 (m, 10H), 4.83 (s, 1H). LRMS (ESI): calc. 303.4, found 302.4 (M)$^-$.

EXAMPLE 7

N-hydroxy-2-phenyl-2-(piperidin-1-yl)acetamide (23)

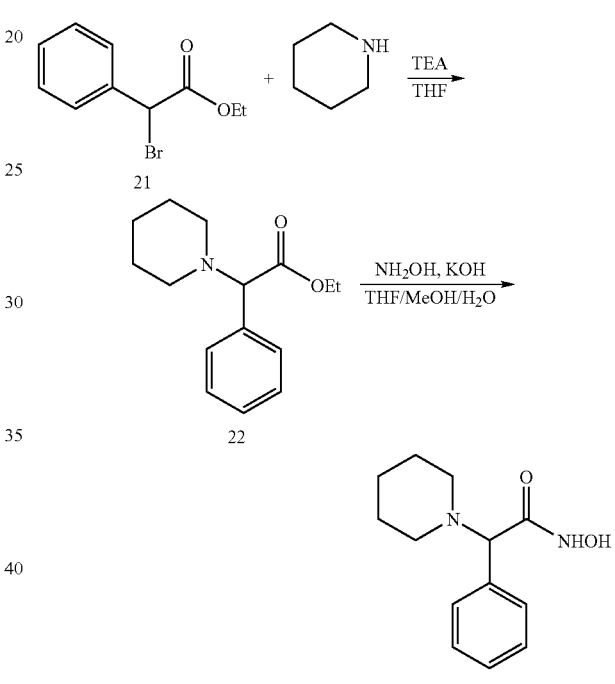

23: Example 7

Step 1: ethyl 2-phenyl-2-(piperidin-1-yl)acetate (22)

To a solution of ethyl 2-bromo-2-phenylacetate 21 (1.50 g, 6.17 mmol) in THF (10 mL) at room temperature was added piperidine (0.641 mL, 6.48 mmol) and TEA (1.72 mL, 12.34 mmol) and the reaction mixture was stirred for 3 h then diluted with brine and extracted with ethyl acetate. The organic layer was dried over Na$_2$SO$_4$, filtered, and concentrated. The crude material was purified by silica gel column chromatography with gradient of ethyl acetate (0-50%) in hexane to afford 22 as a colorless viscous oil (520 mg, 34%). LRMS (ESI): (calc) 247.3 (found) 248.3 (MH)+.

Step 2: N-hydroxy-2-phenyl-2-(piperidin-1-yl)acetamide (23)

Following the same procedure as described in Example 1, step 2, but substituting compound 2 for compound 22, the title compound 23 was obtained as a white solid in 16% yield (78 mg). $^1$H NMR (MeOD-d$_4$) δ (ppm): 7.53-7.49 (m, 2H), 7.38-

7.31 (m, 3H), 3.64 (s, 1H), 2.46-2.30 (m, 4H), 1.67-1.58 (m, 4H), 1.53-1.44 (m, 2H). LRMS (ESI): (calc) 234.3 (found) 235.2 (MH)+.

EXAMPLE 8

N-hydroxy-2-phenyl-2-(4-phenyl-1H-1,2,3-triazol-1-yl)acetamide (25)

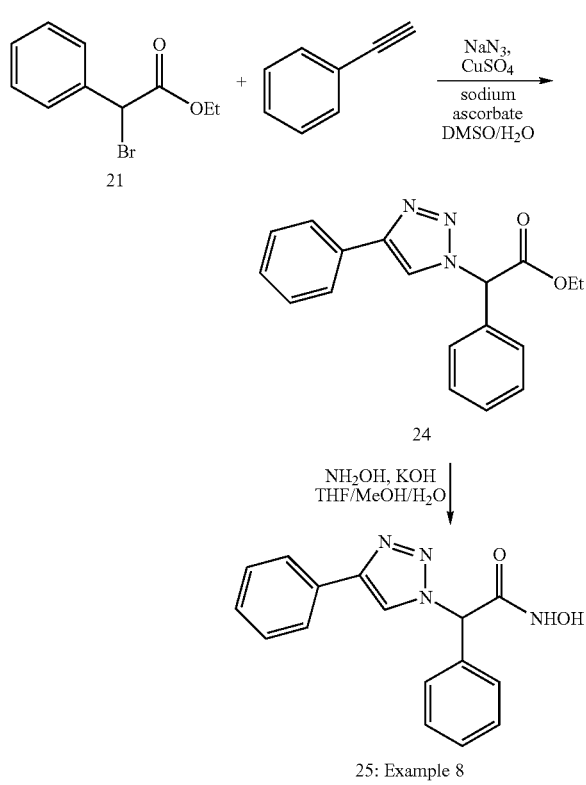

25: Example 8

Step 1: ethyl 2-phenyl-2-(4-phenyl-1H-1,2,3-triazol-1-yl)acetate (24)

To a solution of ethyl 2-bromo-2-phenylacetate 21 (1.60 g, 6.58 mmol) in sodium azide/DMSO solution (0.5 M, 13.16 mL, 6.58 mmol) which had been stirred at room temperature for 1 h was added water (10 mL), sodium ascorbate (0.130 g, 0.658 mmol), phenylacetylene (0.723 mL, 6.58 mmol) and aq. copper(II) sulfate solution (1.0 M, 1.30 mL, 1.30 mmol) (in that order). The reaction mixture was stirred for 16 h. Brine was added and extraction with ethyl acetate. The organic layer was dried over Na₂SO₄, filtered, and concentrated. The crude material was purified by silica gel column chromatography with gradient of ethyl acetate (0-50%) in hexane to afford compound (24) as a light yellow solid (1.31 g, 65%). LRMS: calc. 307.4, found 308.4 (MH)+.

Step 2: N-hydroxy-2-phenyl-2-(4-phenyl-1H-1,2,3-triazol-1-yl)acetamide (25)

Following the same procedure as described in Example 1, step 2, but substituting compound 2 for compound 24, the title compound 25 was obtained as a white solid in 16% yield (135 mg). $^1$H NMR (MeOD-d$_4$) δ (ppm): 7.56 (s, 1H), 7.02 (dd, J=8.4, 1.4 Hz, 2H), 6.78-6.53 (m, 8H), 5.69 (s, 1H). LRMS: calc. 294.3, found 295.4 (MH)+.

EXAMPLE 9

N-hydroxy-2-(N-methylphenylsulfonamido)acetamide (29)

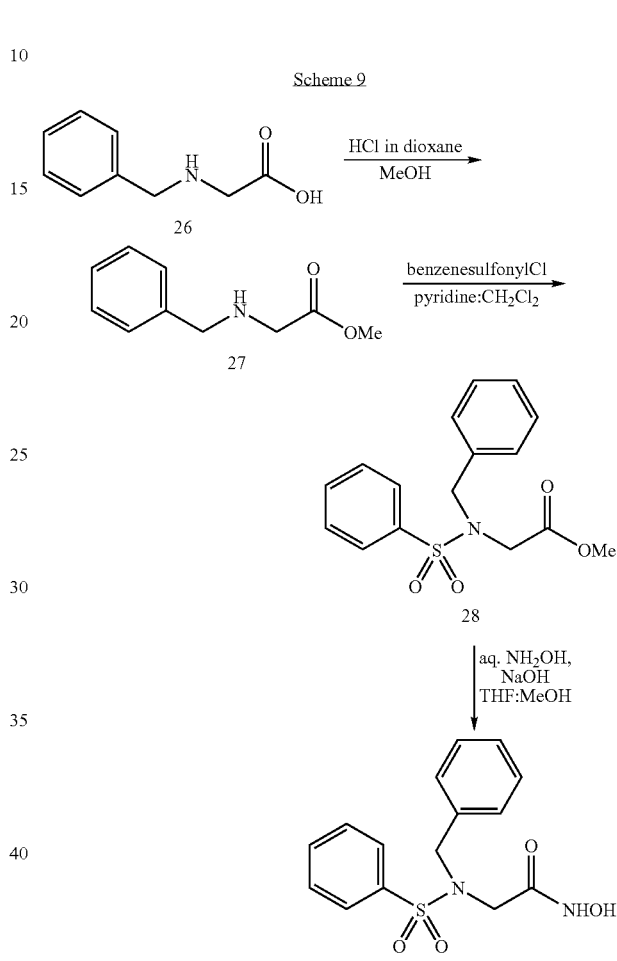

29: Example 9

Step 1: Methyl 2-(benzylamino)acetate hydrochloride (27)

To a N-benzyl glycine 26 (500 mg, 3.0 mmol) in MeOH (6 mL) was added 4M solution of HCl in dioxane (4 mL) and stirred overnight. The reaction mixture was concentrated to afford compound 27 (649 mg, 99%) as a white solid. The crude compound was carried forward without further purification. LRMS (ESI): (calc) 179.2 (found) 180.1 (MH)+.

Step 2: Methyl 2-(N-benzylphenylsulfonamido)acetate (28)

To a solution of compound 27 in CH₂Cl₂ (3 mL) was added pyridine (3 mL) and the stirred overnight. The reaction was partitioned between EtOAc (6 mL) and water (6 mL). The organic layer was separated, dried over Na₂SO₄, filtered and concentrated under vacuum. The crude material was purified by silica gel column chromatography with gradient of ethyl acetate (0-70%) in hexane to afford compound 28 (165 mg, 28%) as a thick oil. LRMS (ESI): (calc) 319.4 (found) 320.2 (MH)+.

Step 3: 2-(N-benzylphenylsulfonamido)-N-hydroxyacetamide (29)

Following the same procedure as described in Example 1, step 2, but substituting compound 2 for compound 28, the title compound 29 (139 mg, 84%) as a white solid. $^1$H NMR (CD$_3$OD-d$_4$) δ (ppm): 7.91 (d, J=7.2 Hz, 2H), 7.57 (m, 3H), 7.28 (m, 5H), 4.47 (s, 2H), 3.72 (s, 2H). LRMS (ESI): (calc.) 320.1 (found) 321.3 (MH)+.

EXAMPLE 10

N-hydroxy-2-phenyl-2-(6-(thiophen-2-yl)-1H-benzo[d]imidazol-2-yl)acetamide (34)

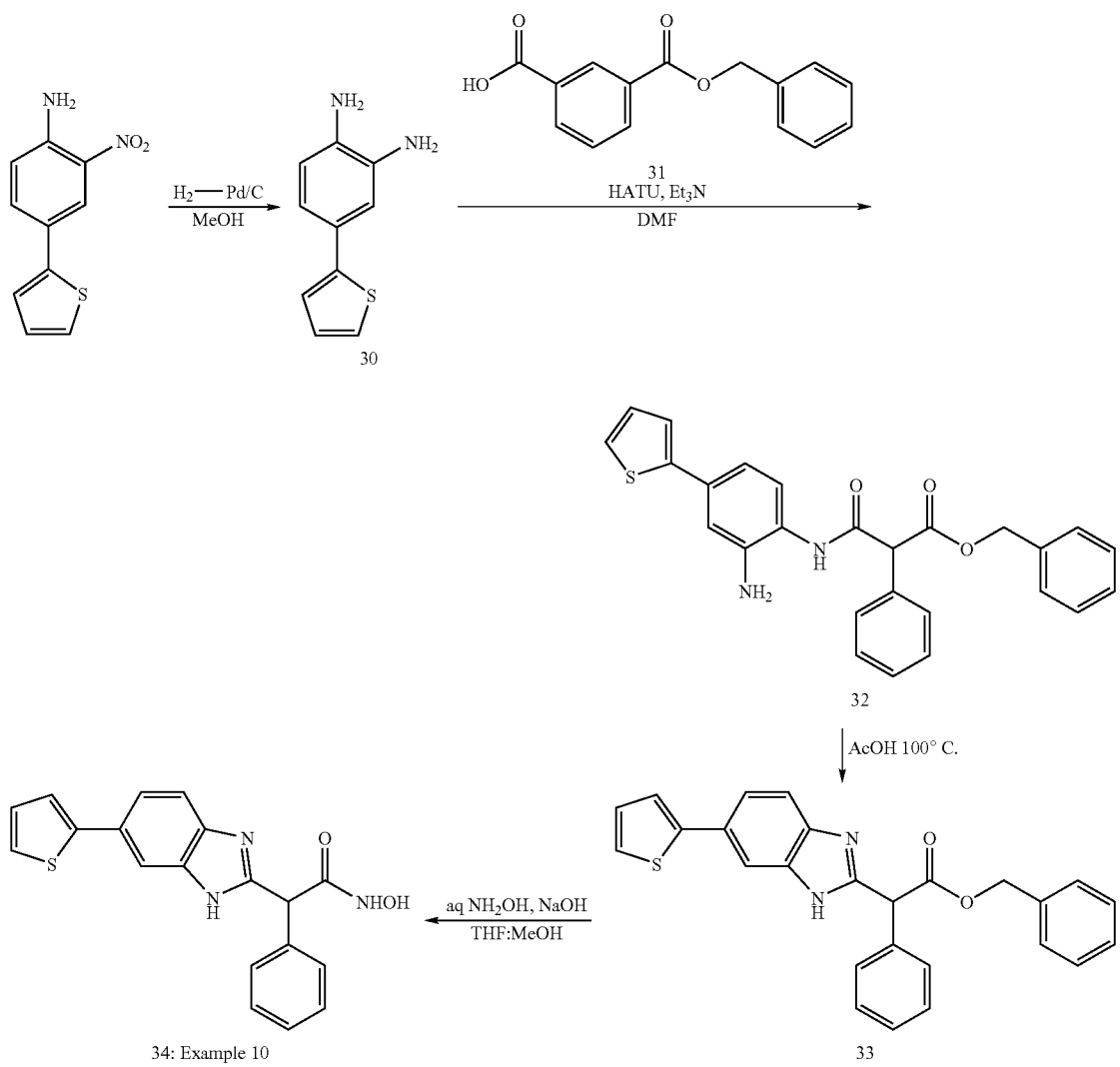

Scheme 10

Step 1: 4-(thiophen-2-yl)benzene-1,2-diamine (30)

To a solution of 4-thienyl-2-nitroaniline (1 equiv, 400 mg, 1.82 mmol) was added 10% Pd/C (0.05 equiv, 97 mg, 0.09 mmol). The resulting suspension was stirred for overnight over 1 atm of hydrogen. The solids were filtered through celite pad and the filtrate was concentrated under vacuum. The crude material was purified by silica gel column chromatography with gradient of MeOH (0-10%) in CH$_2$Cl$_2$ to afford compound 30 (310 mg, 90%) and a white solid. LRMS (ESI): (calc) 190.2 (found) 191.0 (MH)+.

Step 2: Benzyl 3-(2-amino-4-(thiophen-2-yl)phenylamino)-3-oxo-2-phenylpropanoate (32)

To a solution of compound 30 (275 mg, 1.45 mmol), compound 31 (391 mg, 1.45 mmol) and HATU (714 mg, 1.88 mmol) in DMF (3 mL) was added Et$_3$N (0.81 mL, 5.78 mmol) and stirred overnight. The reaction was partitioned between EtOAc (5 mL) and H$_2$O (10 mL). The organic layer was separated, dried over Na$_2$SO$_4$, filtered and concentrated under vacuum. The crude material was purified by silica gel column chromatography with gradient of ethyl acetate (10-90%) in hexane to afford compound 32 (463 mg, 72%) as a clear thick oil. LRMS (ESI): (calc) 442.58 (found) 443.4 (MH)+.

Step 3: Benzyl 2-phenyl-2-(6-(thiophen-2-yl)-1H-benzo[d]imidazol-2-yl)acetate (33)

AcOH (3 mL) was added to compound 32 (463 mg, 1.04 mmol) and the reaction heated at 100° C. for 30 min. The solvent was evaporated under reduced pressure.

The crude material was purified by silica gel column chromatography with gradient of ethyl acetate (10-50%) in hexane to afford compound 33 (378 mg, 85%) as a clear oil. LRMS (ESI): (calc) 424.5 (found) 425.4 (MH)+.

Step 4: N-Hydroxy-2-phenyl-2-(6-(thiophen-2-yl)-1H-benzo[d]imidazol-2-yl)acetamide. Formic salt (34)

Following the same procedure as described in Example 1, step 2, but substituting compound 2 for compound 33, the title compound 34 (4 mg, 7%) as a white solid. $^1$H NMR (CD$_3$OD-d$_4$) δ (ppm): 8.24 (s, 1H), 7.78 (s, 1H), 7.54 (m, 2H), 7.47 (m, 2H), 7.38-7.30 (m, 5H), 7.08-7.06 (m, 1H), 5.11 (s, 1H). LRMS (ESI): (calc.) 349.0 (found) 350.4 (MH)+.

EXAMPLE 11

N-hydroxy-2-(5-(2-methoxyphenyl)-1,3,4-thiadiazol-2-yl)-2-phenylacetamide (38)

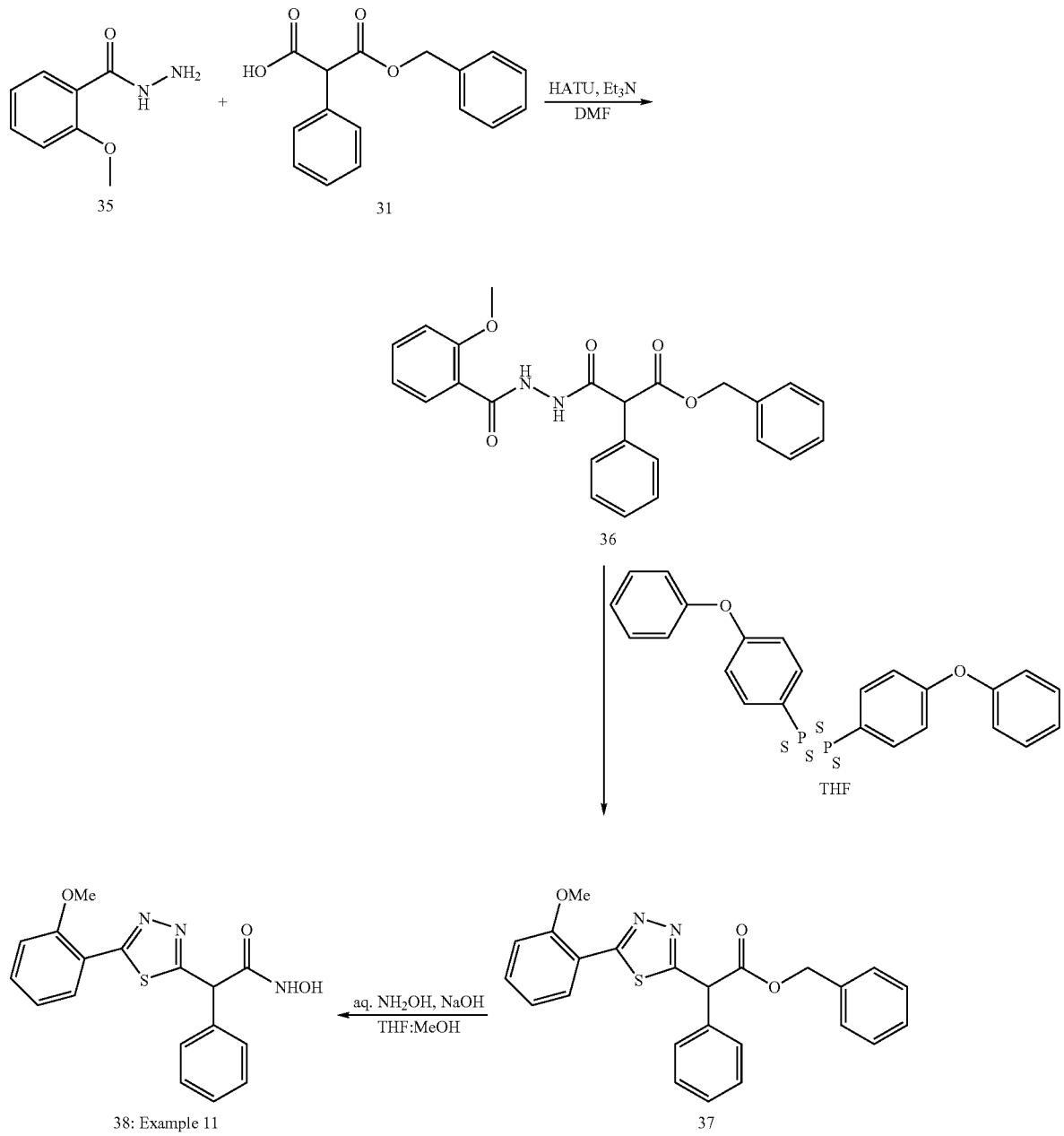

Scheme 11

Step 1: Benzyl 3-(2-(2-methoxybenzoyl)hydrazinyl)-3-oxo-2-phenylpropanoate (36)

Following the same procedure as described in Example 10, step 2, but substituting compound 30 for compound 35, the title compound 36 (427 mg, 55%) as a white solid. LRMS (ESI): (calc) 418.4, (found) 419.5 (MH)+.

Step 2: Benzyl 2-(5-(2-methoxyphenyl)-1,3,4-thiadiazol-2-yl)-2-phenylacetate (37)

To a solution of compound 36 (539 mg, 1.02 mmol) in THF (4 mL) was added 2,4-bis(4-phenoxyphenyl)-1,3-dithia-2,4-diphosphetane-2,4-disulfide (539 mg, 1.02 mmol) and the reaction stirred overnight. The crude material was concentrated and purified by silica gel column chromatography with gradient of ethyl acetate (5-40%) in hexane to afford compound 37 (325 mg, 76%) as a white solid. LRMS (ESI): (calc) 416.4, (found) 417.4 (MH)+.

Step 3: N-Hydroxy-2-(5-(2-methoxyphenyl)-1,3,4-thiadiazol-2-yl)-2-phenylacetamide(38)

Following the same procedure as described in Example 1, step 2, but substituting compound 2 for compound 37, the title compound 38 (93 mg, 35%) as a white solid. $^1$H NMR (CD$_3$OD-d$_4$) δ (ppm): 8.29 (d, J=6.0 Hz, 1H), 7.54-7.48 (m, 3H), 7.39-7.32 (m, 3H), 7.21 (d, J=8.0 Hz, 1H), 7.11 (t, J=7.6 Hz, 1H), 5.38 (s, 1H), 4.02 (s, 3H). LRMS (ESI): (calc.) 341.1, (found) 342.3 (MH)+.

EXAMPLE 12

N-benzhydryl-N-hydroxyformamide

Scheme 12

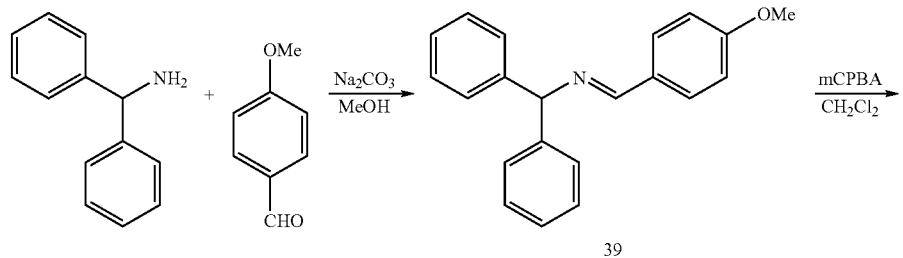

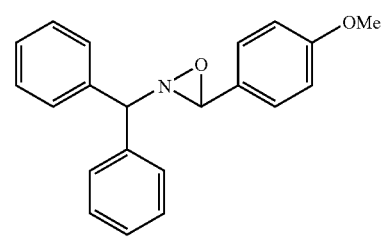

40

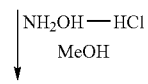

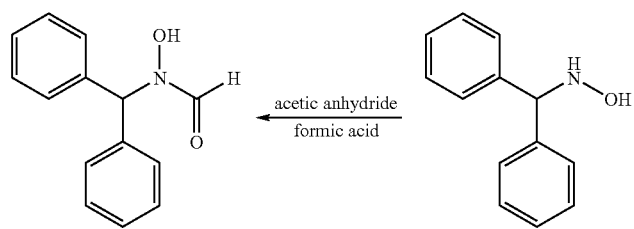

42: Example 12      41

Step 1: (E)-N-(4-methoxybenzylidene)-1,1-diphenylmethanamine (39)

To a solution of diphenylmethanamine (3.00 g, 16.4 mmol) in methanol (80 mL) was added 4-methoxybenzaldehyde (2.45 g, 18.0 mmol) and sodium carbonate (2.60 g, 24.6 mmol). The reaction mixture was stirred at room temperature for 16 h prior to removal of all solvents under vacuum. The residue was then diluted with ethyl acetate, washed with brine, dried over anhydrous $Na_2SO_4$, filtered, and concentrated to afford compound 39 as a white solid (3.62 g, 73%). LRMS (ESI): (calc.) 301.4 (found) 302.4 (MH)+.

Step 2: 2-benzhydryl-3-(4-methoxyphenyl)-1,2-oxaziridine (40)

(E)-N-(4-methoxybenzylidene)-1,1-diphenylmethanamine 39 (3.62 g, 12.0 mmol) was dissolved in dichloromethane (130 mL) at 0° C., followed by the portionwise addition of mCPBA (2.96 g, 13.2 mmol). The resulting solution was warmed to room temperature, and stirred for 16 h prior to being transferred to a separatory funnel, and being washed 3 times with 50 mL of saturated sodium bicarbonate solution. The organic layer was then dried with anhydrous sodium sulfate, filtered, and concentrated to afford 40 as a light yellow oil (3.52 g, 92%). LRMS (ESI): (calc.) 317.4 (found) 318.2 (MH)+.

Step 3: N-benzhydrylhydroxylamine (41)

To a solution of 2-benzhydryl-3-(4-methoxyphenyl)-1,2-oxaziridine 40 (3.52 g, 11.1 mmol) in methanol (100 mL) was added hydroxylamine-HCl (2.31 g, 33.3 mmol) and stirred at room temperature. for 16 h. The reaction mixture was concentrated under vacuum and diluted with aqueous NaOH solution (to pH=13), followed by extraction with ethyl acetate. The combined organic layers were dried over anhydrous $Na_2SO_4$, filtered, and concentrated. The crude material was concentrated and purified by silica gel column chromatography with gradient of ethyl acetate (10-50%) in hexane to afford compound 41 as a light yellow solid (450 mg, 20%). LRMS (ESI): (calc.) 199.3 (found) 167.2 (M-NHOH)+.

Step 4: N-benzhydryl-N-hydroxyformamide (42)

Formic acid (0.53 mL, 14.1 mmol) was added dropwise to acetic anhydride (1.07 mL, 11.3 mmol) at 0° C., stirred for 5 mins. and then warmed to 55° C. for 5 mins prior to cooling back down to room temperature. N-benzhydrylhydroxylamine 41 (225 mg, 1.13 mmol) was added, and stirred at room temperature for 3 days. The reaction mixture was diluted with aqueous NaOH solution (to pH=7), the solution was stirred for 5 mins, and then acidified with aqueous HCl solution (to pH=4). Following extraction with ethyl acetate, the combined organic layers were dried with anhydrous sodium sulfate, filtered, and concentrated. The crude material was concentrated and purified by silica gel column chromatography with gradient of ethyl acetate (0-75%) in hexane to afford compound 42 as a tan solid (169 mg, 66%). $^1$H NMR: (DMSO-$d_6$) 8.41 (br s, 1H), 7.44-7.28 (m, 11H). LRMS (ESI): (calc.) 227.3 (found) 228.2 (MH)+.

The compounds in table I were made according to processes described in the previous examples.

TABLE I

| Strucutre | Cpd | Name | MS | $^1$H NMR | Procedure of Scheme |
|---|---|---|---|---|---|
|  | 1-1 | N-hydroxy-2,2-diphenylacetamide | LRMS (ESI): (calc.) 227.1 (found) 228.2 (MH)+ | $^1$H NMR (DMSO-$d_6$) δ (ppm): 10.91 (s, 1H), 8.95 (s, 1H), 7.33-7.19 (m, 10H), 4.69 (s, 1H). | 1 |
|  | 1-2 (cpd 6, Ex 2) | N-hydroxy-2-phenoxy-2-phenylacetamide | LRMS (ESI): (calc.) 243.1 (found) 242.0 (M − H)− | $^1$H NMR (CD$_3$OD-$d_4$) δ (ppm): 5.57-7.54 (m, 2H), 7.39-7.32 (m, 3H), 7.27-7.22 (m, 2H), 7.00-6.92 (m, 3H), 5.60 (s, 1H). | 2 |
|  | 1-3 (cpd 9, Ex 3) | N-hydroxy-2,2-bis(4-nitrophenyl)-acetamide | LRMS (ESI): (calc.) 317.1 (found) 316.3 (M − H)− | $^1$H NMR (CD$_3$OD-$d_4$) δ (ppm): 8.21 (d, J = 8.8Hz, 4H), 7.61 (d, J = 8.6Hz, 4H), 5.07 (s, 1H). | 3 |

TABLE I-continued

| Strucutre | Cpd | Name | MS | ¹H NMR | Procedure of Scheme |
|---|---|---|---|---|---|
| | 1-4 (cpd 23, Ex 7) | N-hydroxy-2-phenyl-2-(piperidin-1-yl)acetamide | LRMS (ESI): (calc.) 234.3 (found) 235.2 (MH)+ | ¹H NMR (CD$_3$OD-d$_4$) δ (ppm): 7.53-7.49 (m, 2H), 7.38-7.31 (m, 3H), 3.64 (s, 1H), 2.46-2.30 (m, 4H), 1.67-1.58 (m, 4H), 1.53-1.44 (m, 2H) | 7 |
| | 1-5 (cpd 29, Ex 9) | 2-(N-benzylphenyl-sulfonamido)-N-hydroxyacetamide | LRMS (ESI): (calc.) 320.1 (found) 321.3 (MH)+ | ¹H NMR (CD$_3$OD-d$_4$) δ (ppm): 7.91 (d, J = 7.2Hz, 2H), 7.57 (m, 3H), 7.28 (m, 5H), 4.47 (s, 2H), 3.72 (s, 2H) | 9 |
| | 1-6 | N-hydroxy-3,3-diphenylpropan-amide | LRMS (ESI): (calc.) 241.3 (found) 242.2 (MH)+ | ¹H NMR (CD$_3$OD-d$_4$) δ (ppm): 7.30-7.16 (m, 10H), 4.58 (t, J = 8.2Hz, 1H), 2.84 (d, J = 8.0 Hz, 2H) | 1 |
| | 1-7 | N-hydroxy-9H-xanthene-9-carboxamide | LRMS (ESI): (calc.) 241.2 (found) 242.3 (MH)+ | ¹H NMR (CD$_3$OD-d$_4$) δ (ppm): 7.35-7.27 (m, 4H), 7.16-7.09 (m, 4H), 4.80 (s, 1H) | 1 (step 2) |
| | 1-8 (cpd 3, Ex 1) | 2,2-bis(2,3-dihydrobenzo-furan-5-yl)-N-hydroxyacetamide | LRMS (ESI): (calc.) 311.1 (found) 310.3 (M − H)− | ¹H NMR (DMSO-d$_6$) δ (ppm): 10.81 (br s, 1H), 8.88 (br s, 1H), 7.16 (d, J = 1.0 Hz, 2H), 6.99 (dd, J = 8.4, 1.8Hz, 2H), 6.67 (d, J = 8.1Hz, 2H), 4.53-4.45 (m, 5H), 3.12 (t, J = 8.6Hz, 4H). | 1 |
| | 1-9 | 2-(4-benzylpiperidin-1-yl)-N-hydroxy-2-phenylacetamide | LRMS (ESI): (calc.) 324.4 (found) 325.4 (MH)+ | ¹H NMR (CD$_3$OD-d$_4$) δ (ppm): 7.52-7.47 (m, 2H), 7.37-7.23 (m, 5H), 7.19-7.13 (m, 3H), 3.62 (s, 1H), 3.10-3.03 (m, 1H), 2.70-2.63 (m, 1H), 2.55 (d, J = 6.7Hz, 2H), 2.09-2.00 (m, 1H), 1.80-1.71 (m, 1H), 1.69-1.24 (m, 5H) | 7 |

TABLE I-continued

| Strucutre | Cpd | Name | MS | ¹H NMR | Procedure of Scheme |
|---|---|---|---|---|---|
| | 1-10 | 2-cyclohexyl-N-hydroxy-2-phenylacetamide | LRMS (ESI): (calc.) 233.3 (found) 234.3 (MH)+ | ¹H NMR (CD₃OD-d₄) δ (ppm): 7.40-7.35 (m, 2H), 7.33-7.22 (m, 3H), 2.93 (d, J = 11.0 Hz, 1H), 2.16-2.04 (m, 1H), 1.94-1.85 (m, 1H), 1.83-1.74 (m, 1H), 1.73-1.60 (m, 2H), 1.42-1.14 (m, 4H), 1.12-1.00 (m, 1H), 0.84-0.71 (m, 1H) | 1 |
| | 1-11 | N-hydroxy-2,3-diphenylpropan-amide | LRMS (ESI): (calc.) 241.1 (found) 242.2 (MH)+ | ¹H NMR (CD₃OD-d₄) δ (ppm): 7.42-7.38 (m, 2H), 7.30-7.11 (m, 8H), 3.63 (dd, J = 9.4, 5.9Hz, 1H), 3.40 (dd, J = 13.5, 9.6Hz, 1H), 2.98 (dd, J = 13.5, 5.9Hz, 1H). | 1 |
| | 1-12 | N-hydroxy-2-phenyl-2-(phenylthio)-acetamide | LRMS(ESI): (calc.) 259.1 (found) 258.2 (M − H)− | ¹H NMR (DMSO-d₆) δ (ppm): 10.95 (br s, 1H), 9.10 (br s, 1H), 7.49-7.46 (m, 2H), 7.35-7.21 (m, 8H), 4.90 (s, 1H). | 2 |
| | 1-13 | N-hydroxy-2-phenyl-2-(1H-pyrrol-1-yl)acetamide | LRMS (ESI): (calc.) 216.2 (found) 217.1 (MH)+ | ¹H NMR (CD₃OD-d₄) δ (ppm): 7.42-7.26 (m, 5H), 6.82 (t, J = 2.0 Hz, 2H), 6.14 (t, J = 2.2Hz, 2H), 5.76 (s, 1H). | 1 (step 2) |
| | 1-14 | N-hydroxy-2,2-diphenylpropan-amide | LRMS (ESI): (calc.) 241.3 (found) 242.3 (MH)+ | ¹H NMR (CD₃OD-d₄) δ (ppm): 7.37-7.25 (m, 10H), 1.96 (s, 3H). | 1 |
| | 1-15 | 2,2-bis(4-chlorophenyl)-N-hydroxyacetamide | LRMS ESI): (calc.) 295.0 (found) 294.2 (M − H)− | ¹H NMR (CD₃OD-d₄) δ (ppm): 7.29 (s, 8H), 4.78 (s, 1H). | 1 |

TABLE I-continued

| Strucutre | Cpd | Name | MS | ¹H NMR | Procedure of Scheme |
|---|---|---|---|---|---|
| | 1-16 | N-hydroxy-2-phenyl-2-(4-phenylpiperazin-1-yl)acetamide | LRMS (ESI): (calc.) 311.4 (found) 312.4 (MH)+ | ¹H NMR (CD$_3$OD-d$_4$) δ (ppm): 7.55 (d, J = 7.4Hz, 2H), 7.42-7.32 (m, 3H), 7.28-7.21 (m, 2H), 6.98 (d, J = 8.4Hz, 2H), 6.88-6.82 (m, 1H), 3.73 (s, 1H), 3.25-3.20 (m, 4H), 2.70-2.54 (m, 4H). | 7 |
| | 1-17 | 2-(4-benzylpiperazin-1-yl)-N-hydroxy-2-phenylacetamide | LRMS (ESI): (calc.) 325.4 (found) 326.4 (MH)+ | ¹H NMR (CD$_3$OD-d$_4$) δ (ppm): 7.53-7.47 (m, 2H), 7.39-7.25 (m, 8H), 3.66 (s, 1H), 3.56 (s, 2H), 2.64-2.37 (m, 8H). | 7 |
| | 1-18 | 2,2-bis(4-fluorophenyl)-N-hydroxyacetamide | LRMS (ESI): (calc.) 263.1 (found) 264.1 (MH)+ | ¹H NMR (CD$_3$OD-d$_4$) δ (ppm): 7.33 (dd, J = 8.2, 5.7Hz, 4H), 7.04 (t, J = 8.8Hz, 4H), 4.76 (s, 1H). | 4 |
| | 1-19 | 2-(4-(diethylamino)-phenyl)-N-hydroxy-2-phenylacetamide | LRMS (ESI): (calc.) 298.2 (found) 299.2 (MH)+ | ¹H NMR (CD$_3$OD-d$_4$) δ (ppm): 7.31-7.19 (m, 5H), 7.12 (d, J = 8.6Hz, 2H), 6.68 (d, J = 8.6Hz, 2H), 4.66 (s, 1H), 3.34 (q, J = 7.0 Hz, 4H), 1.11 (t, J = 7.0 Hz, 6H). | 5 |
| | 1-20 (cpd 34, Ex 10) | N-hydroxy-2-phenyl-2-(6-(thiophen-2-yl)-1H-benzo[d]imidazol-2-yl)acetamide | LRMS (ESI): (calc.) 349.0 (found) 350.4 (MH)+ | ¹H NMR (CD$_3$OD-d$_4$) δ (ppm): 8.24 (s, 1H; formate proton), 7.78 (s, 1H), 7.54 (m, 2H), 7.47 (m, 2H), 7.38-7.30 (m, 5H), 7.08-7.06 (m, 1H), 5.11 (s, 1H) | 10 |

TABLE I-continued

| Strucutre | Cpd | Name | MS | ¹H NMR | Procedure of Scheme |
|---|---|---|---|---|---|
| | 1-21 | (E)-N-hydroxy-2,3-diphenylacryl-amide | LRMS (ESI): (calc.) 239.3 (found) 240.3 (MH)+ | ¹H NMR (CD₃OD-d₄) δ (ppm): 7.48 (s, 1H), 7.45-7.40 (m, 3H), 7.29-7.13 (m, 5H), 7.06-7.01 (m, 2H). | 4 (step 4) |
| | 1-22 | N-hydroxy-2-(isoindolin-2-yl)-2-phenylacetamide | LRMS (ESI): (calc.) 268.3 (found) 269.3 (MH)+ | ¹H NMR (DMSO-d₆) δ (ppm): 10.96 (s, 1H), 8.94 (s, 1H), 7.59-7.54 (m, 2H), 7.44-7.32 (m, 3H), 7.28-7.20 (m, 4H), 4.12 (s, 1H), 3.89-3.76 (m, 4H). | 7 |
| | 1-23 | N-hydroxy-2,2-di(thiopen-2-yl)acetamide | LRMS (ESI): (calc.) 239.1 (found) 240.2 (MH)+ | ¹H NMR (DMSO-d₆) δ (ppm): 11.01 (s, 1H), 9.14 (s, 1H), 7.39 (dd, J = 5.1, 1.4 Hz, 1H), 6.99-6.97 (m, 2H), 6.94-6.91 (m, 2H), 5.26 (s, 1H). | 1 |
| | 1-24 | 2-(benzo[d]thiazol-2-ylthio)-N-hydroxy-2-phenylacetamide | LRMS (ESI): (calc.) 316.1 (found) 317.3 (MH)+ | ¹H NMR (CD₃OD-d₄) δ (ppm): 7.86-7.80 (m, 2H), 7.61-7.58 (m, 2H), 7.43 (td, J = 7.2, 1.2Hz, 1H), 7.37-7.30 (m, 4H), 5.68 (s, 1H). | 2 |
| | 1-25 | 2-(5-chloro-6-fluoro-1H-benzo[d]imidazol-2-yl)-N-hydroxy-2-phenylacetamide | LRMS (ESI): (calc.) 319.0 (found) 320.3 (MH)+ | ¹H NMR (CD₃OD-d₄) δ (ppm): 7.61 (d, J = 6.4Hz, 1H), 7.46 (m, 2H), 7.44-7.29 (m, 4H), 5.09 (s, 1H). | 10 |
| | 1-26 (cpd 25, Ex 8) | N-hydroxy-2-phenyl-2-(4-phenyl-1H-1,2,3-triazol-1-yl)acetamide | LRMS (ESI): (calc.) 294.3 (found) 295.4 (MH)+ | ¹H NMR (CD₃OD-d₄) δ (ppm): 7.56 (s, 1H), 7.02 (dd, J = 8.4, 1.4Hz, 2H), 6.78-6.53 (m, 8H), 5.69 (s, 1H). | 8 |
| | 1-27 | N-hydroxy-2-(4-phenethyl-1H-1,2,3-triazol-1-yl)-2-phenylacetamide | LRMS (ESI): (calc.) 322.4 (found) 323.5 (MH)+ | ¹H NMR (CD₃OD-d₄) δ (ppm): 7.62 (s, 1H), 7.46-7.36 (m, 5H), 7.26-7.10 (m, 5H), 6.39 (s, 1H), 3.02-2.87 (m, 4H) | 8 |

TABLE I-continued

| Strucutre | Cpd | Name | MS | ¹H NMR | Procedure of Scheme |
|---|---|---|---|---|---|
| | 1-28 | N,2-dihydroxy-2,2-diphenylacetamide | LRMS (ESI): (calc.) 243.3 (found) 242.3 (M − H)− | ¹H NMR (CD₃OD-d₄) δ (ppm): 7.46-7.43 (m, 4H), 7.34-7.26 (m, 6H). | 1 (step 2) |
| | 1-29 (cpd 17, Ex 5) | 2-(4-(dimethylamino)phenyl)-N-hydroxy-2-phenylacetamide | LRMS (ESI): (calc.) 270.3 (found) 271.4 (MH)+ | ¹H NMR (CD₃OD-d₄) δ (ppm): 7.28-7.19 (m, 5H), 7.15 (d, J = 8.4Hz, 2H), 6.72 (d, J = 8.8Hz, 2H), 4.67 (s, 1H), 2.88 (s, 6H). | 5 |
| | 1-30 | 2-(4-(4-fluorobenzyl)-piperidin-1-yl)-N-hydroxy-2-phenylacetamide | LRMS (ESI): (calc.) 342.4 (found) 343.5 (MH)+ | ¹H NMR (CD₃OD-d₄) δ (ppm): 7.53-7.47 (m, 2H), 7.38-7.30 (m, 3H), 7.20-7.13 (m, 2H), 6.99 (t, J = 8.8Hz, 2H), 3.63 (s, 1H), 3.10-3.03 (m, 1H), 2.70-2.64 (m, 1H), 2.55 (d, J = 6.7 Hz, 2H), 2.10-2.00 (m, 1H), 1.80-1.70 (m, 1H), 1.68-1.24 (m, 5H). | 7 |
| | 1-31 | N-hydroxy-2-(4-phenethylpiperidin-1-yl)-2-phenylacetamide | LRMS (ESI): (calc.) 338.4 (found) 339.5 (MH)+ | ¹H NMR (DMSO-d₆) δ (ppm): 7.47-7.42 (m, 2H), 7.38-7.26 (m, 5H), 7.24-7.16 (m, 3H), 3.61 (s, 1H), 2.98-2.90 (m, 1H), 2.66-2.56 (m, 3H), 1.98 (t, J = 9.4Hz, 1H), 1.79-1.46 (m, 5H), 1.31-1.10 (m, 3H). | 7 |
| | 1-32 (cpd 20, Ex 6) | 2-(biphenyl-4-yl)-N-hydroxy-2-phenylacetamide | LRMS (ESI): (calc.) 303.4 (found) 302.4 (M − H)− | ¹H NMR (CD₃OD-d₄) δ (ppm): 7.61-7.55 (m, 4H), 7.43-7.23 (m, 10H), 4.83 (s, 1H). | 6 |
| | 1-33 | N1-hydroxy-2-phenyl-N3-(3-(trifluoromethyl)phenyl)malon-amide | LRMS (ESI): (calc.) 338.0 (found) 337.3 (M − H)− | ¹H NMR (CD₃OD-d₄) δ (ppm): 8.01 (s, 1H), 7.73 (d, J = 8.0 Hz, 1H), 7.49 (m, 3H), 7.39-7.32 (m, 4H), 4.52 (s, 1H) | 10 (step 1) 1 (step 2) |

TABLE I-continued

| Strucutre | Cpd | Name | MS | ¹H NMR | Procedure of Scheme |
|---|---|---|---|---|---|
| | 1-34 | 2-(4-(1H-indol-3-yl)piperidin-1-yl)-N-hydroxy-2-phenylacetamide | LRMS (ESI): (calc.) 349.4 (found) 350.5 (MH)+ | ¹H NMR (CD₃OD-d₄) δ (ppm): 7.62-7.54 (m, 3H), 7.40-7.30 (m, 4H), 7.11-7.05 (m, 1H), 7.03-6.96 (m, 2H), 3.74 (s, 1H), 3.27-3.18 (m, 1H), 2.90-2.76 (m, 2H), 2.36-2.25 (m, 1H), 2.10-1.80 (m, 5H). | 7 |
| | 1-35 | 2-(4-benzyl-1H-1,2,3-triazol-1-yl)-N-hydroxy-2-phenylacetamide | LRMS (ESI): (calc.) 308.3 (found) 309.4 (MH)+ | ¹H NMR (CD₃OD-d₄) δ (ppm): 7.75 (s, 1H), 7.50-7.40 (m, 5H), 7.31-7.16 (m, 5H), 6.41 (s, 1H), 4.04 (s, 2H). | 8 |
| | 1-36 | N-hydroxy-2-phenyl-2-(4-(pyrimidin-2-yl)piperazin-1-yl)acetamide | LRMS (ESI): (calc.) 313.4 (found) 314.5 (MH)+ | ¹H NMR (CD₃OD-d₄) δ (ppm): 8.32 (d, J = 4.7Hz, 2H), 7.54 (dd, J = 7.6, 1.4Hz, 2H), 7.42-7.32 (m, 3H), 6.61 (t, J = 4.7Hz, 1H), 3.87-3.82 (m, 4H), 3.73 (s, 1H), 2.57-2.42 (m, 4H). | 7 |
| | 1-37 | 2-(4-(4-chlorophenyl)-pyrimidin-2-ylthio)-N-hydroxy-2-phenylacetamide | LRMS (ESI): (calc.) 371.8 (found) 372.4 (MH)+ | ¹H NMR (CD₃OD-d₄) δ (ppm): 8.59 (d, J = 5.3Hz, 1H), 8.17 (d, J = 8.8Hz, 2H), 7.65 (d, J = 5.5Hz, 1H), 7.60-7.52 (m, 4H), 7.39-7.30 (m, 3H), 5.56 (s, 1H). | 2 |
| | 1-38 (cpd 38, Ex 11) | N-hydroxy-2-(5-(2-methoxyphenyl)-1,3,4-thiadiazol-2-yl)-2-phenylacetamide | LRMS (ESI): (calc.) 341.08 (found) 342.3 (MH)+ | ¹H NMR (CD₃OD-d₄) δ (ppm): 8.29 (d, J = 6.0 Hz, 1H), 7.54-7.48 (m, 3H), 7.39-7.32 (m, 3H), 7.21 (d, J = 8.0 Hz, 1H), 7.11 (t, J = 7.6Hz, 1H), 5.38 (s, 1H), 4.02 (s, 3H). | 11 |

TABLE I-continued

| Strucutre | Cpd | Name | MS | ¹H NMR | Procedure of Scheme |
|---|---|---|---|---|---|
| | 1-39 | 2-(5-(4-bromophenyl)-1,3,4-thiadiazol-2-yl)-N-hydroxy-2-phenylacetamide | LRMS (ESI): (calc.) 388.9 (found) 390.3 (MH)+ | ¹H NMR (CD$_3$OD-d$_4$) δ (ppm): 7.88 (d, J = 8.8Hz, 2H), 7.68 (d, J = 8.8Hz, 2H), 7.50 (d, J = 8.0 Hz, 2H), 7.39-7.32 (m, 3H), 5.37 (s, 1H) | 11 |
| | 1-40 | 2-(biphenyl-4-yl)-2-(4-(dimethylamino)phenyl)-N-hydroxyacetamide | LRMS (ESI): (calc.) 346.4 (found) 347.4 (MH)+ | ¹H NMR (MeOD-d$_4$) δ (ppm): 7.60-4.53 (m, 4H), 7.43-7.35 (m, 4H), 7.33-7.28 (m, 1H), 7.19 (d, J = 8.8Hz, 2H), 6.74 (d, J = 8.8Hz, 2H), 4.72 (s, 1H), 2.90 (s, 6H). | 5 |
| | 1-41 | N-hydroxy-2-phenyl-2-(4-(pyrrolidin-1-yl)phenyl)-acetamide | LRMS (ESI): (calc.) 296.4 (found) 297.5 (MH)+ | ¹H NMR (MeOD-d$_4$) δ (ppm): 7.18-7.13 (m, 5H), 6.93-6.91 (m, 2H), 6.40-6.30 (m, 2H), 4.63 (s, 1H), 3.14 (s, 4H), 1.89 (s, 4H). | 5 |
| | 1-42 | 2-(4,5-diphenyl-1H-imidazol-2-ylthio)-N-hydroxy-2-phenylacetamide | LRMS (ESI): (calc.) 401.5 (found) 402.5 (MH)+ | ¹H NMR (DMSO-d$_6$) δ (ppm): 12.59 (s, 1H), 11.09 (s, 1H), 9.12 (s, 1H), 7.53-7.50 (m, 2H), 7.45 (d, J = 7.2Hz, 2H), 7.38-7.20 (m, 11H), 5.37 (s, 1H). | 2 |
| | 1-43 | N-hydroxy-2-(4-phenoxypiperidin-1-yl)-2-phenylacetamide | LRMS (ESI): (calc.) 326.4 (found) 327.4 (MH)+ | ¹H NMR (DMSO-d$_6$) δ (ppm): 10.86 (s, 1H), 8.93 (s, 1H), 7.50-7.45 (m, 2H), 7.40-7.26 (m, 5H), 6.99-6.90 (m, 3H), 4.44-4.36 (m, 1H), 3.72 (s, 1H), 2.76-2.56 (m, 2H), 2.33-2.18 (m, 2H), 2.01-1.90 (m, 2H), 1.73-1.60 (m, 2H). | 7 |
| | 1-44 | N-hydroxy-2-phenyl-2-(4-phenylpiperidin-1-yl)acetamide | LRMS (ESI): (calc.) 310.4 (found) 311.4 (MH)+ | ¹H NMR (MeOD-d$_4$) δ (ppm): 7.57-7.53 (m, 2H), 7.41-7.24 (m, 7H), 7.21-15 (m, 1H), 3.72 (s, 1H), 3.26-3.20 (m, 1H), 2.84-2.76 (m, 1H), 2.60-2.50 (m, 1H), 2.30-2.20 (m, 1H), 2.02-1.90 (m, 2H), 1.88-1.68 (m, 3H). | 7 |

TABLE I-continued

| Strucutre | Cpd | Name | MS | $^1$H NMR | Procedure of Scheme |
|---|---|---|---|---|---|
| | 1-45 (cpd 14, Ex 4) | 2-(4'-fluorobiphenyl-4-yl)-N-hydroxy-2-phenylacetamide | LRMS (ESI): (calc.) 321.3 (found) 320.4 (M − H)− | $^1$H NMR (MeOD-d$_4$) δ (ppm): 7.62-7.57 (m, 2H), 7.53 (d, J = 8.2Hz, 2H), 7.40-7.22 (m, 7H), 7.14 (t, J = 8.8Hz, 2H), 4.82 (s, 1H). | 4 |
| | 1-46 | 2-(biphenyl-4-ylthio)-N-hydroxy-2-phenylacetamide | LRMS (ESI) (calc.) 335.4 (found) 336.4 (MH)+ | $^1$H NMR (DMSO-d$_6$) δ (ppm): 10.97 (s, 1H), 9.11 (s, 1H), 7.65-7.59 (m, 4H), 7.53-7.50 (m, 2H), 7.44 (t, J = 7.2Hz, 2H), 7.39-7.26 (m, 6H), 4.96 (s, 1H). | 2 |
| | 1-47 (cpd 42, ex 12) | N-benzhydryl-N-hydroxyformamide | LRMS (ESI) (calc.) 227.3 (found) 228.2 (MH)+ | $^1$H NMR: (DMSO-d$_6$) 8.41 (br s, 1H), 7.44-7.28 (m, 11H). LRMS: calc. 227.3, found 228.2 | |

EXAMPLE 13

N-hydroxy-2-(4'-methoxybiphenyl-4-yl)-2-phenylacetamide (56)

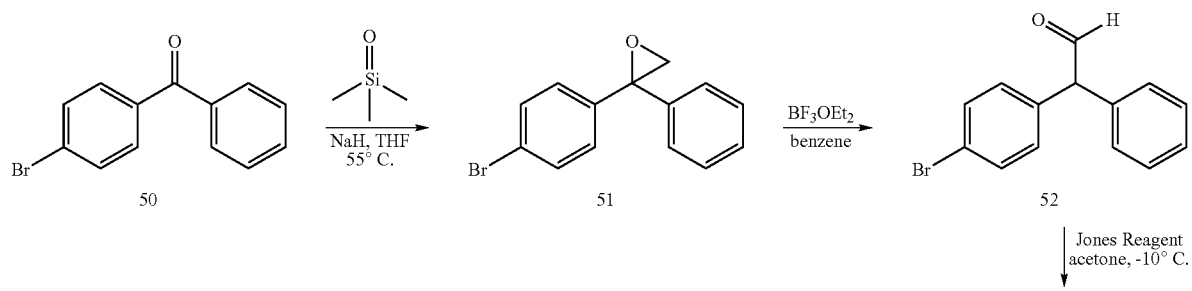

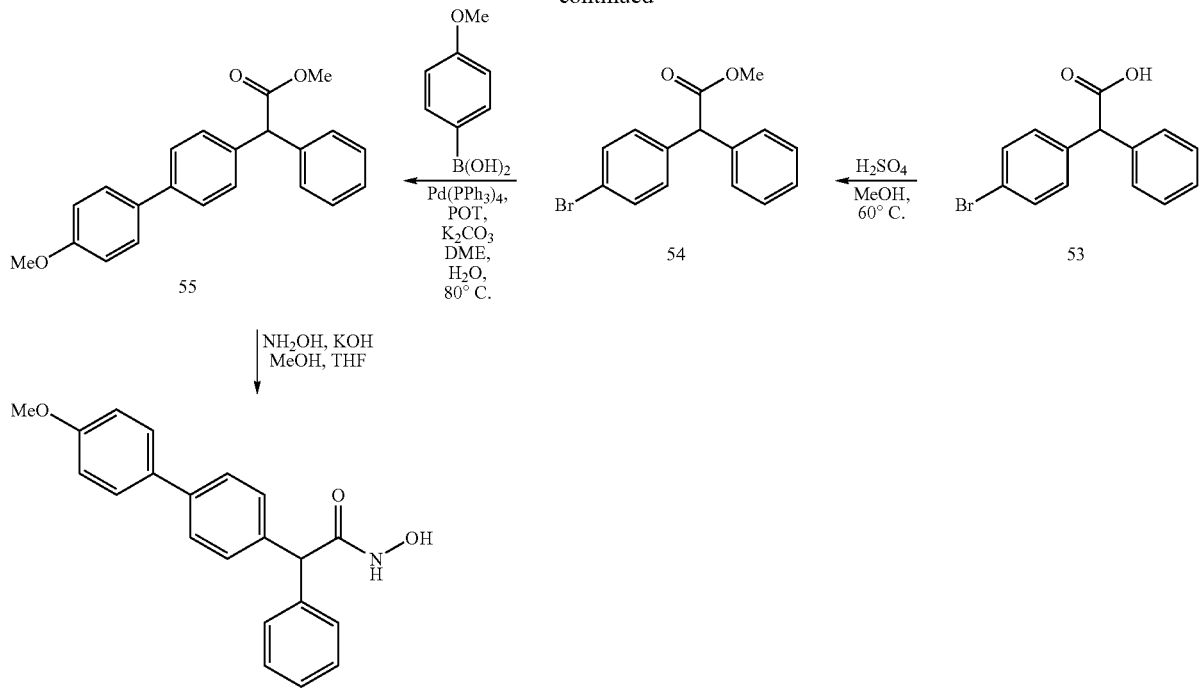

56: Example 13

Step 1: 2-(4-bromophenyl)-2-phenyloxirane (51)

To a stirring solution of trimethylsulfonium iodide (5.27 g, 19.15 mmol) in THF (20 mL) was added sodium hydride (0.957 g, 23.94 mmol) and the reaction mixture was stirred at 55° C. for 6 h. A solution of (4-bromophenyl)(phenyl)methanone 50 (5.0 g, 19.15 mmol) in THF (10 mL) was added and the mixture was stirred an additional 16 h at 55° C. The reaction mixture was quenched with water, diluted with ether and layer separated. The organic layer was dried over $Na_2SO_4$, filtered and concentrated to afford 2-(4-bromophenyl)-2-phenyloxirane 51 (quantitative yield) as a brown oil.

Step 2: 2-(4-bromophenyl)-2-phenylacetaldehyde (52)

A solution of 2-(4-bromophenyl)-2-phenyloxirane 51 (5.27 g, 19.15 mmol) and $BF_3OEt_2$ (3.29 g, 23.20 mmol) in benzene (50 mL) was shaken vigorously in a separatory funnel for 2 minutes then allowed to stand for 3 minutes. The resulting solution was washed twice with aq. sat. $NaHCO_3$ and the organic layer was separated, dried over $Na_2SO_4$ and concentrated to afford 2-(4-bromophenyl)-2-phenylacetaldehyde 52. The crude was used in the next step.

Step 3: 2-(4-bromophenyl)-2-phenylacetic acid (53)

To a stirring solution of compound 52 (5.27 g, 19.15 mmol) in acetone (60 mL) cooled to −10° C. was added Jones Reagent (2.93 mL, 2.5 M solution) drop wise. Isopropyl alcohol was then added until the reaction mixture turned green. The mixture was filtered through Celite, diluted with ethyl acetate and washed with NaOH. The organic layer was discarded and the aqueous layer was acidified with 1M HCl to pH 1 and further extracted with ethyl acetate. The combined organics were dried over $Na_2SO_4$, filtered and concentrated to afford 2-(4-bromophenyl)-2-phenylacetic acid 53 (2 g, 36%) as a beige solid.

Step 4: methyl 2-(4-bromophenyl)-2-phenylacetate (54)

A solution of acid 53 (1.9 g, 6.53 mmol) in methanol (20 mL) was added concentrated sulfuric acid (2 mL) and the reaction mixture was stirred at 60° C. for 4 h. The organic layer was separated, dried over $Na_2SO_4$, filtered and concentrated to afford methyl 2-(4-bromophenyl)-2-phenylacetate 54 (1.7 g, 85% yield) as a brown oil.

Step 5: methyl 2-(4'-methoxybiphenyl-4-yl)-2-phenylacetate (55)

To a degassed solution of bromide 54 (0.33 g, 1.081 mmol), 4-methoxyphenylboronic acid (0.181 g, 1.190 mmol), POT (0.023 g, 0.076 mmol) and potassium carbonate (0.747 g, 5.41 mmol) in DME (15 mL) and water (7.5 mL) was added $Pd(PPh_3)_4$ (0.087 g, 0.076 mmol). The reaction mixture was stirred at 80° C. for 16 h and diluted with ethyl acetate, washed with water, dried over $Na_2SO_4$, filtered and concentrated to afford compound 55 (0.11 g, 31% yield) as a white solid after purification by ISCO (2 to 40% EtOAc/hexane).
Alternate condition for formation of Ar—Ar':
$PdCl_2(dppf)$, aryl boronic acid (1.25 eq), 2N $Na_2CO_3$, toluene, 80° C., 18 h.

Step 6: N-hydroxy-2-(4'-methoxybiphenyl-4-yl)-2-phenylacetamide (56)

Following the same procedure as described in Example 1, step 2, but substituting compound 2 for compound 55, the title compound 56 was obtained as white solid in a 40% yield (0.04 g). $^1$H NMR (DMSO-d$_6$) δ (ppm): 10.94 (s, 1H), 8.98 (s, 1H), 7.55 (t, J=8.8 Hz, 4H), 7.37-7.29 (m, 6H), 7.25-7.23 (m, 1H), 7.00 (d, J=8.8 Hz, 2H), 4.73 (s, 1H), 3.77 (s, 3H). LRMS (ESI): (calc.) 333.4 (found) 334.4 (MH)+.

EXAMPLES 14A AND 14B

N-hydroxy-2-phenyl-2-(4-(3-thio-dioxide-morpholinoprop-1-ynyl)phenyl)acetamide (59)

N-hydroxy-2-phenyl-2-(4-(3-thio-dioxide-morpholinopropyl)phenyl)acetamide (61)

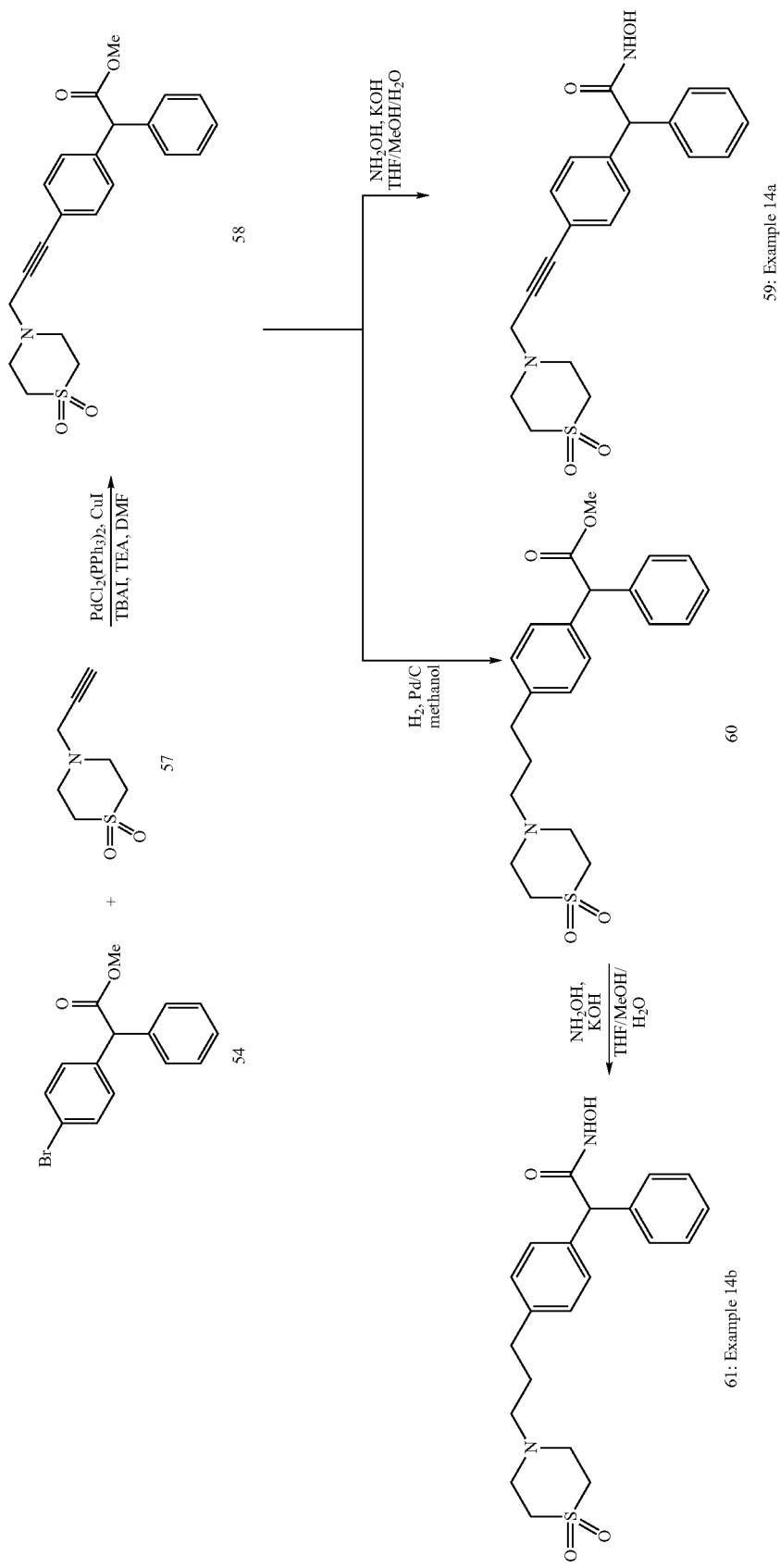

Step 1: methyl 2-phenyl-2-(4-(3-thio-dioxide-morpholinoprop-1-ynyl)phenyl)acetate (58)

To a degassed solution of bromo-ester 54 (0.881 g, 2.89 mmol), alkyne 57 (1.0 g, 5.77 mmol), copper iodide (0.110 g, 0.577 mmol), tetrabutyl ammonium iodide (0.320 g, 0.866 mmol) and triethylamine (4.0 mL) in DMF (8.0 mL) was added PdCl$_2$(PPh$_3$)$_2$ (0.203 g, 0.289 mmol). The reaction mixture was heated at 75° C. for 16 h, cooled to room temperature, diluted with brine and extracted with EtOAc. The combined organic extracts were dried over Na$_2$SO$_4$, filtered and concentrated to afford 58 (0.527 g, 46% yield) as a light yellow solid after purification by flash chromatography (25 to 100% EtOAc in hexanes). LRMS (ESI): (calc) 397.49 (found) 398.5 (MH)+.

Alternate reaction conditions for Sonogashira reaction:
PdCl$_2$(PPh$_3$)$_2$, CuI, piperidine, MeCN, 80° C., 18 h.
PdCl$_2$(PPh$_3$)$_2$, CuI, TEA, 90° C., 18 h.
Pd(PPh$_3$)$_4$, CuI, TEA, 90° C., 18 h.
PdCl$_2$(PPh$_3$)$_2$, CuI, K$_2$CO$_3$, DMF, 110° C., 18 h.
Pd(PPh$_3$)$_4$, CuI, K$_2$CO$_3$, DMF, 110° C., 18 h.
Pd(OAc)$_2$, PPh$_3$, NaOAc, DMF, 110° C., 18 h.

Step 2: N-hydroxy-2-phenyl-2-(4-(3-thio-dioxide-morpholinoprop-1-ynyl)phenyl)acetamide (59)

Following the same procedure as described in Example 1, step 2, but substituting compound 2 for compound 58, the title compound 59 was obtained in 17% yield (51 mg) as dark beige color.

$^1$H NMR (MeOH-d4) δ (ppm): 7.42-7.39 (m, 2H), 7.36-7.27 (m, 7H), 4.81 (s, 1H), 3.72 (s, 2H), 3.22-3.15 (m, 8H). LRMS (ESI): (calc.) 398.5 (found) 397.5 (MH)–.

Step 3: methyl 2-phenyl-2-(4-(3-thio-dioxide-morpholinopropyl)phenyl)acetate (60)

Following the same procedure as described in Example 10, step 1, but substituting 2-nitro-4-(thiophen-2-yl)aniline for compound 58, the title compound 60 (0.205 g, 90%) was obtained as a light yellow oil. LRMS (ESI): (calc) 401.52 (found) 402.3 (MH)+.

Step 4: N-hydroxy-2-phenyl-2-(4-(3-thio-dioxide-morpholinopropyl)phenyl)acetamide (61)

Following the same procedure as described in Example 1, step 2, but substituting compound 2 for compound 60, the title compound 61 (33 mg, 16%) was obtained.

$^1$H NMR (MeOH-d4) δ (ppm): 7.36-7.17 (m, 9H), 4.77 (s, 1H), 3.12-3.06 (m, 4H), 3.01-2.94 (m, 4H), 2.67 (t, J=7.6 Hz, 2H), 2.54 (t, J=7.6 Hz, 2H), 1.88-1.78 (m, 2H). LRMS (ESI): (calc.) 402.5 (found) 403.5 (MH)+.

EXAMPLE 15

N-hydroxy-2-phenyl-2-(4-(4-(pyrimidin-2-yl)piperazin-1-yl)phenyl)acetamide (64)

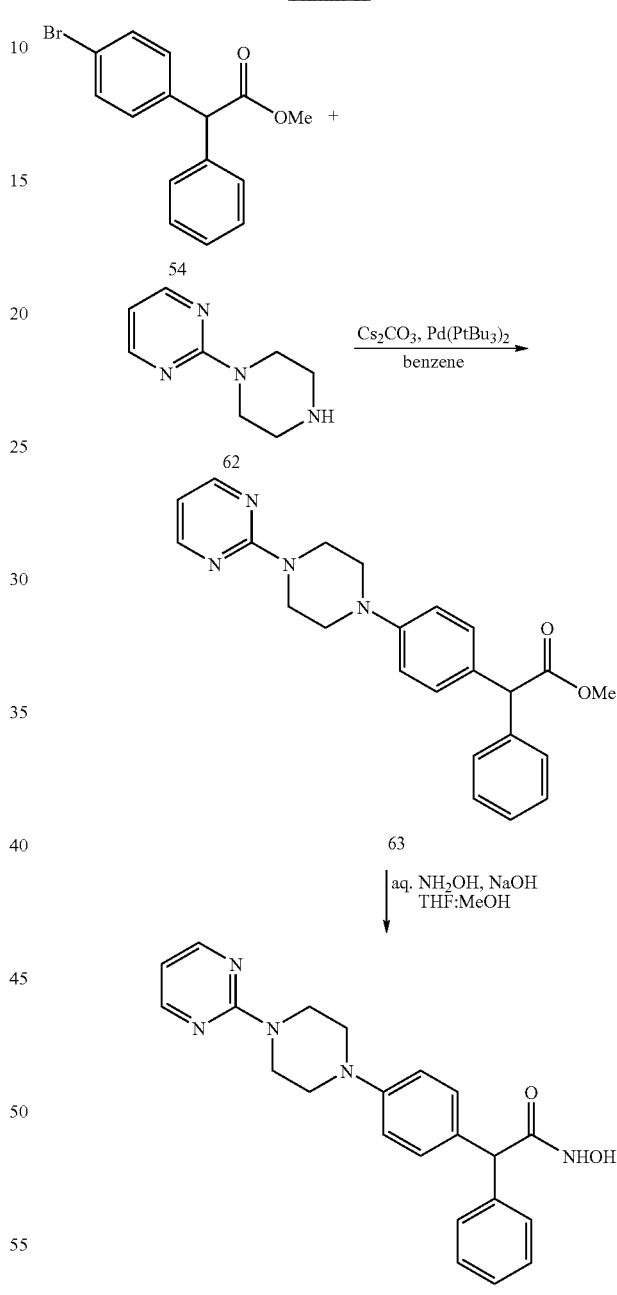

64: Example 15

Step 1: methyl 2-phenyl-2-(4-(4-(pyrimidin-2-yl) piperazin-1-yl)phenyl)acetate (63)

To a stirring solution of 1-phenylpiperazine 62 (0.159 g, 0.983 mmol) and bis(tri-tert-butylphosphine)palladium in benzene (2 mL) was added bromoester 54 (0.250 g, 0.819 mmol) and cesium carbonate (0.587 g, 1.802 mmol). The reaction mixture was heated to 110° C. overnight, diluted with ethyl acetate, washed with water, dried over Na$_2$SO$_4$, filtered and concentrated to afford the methyl ester 63 (0.134 g, 42% yield) after purification by flash chromatography (20 to 90% EtOAc in hexane). Alternate procedures for formation of RR'N—Ar:

1. Pd (II) acetate, cesium carbonate, tri-tert-butylphosphine tetrafluoroborate, THF, 100° C., 2 days.
2. Copper (I) iodide (0.05 eq), (1R,2R)—N1,N2-dimethylcyclohexane-1,2-diamine (0.2 eq), potassium phosphate (2.1 eq) or potassium carbonate (2.2 eq), toluene or DMSO, 110° C., 16 h.
3. Pd$_2$(dba)$_3$ (0.02 eq), Xantphos (0.06 eq), cesium carbonate (1.7 eq), dioxane, 100° C., 16 h.
4. Pd$_2$(dba)$_3$, P(tBu)$_2$(PhPh), NaOtBu, toluene, 100° C., 18 h.

Step 2: N-hydroxy-2-phenyl-2-(4-(4-(pyrimidin-2-yl)piperazin-1-yl)phenyl)acetamide (64)

Following the same procedure as described in Example 1, step 2, but substituting compound 2 for compound 63, the title compound 64 (35 mg, 26%) was obtained as white solid. $^1$H NMR (MeOH-d4) δ (ppm): 8.32 (d, J=4.8 Hz, 2H), 7.29-7.20 (m, 7H), 6.97 (d, J=8.8 Hz, 2H), 6.60 (t, J=4.8 Hz, 1H), 4.69 (s, 1H), 3.93 (m, 4H), 3.20 (m, 4H). LRMS (ESI): (calc.) 389.4 (found) 390.5 (MH)+.

EXAMPLES 16A, 16B AND 16C 2-(4-(benzyloxy)phenyl)-N-hydroxy-2-phenylacetamide (70)

N-hydroxy-2-(4-hydroxyphenyl)-2-phenylacetamide (72)

N-hydroxy-2-(4-(2-morpholinoethoxy)phenyl)-2-phenylacetamide (74)

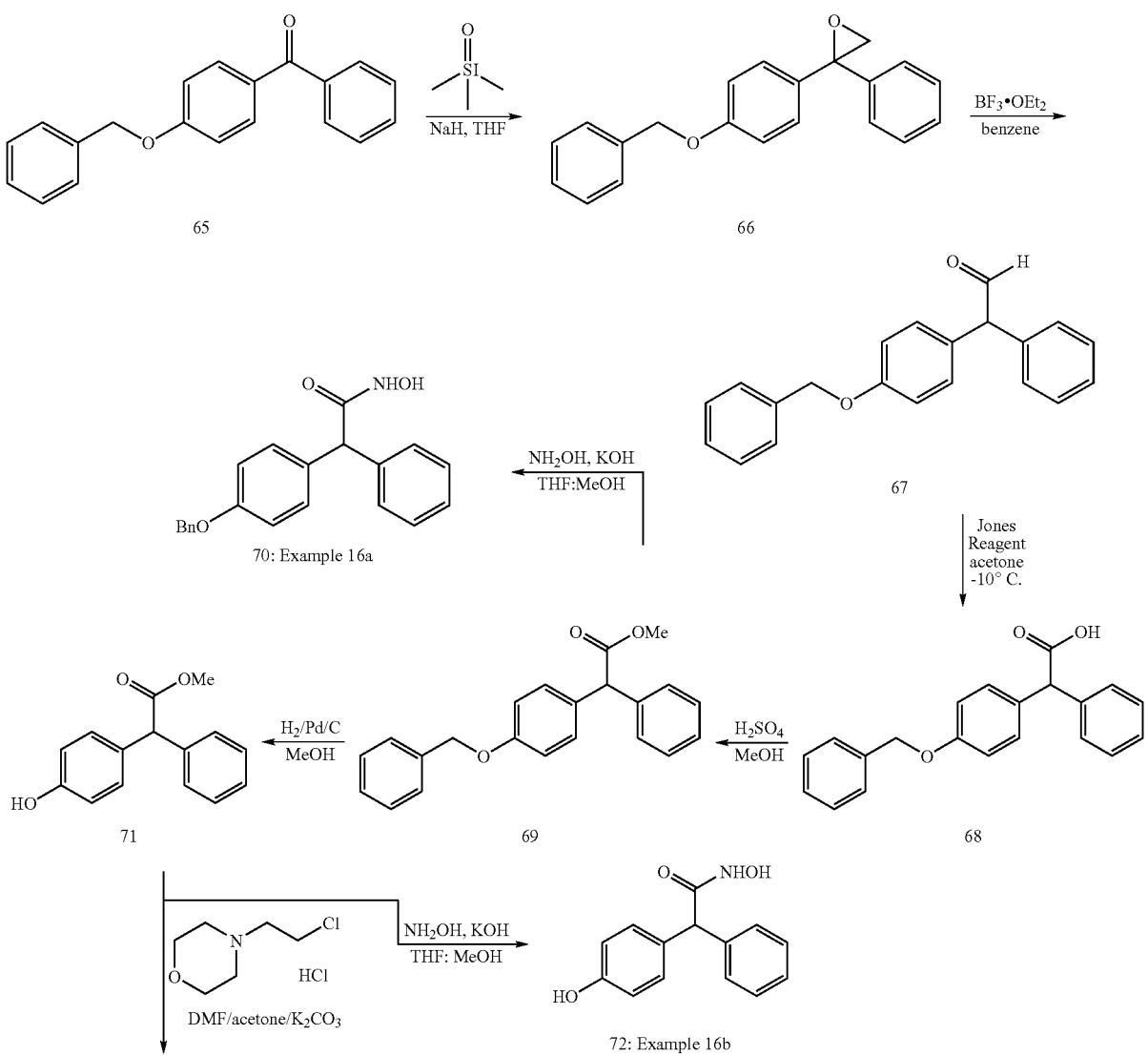

Scheme 16

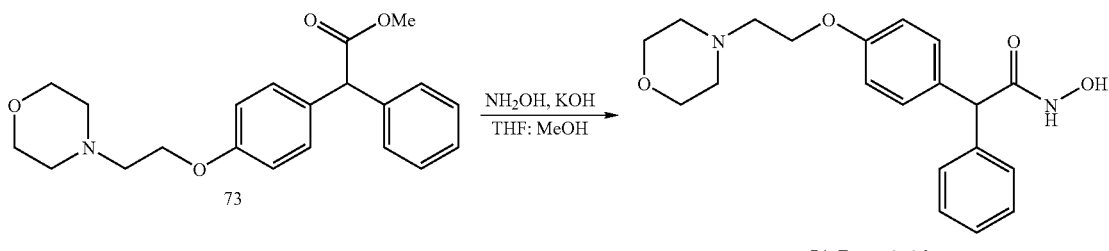

74: Example 16c

Step 1: 2-(4-(benzyloxy)phenyl)-2-phenyloxirane (66)

Following the same procedure as described in Example 13 (Scheme 13), step 1, but substituting compound 50 for compound 65, the title compound 66 (quantitative yield) was obtained as a light yellow oil.

Step 2: 2-(4-(benzyloxy)phenyl)-2-phenylacetaldehyde (67)

Following the same procedure as described in Example 13 (Scheme 13), step 2, but substituting compound 51 for compound 66, the title compound 67 (taken on to Step 3 as a crude mixture).

Step 3: 2-(4-(benzyloxy)phenyl)-2-phenylacetic acid (68)

Following the same procedure as described in Example 13 (Scheme 13), step 3, but substituting compound 52 for compound 67, the title compound 68 (4.2 g, 30.4%) was obtained as a white solid.

Step 4: methyl 2-(4-(benzyloxy)phenyl)-2-phenylacetate (69)

Following the same procedure as described in Example 13 (Scheme 13), step 4, but substituting compound 53 for compound 68, the title compound 69 (3.8 g, 89%) was obtained as a yellow solid.
$^1$H NMR (DMSO-$d_6$) δ (ppm): 7.44-7.21 (m, 12H), 6.99-6.95 (m, 2H), 5.14 (s, 1H), 5.07 (s, 2H), 3.65 (s, 3H).

Step 5: 2-(4-(benzyloxy)phenyl)-N-hydroxy-2-phenylacetamide (70)

Following the same procedure as described in Example 1, step 2, but substituting compound 2 for compound 69, the title compound 70 (0.07 g, 25%) was obtained as a white solid. $^1$H NMR (DMSO-d6) δ (ppm) 1H, 10.86 (s, 1H), 8.92 (s, 1H), 7.42-7.17 (m, 12H), 6.93 (d, J=8.8 Hz, 2H), 5.05 (s, 2H), 4.62 (s, 1H). LRMS (ESI): (calc.) 333.4 (found) 334.4 (MH)+.

Step 6: methyl 2-(4-hydroxyphenyl)-2-phenylacetate (71)

Following the same procedure as described in Example 10, step 1, but substituting 2-nitro-4-(thiophen-2-yl)aniline for compound 69, the title compound 71 (2.65 g, 96%) was obtained as an orange oil.

Step 7: N-hydroxy-2-(4-hydroxyphenyl)-2-phenylacetamide (72)

Following the same procedure as described in Example 1, step 2, but substituting compound 2 for compound 71, the title compound 72 (0.09 g, 35%) was obtained as a white solid. $^1$H NMR (DMSO-d6) δ (ppm) 1H: 10.83 (s, 1H), 9.29 (s, 1H), 8.89 (s, 1H), 7.30-7.16 (m, 5H), 7.10 (d, J=8.6 Hz, 2H), 6.67 (d, J=8.6 Hz, 2H), 4.55 (s, 1H). LRMS (ESI): (calc.) 243.3 (found) 244.3 (MH)+.

Step 8: methyl 2-(4-(2-morpholinoethoxy)phenyl)-2-phenylacetate (73)

A stirring solution of compound 71 (1.5 g, 6.19 mmol), 4-(2-chloroethyl)morpholine hydrochloride (1.152 g, 6.19 mmol) and potassium carbonate (1.709 g, 12.38 mmol) in (1:1) DMF: acetone (60 mL) was heated to 60° C. for 16 h then concentrated. The crude residue was diluted with ethyl acetate and washed with water, dried over Na$_2$SO$_4$, filtered and concentrated to afford compound 73 (0.92 g, 42%) after purification by ISCO-HPLC (20 to 100% ethyl acetate in hexanes).

Supplementary Procedure:

A solution of phenol 71 (3.43 mmol), alcohol (3.43 mmol), DEAD (4.11 mmol) and triphenylphosphine (4.45 mmol) in THF was stirred at room temperature for 16 h then concentrated. The crude product was diluted with ethyl acetate and washed with water, dried over Na$_2$SO$_4$, filtered and concentrated to afford the product (26 to 63% yields) which can be further manipulated using chemistry already described.

Alternate Conditions for Step 8:

KBr, K$_2$CO$_3$, KI, acetone, 50° C., 18 h, followed by scavenging with PS-Ph$_3$ (for remaining hydroxy SM) then ambersep (for remaining alkyl halide).

Step 9: N-hydroxy-2-(4-(2-morpholinoethoxy)phenyl)-2-phenylacetamide (74)

Following the same procedure as described in Example 1, step 2, but substituting compound 2 for compound 73, the title compound 74 (0.315 g, 34%) was obtained as a white solid. $^1$H NMR (DMSO-d6) δ (ppm) 1H, 10.88 (s, 1H), 8.94 (s, 1H), 7.30-7.20 (m, 7H), 6.87 (d, J=8.8 Hz, 2H), 4.62 (s, 1H), 4.03 (t, J=5.7 Hz, 2H), 3.56 (t, J=4.7 Hz, 4H), 2.65 (t, J=5.7 Hz, 2H), 2.46-2.43 (m, 4H).

EXAMPLE 17

N-hydroxy-2-phenyl-2-(pyridin-3-yl)acetamide (80)

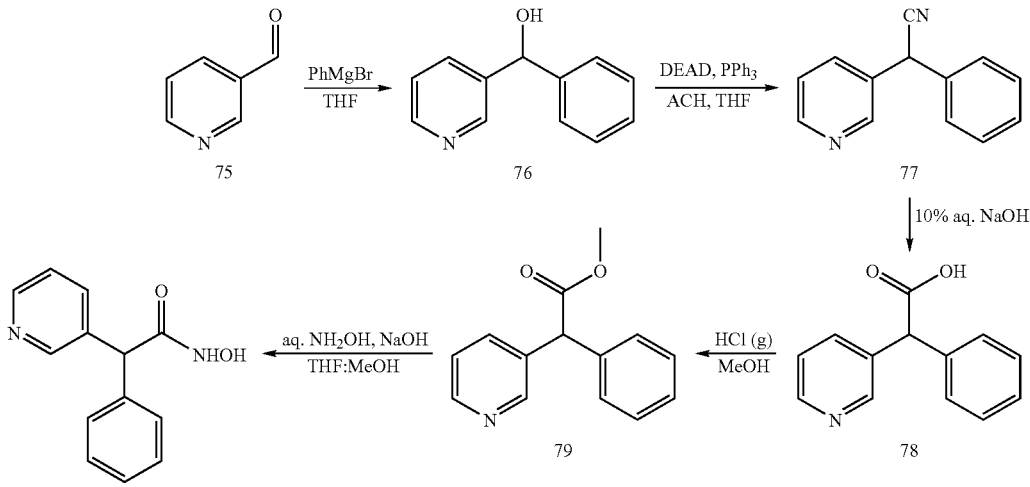

80: Example 17

Step 1: Phenyl(pyridin-3-yl)methanol (76)

To a stirring solution of nicotinaldehyde 75 (0.876 mL, 9.34 mmol) in THF (20 mL) at 0° C. was slowly added a 1M phenylmagnesium bromide solution (9.34 mL, 9.34 mmol) and the reaction mixture was allowed to warm to room temperature over 30 minutes. The crude solution was diluted with ethyl acetate and washed with water, dried over $Na_2SO_4$, filtered and concentrated to afford compound 76 (1.7 g, 98% yield) after purification by flash chromatography (50 to 100% EtOAc in hexanes).

Step 2: 2-phenyl-2-(pyridin-3-yl)acetonitrile (77)

To a solution of triphenylphosphine (3.83 g, 14.61 mmol) in THF (40 mL) at 0° C. was added DEAD (2.54 g, 14.61 mmol) drop wise and the reaction mixture was stirred for 20 minutes. Compound 76 (1.78 g, 9.61 mmol) was added to the reaction mixture and stirred for an additional 20 minutes. Then acetone cyanohydrin (1.319 mL, 14.42 mmol) was added, stirred for 1 h at 0° C. and 18 h at room temperature. The reaction mixture was concentrated then purified by flash chromatography to afford 77 (0.972 g, 52%).

Step 4: 2-phenyl-2-(pyridin-3-yl)acetic acid (78)

A solution of compound 77 (0.822 g, 4.23 mmol) in 10% aqueous NaOH (15.24 mL, 38.1 mmol) was heated at reflux for 2 h then neutralized to pH 7 by the addition of 3M HCl. The crude was concentrated to afford compound 78 (0.380 g, 42%). LRMS (ESI): (calc) 213.23 (found) 214.1 (MH)+

Step 5: methyl 2-phenyl-2-(pyridin-3-yl)acetate (79)

Following the same procedure as described in Example 1, step 1, but substituting compound 1 for compound 78 and $H_2SO_4$ for HCl, the title compound 79 (0.326 g, 80%) was obtained. LRMS (ESI): (calc) 227.26 (found) 228.3 (MH)+

Step 6: N-hydroxy-2-phenyl-2-(pyridin-3-yl)acetamide (80)

Following the same procedure as described in Example 1, step 2, but substituting compound 2 for compound 79, the title compound 80 (0.162 g, 50%) was obtained.

$^1$H NMR (MeOH-d4) δ (ppm): 8.47 (d, J=2.4 Hz, 1H), 8.43 (q, J=1.6, 4.8 Hz, 1H), 7.48 (m, 1H), 7.41-7.28 (m, 6H), 4.83 (s, 1H). LRMS (ESI): (calc.) 228.0 (found) 229.2 (MH)+

EXAMPLE 18

10-benzyl-N-hydroxy-9,10-dihydroacridine-9-carboxamide (85)

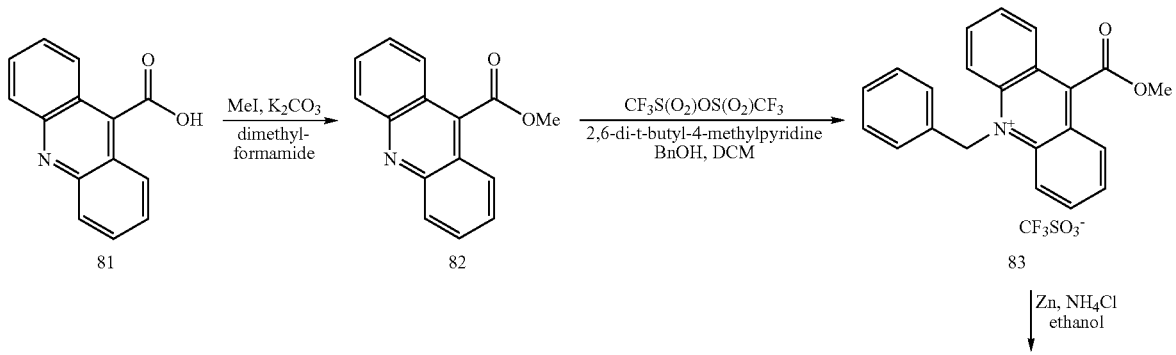

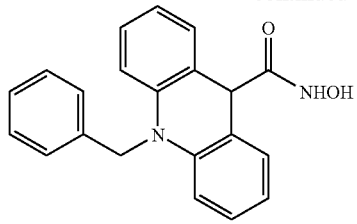

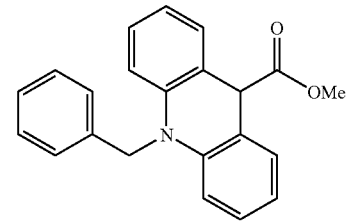

85: Example 18           84

Step 1: methyl acridine-9-carboxylate (82)

A solution of acridine-9-carboxylic acid 81 (2.0 g, 8.96 mmol), methyl iodide (3.82 g, 26.9 mmol) and potassium carbonate (4.95 g, 35.8 mmol) in DMF (25 mL) was stirred at room temperature for 3 h then diluted with brine and extracted with EtOAc. The combined organic layers were dried over $Na_2SO_4$, filtered and concentrated to afford compound 82 (1.65 g, 78%) as a light yellow solid. LRMS (ESI): (calc) 237.25 (found) 238.2 (MH)+

Step 2: 10-benzyl-9-(methoxycarbonyl)acridinium trifluoromethanesulfonate (83)

To a stirred solution of triflic anhydride (0.483 mL, 2.87 mmol) in DCM (6 mL) at −78° C. was slowly added a solution of benzyl alcohol (0.298 mL, 2.87 mmol) and 2,6-di-t-butyl-4-methylpyridine (0.59 g, 2.87 mmol) in DCM (2 mL). After 10 minutes of stirring, the compound 74 (0.620 g, 2.61 mmol) in DCM (2 mL) was added, and the reaction allowed to warm to room temperature. The solution was stirred a further 16 h. The crude was concentrated under reduced pressure, and the residue purified by column chromatography on silica gel using 10% MeOH in DCM as the eluent to afford the title compound 83 (1.05 g, 85%) as a yellow solid. LRMS (ESI): (calc) 328.38 (found) 328.3 (MH)+

Step 3: methyl 10-benzyl-9,10-dihydroacridine-9-carboxylate (84)

To a stirring solution of compound 83 (1.05 g, 3.20 mmol) and ammonium chloride (2.67 g, 49.8 mmol) in ethanol (35 mL) was added zinc (2.67 g, 40.8 mmol) and the reaction mixture was heated at 80° C. for 30 minutes then filtered through a pad of Celite®. The solution was diluted with brine, extracted with EtOAc, and the combined organics were dried over, filtered and concentrated to afford compound 84 (0.248 g, 24%) as a white solid after purification by flash chromatography (10 to 40% EtOAc in hexanes). LRMS (ESI): (calc) 329.39 (found) 330.5 (MH)+

Step 4: 10-benzyl-N-hydroxy-9,10-dihydroacridine-9-carboxamide (85)

Following the same procedure as described in Example 1, step 2, but substituting compound 2 for compound 84, the title compound 85 (29 mg, 12%) as a light yellow solid. $^1$H NMR (MeOH-d4) δ (ppm): 7.36-7.31 (m, 2H), 7.29-7.21 (m, 5H), 7.17-7.11 (m, 2H), 6.91 (td, J=7.4, 1.0 Hz, 2H), 6.81-6.78 (m, 2H), 5.22 (s, 2H), 4.85 (s, 1H). LRMS (ESI): (calc.) 330.4 (found) 331.4 (MH)+

EXAMPLE 19

N-hydroxy-2-phenyl-2-(1-(pyrimidin-2-yl)piperidin-4-yl)acetamide (94)

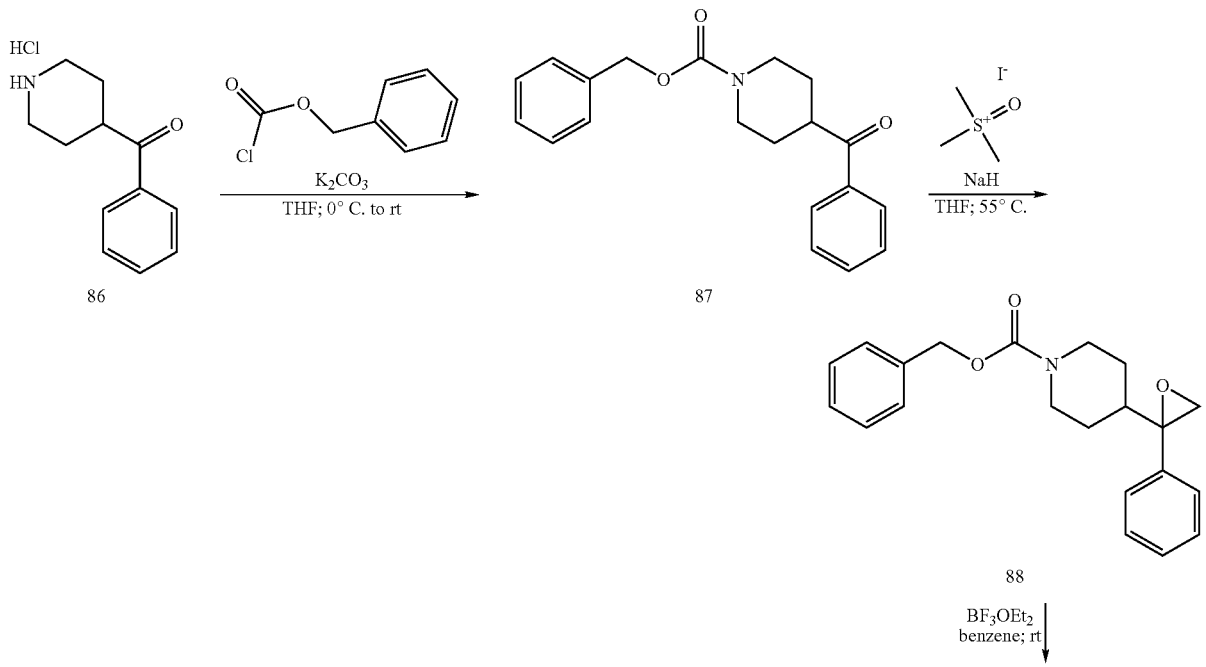

Scheme 19

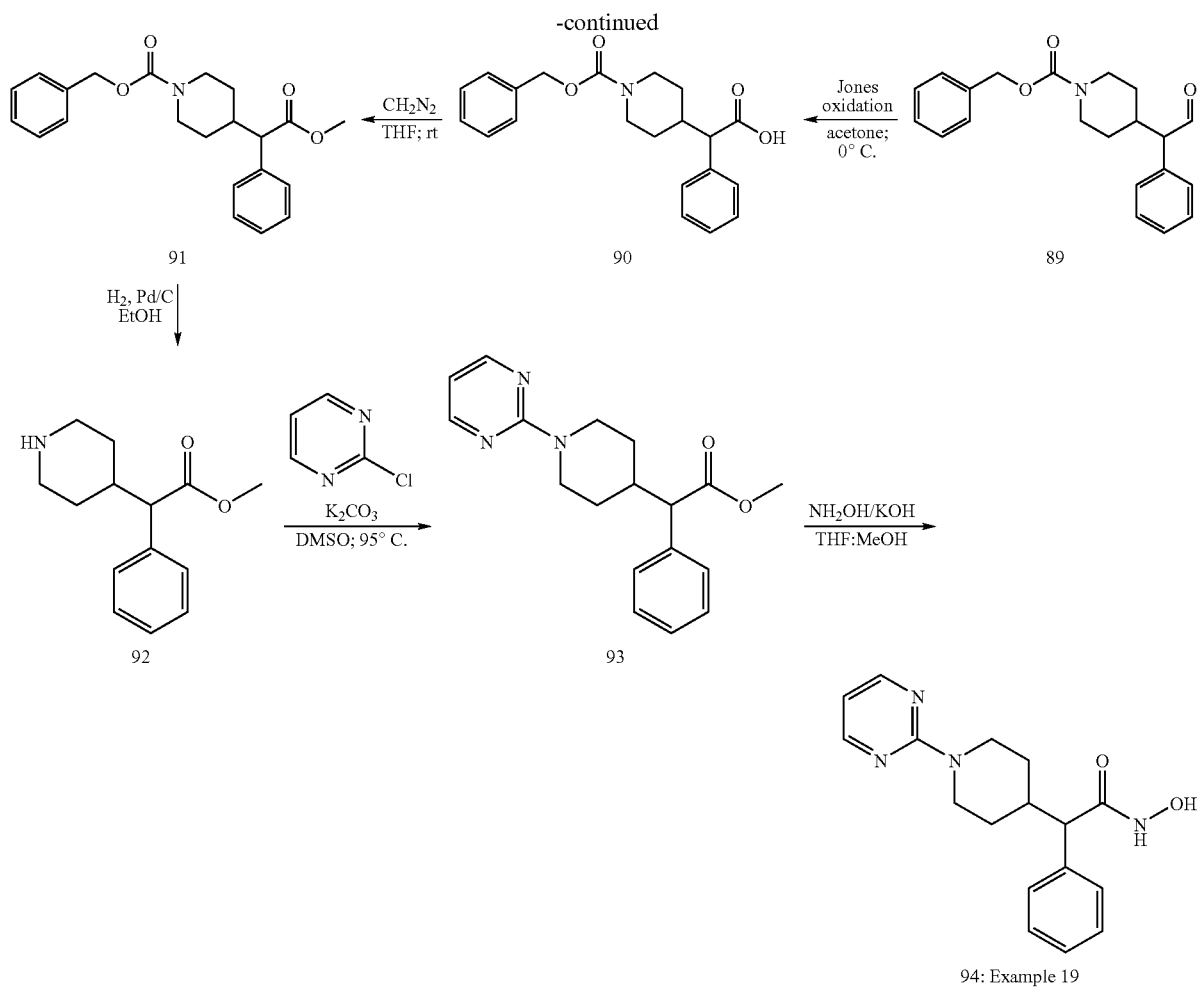

94: Example 19

Step 1: benzyl 4-benzoylpiperidine-1-carboxylate (87)

To a stirring suspension of phenyl(piperidin-4-yl)methanone hydrochloride 86 (1.97 g, 8.73 mmol) and potassium carbonate (3.62 g, 26.2 mmol) in THF (40 mL) at 0° C. was added benzyl chloroformate (1.433 mL, 10.04 mmol) and the reaction mixture was allowed to slowly warm to room temperature and stirred for 2 h. The mixture was diluted with ethyl acetate, washed with brine, water, dried over $Na_2SO_4$, filtered and concentrated to afford compound 87 quantitative yield. LRMS (ESI): (calc) 323.39 (found) 324.31 (MH)+

Step 2: benzyl 4-(2-phenyloxiran-2-yl)piperidine-1-carboxylate (88)

A mixture of trimethylsulfoxonium iodide (2.402 g, 10.91 mmol) and sodium hydride (0.436 g, 10.91 mmol) in THF (20 mL) was heated at 55° C. for 3 h then a solution of compound 87 (2.82 g, 8.73 mmol) in THF (10 mL) was added. The reaction mixture was stirred for 36 h, quenched with water, extracted with ether and the combined organics were washed with water, brine, dried over $Na_2SO_4$, filtered and concentrated to afford compound 88 used as a crude in the next step.

Step 3: benzyl 4-(2-oxo-1-phenylethyl)piperidine-1-carboxylate (89)

Following the same procedure as described in Example 13 (Scheme 13), step 2, but substituting compound 51 for compound 88, the title compound 89 was obtained.

Step 4: 2-(1-(benzyloxycarbonyl)piperidin-4-yl)-2-phenylacetic acid (90)

Following the same procedure as described in Example 13 (Scheme 13), step 3, but substituting compound 52 for compound 89, the title compound 90 (1.281 g, 42%) was obtained as a white foam. LRMS (ESI): (calc) 353.41 (found) 354.31 (MH)+. $^1$H NMR (DMSO-$d_6$) δ (ppm): 12.43 (s, 1H), 7.38-7.23 (m, 10H), 5.04 (s, 2H), 4.03 (d, J=13.5 Hz, 1H), 3.90 (d, J=13.3 Hz, 1H), 3.24 (d, J=10.6 Hz, 1H), 2.89-2.67 (m, 2H), 2.13-2.06 (m, 1H), 1.77 (d, J=12.3 Hz, 1H), 1.21-1.09 (m, 2H), 0.95-0.85 (m, 1H).

Step 5: benzyl 4-(2-methoxy-2-oxo-1-phenylethyl)piperidine-1-carboxylate (91)

To a stirring solution of compound 90 (1.281 g, 3.62 mmol) in THF (40 mL) was added an excess of diazomethane at room temperature and the reaction mixture was stirred for 15 minutes. Nitrogen was bubbled into the reaction mixture for 15 minutes then it was concentrated to afford compound 91

(1.032 g, 77%) as a colorless oil after purification by ISCO (0 to 50% EtOAc in hexanes). LRMS (ESI): (calc) 367.44 (found) 368.16 (MH)+. $^1$H NMR (CD$_3$OD-d4) δ (ppm):7.33-7.23 (m, 10H), 5.09 (s, 2H), 4.18-4.14 (m, 1H), 4.05-4.01 (m, 1H), 3.63 (s, 3H), 3.33-3.30 (m, 1H), 2.86-2.72 (m, 2H), 2.21 (qt, J=11.3, 3.5 Hz, 1H), 1.78 (d, J=12.7 Hz, 1H), 1.28-1.18 (m, 2H), 0.96 (qd, J=12.5, 4.3 Hz, 1H).

Step 6: methyl 2-phenyl-2-(piperidin-4-yl)acetate (92)

Following the same procedure as described in Example 10, step 1, but substituting 2-nitro-4-(thiophen-2-yl)aniline for compound 91, and MeOH for EtOH, the title compound 92 (0.384 g, 99%) was obtained as a colorless oil. LRMS (ESI): (calc) 233.31 (found) 234.14 (MH)+

Step 7: methyl 2-phenyl-2-(1-(pyrimidin-2-yl)piperidin-4-yl)acetate (93)

Following the same procedure as described in Example 15 (Scheme 15), step 1, but substituting compound 54 for 2-chloropyrimidine, compound 62 for compound 92, Cs$_2$CO$_3$/Pd(PtBu$_3$)$_2$ for potassium carbonate and benzene for DMSO, the title compound 93 (0.232 g, 78%) was obtained as a white solid. LRMS (ESI): (calc) 311.38 (found) 312.32 (MH)+

Alternate Procedure for Methyl 2-(1-benzoylpiperidin-4-yl)-2-phenylacetate:

To a stirring solution of compound 92 (0.159 g, 0.682 mmol) and triethylamine (0.2 mL, 1.435 mmol) in MeCN (10 mL) was added benzoyl chloride (0.10 mL, 0.862 mmol) and the reaction mixture was stirred for 2 h at room temperature. The reaction was diluted with ethyl acetate, washed with sat. aq. Na$_2$CO$_3$, water, brine, dried over Na$_2$SO$_4$, filtered and concentrated to afford the desired compound (0.196 g, 85%) as a colorless oil. LRMS (ESI): (calc) 337.41 (found) 338.35 (MH)+

Step 8: N-hydroxy-2-phenyl-2-(1-(pyrimidin-2-yl)piperidin-4-yl)acetamide (94)

Following the same procedure as described in Example 1, step 2, but substituting compound 2 for compound 93, the title compound 94 (29 mg, 12%) was obtained as a white solid. $^1$H NMR (DMSO-d6) δ (ppm): 10.63 (s, 1H), 8.82 (s, 1H), 8.31 (d, J=4.8 Hz, 2H), 7.35-7.28 (m, 4H), 7.25-7.21 (m, 1H), 6.57 (t, J=4.8 Hz, 1H), 4.65 (d, J=13.6 Hz, 1H), 4.51 (d, J=13.6 Hz, 1H), 2.93-2.84 (m, 2H), 2.75 (td, J=12.6, 2.4 Hz, 1H), 2.30-2.22 (m, 1H), 1.77 (d, J=12.0 Hz, 1H), 1.22-1.06 (m, 2H), 0.92-0.82 (m, 1H). LRMS (ESI): (calc) 312.37 (found) 313.27 (MH)+

General Procedures

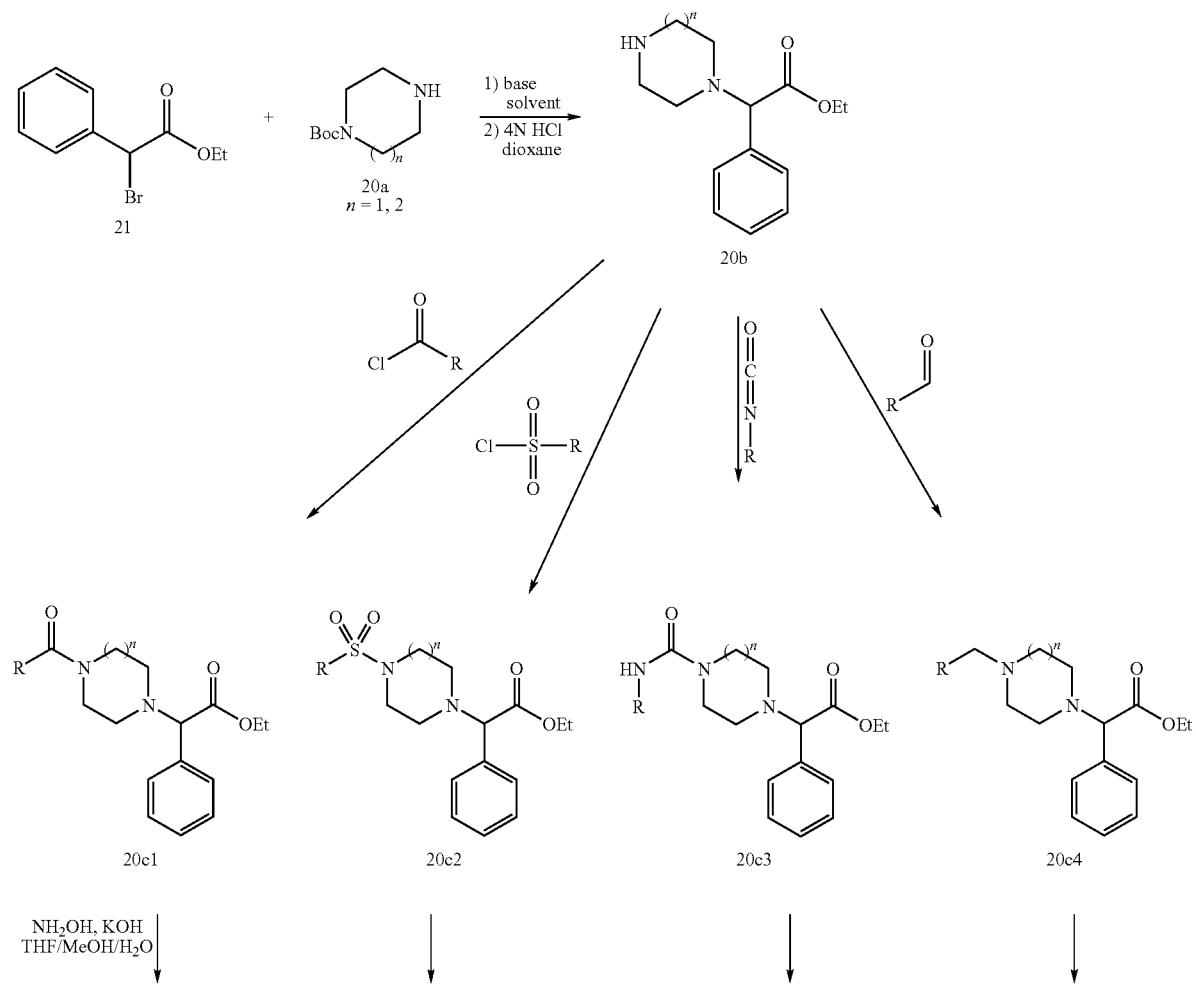

Scheme 20

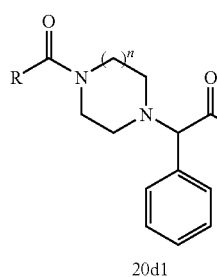 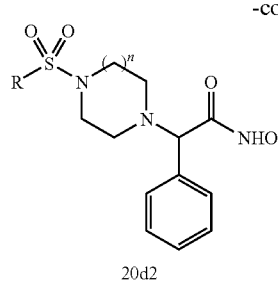 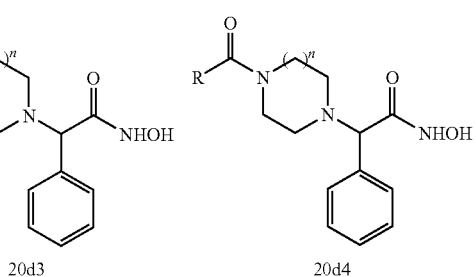

20d1  20d2  20d3  20d4

General Procedure for Scheme 20:

Step 1: General Structure 20b

To a stirring solution of compound 21 (1 eq), and amine 20a (1 eq), in solvent (acetone, THF, DCE or MeCN) was added base (1.5 eq) ($K_2CO_3$, $CsCO_3$, KOH, NaH or DIPEA) at room temperature. The reaction mixture was stirred for 24 then scavenged with PS-NCO and PS-AMPS, filtered and concentrated. To this residue was added 4N HCl in dioxane at room temperature and the reaction mixture was stirred for 2 h then concentrated to provide the HCl salt of 20b.

Step 2: General Structure 20c1, 20c2, 20c3, 20c4

Capping (to Provide Amides, Sulfonamides or Ureas):

A solution of compound 20b with acid chloride, sulfonyl chloride or isocyante was stirred with PS-DIPEA in DCE at room temperature for 18 h. The reaction mixture was filtered and concentrated to provide 20c-1, 20c2 and 20c3.

Reductive Amination (to Provide Amines):

To a stirring solution of compound 20b and aldehyde (1.5-2.0 eq) in DCE was added $NaBH(OAc)_3$ and AcOH at room temperature. The reaction mixture was stirred at room temperature for 18 h followed by basic wash or filtration onto MP-TsOH to provide amine 20c4.

Step 3: General Structure 20d1, 20d2, 20d3, 20d4

To a stirring solution of compound 20c-1, 20c2, 20c3 and 20c4 in MeOH:THF (1:1) was added 50% $NH_2OH$ in $H_2O$: 4N KOH (1:1) at room temperature and the reaction mixture was stirred for 18 h. The reaction mixture was concentrated and the resulting residue was triturated with DCE, dried with $MgSO_4$ then filtered to provide 20d1, 20d2, 20d3 and 20d4. If required, the final compounds were further purified by prep HPLC.

Scheme 21

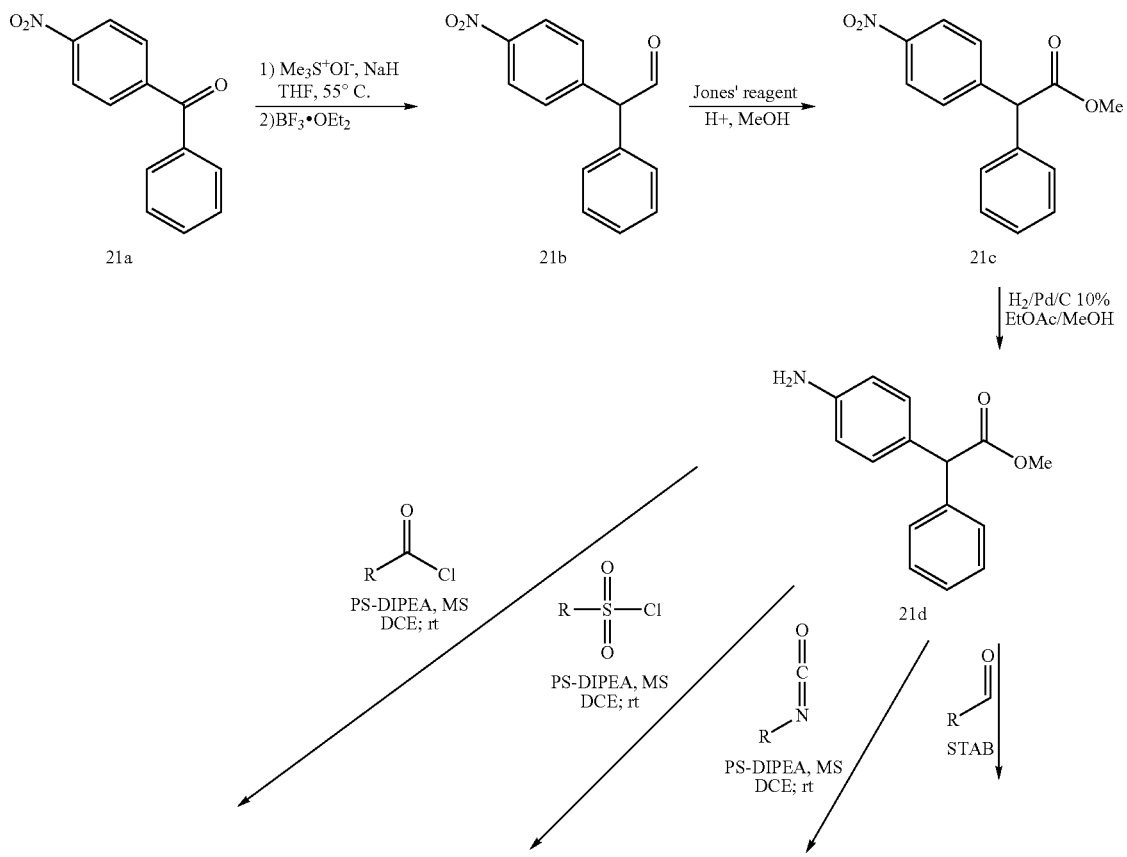

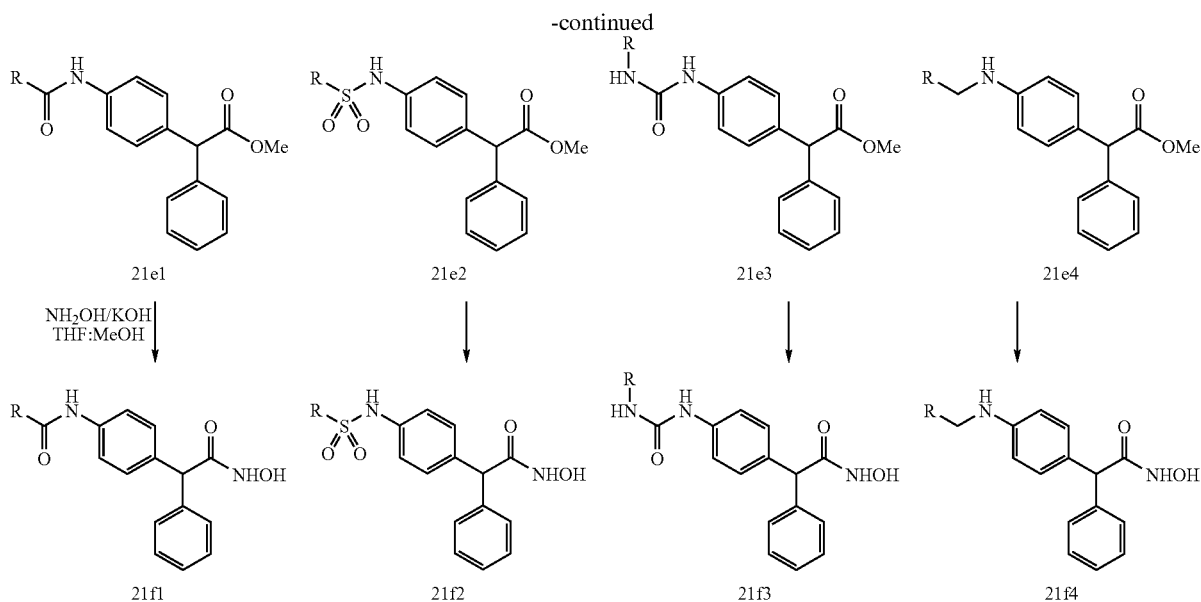

General Procedure for Scheme 21

Steps 1 and 2: methyl 2-(4-nitrophenyl)-2-phenylacetate (21c)

Following the same procedure as described in Scheme 13, steps 1 to 3 but substituting compound 50 with compound 21a, the title compound 21c was obtained.

Step 3: methyl 2-(4-aminophenyl)-2-phenylacetate (21d)

Following the same procedure as described in Scheme 10, step 1 but substituting 2-nitro-4-(thiophen-2-yl)aniline with compound 21c, the title compound 21d was obtained.

Step 4: General Structure (21e1-4)

Capping (to Provide Amides or Sulfonamides)
1. amides: A solution of amine intermediate 21d1, acid chloride and PS-DIPEA was stirred in DCE at room temperature for 18 h. The reaction mixture was then scavenged using PS-AMPS and PS-NCO, filtered and concentrated to provide 21e1.
2. sulfonamides: A solution of amine intermediate 21d2, sulfonyl chloride and DMAP was stirred in pyridine at room temperature for 18 h. The reaction mixture was then scavenged using PS-AMPS and PS-NCO, filtered and concentrated to provide 212e.

Reductive Amination (to Provide Amines)

A solution of amine intermediate 21d4, aldehyde and STAB was stirred in solvent at room temperature. The reaction mixture was then scavenged using PS-AMPS and PS-NCO, filtered and concentrated to provide 21e4.

Step 5: general structure (21f1-4)

To a stirring solution of compound 21e1-4 in MeOH:THF (1:1) was added 50% $NH_2OH$ in $H_2O$: 4N KOH (1:1) at room temperature and the reaction mixture was stirred for 18 h. The reaction mixture was concentrated and the resulting residue was triturated with DCE, dried with $MgSO_4$ then filtered to provide 21f1-4. If required, the final compounds were further purified by prep HPLC.

TABLE II

Compounds prepared according general Schemes 20 and 21 and other Schemes.

| Cpd # | Chemical name | MS | Scheme |
|---|---|---|---|
| 2-5 | 2-(3-butoxyphenyl)-N-hydroxy-2-phenylacetamide | LRMS (ESI): (calc) 299.3642 (found) 300.16 (MH)+ HPLC: 92% RT: 4.13 min 1H NMR (250 MHz, CHLOROFORM-d) d ppm 7.04-7.23 (6H, m), 6.64-6.73 (3H, m), 4.70 (1H, s), 3.79 (2H, t, J = 6.40 Hz), 1.55-1.69 (2H, m), 1.28-1.44 (2H, m), 0.86 (3H, t, J = 7.31 Hz) | 16 |
| 2-6 | 2-(3-(benzyloxy)phenyl)-N-hydroxy-2-phenylacetamide | LRMS (ESI): (calc) 333.3804 (found) 334.18 (MH)+ HPLC: 92% RT: 4.08 min | 16 |
| 2-7 | N-hydroxy-2-(3-phenethoxyphenyl)-2-phenylacetamide | LRMS (ESI): (calc) 347.407 (found) 348.17 (MH)+ HPLC: 91% RT: 4.24 min | 16 |
| 2-8 | 2-(3-(4-fluorobenzyloxy)phenyl)-N-hydroxy-2-phenylacetamide | LRMS (ESI): (calc) 351.3709 (found) 352.15 (MH)+ HPLC: 92% RT: 4.13 min | 16 |

TABLE II-continued

Compounds prepared according general Schemes 20 and 21 and other Schemes.

| Cpd # | Chemical name | MS | Scheme |
|---|---|---|---|
| 2-9 | N-hydroxy-2-(3-(3-methoxybenzyloxy)phenyl)-2-phenylacetamide | LRMS (ESI): (calc) 363.4064 (found) 364.17 (MH)+ HPLC: 100% RT: 4.08 min 1H NMR (360 MHz, CHCl$_3$-d) d ppm 7.19-7.33 (7H, m), 6.96-7.01 (2H, m), 6.87-6.92 (3H, m), 6.82 (1H, d, J = 7.72 Hz), 4.99 (2H, s), 4.84 (1H, s), 3.82 (3H, s) | 16 |
| 2-10 | 2-(4-butoxyphenyl)-N-hydroxy-2-phenylacetamide | LRMS (ESI): (calc) 299.3642 (found) 300.16 (MH)+ HPLC: 97% RT: 4.14 min 1H NMR (250 MHz, CHCl$_3$-d) d ppm 7.17-7.24 (3H, m), 7.10-7.17 (2H, m), 7.03 (2H, d, J = 8.53 Hz), 6.75 (2H, d, J = 8.53 Hz), 4.75 (1H, s), 3.85 (2H, t, J = 6.55 Hz), 1.61-1.74 (2H, m), 1.33-1.48 (2H, m), 0.89 (3H, t, J = 7.31 Hz) | 16 |
| 2-11 | N-hydroxy-2-(4-(2-morpholino-2-oxoethoxy)phenyl)-2-phenylacetamide | LRMS (ESI): (calc) 370.399 (found) 371.2 (MH)+ HPLC: 100% RT: 3.06 min | 16 |
| 2-12 | N-hydroxy-2-(4-phenethoxyphenyl)-2-phenylacetamide | LRMS (ESI): (calc) 347.407 (found) 348.17 (MH)+ HPLC: 91% RT: 4.25 min | 16 |
| 2-13 | (2-(4-(4-fluorobenzyloxy)phenyl)-N-hydroxy-2-phenylacetamide | LRMS (ESI): (calc) 351.3709 (found) 352.14 (MH)+ HPLC: 93% RT: 4.14 min | 16 |
| 2-14 | N-hydroxy-2-(4-(3-methoxybenzyloxy)phenyl)-2-phenylacetamide | LRMS (ESI): (calc) 363.4064 (found) 364.17 (MH)+ HPLC: 90% RT: 4.09 min | 16 |
| 2-15 | N-hydroxy-2-phenyl-2-(p-tolyloxy)acetamide | LRMS (ESI): (calc) 257.2845 (found) 258.05 (MH)+ HPLC: 91% RT: 3.64 min | 2 |
| 2-16 | 2-(2,3-dihydro-1H-inden-5-yloxy)-N-hydroxy-2-phenylacetamide | LRMS (ESI): (calc) 283.3217 (found) 284.08 (MH)+ HPLC: 86% RT: 3.90 min | 2 |
| 2-17 | N-hydroxy-2-phenyl-2-(5,6,7,8-tetrahydronaphthalen-1-yloxy)acetamide | LRMS (ESI): (calc) 297.3483 (found) 298.14 (MH)+ HPLC: 100% RT: 4.11 min | 2 |
| 2-18 | N-hydroxy-2-(4-(2-methoxyethyl)phenoxy)-2-phenylacetamide | LRMS (ESI): (calc) 301.337 (found) 302.11 (MH)+ HPLC: 93% RT: 3.50 min | 2 |
| 2-19 | N-hydroxy-2-phenyl-2-(2-(pyrrolidin-1-yl)phenoxy)acetamide | LRMS (ESI): (calc) 312.363 (found) 313.14 (MH)+ HPLC: 99% RT: 2.63 min | 2 |
| 2-20 | N-hydroxy-2-phenyl-2-(p-tolylthio)acetamide | LRMS (ESI): (calc) 273.3501 (found) 274.06 (MH)+ HPLC: 100% RT: 3.77 min 1H NMR (400 MHz, DMSO-d6) d ppm 10.93 (1H, br. s.), 9.13 (1H, br. s.), 7.50-7.54 (2H, m), 7.31-7.41 (3H, m), 7.24-7.28 (2H, m), 7.15-7.19 (2H, m), 4.87 (1H, s), 2.31 (3H, s) | 2 |
| 2-21 | N-hydroxy-2-(4-isopropylphenylthio)-2-phenylacetamide | LRMS (ESI): (calc) 301.4032 (found) 302.11 (MH)+ HPLC: 100% RT: 4.16 min | 2 |
| 2-22 | 2-(4-butyryl-1,4-diazepan-1-yl)-N-hydroxy-2-phenylacetamide | LRMS (ESI): (calc) 319.3987 (found) 320.2 (MH)+ HPLC: 91% RT: 2.23 min | 20 |
| 2-23 | 2-(4-butyrylpiperazin-1-yl)-N-hydroxy-2-phenylacetamide | LRMS (ESI): (calc) 305.3721 (found) 306.21 (MH)+ HPLC: 100% RT: 2.37 min | 20 |
| 2-24 | N-hydroxy-2-phenyl-2-(4-pivaloyl-1,4-diazepan-1-yl)acetamide | LRMS (ESI): (calc) 333.4252 (found) 334.2 (MH)+ HPLC: 91% RT: 2.44 min | 20 |
| 2-25 | N-hydroxy-2-phenyl-2-(4-pivaloylpiperazin-1-yl)acetamide | LRMS (ESI): (calc) 319.3987 (found) 320.2 (MH)+ HPLC: 90% RT: 2.56 min | 20 |
| 2-26 | 2-(4-(furan-2-carbonyl)-1,4-diazepan-1-yl)-N-hydroxy-2-phenylacetamide | LRMS (ESI): (calc) 343.377 (found) 344.2 (MH)+ HPLC: 92% RT: 2.23 min | 20 |
| 2-27 | 2-(4-(furan-2-carbonyl)piperazin-1- | LRMS (ESI): (calc) 329.3504 (found) 330.15 (MH)+ HPLC: 94% RT: 2.43 min | 20 |

TABLE II-continued

Compounds prepared according general Schemes 20 and 21 and other Schemes.

| Cpd # | Chemical name | MS | Scheme |
|---|---|---|---|
| | yl)-N-hydroxy-2-phenylacetamide | | |
| 2-28 | N-hydroxy-2-phenyl-2-(4-(2-phenylacetyl)piperazin-1-yl)acetamide | LRMS (ESI): (calc) 353.4149 (found) 354.22 (MH)+ HPLC: 100% RT: 2.79 min | 20 |
| 2-29 | N-hydroxy-2-(4-(3-methylbenzoyl)-1,4-diazepan-1-yl)-2-phenylacetamide | LRMS (ESI): (calc) 367.4415 (found) 368.2 (MH)+ HPLC: 88% RT: 1.36 min | 20 |
| 2-30 | N-hydroxy-2-(4-(3-methylbenzoyl)piperazin-1-yl)-2-phenylacetamide | LRMS (ESI): (calc) 353.4149 (found) 354.22 (MH)+ HPLC: 100% RT: 2.92 min | 20 |
| 2-31 | 4-(2-(hydroxyamino)-2-oxo-1-phenylethyl)-N-isopropyl-1,4-diazepane-1-carboxamide | LRMS (ESI): (calc) 334.4133 (found) 335.24 (MH)+ HPLC: 95% RT: 2.10 min | 20 |
| 2-32 | 4-(2-(hydroxyamino)-2-oxo-1-phenylethyl)-N-isopropylpiperazine-1-carboxamide | LRMS (ESI): (calc) 320.3867 (found) 321.2 (MH)+ HPLC: 93% RT: 2.07 min | 20 |
| 2-33 | 4-(2-(hydroxyamino)-2-oxo-1-phenylethyl)-N-(pyridin-3-yl)-1,4-diazepane-1-carboxamide | LRMS (ESI): (calc) 369.4176 (found) 370.18 (MH)+ HPLC: 90% RT: 2.91 min | 20 |
| 2-34 | 4-(2-(hydroxyamino)-2-oxo-1-phenylethyl)-N-(pyridin-3-yl)piperazine-1-carboxamide | LRMS (ESI): (calc) 355.391 (found) 356.17 (MH)+ HPLC: 95% RT: 1.41 min | 20 |
| 2-35 | 4-(2-(hydroxyamino)-2-oxo-1-phenylethyl)-N-o-tolyl-1,4-diazepane-1-carboxamide | LRMS (ESI): (calc) 382.4561 (found) 383.26 (MH)+ HPLC: 92% RT: 2.49 min | 20 |
| 2-36 | 4-(2-(hydroxyamino)-2-oxo-1-phenylethyl)-N-o-tolylpiperazine-1-carboxamide | LRMS (ESI): (calc) 368.4295 (found) 369.2 (MH)+ HPLC: 91% RT: 2.63 min | 20 |
| 2-37 | 4-(2-(hydroxyamino)-2-oxo-1-phenylethyl)-N-(3-methoxyphenyl)-1,4-diazepane-1-carboxamide | LRMS (ESI): (calc) 398.4555 (found) 399.2 (MH)+ HPLC: 89% RT: 2.58 min | 20 |
| 2-38 | N-hydroxy-2-(4-(1-methyl-1H-imidazol-4-ylsulfonyl)piperazin-1-yl)-2-phenylacetamide | LRMS (ESI): (calc) 379.434 (found) 380.17 (MH)+ HPLC: 97% RT: 2.35 min | 20 |
| 2-39 | N-hydroxy-2-(4-(1-methyl-1H-imidazol-4-ylsulfonyl)-1,4- | LRMS (ESI): (calc) 393.4606 (found) 394.2 (MH)+ HPLC: 94% RT: 2.20 min | 20 |

TABLE II-continued

Compounds prepared according general Schemes 20 and 21 and other Schemes.

| Cpd # | Chemical name | MS | Scheme |
|---|---|---|---|
| 2-40 | diazepan-1-yl)-2-phenylacetamide N-hydroxy-2-phenyl-2-(4-(pyridin-3-ylmethyl)piperazin-1-yl)acetamide | LRMS (ESI): (calc) 326.3928 (found) 327.19 (MH)+ HPLC: 99% RT: 1.09 min | 20 |
| 2-41 | N-hydroxy-2-phenyl-2-(1,4-dioxa-8-azaspiro[4.5]decan-8-yl)acetamide | LRMS (ESI): (calc) 292.3303 (found) 293.16 (MH)+ HPLC: 100% RT: 2.00 min | 7 |
| 2-42 | N-hydroxy-2-(4-morpholinopiperidin-1-yl)-2-phenylacetamide | LRMS (ESI): (calc) 319.3987 (found) 320.2 (MH)+ HPLC: 95% RT: 2.97 min | 7 |
| 2-43 | N-hydroxy-2-phenyl-2-(4-(3-(pyridin-3-yl)-1,2,4-oxadiazol-5-yl)piperidin-1-yl)acetamide | LRMS (ESI): (calc) 379.4124 (found) 380.17 (MH)+ HPLC: 91% RT: 2.46 min | |
| 2-44 | 2-(4-(3-(benzo[d][1,3]dioxol-5-yl)-1,2,4-oxadiazol-5-yl)piperidin-1-yl)-N-hydroxy-2-phenylacetamide | LRMS (ESI): (calc) 422.4338 (found) 423.19 (MH)+ HPLC: 91% RT: 2.99 min | |
| 2-45 | N-hydroxy-2-phenyl-2-(pyridin-4-ylthio)acetamide | LRMS (ESI): (calc) 260.3115 (found) 261.01 (MH)+ HPLC: 100% RT: 2.10 min | 2 |
| 2-46 | N-hydroxy-2-(2-methylfuran-3-ylthio)-2-phenylacetamide | LRMS (ESI): (calc) 263.3122 (found) 264.04 (MH)+ HPLC: 100% RT: 3.53 min | 2 |
| 2-47 | N-hydroxy-2-phenyl-2-(5-(trifluoromethyl)pyridin-2-ylthio)acetamide | LRMS (ESI): (calc) 328.3095 (found) 329.08 (MH)+ HPLC: 90% RT: 3.83 min | |
| 2-48 | N-hydroxy-2-phenyl-2-(4-(thiophen-2-yl)pyrimidin-2-ylthio)acetamide | LRMS (ESI): (calc) 343.4233 (found) 344.08 (MH)+ HPLC: 94% RT: 3.68 min | 2 |
| 2-49 | N-hydroxy-2-phenyl-2-(7-(trifluoromethyl)quinolin-4-ylthio)acetamide | LRMS (ESI): (calc) 378.3682 (found) 379.1 (MH)+ HPLC: 100% RT: 3.91 min 1H NMR (400 MHz, DMSO-d6) d ppm 11.38 (1H, s), 9.45 (1H, s), 9.05 (1H, d, J = 4.65 Hz), 8.57 (1H, d, J = 8.80 Hz), 8.53 (1H, s), 8.11 (1H, dd, J = 8.80, 1.96 Hz), 7.79-7.84 (2H, m), 7.66 (1H, d, J = 4.89 Hz), 7.51-7.61 (3H, m), 5.56 (1H, s) | 2 |
| 2-50 | 2-(3-(4-fluorobenzylamino)phenyl)-N-hydroxy-2-phenylacetamide | LRMS (ESI): (calc) 350.3861 (found) 351.4 (MH)+ HPLC: 94% RT: 3.87 min | 21 |
| 2-51 | 2-(4-(4-fluorobenzylamino)phenyl)-N-hydroxy-2-phenylacetamide | LRMS (ESI): (calc) 350.3861 (found) 351.4 (MH)+ HPLC: 92% RT: 3.87 min 1H NMR (360 MHz, MeOH) d ppm 7.31-7.38 (2H, m), 7.18-7.28 (5H, m), 6.97-7.05 (4H, m), 6.53-6.59 (2H, m), 4.62 (1H, s), 4.28 (2H, s) | 21 |
| 2-52 | 2-(3-acetamidophenyl)-N-hydroxy-2-phenylacetamide | LRMS (ESI): (calc) 284.3098 (found) 285 (MH)+ HPLC: 87% RT: 2.95 min | 21 |
| 2-53 | N-(4-(2-(hydroxyamino)-2-oxo-1-phenylethyl)phenyl)-3-methylbutanamide | LRMS (ESI): (calc) 326.3895 (found) 327.1 (MH)+ HPLC: 95% RT: 3.49 min | 21 |
| 2-54 | N-(3-(2-(hydroxyamino)-2-oxo-1-phenylethyl)phenyl)-3-methylbutanamide | LRMS (ESI): (calc) 326.3895 (found) 327.1 (MH)+ HPLC: 100% RT: 3.53 min | 21 |
| 2-55 | N-(4-(2-(hydroxyamino)-2-oxo-1-phenylethyl)phenyl)benzamide | LRMS (ESI): (calc) 346.3792 (found) 347.1 (MH)+ HPLC: 98% RT: 3.57 min | 21 |
| 2-56 | N-(3-(2-(hydroxyamino)-2-oxo-1- | LRMS (ESI): (calc) 346.3792 (found) 347.1 (MH)+ HPLC: 100% RT: 3.59 min 1H NMR (400 MHz, MeOD) d ppm 7.90-7.93 (2H, | 21 |

TABLE II-continued

Compounds prepared according general Schemes 20 and 21 and other Schemes.

| Cpd # | Chemical name | MS | Scheme |
|---|---|---|---|
| | phenylethyl)phenyl)benzamide | m), 7.63-7.68 (2H, m), 7.55-7.60 (1H, m), 7.48-7.53 (2H, m), 7.31-7.39 (5H, m), 7.24-7.29 (1H, m), 7.12-7.17 (1H, m), 4.82 (1H, s) | |
| 2-57 | N-(4-(2-(hydroxyamino)-2-oxo-1-phenylethyl)phenyl)cyclohexanecarboxamide | LRMS (ESI): (calc) 352.4268 (found) 353.1 (MH)+ HPLC: 91% RT: 3.75 min | 21 |
| 2-58 | N-(3-(2-(hydroxyamino)-2-oxo-1-phenylethyl)phenyl)cyclohexanecarboxamide | LRMS (ESI): (calc) 352.4268 (found) 353.1 (MH)+ HPLC: 90% RT: 3.79 min | 21 |
| 2-59 | N-hydroxy-2-phenyl-2-(4-(2-phenylacetamido)phenyl)acetamide | LRMS (ESI): (calc) 360.4058 (found) 361.1 (MH)+ HPLC: 94% RT: 3.60 min | 21 |
| 2-60 | N-hydroxy-2-phenyl-2-(3-(2-phenylacetamido)phenyl)acetamide | LRMS (ESI): (calc) 360.4058 (found) 361.1 (MH)+ HPLC: 92% RT: 3.63 min | 21 |
| 2-61 | 4-fluoro-N-(4-(2-(hydroxyamino)-2-oxo-1-phenylethyl)phenyl)benzamide | LRMS (ESI): (calc) 364.3696 (found) 365.1 (MH)+ HPLC: 99% RT: 3.65 min | 21 |
| 2-62 | 4-fluoro-N-(3-(2-(hydroxyamino)-2-oxo-1-phenylethyl)phenyl)benzamide | LRMS (ESI): (calc) 364.3696 (found) 365.1 (MH)+ HPLC: 87% RT: 3.68 min | 21 |
| 2-63 | N-(4-(2-(hydroxyamino)-2-oxo-1-phenylethyl)phenyl)-2,5-dimethylfuran-3-carboxamide | LRMS (ESI): (calc) 364.3945 (found) 365.1 (MH)+ HPLC: 98% RT: 3.74 min | 21 |
| 2-64 | N-(3-(2-(hydroxyamino)-2-oxo-1-phenylethyl)phenyl)-2,5-dimethylfuran-3-carboxamide | LRMS (ESI): (calc) 364.3945 (found) 365.1 (MH)+ HPLC: 91% RT: 3.77 min | 21 |
| 2-65 | N-(4-(2-(hydroxyamino)-2-oxo-1-phenylethyl)phenyl)-3-methylthiophene-2-carboxamide | LRMS (ESI): (calc) 366.4335 (found) 367.1 (MH)+ HPLC: 95% RT: 3.66 min | 21 |
| 2-66 | N-(3-(2-(hydroxyamino)-2-oxo-1-phenylethyl)phenyl)-3-methylthiophene-2-carboxamide | LRMS (ESI): (calc) 366.4335 (found) 367.1 (MH)+ HPLC: 93% RT: 3.68 min | 21 |
| 2-67 | N-hydroxy-2-(4-(2-phenoxyacetamido)phenyl)-2-phenylacetamide | LRMS (ESI): (calc) 376.4052 (found) 753 (2M + H)+ HPLC: 100% RT: 3.72 min 1H NMR (400 MHz, MeOD) d ppm 7.53-7.59 (2H, m), 7.23-7.33 (9H, m), 6.98-7.06 (3H, m), 4.77 (1H, s), 4.65 (2H, s) | 21 |
| 2-68 | N-hydroxy-2-(3-(2-phenoxyacetamido)phenyl)-2-phenylacetamide | LRMS (ESI): (calc) 376.4052 (found) 377.1 (MH)+ HPLC: 100% RT: 3.74 min | 21 |
| 2-69 | N-(3-(2-(hydroxyamino)-2-oxo-1-phenylethyl)phenyl)-4-methoxybenzamide | LRMS (ESI): (calc) 376.4052 (found) 377.1 (MH)+ HPLC: 95% RT: 3.61 min | 21 |
| 2-70 | 3-cyclohexyl-N-(4-(2-(hydroxyamino)-2-oxo-1-phenylethyl)phenyl)propanamide | LRMS (ESI): (calc) 380.48 (found) 381.2 (MH)+ HPLC: 98% RT: 4.18 min | 21 |
| 2-71 | 3-cyclohexyl-N-(3-(2-(hydroxyamino)-2-oxo-1-phenylethyl)phenyl)propanamide | LRMS (ESI): (calc) 380.48 (found) 381.2 (MH)+ HPLC: 100% RT: 4.20 min | 21 |
| 2-72 | 3-chloro-N-(4-(2-(hydroxyamino)-2-oxo-1-phenylethyl)phenyl)benzamide | LRMS (ESI): (calc) 380.8242 (found) 381.5 (MH)+ HPLC: 91% RT: 3.87 min | 21 |

TABLE II-continued

Compounds prepared according general Schemes 20 and 21 and other Schemes.

| Cpd # | Chemical name | MS | Scheme |
|---|---|---|---|
| 2-73 | 3-chloro-N-(3-(2-(hydroxyamino)-2-oxo-1-phenylethyl)phenyl)benzamide | LRMS (ESI): (calc) 380.8242 (found) 381.5 (MH)+ HPLC: 99% RT: 3.89 min | 21 |
| 2-74 | 2-chloro-N-(4-(2-(hydroxyamino)-2-oxo-1-phenylethyl)phenyl)isonicotinamide | LRMS (ESI): (calc) 381.8123 (found) 382.5 (MH)+ HPLC: 91% RT: 3.52 min | 21 |
| 2-75 | N-(4-(2-(hydroxyamino)-2-oxo-1-phenylethyl)phenyl)benzo[d][1,3]dioxole-5-carboxamide | LRMS (ESI): (calc) 390.3887 (found) 391.1 (MH)+ HPLC: 98% RT: 3.57 min | 21 |
| 2-76 | N-(3-(2-(hydroxyamino)-2-oxo-1-phenylethyl)phenyl)benzo[d][1,3]dioxole-5-carboxamide | LRMS (ESI): (calc) 390.3887 (found) 391.1 (MH)+ HPLC: 100% RT: 3.61 min | 21 |
| 2-77 | N-hydroxy-2-(4-(isopentylamino)phenyl)-2-phenylacetamide | LRMS (ESI): (calc) 312.406 (found) 313.4 (MH)+ HPLC: 92% RT: 3.35 min | 21 |
| 2-78 | 2-(4-(benzylamino)phenyl)-N-hydroxy-2-phenylacetamide | LRMS (ESI): (calc) 332.3957 (found) 333.4 (MH)+ HPLC: 93% RT: 3.79 min | 21 |
| 2-79 | 2-(3-(benzylamino)phenyl)-N-hydroxy-2-phenylacetamide | LRMS (ESI): (calc) 332.3957 (found) 333.4 (MH)+ HPLC: 92% RT: 3.80 min | 21 |
| 2-80 | N-hydroxy-2-phenyl-2-(4-(pyridin-4-ylmethylamino)phenyl)acetamide | LRMS (ESI): (calc) 333.3837 (found) 334.4 (MH)+ HPLC: 90% RT: 2.49 min | 21 |
| 2-81 | N-hydroxy-2-phenyl-2-(3-(pyridin-4-ylmethylamino)phenyl)acetamide | LRMS (ESI): (calc) 333.3837 (found) 334.4 (MH)+ HPLC: 90% RT: 2.49 min 1H NMR (360 MHz, MeOH) d ppm 8.40 (2H, d, J = 6.36 Hz), 7.38 (2H, d, J = 6.36 Hz), 7.19-7.30 (5H, m), 6.99-7.05 (1H, m), 6.45-6.59 (3H, m), 4.62 (1H, s), 4.36 (2H, s) | 21 |
| 2-82 | 2-(4-(cyclohexylmethylamino)phenyl)-N-hydroxy-2-phenylacetamide | LRMS (ESI): (calc) 338.4433 (found) 339.4 (MH)+ HPLC: 94% RT: 3.99 min | 21 |
| 2-83 | 2-(3-(cyclohexylmethylamino)phenyl)-N-hydroxy-2-phenylacetamide | LRMS (ESI): (calc) 338.4433 (found) 339.4 (MH)+ HPLC: 87% RT: 4.06 min | 21 |
| 2-84 | N-hydroxy-2-(4-(3-methoxybenzylamino)phenyl)-2-phenylacetamide | LRMS (ESI): (calc) 362.4216 (found) 363.4 (MH)+ HPLC: 92% RT: 3.80 min | 21 |
| 2-85 | N-hydroxy-2-(3-(3-methoxybenzylamino)phenyl)-2-phenylacetamide | LRMS (ESI): (calc) 362.4216 (found) 302 (M − CONHOH)+ HPLC: 92% RT: 3.81 min | 21 |
| 2-86 | N-hydroxy-2-phenyl-2-(4-(propylsulfonamido)phenyl)acetamide | LRMS (ESI): (calc) 348.4167 (found) 349.1 (MH)+ HPLC: 96% RT: 3.33 min 1H NMR (400 MHz, MeOD) d ppm 7.22-7.33 (7H, m), 7.16-7.19 (2H, m), 4.74 (1H, s), 2.99-3.05 (2H, m), 1.73-1.82 (2H, m), 0.98 (3H, t, J = 7.58 Hz) | 21 |
| 2-87 | N-hydroxy-2-phenyl-2-(3-(propylsulfonamido)phenyl)acetamide | LRMS (ESI): (calc) 348.4167 (found) 349.1 (MH)+ HPLC: 92% RT: 3.57 min | 21 |
| 2-88 | N-hydroxy-2-phenyl-2-(4-(phenylsulfonamido)phenyl)acetamide | LRMS (ESI): (calc) 382.4329 (found) 383.1 (MH)+ HPLC: 95% RT: 3.53 min | 21 |
| 2-89 | N-hydroxy-2-phenyl-2-(3-(phenylsulfonamido)phenyl)acetamide | LRMS (ESI): (calc) 382.4329 (found) 383.1 (MH)+ HPLC: 95% RT: 3.54 min 1H NMR (360 MHz, MeOH) d ppm 7.64-7.69 (2H, m), 7.51-7.57 (1H, m), 7.39-7.45 (2H, m), 7.24-7.31 (3H, m), 7.08-7.22 (4H, m), 6.96-7.03 (2H, m), 4.67 (1H, s) | 21 |

TABLE II-continued

Compounds prepared according general Schemes 20 and 21 and other Schemes.

| Cpd # | Chemical name | MS | Scheme |
|---|---|---|---|
| 2-90 | N-hydroxy-2-phenyl-2-(4-(thiophene-2-sulfonamido)phenyl)acetamide | LRMS (ESI): (calc) 388.4606 (found) 389.1 (MH)+ HPLC: 95% RT: 3.47 min | 21 |
| 2-91 | N-hydroxy-2-(3-(4-methoxyphenylsulfonamido)phenyl)-2-phenylacetamide | LRMS (ESI): (calc) 412.4589 (found) 413.1 (MH)+ HPLC: 94% RT: 3.58 min | 21 |
| 2-92 | 2-(4-(4-chlorophenylsulfonamido)phenyl)-N-hydroxy-2-phenylacetamide | LRMS (ESI): (calc) 416.8779 (found) 417.6 (MH)+ HPLC: 95% RT: 3.78 min | 21 |
| 2-93 | 2-(3-(4-chlorophenylsulfonamido)phenyl)-N-hydroxy-2-phenylacetamide | LRMS (ESI): (calc) 416.8779 (found) 417.6 (MH)+ HPLC: 93% RT: 3.80 min | 21 |
| 2-94 | N-hydroxy-2-phenyl-2-(3-(phenylethynyl)phenyl)acetamide | LRMS (ESI): (calc) 327.3758 (found) 328.4 (MH)+ HPLC: 93% RT: 4.34 min | 14 |
| 2-95 | N-hydroxy-2-phenyl-2-(3-(pyridin-3-ylethynyl)phenyl)acetamide | LRMS (ESI): (calc) 328.3639 (found) 329.4 (MH)+ HPLC: 89% RT: 3.58 min | 14 |
| 2-96 | 2-(3-(3-cyclopentylprop-1-ynyl)phenyl)-N-hydroxy-2-phenylacetamide | LRMS (ESI): (calc) 333.4235 (found) 334.4 (MH)+ HPLC: 86% RT: 4.71 min 1H NMR (400 MHz, DMSO-d6) d ppm 11.00 (1H, s), 9.01 (1H, br. s.), 7.20-7.34 (9H, m), 4.73 (1H, s), 2.40 (2H, d, J = 6.85 Hz), 1.98-2.18 (1H, m), 1.72-1.82 (2H, m), 1.47-1.65 (4H, m), 1.20-1.34 (2H, m) | 14 |
| 2-97 | N-hydroxy-2-phenyl-2-(4-(phenylethynyl)phenyl)acetamide | LRMS (ESI): (calc) 327.3758 (found) 328.4 (MH)+ HPLC: 95% RT: 4.36 min | 14 |
| 2-98 | 2-(4-(3-cyclopentylprop-1-ynyl)phenyl)-N-hydroxy-2-phenylacetamide | LRMS (ESI): (calc) 333.4235 (found) 334.4 (MH)+ HPLC: 93% RT: 4.76 min | 14 |
| 2-99 | 2-(4-((4-butoxyphenyl)ethynyl)phenyl)-N-hydroxy-2-phenylacetamide | LRMS (ESI): (calc) 399.4816 (found) 400.5 (MH)+ HPLC: 87% RT: 5.08 min | 14 |
| 2-100 | N-hydroxy-2-(4'-phenoxybiphenyl-3-yl)-2-phenylacetamide | LRMS (ESI): (calc) 395.4498 (found) 396.4 (MH)+ HPLC: 89% RT: 4.65 min | 13 |
| 2-101 | N-hydroxy-2-phenyl-2-(3-propylphenyl)acetamide | LRMS (ESI): (calc) 269.3382 (found) 270.3 (MH)+ HPLC: 94% RT: 4.02 min 1H NMR (400 MHz, DMSO-d6) d ppm 10.92 (1H, s), 8.96 (1H, br. s.), 7.28-7.33 (4H, m), 7.19-7.26 (2H, m), 7.11-7.17 (2H, m), 7.03-7.09 (1H, m), 4.68 (1H, s), 2.37-2.61 (2H under DMSO), 1.54 (2H, qt, J = 7.50, 7.34 Hz), 0.87 (3H, t, J = 7.3) | 14 |
| 2-102 | 2-(4'-ethylbiphenyl-3-yl)-N-hydroxy-2-phenylacetamide | LRMS (ESI): (calc) 331.4076 (found) 332.4 (MH)+ HPLC: 90% RT: 4.46 min | 13 |
| 2-103 | 2-(4'-chlorobiphenyl-3-yl)-N-hydroxy-2-phenylacetamide | LRMS (ESI): (calc) 337.7995 (found) 338.8 (MH)+ HPLC: 91% RT: 4.32 min | 13 |
| 2-104 | 2-(3-(2,3-dihydrobenzofuran-5-yl)phenyl)-N-hydroxy-2-phenylacetamide | LRMS (ESI): (calc) 345.3911 (found) 346.4 (MH)+ HPLC: 92% RT: 4.01 min | 13 |
| 2-105 | 2-(4'-(dimethylamino)biphenyl-3-yl)-N-hydroxy-2-phenylacetamide | LRMS (ESI): (calc) 346.4222 (found) 347.4 (MH)+ HPLC: 86% RT: 3.53 min | 13 |
| 2-106 | 2-(3',4'-dimethoxybiphenyl-3-yl)-N-hydroxy-2-phenylacetamide | LRMS (ESI): (calc) 363.4064 (found) 364.4 (MH)+ HPLC: 91% RT: 3.84 min | 13 |
| 2-107 | 2-(4'-(ethylthio)biphenyl-3-yl)-N-hydroxy-2-phenylacetamide | LRMS (ESI): (calc) 363.4726 (found) 364.5 (MH)+ HPLC: 86% RT: 4.48 min | 13 |

TABLE II-continued

Compounds prepared according general Schemes 20 and 21 and other Schemes.

| Cpd # | Chemical name | MS | Scheme |
|---|---|---|---|
| 2-108 | N-hydroxy-2-phenyl-2-(2'-(trifluoromethyl)biphenyl-3-yl)acetamide | LRMS (ESI): (calc) 371.3524 (found) 372.4 (MH)+ HPLC: 91% RT: 4.25 min | 13 |
| 2-109 | 3'-(2-(hydroxyamino)-2-oxo-1-phenylethyl)-N,N-dimethylbiphenyl-4-carboxamide | LRMS (ESI): (calc) 374.4323 (found) 375.4 (MH)+ HPLC: 89% RT: 3.54 min | 13 |
| 2-110 | N-hydroxy-2-(4'-(methylsulfonyl)biphenyl-3-yl)-2-phenylacetamide | LRMS (ESI): (calc) 381.4448 (found) 382.4 (MH)+ HPLC: 93% RT: 3.58 min | 13 |
| 2-111 | 2-(4'-ethylbiphenyl-4-yl)-N-hydroxy-2-phenylacetamide | LRMS (ESI): (calc) 331.4076 (found) 332.4 (MH)+ HPLC: 93% RT: 4.48 min 1H NMR (400 MHz, DMSO-d6) d ppm 8.99 (1H, br. s.), 7.53-7.60 (4H, m), 7.23-7.40 (9H, m), 4.75 (1H, s), 2.63 (2H, q, J = 7.34 Hz), 1.20 (3H, t) | 13 |
| 2-112 | 2-(4'-chlorobiphenyl-4-yl)-N-hydroxy-2-phenylacetamide | LRMS (ESI): (calc) 337.7995 (found) 338.8 (MH)+ HPLC: 94% RT: 4.36 min | 13 |
| 2-113 | 2-(4-(2,3-dihydrobenzofuran-5-yl)phenyl)-N-hydroxy-2-phenylacetamide | LRMS (ESI): (calc) 345.3911 (found) 346.4 (MH)+ HPLC: 94% RT: 4.03 min | 13 |
| 2-114 | 2-(3',4'-dimethoxybiphenyl-4-yl)-N-hydroxy-2-phenylacetamide | LRMS (ESI): (calc) 363.4064 (found) 364.4 (MH)+ HPLC: 95% 1H NMR (400 MHz, DMSO-d6) d ppm 10.93 (1H, br. s.), 8.98 (1H, s), 7.57 (2H, d, J = 8.31 Hz), 7.29-7.38 (6H, m), 7.20-7.27 (1H, m), 7.13-7.18 (2H, m), 7.01 (1H, d, J = 8.31 Hz), 4.73 (1H, s), 3.81 (3H, s), 3.77 (3H, s) | 13 |
| 2-115 | 2-(4'-(ethylthio)biphenyl-4-yl)-N-hydroxy-2-phenylacetamide | LRMS (ESI): (calc) 363.4726 (found) 364.5 (MH)+ HPLC: 95% | 13 |
| 2-116 | 4'-(2-(hydroxyamino)-2-oxo-1-phenylethyl)-N,N-dimethylbiphenyl-4-carboxamide | LRMS (ESI): (calc) 374.4323 (found) 375.4 (MH)+ HPLC: 95% | 13 |
| 2-117 | N-hydroxy-2-(4'-phenoxybiphenyl-4-yl)-2-phenylacetamide | LRMS (ESI): (calc) 395.4498 (found) 396.4 (MH)+ HPLC: 92% | 13 |

TABLE III

Compounds prepared according general Schemes 20 and 21 and other Schemes.

| Cpd # | Name | Characterization |
|---|---|---|
| 3-5 | N-hydroxy-2-(3-(3-methylbut-2-enyloxy)phenyl)-2-phenylacetamide | LRMS (ESI): (calc) 311.3749 (found) 312 (MH)+ HPLC: 98% RT: 4.08 min |
| 3-6 | N-hydroxy-2-(3-(4-methoxybenzyloxy)phenyl)-2-phenylacetamide | LRMS (ESI): (calc) 363.4064 (found) 364 (MH)+ HPLC: 98% RT: 4.04 min |
| 3-7 | 2-(3-(benzo[d][1,3]dioxol-5-ylmethylbenzo[d][1,3]dioxol-5-ylmethoxy)phenyl)-N-hydroxy-2-phenylacetamide | LRMS (ESI): (calc) 377.3899 (found) 378 (MH)+ HPLC: 98% RT: 3.99 min |
| 3-8 | N-hydroxy-2-phenyl-2-(3-(1-phenylethoxy)phenyl)acetamide | LRMS (ESI): (calc) 347.407 (found) 348 (MH)+ HPLC: 100% RT: 4.15 min |
| 3-9 | (E)-2-(3-(cinnamyloxy)phenyl)-N-hydroxy-2-phenylacetamide | LRMS (ESI): (calc) 359.4177 (found) 360 (MH)+ HPLC: 95% RT: 4.32 min 1H NMR (360 MHz, MeOH) d ppm 7.37-7.42 (2H, m), 7.19-7.34 (9H, m), 6.98 (1H, s), 6.84-6.92 (2H, m), 6.70 (1H, d, J = 15.89 Hz), 6.34-6.44 (1H, m), 4.76 (1H, s), 4.65 (2H, d, J = 5.90 Hz) |
| 3-10 | 2-(3-(3-chlorobenzyloxy)phenyl)-N-hydroxy-2-phenylacetamide | LRMS (ESI): (calc) 367.8255 (found) 368 (MH)+ HPLC: 100% RT: 4.31 min |

TABLE III-continued

Compounds prepared according general Schemes 20 and 21 and other Schemes.

| Cpd # | Name | Characterization |
|---|---|---|
| 3-11 | 2-(4-(benzo[d][1,3]dioxol-5-ylmethylbenzo[d][1,3]dioxol-5-ylmethoxy)phenyl)-N-hydroxy-2-phenylacetamide | LRMS (ESI): (calc) 377.3899 (found) 378 (MH)+ HPLC: 100% RT: 3.99 min 1H NMR (360 MHz, MeOH) d ppm 7.27-7.31 (4H, m), 7.19-7.26 (3H, m), 6.86-6.93 (4H, m), 6.79 (1H, d, J = 7.72 Hz), 5.93 (2H, s), 4.95 (2H, s), 4.72 (1H, s) |
| 3-12 | N-hydroxy-2-phenyl-2-(3-(4-(pyridin-4-ylmethyl)piperazin-1-yl)phenyl)acetamide | LRMS (ESI): (calc) 402.4888 (found) 202 ((M2H/2)+ HPLC: 100% RT: 2.45 min |
| 3-13 | 2-(4-acetamidophenyl)-N-hydroxy-2-phenylacetamide | LRMS (ESI): (calc) 284.3098 (found) 285 (MH)+ HPLC: 86% RT: 2.88 min |
| 3-14 | 2-chloro-N-(3-(2-(hydroxyamino)-2-oxo-1-phenylethyl)phenyl)isonicotinamide | LRMS (ESI): (calc) 381.8123 (found) 382 (MH)+ HPLC: 100% RT: 3.53 min 1H NMR (250 MHz, MeOD) d ppm 8.52 (1H, d, J = 5.18 Hz), 7.90 (1H, s), 7.78 (1H, dd, J = 5.10, 1.29 Hz), 7.62-7.71 (2H, m), 7.23-7.39 (7H, m), 7.16 (1H, d, J = 7.77 Hz), 4.81 (1H, s) |
| 3-15 | 2-(3-(3-(dimethylamino)propoxy)phenyl)-N-hydroxy-2-phenylacetamide | LRMS (ESI): (calc) 328.4054 (found) 329 (MH)+ HPLC: 99% RT: 2.57 min |
| 3-16 | 2-(4-(3-(dimethylamino)propoxy)phenyl)-N-hydroxy-2-phenylacetamide | LRMS (ESI): (calc) 328.4054 (found) 329 (MH)+ HPLC: 97% RT: 2.54 min |
| 3-17 | 2-(3-(3-(dimethylamino)-2-methylpropoxy)phenyl)-N-hydroxy-2-phenylacetamide | LRMS (ESI): (calc) 342.432 (found) 343 (MH)+ HPLC: 100% RT: 2.68 min |
| 3-18 | 2-(4-(3-(dimethylamino)-2-methylpropoxy)phenyl)-N-hydroxy-2-phenylacetamide | LRMS (ESI): (calc) 342.432 (found) 343 (MH)+ HPLC: 100% RT: 2.64 min |
| 3-19 | N-hydroxy-2-phenyl-2-(3-(2-(pyrrolidin-1-yl)ethoxy)phenyl)acetamide | LRMS (ESI): (calc) 340.4161 (found) 341 (MH)+ HPLC: 100% RT: 2.55 min |
| 3-20 | N-hydroxy-2-(3-(2-(1-methylpyrrolidin-2-yl)ethoxy)phenyl)-2-phenylacetamide | LRMS (ESI): (calc) 354.4427 (found) 355 (MH)+ HPLC: 100% RT: 2.65 min |
| 3-21 | N-hydroxy-2-(3-methoxyphenyl)-2-phenylacetamide | LRMS (ESI): (calc) 257.2845 (found) 258 (MH)+ HPLC: 96% RT: 3.38 min |
| 3-22 | 2-(3-ethoxyphenyl)-N-hydroxy-2-phenylacetamide | LRMS (ESI): (calc) 271.311 (found) 543 (2MH)+ HPLC: 100% RT: 3.6 min 1H NMR (360 MHz, MeOH) d ppm 7.17-7.33 (6H, m), 6.84-6.89 (2H, m), 6.76-6.82 (1H, m), 4.74 (1H, s), 3.98 (2H, q, J = 7.11 Hz), 1.34 (3H, t, J = 7.04 Hz) |
| 3-23 | N-hydroxy-2-phenyl-2-(3-(prop-2-ynyloxy)phenyl)acetamide | LRMS (ESI): (calc) 281.3059 (found) 282 (MH)+ HPLC: 94% RT: 3.53 min |
| 3-24 | 2-(3-(allyloxy)phenyl)-N-hydroxy-2-phenylacetamide | LRMS (ESI): (calc) 283.3217 (found) 567 (2MH)+ HPLC: 97% RT: 3.72 min |
| 3-25 | 2-(3-(cyclopropylmethoxy)phenyl)-N-hydroxy-2-phenylacetamide | LRMS (ESI): (calc) 297.3483 (found) 595 (2MH)+ HPLC: 100% RT: 3.83 min |
| 3-26 | 2-(3-(but-3-enyloxy)phenyl)-N-hydroxy-2-phenylacetamide | LRMS (ESI): (calc) 297.3483 (found) 595 (2MH)+ HPLC: 86% RT: 3.91 min |
| 3-27 | N-hydroxy-2-(3-(2-methoxyethoxy)phenyl)-2-phenylacetamide | LRMS (ESI): (calc) 301.337 (found) 603 (2MH)+ HPLC: 90% RT: 3.37 min |
| 3-28 | 2-(3-((3,5-dimethylisoxazol-4-yl)methoxy)phenyl)-N-hydroxy-2-phenylacetamide | LRMS (ESI): (calc) 352.3838 (found) 353 (MH)+ HPLC: 98% RT: 3.62 min |
| 3-29 | 2-(3-(cyclopentyloxy)phenyl)-N-hydroxy-2-phenylacetamide | LRMS (ESI): (calc) 311.3749 (found) 623 (2MH)+ HPLC: 100% RT: 4.09 min |
| 3-30 | N-hydroxy-2-(3-(isopentyloxy)phenyl)-2-phenylacetamide | LRMS (ESI): (calc) 313.3908 (found) 627 (2MH)+ HPLC: 98% RT: 4.3 min |
| 3-31 | 2-(3-(2-ethylbutoxy)phenyl)-N-hydroxy-2-phenylacetamide | LRMS (ESI): (calc) 327.4174 (found) 655 (2MH)+ HPLC: 89% RT: 4.52 min |
| 3-32 | 2-(3-(cyclohexylmethoxy)phenyl)-N-hydroxy-2-phenylacetamide | LRMS (ESI): (calc) 339.4281 (found) 679 (2MH)+ HPLC: 100% RT: 4.63 min |
| 3-33 | N-hydroxy-2-(3-(3-methylbenzyloxy)phenyl)-2-phenylacetamide | LRMS (ESI): (calc) 347.407 (found) 695 (2MH)+ HPLC: 94% RT: 4.26 min |
| 3-34 | 2-(3-(2-fluorobenzyloxy)phenyl)-N-hydroxy-2-phenylacetamide | LRMS (ESI): (calc) 351.3709 (found) 352 (MH)+ HPLC: 93% RT: 4.08 min |

TABLE III-continued

Compounds prepared according general Schemes 20 and 21 and other Schemes.

| Cpd # | Name | Characterization |
|---|---|---|
| 3-35 | 2-(3-(3,5-dimethylbenzyloxy)phenyl)-N-hydroxy-2-phenylacetamide | LRMS (ESI): (calc) 361.4336 (found) 723 (2MH)+ HPLC: 93% RT: 4.46 min |
| 3-36 | N-hydroxy-2-phenyl-2-(3-(3-phenylpropoxy)phenyl)acetamide | LRMS (ESI): (calc) 361.4336 (found) 723 (2MH)+ HPLC: 95% RT: 4.42 min |
| 3-37 | 2-(3-(2-chlorobenzyloxy)phenyl)-N-hydroxy-2-phenylacetamide | LRMS (ESI): (calc) 367.8255 (found) 735 (2MH)+ HPLC: 93% RT: 4.28 min |
| 3-38 | 2-(3-(2,4-difluorobenzyloxy)phenyl)-N-hydroxy-2-phenylacetamide | LRMS (ESI): (calc) 369.3613 (found) 739 (2MH)+ HPLC: 95% RT: 4.14 min |
| 3-39 | 2-(3-(2-(benzyloxy)ethoxy)phenyl)-N-hydroxy-2-phenylacetamide | LRMS (ESI): (calc) 377.433 (found) 755 (2MH)+ HPLC: 87% RT: 4.08 min |
| 3-40 | 2-(3-(2-(4-fluorophenoxy)ethoxy)phenyl)-N-hydroxy-2-phenylacetamide | LRMS (ESI): (calc) 381.3969 (found) 382 (MH)+ HPLC: 95% RT: 4.12 min |
| 3-41 | 2-(3-(4-tert-butylbenzyloxy)phenyl)-N-hydroxy-2-phenylacetamide | LRMS (ESI): (calc) 389.4867 (found) 779 (2MH)+ HPLC: 96% RT: 4.78 min |
| 3-42 | N-hydroxy-2-phenyl-2-(3-(3-(trifluoromethyl)benzyloxy)phenyl)acetamide | LRMS (ESI): (calc) 401.3784 (found) 402 (MH)+ HPLC: 96% RT: 4.38 min |
| 3-43 | N-hydroxy-2-(4-methoxyphenyl)-2-phenylacetamide | LRMS (ESI): (calc) 257.2845 (found) 258 (MH)+ HPLC: 100% RT: 3.37 min |
| 3-44 | 2-(4-ethoxyphenyl)-N-hydroxy-2-phenylacetamide | LRMS (ESI): (calc) 271.311 (found) 272 (MH)+ HPLC: 91% RT: 3.6 min |
| 3-45 | N-hydroxy-2-phenyl-2-(4-(prop-2-ynyloxy)phenyl)acetamide | LRMS (ESI): (calc) 281.3059 (found) 282 (MH)+ HPLC: 99% RT: 3.53 min |
| 3-46 | 2-(4-(allyloxy)phenyl)-N-hydroxy-2-phenylacetamide | LRMS (ESI): (calc) 283.3217 (found) 284 (MH)+ HPLC: 87% RT: 3.71 min 1H NMR (400 MHz, MeOD) d ppm 7.26-7.31 (4H, m), 7.20-7.25 (3H, m), 6.87 (2H, d, J = 8.80 Hz), 5.99-6.09 (1H, m), 5.34-5.41 (1H, m, J = 17.30, 1.62, 1.62, 1.47 Hz), 5.20-5.25 (1H, m, J = 10.51, 1.59, 1.59, 1.47 Hz), 4.71 (1H, s), 4.51 (2H, d |
| 3-47 | N-hydroxy-2-(4-isopropoxyphenyl)-2-phenylacetamide | LRMS (ESI): (calc) 285.3376 (found) 571 (2MH)+ HPLC: 90% RT: 3.75 min |
| 3-48 | 2-(4-(cyclopropylmethoxy)phenyl)-N-hydroxy-2-phenylacetamide | LRMS (ESI): (calc) 297.3483 (found) 298 (MH)+ HPLC: 98% RT: 3.82 min |
| 3-49 | 2-(4-(but-3-enyloxy)phenyl)-N-hydroxy-2-phenylacetamide | LRMS (ESI): (calc) 297.3483 (found) 298 (MH)+ HPLC: 97% RT: 3.92 min |
| 3-50 | N-hydroxy-2-(4-(2-methoxyethoxy)phenyl)-2-phenylacetamide | LRMS (ESI): (calc) 301.337 (found) 603 (2MH)+ HPLC: 93% RT: 3.34 min |
| 3-51 | 2-(4-((3,5-dimethylisoxazol-4-yl)methoxy)phenyl)-N-hydroxy-2-phenylacetamide | LRMS (ESI): (calc) 352.3838 (found) 353 (MH)+ HPLC: 86% RT: 3.62 min |
| 3-52 | N-hydroxy-2-(4-(3-methylbut-2-enyloxy)phenyl)-2-phenylacetamide | LRMS (ESI): (calc) 311.3749 (found) 312 (MH)+ HPLC: 88% RT: 4.08 min |
| 3-53 | 2-(4-(cyclopentyloxy)phenyl)-N-hydroxy-2-phenylacetamide | LRMS (ESI): (calc) 311.3749 (found) 312 (MH)+ HPLC: 100% RT: 4.11 min |
| 3-54 | N-hydroxy-2-(4-(isopentyloxy)phenyl)-2-phenylacetamide | LRMS (ESI): (calc) 313.3908 (found) 627 (MH)+ HPLC: 86% RT: 4.31 min 1H NMR (400 MHz, MeOD) d ppm 7.25-7.32 (4H, m), 7.17-7.25 (3H, m), 6.84 (2H, d, J = 8.80 Hz), 4.71 (1H, s), 3.97 (2H, t, J = 6.60 Hz), 1.76-1.88 (1H, m), 1.58-1.67 (2H, m), 0.96 (6H, d, J = 6.85 Hz) |
| 3-55 | 2-(4-(2-ethylbutoxy)phenyl)-N-hydroxy-2-phenylacetamide | LRMS (ESI): (calc) 327.4174 (found) 655 (2MH)+ HPLC: 91% RT: 4.56 min |
| 3-56 | N-hydroxy-2-(4-(4-methylpentyloxy)phenyl)-2-phenylacetamide | LRMS (ESI): (calc) 327.4174 (found) 328 (MH)+ HPLC: 92% RT: 4.55 min 1H NMR (400 MHz, MeOD) d ppm 7.26-7.31 (4H, m), 7.17-7.25 (3H, m), 6.84 (2H, d, J = 8.80 Hz), 4.71 (1H, s), 3.93 (2H, t, J = 6.60 Hz), 1.71-1.80 (2H, m), 1.53-1.66 (1H, m), 1.28-1.38 (2H, m), 0.93 (6H, d, J = 6.85 Hz) |
| 3-57 | 2-(4-(cyclohexylmethoxy)phenyl)-N-hydroxy-2-phenylacetamide | LRMS (ESI): (calc) 339.4281 (found) 340 (MH)+ HPLC: 93% RT: 4.65 min |
| 3-58 | N-hydroxy-2-(4-(3-methylbenzyloxy)phenyl)-2-phenylacetamide | LRMS (ESI): (calc) 347.407 (found) 695 (2MH)+ HPLC: 100% RT: 4.26 min |

TABLE III-continued

Compounds prepared according general Schemes 20 and 21 and other Schemes.

| Cpd # | Name | Characterization |
|---|---|---|
| 3-59 | N-hydroxy-2-phenyl-2-(4-(1-phenylethoxy)phenyl)acetamide | LRMS (ESI): (calc) 347.407 (found) 695 (2MH)+ HPLC: 86% RT: 4.17 min 1H NMR (400 MHz, MeOD) d ppm 7.17-7.36 (10H, m), 7.05-7.14 (2H, m), 6.79 (2H, d, J = 8.80 Hz), 5.34 (1H, q, J = 6.36 Hz), 4.65 (1H, s), 1.56 (3H, d, J = 6.36 Hz) |
| 3-60 | 2-(4-(2-fluorobenzyloxy)phenyl)-N-hydroxy-2-phenylacetamide | LRMS (ESI): (calc) 351.3709 (found) 703 (2MH)+ HPLC: 100% RT: 4.1 min |
| 3-61 | 2-(4-(2-cyanobenzyloxy)phenyl)-N-hydroxy-2-phenylacetamide | LRMS (ESI): (calc) 358.3899 (found) 717 (2MH)+ HPLC: 100% RT: 3.89 min |
| 3-62 | 2-(4-(3,5-dimethylbenzyloxy)phenyl)-N-hydroxy-2-phenylacetamide | LRMS (ESI): (calc) 361.4336 (found) 723 (2MH)+ HPLC: 86% RT: 4.46 min 1H NMR (400 MHz, MeOD) d ppm 7.26-7.31 (4H, m), 7.18-7.25 (3H, m), 7.01 (2H, s), 6.85-6.96 (3H, m), 4.96 (2H, s), 4.71 (1H, s), 2.28 (6H, s) |
| 3-63 | N-hydroxy-2-phenyl-2-(4-(3-phenylpropoxy)phenyl)acetamide | LRMS (ESI): (calc) 361.4336 (found) 362 (MH)+ HPLC: 90% RT: 4.41 min |
| 3-64 | N-hydroxy-2-(4-(2-phenoxyethoxy)phenyl)-2-phenylacetamide | LRMS (ESI): (calc) 363.4064 (found) 727 (2MH)+ HPLC: 100% RT: 4.08 min |
| 3-65 | 2-(4-(2-chlorobenzyloxy)phenyl)-N-hydroxy-2-phenylacetamide | LRMS (ESI): (calc) 367.8255 (found) 368 (MH)+ HPLC: 100% RT: 4.29 min |
| 3-66 | 2-(4-(3-chlorobenzyloxy)phenyl)-N-hydroxy-2-phenylacetamide | LRMS (ESI): (calc) 367.8255 (found) 368 (MH)+ HPLC: 88% RT: 4.31 min |
| 3-67 | 2-(4-(2,4-difluorobenzyloxy)phenyl)-N-hydroxy-2-phenylacetamide | LRMS (ESI): (calc) 369.3613 (found) 370 (MH)+ HPLC: 86% RT: 4.15 min |
| 3-68 | 2-(4-(2-(benzyloxy)ethoxy)phenyl)-N-hydroxy-2-phenylacetamide | LRMS (ESI): (calc) 377.433 (found) 755 (2MH)+ HPLC: 88% RT: 4.08 min |
| 3-69 | 2-(4-(2-(4-fluorophenoxy)ethoxy)phenyl)-N-hydroxy-2-phenylacetamide | LRMS (ESI): (calc) 381.3969 (found) 382 (MH)+ HPLC: 100% RT: 4.12 min |
| 3-70 | 2-(4-(4-tert-butylbenzyloxy)phenyl)-N-hydroxy-2-phenylacetamide | LRMS (ESI): (calc) 389.4867 (found) 390 (MH)+ HPLC: 90% RT: 4.8 min |
| 3-71 | N-hydroxy-2-phenyl-2-(4-(3-(trifluoromethyl)benzyloxy)phenyl)acetamide | LRMS (ESI): (calc) 401.3784 (found) 402 (MH)+ HPLC: 85% RT: 4.38 min |
| 3-72 | N-hydroxy-2-(3-(isopropylamino)phenyl)-2-phenylacetamide | LRMS (ESI): (calc) 284.3529 (found) 285 (MH)+ HPLC: 90% RT: 2.53 min |
| 373 | N-hydroxy-2-phenyl-2-(3-(phenylamino)phenyl)acetamide | LRMS (ESI): (calc) 318.3691 (found) 319 (MH)+ HPLC: 94% RT: 3.93 min |
| 3-74 | N-hydroxy-2-phenyl-2-(3-(pyridin-2-ylmethylamino)phenyl)acetamide | LRMS (ESI): (calc) 333.3837 (found) 334 (MH)+ HPLC: 91% RT: 2.56 min |
| 3-75 | 2-(3-(4-acetylpiperazin-1-yl)phenyl)-N-hydroxy-2-phenylacetamide | LRMS (ESI): (calc) 353.4149 (found) 354 (MH)+ HPLC: 90% RT: 3.13 min |
| 3-76 | N-hydroxy-2-phenyl-2-(3-(4-(pyrrolidin-1-yl)piperidin-1-yl)phenyl)acetamide | LRMS (ESI): (calc) 379.4952 (found) 380 (MH)+ HPLC: 85% RT: 2.61 min |
| 3-77 | 2-(3-(4-benzylpiperidin-1-yl)phenyl)-N-hydroxy-2-phenylacetamide | LRMS (ESI): (calc) 400.5127 (found) 401 (MH)+ HPLC: 87% RT: 3.57 min |
| 3-78 | 2-(3-(4-(4-fluorophenyl)piperazin-1-yl)phenyl)-N-hydroxy-2-phenylacetamide | LRMS (ESI): (calc) 405.4646 (found) 406 (MH)+ HPLC: 93% RT: 4.06 min |
| 3-79 | N-hydroxy-2-(4-(isopropylamino)phenyl)-2-phenylacetamide | LRMS (ESI): (calc) 284.3529 (found) 285 (MH)+ HPLC: 93% RT: 2.48 min |
| 3-80 | N-hydroxy-2-phenyl-2-(4-(phenylamino)phenyl)acetamide | LRMS (ESI): (calc) 318.3691 (found) 319 (MH)+ HPLC: 98% RT: 3.92 min 1H NMR (400 MHz, MeOD) d ppm 7.27-7.34 (4H, m), 7.15-7.25 (5H, m), 6.99-7.09 (4H, m), 6.79-6.85 (1H, m), 4.70 (1H, s) |
| 3-81 | N-hydroxy-2-phenyl-2-(4-(pyridin-2-ylmethylamino)phenyl)acetamide | LRMS (ESI): (calc) 333.3837 (found) 334 (MH)+ HPLC: 92% RT: 2.54 min |
| 3-82 | 2-(4-(4-acetylpiperazin-1-yl)phenyl)-N-hydroxy-2-phenylacetamide | LRMS (ESI): (calc) 353.4149 (found) 354 (MH)+ HPLC: 91% RT: 3.07 min |
| 3-83 | N-hydroxy-2-phenyl-2-(4-(4-(pyrrolidin-1-yl)piperidin-1-yl)phenyl)acetamide | LRMS (ESI): (calc) 379.4952 (found) 380 (MH)+ HPLC: 91% RT: 2.54 min |

TABLE III-continued

Compounds prepared according general Schemes 20 and 21 and other Schemes.

| Cpd # | Name | Characterization |
|---|---|---|
| 3-84 | 2-(4-(4-(4-fluorophenyl)piperazin-1-yl)phenyl)-N-hydroxy-2-phenylacetamide | LRMS (ESI): (calc) 405.4646 (found) 406 (MH)+ HPLC: 92% RT: 4.04 min |
| 3-85 | (E)-2-(4-(cinnamyloxy)phenyl)-N-hydroxy-2-phenylacetamide | LRMS (ESI): (calc) 359.4177 (found) 360 (MH)+ HPLC: 85% RT: 4.31 min |
| 3-86 | N-hydroxy-2-phenyl-2-(4-(3-(trifluoromethoxy)benzyloxy)phenyl)acetamide | LRMS (ESI): (calc) 417.3778 (found) 418 (MH)+ HPLC: 94% RT: 4.47 min |
| 3-87 | N-hydroxy-2-phenyl-2-(3-(3-(trifluoromethoxy)benzyloxy)phenyl)acetamide | LRMS (ESI): (calc) 417.3778 (found) 418 (MH)+ HPLC: 92% RT: 4.47 min |
| 3-88 | 2-(3-(2-(dimethylamino)ethoxy)phenyl)-N-hydroxy-2-phenylacetamide | LRMS (ESI): (calc) 314.3788 (found) 315 (MH)+ HPLC: 100% RT: 2.44 min 1H NMR (400 MHz, MeOD) d ppm 7.24-7.36 (6H, m), 6.92-7.03 (3H, m), 4.80 (1H, s), 4.26-4.34 (2H, m), 3.54-3.59 (2H, m), 2.96 (6H, s) |
| 3-89 | N-hydroxy-2-(3-(2-(2-methoxyethoxy)ethoxy)phenyl)-2-phenylacetamide | LRMS (ESI): (calc) 345.3896 (found) 691 (2MH)+ HPLC: 89% RT: 3.4 min |
| 3-90 | N-hydroxy-2-(4-(2-(2-methoxyethoxy)ethoxy)phenyl)-2-phenylacetamide | LRMS (ESI): (calc) 345.3896 (found) 346 (MH)+ HPLC: 91% RT: 3.36 min |

TABLE IV

Compounds prepared according general Schemes 20 and 21 and other Schemes.

| Cpd # | Name | Characterization |
|---|---|---|
| 4-1 | 2-(3-(3-fluorobenzylamino)phenyl)-N-hydroxy-2-phenylacetamide | LRMS (ESI): (calc) 350.386 (found) 351 [M + H]+ HPLC: 89% RT: 3.91 min |
| 4-3 | 2-(4-(4-chlorobenzylamino)phenyl)-N-hydroxy-2-phenylacetamide | LRMS (ESI): (calc) 366.841 (found) 367 [M + H]+ HPLC: 87% RT: 4.1 min |
| 4-4 | N-(4-(2-(hydroxyamino)-2-oxo-1-phenylethyl)phenyl)propionamide | LRMS (ESI): (calc) 298.336 (found) 299 [M + H]+ HPLC: 100% RT: 3.07 min |
| 4-5 | N-(4-(2-(hydroxyamino)-2-oxo-1-phenylethyl)phenyl)cyclopropanecarboxamide | LRMS (ESI): (calc) 310.347 (found) 311 [M + H]+ HPLC: 93% RT: 3.2 min |
| 4-6 | N-(4-(2-(hydroxyamino)-2-oxo-1-phenylethyl)phenyl)butyramide | LRMS (ESI): (calc) 312.363 (found) 313 [M + H]+ HPLC: 100% RT: 3.29 min 1H NMR (250 MHz, MeOD) d ppm 7.50 (2H, d, J = 8.68 Hz), 7.20-7.34 (7H, m), 4.75 (1H, s), 2.33 (2H, t, J = 7.39 Hz), 1.63-1.78 (2H, m), 0.99 (3H, t, J = 7.39 Hz) |
| 4-8 | N-(4-(2-(hydroxyamino)-2-oxo-1-phenylethyl)phenyl)isobutyramide | LRMS (ESI): (calc) 312.363 (found) 313 [M + H]+ HPLC: 93% RT: 3.26 min |
| 4-9 | N-hydroxy-2-(4-(2-methoxyacetamido)phenyl)-2-phenylacetamide | LRMS (ESI): (calc) 314.336 (found) 315 [M + H]+ HPLC: 100% RT: 3.02 min 1H NMR (250 MHz, MeOD) d ppm 7.55 (2H, d, J = 8.68 Hz), 7.30 (2H, d, J = 2.44 Hz), 7.20-7.35 (5H, m), 4.77 (1H, s), 4.01 (2H, s), 3.46 (3H, s) |
| 4-10 | N-hydroxy-2-(3-(2-methoxyacetamido)phenyl)-2-phenylacetamide | LRMS (ESI): (calc) 314.336 (found) 315 [M + H]+ HPLC: 100% RT: 3.06 min |
| 4-11 | N-(4-(2-(hydroxyamino)-2-oxo-1-phenylethyl)phenyl)-3-methylbut-2-enamide | LRMS (ESI): (calc) 324.374 (found) 325 [M + H]+ HPLC: 100% RT: 3.48 min |
| 4-12 | N-(4-(2-(hydroxyamino)-2-oxo-1-phenylethyl)phenyl)cyclobutanecarboxamide | LRMS (ESI): (calc) 324.374 (found) 325 [M + H]+ HPLC: 100% RT: 3.48 min |
| 4-13 | N-(4-(2-(hydroxyamino)-2-oxo-1-phenylethyl)phenyl)-2-methylbutanamide | LRMS (ESI): (calc) 326.39 (found) 327 [M + H]+ HPLC: 90% RT: 3.45 min |
| 4-14 | N-(3-(2-(hydroxyamino)-2-oxo-1-phenylethyl)phenyl)-2-methylbutanamide | LRMS (ESI): (calc) 326.39 (found) 327 [M + H]+ HPLC: 88% RT: 3.51 min |
| 4-15 | N-(4-(2-(hydroxyamino)-2-oxo-1-phenylethyl)phenyl)pivalamide | LRMS (ESI): (calc) 326.39 (found) 327 [M + H]+ HPLC: 95% RT: 3.6 min |

TABLE IV-continued

Compounds prepared according general Schemes 20 and 21 and other Schemes.

| Cpd # | Name | Characterization |
|---|---|---|
| 4-16 | N-(3-(2-(hydroxyamino)-2-oxo-1-phenylethyl)phenyl)pivalamide | LRMS (ESI): (calc) 326.39 (found) 327 [M + H]+ HPLC: 91% RT: 3.52 min |
| 4-17 | N-(4-(2-(hydroxyamino)-2-oxo-1-phenylethyl)phenyl)furan-2-carboxamide | LRMS (ESI): (calc) 336.341 (found) 337 [M + H]+ HPLC: 100% RT: 3.3 min |
| 4-18 | N-(4-(2-(hydroxyamino)-2-oxo-1-phenylethyl)phenyl)furan-3-carboxamide | LRMS (ESI): (calc) 336.341 (found) 337 [M + H]+ HPLC: 100% RT: 3.42 min |
| 4-19 | N-(4-(2-(hydroxyamino)-2-oxo-1-phenylethyl)phenyl)pyrrolidine-1-carboxamide | LRMS (ESI): (calc) 339.388 (found) 340 [M + H]+ HPLC: 90% RT: 3.28 min |
| 4-20 | N-(4-(2-(hydroxyamino)-2-oxo-1-phenylethyl)phenyl)-3,3-dimethylbutanamide | LRMS (ESI): (calc) 340.416 (found) 341 [M + H]+ HPLC: 95% RT: 3.64 min 1H NMR (250 MHz, MeOD) d ppm 7.45 (2H, d, J = 8.68 Hz), 7.13-7.33 (7H, m), 4.72 (1H, s), 2.18 (2H, s), 1.02 (9H, s) |
| 4-21 | N-(3-(2-(hydroxyamino)-2-oxo-1-phenylethyl)phenyl)-3,3-dimethylbutanamide | LRMS (ESI): (calc) 340.416 (found) 341 [M + H]+ HPLC: 98% RT: 3.67 min |
| 4-22 | 2-ethyl-N-(4-(2-(hydroxyamino)-2-oxo-1-phenylethyl)phenyl)butanamide | LRMS (ESI): (calc) 340.416 (found) 341 [M + H]+ HPLC: 92% RT: 3.61 min |
| 4-23 | 2-ethyl-N-(3-(2-(hydroxyamino)-2-oxo-1-phenylethyl)phenyl)butanamide | LRMS (ESI): (calc) 340.416 (found) 341 [M + H]+ HPLC: 87% RT: 3.75 min |
| 4-24 | N-(4-(2-(hydroxyamino)-2-oxo-1-phenylethyl)phenyl)-2,2-dimethylbutanamide | LRMS (ESI): (calc) 340.416 (found) 341 [M + H]+ HPLC: 95% RT: 3.66 min |
| 4-25 | N-(4-(2-(hydroxyamino)-2-oxo-1-phenylethyl)phenyl)-2-methylpentanamide | LRMS (ESI): (calc) 340.416 (found) 341 [M + H]+ HPLC: 95% RT: 3.67 min |
| 4-26 | N-(4-(2-(hydroxyamino)-2-oxo-1-phenylethyl)phenyl)isonicotinamide | LRMS (ESI): (calc) 347.367 (found) 348 [M + H]+ HPLC: 88% RT: 2.9 min |
| 4-27 | N-(4-(2-(hydroxyamino)-2-oxo-1-phenylethyl)phenyl)-5-methylisoxazole-3-carboxamide | LRMS (ESI): (calc) 351.356 (found) 352 [M + H]+ HPLC: 94% RT: 3.55 min |
| 4-28 | N-(4-(2-(hydroxyamino)-2-oxo-1-phenylethyl)phenyl)thiophene-2-carboxamide | LRMS (ESI): (calc) 352.407 (found) 353 [M + H]+ HPLC: 99% RT: 3.5 min |
| 4-29 | N-(3-(2-(hydroxyamino)-2-oxo-1-phenylethyl)phenyl)thiophene-2-carboxamide | LRMS (ESI): (calc) 352.407 (found) 353 [M + H]+ HPLC: 95% RT: 3.55 min 1H NMR (250 MHz, MeOD) d ppm 7.84 (1H, d, J = 3.65 Hz), 7.66 (1H, d, J = 5.03 Hz), 7.55-7.62 (2H, m), 7.18-7.35 (6H, m), 7.04-7.15 (2H, m), 4.77 (1H, s) |
| 4-31 | N-(4-(2-(hydroxyamino)-2-oxo-1-phenylethyl)phenyl)tetrahydro-2H-pyran-4-carboxamide | LRMS (ESI): (calc) 354.4 (found) 355 [M + H]+ HPLC: 96% RT: 3.05 min |
| 4-32 | N-(4-(2-(hydroxyamino)-2-oxo-1-phenylethyl)phenyl)morpholine-4-carboxamide | LRMS (ESI): (calc) 355.388 (found) 356 [M + H]+ HPLC: 90% RT: 2.97 min |
| 4-33 | N-(4-(2-(hydroxyamino)-2-oxo-1-phenylethyl)phenyl)-4-methylbenzamide | LRMS (ESI): (calc) 360.406 (found) 361 [M + H]+ HPLC: 98% RT: 3.73 min |
| 4-34 | N-(4-(2-(hydroxyamino)-2-oxo-1-phenylethyl)phenyl)-2-methylbenzamide | LRMS (ESI): (calc) 360.406 (found) 361 [M + H]+ HPLC: 100% RT: 3.62 min |
| 4-35 | N-(4-(2-(hydroxyamino)-2-oxo-1-phenylethyl)phenyl)-3-methylbenzamide | LRMS (ESI): (calc) 360.406 (found) 361 [M + H]+ HPLC: 98% RT: 3.84 min |
| 4-36 | N-(3-(2-(hydroxyamino)-2-oxo-1-phenylethyl)phenyl)-3-methylbenzamide | LRMS (ESI): (calc) 360.406 (found) 361 [M + H]+ HPLC: 90% RT: 3.78 min |
| 4-37 | 5-chloro-N-(4-(2-(hydroxyamino)-2-oxo-1-phenylethyl)phenyl)pentanamide | LRMS (ESI): (calc) 360.835 (found) 361 [M + H]+ HPLC: 92% RT: 3.53 min |

TABLE IV-continued

Compounds prepared according general Schemes 20 and 21 and other Schemes.

| Cpd # | Name | Characterization |
|---|---|---|
| 4-38 | 2-fluoro-N-(4-(2-(hydroxyamino)-2-oxo-1-phenylethyl)phenyl)benzamide | LRMS (ESI): (calc) 364.37 (found) 365 [M + H]+ HPLC: 97% RT: 3.68 min |
| 4-39 | 2-fluoro-N-(3-(2-(hydroxyamino)-2-oxo-1-phenylethyl)phenyl)benzamide | LRMS (ESI): (calc) 364.37 (found) 365 [M + H]+ HPLC: 91% RT: 3.62 min |
| 4-40 | 3-fluoro-N-(4-(2-(hydroxyamino)-2-oxo-1-phenylethyl)phenyl)benzamide | LRMS (ESI): (calc) 364.37 (found) 365 [M + H]+ HPLC: 100% RT: 3.66 min |
| 4-41 | N-(4-(2-(hydroxyamino)-2-oxo-1-phenylethyl)phenyl)-1,3-dimethyl-1H-pyrazole-5-carboxamide | LRMS (ESI): (calc) 364.398 (found) 365 [M + H]+ HPLC: 88% RT: 3.34 min |
| 4-42 | N-hydroxy-2-phenyl-2-(4-(2-(thiophen-2-yl)acetamido)phenyl)acetamide | LRMS (ESI): (calc) 366.434 (found) 367 [M + H]+ HPLC: 93% RT: 3.5 min |
| 4-43 | N-hydroxy-2-phenyl-2-(3-(2-(thiophen-2-yl)acetamido)phenyl)acetamide | LRMS (ESI): (calc) 366.434 (found) 367 [M + H]+ HPLC: 87% RT: 3.57 min |
| 4-44 | 3-cyclopentyl-N-(4-(2-(hydroxyamino)-2-oxo-1-phenylethyl)phenyl)propanamide | LRMS (ESI): (calc) 366.453 (found) 367 [M + H]+ HPLC: 93% RT: 3.97 min |
| 4-45 | 3-cyclopentyl-N-(3-(2-(hydroxyamino)-2-oxo-1-phenylethyl)phenyl)propanamide | LRMS (ESI): (calc) 366.453 (found) 367 [M + H]+ HPLC: 99% RT: 3.99 min 1H NMR (250 MHz, MeOD) d ppm 7.46 (1H, d, J = 1.98 Hz), 7.50 (1H, s), 7.15-7.33 (6H, m), 7.02 (1H, d, J = 7.77 Hz), 4.73 (1H, s), 2.25-2.37 (2H, m), 1.45-1.82 (9H, m), 1.02-1.19 (2H, m) |
| 4-46 | N-(4-(2-(hydroxyamino)-2-oxo-1-phenylethyl)phenyl)cinnamamide | LRMS (ESI): (calc) 372.417 (found) 373 [M + H]+ HPLC: 100% RT: 3.89 min |
| 4-47 | N-(4-(2-(hydroxyamino)-2-oxo-1-phenylethyl)phenyl)-3-phenylpropanamide | LRMS (ESI): (calc) 374.432 (found) 375 [M + H]+ HPLC: 92% RT: 3.71 min |
| 4-48 | N-(3-(2-(hydroxyamino)-2-oxo-1-phenylethyl)phenyl)-3-phenylpropanamide | LRMS (ESI): (calc) 374.432 (found) 375 [M + H]+ HPLC: 98% RT: 3.85 min |
| 4-49 | N-(4-(2-(hydroxyamino)-2-oxo-1-phenylethyl)phenyl)-3,4-dimethylbenzamide | LRMS (ESI): (calc) 374.432 (found) 375 [M + H]+ HPLC: 95% RT: 3.88 min 1H NMR (250 MHz, MeOD) d ppm 7.58-7.73 (4H, m), 7.17-7.37 (8H, m), 4.78 (1H, s), 2.33 (3H, s), 2.33 (3H, s) |
| 4-50 | N-(3-(2-(hydroxyamino)-2-oxo-1-phenylethyl)phenyl)-3,4-dimethylbenzamide | LRMS (ESI): (calc) 374.432 (found) 375 [M + H]+ HPLC: 91% RT: 3.93 min |
| 4-51 | 4-ethyl-N-(4-(2-(hydroxyamino)-2-oxo-1-phenylethyl)phenyl)benzamide | LRMS (ESI): (calc) 374.432 (found) 375 [M + H]+ HPLC: 92% RT: 3.93 min |
| 4-52 | 4-ethyl-N-(3-(2-(hydroxyamino)-2-oxo-1-phenylethyl)phenyl)benzamide | LRMS (ESI): (calc) 374.432 (found) 375 [M + H]+ HPLC: 91% RT: 3.96 min |
| 4-53 | N-(4-(2-(hydroxyamino)-2-oxo-1-phenylethyl)phenyl)-3-methoxybenzamide | LRMS (ESI): (calc) 376.405 (found) 377 [M + H]+ HPLC: 100% RT: 3.63 min |
| 4-54 | 2-(4-(2-(4-fluorophenyl)acetamido)phenyl)-N-hydroxy-2-phenylacetamide | LRMS (ESI): (calc) 378.396 (found) 379 [M + H]+ HPLC: 95% RT: 3.64 min |
| 4-55 | 2-(3-(2-(4-fluorophenyl)acetamido)phenyl)-N-hydroxy-2-phenylacetamide | LRMS (ESI): (calc) 378.396 (found) 379 [M + H]+ HPLC: 88% RT: 3.69 min |
| 4-56 | 5-fluoro-N-(4-(2-(hydroxyamino)-2-oxo-1-phenylethyl)phenyl)-2-methylbenzamide | LRMS (ESI): (calc) 378.396 (found) 379 [M + H]+ HPLC: 98% RT: 3.72 min |
| 4-58 | 3-fluoro-N-(4-(2-(hydroxyamino)-2-oxo-1-phenylethyl)phenyl)-4-methylbenzamide | LRMS (ESI): (calc) 378.396 (found) 379 [M + H]+ HPLC: 88% RT: 3.83 min |
| 4-59 | 4-fluoro-N-(4-(2-(hydroxyamino)-2-oxo-1-phenylethyl)phenyl)-3-methylbenzamide | LRMS (ESI): (calc) 378.396 (found) 379 [M + H]+ HPLC: 94% RT: 3.83 min |
| 5-60 | 2-chloro-N-(3-(2-(hydroxyamino)-2-oxo-1-phenylethyl)phenyl)benzamide | LRMS (ESI): (calc) 380.824 (found) 381 [M + H]+ HPLC: 91% RT: 3.64 min |

TABLE IV-continued

Compounds prepared according general Schemes 20 and 21 and other Schemes.

| Cpd # | Name | Characterization |
|---|---|---|
| 4-61 | 4-chloro-N-(4-(2-(hydroxyamino)-2-oxo-1-phenylethyl)phenyl)benzamide | LRMS (ESI): (calc) 380.824 (found) 381 [M + H]+ HPLC: 98% RT: 3.83 min |
| 4-62 | 6-chloro-N-(4-(2-(hydroxyamino)-2-oxo-1-phenylethyl)phenyl)nicotinamide | LRMS (ESI): (calc) 381.812 (found) 382 [M + H]+ HPLC: 100% RT: 3.48 min 1H NMR (250 MHz, MeOD) d ppm 8.90 (1H, d, J = 1.83 Hz), 8.30 (1H, dd, J = 8.38, 2.28 Hz), 7.56-7.71 (3H, m), 7.21-7.39 (7H, m), 4.79 (1H, s) |
| 4-63 | 3,4-difluoro-N-(4-(2-(hydroxyamino)-2-oxo-1-phenylethyl)phenyl)benzamide | LRMS (ESI): (calc) 382.36 (found) 383 [M + H]+ HPLC: 92% RT: 3.75 min |
| 4-64 | 3,4-difluoro-N-(3-(2-(hydroxyamino)-2-oxo-1-phenylethyl)phenyl)benzamide | LRMS (ESI): (calc) 382.36 (found) 383 [M + H]+ HPLC: 100% RT: 3.9 min |
| 4-65 | 3,5-difluoro-N-(4-(2-(hydroxyamino)-2-oxo-1-phenylethyl)phenyl)benzamide | LRMS (ESI): (calc) 382.36 (found) 383 [M + H]+ HPLC: 95% RT: 3.78 min |
| 4-66 | 2,5-difluoro-N-(4-(2-(hydroxyamino)-2-oxo-1-phenylethyl)phenyl)benzamide | LRMS (ESI): (calc) 382.36 (found) 383 [M + H]+ HPLC: 99% RT: 3.67 min |
| 4-67 | 5-chloro-N-(4-(2-(hydroxyamino)-2-oxo-1-phenylethyl)phenyl)-1-methyl-1H-pyrazole-4-carboxamide | LRMS (ESI): (calc) 384.816 (found) 385 [M + H]+ HPLC: 99% RT: 3.27 min |
| 4-68 | N-(4-(2-(hydroxyamino)-2-oxo-1-phenylethyl)phenyl)-2-phenylbutanamide | LRMS (ESI): (calc) 388.459 (found) 389 [M + H]+ HPLC: 94% RT: 3.92 min |
| 4-69 | N-(4-(2-(hydroxyamino)-2-oxo-1-phenylethyl)phenyl)-4-propylbenzamide | LRMS (ESI): (calc) 388.459 (found) 389 [M + H]+ HPLC: 97% RT: 4.14 min |
| 4-70 | N-(3-(2-(hydroxyamino)-2-oxo-1-phenylethyl)phenyl)-4-propylbenzamide | LRMS (ESI): (calc) 388.459 (found) 389 [M + H]+ HPLC: 92% RT: 4.17 min |
| 4-71 | 4-(dimethylamino)-N-(4-(2-(hydroxyamino)-2-oxo-1-phenylethyl)phenyl)benzamide | LRMS (ESI): (calc) 389.447 (found) 390 [M + H]+ HPLC: 95% RT: 3.68 min |
| 4-73 | N-hydroxy-2-(4-(2-(4-methoxyphenyl)acetamido)phenyl)-2-phenylacetamide | LRMS (ESI): (calc) 390.432 (found) 391 [M + H]+ HPLC: 93% RT: 3.57 min |
| 4-74 | N-hydroxy-2-(4-(2-(3-methoxyphenyl)acetamido)phenyl)-2-phenylacetamide | LRMS (ESI): (calc) 390.432 (found) 391 [M + H]+ HPLC: 100% RT: 3.59 min |
| 4.75 | N-hydroxy-2-(3-(2-(3-methoxyphenyl)acetamido)phenyl)-2-phenylacetamide | LRMS (ESI): (calc) 390.432 (found) 391 [M + H]+ HPLC: 90% RT: 3.62 min 1H NMR (250 MHz, MeOD) d ppm 7.43-7.52 (2H m), 7.13-7.32 (7H, m), 7.02 (1H, d, J = 7.77 Hz), 6.82-6.88 (2H, m), 6.67-6.82 (1H, m), 4.72 (1H, s), 3.72 (3H, s), 3.56 (2H, s) |
| 4-76 | N-(4-(2-(hydroxyamino)-2-oxo-1-phenylethyl)phenyl)-2-phenoxypropanamide | LRMS (ESI): (calc) 390.432 (found) 391 [M + H]+ HPLC: 90% RT: 3.78 min |
| 4-78 | 2-(4-(2-(benzyloxy)acetamido)phenyl)-N-hydroxy-2-phenylacetamide | LRMS (ESI): (calc) 390.432 (found) 391 [M + H]+ HPLC: 88% RT: 3.74 min |
| 4-79 | 2-(3-(2-(benzyloxy)acetamido)phenyl)-N-hydroxy-2-phenylacetamide | LRMS (ESI): (calc) 390.432 (found) 391 [M + H]+ HPLC: 100% RT: 3.77 min |
| 4-80 | 4-ethoxy-N-(4-(2-(hydroxyamino)-2-oxo-1-phenylethyl)phenyl)benzamide | LRMS (ESI): (calc) 390.432 (found) 391 [M + H]+ HPLC: 94% RT: 3.78 min |
| 4-81 | 4-ethoxy-N-(3-(2-(hydroxyamino)-2-oxo-1-phenylethyl)phenyl)benzamide | LRMS (ESI): (calc) 390.432 (found) 391 [M + H]+ HPLC: 91% RT: 3.92 min |
| 4-82 | 2-ethoxy-N-(4-(2-(hydroxyamino)-2-oxo-1-phenylethyl)phenyl)benzamide | LRMS (ESI): (calc) 390.432 (found) 391 [M + H]+ HPLC: 91% RT: 3.93 min |
| 4-83 | N-(4-(2-(hydroxyamino)-2-oxo-1-phenylethyl)phenyl)-2-nitrobenzamide | LRMS (ESI): (calc) 391.377 (found) 392 [M + H]+ HPLC: 88% RT: 3.45 min |
| 4-84 | N-(4-(2-(hydroxyamino)-2-oxo-1-phenylethyl)phenyl)-3-nitrobenzamide | LRMS (ESI): (calc) 391.377 (found) 392 [M + H]+ HPLC: 87% RT: 3.65 min |

TABLE IV-continued

Compounds prepared according general Schemes 20 and 21 and other Schemes.

| Cpd # | Name | Characterization |
|---|---|---|
| 4-85 | N-hydroxy-2-phenyl-2-(4-(2-(phenylthio)acetamido)phenyl)acetamide | LRMS (ESI): (calc) 392.471 (found) 393 [M + H]+ HPLC: 100% RT: 3.72 min |
| 4-86 | N-hydroxy-2-phenyl-2-(3-(2-(phenylthio)acetamido)phenyl)acetamide | LRMS (ESI): (calc) 392.471 (found) 393 [M + H]+ HPLC: 100% RT: 3.83 min |
| 4-87 | 3-fluoro-N-(4-(2-(hydroxyamino)-2-oxo-1-phenylethyl)phenyl)-4-methoxybenzamide | LRMS (ESI): (calc) 394.396 (found) 395 [M + H]+ HPLC: 88% RT: 3.65 min |
| 4-88 | 2-(4-(2-(4-chlorophenyl)acetamido)phenyl)-N-hydroxy-2-phenylacetamide | LRMS (ESI): (calc) 394.1 (found) 395 [M + H]+ HPLC: 89% RT: 3.82 min |
| 4-89 | 2-(3-(2-(4-chlorophenyl)acetamido)phenyl)-N-hydroxy-2-phenylacetamide | LRMS (ESI): (calc) 394.1 (found) 395 [M + H]+ HPLC: 100% RT: 3.87 min 1H NMR (250 MHz, MeOD) d ppm 7.40-7.58 (2H, m), 7.17-7.32 (10H, m), 7.03 (1H, d, J = 7.61 Hz), 4.72 (1H, s), 3.59 (2H, s) |
| 4-90 | 1-acetyl-N-(4-(2-(hydroxyamino)-2-oxo-1-phenylethyl)phenyl)piperidine-4-carboxamide | LRMS (ESI): (calc) 395.452 (found) 396 [M + H]+ HPLC: 100% RT: 2.99 min |
| 4-91 | N-(4-(2-(hydroxyamino)-2-oxo-1-phenylethyl)phenyl)-1-naphthamide | LRMS (ESI): (calc) 396.438 (found) 397 [M + H]+ HPLC: 89% RT: 3.84 min |
| 4-92 | N-(4-(2-(hydroxyamino)-2-oxo-1-phenylethyl)phenyl)quinoline-2-carboxamide | LRMS (ESI): (calc) 397.426 (found) 398 [M + H]+ HPLC: 100% RT: 4.05 min |
| 4-93 | 2-chloro-4-fluoro-N-(4-(2-(hydroxyamino)-2-oxo-1-phenylethyl)phenyl)benzamide | LRMS (ESI): (calc) 398.083 (found) 399 [M + H]+ HPLC: 95% RT: 3.69 min |
| 4-94 | 2,4,5-trifluoro-N-(4-(2-(hydroxyamino)-2-oxo-1-phenylethyl)phenyl)benzamide | LRMS (ESI): (calc) 400.351 (found) 401 [M + H]+ HPLC: 100% RT: 3.78 min |
| 4-95 | N-(4-(2-(hydroxyamino)-2-oxo-1-phenylethyl)phenyl)-3-methylbenzofuran-2-carboxamide | LRMS (ESI): (calc) 400.427 (found) 401 [M + H]+ HPLC: 99% RT: 4.23 min |
| 4-96 | N-(3-(2-(hydroxyamino)-2-oxo-1-phenylethyl)phenyl)-3-methylbenzofuran-2-carboxamide | LRMS (ESI): (calc) 400.427 (found) 401 [M + H]+ HPLC: 100% RT: 4.14 min 1H NMR (250 MHz, MeOD) d ppm 7.58-7.69 (3H, m), 7.49-7.56 (1H, m), 7.36-7.46 (1H, m), 7.19-7.36 (7H, m), 7.11 (1H, d, J = 7.61 Hz), 4.78 (1H, s), 2.56 (3H, s) |
| 4-97 | N-(4-(2-(hydroxyamino)-2-oxo-1-phenylethyl)phenyl)chroman-3-carboxamide | LRMS (ESI): (calc) 402.442 (found) 403 [M + H]+ HPLC: 100% RT: 3.93 min |
| 4-98 | N-(3-(2-(hydroxyamino)-2-oxo-1-phenylethyl)phenyl)benzo[b]thiophene-2-carboxamide | LRMS (ESI): (calc) 402.466 (found) 403 [M + H]+ HPLC: 91% RT: 4.12 min |
| 4-99 | N-(4-(2-(hydroxyamino)-2-oxo-1-phenylethyl)phenyl)benzo[b]thiophene-3-carboxamide | LRMS (ESI): (calc) 402.466 (found) 403 [M + H]+ HPLC: 97% RT: 4.06 min |
| 4-100 | 4-tert-butyl-N-(4-(2-(hydroxyamino)-2-oxo-1-phenylethyl)phenyl)benzamide | LRMS (ESI): (calc) 402.486 (found) 403 [M + H]+ HPLC: 95% RT: 4.23 min 1H NMR (250 MHz, MeOD) d ppm 7.87 (2H, d, J = 8.53 Hz), 7.65 (2H, d, J = 8.53 Hz), 7.53 (2H, d, J = 8.38 Hz), 7.21-7.37 (7H, m), 4.80 (1H, s), 1.35 (9H, s) |
| 4-101 | 4-tert-butyl-N-(3-(2-(hydroxyamino)-2-oxo-1-phenylethyl)phenyl)benzamide | LRMS (ESI): (calc) 402.486 (found) 403 [M + H]+ HPLC: 92% RT: 4.26 min |
| 4-102 | N-(4-(2-(hydroxyamino)-2-oxo-1-phenylethyl)phenyl)-2,3-dihydrobenzo[b][1,4]dioxine-2-carboxamide | LRMS (ESI): (calc) 404.415 (found) 405 [M + H]+ HPLC: 100% RT: 3.8 min 1H NMR (250 MHz, MeOD) d ppm 7.52 (2H, d, J = 8.68 Hz), 7.17-7.31 (7H, m), 6.99-7.08 (1H, m), 6.80-6.90 (3H, m), 4.80 (1H, dd, J = 6.85, 2.59 Hz), 4.73 (1H, s), 4.45 (1H, dd, J = 11.42, 2.74 Hz), 4.20-4.30 (1H, m) |
| 4-103 | N-(3-(2-(hydroxyamino)-2-oxo-1-phenylethyl)phenyl)-2,3-dihydrobenzo[b][1,4]dioxine-2-carboxamide | LRMS (ESI): (calc) 404.415 (found) 405 [M + H]+ HPLC: 100% RT: 3.92 min 1H NMR (250 MHz, MeOD) d ppm 7.45-7.56 (2H, m), 7.16-7.33 (6H, m), 7.08 (1H, d, J = 7.61 Hz), 6.95-7.04 (1H, m), 6.78-6.89 (3H, m), 4.74 (1H, s), 4.78 (1H, d, |

TABLE IV-continued

Compounds prepared according general Schemes 20 and 21 and other Schemes.

| Cpd # | Name | Characterization |
|---|---|---|
| | | J = 2.44 Hz), 4.35-4.46 (1H, m), 4.16-4.28 (1H, m) |
| 4-104 | N-(4-(2-(hydroxyamino)-2-oxo-1-phenylethyl)phenyl)-2,6-dimethoxybenzamide | LRMS (ESI): (calc 406.431 (found) 407 [M + H]+ HPLC: 100% RT: 3.44 min |
| 4-105 | N-(4-(2-(hydroxyamino)-2-oxo-1-phenylethyl)phenyl)-3,5-dimethoxybenzamide | LRMS (ESI): (calc 406.431 (found) 407 [M + H]+ HPLC: 93% RT: 3.72 min |
| 4-106 | N-hydroxy-2-(3-(2-(naphthalen-1-yl)acetamido)phenyl)-2-phenylacetamide | LRMS (ESI): (calc) 410.464 (found) 411 [M + H]+ HPLC: 100% RT: 4.05 min |
| 4-107 | 2-(4-(2-(4-chlorophenoxy)acetamido)phenyl)-N-hydroxy-2-phenylacetamide | LRMS (ESI): (calc) 410.85 (found) 411 [M + H]+ HPLC: 100% RT: 3.93 min |
| 4-108 | 2-chloro-N-(4-(2-(hydroxyamino)-2-oxo-1-phenylethyl)phenyl)-6-methoxyisonicotinamide | LRMS (ESI): (calc) 411.838 (found) 412 [M + H]+ HPLC: 93% RT: 3.9 min |
| 4-109 | 6-chloro-2-fluoro-N-(4-(2-(hydroxyamino)-2-oxo-1-phenylethyl)phenyl)-3-methylbenzamide | LRMS (ESI): (calc) 412.841 (found) 413 [M + H]+ HPLC: 94% RT: 3.78 min |
| 4-110 | N-(4-(2-(hydroxyamino)-2-oxo-1-phenylethyl)phenyl)-4-(trifluoromethyl)benzamide | LRMS (ESI): (calc) 414.377 (found) 415 [M + H]+ HPLC: 94% RT: 4.09 min |
| 4-111 | N-(4-(2-(hydroxyamino)-2-oxo-1-phenylethyl)phenyl)-3-(trifluoromethyl)benzamide | LRMS (ESI): (calc) 414.377 (found) 415 [M + H]+ HPLC: 95% RT: 3.97 min |
| 4-112 | N-(3-(2-(hydroxyamino)-2-oxo-1-phenylethyl)phenyl)-3-(trifluoromethyl)benzamide | LRMS (ESI): (calc) 414.377 (found) 415 [M + H]+ HPLC: 85% RT: 4.01 min |
| 4-113 | 3,4-dichloro-N-(4-(2-(hydroxyamino)-2-oxo-1-phenylethyl)phenyl)benzamide | LRMS (ESI): (calc) 414.05 (found) 415 [M + H]+ HPLC: 91% RT: 4.11 min |
| 4-114 | 3,4-dichloro-N-(3-(2-(hydroxyamino)-2-oxo-1-phenylethyl)phenyl)benzamide | LRMS (ESI): (calc) 414.05 (found) 415 [M + H]+ HPLC: 100% RT: 4.23 min |
| 4-115 | 3,5-dichloro-N-(4-(2-(hydroxyamino)-2-oxo-1-phenylethyl)phenyl)benzamide | LRMS (ESI): (calc) 414.05 (found) 415 [M + H]+ HPLC: 88% RT: 4.19 min |
| 4-116 | N-(4-(2-(hydroxyamino)-2-oxo-1-phenylethyl)phenyl)-4-methyl-3,4-dihydro-2H-benzo[b][1,4]oxazine-7-carboxamide | LRMS (ESI): (calc) 417.457 (found) 418 [M + H]+ HPLC: 100% RT: 3.63 min |
| 4-117 | 4-butoxy-N-(4-(2-(hydroxyamino)-2-oxo-1-phenylethyl)phenyl)benzamide | LRMS (ESI): (calc) 418.485 (found) 419 [M + H]+ HPLC: 94% RT: 4.23 min |
| 4-118 | 2-(4-(2-(3,4-dimethoxyphenyl)acetamido)phenyl)-N-hydroxy-2-phenylacetamide | LRMS (ESI): (calc) 420.458 (found) 421 [M + H]+ HPLC: 93% RT: 3.4 min |
| 4-119 | 2-(3-(2-(3,4-dimethoxyphenyl)acetamido)phenyl)-N-hydroxy-2-phenylacetamide | LRMS (ESI): (calc) 420.458 (found) 421 [M + H]+ HPLC: 93% RT: 3.47 min |
| 4-120 | N-(4-(2-(hydroxyamino)-2-oxo-1-phenylethyl)phenyl)-5-methyl-3-phenylisoxazole-4-carboxamide | LRMS (ESI): (calc) 427.452 (found) 428 [M + H]+ HPLC: 100% RT: 3.77 min |
| 4-121 | N-(3-(2-(hydroxyamino)-2-oxo-1-phenylethyl)phenyl)-5-methyl-3-phenylisoxazole-4-carboxamide | LRMS (ESI): (calc) 427.452 (found) 428 [M + H]+ HPLC: 87% RT: 3.81 min |
| 4-123 | N-(4-(2-(hydroxyamino)-2-oxo-1-phenylethyl)phenyl)-4-(trifluoromethoxy)benzamide | LRMS (ESI): (calc) 430.377 (found) 431 [M + H]+ HPLC: 95% RT: 4.03 min |
| 4-124 | N-(3-(2-(hydroxyamino)-2-oxo-1-phenylethyl)phenyl)-4-(trifluoromethoxy)benzamide | LRMS (ESI): (calc) 430.377 (found) 431 [M + H]+ HPLC: 92% RT: 4.07 min 1H NMR (250 MHz, MeOD) d ppm 7.96 (2H, d, J = 8.83 Hz), 7.50-7.69 (2H, m), 7.18-7.37 (8H, m), 7.10 (1H, d, J = 7.77 Hz), 4.78 (1H, s) |

TABLE IV-continued

Compounds prepared according general Schemes 20 and 21 and other Schemes.

| Cpd # | Name | Characterization |
|---|---|---|
| 4-125 | N-(4-(2-(hydroxyamino)-2-oxo-1-phenylethyl)phenyl)-3-(trifluoromethoxy)benzamide | LRMS (ESI): (calc) 430.377 (found) 431 [M + H]+ HPLC: 94% RT: 4.04 min |
| 4-126 | N-(3-(2-(hydroxyamino)-2-oxo-1-phenylethyl)phenyl)-3-(trifluoromethoxy)benzamide | LRMS (ESI): (calc) 430.377 (found) 431 [M + H]+ HPLC: 90% RT: 4.87 min |
| 4-127 | 2-fluoro-N-(4-(2-(hydroxyamino)-2-oxo-1-phenylethyl)phenyl)-4-(trifluoromethyl)benzamide | LRMS (ESI): (calc) 432.368 (found) 433 [M + H]+ HPLC: 99% RT: 4.1 min |
| 4-128 | 2-fluoro-N-(3-(2-(hydroxyamino)-2-oxo-1-phenylethyl)phenyl)-4-(trifluoromethyl)benzamide | LRMS (ESI): (calc) 432.368 (found) 433 [M + H]+ HPLC: 99% RT: 4.14 min |
| 4-129 | 4-fluoro-N-(4-(2-(hydroxyamino)-2-oxo-1-phenylethyl)phenyl)-2-(trifluoromethyl)benzamide | LRMS (ESI): (calc) 432.368 (found) 433 [M + H]+ HPLC: 95% RT: 3.79 min |
| 4-130 | 2-(4-(2-(4-tert-butylphenoxy)acetamido)phenyl)-N-hydroxy-2-phenylacetamide | LRMS (ESI): (calc) 432.512 (found) 433 [M + H]+ HPLC: 100% RT: 4.48 min |
| 4-131 | N-(4-(2-(hydroxyamino)-2-oxo-1-phenylethyl)phenyl)-4-methoxy-3-(trifluoromethyl)benzamide | LRMS (ESI): (calc) 444.403 (found) 445 [M + H]+ HPLC: 94% RT: 3.97 min |
| 4-132 | N-(4-(2-(hydroxyamino)-2-oxo-1-phenylethyl)phenyl)-4-(trifluoromethylthio)benzamide | LRMS (ESI): (calc) 446.442 (found) 447 [M + H]+ HPLC: 93% RT: 4.19 min |
| 4-133 | N-(4-(2-(hydroxyamino)-2-oxo-1-phenylethyl)phenyl)-5-nitrobenzo[b]thiophene-2-carboxamide | LRMS (ESI): (calc) 447.463 (found) 448 [M + H]+ HPLC: 100% RT: 4.17 min |
| 4-134 | 2-(4-(cyclopropylmethylamino)phenyl)-N-hydroxy-2-phenylacetamide | LRMS (ESI): (calc) 296.364 (found) 297 [M + H]+ HPLC: 94% RT: 2.77 min |
| 4-135 | N-hydroxy-2-(4-(isobutylamino)phenyl)-2-phenylacetamide | LRMS (ESI): (calc) 298.379 (found) 299 [M + H]+ HPLC: 95% RT: 3.42 min 1H NMR (250 MHz, MeOD) d ppm 7.12-7.30 (5H, m), 7.01 (2H, d, J = 8.53 Hz), 6.53 (2H, d, J = 8.68 Hz), 4.60 (1H, s), 2.83 (2H, d, J = 6.85 Hz), 1.66-1.94 (1H, m), 0.92 (6H, d, J = 6.55 Hz) |
| 4-136 | N-hydroxy-2-(4-(3-methylbut-2-enylamino)phenyl)-2-phenylacetamide | LRMS (ESI): (calc) 310.39 (found) 311 [M + H]+ HPLC: 91% RT: 3.14 min |
| 4-137 | N-hydroxy-2-(4-(neopentylamino)phenyl)-2-phenylacetamide | LRMS (ESI): (calc) 312.406 (found) 313 [M + H]+ HPLC: 95% RT: 3.98 min 1H NMR (250 MHz, MeOD) d ppm 7.10-7.30 (5H, m), 6.99 (2H, d, J = 7.01 Hz), 6.55 (2H, d, J = 7.01 Hz), 4.59 (1H, s), 2.82 (2H, s), 0.93 (9H, s) |
| 4-138 | N-hydroxy-2-(3-(neopentylamino)phenyl)-2-phenylacetamide | LRMS (ESI): (calc) 312.406 (found) 313 [M + H]+ HPLC: 99% RT: 4.01 min 1H NMR (250 MHz, MeOD) d ppm 7.14-7.31 (5H, m), 6.92-7.07 (1H, m), 6.65 (1H, s), 6.50-6.60 (2H, m), 4.64 (1H, s), 2.82 (2H, s), 0.92 (9H, s) |
| 4-139 | N-hydroxy-2-(4-(2-methylbutylamino)phenyl)-2-phenylacetamide | LRMS (ESI): (calc) 312.406 (found) 313 [M + H]+ HPLC: 92% RT: 3.73 min |
| 4-140 | 2-(4-(cyclopentylmethylamino)phenyl)-N-hydroxy-2-phenylacetamide | LRMS (ESI): (calc) 324.417 (found) 325 [M + H]+ HPLC: 90% RT: 3.65 min |
| 4-141 | 2-(4-(2-ethylbutylamino)phenyl)-N-hydroxy-2-phenylacetamide | LRMS (ESI): (calc) 326.433 (found) 327 [M + H]+ HPLC: 87% RT: 4.04 min |
| 4-142 | N-hydroxy-2-(4-(2-methylpentylamino)phenyl)-2-phenylacetamide | LRMS (ESI): (calc) 326.433 (found) 327 [M + H]+ HPLC: 91% RT: 4.05 min |
| 4-143 | 2-(4-(3,3-dimethylbutylamino)phenyl)-N-hydroxy-2-phenylacetamide | LRMS (ESI): (calc) 326.433 (found) 327 [M + H]+ HPLC: 95% RT: 3.52 min |

TABLE IV-continued

Compounds prepared according general Schemes 20 and 21 and other Schemes.

| Cpd # | Name | Characterization |
|---|---|---|
| 4-144 | N-hydroxy-2-phenyl-2-(4-(pyridin-3-ylmethylamino)phenyl)acetamide | LRMS (ESI): (calc) 333.384 (found) 334 [M + H]+ HPLC: 91% RT: 2.51 min |
| 4-145 | N-hydroxy-2-(4-((1-methyl-1H-imidazol-2-yl)methylamino)phenyl)-2-phenylacetamide | LRMS (ESI): (calc) 336.388 (found) 337 [M + H]+ HPLC: 92% RT: 2.39 min |
| 4-146 | 2-(4-(cyclohex-3-enylmethylamino)phenyl)-N-hydroxy-2-phenylacetamide | LRMS (ESI): (calc) 336.427 (found) 337 [M + H]+ HPLC: 90% RT: 3.89 min |
| 4-147 | N-hydroxy-2-phenyl-2-(4-(thiazol-2-ylmethylamino)phenyl)acetamide | LRMS (ESI): (calc) 339.411 (found) 340 [M + H]+ HPLC: 100% RT: 3.29 min |
| 4-148 | N-hydroxy-2-phenyl-2-(3-(thiazol-2-ylmethylamino)phenyl)acetamide | LRMS (ESI): (calc) 339.411 (found) 340 [M + H]+ HPLC: 97% RT: 3.32 min |
| 4-149 | N-hydroxy-2-(4-(2-methylbenzylamino)phenyl)-2-phenylacetamide | LRMS (ESI): (calc) 346.422 (found) 347 [M + H]+ HPLC: 97% RT: 4 min |
| 4-150 | N-hydroxy-2-(4-(3-methylbenzylamino)phenyl)-2-phenylacetamide | LRMS (ESI): (calc) 346.422 (found) 347 [M + H]+ HPLC: 89% RT: 3.99 min |
| 4-151 | N-hydroxy-2-(4-((6-methylpyridin-2-yl)methylamino)phenyl)-2-phenylacetamide | LRMS (ESI): (calc) 347.41 (found) 348 [M + H]+ HPLC: 99% RT: 2.54 min |
| 4-152 | N-hydroxy-2-(4-(3-hydroxybenzylamino)phenyl)-2-phenylacetamide | LRMS (ESI): (calc) 348.395 (found) 349 [M + H]+ HPLC: 93% RT: 3.34 min |
| 4-153 | 2-(4-(2-fluorobenzylamino)phenyl)-N-hydroxy-2-phenylacetamide | LRMS (ESI): (calc) 350.386 (found) 351 [M + H]+ HPLC: 86% RT: 3.9 min |
| 4-154 | (E)-N-hydroxy-2-phenyl-2-(4-(3-(pyridin-3-yl)allylamino)phenyl)acetamide | LRMS (ESI): (calc) 359.421 (found) 360 [M + H]+ HPLC: 92% RT: 2.7 min |
| 4-155 | N-hydroxy-2-phenyl-2-(4-(2-phenylpropylamino)phenyl)acetamide | LRMS (ESI): (calc) 360.449 (found) 361 [M + H]+ HPLC: 93% RT: 4.22 min |
| 4-156 | 2-(4-(3,5-dimethylbenzylamino)phenyl)-N-hydroxy-2-phenylacetamide | LRMS (ESI): (calc) 360.449 (found) 361 [M + H]+ HPLC: 100% RT: 4.15 min |
| 4-157 | N-hydroxy-2-(4-(2-methoxybenzylamino)phenyl)-2-phenylacetamide | LRMS (ESI): (calc) 362.422 (found) 363 [M + H]+ HPLC: 85% RT: 3.63 min |
| 4-158 | 2-(4-(2-chlorobenzylamino)phenyl)-N-hydroxy-2-phenylacetamide | LRMS (ESI): (calc) 366.841 (found) 367 [M + H]+ HPLC: 89% RT: 4.11 min |
| 4-159 | 2-(3-(2-chlorobenzylamino)phenyl)-N-hydroxy-2-phenylacetamide | LRMS (ESI): (calc) 366.841 (found) 367 [M + H]+ HPLC: 98% RT: 4.2 min |
| 4-160 | 2-(4-((1H-indol-5-yl)methylamino)phenyl)-N-hydroxy-2-phenylacetamide | LRMS (ESI): (calc) 371.432 (found) 372 [M + H]+ HPLC: 87% RT: 3.36 min |
| 4-161 | 2-(3-((1H-indol-5-yl)methylamino)phenyl)-N-hydroxy-2-phenylacetamide | LRMS (ESI): (calc) 371.432 (found) 372 [M + H]+ HPLC: 89% RT: 3.37 min |
| 4-162 | 2-(4-(benzo[d][1,3]dioxol-5-ylmethylamino)phenyl)-N-hydroxy-2-phenylacetamide | LRMS (ESI): (calc) 376.405 (found) 377 [M + H]+ HPLC: 86% RT: 3.7 min |
| 4-163 | 2-(3-(benzo[d][1,3]dioxol-5-ylmethylamino)phenyl)-N-hydroxy-2-phenylacetamide | LRMS (ESI): (calc) 376.405 (found) 377 [M + H]+ HPLC: 88% RT: 3.7 min |
| 4-164 | N-hydroxy-2-(4-(4-methoxy-3-methylbenzylamino)phenyl)-2-phenylacetamide | LRMS (ESI): (calc) 376.448 (found) 377 [M + H]+ HPLC: 99% RT: 3.88 min |
| 4-165 | N-hydroxy-2-(4-(4-(methylthio)benzylamino)phenyl)-2-phenylacetamide | LRMS (ESI): (calc) 378.487 (found) 379 [M + H]+ HPLC: 100% RT: 4 min |
| 4-166 | N-hydroxy-2-(3-(4-(methylthio)benzylamino)phenyl)-2-phenylacetamide | LRMS (ESI): (calc) 378.487 (found) 379 [M + H]+ HPLC: 95% RT: 3.99 min |

TABLE IV-continued

Compounds prepared according general Schemes 20 and 21 and other Schemes.

| Cpd # | Name | Characterization |
|---|---|---|
| 4-167 | N-hydroxy-2-phenyl-2-(3-(quinolin-4-ylmethylamino)phenyl)acetamide | LRMS (ESI): (calc) 383.442 (found) 384 [M + H]+ HPLC: 90% RT: 2.85 min |
| 4-168 | (E)-N-hydroxy-2-(4-(3-(4-methoxyphenyl)allylamino)phenyl)-2-phenylacetamide | LRMS (ESI): (calc) 388.459 (found) 777 [2M + H]+ HPLC: 92% RT: 3.83 min |
| 4-169 | (E)-N-hydroxy-2-(4-(3-(2-methoxyphenyl)allylamino)phenyl)-2-phenylacetamide | LRMS (ESI): (calc) 388.459 (found) 389 [M + H]+ HPLC: 92% RT: 3.92 min |
| 4-170 | 2-(4-(4-tert-butylbenzylamino)phenyl)-N-hydroxy-2-phenylacetamide | LRMS (ESI): (calc) 388.502 (found) 389 [M + H]+ HPLC: 91% RT: 4.5 min |
| 4-171 | 2-(4-((2,3-dihydrobenzo[b][1,4]dioxin-6-yl)methylamino)phenyl)-N-hydroxy-2-phenylacetamide | LRMS (ESI): (calc) 390.432 (found) 391 [M + H]+ HPLC: 92% RT: 3.67 min |
| 4-173 | N-hydroxy-2-phenyl-2-(4-(3-(trifluoromethyl)benzylamino)phenyl)acetamide | LRMS (ESI): (calc) 400.394 (found) 401 [M + H]+ HPLC: 98% RT: 4.18 min 1H NMR (250 MHz, MeOD) d ppm 7.36-7.61 (4H, m), 7.09-7.25 (5H, m), 7.00 (2H, d, J = 7.77 Hz), 6.52 (2H, d, J = 7.61 Hz), 4.59 (1H, s), 4.31 (2H, s) |
| 4-174 | N-hydroxy-2-phenyl-2-(3-(3-(trifluoromethyl)benzylamino)phenyl)acetamide | LRMS (ESI): (calc) 400.394 (found) 401 [M + H]+ HPLC: 99% RT: 4.18 min |
| 4-175 | N-hydroxy-2-phenyl-2-(4-(4-(trifluoromethyl)benzylamino)phenyl)acetamide | LRMS (ESI): (calc) 400.394 (found) 401 [M + H]+ HPLC: 86% RT: 4.21 min |
| 4-176 | 2-(4-(biphenyl-4-ylmethylamino)phenyl)-N-hydroxy-2-phenylacetamide | LRMS (ESI): (calc) 408.492 (found) 409 [M + H]+ HPLC: 93% RT: 4.41 min |
| 4-177 | 2-(3-(biphenyl-4-ylmethylamino)phenyl)-N-hydroxy-2-phenylacetamide | LRMS (ESI): (calc) 408.492 (found) 409 [M + H]+ HPLC: 99% RT: 4.38 min |
| 4-178 | N-hydroxy-2-(4-(methylsulfonamido)phenyl)-2-phenylacetamide | LRMS (ESI): (calc) 320.364 (found) 321 [M + H]+ HPLC: 91% RT: 2.99 min |
| 4-179 | 2-(4-(ethylsulfonamido)phenyl)-N-hydroxy-2-phenylacetamide | LRMS (ESI): (calc) 334.39 (found) 335 [M + H]+ HPLC: 95% RT: 3.13 min |
| 4-180 | 2-(3-(ethylsulfonamido)phenyl)-N-hydroxy-2-phenylacetamide | LRMS (ESI): (calc) 334.39 (found) 335 [M + H]+ HPLC: 85% RT: 3.17 min |
| 4-181 | N-hydroxy-2-(4-(1-methylethylsulfonamido)phenyl)-2-phenylacetamide | LRMS (ESI): (calc) 348.417 (found) 349 [M + H]+ HPLC: 95% RT: 3.28 min |
| 4-182 | 2-(4-(butylsulfonamido)phenyl)-N-hydroxy-2-phenylacetamide | LRMS (ESI): (calc) 362.443 (found) 363 [M + H]+ HPLC: 92% RT: 3.53 min |
| 4-183 | 2-(3-(butylsulfonamido)phenyl)-N-hydroxy-2-phenylacetamide | LRMS (ESI): (calc) 362.443 (found) 363 [M + H]+ HPLC: 89% RT: 3.56 min |
| 4-184 | 2-(4-(3-chloropropylsulfonamido)phenyl)-N-hydroxy-2-phenylacetamide | LRMS (ESI): (calc) 382.862 (found) 383 [M + H]+ HPLC: 100% RT: 3.53 min 1H NMR (360 MHz, MeOH) d ppm 7.25-7.31 (6H, m), 7.20-7.24 (1H, m), 7.15-7.20 (2H, m), 4.74 (1H, s), 3.62 (2H, t, J = 6.36 Hz), 3.13-3.23 (2H, m), 2.10-2.23 (2H, m) |
| 4-185 | N-hydroxy-2-(3-(1-methyl-1H-imidazole-4-sulfonamido)phenyl)-2-phenylacetamide | LRMS (ESI): (calc) 386.425 (found) 387 [M + H]+ HPLC: 88% RT: 2.98 min |
| 4-186 | N-hydroxy-2-phenyl-2-(4-(2,2,2-trifluoroethylsulfonamido)phenyl)acetamide | LRMS (ESI): (calc) 388.362 (found) 389 [M + H]+ HPLC: 100% RT: 3.47 min |
| 4-187 | N-hydroxy-2-phenyl-2-(3-(2,2,2-trifluoroethylsulfonamido)phenyl)acetamide | LRMS (ESI): (calc) 388.362 (found) 389 [M + H]+ HPLC: 100% RT: 3.59 min |
| 4-188 | N-hydroxy-2-phenyl-2-(4-(phenylmethylsulfonamido)phenyl)acetamide | LRMS (ESI): (calc) 396.46 (found) 397 [M + H]+ HPLC: 91% RT: 3.6 min |
| 4-189 | N-hydroxy-2-phenyl-2-(3-(phenylmethylsulfonamido)phenyl)acetamide | LRMS (ESI): (calc) 396.46 (found) 397 [M + H]+ HPLC: 89% RT: 3.64 min |

TABLE IV-continued

Compounds prepared according general Schemes 20 and 21 and other Schemes.

| Cpd # | Name | Characterization |
|---|---|---|
| 4-190 | N-hydroxy-2-(4-(4-methylphenylsulfonamido)phenyl)-2-phenylacetamide | LRMS (ESI): (calc) 396.46 (found) 397 [M + H]+ HPLC: 94% RT: 3.68 min |
| 4-191 | N-hydroxy-2-(4-(2-methylphenylsulfonamido)phenyl)-2-phenylacetamide | LRMS (ESI): (calc) 396.46 (found) 397 [M + H]+ HPLC: 94% RT: 3.75 min |
| 4-192 | N-hydroxy-2-(4-(3-methylphenylsulfonamido)phenyl)-2-phenylacetamide | LRMS (ESI): (calc) 396.46 (found) 397 [M + H]+ HPLC: 91% RT: 3.68 min |
| 4-193 | N-hydroxy-2-(3-(3-methylphenylsulfonamido)phenyl)-2-phenylacetamide | LRMS (ESI): (calc) 396.46 (found) 397 [M + H]+ HPLC: 91% RT: 3.69 min |
| 4-194 | 2-(4-(4-fluorophenylsulfonamido)phenyl)-N-hydroxy-2-phenylacetamide | LRMS (ESI): (calc) 400.423 (found) 401 [M + H]+ HPLC: 91% RT: 3.7 min |
| 4-195 | 2-(3-(4-fluorophenylsulfonamido)phenyl)-N-hydroxy-2-phenylacetamide | LRMS (ESI): (calc) 400.423 (found) 401 [M + H]+ HPLC: 90% RT: 3.63 min |
| 4-196 | 2-(4-(3-fluorophenylsulfonamido)phenyl)-N-hydroxy-2-phenylacetamide | LRMS (ESI): (calc) 400.423 (found) 401 [M + H]+ HPLC: 100% RT: 3.72 min |
| 4-197 | 2-(4-(2-fluorophenylsulfonamido)phenyl)-N-hydroxy-2-phenylacetamide | LRMS (ESI): (calc) 400.423 (found) 401 [M + H]+ HPLC: 91% RT: 3.56 min |
| 4-198 | 2-(3-(2-fluorophenylsulfonamido)phenyl)-N-hydroxy-2-phenylacetamide | LRMS (ESI): (calc) 400.423 (found) 401 [M + H]+ HPLC: 87% RT: 3.55 min |
| 4-199 | 2-(4-(1,2-dimethyl-1H-imidazole-4-sulfonamido)phenyl)-N-hydroxy-2-phenylacetamide | LRMS (ESI): (calc) 400.452 (found) 401 [M + H]+ HPLC: 90% RT: 3.05 min |
| 4-200 | 2-(4-(3,5-dimethylisoxazole-4-sulfonamido)phenyl)-N-hydroxy-2-phenylacetamide | LRMS (ESI): (calc) 401.436 (found) 402 [M + H]+ HPLC: 94% RT: 3.5 min |
| 4-201 | 2-(4-(3,4-dimethylphenylsulfonamido)phenyl)-N-hydroxy-2-phenylacetamide | LRMS (ESI): (calc) 410.486 (found) 411 [M + H]+ HPLC: 93% RT: 3.8 min |
| 4-202 | 2-(3-(3,4-dimethylphenylsulfonamido)phenyl)-N-hydroxy-2-phenylacetamide | LRMS (ESI): (calc) 410.486 (found) 411 [M + H]+ HPLC: 93% RT: 3.8 min 1H NMR (250 MHz, MeOD) d ppm 7.42 (1H, s), 7.30-7.38 (1H, m), 7.12-7.26 (6H, m), 7.03-7.11 (2H, m), 6.90-7.01 (2H, m), 4.63 (1H, s), 2.22 (3H, s), 2.17 (3H, s) |
| 4-203 | 2-(4-(2,5-dimethylphenylsulfonamido)phenyl)-N-hydroxy-2-phenylacetamide | LRMS (ESI): (calc) 410.486 (found) 411 [M + H]+ HPLC: 92% RT: 3.82 min |
| 4-204 | 2-(4-(4-ethylphenylsulfonamido)phenyl)-N-hydroxy-2-phenylacetamide | LRMS (ESI): (calc) 410.486 (found) 411 [M + H]+ HPLC: 87% RT: 3.84 min |
| 4-205 | 2-(4-(3,5-dimethylphenylsulfonamido)phenyl)-N-hydroxy-2-phenylacetamide | LRMS (ESI): (calc) 410.486 (found) 411 [M + H]+ HPLC: 94% RT: 3.83 min |
| 4-206 | N-hydroxy-2-(4-(3-methoxyphenylsulfonamido)phenyl)-2-phenylacetamide | LRMS (ESI): (calc) 412.459 (found) 413 [M + H]+ HPLC: 93% RT: 3.61 min 1H NMR (250 MHz, MeOD) d ppm 7.10-7.33 (10H, m), 6.87-7.08 (3H, m), 4.67 (1H, s), 3.63 (3H, s) |
| 4-207 | N-hydroxy-2-(3-(3-methoxyphenylsulfonamido)phenyl)-2-phenylacetamide | LRMS (ESI): (calc) 412.459 (found) 413 [M + H]+ HPLC: 91% RT: 3.62 min |
| 4-208 | 2-(4-(4-fluoro-2-methylphenylsulfonamido)phenyl)-N-hydroxy-2-phenylacetamide | LRMS (ESI): (calc) 414.45 (found) 415 [M + H]+ HPLC: 93% RT: 3.75 min |
| 4-209 | 2-(3-(4-fluoro-2-methylphenylsulfonamido)phenyl)-N-hydroxy-2-phenylacetamide | LRMS (ESI): (calc) 414.45 (found) 415 [M + H]+ HPLC: 89% RT: 3.74 min |

TABLE IV-continued

Compounds prepared according general Schemes 20 and 21 and other Schemes.

| Cpd # | Name | Characterization |
|---|---|---|
| 4-210 | 2-(4-(2-chlorophenylsulfonamido)phenyl)-N-hydroxy-2-phenylacetamide | LRMS (ESI): (calc) 416.878 (found) 417 [M + H]+ HPLC: 94% RT: 3.65 min |
| 4-211 | 2-(4-(3-chlorophenylsulfonamido)phenyl)-N-hydroxy-2-phenylacetamide | LRMS (ESI): (calc) 416.878 (found) 417 [M + H]+ HPLC: 95% RT: 3.78 min 1H NMR (250 MHz, MeOD) d ppm 7.56-7.69 (2H, m), 7.45-7.54 (1H, m), 7.33-7.44 (1H, m), 7.12-7.27 (7H, m), 6.95-7.07 (2H, m), 4.67 (1H, s) |
| 4-212 | 2-(4-(2,6-difluorophenylsulfonamido)phenyl)-N-hydroxy-2-phenylacetamide | LRMS (ESI): (calc) 418.414 (found) 419 [M + H]+ HPLC: 91% RT: 3.55 min |
| 4-213 | 2-(4-(2,4-difluorophenylsulfonamido)phenyl)-N-hydroxy-2-phenylacetamide | LRMS (ESI): (calc) 418.414 (found) 419 [M + H]+ HPLC: 93% RT: 3.73 min |
| 4-214 | 2-(3-(2,4-difluorophenylsulfonamido)phenyl)-N-hydroxy-2-phenylacetamide | LRMS (ESI): (calc) 418.414 (found) 419 [M + H]+ HPLC: 89% RT: 3.64 min |
| 4-215 | 2-(4-(5-chlorothiophene-2-sulfonamido)phenyl)-N-hydroxy-2-phenylacetamide | LRMS (ESI): (calc) 422.016 (found) 422 [M + H]+ HPLC: 91% RT: 3.79 min |
| 4-216 | 2-(3-(5-chlorothiophene-2-sulfonamido)phenyl)-N-hydroxy-2-phenylacetamide | LRMS (ESI): (calc) 422.016 (found) 422 [M + H]+ HPLC: 99% RT: 3.89 min 1H NMR (250 MHz, MeOD) d ppm 6.97-7.29 (10H, m), 6.86 (1H, d, J = 4.11 Hz), 4.67 (1H, s) |
| 4-217 | N-hydroxy-2-(4-(2-methoxy-4-methylphenylsulfonamido)phenyl)-2-phenylacetamide | LRMS (ESI): (calc) 426.485 (found) 427 [M + H]+ HPLC: 100% RT: 3.75 min |
| 4-218 | N-hydroxy-2-(3-(2-methoxy-4-methylphenylsulfonamido)phenyl)-2-phenylacetamide | LRMS (ESI): (calc) 426.485 (found) 427 [M + H]+ HPLC: 91% RT: 3.67 min |
| 4-219 | N-hydroxy-2-(3-(4-nitrophenylsulfonamido)phenyl)-2-phenylacetamide | LRMS (ESI): (calc) 427.43 (found) 428 [M + H]+ HPLC: 100% RT: 3.78 min |
| 4-220 | N-hydroxy-2-(4-(2-nitrophenylsulfonamido)phenyl)-2-phenylacetamide | LRMS (ESI): (calc) 427.43 (found) 428 [M + H]+ HPLC: 88% RT: 3.64 min |
| 4-221 | 2-(4-(3-chloro-4-methylphenylsulfonamido)phenyl)-N-hydroxy-2-phenylacetamide | LRMS (ESI): (calc) 430.905 (found) 431 [M + H]+ HPLC: 100% RT: 4.01 min |
| 4-222 | 2-(3-(3-chloro-4-methylphenylsulfonamido)phenyl)-N-hydroxy-2-phenylacetamide | LRMS (ESI): (calc) 430.905 (found) 431 [M + H]+ HPLC: 91% RT: 3.93 min |
| 4-223 | N-hydroxy-2-(4-(naphthalene-1-sulfonamido)phenyl)-2-phenylacetamide | LRMS (ESI): (calc) 432.492 (found) 433 [M + H]+ HPLC: 100% RT: 3.93 min |
| 4-224 | N-hydroxy-2-(3-(naphthalene-1-sulfonamido)phenyl)-2-phenylacetamide | LRMS (ESI): (calc) 432.492 (found) 433 [M + H]+ HPLC: 91% RT: 3.83 min |
| 4-225 | N-hydroxy-2-(4-(naphthalene-2-sulfonamido)phenyl)-2-phenylacetamide | LRMS (ESI): (calc) 432.492 (found) 433 [M + H]+ HPLC: 100% RT: 3.95 min |
| 4-226 | 2-(4-(4-tert-butylphenylsulfonamido)phenyl)-N-hydroxy-2-phenylacetamide | LRMS (ESI): (calc) 438.539 (found) 439 [M + H]+ HPLC: 94% RT: 4.1 min |
| 4-227 | 2-(3-(4-tert-butylphenylsulfonamido)phenyl)-N-hydroxy-2-phenylacetamide | LRMS (ESI): (calc) 438.539 (found) 439 [M + H]+ HPLC: 100% RT: 4.2 min |
| 4-228 | 2-(4-(4-acetamidophenylsulfonamido)phenyl)-N-hydroxy-2-phenylacetamide | LRMS (ESI): (calc) 439.484 (found) 440 [M + H]+ HPLC: 100% RT: 3.32 min 1H NMR (250 MHz, MeOD) d ppm 7.62 (4H, s), 7.08-7.28 (7H, m), 6.93-7.07 (2H, m), 4.66 (1H, s), 2.08 (3H, s) |
| 4-229 | N-hydroxy-2-(4-((2-nitrophenyl)methylsulfonamido)phenyl)- | LRMS (ESI): (calc) 441.457 (found) 442 [M + H]+ HPLC: 100% RT: 3.7 min |

TABLE IV-continued

Compounds prepared according general Schemes 20 and 21 and other Schemes.

| Cpd # | Name | Characterization |
|---|---|---|
| 4-230 | 2-phenylacetamide 2-(4-(3,4-dimethoxyphenylsulfonamido)phenyl)-N-hydroxy-2-phenylacetamide | LRMS (ESI): (calc) 442.485 (found) 443 [M + H]+ HPLC: 95% RT: 3.55 min |
| 4-231 | 2-(3-(3,4-dimethoxyphenylsulfonamido)phenyl)-N-hydroxy-2-phenylacetamide | LRMS (ESI): (calc) 442.485 (found) 443 [M + H]+ HPLC: 92% RT: 3.46 min |
| 4-232 | N-hydroxy-2-phenyl-2-(4-(3-(trifluoromethyl)phenylsulfonamido)phenyl)acetamide | LRMS (ESI): (calc) 450.431 (found) 451 [M + H]+ HPLC: 91% RT: 3.89 min |
| 4-233 | N-hydroxy-2-phenyl-2-(3-(3-(trifluoromethyl)phenylsulfonamido)phenyl)acetamide | LRMS (ESI): (calc) 450.431 (found) 451 [M + H]+ HPLC: 91% RT: 3.91 min 1H NMR (250 MHz, MeOD) d ppm 7.91 (1H, s), 7.81 (2H, d, J = 8.07 Hz), 7.46-7.65 (1H, m), 7.07-7.28 (6H, m), 6.92-7.07 (3H, m), 4.64 (1H, s) |
| 4-234 | 2-(4-(2,5-dichlorothiophene-3-sulfonamido)phenyl)-N-hydroxy-2-phenylacetamide | LRMS (ESI): (calc) 455.977 (found) 457 [M + H]+ HPLC: 92% RT: 3.93 min |
| 4-235 | 2-(4-(4,5-dichlorothiophene-2-sulfonamido)phenyl)-N-hydroxy-2-phenylacetamide | LRMS (ESI): (calc) 455.977 (found) 457 [M + H]+ HPLC: 94% RT: 4.04 min |
| 4-236 | 2-(3-(4,5-dichlorothiophene-2-sulfonamido)phenyl)-N-hydroxy-2-phenylacetamide | LRMS (ESI): (calc) 455.977 (found) 457 [M + H]+ HPLC: 88% RT: 4.05 min |
| 4-237 | (E)-2-(4-(cinnamylamino)phenyl)-N-hydroxy-2-phenylacetamide | LRMS (ESI): (calc) 358.433 (found) 359 [M + H]+ HPLC: 89% RT: 3.93 min |
| 4-238 | 2-(4-(benzo[c][1,2,5]thiadiazole-5-sulfonamido)phenyl)-N-hydroxy-2-phenylacetamide | LRMS (ESI): (calc) 440.495 (found) 441 [M + H]+ HPLC: 100% RT: 3.7 min |

TABLE V

Other Compounds prepared according general Schemes above 5-1

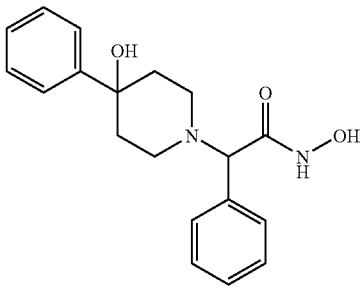 [SMILES: O=C(NO)C(c1ccccc1)N1CCC(O)(c2ccccc2)CC1]

N-hydroxy-2-(4-hydroxy-4-phenylpiperidin-1-yl)-2-phenylacetamide
Mol wt. 326.39
LRMS(ESI): (calc.) 326.4 (found) 327.5 (MH)+
1H NMR (MeOD-d4) 7.60-7.51 (m, 4H), 7.41-7.31 (m, 5H), 7.27-7.21 (m, 1H), 3.75 (s, 1H), 3.00-2.92 (m, 1H), 2.68-2.60 (m, 1H), 2.57-2.50 (m, 1H), 2.39-2.26 (m, 2H), 2.20-2.10 (m, 1H), 1.80-1.72 (m, 1H), 1.67-1.60 (m, 1H)

5-2

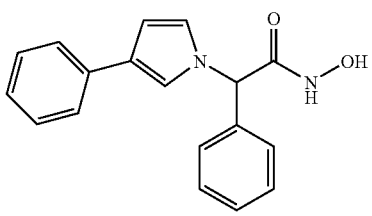 [SMILES: O=C(NO)C(c1ccccc1)n1ccc(-c2ccccc2)c1]

N-hydroxy-2-phenyl-2-(3-phenyl-1H-pyrrol-1-yl)acetamide
Mol wt. 292.332
LRMS(ESI): (calc.) 292.3 (found) 293.4 (MH)+

TABLE V-continued

Other Compounds prepared according general Schemes above (MeOD-d4) 7.53-7.47 (m, 2H), 7.44-7.34 (m, 5H), 7.32-7.26 (m, 2H), 7.19 (t, J = 2.0 Hz, 1H), 7.15-7.09 (m, 1H), 6.85 (t, J = 2.5Hz, 1H), 6.49 (dd, J = 2.9, 1.8Hz, 1H), 5.77 (s, 1H)

5-3

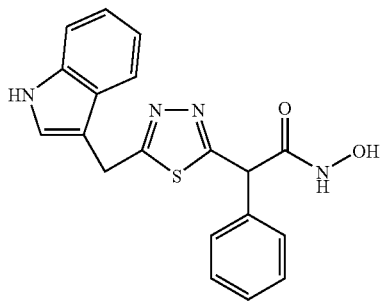 [SMILES: O=C(NO)C(c1ccccc1)c1nnc(Cc2c[nH]c3ccccc23)s1]

2-(5-((1H-indol-3-yl)methyl)-1,3,4-thiadiazol-2-yl)-N-hydroxy-2-phenylacetamide
Mol wt. 364.421
LRMS(ESI): (calc.) 364.1 (found) 365.4 (MH)+
(CD3OD) d(ppm) 1H: 7.41 (d, J = 8.0 Hz, 1H), 7.37-7.23 (m, 7H), 7.10 (t, J = 6.8Hz, 1H), 6.98 (t, J = 6.8Hz, 1H), 5.22 (s, 1H), 4.51 (s, 2H)

5-4

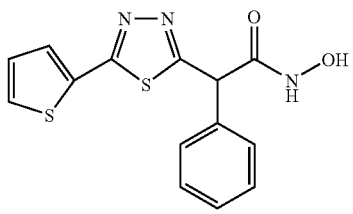 [SMILES: O=C(NO)C(c1ccccc1)c1nnc(-c2cccs2)s1]

N-hydroxy-2-phenyl-2-(5-(thiophen-2-yl)-1,3,4-thiadiazol-2-yl)acetamide
Mol wt. 317.386
LRMS(ESI): (calc.) 317.0 (found) 318.3 (MH)+
(CD3OD) d(ppm) 1H: 7.67 (m, 2H), 7.48 (m, 2H), 7.39-7.32 (m, 3H), 7.17 (m, 1H), 5.34 (s, 1H)

5-5

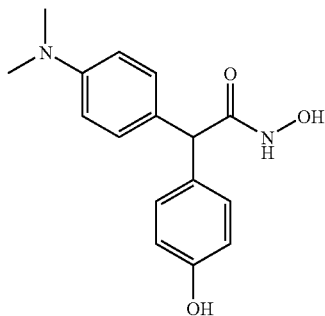 [SMILES: CN(C)c1ccc(C(C(=O)NO)c2ccc(O)cc2)cc1]

2-(4-(dimethylamino)phenyl)-N-hydroxy-2-(4-hydroxyphenyl)acetamide
Mol wt. 286.326
LRMS(ESI): (calc.) 286.3 (found) 287.4 (MH)+
(MeOD) d(ppm) 1H: 7.11 (dd, J = 11.3, 8.8Hz, 4H), 6.71 (t, J = 8.6Hz, 4H), 4.58 (s, 1H), 2.89 (s, 6H).

5-6

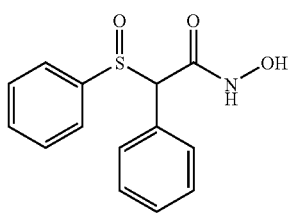 [SMILES: O=C(NO)C(c1ccccc1)S(=O)c1ccccc1]

N-hydroxy-2-phenyl-2-(phenylsulfinyl)acetamide
Mol. Wt. 275.323
LRMS(ESI): (calc.) 275.3 (found) 274.1 (M − H)−
(DMSO-d6) d(ppm) 1H: 10.93 (br s, 1H), 9.32 (br s, 1H), 7.58-6.95 (m, 10H), 4.37 (s, 1H)

TABLE V-continued

Other Compounds prepared according general Schemes above 5-7

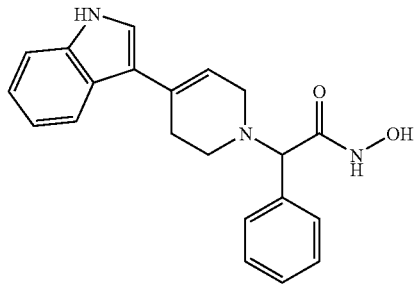 [SMILES: O=C(NO)C(c1ccccc1)N1CC=C(c2c[nH]c3ccccc23)CC1]

2-(4-(1H-indol-3-yl)-5,6-dihydropyridin-1(2H)-yl)-N-hydroxy-2-phenylacetamide
Mol. Wt. 347.41
LRMS(ESI): (calc.) 347.4 (found) 348.2 (MH)+
(MeOD-d4) 7.82 (d, J = 8.0 Hz, 1H), 7.63-7.58 (m, 2H), 7.43-7.35 (m, 4H), 7.27 (s, 1H), 7.15-7.10 (m, 1H), 7.08-7.02 (m, 1H), 6.18-6.12 (m, 1H), 3.87 (s, 1H), 3.30-3.12 (m, 2H), 2.81-2.74 (m, 2H), 2.70-2.61 (m, 2H)__

5-8

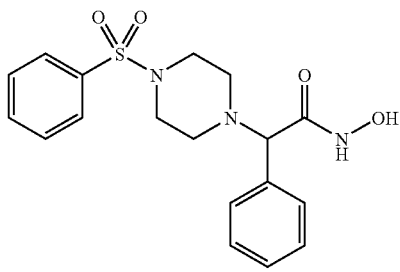 [SMILES: O=C(NO)C(c1ccccc1)N1CCN(S(=O)(=O)c2ccccc2)CC1]

N-hydroxy-2-phenyl-2-(4-(phenylsulfonyl)piperazin-1-yl)acetamide
Mol. Wt. 375.442
LRMS(ESI): (calc.) 375.4 (found) 376.5 (MH)+
(MeOD-d4) 7.83-7.78 (m, 2H), 7.76-7.70 (m, 1H), 7.69-7.63 (m, 2H), 7.45-7.40 (m, 2H), 7.36-7.30 (m, 3H), 3.71 (s, 1H), 3.10-3.02 (m, 4H), 2.58-2.44 (m, 4H)__

5-9 Cpd 56

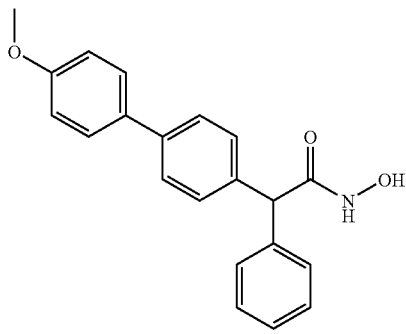 [SMILES: COc1ccc(-c2ccc(C(C(=O)NO)c3ccccc3)cc2)cc1]

N-hydroxy-2-(4'-methoxybiphenyl-4-yl)-2-phenylacetamide
Mol. Wt. 333.38
LRMS(ESI): (calc.) 333.4 (found) 334.4 (MH)+
(DMSO-d6) d(ppm) 1H: 10.94 (s, 1H), 8.98 (s, 1H), 7.55 (t, J = 8.8Hz, 4H), 7.37-7.29 (m, 6H), 7.25-7.23 (m, 1H), 7.00 (d, J = 8.8Hz, 2H), 4.73 (s, 1H), 3.77 (s, 3H).__

TABLE V-continued

Other Compounds prepared according general Schemes above 5-10

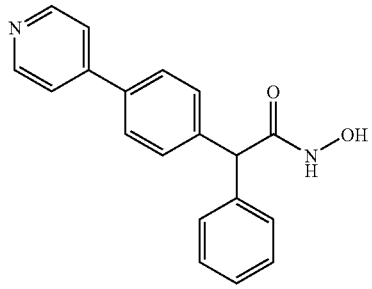 [SMILES: O=C(NO)C(c1ccccc1)c1ccc(-c2ccncc2)cc1]

N-hydroxy-2-phenyl-2-(4-(pyridin-4-yl)phenyl)acetamide
Mol. Wt. 304.342
LRMS(ESI): (calc.) 304.3 (found) 305.4 (MH)+
(DMSO-d6) d(ppm) 1H: 10.97 (s, 1H), 9.01 (s, 1H), 8.61 (d, J = 6.3Hz, 2H), 7.75 (d, J = 8.4Hz, 2H), 7.68 (d, J = 7.3Hz, 2H), 7.45 (d, J = 8.4Hz, 2H), 7.37-7.22 (m, 5H), 4.78 (s, 1H).

5-11

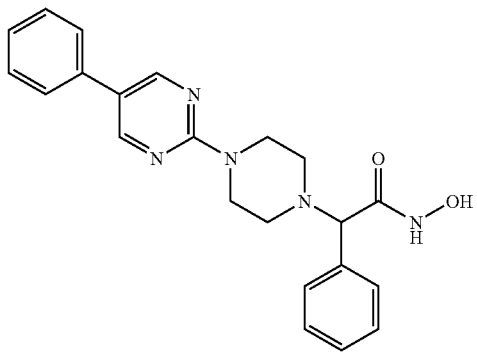 [SMILES: O=C(NO)C(c1ccccc1)N1CCN(c2ncc(-c3ccccc3)cn2)CC1]

N-hydroxy-2-phenyl-2-(4-(5-phenylpyrimidin-2-yl)piperazin-1-yl)acetamide
Mol. Wt. 389.45
LRMS(ESI): (calc.) 389.5 (found) 390.6 (MH)+
(DMSO-d6) 10.92 (s, 1H), 8.98 (s, 1H), 8.73 (s, 2H), 7.69-7.65 (m, 2H), 7.54-7.45 (m, 4H), 7.42-7.31 (m, 4H), 3.85-3.79 (m, 4H), 3.72 (s, 1H), 2.51-2.40 (m, 4H)

5-12

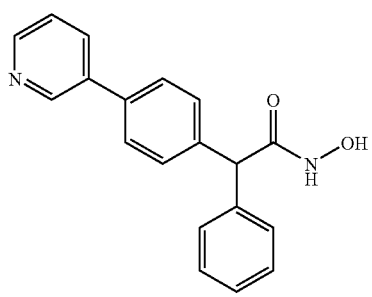 [SMILES: O=C(NO)C(c1ccccc1)c1ccc(-c2cccnc2)cc1]

N-hydroxy-2-phenyl-2-(4-(pyridin-3-yl)phenyl)acetamide
Mol. Wt. 304.342
LRMS(ESI): (calc.) 304.3 (found) 305.4 (MH)+
(MeOD) d(ppm) 1H: 8.77 (d, J = 1.8Hz, 1H), 8.50-8.48 (m, 1H), 8.07 (dt, J = 8.0, 2.0 Hz, 1H), 7.61 (d, J = 8.4Hz, 2H), 7.51-7.45 (m, 3H), 7.38-7.23 (m, 5H), 4.85 (s, 1H).

TABLE V-continued

Other Compounds prepared according general Schemes above 5-13

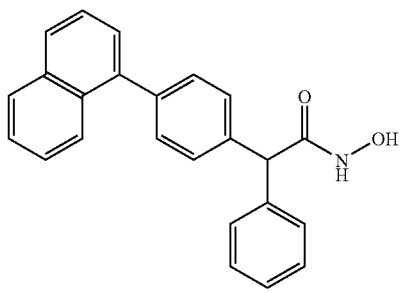 [SMILES: O=C(NO)C(c1ccccc1)c1ccc(-c2cccc3ccccc23)cc1]

N-hydroxy-2-(4-(naphthalen-1-yl)phenyl)-2-phenylacetamide
Mol. Wt. 353.413
LRMS(ESI): (calc.) 353.4 (found) 354.5 (MH)+
(DMSO-d6) d(ppm) 1H: 10.97 (s, 1H), 9.01 (s, 1H), 8.18 (s, 1H), 8.00-7.92 (m, 3H), 7.84-7.75 (m, 3H), 7.54-7.25 (m, 9H), 4.78 (s, 1H).

5-14

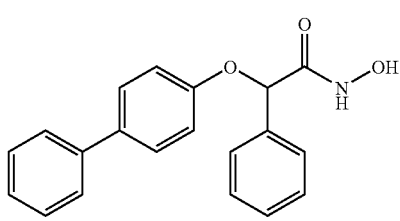 [SMILES: O=C(NO)C(Oc1ccc(-c2ccccc2)cc1)c1ccccc1]

2-(biphenyl-4-yloxy)-N-hydroxy-2-phenylacetamide
Mol. Wt. 319.354
LRMS(ESI): (calc.) 319.4 (found) 320.4 (MH)+
(DMSO-d6) d(ppm) 1H: 11.17 (br s, 1H), 9.04 (br s, 1H), 7.60-7.54 (m, 6H), 7.43-7.27 (m, 6H), 7.05 (d, J = 8.8Hz, 2H), 5.67 (s, 1H).

5-15 and Cpd 80

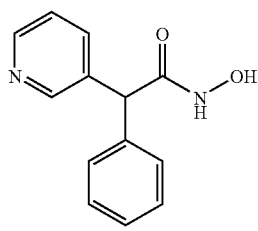 [SMILES: O=C(NO)C(c1ccccc1)c1cccnc1]

N-hydroxy-2-phenyl-2-(pyridin-3-yl)acetamide
Mol. Wt. 228.247
LRMS(ESI): (calc.) 228.0 (found) 229.2 (MH)+
(CD3OD) d(ppm) 1H: 8.47 (d, J = 2.4Hz, 1H), 8.43 (q, J = 1.6, 4.8Hz, 1H), 7.48 (m, 1H), 7.41-7.28 (m, 6H), 4.83 (s, 1H)

5-16

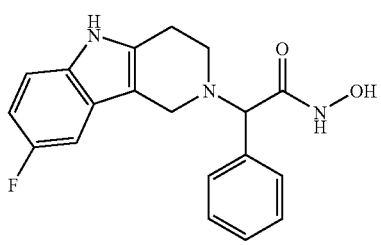 [SMILES: O=C(NO)C(c1ccccc1)N1CCc2[nH]c3ccc(F)cc3c2C1]

2-(8-fluoro-3,4-dihydro-1H-pyrido[4,3-b]indol-2(5H)-yl)-N-hydroxy-2-phenylacetamide
Mol. Wt. 339.363
LRMS(ESI): (calc.) 339.4 (found) 340.2 (MH)+
(DMSO-d6) 10.98 (s, 2H), 9.00 (s, 1H), 7.57-7.51 (m, 2H), 7.43-7.33 (m, 3H), 7.28 (dd, J = 8.6, 4.5 Hz, 1H), 6.99 (dd, J = 7.6, 2.5Hz, 1H), 6.89-6.82 (m, 1H), 4.02 (s, 1H), 3.64 (d, J = 13.7Hz, 1H), 3.54 (d, J = 13.5Hz, 1H), 2.86-2.70 (m, 4H)

5-17

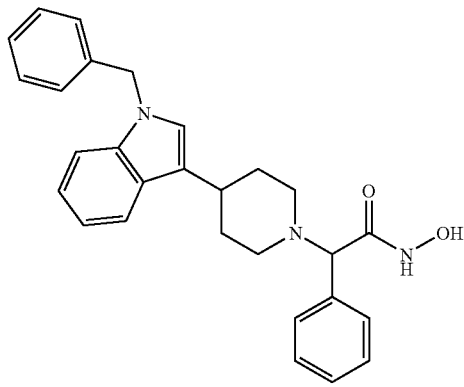 [SMILES: O=C(NO)C(c1ccccc1)N1CCC(c2cn(Cc3ccccc3)c3ccccc23)CC1]

2-(4-(1-benzyl-1H-indol-3-yl)piperidin-1-yl)-N-hydroxy-2-phenylacetamide

Mol. Wt. 439.549

LRMS(ESI): (calc.) 439.6 (found) 440.6 (MH)+

(DMSO-d6) 10.89 (s, 1H), 8.93 (s, 1H), 7.61 (d, J = 7.6Hz, 1H), 7.52-7.48 (m, 2H), 7.44-7.30 (m, 7H), 7.29-7.20 (m, 3H), 7.13-7.07 (m, 1H), 7.04-6.99 (m, 1H), 5.40 (s, 2H), 3.72 (s, 1H), 3.11-3.04 (m, 1H), 2.84-2.70 (m, 2H), 2.3-2.2 (m, 1H), 2.02-1.65 (m, 5H)

5-18

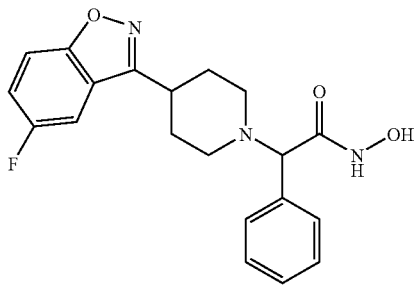 [SMILES: O=C(NO)C(c1ccccc1)N1CCC(c2noc3ccc(F)cc23)CC1]

2-(4-(5-fluorobenzo[d]isoxazol-3-yl)piperidin-1-yl)-N-hydroxy-2-phenylacetamide

Mol. Wt. 369.39

LRMS(ESI): (calc.) 369.4 (found) 370.4 (MH)+

(MeOD-d4) 7.73 (dd, J = 8.2, 2.1Hz, 1H), 7.63 (dd, J = 9.0, 4.9Hz, 1H), 7.58-7.53 (m, 2H), 7.45-7.32 (m, 4H), 3.79 (s, 1H), 3.27-3.11 (m, 2H), 2.89-2.82 (m, 1H), 2.40-2.32 (m, 1H), 2.29-2.17 (m, 1H), 2.13-1.95 (m, 4H)

5-19

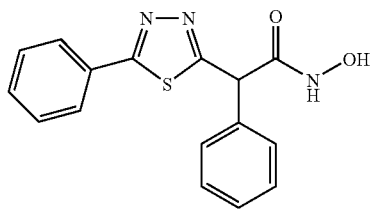 [SMILES: O=C(NO)C(c1ccccc1)c1nnc(-c2ccccc2)s1]

N-hydroxy-2-phenyl-2-(5-phenyl-1,3,4-thiadiazol-2-yl)acetamide

Mol. Wt. 311.358

LRMS(ESI): (calc.) 311.0 (found) 312.3 (MH)+

(CD3OD) d(ppm) 1H: 7.95 (m, 2H), 7.51 (m, 5H), 7.38-7.32 (m, 3H), 5.37 (s, 1H)

5-20 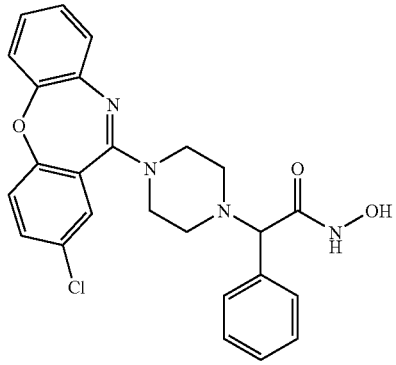 [SMILES: O=C(NO)C(c1ccccc1)N1CCN(C2=Nc3ccccc3Oc3ccc(Cl)cc32)CC1]

(E)-2-(4-(2-chlorodibenzo[b,f][1,4]oxazepin-11-yl)piperazin-1-yl)-N-hydroxy-2-phenylacetamide
Mol. Wt. 462.928
LRMS(ESI): (calc.) 462.9 (found) 463.6 (MH)+
(MeOD-d4) 7.58-7.50 (m, 3H), 7.42-7.34 (m, 4H), 7.30 (d, J = 8.6Hz, 1H), 7.16-7.09 (m, 3H), 7.06-7.01 (m, 1H), 3.80 (s, 1H), 3.62-3.50 (m, 4H), 2.68-2.50 (m, 4H)

5-21 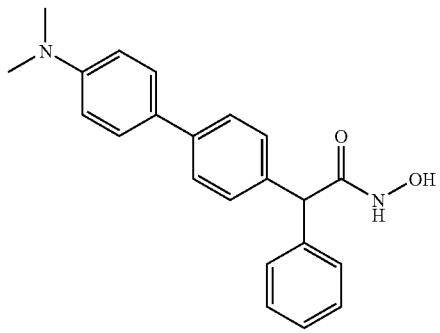 [SMILES: CN(C)c1ccc(-c2ccc(C(C(=O)NO)c3ccccc3)cc2)cc1]

2-(4'-(dimethylamino)biphenyl-4-yl)-N-hydroxy-2-phenylacetamide
Mol. Wt. 346.422
LRMS(ESI): (calc.) 346.4 (found) 347.5 (MH)+
(DMSO-d6) d(ppm) 1H: 10.92 (s, 1H), 8.96 (s, 1H), 7.52-7.46 (m, 4H), 7.36-7.21 (m, 7H), 6.77 (d, J = 9.0 Hz, 2H), 4.70 (s, 1H), 2.91 (s, 6H).

5-22 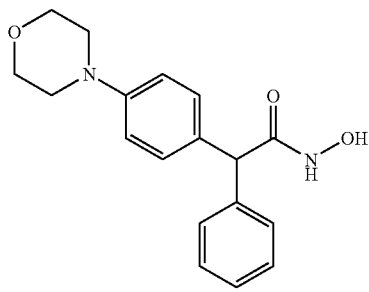 [SMILES: O=C(NO)C(c1ccccc1)c1ccc(N2CCOCC2)cc1]

N-hydroxy-2-(4-morpholinophenyl)-2-phenylacetamide
Mol. Wt. 312.363
LRMS(ESI): (calc.) 312.4 (found) 313.4 (MH)+
(DMSO-d6) d(ppm) 1H: 10.85 (s, 1H), 8.91 (s, 1H), 7.29-7.15 (m, 7H), 6.87 (d, J = 8.8Hz, 2H), 4.58 (s, 1H), 3.71 (t, J = 4.7Hz, 4H), 3.04 (t, J = 4.7Hz, 4H).

5-23
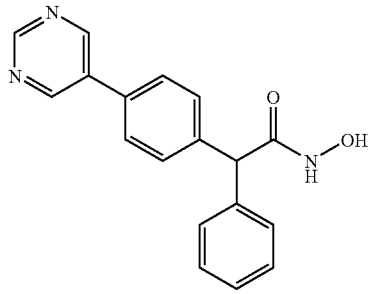 [SMILES: O=C(NO)C(c1ccccc1)c1ccc(-c2cncnc2)cc1]
N-hydroxy-2-phenyl-2-(4-(pyrimidin-5-yl)phenyl)acetamide
Mol. Wt. 305.331
LRMS(ESI): (calc.) 305.3 (found) 306.3 (MH)+
(DMSO-d6) d(ppm) 1H: 10.98 (s, 1H), 9.17 (s, 1H), 9.11 (s, 2H), 9.01 (s, 1H), 7.76 (d, J = 8.2Hz, 2H), 7.47 (d, J = 8.4Hz, 2H), 7.37-7.23 (m, 5H), 4.78 (s, 1H).
5-24
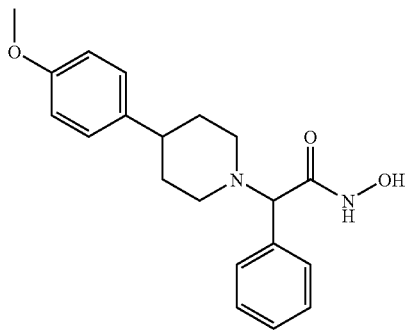 [SMILES: COc1ccc(C2CCN(C(C(=O)NO)c3ccccc3)CC2)cc1]
N-hydroxy-2-(4-(4-methoxyphenyl)piperidin-1-yl)-2-phenylacetamide
Mol. Wt. 340.416
LRMS(ESI): (calc.) 340.4 (found) 341.4 (MH)+
(DMSO-d6) 10.87 (s, 1H), 8.93 (s, 1H), 7.52-7.46 (m, 2H), 7.40-7.28 (m, 3H), 7.22-7.16 (m, 2H), 6.90-6.85 (m, 2H), 3.75 (s, 3H), 3.69 (s, 1H), 3.10-3.03 (m, 1H), 2.76-2.69 (m, 1H), 2.51-2.40 (m, 1H), 2.20-2.11 (m, 1H), 1.92-1.83 (m, 1H), 1.78-1.55 (m, 4H)
5-25
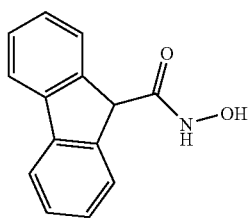 [SMILES: O=C(NO)C1c2ccccc2-c2ccccc21]
N-hydroxy-9H-fluorene-9-carboxamide
Mol wt. 225.243
LRMS(ESI): (calc.) 225.2 (found) 224.0 (M − H+)
(MeOD-d4) 7.85 (d, J = 7.4Hz, 2H), 7.59-7.55 (m, 2H), 7.47-7.43 (m, 2H), 7.39-7.33 (m, 2H), 4.68 (s, 1H)

5-26
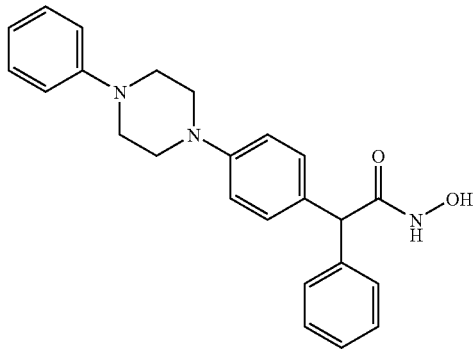 [SMILES: O=C(NO)C(c1ccccc1)c1ccc(N2CCN(c3ccccc3)CC2)cc1]
N-hydroxy-2-phenyl-2-(4-(4-phenylpiperazin-1-yl)phenyl)acetamide
Mol wt. 387.474
LRMS(ESI): (calc.) 387.4 (found) 388.4 (MH)+
(CD3OD) d(ppm) 1H: 7.30-7.21 (m, 9H), 7.02-6.96 (m, 4H), 6.85 (t, J = 14.8Hz, 1H), 4.71 (s, 1H), 3.29 (m, 8H)
5-27 and cpd 64
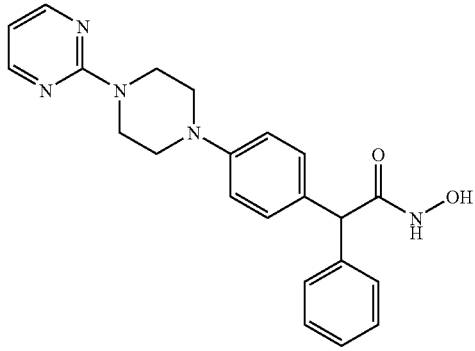
N-hydroxy-2-phenyl-2-(4-(4-(pyrimidin-2-yl)piperazin-1-yl)phenyl)acetamide
Mol wt. 389.45
LRMS(ESI): (calc.) 389.4 (found) 390.5 (MH)+
(CD3OD) d(ppm) 1H: 8.32 (d, J = 4.8Hz, 2H), 7.29-7.20 (m, 7H), 6.97 (d, J = 8.8Hz, 2H), 6.60 (t, J = 4.8Hz, 1H), 4.69 (s, 1H), 3.93 (m, 4H), 3.20 (m, 4H)
5-28
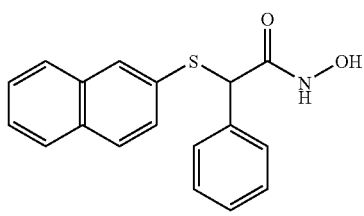 [SMILES: O=C(NO)C(Sc1ccc2ccccc2c1)c1ccccc1]
N-hydroxy-2-(naphthalen-2-ylthio)-2-phenylacetamide
Mol wt. 309.382
LRMS(ESI): (calc.) 309.4 (found) 310.3 (MH)+
(DMSO-d6) d(ppm) 1H: 10.98 (s, 1H), 9.11 (s, 1H), 7.87-7.77 (m, 4H), 7.53-7.40 (m, 5H), 7.34-7.25 (m, 3H), 5.04 (s, 1H).

| | |
|---|---|
| 5-29 | 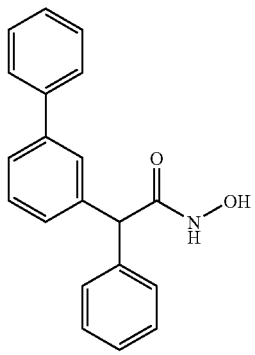 [SMILES: O=C(NO)C(c1ccccc1)c1cccc(-c2ccccc2)c1]<br>2-(biphenyl-3-yl)-N-hydroxy-2-phenylacetamide<br>Mol wt. 303.354<br>LRMS(ESI): (calc.) 303.4 (found) 302.3 (M − H)−<br>(DMSO-d6) d(ppm) 1H: 10.95 (s, 1H), 8.98 (s, 1H), 7.60-7.22 (m, 14H), 4.78 (s, 1H). |
| 5-30 | 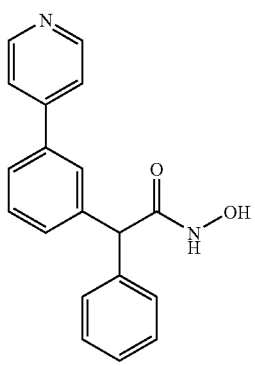 [SMILES: O=C(NO)C(c1ccccc1)c1cccc(-c2ccncc2)c1]<br>N-hydroxy-2-phenyl-2-(3-(pyridin-4-yl)phenyl)acetamide<br>Mol. Wt. 304.342<br>LRMS(ESI): (calc.) 304.3 (found) 305.2 (MH)+<br>(DMSO-d6) d(ppm) 1H: 10.96 (s, 1H), 9.00 (s, 1H), 8.62 (d, J = 6.1Hz, 2H), 7.72 (s, 1H),<br>7.67-7.65 (m, 1H), 7.61 (d, J = 6.4Hz, 2H), 7.48-7.21 (m, 7H), 4.80 (s, 1H). |
| 5-31 | 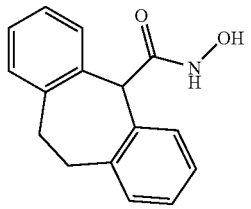 [SMILES: O=C(NO)C1c2ccccc2CCc2ccccc21]<br>Mol wt. 253.296<br>LRMS(ESI): (calc.) 253.3 (found) 254.2 (MH)+<br>(DMSO-d6) 10.47 (s, 1H), 8.87 (s, 1H), 7.33-7.29 (m, 2H), 7.21-7.14 (m, 6H), 4.81 (s, 1H), 3.67-3.57<br>(m, 2H), 2.85-2.75 (m, 2H) |
| 5-32 | 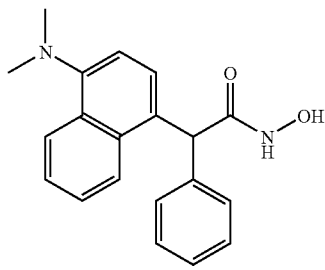 [SMILES: CN(C)c1ccc(C(C(=O)NO)c2ccccc2)c2ccccc12]<br>2-(4-(dimethylamino)naphthalen-1-yl)-N-hydroxy-2-phenylacetamide<br>Mol wt. 320.385<br>LRMS(ESI): (calc.) 320.4 (found) 321.4 (MH)+ |

(DMSO-d6) d(ppm) 1H: 10.95 (s, 1H), 8.96 (s, 1H), 8.19-8.16 (m, 1H), 8.00-7.96 (m, 1H), 7.49-7.41 (m, 3H), 7.31-7.18 (m, 5H), 7.07 (d, J = 8.0 Hz, 1H), 5.43 (s, 1H), 2.77 (s, 6H).

5-33 cpd 70

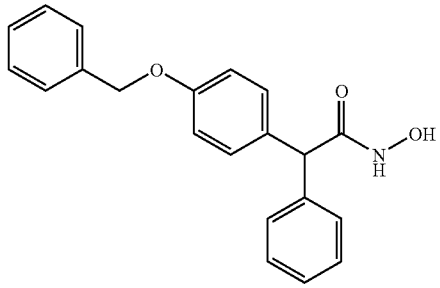 [SMILES: O=C(NO)C(c1ccccc1)c1ccc(OCc2ccccc2)cc1]

2-(4-(benzyloxy)phenyl)-N-hydroxy-2-phenylacetamide
Mol wt. 333.38
LRMS(ESI): (calc.) 333.4 (found) 334.4 (MH)+
(DMSO-d6) d(ppm) 1H: 10.86 (s, 1H), 8.92 (s, 1H), 7.42-7.17 (m, 12H), 6.93 (d, J = 8.8Hz, 2H), 5.05 (s, 2H), 4.62 (s, 1H).

5-34

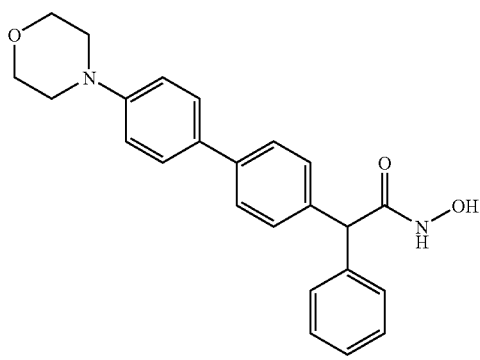 [SMILES: O=C(NO)C(c1ccccc1)c1ccc(-c2ccc(N3CCOCC3)cc2)cc1]

N-hydroxy-2-(4'-morpholinobiphenyl-4-yl)-2-phenylacetamide
Mol wt. 388.459
LRMS(ESI): (calc.) 388.5 (found) 389.5 (MH)+
(DMSO-d6) d(ppm) 1H: 10.92 (s, 1H), 8.96 (s, 1H), 7.51 (t, J = 8.6Hz, 4H), 7.34-7.20 (m, 7H), 6.98 (d, J = 8.8Hz, 2H), 4.70 (s, 1H), 3.72 (t, J = 4.7Hz, 4H), 3.12 (t, J = 4.7Hz, 4H).

5-35

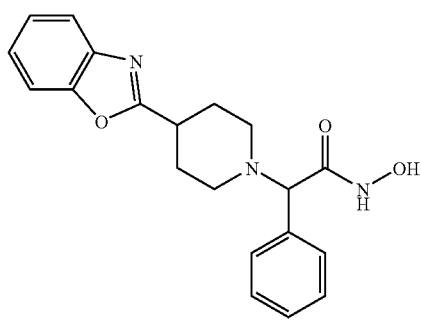 [SMILES: O=C(NO)C(c1ccccc1)N1CCC(c2nc3ccccc3o2)CC1]

2-(4-(benzo[d]oxazol-2-yl)piperidin-1-yl)-N-hydroxy-2-phenylacetamide
Mol. Wt. 351.399
LRMS(ESI): (calc.) 351.4 (found) 352.5 (MH)+
(MeOD-d4) 7.68-7.64 (m, 1H), 7.60-7.51 (m, 3H), 7.41-7.31 (m, 5H), 3.78 (s, 1H), 3.18-2.98 (m, 2H), 2.84-2.75 (m, 1H), 2.37-2.28 (m, 1H), 2.23-1.97 (m, 5H)

TABLE V-continued

Other Compounds prepared according general Schemes above 5-36 cpd 72

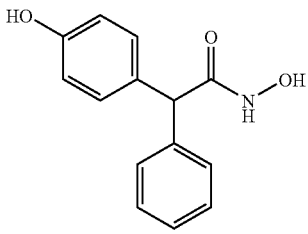 [SMILES: O=C(NO)C(c1ccccc1)c1ccc(O)cc1]

N-hydroxy-2-(4-hydroxyphenyl)-2-phenylacetamide
Mol wt. 243.258
LRMS(ESI): (calc.) 243.3 (found) 244.3 (MH)+
(DMSO-d6) d(ppm) 1H: 10.83 (s, 1H), 9.29 (s, 1H), 8.89 (s, 1H), 7.30-7.16 (m, 5H), 7.10 (d, J = 8.6Hz, 2H), 6.67 (d, J = 8.6Hz, 2H), 4.55 (s, 1H).

5-37

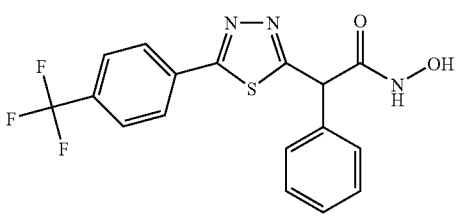 [SMILES: O=C(NO)C(c1ccccc1)c1nnc(-c2ccc(C(F)(F)F)cc2)s1]

N-hydroxy-2-phenyl-2-(5-(4-(trifluoromethyl)phenyl)-1,3,4-thiadiazol-2-yl)acetamide
Mol wt. 379.356
LRMS(ESI): (calc.) 379.0 (found) 380.3 (MH)+
(CD3OD) d(ppm) 1H: 8.16 (d, J = 8.0 Hz, 2H), 7.82 (d, J = 8.4Hz, 2H), 7.50 (d, J = 8.4Hz, 2H), 7.38-7.34 (m, 3H), 5.40 (s, 1H)

5-38

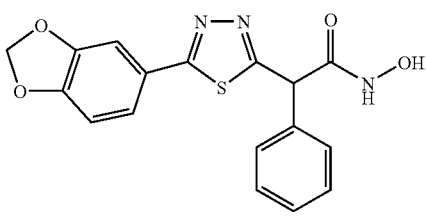 [SMILES: O=C(NO)C(c1ccccc1)c1nnc(-c2ccc3c(c2)OCO3)s1]

2-(5-(benzo[d][1,3]dioxol-5-yl)-1,3,4-thiadiazol-2-yl)-N-hydroxy-2-phenylacetamide
Mol wt. 355.368
LRMS(ESI): (calc.) 355.0 (found) 356.3 (MH)+
(CD3OD) d(ppm) 1H: 7.49-7.43 (m, 4H), 7.37-7.35 (m, 3H), 6.93 (m, 1H), 6.04 (s, 2H), 5.33 (s, 1H)

5-39

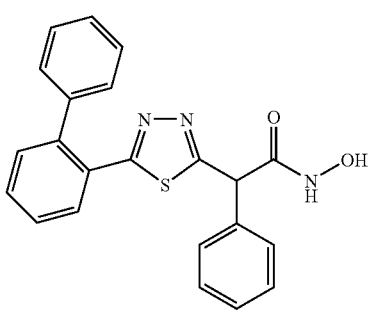 [SMILES: O=C(NO)C(c1ccccc1)c1nnc(-c2ccccc2-c2ccccc2)s1]

2-(5-(biphenyl-2-yl)-1,3,4-thiadiazol-2-yl)-N-hydroxy-2-phenylacetamide
Mol wt. 387.454
LRMS(ESI): (calc.) 387.1 (found) 388.4 (MH)+
(CD3OD) d(ppm) 1H: 7.86 (d, J = 7.6Hz, 1H), 7.61 (t, J = 6.0 Hz, 1H), 7.52 (t, J = 7.6Hz, 1H), 7.46 (d, J = 8.0 Hz, 1H), 7.35-7.25 (m, 8H), 7.17 (m, 2H), 5.23 (s, 1H)

TABLE V-continued

Other Compounds prepared according general Schemes above 5-40 cpd 74

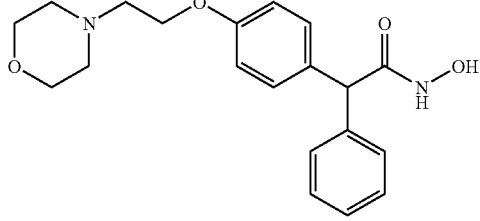

N-hydroxy-2-(4-(2-morpholinoethoxy)phenyl)-2-phenylacetamide
Mol wt. 356.416
LRMS(ESI): (calc.) 356.4 (found) 357.3 (MH)+
(MeOD) d(ppm) 1H: 8.36 (s, 1H), 7.30-7.20 (m, 7H), 6.90 (d, J = 8.2Hz, 2H), 4.72 (s, 1H),
4.20-4.16 (m, 2H), 3.78-3.72 (m, 4H), 3.00-2.94 (m, 2H), 2.80-2.74 (m, 4H).

5-41

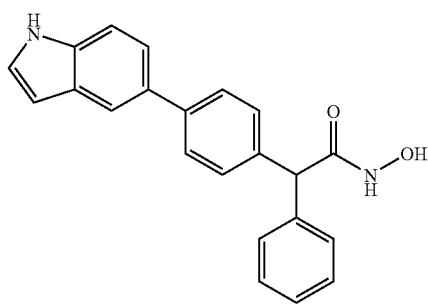 [SMILES: O=C(NO)C(c1ccccc1)c1ccc(-c2ccc3[nH]ccc3c2)cc1]

2-(4-(1H-indol-5-yl)phenyl)-N-hydroxy-2-phenylacetamide
Mol wt 342.39
LRMS(ESI): (calc.) 342.4 (found) 343.5 (MH)+
(DMSO-d6) d(ppm) 1H: 11.12 (s, 1H), 10.94 (s, 1H), 8.97 (s, 1H), 7.76 (d, J = 1.6Hz, 1H), 7.59 (d,
J = 8.4Hz, 2H), 7.44-7.21 (m, 10H), 6.46-6.44 (m, 1H), 4.72 (s, 1H).

5-42

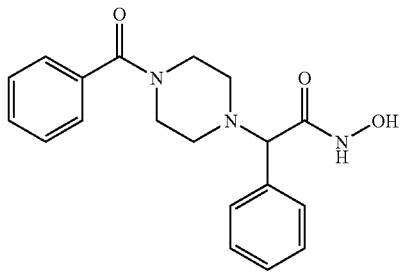

2-(4-benzoylpiperazin-1-yl)-N-hydroxy-2-phenylacetamide
Mol wt. 339.388
LRMS(ESI): (calc.) 339.4 (found) 340.5 (MH)+
(DMSO-d6) 10.85 (s, 1H), 8.91 (s, 1H), 7.44-7.39 (m, 5H), 7.36-7.24 (m, 5H), 3.68 (s, 1H), 3.65-3.50
(m, 2H), 3.35-3.30 (m, 2H), 2.43-2.20 (m, 4H)

5-43

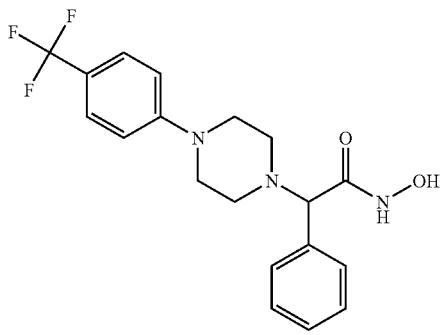 [SMILES: O=C(NO)C(c1ccccc1)N1CCN(c2ccc(C(F)(F)F)cc2)CC1]

N-hydroxy-2-phenyl-2-(4-(4-(trifluoromethyl)phenyl)piperazin-1-yl)acetamide
Mol wt. 379.376
LRMS(ESI): (calc.) 379.4 (found) 380.5 (MH)+

(MeOD-d4) 7.58-7.53 (m, 2H), 7.51-7.46 (m, 2H), 7.42-7.33 (m, 3H), 7.07-7.02 (m, 2H), 3.74 (s, 1H), 3.38-3.33 (m, 4H), 2.68-2.53 (m, 4H).

5-44

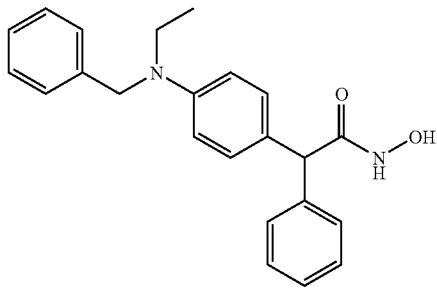 [SMILES: CCN(Cc1ccccc1)c1ccc(C(C(=O)NO)c2ccccc2)cc1]

2-(4-(benzyl(ethyl)amino)phenyl)-N-hydroxy-2-phenylacetamide
Mol wt. 360.449
LRMS(ESI): (calc.) 360.5 (found) 361.6 (MH)+
(DMSO-d6) d(ppm) 1H: 10.79 (s, 1H), 8.85 (s, 1H), 7.30-7.15 (m, 10H), 7.05 (d, J = 8.8Hz, 2H), 6.57 (d, J = 9.0 Hz, 2H), 4.50 (s, 1H), 4.46 (s, 2H), 3.41 (q, J = 7.0 Hz, 2H), 1.08 (t, J = 6.9Hz, 3H).

5-45

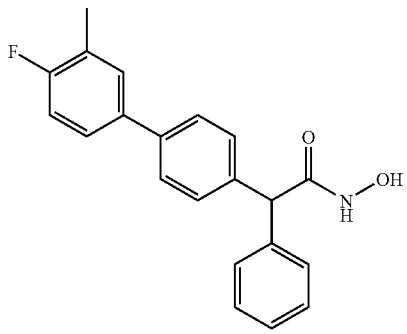 [SMILES: Cc1cc(-c2ccc(C(C(=O)NO)c3ccccc3)cc2)ccc1F]

2-(4'-fluoro-3'-methylbiphenyl-4-yl)-N-hydroxy-2-phenylacetamide
Mol wt. 335.372
LRMS(ESI): (calc.) 335.4 (found) 334.3 (M − H)−
(DMSO-d6) d(ppm) 1H: 10.90 (br s, 1H), 8.99 (br s, 1H), 7.57-7.53 (m, 3H), 7.49-7.43 (m, 1H), 7.38-7.28 (m, 6H), 7.25-7.16 (m, 2H), 4.73 (s, 1H), 2.27 (d, J = 1.7Hz, 3H).

5-46

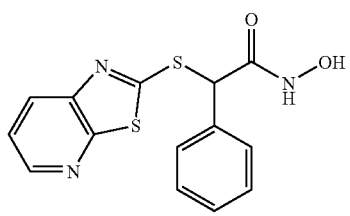 [SMILES: O=C(NO)C(Sc1nc2cccnc2s1)c1ccccc1]

N-hydroxy-2-phenyl-2-(thiazolo[5,4-b]pyridin-2-ylthio)acetamide
Mol wt. 317.386
LRMS(ESI): (calc.) 317.4 (found) 318.0 (MH)+
(DMSO-d6) d(ppm) 1H: 11.24 (s, 1H), 9.24 (s, 1H), 8.49 (dd, J = 4.5, 1.4Hz, 1H), 8.20 (dd, J = 8.2, 1.5Hz, 1H), 7.60-7.58 (m, 2H), 7.54-7.50 (m, 1H), 7.39-7.29 (m, 3H), 5.70 (s, 1H).

5-47

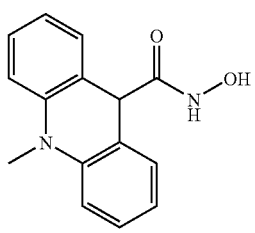 [SMILES: CN1c2ccccc2C(C(=O)NO)c2ccccc21]

N-hydroxy-10-methyl-9,10-dihydroacridine-9-carboxamide
Mol wt. 254.284

LRMS(ESI): (calc.) 254.3 (found) 255.2 (MH)+
(MeOD-d4) 7.32-7.27 (m, 2H), 7.26-7.22 (m, 2H), 7.05 (d, J = 7.6Hz, 2H), 6.96 (td, J = 7.4, 1.2Hz, 2H), 4.74 (s, 1H), 3.42 (s, 3H)

5-48

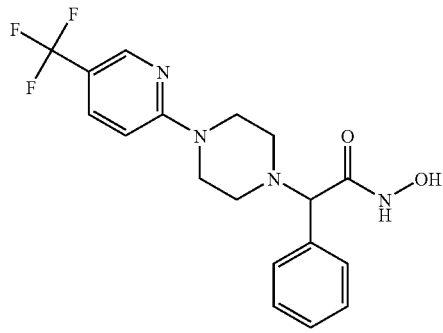 [SMILES: O=C(NO)C(c1ccccc1)N1CCN(c2ccc(C(F)(F)F)cn2)CC1]

N-hydroxy-2-phenyl-2-(4-(5-(trifluoromethyl)pyridin-2-yl)piperazin-1-yl)acetamide
Mol wt. 380.364
LRMS(ESI): (calc.) 380.4 (found) 381.5 (MH)+
(MeOD-d4) 8.34 (dd, J = 1.8, 0.8Hz, 1H), 7.72 (dd, J = 9.1, 2.3Hz, 1H), 7.58-7.52 (m, 2H), 7.43-7.34 (m, 3H), 6.88 (d, J = 9.0 Hz, 1H), 3.74 (s, 1H), 3.73-3.69 (m, 4H), 2.62-2.47 (m, 4H)

5-49

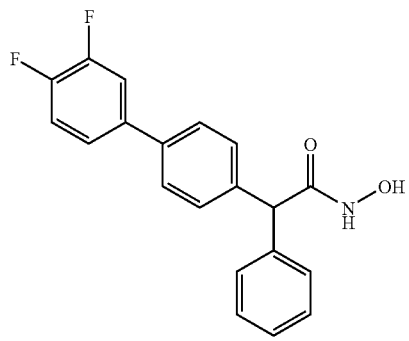 [SMILES: O=C(NO)C(c1ccccc1)c1ccc(-c2ccc(F)c(F)c2)cc1]

2-(3',4'-difluorobiphenyl-4-yl)-N-hydroxy-2-phenylacetamide
Mol wt. 339.335
LRMS(ESI): (calc.) 339.3 (found) 338.4 (M − H)−
(DMSO-d6) d(ppm) 1H: 10.95 (s, 1H), 8.99 (s, 1H), 7.76-7.70 (m, 1H), 7.62 (d, J = 8.2Hz, 2H), 7.51-7.47 (m, 2H), 7.39-7.20 (m, 7H), 4.74 (s, 1H).

5-50

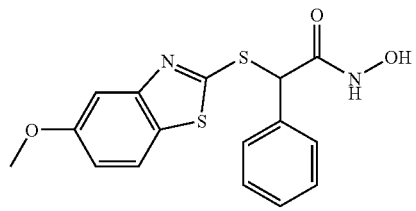 [SMILES: COc1ccc2sc(SC(C(=O)NO)c3ccccc3)nc2c1]

N-hydroxy-2-(5-methoxybenzo[d]thiazol-2-ylthio)-2-phenylacetamide
Mol wt. 346.424
LRMS(ESI): (calc.) 346.4 (found) 347.4 (MH)+
(DMSO-d6) d(ppm) 1H: 11.22 (s, 1H), 9.23 (s, 1H), 7.84 (d, J = 8.8Hz, 1H), 7.58 (d, J = 6.9Hz, 2H), 7.38-7.29 (m, 4H), 6.99 (dd, J = 8.8, 2.5Hz, 1H), 5.59 (s, 1H), 3.81 (s, 3H).

5-51

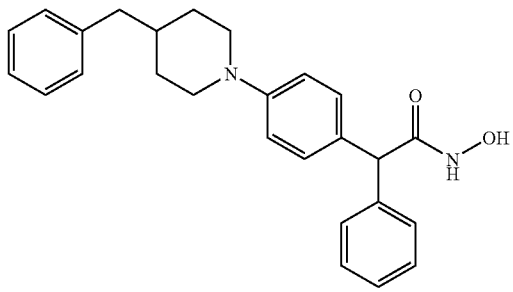 [SMILES: O=C(NO)C(c1ccccc1)c1ccc(N2CCC(Cc3ccccc3)CC2)cc1]

2-(4-(4-benzylpiperidin-1-yl)phenyl)-N-hydroxy-2-phenylacetamide
Mol wt. 400.513
LRMS(ESI): (calc.) 400.5 (found) 401.6 (MH)+
(MeOD) d(ppm) 1H: 7.30-7.13 (m, 12H), 6.91 (d, J = 8.8Hz, 2H), 4.68 (s, 1H), 3.60 (d, J = 12.4 Hz, 2H), 2.62-2.54 (m, 4H), 1.73-1.60 (m, 3H), 1.42-1.31 (m, 2H).

5-52

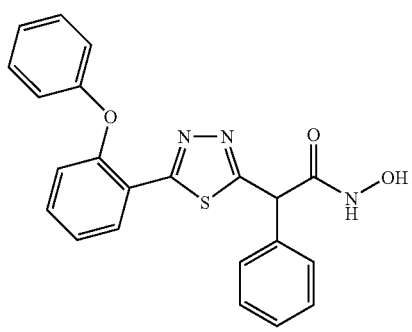 [SMILES: O=C(NO)C(c1ccccc1)c1nnc(-c2ccccc2Oc2ccccc2)s1]

N-hydroxy-2-(5-(2-phenoxyphenyl)-1,3,4-thiadiazol-2-yl)-2-phenylacetamide
Mol wt. 403.454
LRMS(ESI): (calc.) 403.1 (found) 404.4 (MH)+
(CD3OD) d(ppm) 1H: 8.38 (d, J = 8.0 Hz, 1H), 7.48-7.20 (m, 10H), 7.06 (d, J = 8.0 Hz, 2H), 6.97 (d, J = 8.0 Hz, 1H), 5.36 (s, 1H)

5-53

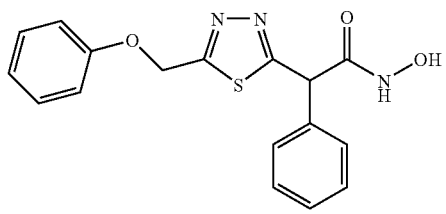 [SMILES: O=C(NO)C(c1ccccc1)c1nnc(COc2ccccc2)s1]

N-hydroxy-2-(5-(phenoxymethyl)-1,3,4-thiadiazol-2-yl)-2-phenylacetamide
Mol wt. 341.384
LRMS(ESI): (calc.) 341.0 (found) 342.3 (MH)+
(CD3OD) d(ppm) 1H: 7.45 (m, 2H), 7.38-7.27 (m, 5H), 7.03-6.96 (m, 3H), 5.48 (s, 2H), 5.34 (s, 1H)

5-54

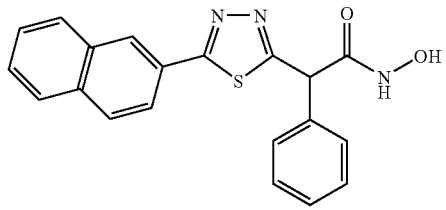 [SMILES: O=C(NO)C(c1ccccc1)c1nnc(-c2ccc3ccccc3c2)s1]

N-hydroxy-2-(5-(naphthalen-2-yl)-1,3,4-thiadiazol-2-yl)-2-phenylacetamide
Mol wt. 361.417
LRMS(ESI): (calc.) 361.0 (found) 362.3 (MH)+
(CD3OD) d(ppm) 1H: 8.43 (s, 1H), 8.09-7.88 (m, 4H), 7.56-7.50 (m, 4H), 7.38-7.31 (m, 3H), 5.38 (s, 1H)

TABLE V-continued

Other Compounds prepared according general Schemes above 5-55

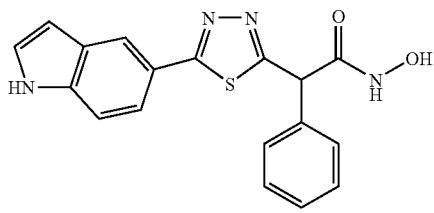 [SMILES: O=C(NO)C(c1ccccc1)c1nnc(-c2ccc3[nH]ccc3c2)s1]

2-(5-(1H-indol-5-yl)-1,3,4-thiadiazol-2-yl)-N-hydroxy-2-phenylacetamide
Mol wt. 350.394
LRMS(ESI): (calc.) 350.0 (found) 351.2 (MH)+
(CD3OD) d(ppm) 1H: 8.16 (s, 1H), 7.71 (d, J = 2.0 Hz, 1H), 7.52-7.47 (m, 3H), 7.40-7.32 (m, 4H), 6.56 (d, J = 3.2Hz, 1H), 5.34 (s, 1H)

5-56 cpd 85

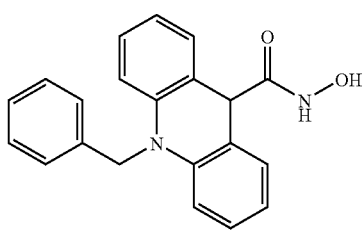 [SMILES: O=C(NO)C1c2ccccc2N(Cc2ccccc2)c2ccccc21]

10-benzyl-N-hydroxy-9,10-dihydroacridine-9-carboxamide
Mol wt. 330.38
LRMS(ESI): (calc.) 330.4 (found) 331.4 (MH)+
(MeOD-d4) 7.36-7.31 (m, 2H), 7.29-7.21 (m, 5H), 7.17-7.11 (m, 2H), 6.91 (td, J = 7.4, 1.0 Hz, 2H), 6.81-6.78 (m, 2H), 5.22 (s, 2H), 4.85 (s, 1H)

5-57

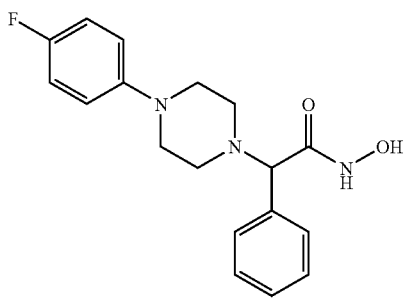

2-(4-(4-fluorophenyl)piperazin-1-yl)-N-hydroxy-2-phenylacetamide
Mol wt. 329.369
LRMS(ESI): (calc.) 329.4 (found) 330.4 (MH)+
(MeOD-d4) 7.59-7.53 (m, 2H), 7.42-7.32 (m, 3H), 7.02-6.92 (m, 4H), 3.75 (s, 1H), 3.20-3.10 (m, 4H), 2.68-2.52 (m, 4H)

5-58

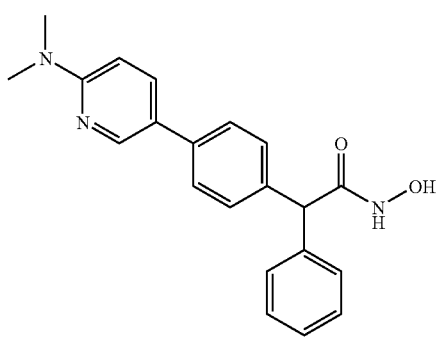

2-(4-(6-(dimethylamino)pyridin-3-yl)phenyl)-N-hydroxy-2-phenylacetamide
Mol wt. 347.41
LRMS(ESI): (calc.) 347.4 (found) 348.5 (MH)+
(DLRMSOD6) d(ppm) 1H: 10.94 (s, 1H), 8.98 (s, 1H), 8.40 (d, J = 2.4Hz, 1H), 7.79 (dd, J = 8.8, 2.5 Hz, 1H), 7.54 (d, J = 8.2Hz, 2H), 7.36-7.23 (m, 7H), 6.70 (d, J = 8.8Hz, 1H), 4.72 (s, 1H), 3.05 (s, 6H).

TABLE V-continued

Other Compounds prepared according general Schemes above 5-59

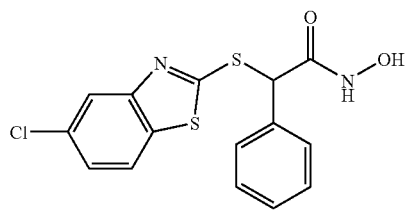 [SMILES: O=C(NO)C(Sc1nc2cc(Cl)ccc2s1)c1ccccc1]

2-(5-chlorobenzo[d]thiazol-2-ylthio)-N-hydroxy-2-phenylacetamide
Mol wt. 350.843
LRMS(ESI): (calc.) 350.0 (found) 351.3 (MH)+
(DLRMSOD6) d(ppm) 1H: 11.24 (s, 1H), 9.25 (s, 1H), 8.04 (d, J = 8.6Hz, 1H), 7.91 (d, J = 2.2Hz, 1H), 7.61-7.58 (m, 2H), 7.44-7.29 (m, 4H), 5.62 (s, 1H).

5-60

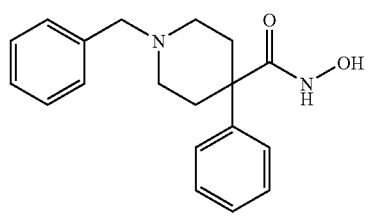 [SMILES: O=C(NO)C1(c2ccccc2)CCN(Cc2ccccc2)CC1]

1-benzyl-N-hydroxy-4-phenylpiperidine-4-carboxamide
Mol wt. 310.39
LRMS(ESI): (calc.) 310.4 (found) 311.4 (MH)+
(DLRMSOD6) d(ppm) 1H: 10.49 (s, 1H), 8.69 (s, 1H), 7.37-7.18 (m, 10H), 3.39 (s, 2H), 2.68-2.55 (m, 2H), 2.48-2.43 (m, 2H), 2.15 (t, J = 11.1Hz, 2H), 1.85-1.75 (m, 2H).

5-61

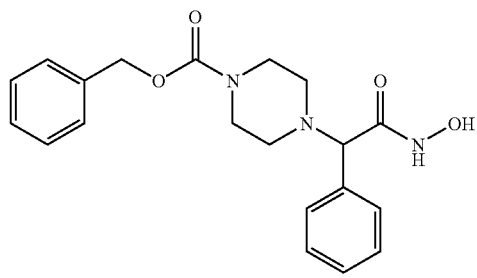 [SMILES: O=C(NO)C(c1ccccc1)N1CCN(C(=O)OCc2ccccc2)CC1]

benzyl 4-(2-(hydroxyamino)-2-oxo-1-phenylethyl)piperazine-1-carboxylate
Mol wt. 369.414
LRMS(ESI): (calc.) 369.4 (found) 370.6 (MH)+
(MeOD-d4) 7.53-7.49 (m, 2H), 7.40-7.32 (m, 8H), 5.13 (s, 2H), 3.72 (s, 1H), 3.60-3.50 (m, 4H), 2.49-2.34 (m, 4H)

5-62

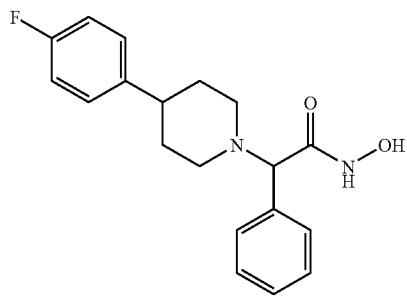 [SMILES: O=C(NO)C(c1ccccc1)N1CCC(c2ccc(F)cc2)CC1]

2-(4-(4-fluorophenyl)piperidin-1-yl)-N-hydroxy-2-phenylacetamide
Mol wt. 328.381
LRMS(ESI): (calc.) 328.4 (found) 329.5 (MH)+
(MeOD-d4) 7.58-7.52 (m, 2H), 7.41-7.33 (m, 3H), 7.30-7.25 (m, 2H), 7.06-6.99 (m, 2H), 3.72 (s, 1H), 3.25-3.18 (m, 1H), 2.84-2.76 (m, 1H), 2.61-2.51 (m, 1H), 2.29-2.20 (m, 1H), 1.99-1.67 (m, 5H)

TABLE V-continued

Other Compounds prepared according general Schemes above 5-63

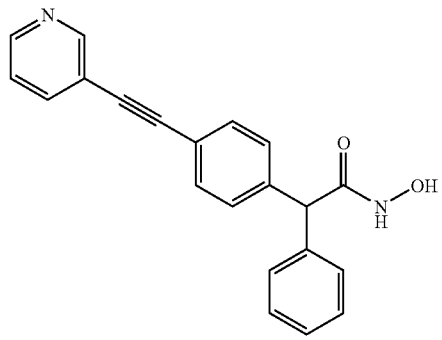 [SMILES: O=C(NO)C(c1ccccc1)c1ccc(C#Cc2cccnc2)cc1]

N-hydroxy-2-phenyl-2-(4-(pyridin-3-ylethynyl)phenyl)acetamide
Mol wt. 328.364
LRMS(ESI): (calc.) 328.4 (found) 329.4 (MH)+
(DMSO-d6) 11.03 (s, 1H), 9.08 (s, 1H), 8.78 (dd, J = 2.2, 0.8Hz, 1H), 8.62 (dd, J = 4.8, 1.8Hz, 1H),
8.01 (dt, J = 8.0, 2.0 Hz, 1H), 7.61-7.57 (m, 2H), 7.52-7.48 (m, 1H), 7.45-7.41 (m, 2H), 7.40-7.36
(m, 4H), 7.33-7.27 (m, 1H), 4.80 (s, 1H)__

5-64

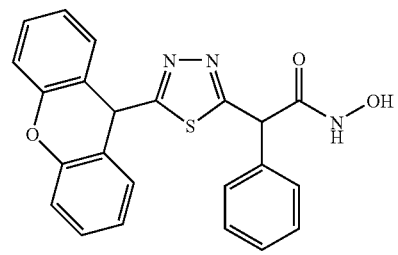 [SMILES: O=C(NO)C(c1ccccc1)c1nnc(C2c3ccccc3Oc3ccccc32)s1]

2-(5-(9H-xanthen-9-yl)-1,3,4-thiadiazol-2-yl)-N-hydroxy-2-phenylacetamide
Mol wt. 415.464
LRMS(ESI): (calc.) 415.1 (found) 416.2 (MH)+
(CD3OD) d(ppm) 1H: 7.35-7.26 (m, 9H), 7.18-7.07 (m, 4H), 5.95 (s, 1H), 5.20 (s, 1H)__

5-65

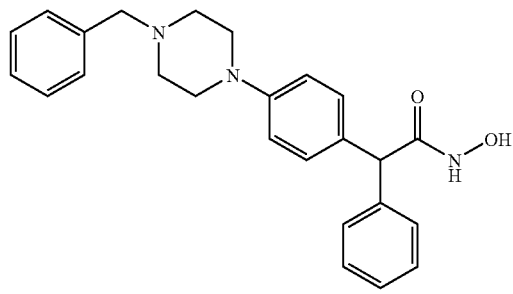 [SMILES: O=C(NO)C(c1ccccc1)c1ccc(N2CCN(Cc3ccccc3)CC2)cc1]

2-(4-(4-benzylpiperazin-1-yl)phenyl)-N-hydroxy-2-phenylacetamide
Mol wt. 401.501
LRMS(ESI): (calc.) 401.2 (found) 402.6 (MH)+
(CD3OD) d(ppm) 1H: 7.35-7.17 (m, 12H), 6.91 (d, J = 8.8Hz, 2H), 4.68 (s, 1H), 3.57 (s, 2H),
3.16 (m, 4H), 2.61 (m, 4H)__

5-66

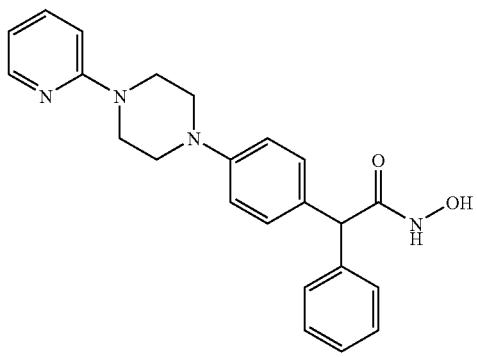 [SMILES: O=C(NO)C(c1ccccc1)c1ccc(N2CCN(c3ccccn3)CC2)cc1]

N-hydroxy-2-phenyl-2-(4-(4-(pyridin-2-yl)piperazin-1-yl)phenyl)acetamide
Mol wt. 388.462
LRMS(ESI): (calc.) 388.1 (found) 389.5 (MH)+
(CD3OD) d(ppm) 1H: 8.09 (d, J = 4.8Hz, 1H), 7.57 (t, J = 9.2Hz, 1H), 7.30-7.21 (m, 7H), 6.97
(d, J = 6.8Hz, 2H), 6.87 (d, J = 8.8Hz, 1H), 6.69 (t, J = 6.4Hz, 1H), 4.70 (s, 1H), 3.63 (m, 4H),
3.25 (m, 4H)

5-67

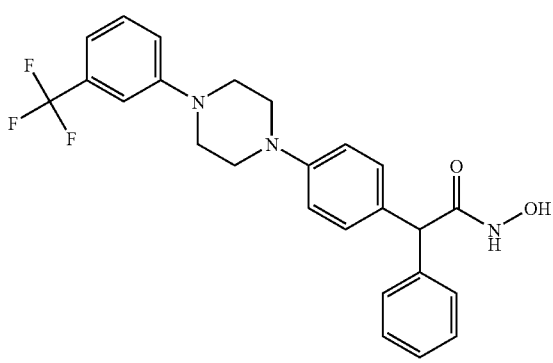 [SMILES: O=C(NO)C(c1ccccc1)c1ccc(N2CCN(c3cccc(C(F)(F)F)c3)CC2)cc1]

N-hydroxy-2-phenyl-2-(4-(4-(3-(trifluoromethyl)phenyl)piperazin-1-yl)phenyl)acetamide
Mol wt. 455.472
LRMS(ESI): (calc.) 455.1 (found) 456.6 (MH)+
(CD3OD) d(ppm) 1H: 7.43-7.21 (m, 10H), 7.09 (d, J = 8.0 Hz, 1H), 6.98 (m, 2H), 4.70 (s, 1H),
3.36 (m, 4H), 3.32 (m, 4H)

5-68

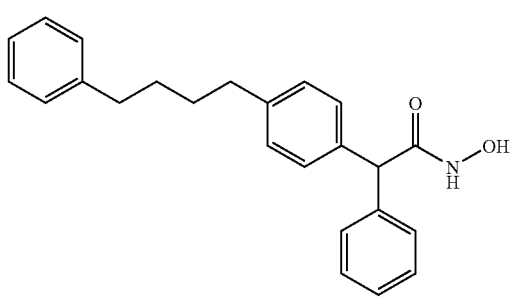 [SMILES: O=C(NO)C(c1ccccc1)c1ccc(CCCCc2ccccc2)cc1]

N-hydroxy-2-phenyl-2-(4-(4-phenylbutyl)phenyl)acetamide
Mol wt. 359.461
LRMS(ESI): (calc.) 359.2 (found) 360.4 (MH)+
(CD3OD) d(ppm) 1H: 7.30-7.11 (m, 14H), 4.73 (s, 1H), 2.60 (m, 4H), 1.61 (m, 4H)

5-69

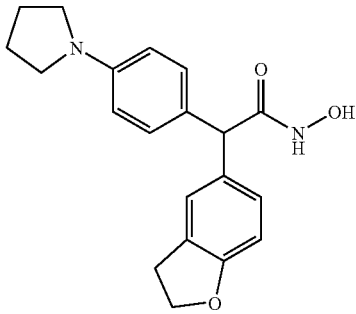 [SMILES: O=C(NO)C(c1ccc(N2CCCC2)cc1)c1ccc2c(c1)CCO2]

2-(2,3-dihydrobenzofuran-5-yl)-N-hydroxy-2-(4-(pyrrolidin-1-yl)phenyl)acetamide
Mol wt. 338.4
LRMS(ESI): (calc.) 338.4 (found) 339.4 (MH)+
(DMSO-d6) d(ppm) 1H: 10.76 (s, 1H), 8.84 (s, 1H), 7.12-7.07 (m, 3H), 6.95 (dd, J = 8.2, 1.6Hz, 1H), 6.64 (d, J = 8.2Hz, 1H), 6.45 (d, J = 8.2Hz, 2H), 4.49-4.44 (m, 3H), 3.18-3.08 (m, 6H), 1.94-1.90 (m, 4H).

5-70

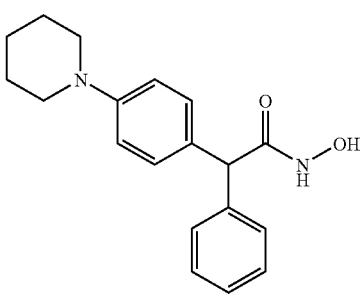 [SMILES: O=C(NO)C(c1ccccc1)c1ccc(N2CCCCC2)cc1]

N-hydroxy-2-phenyl-2-(4-(piperidin-1-yl)phenyl)acetamide
Mol wt. 310.39
LRMS(ESI): (calc.) 310.4 (found) 311.5 (MH)+
(DLRMSOD6) d(ppm) 1H: 10.83 (br s, 1H), 9.51 (br s, 1H), 7.29-7.17 (m, 5H), 7.13 (d, J = 8.8 Hz, 2H), 6.85 (d, J = 8.8Hz, 2H), 4.57 (s, 1H), 3.07 (t, J = 5.1Hz, 4H), 1.59-1.49 (m, 6H).

5-71

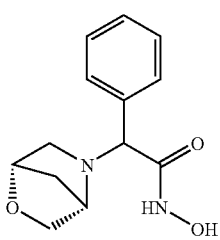 [SMILES: O=C(NO)C(c1ccccc1)N1C[C@@H]2C[C@H]1CO2]

2-((1S,4S)-2-oxa-5-azabicyclo[2.2.1]heptan-5-yl)-N-hydroxy-2-phenylacetamide
Mol wt. 248.278
LRMS(ESI): (calc.) 248.1 (found) 249.3 (MH)+
(MeOD) d(ppm) 1H: 7.52 (d, J = 6.8Hz, 2H), 7.37-7.27 (m, 3H), 4.42-4.27 (m, 1H), 4.15 and 4.10 (2 s, 1H), 4.07 and 4.04 (2 d, J = 8.0 Hz, 1H), 3.60 and 3.47 (2 dd, J = 7.8 and 1.8Hz, 1H), 3.48 (s, 1H), 3.00 and 2.67 (2 dd, J = 10.2 and 0.9Hz, 1H), 2.55 and 2.44 (2 d, J = 10.3Hz, 1H), 2.00-1.93 (m, 1H), 1.74-1.65 (m, 1H).

5-72

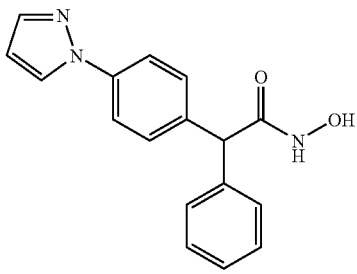 [SMILES: O=C(NO)C(c1ccccc1)c1ccc(-n2cccn2)cc1]

2-(4-(1H-pyrazol-1-yl)phenyl)-N-hydroxy-2-phenylacetamide
Mol wt. 293.32
LRMS(ESI): (calc.) 293.3 (found) 294.3 (MH)+
(DMSO-d6) 11.02 (br s, 1H), 9.06 (br s, 1H), 8.49 (d, J = 2.1Hz, 1H), 7.84-7.80 (m, 2H), 7.76 (d, J = 1.4Hz, 1H), 7.49-7.45 (m, 2H), 7.40-7.34 (m, 4H), 7.32-7.26 (m, 1H), 6.57 (q, J = 2.5, 1.8Hz, 1H), 4.80 (s, 1H).

5-73

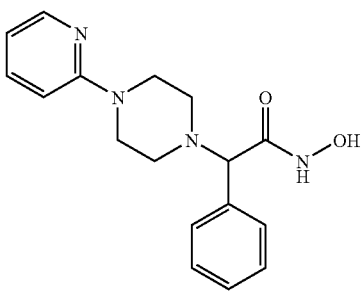 [SMILES: O=C(NO)C(c1ccccc1)N1CCN(c2ccccn2)CC1]

N-hydroxy-2-phenyl-2-(4-(pyridin-2-yl)piperazin-1-yl)acetamide
Mol wt 312.366
LRMS(ESI): (calc.) 312.4 (found) 313.5 (MH)+
(DMSO-d6) 10.91 (br s, 1H), 8.97 (br s, 1H), 8.14-8.12 (m, 1H), 7.58-7.48 (m, 3H), 7.42-7.30 (m, 3H), 6.82 (d, J = 8.6Hz, 1H), 6.69-6.64 (m, 1H), 3.69 (s, 1H), 3.53-3.47 (m, 4H), 2.52-2.36 (m, 4H).

5-74

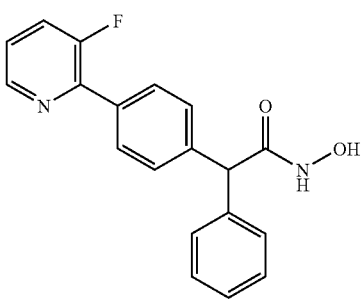 [SMILES: O=C(NO)C(c1ccccc1)c1ccc(-c2ncccc2F)cc1]

2-(4-(3-fluoropyridin-2-yl)phenyl)-N-hydroxy-2-phenylacetamide
Mol wt. 322.333
LRMS(ESI): (calc.) 322.3 (found) 323.2 (MH)+
(MeOD) d(ppm) 1H: 8.39 (d, J = 2.2Hz, 1H), 8.13 (td, J = 8.4, 2.5Hz, 1H), 7.55 (d, J = 8.2Hz, 2H), 7.44 (d, J = 8.2Hz, 2H), 7.37-7.22 (m, 5H), 7.11 (dd, J = 8.4, 2.3Hz, 1H), 4.85 (s, 1H).

TABLE V-continued

Other Compounds prepared according general Schemes above 5-75

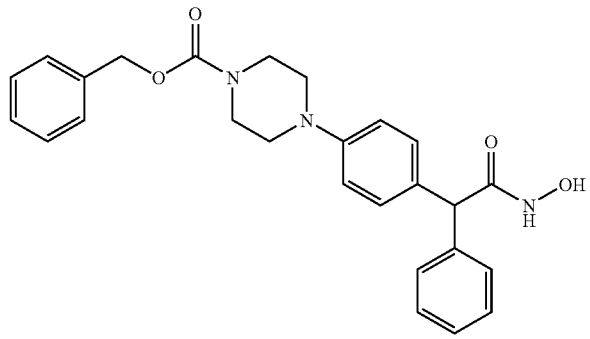 [SMILES: O=C(NO)C(c1ccccc1)c1ccc(N2CCN(C(=O)OCc3ccccc3)CC2)cc1]

benzyl 4-(4-(2-(hydroxyamino)-2-oxo-1-phenylethyl)phenyl)piperazine-1-carboxylate
Mol wt. 445.51
LRMS(ESI): (calc.) 445.2 (found) 446.5 (MH)+
(CD3OD) d(ppm) 1H: 7.38-7.18 (m, 12H), 6.92 (d, J = 8.8Hz, 2H), 5.13 (s, 2H), 4.68 (s, 1H), 3.62 (m, 4H), 3.11 (m, 4H)__

5-76

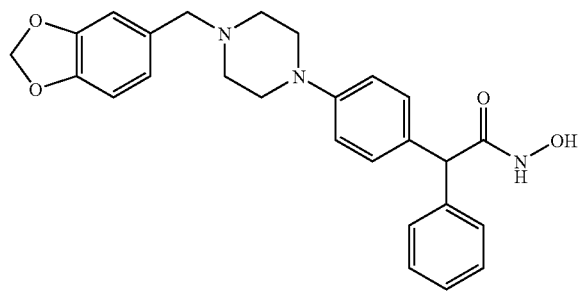 [SMILES: O=C(NO)C(c1ccccc1)c1ccc(N2CCN(Cc3ccc4c(c3)OCO4)CC2)cc1]

2-(4-(4-(benzo[d][1,3]dioxol-5-ylmethyl)piperazin-1-yl)phenyl)-N-hydroxy-2-phenylacetamide
Mol wt. 445.51
LRMS(ESI): (calc.) 445.2 (found) 446.5 (MH)+
(CD3OD) d(ppm) 1H: 7.28-7.17 (m, 7H), 6.92-6.88 (m, 3H), 6.79-6.75 (m, 2H), 5.92 (s, 2H), 4.68 (s, 1H), 3.51 (s, 2H), 3.17 (t, J = 4.8Hz, 4H), 2.62 (t, J = 5.2Hz, 4H)__

5-77

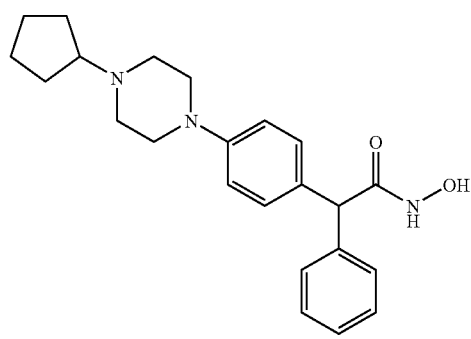 [SMILES: O=C(NO)C(c1ccccc1)c1ccc(N2CCN(C3CCCC3)CC2)cc1]

2-(4-(4-cyclopentylpiperazin-1-yl)phenyl)-N-hydroxy-2-phenylacetamide
Mol wt. 379.495
LRMS(ESI): (calc.) 379.2 (found) 380.5 (MH)+
(CD3OD) d(ppm) 1H: 7.29-7.18 (m, 7H), 6.92 (d, J = 8.8Hz, 2H), 4.68 (s, 1H), 3.18 (t, J = 5.2 Hz, 4H), 2.69 (t, J = 5.2Hz, 4H), 2.57 (m, 1H), 1.93 (m, 2H), 1.73 (m, 2H), 1.60 (m, 2H), 1.44 (m, 2H)__

5-78

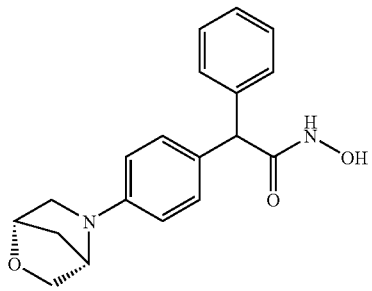 [SMILES: O=C(NO)C(c1ccccc1)c1ccc(N2C[C@@H]3C[C@H]2CO3)cc1]

2-(4-((1S,4S)-2-oxa-5-azabicyclo[2.2.1]heptan-5-yl)phenyl)-N-hydroxy-2-phenylacetamide
Mol wt. 324.374
LRMS(ESI): (calc.) 324.2 (found) 325.4 (MH)+
(dLRMSo) d(ppm) 1H: 10.84 (s, 1H), 8.90 (s, 1H), 7.42-7.16 (m, 5H), 7.12 (d, J = 8.2Hz, 2H), 6.55 (d, J = 7.5Hz, 2H), 4.58 (s, 1H), 4.56 (s, 1H), 4.49 (s, 1H), 3.71 (d, J = 7.2Hz, 1H), 6.63 (d, J = 7.2Hz, 1H), 3.46 (d, J = 9.2Hz, 1H), 2.91 (d, J = 7.2 z, 1H), 1.89 (d, J = 9.3Hz, 1H), 1.81 (d, J = 9.6Hz, 1H).

5-79

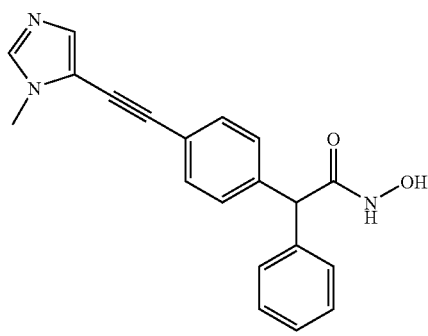 [SMILES: Cn1cncc1C#Cc1ccc(C(C(=O)NO)c2ccccc2)cc1]

N-hydroxy-2-(4-((1-methyl-1H-imidazol-5-yl)ethynyl)phenyl)-2-phenylacetamide
Mol wt. 331.368
LRMS(ESI): (calc.) 331.4 (found) 332.4 (MH)+
(DMSO-d6) 11.02 (br s, 1H), 9.07 (br s, 1H), 7.81 (s, 1H), 7.58-7.53 (m, 2H), 7.44-7.27 (m, 8H), 4.79 (s, 1H), 3.73 (s, 3H)

5-80

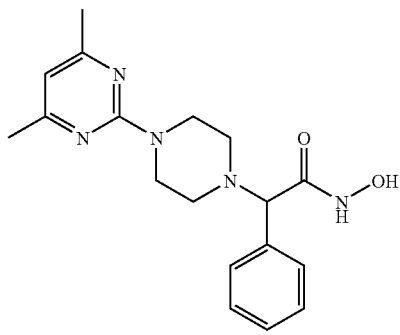 [SMILES: Cc1cc(C)nc(N2CCN(C(C(=O)NO)c3ccccc3)CC2)n1]

2-(4-(4,6-dimethylpyrimidin-2-yl)piperazin-1-yl)-N-hydroxy-2-phenylacetamide
Mol wt. 341.408
LRMS(ESI): (calc.) 341.4 (found) 342.3 (MH)+
(MeOD-d4) 7.59-7.52 (m, 2H), 7.43-7.34 (m, 3H), 6.40 (s, 1H), 3.87-3.81 (m, 4H), 3.71 (s, 1H), 2.55-2.40 (m, 4H), 2.28 (s, 6H)

5-81

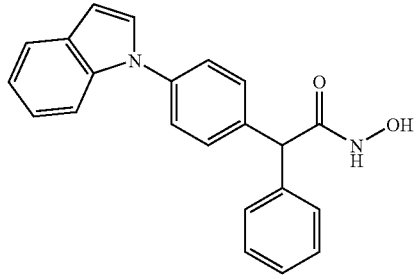 [SMILES: O=C(NO)C(c1ccccc1)c1ccc(-n2ccc3ccccc32)cc1]

2-(4-(1H-indol-1-yl)phenyl)-N-hydroxy-2-phenylacetamide

Mol wt. 342.39

LRMS(ESI): (calc.) 342.4 (found) 343.4 (MH)+

(MeOD-d4) 7.66-7.62 (m, 1H), 7.57-7.50 (m, 5H), 7.46-7.41 (m, 3H), 7.40-7.35 (m, 2H), 7.33-7.28 (m, 1H), 7.22-7.17 (m, 1H), 7.15-7.10 (m, 1H), 6.67 (d, J = 3.3Hz, 1H), 4.91 (s, 1H)

5-82

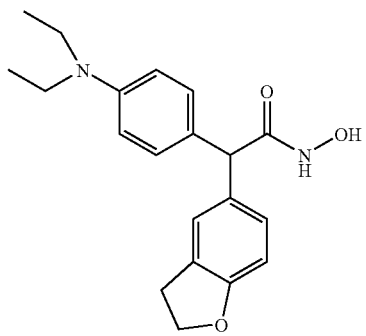 [SMILES: CCN(CC)c1ccc(C(C(=O)NO)c2ccc3c(c2)CCO3)cc1]

2-(4-(diethylamino)phenyl)-2-(2,3-dihydrobenzofuran-5-yl)-N-hydroxyacetamide

Mol wt. 340.416

LRMS(ESI): (calc.) 340.4 (found) 341.5 (MH)+

(DLRMSOD6) d(ppm) 1H: 10.75 (s, 1H), 8.83 (s, 1H), 7.15 (s, 1H), 7.07 (d, J = 8.8Hz, 2H), 6.98 (dd, J = 8.4, 1.8Hz, 1H), 6.65 (d, J = 8.2Hz, 1H), 6.56 (d, J = 9.0 Hz, 2H), 4.49-4.43 (m, 3H), 3.28 (q, J = 7.0 Hz, 4H), 3.11 (t, J = 8.6Hz, 2H), 1.04 (t, J = 7.0 Hz, 6H).

5-83

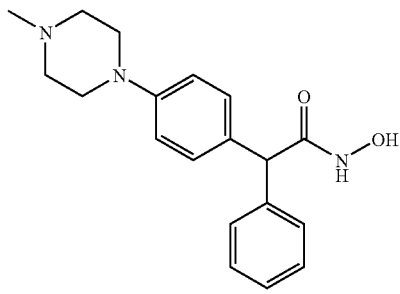 [SMILES: CN1CCN(c2ccc(C(C(=O)NO)c3ccccc3)cc2)CC1]

N-hydroxy-2-(4-(4-methylpiperazin-1-yl)phenyl)-2-phenylacetamide

Mol wt. 325.405

LRMS(ESI): (calc.) 325.4 (found) 326.4 (MH)+

(DLRMSOD6) d(ppm) 1H: 10.84 (s, 1H), 8.91 (s, 1H), 7.29-7.19 (m, 5H), 7.15 (d, J = 8.6Hz, 2H), 6.86 (d, J = 8.8Hz, 2H), 4.57 (s, 1H), 3.07 (t, J = 4.7Hz, 4H), 2.42 (t, J = 4.9Hz, 4H), 2.20 (s, 3H).

5-84 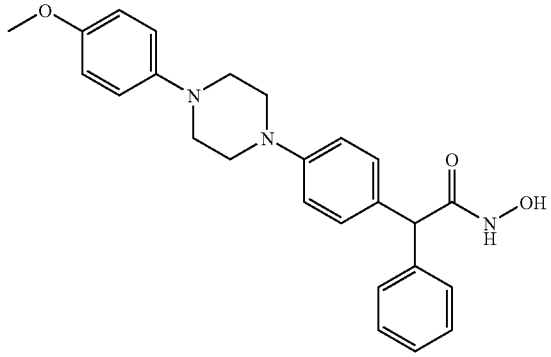 [SMILES: COc1ccc(N2CCN(c3ccc(C(C(=O)NO)c4ccccc4)cc3)CC2)cc1]

N-hydroxy-2-(4-(4-(4-methoxyphenyl)piperazin-1-yl)phenyl)-2-phenylacetamide
Mol wt. 417.5
LRMS(ESI): (calc.) 417.2 (found) 418.5 (MH)+
(CD3OD) d(ppm) 1H: 7.30-7.21 (m, 7H), 6.98 (t, J = 8.8Hz, 4H), 6.85 (d, J = 9.2Hz, 2H), 4.70 (s, 1H), 3.74 (s, 3H), 3.28 (m, 4H), 3.18 (m, 4H)

5-85 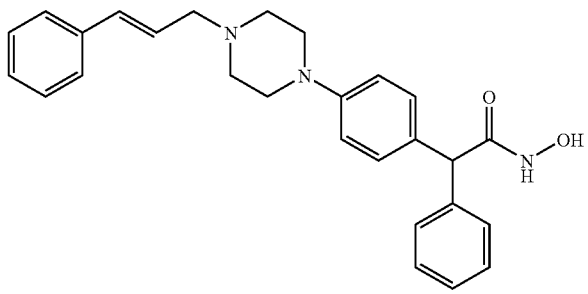 [SMILES: O=C(NO)C(c1ccccc1)c1ccc(N2CCN(C/C=C/c3ccccc3)CC2)cc1]

(E)-2-(4-(4-cinnamylpiperazin-1-yl)phenyl)-N-hydroxy-2-phenylacetamide
Mol wt. 427.538
LRMS(ESI): (calc.) 427.3 (found) 428.4 (MH)+
(CD3OD) d(ppm) 1H: 7.41 (d, J = 6.8Hz, 2H), 7.32-7.18 (m, 10H), 6.92 (d, J = 9.2Hz, 2H), 6.62 (d, J = 16.0 Hz, 1H), 6.31 (m, 1H), 4.68 (s, 1H), 3.21 (m, 6H), 2.69 (m, 4H)

5-86 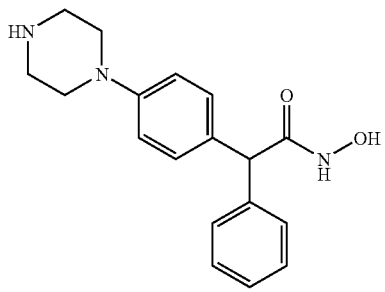 [SMILES: O=C(NO)C(c1ccccc1)c1ccc(N2CCNCC2)cc1]

N-hydroxy-2-phenyl-2-(4-(piperazin-1-yl)phenyl)acetamide
Mol wt. 311.378
LRMS(ESI): (calc.) 311.1 (found) 312.4 (MH)+
(CD3OD) d(ppm) 1H: 7.29-7.18 (m, 7H), 6.91 (d, J = 9.2Hz, 2H), 4.69 (s, 1H), 3.10 (m, 4H), 2.95 (m, 4H)

TABLE V-continued

Other Compounds prepared according general Schemes above 5-87

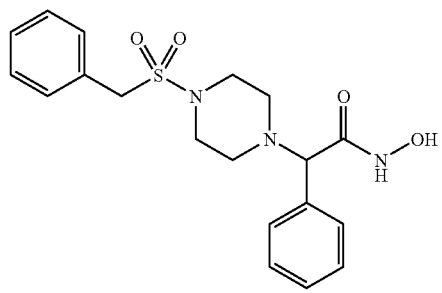 [SMILES: O=C(NO)C(c1ccccc1)N1CCN(S(=O)(=O)Cc2ccccc2)CC1]

2-(4-(benzylsulfonyl)piperazin-1-yl)-N-hydroxy-2-phenylacetamide
Mol wt. 389.469
LRMS(ESI): (calc.) 389.5 (found) 390.5 (MH)+
(MeOD-d4) 7.52-7.33 (m, 10H), 4.36 (s, 2H), 3.71 (s, 1H), 3.26-3.20 (m, 4H), 2.50-2.36 (m, 4H)__

5-88

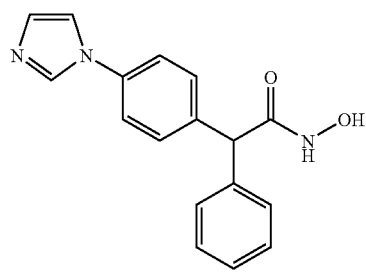 [SMILES: O=C(NO)C(c1ccccc1)c1ccc(-n2ccnc2)cc1]

2-(4-(1H-imidazol-1-yl)phenyl)-N-hydroxy-2-phenylacetamide
Mol wt. 293.32
LRMS(ESI): (calc.) 293.3 (found) 294.4 (MH)+
(MeOD-d4) 8.14 (s, 1H), 7.60-7.47 (m, 5H), 7.42-7.25 (m, 5H), 7.16 (s, 1H), 4.88 (s, 1H)__

5-89

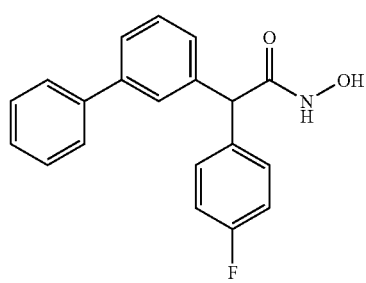 [SMILES: O=C(NO)C(c1ccc(F)cc1)c1cccc(-c2ccccc2)c1]

2-(biphenyl-3-yl)-2-(4-fluorophenyl)-N-hydroxyacetamide
Mol wt. 321.345
LRMS(ESI): (calc.) 321.3 (found) 322.4 (MH)+
(DLRMSOD6) d(ppm) 1H: 10.98 (s, 1H), 9.02 (s, 1H), 7.60-7.28 (m, 11H), 7.16 (t, J = 8.8Hz, 2H), 4.80 (s, 1H).__

5-90

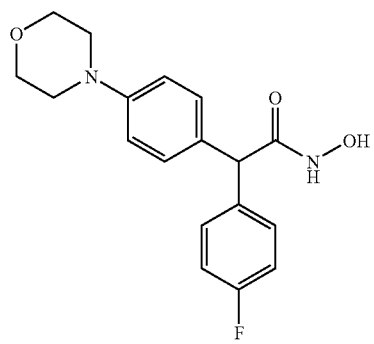 [SMILES: O=C(NO)C(c1ccc(F)cc1)c1ccc(N2CCOCC2)cc1]

2-(4-fluorophenyl)-N-hydroxy-2-(4-morpholinophenyl)acetamide
Mol wt. 330.354
LRMS(ESI): (calc.) 330.4 (found) 331.5 (MH)+

(DLRMSOD6) d(ppm) 1H: 10.87 (s, 1H), 8.94 (s, 1H), 7.34-7.29 (m, 2H), 7.17-7.09 (m, 4H), 6.87 (d, J = 8.8Hz, 2H), 4.60 (s, 1H), 3.71 (t, J = 4.7Hz, 4H), 3.05 (t, J = 4.9Hz, 4H).
5-91
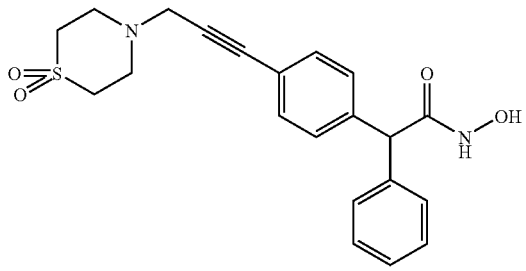 [SMILES: O=C(NO)C(c1ccccc1)c1ccc(C#CCN2CCS(=O)(=O)CC2)cc1]
Mol wt. 398.475
LRMS(ESI): (calc.) 398.5 (found) 397.5 (M − H+)
(MeOD-d4) 7.42-7.39 (m, 2H), 7.36-7.27 (m, 7H), 4.81 (s, 1H), 3.72 (s, 2H), 3.22-3.15 (m, 8H)
5-92
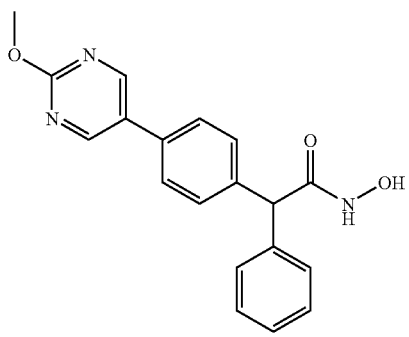 [SMILES: COc1ncc(-c2ccc(C(C(=O)NO)c3ccccc3)cc2)cn1]
N-hydroxy-2-(4-(2-methoxypyrimidin-5-yl)phenyl)-2-phenylacetamide
Mol wt. 335.357
LRMS(ESI): (calc.) 335.4 (found) 336.5 (MH)+
(DLRMSOD6) d(ppm) 1H: 10.96 (s, 1H), 8.96 (s, 1H), 8.90 (s, 2H), 7.67 (d, J = 8.4Hz, 2H), 7.43 (d, J = 8.4Hz, 2H), 7.37-7.22 (m, 5H), 4.76 (s, 1H), 3.95 (s, 3H).
5-93
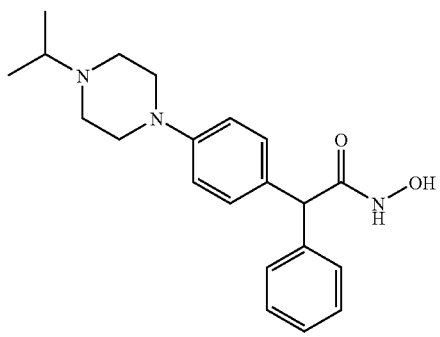 [SMILES: CC(C)N1CCN(c2ccc(C(C(=O)NO)c3ccccc3)cc2)CC1]
N-hydroxy-2-(4-(4-isopropylpiperazin-1-yl)phenyl)-2-phenylacetamide
Mol wt. 353.458
LRMS(ESI): (calc.) 353.2 (found) 354.3 (MH)+
(CD3OD) d(ppm) 1H: 7.29-7.23 (m, 7H), 6.96 (d, J = 8.8Hz, 2H), 4.70 (s, 1H), 3.50-3.33 (m, 9H), 1.37 (d, J = 8.0 Hz, 6H)

5-94

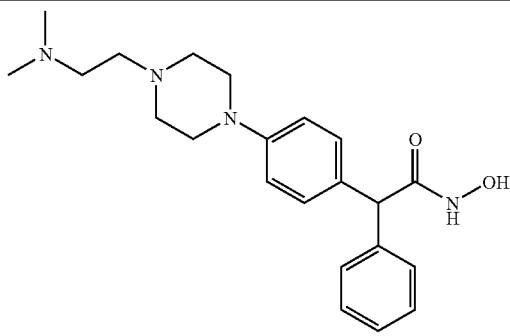

2-(4-(4-(2-(dimethylamino)ethyl)piperazin-1-yl)phenyl)-N-hydroxy-2-phenylacetamide
Mol wt. 382.499
LRMS(ESI): (calc.) 382.2 (found) 383.5 (MH)+
(CD3OD) d(ppm) 1H: 7.29-7.19 (m, 7H), 6.92 (d, J = 8.8Hz, 2H), 4.69 (s, 1H), 3.28 (t, J = 5.2 Hz, 2H), 3.19 (t, J = 4.8Hz, 4H), 3.89 (s, 6H), 2.75 (t, J = 6.0 Hz, 2H), 2.69 (t, J = 5.2Hz, 4H)

5-95

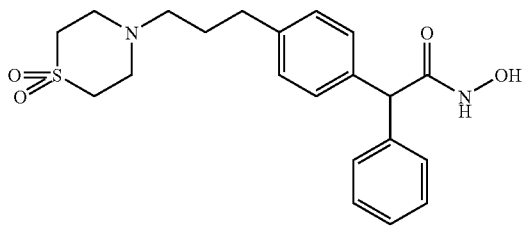 [SMILES: O=C(NO)C(c1ccccc1)c1ccc(CCCN2CCS(=O)(=O)CC2)cc1]

Mol wt. 402.507
LRMS(ESI): (calc.) 402.5 (found) 403.5 (MH)+
(MeOD-d4) 7.36-7.17 (m, 9H), 4.77 (s, 1H), 3.12-3.06 (m, 4H), 3.01-2.94 (m, 4H), 2.67 (t, J = 7.6 Hz, 2H), 2.54 (t, J = 7.6Hz, 2H), 1.88-1.78 (m, 2H)

5-96

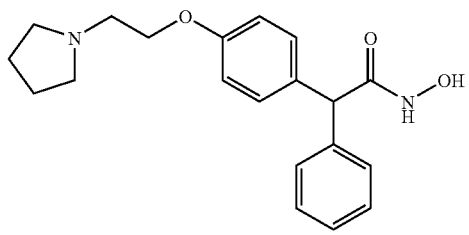 [SMILES: O=C(NO)C(c1ccccc1)c1ccc(OCCN2CCCC2)cc1]

N-hydroxy-2-phenyl-2-(4-(2-(pyrrolidin-1-yl)ethoxy)phenyl)acetamide
Mol wt. 340.416
LRMS(ESI): (calc.) 340.4 (found) 341.5 (MH)+
(DLRMSOD6) d(ppm) 1H: 10.89 (br s, 1H), 8.95 (br s, 1H), 7.30-7.21 (m, 7H), 6.87 (d, J = 8.8 Hz, 2H), 4.63 (s, 1H), 4.01 (t, J = 5.9Hz, 2H), 2.74 (t, J = 5.9Hz, 2H), 2.50-2.46 (m, 4H), 1.68-1.64 (m, 4H).

5-97

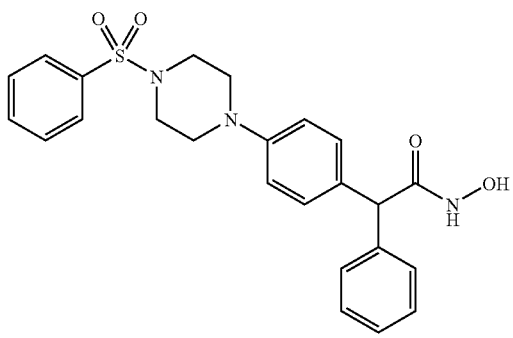 [SMILES: O=C(NO)C(c1ccccc1)c1ccc(N2CCN(S(=O)(=O)c3ccccc3)CC2)cc1]

N-hydroxy-2-phenyl-2-(4-(4-(phenylsulfonyl)piperazin-1-yl)phenyl)acetamide
Mol wt. 451.538

LRMS(ESI): (calc.) 451.16 (found) 452.4 (MH)+

(CD3OD) d(ppm) 1H: 7.80 (m, 2H), 7.71-7.61 (m, 3H), 7.27-7.15 (m, 7H), 6.87 (d, J = 8.8Hz, 2H), 4.66 (s, 1H), 3.18 (m, 4H), 3.11 (m, 4H)__

5-98

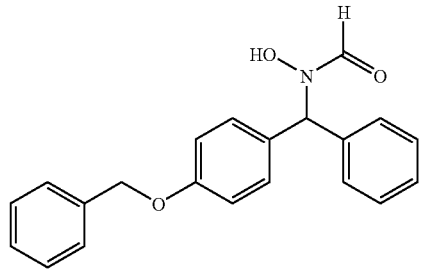 [SMILES: O=CN(O)C(c1ccccc1)c1ccc(OCc2ccccc2)cc1]

N-((4-(benzyloxy)phenyl)(phenyl)methyl)-N-hydroxyformamide

Mol wt. 333.38

LRMS(ESI): (calc.) 333.4 (found) 356.2 (MNa)+

(DLRMSOD6) d(ppm) 1H: 7.46-7.24 (m, 11H), 7.18 (d, J = 8.6Hz, 2H), 7.00 (d, J = 8.6Hz, 2H), 8.34 (br s, 1H), 5.09 (s, 2H).__

5-99

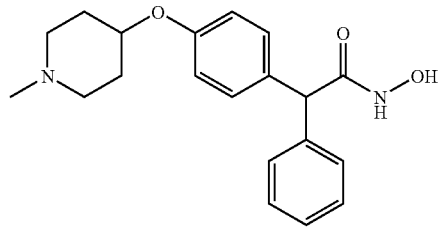 [SMILES: CN1CCC(Oc2ccc(C(C(=O)NO)c3ccccc3)cc2)CC1]

N-hydroxy-2-(4-(1-methylpiperidin-4-yloxy)phenyl)-2-phenylacetamide

Mol wt. 340.416

LRMS(ESI): (calc.) 340.4 (found) 341.3 (MH)+

(DLRMSOD6) d(ppm) 1H: 10.87 (br s, 1H), 8.94 (br s, 1H), 7.35-7.18 (m, 7H), 6.87 (d, J = 8.8 Hz, 2H), 4.62 (s, 1H), 4.32-4.27 (m, 1H), 2.58-2.54 (m, 2H), 2.20-2.10 (m, 5H), 1.90-1.87 (m, 2H), 1.63-1.54 (m, 2H).__

5-100

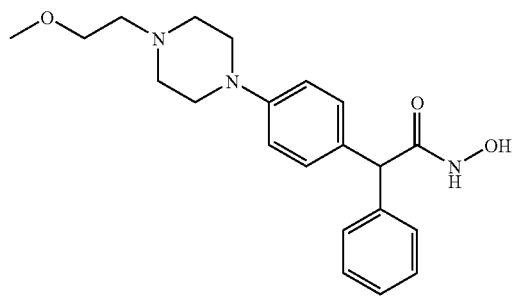 [SMILES: COCCN1CCN(c2ccc(C(C(=O)NO)c3ccccc3)cc2)CC1]

N-hydroxy-2-(4-(4-(2-methoxyethyl)piperazin-1-yl)phenyl)-2-phenylacetamide

Mol wt. 369.457

LRMS(ESI): (calc.) 369.2 (found) 370.4 (MH)+

(CD3OD) d(ppm) 1H: 7.29-7.20 (m, 7H), 6.91 (d, J = 8.8Hz, 2H), 4.69 (s, 1H), 3.57 (t, J = 5.2 Hz, 2H), 3.34 (s, 3H), 3.17 (m, 4H), 2.67 (m, 4H), 2.63 (t, J = 4.0 Hz, 2H)__

| | |
|---|---|
| 5-101 | 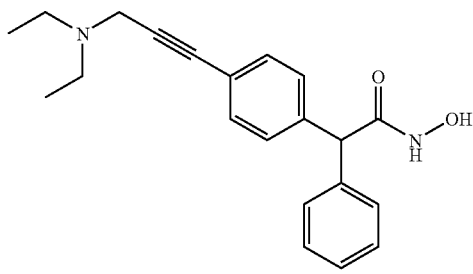 [SMILES: CCN(CC)CC#Cc1ccc(C(C(=O)NO)c2ccccc2)cc1] |

2-(4-(3-(diethylamino)prop-1-ynyl)phenyl)-N-hydroxy-2-phenylacetamide
Mol wt. 336.428
LRMS(ESI): (calc.) 336.4 (found) 337.4 (MH)+
(DMSO-d6) 10.98 (br s, 1H), 9.04 (br s, 1H), 7.42-7.38 (m, 2H), 7.37-7.26 (m, 7H), 4.75 (s, 1H), 3.61 (s, 2H), 2.58-2.51 (m, 4H), 1.04 (t, J = 7.2Hz, 6H)

| | |
|---|---|
| 5-102 | 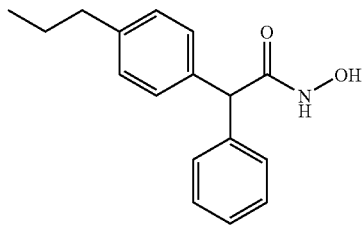 [SMILES: CCCc1ccc(C(C(=O)NO)c2ccccc2)cc1] |

N-hydroxy-2-phenyl-2-(4-propylphenyl)acetamide
Mol wt. 269.338
LRMS(ESI): (calc.) 269.3 (found) 270.3 (MH)+
(MeOd-d4) 7.36-7.22 (m, 7H), 7.17-7.13 (m, 2H), 4.77 (s, 1H), 2.62-2.57 (m, 2H), 1.70-1.60 (m, 2H), 0.96 (t, J = 7.4Hz, 3H)

| | |
|---|---|
| 5-103 | 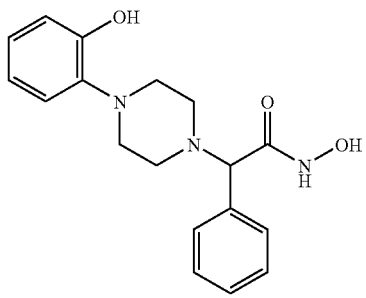 [SMILES: O=C(NO)C(c1ccccc1)N1CCN(c2ccccc2O)CC1] |

N-hydroxy-2-(4-(2-hydroxyphenyl)piperazin-1-yl)-2-phenylacetamide
Mol wt. 327.378
C18H21N3O3
LRMS(ESI): (calc.) 327.4 (found) 328.2 (MH)+
(MeOD-d4) 7.58-7.53 (m, 2H), 7.42-7.32 (m, 3H), 7.10-7.05 (m, 1H), 6.97-6.91 (m, 1H), 6.85-6.80 (m, 2H), 3.76 (s, 1H), 3.10-3.00 (m, 4H), 2.73-2.56 (m, 4H)

| | |
|---|---|
| 5-104 | 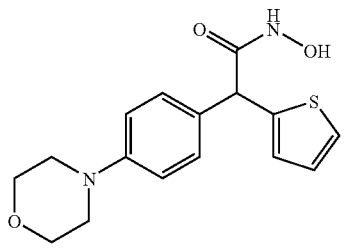 [SMILES: O=C(NO)C(c1ccc(N2CCOCC2)cc1)c1cccs1] |

N-hydroxy-2-(4-morpholinophenyl)-2-(thiophen-2-yl)acetamide
Mol wt. 318.391
LRMS(ESI): (calc.) 318.4 (found) 319.3 (MH)+
(MeOD) d(ppm) 1H: 7.30-7.26 (m, 3H), 6.97-6.88 (m, 4H), 4.91 (s, 1H), 3.81 (t, J = 4.9Hz, 4H), 3.11 (t, J = 4.9Hz, 4H).

TABLE V-continued

Other Compounds prepared according general Schemes above 5-105

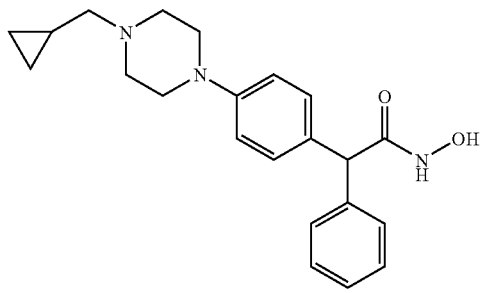 [SMILES: O=C(NO)C(c1ccccc1)c1ccc(N2CCN(CC3CC3)CC2)cc1]

2-(4-(4-(cyclopropylmethyl)piperazin-1-yl)phenyl)-N-hydroxy-2-phenylacetamide
Mol wt. 365.469
LRMS(ESI): (calc.) 365.4 (found) 366.4 (MH)+
(CD3OD) d(ppm) 1H: 6.92-6.85 (m, 7H), 6.59 (d, J = 8.4Hz, 2H), 4.33 (s, 1H), 3.00 (m, 4H),
2.87 (m, 4H), 2.50 (d, J = 6.8Hz, 2H), 0.71 (m, 1H), 0.37 (m, 2H), 0.01 (m, 2H)

5-106

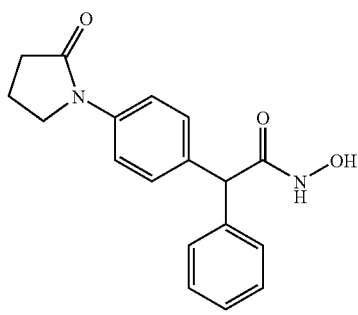 [SMILES: O=C(NO)C(c1ccccc1)c1ccc(N2CCCC2=O)cc1]

N-hydroxy-2-(4-(2-oxopyrrolidin-1-yl)phenyl)-2-phenylacetamide
Mol wt. 310.347
LRMS(ESI): (calc.) 310.3 (found) 309.2 (M − H+)
(DMSO-d6) 10.96 (br s, 1H), 9.01 (br s, 1H), 7.64-7.60 (m, 2H), 7.38-7.24 (m, 7H), 4.72 (s, 1H),
3.84 (t, J = 7.0 Hz, 2H), 2.51 (t, J = 8.4Hz, 2H), 2.13-2.03 (m, 2H)

5-107

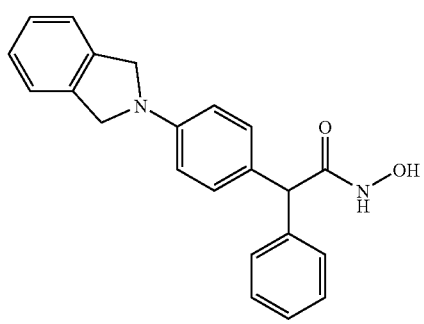 [SMILES: O=C(NO)C(c1ccccc1)c1ccc(N2Cc3ccccc3C2)cc1]

N-hydroxy-2-(4-(isoindolin-2-yl)phenyl)-2-phenylacetamide
Mol wt. 344.406
LRMS(ESI): (calc.) 344.4 (found) 345.4 (MH)+
(MeOD-d4) 7.42-7.22 (m, 11H), 6.74-6.67 (m, 2H), 4.73 (s, 1H), 4.63 (s, 4H)

5-108

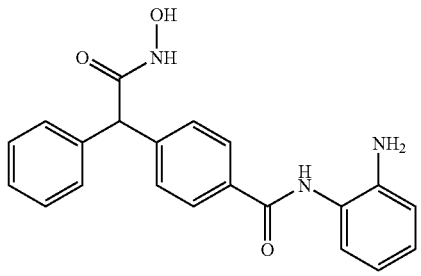 [SMILES: Nc1ccccc1NC(=O)c1ccc(C(C(=O)NO)c2ccccc2)cc1]

N-(2-aminophenyl)-4-(2-(hydroxyamino)-2-oxo-1-phenylethyl)benzamide

Mol wt. 361.394

LRMS(ESI): (calc.) 361.39 (found) 362.2 (MH)+

(DMSO-d6) d(ppm) 1H: 10.98 (s, 1H), 9.60 (s, 1H), 9.02 (s, 1H), 7.92 (d, J = 8.2Hz, 2H), 7.44 (d, J = 8.4Hz, 2H), 7.34-7.30 (m, 4H), 7.29-7.23 (m, 1H), 7.15 (d, J = 7.1Hz, 1H), 6.96 (td, J = 8.0, 1.6 Hz, 1H), 6.76 (dd, J = 8.0, 1.4Hz, 1H), 6.58 (td, J = 7.6, 1.4 z, 1H), 4.88 (s, 2H), 4.80 (s, 1H).

5-109

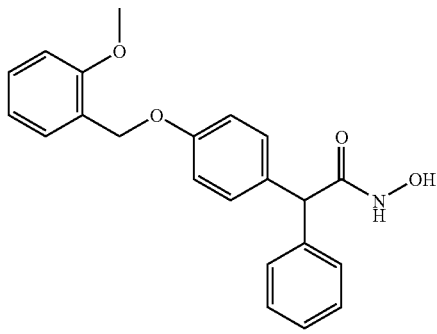 [SMILES: COc1ccccc1COc1ccc(C(C(=O)NO)c2ccccc2)cc1]

N-hydroxy-2-(4-(2-methoxybenzyloxy)phenyl)-2-phenylacetamide

Mol wt. 363.406

LRMS(ESI): (calc.) 363.4 (found) 364.4 (MH)+

(DLRMSOD6) d(ppm) 1H: 10.89 (s, 1H), 8.94 (s, 1H), 7.38-7.20 (m, 9H), 7.03 (d, J = 7.7Hz, 1H), 6.97-6.90 (m, 3H), 5.01 (s, 2H), 4.63 (s, 1H), 3.80 (s, 3H).

5-110

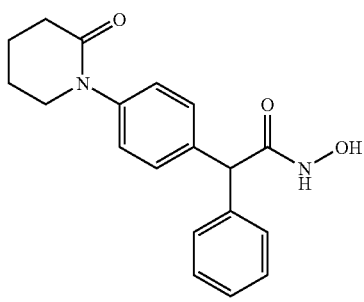 [SMILES: O=C(NO)C(c1ccccc1)c1ccc(N2CCCCC2=O)cc1]

N-hydroxy-2-(4-(2-oxopiperidin-1-yl)phenyl)-2-phenylacetamide

Mol wt. 324.374

LRMS(ESI): (calc.) 324.4 (found) 323.3 (M − H+)

(DMSO-d6) 10.98 (br s, 1H), 9.01 (br s, 1H), 7.41-7.20 (m, 9H), 4.74 (s, 1H), 3.62-3.57 (m, 2H), 2.43-2.37 (m, 2H), 1.92-1.78 (m, 4H)

TABLE V-continued

Other Compounds prepared according general Schemes above 5-111 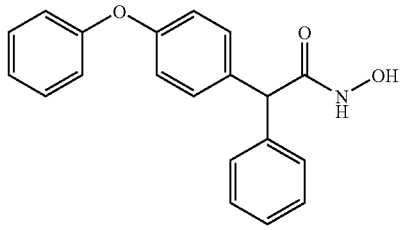 [SMILES: O=C(NO)C(c1ccccc1)c1ccc(Oc2ccccc2)cc1]

N-hydroxy-2-(4-phenoxyphenyl)-2-phenylacetamide
Mol wt. 319.354
LRMS(ESI): (calc.) 319.4 (found) 320.3 (MH)+
(DMSO-d6) 10.97 (s, 1H), 9.03 (s, 1H), 7.46-7.32 (m, 8H), 7.31-7.26 (m, 1H), 7.19-7.14 (m, 1H),
7.04-6.98 (m, 4H), 4.74 (s, 1H).

5-112 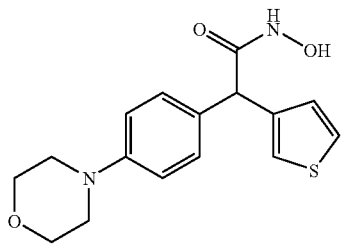 [SMILES: O=C(NO)C(c1ccc(N2CCOCC2)cc1)c1ccsc1]

N-hydroxy-2-(4-morpholinophenyl)-2-(thiophen-3-yl)acetamide
Mol wt. 318.391
LRMS(ESI): (calc.) 318.4 (found) 319.3 (MH)+
(DLRMSOD6) d(ppm) 1H: 10.83 (s, 1H), 8.91 (s, 1H), 7.45 (dd, J = 5.1, 3.1Hz, 1H), 7.29-7.27
(m, 1H), 7.17 (d, J = 8.8Hz, 2H), 7.04-7.01 (m, 1H), 6.87 (d, J = 8.8Hz, 2H), 4.64 (s, 1H), 3.72 (t,
J = 4.5Hz, 4H), 3.05 (t, J = 4.9Hz, 4H).

5-113 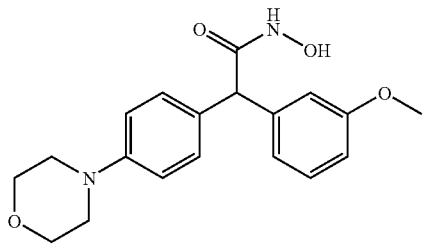 [SMILES: COc1cccc(C(C(=O)NO)c2ccc(N3CCOCC3)cc2)c1]

N-hydroxy-2-(3-methoxyphenyl)-2-(4-morpholinophenyl)acetamide
Mol wt. 342.389
LRMS(ESI): (calc.) 342.4 (found) 343.4 (MH)+
(DLRMSOD6) d(ppm) 1H: 10.83 (s, 1H), 8.91 (s, 1H), 7.23-7.16 (m, 3H), 6.84-6.78 (m, 5H),
4.55 (s, 1H), 3.73-3.70 (m, 7H), 3.05 (t, J = 4.9Hz, 4H).

5-113b 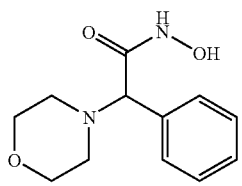 [SMILES: O=C(NO)C(c1ccccc1)N1CCOCC1]

N-hydroxy-2-morpholino-2-phenylacetamide
Mol wt. 236.267
LRMS(ESI): (calc.) 236.3 (found) 237.2 (MH)+
(DLRMSOD6) d(ppm) 1H: 10.84 (s, 1H), 8.90 (s, 1H), 7.45-7.41 (m, 2H), 7.35-7.25 (m, 3H),
3.59-3.54 (m, 5H), 2.30-2.23 (m, 4H).

TABLE V-continued

Other Compounds prepared according general Schemes above 5-114

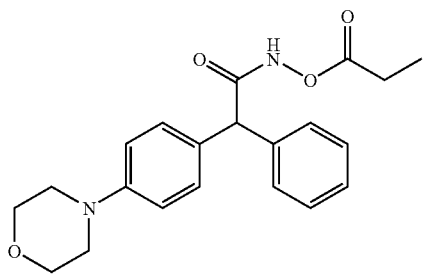 [SMILES: CCC(=O)ONC(=O)C(c1ccccc1)c1ccc(N2CCOCC2)cc1]

2-(4-morpholinophenyl)-2-phenyl-N-(propionyloxy)acetamide
Mol wt. 368.426
LRMS(ESI): (calc.) 368.4 (found) 369.2 (MH)+
(DLRMSOD6) d(ppm) 1H: 12.13 (s, 1H), 7.33-7.21 (m, 5H), 7.16 (d, J = 8.8Hz, 2H), 6.89 (d,
J = 8.8Hz, 2H), 4.81 (s, 1H), 3.71 (t, J = 4.7Hz, 4H), 3.06 (t, J = 4.9Hz, 4H), 2.46 (q, J = 7.4Hz, 2H),
1.07 (t, J = 7.4Hz, 3H).

5-115

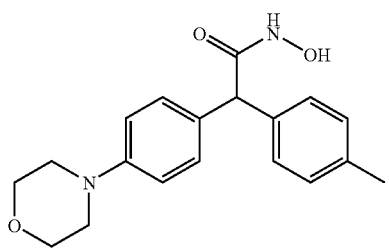 [SMILES: Cc1ccc(C(C(=O)NO)c2ccc(N3CCOCC3)cc2)cc1]

N-hydroxy-2-(4-morpholinophenyl)-2-p-tolylacetamide
Mol wt. 326.39
LRMS(ESI): (calc.) 326.4 (found) 327.3 (MH)+
(DLRMSOD6) d(ppm) 1H: 10.81 (s, 1H), 8.88 (s, 1H), 7.17-7.07 (m, 6H), 6.85 (d, J = 8.8Hz,
2H), 4.53 (s, 1H), 3.70 (t, J = 4.7Hz, 4H), 3.03 (t, J = 4.9Hz, 4H), 2.24 (s, 3H).

5-116

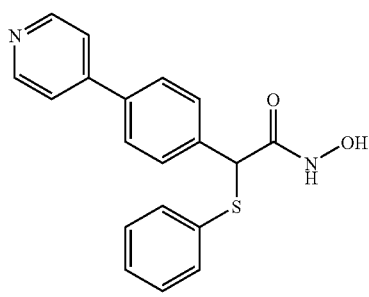 [SMILES: O=C(NO)C(Sc1ccccc1)c1ccc(-c2ccncc2)cc1]

N-hydroxy-2-(phenylthio)-2-(4-(pyridin-4-yl)phenyl)acetamide
Mol wt. 336.408
LRMS(ESI): (calc.) 336.4 (found) 337.3 (MH)+
(DMSO-d6) 11.07 (s, 1H), 9.19 (s, 1H), 8.61-8.71 (m, 2H), 7.85-7.80 (m, 2H), 7.76-7.71 (m, 2H),
7.69-7.64 (m, 2H), 7.40-7.24 (m, 5H), 5.06 (s, 1H)

5-117

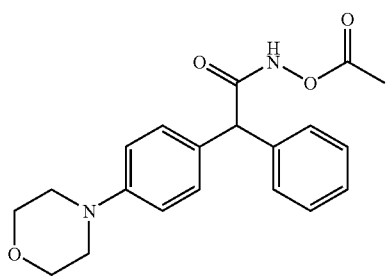 [SMILES: CC(=O)ONC(=O)C(c1ccccc1)c1ccc(N2CCOCC2)cc1]

N-acetoxy-2-(4-morpholinophenyl)-2-phenylacetamide
Mol wt. 354.4
LRMS(ESI): (calc.) 354.4 (found) 355.3 (MH)+

(DMSO-d6) d(ppm) 1H: 12.13 (br s, 1H), 7.34-7.21 (m, 5H), 7.16 (d, J = 8.8Hz, 2H), 6.89 (d, J = 8.8Hz, 2H), 4.81 (s, 1H), 3.72 (t, J = 4.7Hz, 4H), 3.06 (t, J = 4.7Hz, 4H), 2.15 (s, 3H).

5-118

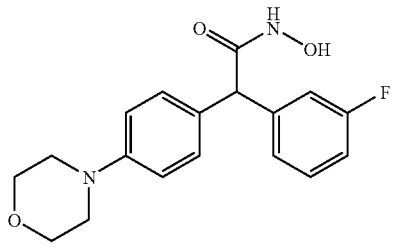 [SMILES: O=C(NO)C(c1ccc(N2CCOCC2)cc1)c1cccc(F)c1]

2-(3-fluorophenyl)-N-hydroxy-2-(4-morpholinophenyl)acetamide
Mol wt. 330.354
LRMS(ESI): (calc.) 330.4 (found) 331.3 (MH)+
(DMSO-d6) d(ppm) 1H: 10.89 (s, 1H), 8.97 (s, 1H), 7.37-7.31 (m, 1H), 7.19-7.03 (m, 5H), 6.89 (d, J = 8.8Hz, 2H), 4.63 (s, 1H), 3.71 (t, J = 4.7Hz, 4H), 3.06 (t, J = 4.7Hz, 4H).

5-119

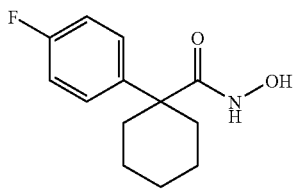 [SMILES: O=C(NO)C1(c2ccc(F)cc2)CCCCC1]

1-(4-fluorophenyl)-N-hydroxycyclohexanecarboxamide
Mol wt. 237.27
LRMS(ESI): (calc.) 237.1 (found) 238.1 (MH)+
(CD3OD) d(ppm) 1H: 7.42 (m, 2H), 7.02 t, J = 8.8Hz, 2H), 2.37 (m, 2H), 1.77 (m, 2H), 1.64-1.54 (m, 5H), 1.35 (m, 1H)

5-120

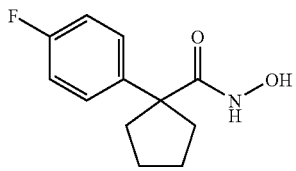 [SMILES: O=C(NO)C1(c2ccc(F)cc2)CCCC1]

1-(4-fluorophenyl)-N-hydroxycyclopentanecarboxamide
Mol wt. 223.244
LRMS(ESI): (calc.) 223.1 (found) 224.1 (MH)+
(CD3OD) d(ppm) 1H: 7.38 (m, 2H), 7.02 (t, J = 8.8Hz, 2H), 2.47 (m, 2H), 1.93 (m, 2H), 1.71 (m, 4H)

5-121

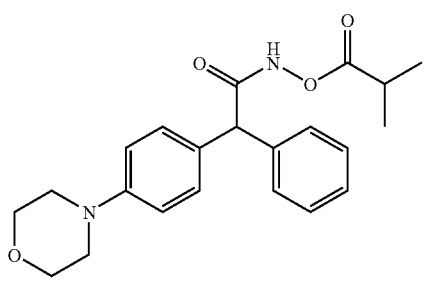 [SMILES: CC(C)C(=O)ONC(=O)C(c1ccccc1)c1ccc(N2CCOCC2)cc1]

N-(isobutyryloxy)-2-(4-morpholinophenyl)-2-phenylacetamide
Mol wt. 382.453
LRMS(ESI): (calc.) 382.5 (found) 383.5 (MH)+
(DLRMSOD6) d(ppm) 1H: 12.12 (br s, 1H), 7.35-7.21 (m, 5H), 7.16 (d, J = 8.8Hz, 2H), 6.89 (d, J = 8.8Hz, 2H), 4.80 (s, 1H), 3.72 (t, J = 4.7Hz, 4H), 3.06 (t, J = 4.9Hz, 4H), 2.75-2.67 (m, 1H), 1.14 (d, J = 5.8Hz, 6H).

TABLE V-continued

Other Compounds prepared according general Schemes above 5-122

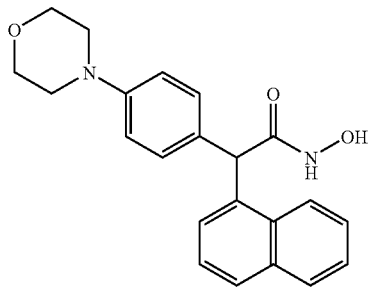 [SMILES: O=C(NO)C(c1ccc(N2CCOCC2)cc1)c1cccc2ccccc12]

N-hydroxy-2-(4-morpholinophenyl)-2-(naphthalen-1-yl)acetamide

Mol wt. 362.422

LRMS(ESI): (calc.) 362.4 (found) 363.4 (MH)+

(DLRMSOD6) d(ppm) 1H: 10.95 (s, 1H), 8.95 (br s, 1H), 8.07-8.04 (m, 1H), 7.94-7.91 (m, 1H), 7.82 (d, J = 8.2Hz, 1H), 7.56-7.44 (m, 4H), 7.16 (d, J = 8.8Hz, 2H), 6.88 (d, J = 8.8Hz, 2H), 5.43 (s, 1H), 3.71 (t, J = 4.7Hz, 4H), 3.05 (t, J = 4.9Hz, 4H).

5-123

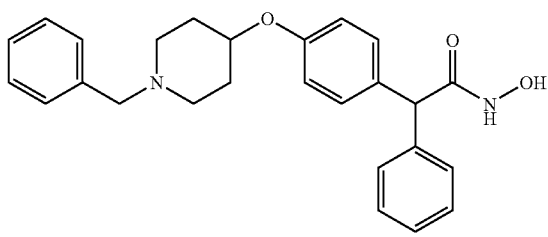 [SMILES: O=C(NO)C(c1ccccc1)c1ccc(OC2CCN(Cc3ccccc3)CC2)cc1]

2-(4-(1-benzylpiperidin-4-yloxy)phenyl)-N-hydroxy-2-phenylacetamide

Mol wt. 416.512

LRMS(ESI): (calc.) 416.5 (found) 417.4 (MH)+

(DLRMSOD6) d(ppm) 1H: 10.87 (s, 1H), 8.94 (s, 1H), 7.32-7.16 (m, 12H), 6.87 (d, J = 8.8Hz, 2H), 4.61 (s, 1H), 4.35-4.30 (m, 1H), 3.46 (s, 2H), 2.66-2.62 (m, 2H), 2.20 (t, J = 8.8Hz, 2H), 1.95-1.85 (m, 2H), 1.62-1.55 (m, 2H).

5-124

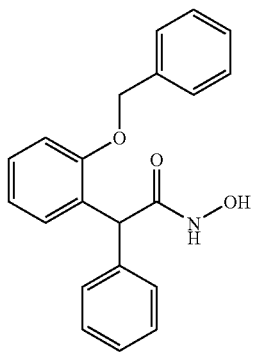 [SMILES: O=C(NO)C(c1ccccc1)c1ccccc1OCc1ccccc1]

2-(2-(benzyloxy)phenyl)-N-hydroxy-2-phenylacetamide

Mol wt. 333.38

LRMS (ESI): (calc) 333.38 (found) 334.36 (MH)+

(DMSO-d6) d(ppm) 1H: 10.90 (s, 1H), 8.88 (s, 1H), 7.45 (dd, J = 7.6, 1.6Hz, 1H), 7.36-7.27 (m, 7H), 7.24-7.18 (m, 4H), 7.03-7.01 (m, 1H), 6.91 (td, J = 7.6, 0.8Hz, 1H), 5.12 (s, 1H), 5.10 (d, rotamers, J = 12.4Hz, 1H), 5.04 (d, rotamers, 12.4Hz, 1H)

| | |
|---|---|
| 5-125 | 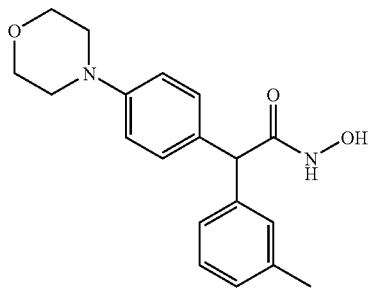 [SMILES: Cc1cccc(C(C(=O)NO)c2ccc(N3CCOCC3)cc2)c1] |

N-hydroxy-2-(4-morpholinophenyl)-2-m-tolylacetamide
Mol wt. 326.39
LRMS(ESI): (calc.) 326.4 (found) 327.3 (MH)+
(DLRMSOD6) d(ppm) 1H: 10.83 (s, 1H), 8.90 (s, 1H), 7.23-7.01 (m, 6H), 6.87 (d, J = 9.0 Hz, 2H), 4.55 (s, 1H), 3.71 (t, J = 4.7Hz, 4H), 3.05 (t, J = 4.9Hz, 4H), 2.25 (s, 3H).

| | |
|---|---|
| 5-126 and cpd-94 | 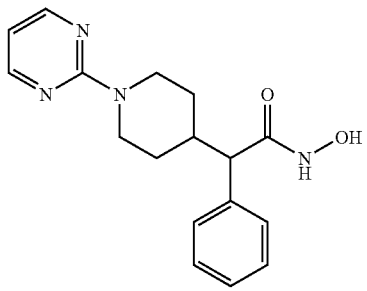 [SMILES: O=C(NO)C(c1ccccc1)C1CCN(c2ncccn2)CC1] |

N-hydroxy-2-phenyl-2-(1-(pyrimidin-2-yl)piperidin-4-yl)acetamide
Mol wt. 312.366
LRMS (ESI): (calc) 312.37 (found) 313.27 (MH)+
(DMSO-d6) d(ppm) 1H: 10.63 (s, 1H), 8.82 (s, 1H), 8.31 (d, J = 4.8Hz, 2H), 7.35-7.28 (m, 4H), 7.25-7.21 (m, 1H), 6.57 (t, J = 4.8Hz, 1H), 4.65 (d, J = 13.6Hz, 1H), 4.51 (d, J = 13.6Hz, 1H), 2.93-2.84 (m, 2H), 2.75 (td, J = 12.6, 2.4Hz, 1H), 2.30-2.22 (m, 1H), 1.77 (d, J = 12.0 Hz, 1H), 1.22-1.06 (m, 2H), 0.92-0.82 (m, 1H)

| | |
|---|---|
| 5-127 | 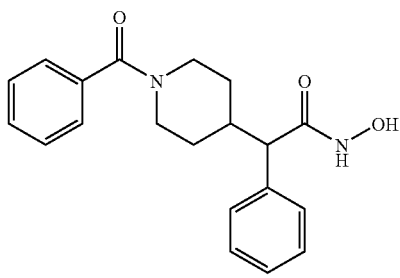 [SMILES: O=C(NO)C(c1ccccc1)C1CCN(C(=O)c2ccccc2)CC1] |

2-(1-benzoylpiperidin-4-yl)-N-hydroxy-2-phenylacetamide
Mol wt. 338.4
LRMS (ESI): (calc) 338.40 (found) 339.2 (MH)+
(MeOH d-4) d(ppm) 1H: 7.46-7.24 (m, 10H), 4.58 (d, J = 12.0 Hz, 0.5H, rotamers), 4.52 (d, J = 10.8Hz, 0.5H, rotamers), 3.75 (d, J = 12.0 Hz, 0.5H, rotamers), 3.62 (d, J = 13.2Hz, 0.5H, rotamers), 3.19-2.73 (m, 3H), 2.44-2.35 (m, 1H), 1.98 (d, J = 11.2Hz, 0.5H, rotamers), 1.79 (d, J = 11.2Hz, 0.5H, rotamers), 1.41-0.98 (m, 3H)

TABLE V-continued

Other Compounds prepared according general Schemes above 5-128

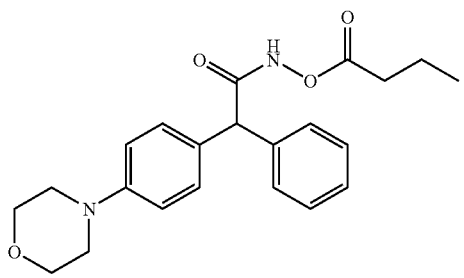 [SMILES: CCCC(=O)ONC(=O)C(c1ccccc1)c1ccc(N2CCOCC2)cc1]

N-(butyryloxy)-2-(4-morpholinophenyl)-2-phenylacetamide
Mol wt. 382.453
LRMS(ESI): (calc.) 382.4 (found) 383.1 (MH)+
(DMSO-d6) d(ppm) 1H: 12.12 (br s, 1H), 7.33-7.21 (m, 5H), 7.16 (d, J = 8.8Hz, 2H), 6.89 (d,
J = 8.8Hz, 2H), 4.80 (s, 1H), 3.71 (t, J = 4.5Hz, 4H), 3.06 (t, J = 5.1Hz, 4H), 2.41 (t, J = 7.0 Hz, 2H),
1.58 (hextet, J = 7.2Hz, 2H), 0.92 (t, J = 7.4Hz, 3H).

5-129

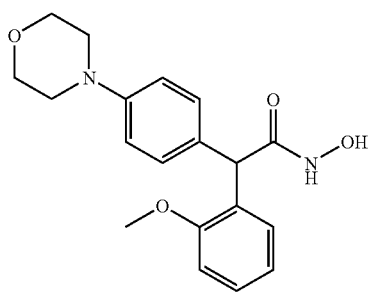 [SMILES: COc1ccccc1C(C(=O)NO)c1ccc(N2CCOCC2)cc1]

N-hydroxy-2-(2-methoxyphenyl)-2-(4-morpholinophenyl)acetamide
Mol wt. 342.389
LRMS(ESI): (calc.) 342.4 (found) 343.4 (MH)+
(DLRMSOD6) d(ppm) 1H: 10.73 (s, 1H), 8.78 (s, 1H), 7.33-7.30 (m, 1H), 7.23-7.08 (m, 1H),
7.10 (d, J = 8.8Hz, 2H), 6.96-6.93 (m, 1H), 6.89-6.84 (m, 3H), 4.94 (s, 1H), 3.74-3.70 (m, 7H),
3.05 (t, J = 4.7Hz, 4H).

5-130

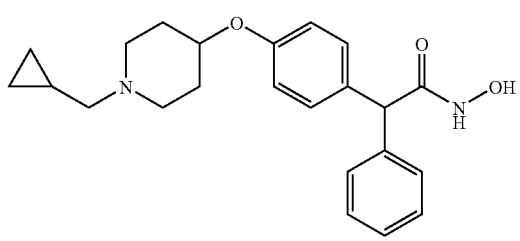 [SMILES: O=C(NO)C(c1ccccc1)c1ccc(OC2CCN(CC3CC3)CC2)cc1]

2-(4-(1-(cyclopropylmethyl)piperidin-4-yloxy)phenyl)-N-hydroxy-2-phenylacetamide
Mol wt. 380.48
LRMS(ESI): (calc.) 380.5 (found) 381.5 (MH)+
(DLRMSOD6) d(ppm) 1H: 10.85 (br s, 1H), 8.91 (br s, 1H), 7.27-7.13 (m, 7H), 6.84 (d, J = 8.8
Hz, 2H), 4.59 (s, 1H), 4.28-4.26 (m, 1H), 2.72-2.70 (m, 2H), 2.21-2.12 (m, 4H), 1.89-1.86
(m, 2H), 1.59-1.51 (m, 2H), 0.80-0.76 (m, 1H), 0.44-0.38 (m, 2H), 0.04-0.00 (m, 2H).

5-131

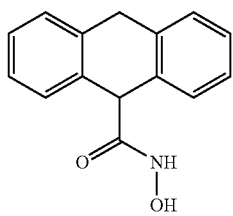 [SMILES: O=C(NO)C1c2ccccc2Cc2ccccc21]

N-hydroxy-9,10-dihydroanthracene-9-carboxamide
Mol wt. 239.269
LRMS(ESI): (calc.) 239.09 (found) 240.2 (MH)+
(MeOD) d(ppm) 1H: 7.34 (d, J = 7.2Hz, 4H), 7.28-7.18 (m, 4H), 4.68 (s, 1H), 4.46 (d, J = 18.5
Hz, 1H), 3.87 (d, J = 18.4Hz, 1H).

TABLE V-continued

Other Compounds prepared according general Schemes above 5-132

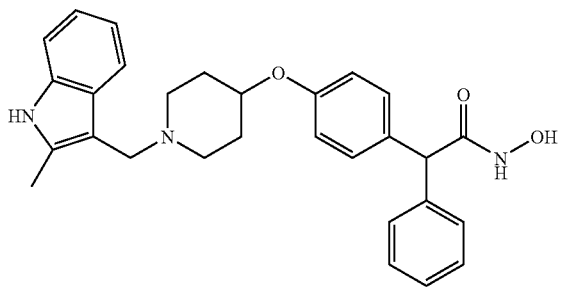 [SMILES: Cc1[nH]c2ccccc2c1CN1CCC(Oc2ccc(C(C(=O)NO)c3ccccc3)cc2)CC1]

N-hydroxy-2-(4-(1-((2-methyl-1H-indol-3-yl)methyl)piperidin-4-yloxy)phenyl)-2-phenylacetamide Mol wt. 469.575

LRMS(ESI): (calc.) 469.6 (found) 470.6 (MH)+

(DMSOD6) d(ppm) 1H: 10.86 (s, 1H), 10.80 (s, 1H), 8.93 (s, 1H), 7.48 (d, J = 7.4Hz, 1H), 7.34-7.17 (m, 8H), 6.98-6.84 (m, 4H), 4.60 (s, 1H), 4.32-4.25 (m, 1H), 3.55 (s, 2H), 2.72-2.65 (m, 2H), 2.33 (s, 3H), 2.22-2.18 (m, 2H), 1.90-1.82 (m, 2H), 1.58-1.50 (m, 2H).

TABLE VI

Compounds prepared according general Schemes above

| Structure | Cmpd # | MS | ¹H NMR | Name |
|---|---|---|---|---|
| 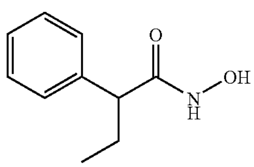 | 6-1 | LRMS (ESI): (calc.) 179.2 (found) 180.2 (MH)+ | 1H NMR (CD3OD-d4) d (ppm): 7.41-7.22 (m, 5H), 3.28-3.18 (m, 1H), 2.18-2.03 (m, 1H), 1.89-1.73 (m, 1H), 0.94 (t, J = 7.2 Hz, 3H) | N-hydroxy-2-phenylbutanamide |
| 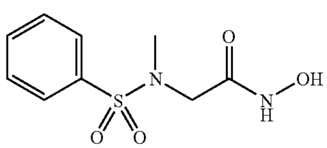 [SMILES: CN(CC(=O)NO)S(=O)(=O)c1ccccc1] | 6-2 | LRMS (ESI): (calc.) 244.05 (found) 243.2 (MH)− | 1H NMR (CD3OD-d4) d (ppm): 7.84 (d, J = 7.2 Hz, 2H), 7.63 (m, 3H), 3.67 (s, 2H), 2.80 (s, 3H) | N-hydroxy-2-(N-methylphenylsulfona-mido)acetamide |
| 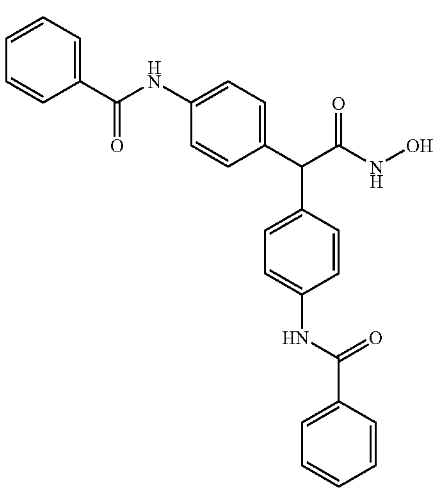 [SMILES: O=C(Nc1ccc(C(C(=O)NO)c2ccc(NC(=O)c3ccccc3)cc2)cc1)c1ccccc1] | 6-3 | LRMS (ESI): (calc.) 465.2 (found) 464.5 (MH)− | 1H NMR (CD3OD-d4) d (ppm): 7.93-7.90 (m, 4H), 7.66 (d, J = 8.6 Hz, 4H), 7.59-7.54 (m, 2H) 7.52-7.47 (m, 4H), 7.35 (d, J = 8.6 Hz, 4H), 4.80 (s, 1H). | N,N'-(4,4'-(2-(hydroxyamino)-2-oxoethane-1,1-diyl)bis(4,1-phenylene))dibenzamide |

TABLE VI-continued

Compounds prepared according general Schemes above

| Structure | Cmpd # | MS | ¹H NMR | Name |
|---|---|---|---|---|
| 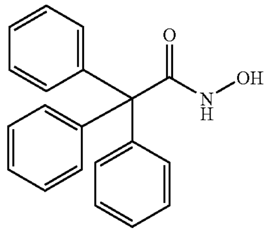 [SMILES: O=C(NO)C(c1ccccc1)(c1ccccc1)c1ccccc1] | 6-4 | LRMS (ESI): (calc.) 303.1 (found) 304.3 (MH)+ | 1H NMR (CD3OD-d4) d (ppm): 1H: 7.32-7.22 (m, 15H). | N-hydroxy-2,2,2-triphenylacetamide |
| 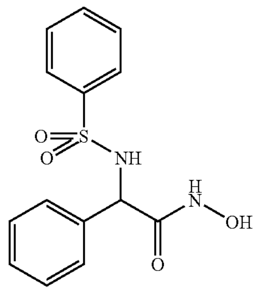 [SMILES: O=C(NO)C(NS(=O)(=O)c1ccccc1)c1ccccc1] | 6-5 | LRMS (ESI): (calc.) 306.1 (found) 305.3 (MH)− | 1H NMR (CD3OD-d4) d (ppm): 7.76 (d, J = 8.2 Hz, 2H), 7.53 (t, J = 7.6 Hz, 1H), 7.43 (t, J = 7.6 Hz, 2H), 7.21 (s, 5H), 4.81 (s, 1H). | N-hydroxy-2-phenyl-2-(phenylsulfonamido)acetamide |
| 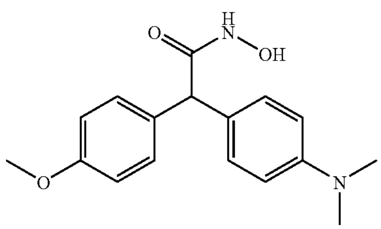 | 6-6 | LRMS (ESI): (calc.) 300.4 (found) 301.4 (MH)+ | 1H NMR (CD3OD-d4) d (ppm): 7.19 (d, J = 8.4 Hz, 2H), 7.13 (d, J = 8.4 Hz, 2H), 6.84 (d, J = 8.8 Hz, 2H), 6.72 (d, J = 8.6 Hz, 2H), 4.61 (s, 2H), 3.76 (s, 3H), 2.89 (s, 6H). | 2-(4-(dimethylamino)phenyhl)-N-hydroxy-2-(4-methoxyphenyl)acetamide |
| 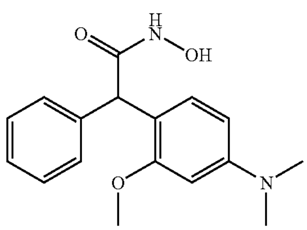 [SMILES: COc1cc(N(C)C)ccc1C(C(=O)NO)c1ccccc1] | 6-7 | LRMS (ESI): (calc.) 300.4 (found) 301.4 (MH)+ | 1H NMR (CD3OD-d4) d (ppm): 7.31-7.19 (m, 5H), 6.91 (d, J = 8.6 Hz, 1H), 6.34 (d, J = 2.6 Hz, 1H), 6.26 (dd, J = 8.6, 2.5 Hz, 1H), 5.03 (s, 1H), 3.79 (s, 3H), 2.90 (s, 6H). | 2-(4-(dimethylamino)-2-methoxyphenyl)-N-hydroxy-2-phenylacetamide |
| 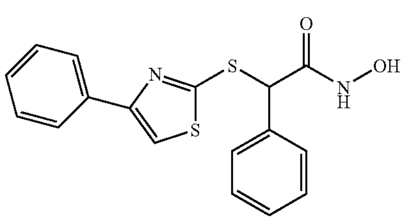 [SMILES: O=C(NO)C(Sc1nc(-c2ccccc2)cs1)c1ccccc1] | 6-8 | LRMS (ESI): (calc.) 342.4 (found) 343.4 (MH)+ | (DMSOD6) d (ppm): 1H: 11.17 (s, 1H), 9.21 (s, 1H), 8.02 (s, 1H), 7.95-7.92 (m, 2H), 7.57 (dd, J = 8.4, 1.4 Hz, 2H), 7.47-7.42 (m, 2H), 7.38-7.30 (m, 4H), 5.50 (s, 1H). | N-hydroxy-2-phenyl-2-(4-phenylthiazol-2-ylthio)acetamide |
| 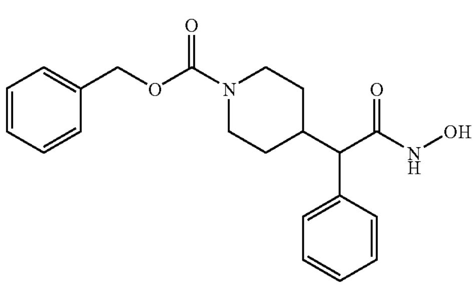 [SMILES: O=C(NO)C(c1ccccc1)C1CCN(C(=O)OCc2ccccc2)CC1] | 6-9a | LRMS (ESI): (calc) 368.43 (found) 369.41 (MH)+ | (MeOH-d4) d (ppm) 1H: 7.38-7.22 (m, 10H), 5.09 (s, 2H), 4.16 (d, J = 13.5 Hz, 1H), 4.03 (d, J = 13.3 Hz, 1H), 2.94-2.75 (m, 3H), 2.32-2.22 (m, 1H), 1.83 (d, J = 12.5 Hz, 1H), 1.28-1.14 (m, 2H), 0.98-0.88 (m, 1H) | benzyl 4-(2-(hydroxyamino)-2-oxo-1-phenylethyl)piperidine-1-carboxylate |

TABLE VI-continued

Compounds prepared according general Schemes above

| Structure | Cmpd # | MS | ¹H NMR | Name |
|---|---|---|---|---|
| 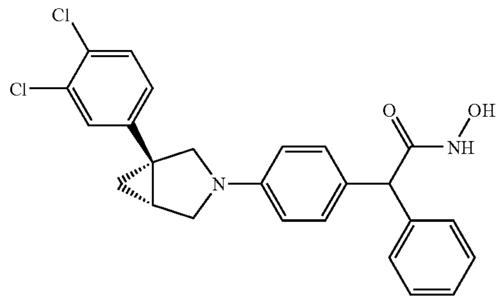 [SMILES: O=C(NO)C(c1ccccc1)c1ccc(N2C[C@@H]3C[C@]3(c3ccc(Cl)c(Cl)c3)C2)cc1] | 6-16 | LRMS (ESI): (calc.) 452.1/454.1 (found) 451.39/453.4 (MH)− | 1H NMR (CD3OD-d4) d(ppm): 7.43 (m, 2H), 7.12-7.28 (m, 8H), 6.61 (d, J = 8.4 Hz, 2H), 4.66 (s, 1H), 3.93 (d, J = 8.8 Hz, 1H), 3.66 (d, J = 8.8 Hz, 1H), 3.31 (m, 2H), 2.10 (m, 1H), 1.10 (m, 2H). | 2-(4-((1S,5R)-1-(3,4-dichlorophenyl)-3-azabicyclo[3.1.0]hexan-3-yl)phenyl)-N-hydroxy-2-phenylacetamide |
| 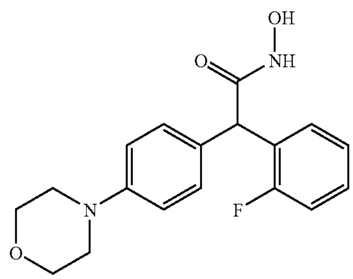 [SMILES: O=C(NO)C(c1ccc(N2CCOCC2)cc1)c1ccccc1F] | 6-17 | LRMS (ESI): (calc.) 330.4 (found) 331.4 (MH)+ | 1H NMR (DMSO-d6) δ (ppm): 10.89 (s, 1H), 8.94 (s, 1H), 7.46-7.41 (m, 1H), 7.31-7.25 (m, 1H), 7.16-7.09 (m, 4H), 6.89 (d, J = 9.0 Hz, 2H), 4.89 (s, 1H), 3.71 (t, J = 4.5 Hz, 4H), 3.05 (t, J = 4.9 Hz, 4H). | 2-(2-fluorophenyl)-N-hydroxy-2-(4-morpholinophenyl)acetamide |
| 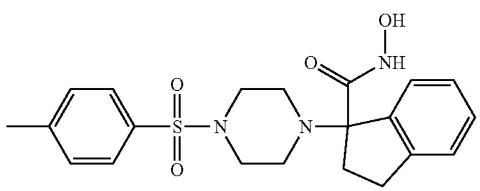 [SMILES: Cc1ccc(S(=O)(=O)N2CCN(C3(C(=O)NO)CCc4ccccc43)CC2)cc1] | 6-18 | LRMS (ESI): (calc.) 415.51 (found) 416.5 (MH)+ | 1H NMR (CD3OD-d4) d (ppm): 6.76 (d, J = 8.2 Hz, 2H), 7.44 (d, J = 8.2 Hz, 2H), 7.27 (d, J = 7.4 Hz, 1H), 7.25-7.13 (m, 3H), 3.18-2.96 (m, 5.5H), 2.60-2.40 (m, 5.5H), 2.46 (s, 3H), 2.18-2.08 (m, 1H). | N-hydroxy-1-(4-(p-tolylsulfonyl)piperazin-1-yl)-2,3-dihydro-1H-indene-1-carboxamide |
| 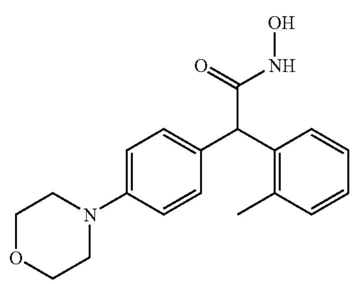 [SMILES: Cc1ccccc1C(C(=O)NO)c1ccc(N2CCOCC2)cc1] | 6-19 | LRMS (ESI): (calc.) 326.4 (found) 327.3 (MH)+ | 1H NMR (DMSO-d6) δ (ppm): 10.79 (s, 1H), 8.88 (s, 1H), 7.41-7.38 (m, 1H), 7.13-7.03 (m, 5H), 6.85 (d, J = 8.8 Hz, 2H), 4.76 (s, 1H), 3.69 (t, J = 4.7 Hz, 4H), 3.03 (t, J = 4.7 Hz, 4H), 2.19 (s, 3H). | N-hydroxy-2-(4-morpholinophenyl)-2-o-tolylacetamide |
| 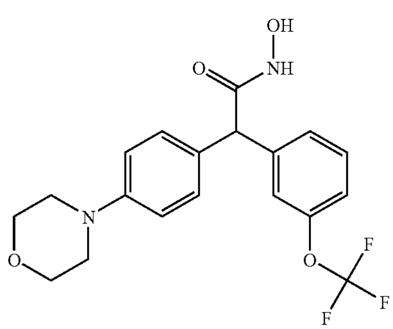 [SMILES: O=C(NO)C(c1ccc(N2CCOCC2)cc1)c1cccc(OC(F)(F)F)c1] | 6-20 | LRMS (ESI): (calc.) 396.4 (found) 397.4 (MH)+ | 1H NMR (DMSO-d6) δ (ppm): 10.90 (s, 1H), 8.98 (s, 1H), 7.43 (t, J = 8.2 Hz, 1H), 7.29-7.28 (m, 2H), 7.24-7.21 (m, 1H), 7.16 (d, J = 8.8 Hz, 2H), 6.88 (d, J = 8.8 Hz, 2H), 4.64 (s, 1H), 3.70 (t, J = 4.7 Hz, 4H), 3.04 (t, J = 4.9 Hz, 4H). | N-hydroxy-2-(4-morpholinophenyl)-2-(3-(trifluoromethoxy)phenyl)acetamide |

TABLE VI-continued

Compounds prepared according general Schemes above

| Structure | Cmpd # | MS | ¹H NMR | Name |
|---|---|---|---|---|
| 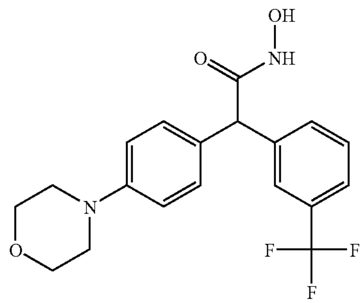 [SMILES: O=C(NO)C(c1ccc(N2CCOCC2)cc1)c1cccc(C(F)(F)F)c1] | 6-21 | LRMS (ESI): (calc.) 380.4 (found) 381.3 (MH)+ | 1H NMR (DMSO-d6) δ (ppm): 10.92 (s, 1H), 9.00 (s, 1H), 7.65-7.52 (m, 4H), 7.16 (d, J = 8.6 Hz, 2H), 6.88 (d, J = 8.8 Hz, 2H), 4.71 (s, 1H), 3.70 (t, J = 4.5 Hz, 4H), 3.14 (t, J = 4.9 Hz, 4H). | N-hydroxy-2-(4-morpholinophenyl)-2-(3-(trifluoromethyl)phenyl)acetamide |
| 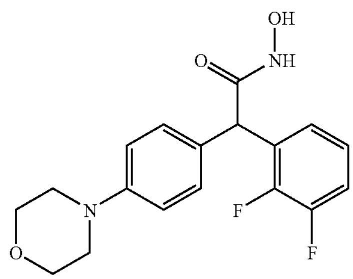 [SMILES: O=C(NO)C(c1ccc(N2CCOCC2)cc1)c1cccc(F)c1F] | 6-22 | LRMS (ESI): (calc.) 348.3 (found) 349.4 (MH)+ | 1H NMR (DMSO-d6) δ (ppm): 10.93 (s, 1H), 8.99 (s, 1H), 7.36-7.11 (m, 5H), 6.90 (d, J = 9.0 Hz, 2H), 4.93 (s, 1H), 3.72 (t, J = 4.7 Hz, 4H), 3.07 (t, J = 4.7 Hz, 4H). | 2-(2,3-difluorophenyl)-N-2-(3-hydroxy-2-(4-morpholinophenyl)acetamide |
| 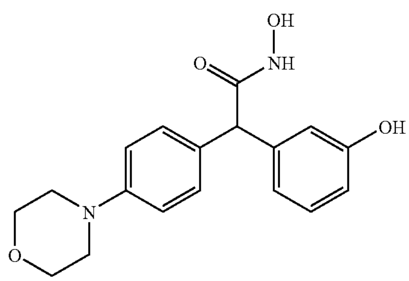 [SMILES: O=C(NO)C(c1ccc(N2CCOCC2)cc1)c1cccc(O)c1] | 6-23 | LRMS (ESI): (calc.) 328.4 (found) 329.4 (MH)+ | 1H NMR (DMSO-d6) δ (ppm): 10.79 (d, J = 1.2 Hz, 1H), 9.27 (s, 1H), 8.87 (d, J = 1.4 Hz, 1H), 7.15 (d, J = 8.6 Hz, 2H), 7.04 (t, J = 7.8 Hz, 1H), 6.85 (d, J = 8.8 Hz, 2H), 6.72 (t, J = 2.0 Hz, 1H), 6.67 (d, J = 7.6 Hz, 1H), 6.59-6.55 (m, 1H), 4.47 (s, 1H), 3.70 (t, J = 4.7 Hz, 4H), 3.03 (t, J = 4.7 Hz, 4H). | N-hydroxy-2-(3-hydroxyphenyl)-2-(4-morpholinophenyl)acetamide |
| 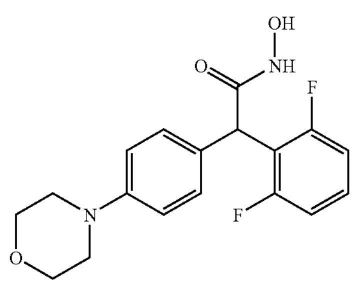 [SMILES: O=C(NO)C(c1ccc(N2CCOCC2)cc1)c1c(F)cccc1F] | 6-24 | LRMS (ESI): (calc.) 348.3 (found) 349.4 (MH)+ | 1H NMR (DMSO-d6) δ (ppm): 10.90 (s, 1H), 8.95 (s, 1H), 7.47-7.40 (m, 1H), 7.21-7.00 (m, 4H), 6.88 (d, J = 8.8 Hz, 2H), 4.83 (s, 1H), 3.70 (t, J = 4.5 Hz, 4H), 3.04 (t, J = 4.9 Hz, 4H). | 2-(2,6-difluorophenyl)-N-hydroxy-2-(4-morpholinophenyl)acetamide |
| 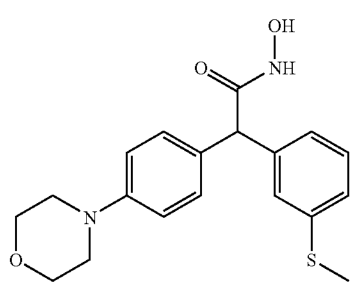 [SMILES: CSc1cccc(C(C(=O)NO)c2ccc(N3CCOCC3)cc2)c1] | 6-25 | LRMS (ESI): (calc.) 358.5 (found) 359.4 (MH)+ | 1H NMR (DMSO-d6) δ (ppm): 10.83 (s, 1H), 8.92 (s, 1H), 7.28-7.08 (m, 5H), 7.05-7.02 (m, 1H), 6.86 (d, J = 8.8 Hz, 2H), 4.55 (s, 1H), 3.70 (t, J = 4.7 Hz, 4H), 3.03 (t, J = 4.7 Hz, 4H), 2.41 (s, 3H). | N-hydroxy-2-(3-(methylthio)phenyl)-2-(4-morpholinophenyl)acetamide |

TABLE VI-continued

Compounds prepared according general Schemes above

| Structure | Cmpd # | MS | ¹H NMR | Name |
|---|---|---|---|---|
| 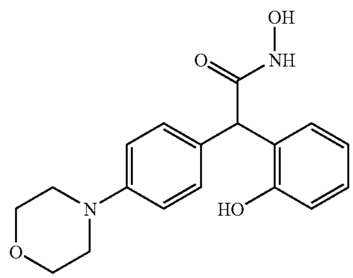 [SMILES: O=C(NO)C(c1ccc(N2CCOCC2)cc1)c1ccccc1O] | 6-26 | LRMS (ESI): (calc.) 328.4 (found) 329.2 (MH)+ | 1H NMR (DMSO-d6) δ (ppm): 10.84 (d, J = 1.6 Hz, 1H), 9.67 (s, 1H), 8.86 (d, J = 1.8 Hz, 1H), 7.24 (dd, J = 7.6, 1.4 Hz, 1H), 7.08-6.99 (m, 3H), 6.83 (d, J = 8.8 Hz, 2H), 6.76-6.68 (m, 2H), 4.86 (s, 1H), 3.69 (t, J = 4.5 Hz, 4H), 3.02 (t, J = 4.7 Hz, 4H). | N-hydroxy-2-(2-hydroxyphenyl)-2-(4-morpholinophenyl)acetamide |
| 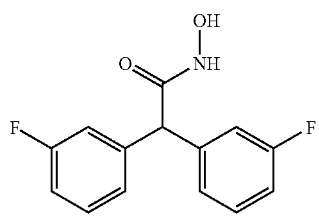 [SMILES: O=C(NO)C(c1cccc(F)c1)c1cccc(F)c1] | 6-27 | LRMS (ESI): (calc.) 263.2 (found) 264.2 (MH)+ | 1H NMR (DMSO-d6) δ (ppm): 10.99 (s, 1H), 9.05 (s, 1H), 7.39-7.33 (m, 2H), 7.16-7.06 (m, 6H), 4.76 (s, 1H). | 2,2-bis(3-fluorophenyl)-N-hydroxyacetamide |
| 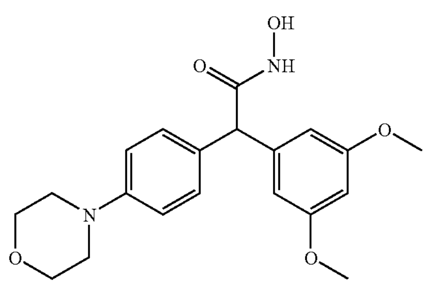 [SMILES: COc1cc(OC)cc(C(C(=O)NO)c2ccc(N3CCOCC3)cc2)c1] | 6-28 | LRMS (ESI): (calc.) 372.4 (found) 373.5 (MH)+ | 1H NMR (DMSO-d6) δ (ppm): 10.79 (s, 1H), 8.89 (s, 1H), 7.15 (d, J = 8.8 Hz, 2H), 6.85 (d, J = 9.0 Hz, 2H), 6.44 (d, J = 2.4 Hz, 2H), 6.35 (t, J = 2.4 Hz, 1H), 4.48 (s, 1H), 3.71-3.66 (m, 10H), 3.03 (t, J = 4.7 Hz, 4H). | 2-(3,5-dimethoxyphenyl)-N-hydroxy-2-(4-morpholinophenyl)acetamide |
| 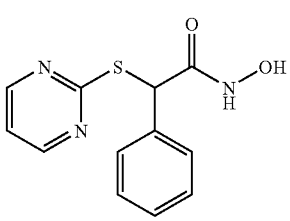 [SMILES: O=C(NO)C(Sc1ncccn1)c1ccccc1] | 6-29 | LRMS (ESI): (calc.) 261.3 (found) 262.0 (MH)+ | 1H NMR (DMSO-d6) δ (ppm): 11.09 (s, 1H), 9.07 (s, 1H), 8.60 (d, J = 4.9 Hz, 2H), 7.54-7.51 (m, 2H), 7.34-7.23 (m, 3H), 7.20 (t, J = 4.9 Hz, 1H), 5.48 (s, 1H). | N-hydroxy-2-phenyl-2-(pyrimidin-2-ylthio)acetamide |
| 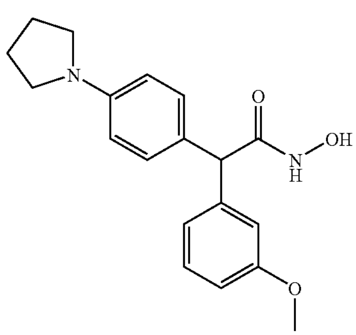 [SMILES: COc1cccc(C(C(=O)NO)c2ccc(N3CCCC3)cc2)c1] | 6-30 | LRMS (ESI): (calc.) 326.4 (found) 327.2 (MH)+ | 1H NMR (DMSO-d6) δ (ppm): 10.78 (s, 1H), 8.86 (s, 1H), 7.17 (t, J = 8.2 Hz, 1H), 7.09 (d, J = 8.7 Hz, 2H), 6.83-6.74 (m, 3H), 6.44 (d, J = 8.8 Hz, 2H), 4.49 (s, 1H), 3.68 (s, 3H), 3.15 (t, J = 6.5 Hz, 4H), 1.92-1.88 (m, 4H). | N-hydroxy-2-(3-methoxyphenyl)-2-(4-(pyrrolidin-1-yl)phenyl)acetamide |

TABLE VI-continued

Compounds prepared according general Schemes above

| Structure | Cmpd # | MS | ¹H NMR | Name |
|---|---|---|---|---|
| 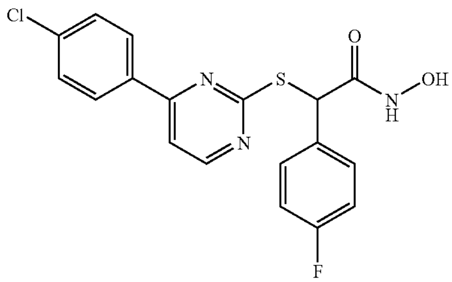 [SMILES: O=C(NO)C(Sc1nccc(-c2ccc(Cl)cc2)n1)c1ccc(F)cc1] | 6-31 | LRMS (ESI): (calc.) 389.8 (found) 390.4 (MH)+ | 1H NMR (DMSO-d6) δ (ppm): 11.17 (s, 1H), 9.14 (s, 1H), 8.67 (d, J = 5.3 Hz, 1H), 8.20 (d, J = 8.6 Hz, 2H), 7.79 (d, J = 5.3 Hz, 1H), 7.62-7.58 (m, 4H), 7.18 (t, J = 8.8 Hz, 2H), 5.59 (s, 1H). | 2-(4-(4-chlorophenyl)pyrimidin-2-ylthio)-2-(4-fluorophenyl)-N-hydroxyacetamide |
| 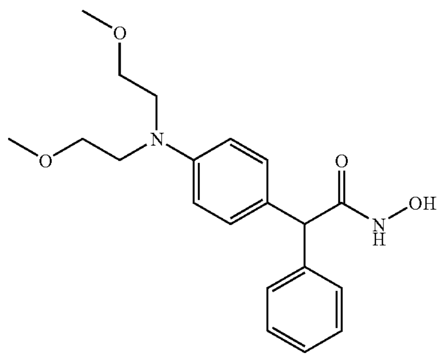 [SMILES: COCCN(CCOC)c1ccc(C(C(=O)NO)c2ccccc2)cc1] | 6-32 | LRMS (ESI): (calc.) 358.4 (found) 359.5 (MH)+ | 1H NMR (CD3OD-d4) d (ppm): 7.32-7.17 (m, 5H), 7.10 (d, J = 8.6 Hz, 2H), 6.65 (d, J = 8.8 Hz, 2H), 4.65 (s, 1H), 3.56-3.48 (m, 8H), 3.34-3.00 (s, 6H) | 2-(4-(bis(2-methoxyethyl)amino)phenyl)-N-hydroxy-2-phenylacetamide |
| 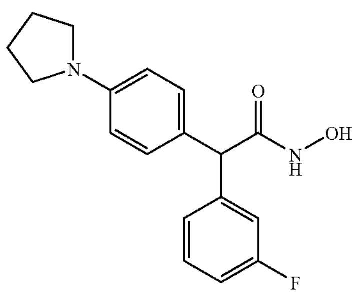 [SMILES: O=C(NO)C(c1ccc(N2CCCC2)cc1)c1cccc(F)c1] | 6-33 | LRMS (ESI): (calc.) 314.4 (found) 315.4 (MH)+ | 1H NMR (DMSO-d6) δ (ppm): 10.84 (s, 1H), 8.91 (s, 1H), 7.34-7.28 (m, 1H), 7.12-6.99 (m, 5H), 6.45 (d, J = 8.8 Hz, 2H), 4.56 (s, 1H), 3.16 (t, J = 6.5 Hz, 4H), 1.93-1.87 (m, 4H). | 2-(3-fluorophenyl)-N-hydroxy-2-(4-(pyrrolidin-1-yl)phenyl)acetamide |
| 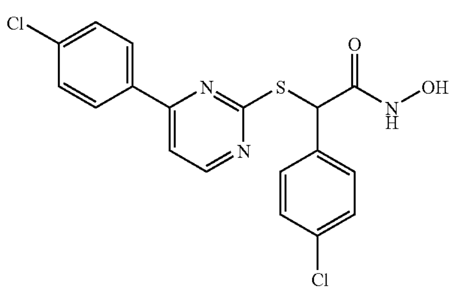 [SMILES: O=C(NO)C(Sc1nccc(-c2ccc(Cl)cc2)n1)c1ccc(Cl)cc1] | 6-34 | LRMS (ESI): (calc.) 405.0/ 407.0 (found) 406.4/ 408.4 (MH)+ | 1H NMR (DMSO-d6) δ (ppm): 11.19 (s, 1H), 9.16 (s, 1H), 8.67 (d, J = 5.3 Hz, 1H), 8.19 (d, J = 8.8 Hz, 2H), 7.79 (d, J = 5.3 Hz, 1H), 7.63-7.58 (m, 4H), 7.41 (d, J = 8.6 Hz, 2H), 5.59 (s, 1H). | 2-(4-chlorophenyl)-2-(4-(4-chlorophenyl)pyrimidin-2-ylthio)-N-hydroxyacetamide |
| 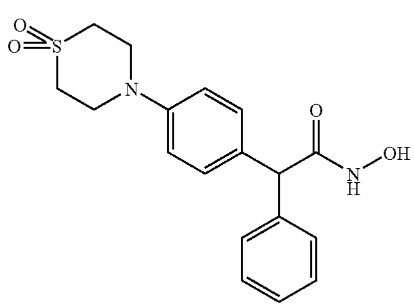 [SMILES: O=C(NO)C(c1ccccc1)c1ccc(N2CCS(=O)(=O)CC2)cc1] | 6-35 | LRMS (ESI): (calc.) 360.4 (found) 361.4 (MH)+ | 1H NMR (CD3OD-d4) d (ppm): 7.37-7.23 (m, 7H), 7.04-6.98 (m, 2H), 4.73 (s, 1H), 3.90-3.83 (m, 4H), 3.16-3.11 (m, 4H) | N-hydroxy-2-phenyl-2-(4-thiomorpholino dioxide-phenyl)acetamide |

TABLE VI-continued

Compounds prepared according general Schemes above

| Structure | Cmpd # | MS | ¹H NMR | Name |
|---|---|---|---|---|
| 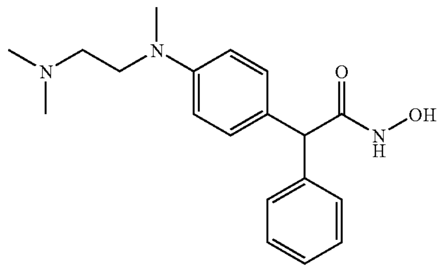 [SMILES: CN(C)CCN(C)c1ccc(C(C(=O)NO)c2ccccc2)cc1] | 6-36 | LRMS (ESI): (calc.) 327.4 (found) 328.5 (MH)+ | 1H NMR (DMSO-d6) δ (ppm): 10.86 (s, 1H), 8.92 (s, 1H), 7.37-7.30 (m, 4H), 7.28-7.22 (m, 1H), 7.18-7.13 (m, 2H), 6.68-6.62 (m, 2H), 4.58 (s, 1H), 3.44-3.36 (m, 2H), 2.89 (s, 3H), 2.40-2.35 (m, 2H), 2.20 (s, 6H) | 2-(4-((2-(dimethylamino)ethyl)(methyl)amino)phenyl)-N-hydroxy-2-phenylacetamide |
| 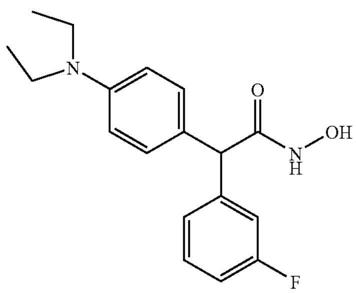 [SMILES: CCN(CC)c1ccc(C(C(=O)NO)c2cccc(F)c2)cc1] | 6-37 | LRMS (ESI): (calc.) 316.4 (found) 317.4 (MH)+ | 1H NMR (DMSO-d6) δ (ppm): 10.83 (s, 1H), 8.91 (s, 1H), 7.35-7.28 (m, 1H), 7.11-7.00 (m, 5H), 6.57 (d, J = 9.0 Hz, 2H), 4.54 (s, 1H), 3.27 (q, J = 7.0 Hz, 4H), 1.03 (t, J = 7.0 Hz, 6H). | 2-(4-(dimethylamino)phenyl)-2-(3-fluorophenyl)-N-hydroxyacetamide |
| 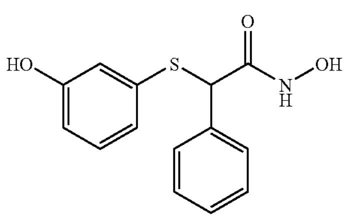 [SMILES: O=C(NO)C(Sc1cccc(O)c1)c1ccccc1] | 6-38 | LRMS (ESI): (calc.) 275.3 (found) 276.3 (MH)+ | 1H NMR (DMSO-d6) δ (ppm): 10.92 (br s, 1H), 9.54 (br s, 1H), 9.08 (br s, 1H), 7.48-7.44 (m, 2H), 7.34-7.23 (m, 3H), 7.06 (t, J = 8.0 Hz, 1H), 6.70-6.65 (m, 2H), 6.60-6.57 (m, 1H), 4.85 (s, 1H) | N-hydroxy-2-(3-hydroxyphenylthio)-2-phenylacetamide |
| 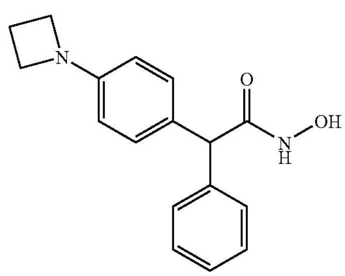 [SMILES: O=C(NO)C(c1ccccc1)c1ccc(N2CCC2)cc1] | 6-39 | LRMS (ESI): (calc.) 282.3 (found) 283.2 (MH)+ | 1H NMR (DMSO-d6) δ (ppm): 10.87 (s, 1H), 8.94 (s, 1H), 7.34-7.30 (m, 4H), 7.28-7.21 (m, 1H), 7.18-7.14 (m, 2H), 6.40-6.36 (m, 2H), 4.59 (s, 1H), 3.78 (t, J = 7.2 Hz, 4H), 2.35-2.26 (m, 2H), | 2-(4-(azetidin-1-yl)phenyl)-N-hydroxy-2-phenylacetamide |
| 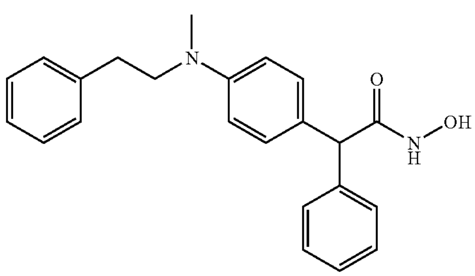 [SMILES: CN(CCc1ccccc1)c1ccc(C(C(=O)NO)c2ccccc2)cc1] | 6-40 | LRMS (ESI): (calc.) 360.5 (found) 361.5 (MH)+ | 1H NMR (DMSO-d6) δ (ppm): 10.81 (s, 1H), 8.87 (s, 1H), 7.31-7.11 (m, 12H), 6.65 (d, J = 9.0 Hz, 2H), 4.54 (s, 1H), 3.47 (t, J = 7.6 Hz, 2H), 2.81 (s, 3H), 2.72 (t, J = 8.0 Hz, 2H). | N-hydroxy-2-(4-(methyl(phenethyl)amino)phenyl)-2-phenylacetamide |

TABLE VI-continued

Compounds prepared according general Schemes above

| Structure | Cmpd # | MS | ¹H NMR | Name |
|---|---|---|---|---|
| 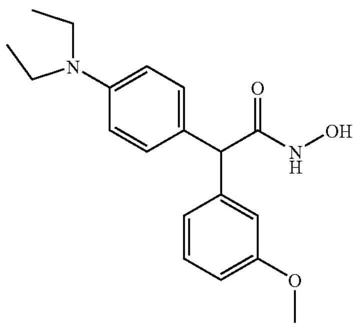 [SMILES: CCN(CC)c1ccc(C(C(=O)NO)c2cccc(OC)c2)cc1] | 6-41 | LRMS (ESI): (calc.) 328.4 (found) 329.4 (MH)+ | 1H NMR (DMSO-d6) δ (ppm): 10.77 (s, 1H), 8.86 (s, 1H), 7.18 (t, J = 7.8 Hz, 1H), 7.07 (d, J = 8.8 Hz, 2H), 6.84-6.82 (m, 2H), 6.79-6.75 (m, 1H), 6.55 (d, J = 8.8 Hz, 2H), 4.47 (s, 1H), 3.68 (s, 3H), 3.26 (q, J = 7.2 Hz, 4H), 1.03 (t, J = 6.8 Hz, 6H). | 2-(4-(diethylamino) phenyl)-N-hydroxy-2-(3-methoxyphenyl) acetamide |
| 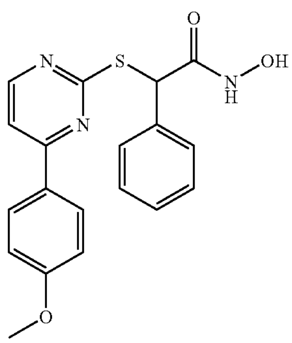 [SMILES: COc1ccc(-c2ccnc(SC(C(=O)NO)c3ccccc3)n2)cc1] | 6-42 | LRMS (ESI): (calc.) 367.4 (found) 368.4 (MH)+ | 1H NMR (DMSO-d6) δ (ppm): 11.16 (s, 1H), 9.09 (s, 1H), 8.56 (d, J = 5.5 Hz, 1H), 8.17 (d, J = 9.0 Hz, 2H), 7.69 (d, J = 5.3 Hz, 1H), 7.59-7.56 (m, 2H), 7.35-7.23 (m, 3H), 7.07 (d, J = 9.0 Hz, 2H), 5.59 (s, 1H), 3.84 (s, 3H). | N-hydroxy-2-(4-(4-methoxyphenyl) pyrimidin-2-ylthio)-2-phenylacetamide |
| 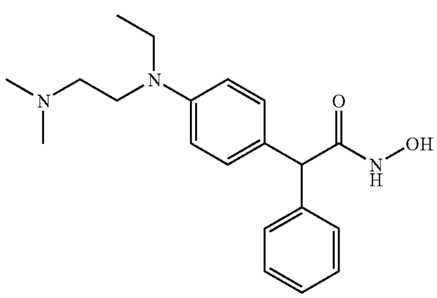 [SMILES: CCN(CCN(C)C)c1ccc(C(C(=O)NO)c2ccccc2)cc1] | 6-43 | LRMS (ESI): (calc.) 341.5 (found) 342.4 (MH)+ | 1H NMR (DMSO-d6) δ (ppm): 10.85 (s, 1H), 8.92 (s, 1H), 7.37-7.30 (m, 4H), 7.27-7.22 (m, 1H), 7.16-7.11 (m, 2H), 6.64-6.58 (m, 2H), 4.57 (s, 1H), 3.44-3.30 (m, 4H), 2.38 (t, J = 7.2 Hz, 2H), 2.22 (s, 6H), 1.08 (t, J = 6.9 Hz, 3H) | 2-(4-((2-(dimethylamino) ethyl(ethyl)amino) phenyl)-N-hydroxy-2-phenylacetamide |
| 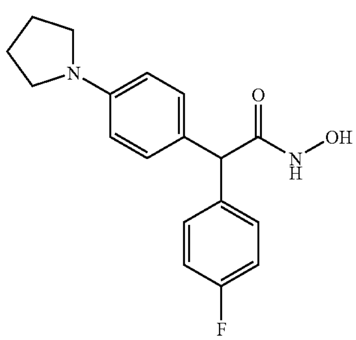 [SMILES: O=C(NO)C(c1ccc(F)cc1)c1ccc(N2CCCC2)cc1] | 6-44 | LRMS (ESI): (calc.) 314.4 (found) 315.3 (MH)+ | 1H NMR (DMSO-d6) δ (ppm): 10.81 (s, 1H), 8.88 (s, 1H),7.30-7.25 (m, 2H), 7.11-7.06 (m, 4H), 6.44 (d, J = 8.8 Hz, 2H), 4.53 (s, 1H), 3.17-3.13 (m, 4H), 1.92-1.88 (m, 4H). | 2-(4-fluorophenyl)-N-hydroxy-2-(4-(pyrrolidin-1-yl)phenyl)acetamide |

TABLE VI-continued

Compounds prepared according general Schemes above

| Structure | Cmpd # | MS | ¹H NMR | Name |
|---|---|---|---|---|
| 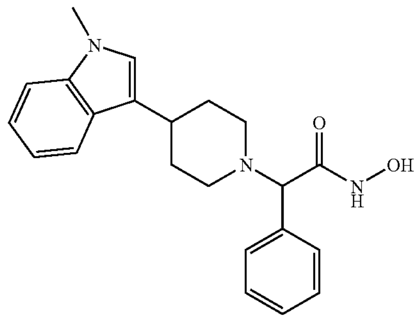 [SMILES: Cn1cc(C2CCN(C(C(=O)NO)c3ccccc3)CC2)c2ccccc21] | 6-45 | LRMS (ESI): (calc.) 363.5 (found) 364.5 (MH)+ | 1H NMR (CD3OD-d4) d (ppm): 7.62-7.54 (m, 3H), 7.41-7.30 (m, 4H), 7.18-7.13 (m, 1H), 7.04-6.99 (m, 1H), 6.96 (s, 1H), 3.76 (s, 3H), 3.74 (s, 1H), 3.30-3.20 (m, 1H), 2.90-2.78 (m, 2H), 2.36-2.26 (m, 1H), 2.07-1.80 (m, 5H) | N-hydroxy-2-(4-(1-methyl-1H-indol-3-yl)piperidin-1-yl)-2-phenylacetamide |
| 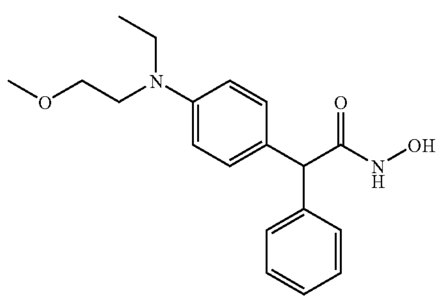 [SMILES: CCN(CCOC)c1ccc(C(C(=O)NO)c2ccccc2)cc1] | 6-46 | LRMS (ESI): (calc.) 328.4 (found) 329.4 (MH)+ | 1H NMR (DMSO-d6) δ (ppm): 10.85 (s, 1H), 8.91 (s, 1H), 7.37-7.30 (m, 4H), 7.28-7.22 (m, 1H), 7.16-7.10 (m, 2H), 6.66-6.60 (m, 2H), 4.57 (s, 1H), 3.50-3.42 (m, 4H), 3.40-3.34 (m, 2H), 3.29 (s, 3H), 1.07 (t, J = 7.0 Hz, 3H) | 2-(4-(ethyl(2-methoxyethyl)amino)phenyl)-N-hydroxy-2-phenylacetamide |
| 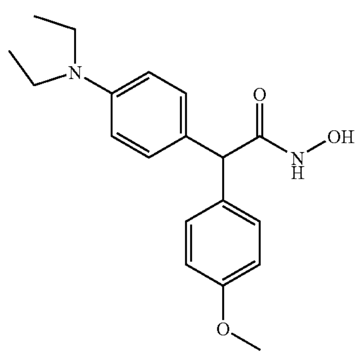 [SMILES: CCN(CC)c1ccc(C(C(=O)NO)c2ccc(OC)cc2)cc1] | 6-47 | LRMS (ESI): (calc.) 328.4 (found) 329.4 (MH)+ | 1H NMR (DMSO-d6) δ (ppm): 10.75 (s, 1H), 8.82 (s, 1H), 7.19 (d, J = 8.6 Hz, 2H), 7.04 (d, J = 8.8 Hz, 2H), 6.82 (d, J = 8.8 Hz, 2H), 6.55 (d, J = 9.0 Hz, 2H), 4.44 (s, 1H), 3.69 (s, 3H), 3.26 (q, J = 7.1 Hz, 4H), 1.02 (t, J = 7.0 Hz, 6H). | 2-(4-(dimethylamino)phenyl)-N-hydroxy-2-(4-methoxyphenyl)acetamide |

| Structure | Name | Cpd No. | HPLC | MS |
|---|---|---|---|---|
| 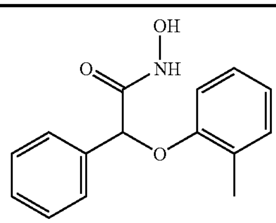 | N-hydroxy-2-phenyl-2-(o-tolyloxy)acetamide | 7-1 | 96% RT: 3.62 min | LRMS (ESI): (calc) 257.2845 (found) 258.05 (MH)+ |
| 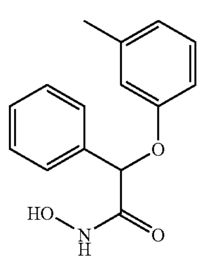 [SMILES: Cc1cccc(OC(C(=O)NO)c2ccccc2)c1] | N-hydroxy-2-phenyl-2-(m-tolyloxy)acetamide | 7-2 | 96% RT: 3.59 min | LRMS (ESI): (calc) 257.2845 (found) 258.05 (MH)+ |

-continued

| Structure | Name | Cpd No. | HPLC | MS |
|---|---|---|---|---|
| 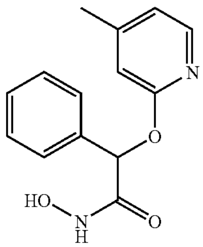 [SMILES: Cc1ccnc(OC(C(=O)NO)c2ccccc2)c1] | N-hydroxy-2-(4-methylpyridin-2-yloxy)-2-phenylacetamide | 7-3 | 94% RT: 2.9 min | LRMS (ESI): (calc) 258.2726 (found) 259.06 (MH)+ |
| 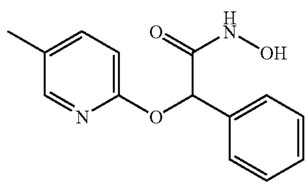 [SMILES: Cc1ccc(OC(C(=O)NO)c2ccccc2)nc1] | N-hydroxy-2-(5-methylpyridin-2-yloxy)-2-phenylacetamide | 7-4 | 95% RT: 2.88 min | LRMS (ESI): (calc) 258.2726 (found) 259.06 (MH)+ |
| 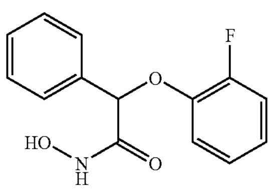 [SMILES: O=C(NO)C(Oc1ccccc1F)c1ccccc1] | 2-(2-fluorophenoxy)-N-hydroxy-2-phenylacetamide | 7-5 | 89% RT: 3.41 min | LRMS (ESI): (calc) 261.2484 (found) 262.02 (MH)+ |
| 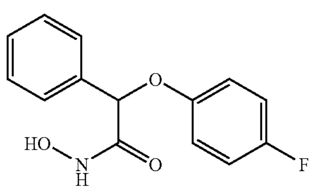 [SMILES: O=C(NO)C(Oc1ccc(F)cc1)c1ccccc1] | 2-(4-fluorophenoxy)-N-hydroxy-2-phenylacetamide | 7-6 | 91% RT: 3.45 min | LRMS (ESI): (calc) 261.2484 (found) 262.02 (MH)+ |
| 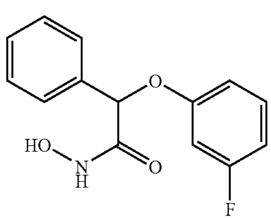 [SMILES: O=C(NO)C(Oc1cccc(F)c1)c1ccccc1] | 2-(3-fluorophenoxy)-N-hydroxy-2-phenylacetamide | 7-8 | 94% RT: 3.48 min | LRMS (ESI): (calc) 261.2484 (found) 262.02 (MH)+ |
| 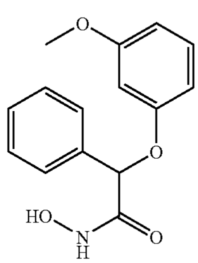 [SMILES: COc1cccc(OC(C(=O)NO)c2ccccc2)c1] | N-hydroxy-2-(3-methoxyphenoxy)-2-phenylacetamide | 7-9 | 96% RT: 3.43 min | LRMS (ESI): (calc) 273.2839 (found) 274.06 (MH)+ |
| 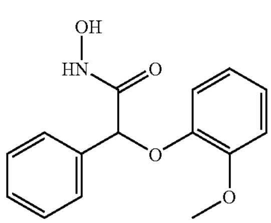 [SMILES: COc1ccccc1OC(C(=O)NO)c1ccccc1] | N-hydroxy-2-(2-methoxyphenoxy)-2-phenylacetamide | 7-10 | 90% RT: 3.39 min | LRMS (ESI): (calc) 273.2839 (found) 274.06 (MH)+ |

-continued

| Structure | Name | Cpd No. | HPLC | MS |
|---|---|---|---|---|
| 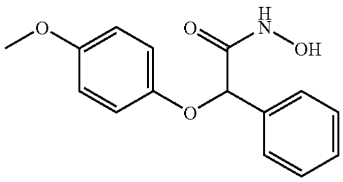 | N-hydroxy-2-(4-methoxyphenoxy)-2-phenylacetamide | 7-11 | 93% RT: 3.36 min | LRMS (ESI): (calc) 273.2839 (found) 274.06 (MH)+ |
| 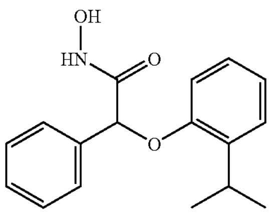 [SMILES: CC(C)c1ccccc1OC(C(=O)NO)c1ccccc1] | N-hydroxy-2-(2-isopropylphenoxy)-2-phenylacetamide | 7-12 | 92% RT: 4 min | LRMS (ESI): (calc) 285.3376 (found) 286.1 (MH)+ |
| 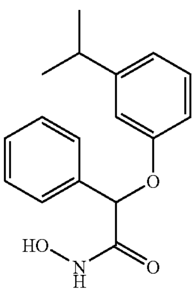 [SMILES: CC(C)c1cccc(OC(C(=O)NO)c2ccccc2)c1] | N-hydroxy-2-(3-isopropylphenoxy)-2-phenylacetamide | 7-13 | 92% RT: 3.98 min | LRMS (ESI): (calc) 285.3376 (found) 286.1 (MH)+ |
| 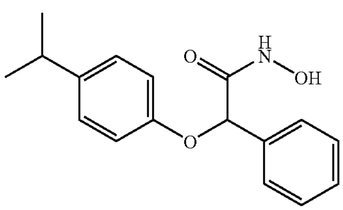 [SMILES: CC(C)c1ccc(OC(C(=O)NO)c2ccccc2)cc1] | N-hydroxy-2-(4-isopropylphenoxy)-2-phenylacetamide | 7-14 | 90% RT: 4 min | LRMS (ESI): (calc) 285.3376 (found) 286.1 (MH)+ |
| 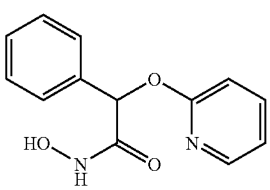 [SMILES: O=C(NO)C(Oc1ccccn1)c1ccccc1] | N-hydroxy-2-phenyl-2-(pyridin-2-yloxy)acetamide | 7-15 | 96% RT: 2.66 min | LRMS (ESI): (calc) 244.246 (found) 245.01 (MH)+ 1H NMR (360 MHz, DMSO-d6) d ppm 11.36 (1H, s), 9.29 (1H, s), 7.44-7.53 (4H, m), 7.41 (1H, dd, J = 7.04, 1.59 Hz), 7.34 (2H, d, J = 6.81 Hz), 6.66 (1H, s), 6.51 (1H, d, J = 9.08 Hz), 6.25 (1H, td, J = 6.81, 1.36 Hz) |
| 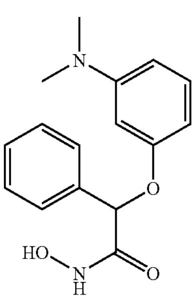 | 2-(3-(dimethylamino)phenoxy)-N-hydroxy-2-phenylacetamide | 7-16 | 89% RT: 2.87 min | LRMS (ESI): (calc) 286.3257 (found) 287.11 (MH)+ |

-continued

| Structure | Name | Cpd No. | HPLC | MS |
|---|---|---|---|---|
| | 2-(benzo[d][1,3]dioxol-5-yloxy)-N-hydroxy-2-phenylacetamide | 7-17 | 96% RT: 3.35 min | LRMS (ESI): (calc) 287.2674 (found) 288.06 (MH)+ |
| 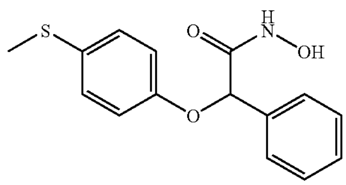 [SMILES: CSc1ccc(OC(C(=O)NO)c2ccccc2)cc1] | N-hydroxy-2-(4-(methylthio)phenoxy)-2-phenylacetamide | 7-18 | 100% RT: 3.65 min | LRMS (ESI): (calc) 289.3495 (found) 290.02 (MH)+ |
| 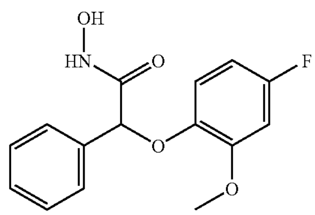 [SMILES: COc1cc(F)ccc1OC(C(=O)NO)c1ccccc1] | 2-(4-fluoro-2-methoxyphenoxy)-N-hydroxy-2-phenylacetamide | 7-19 | 94% RT: 3.49 min | LRMS (ESI): (calc) 291.2744 (found) 292.06 (MH)+ |
| 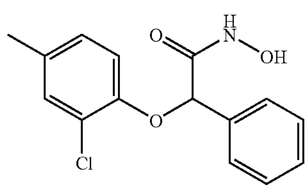 [SMILES: Cc1ccc(OC(C(=O)NO)c2ccccc2)c(Cl)c1] | 2-(2-chloro-4-methylphenoxy)-N-hydroxy-2-phenylacetamide | 7-20 | 90% RT: 3.38 min | LRMS (ESI): (calc) 291.7296 (found) 292.03 (MH)+ |
| 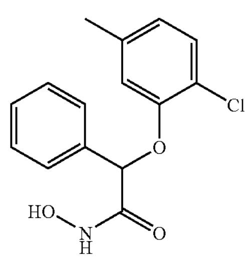 [SMILES: Cc1ccc(Cl)c(OC(C(=O)NO)c2ccccc2)c1] | 2-(2-chloro-5-methylphenoxy)-N-hydroxy-2-phenylacetamide | 7-21 | 95% RT: 3.81 min | LRMS (ESI): (calc) 291.7296 (found) 292.03 (MH)+ |
| 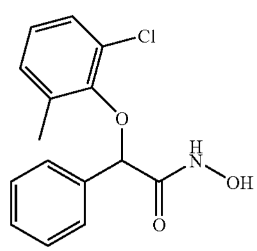 [SMILES: Cc1cccc(Cl)c1OC(C(=O)NO)c1ccccc1] | 2-(2-chloro-6-methylphenoxy)-N-hydroxy-2-phenylacetamide | 7-30 | 97% RT: 369 min | LRMS (ESI): (calc) 291.7296 (found) 292.03 (MH)+ |
| 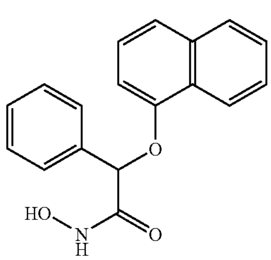 [SMILES: O=C(NO)C(Oc1cccc2ccccc12)c1ccccc1] | N-hydroxy-2-(naphthalen-1-yloxy)-2-phenylacetamide | 7-31 | 92% RT: 3.85 min | LRMS (ESI): (calc) 293.3166 (found) 294.05 (MH)+ |

-continued

| Structure | Name | Cpd No. | HPLC | MS |
|---|---|---|---|---|
| 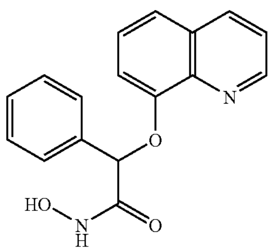 [SMILES: O=C(NO)C(Oc1cccc2cccnc12)c1ccccc1] | N-hydroxy-2-phenyl-2-(quinolin-8-yloxy)acetamide | 7-32 | 100% RT: 2.76 min | LRMS (ESI): (calc) 294.3047 (found) 295.11 (MH)+ |
| 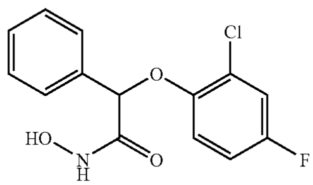 [SMILES: O=C(NO)C(Oc1ccc(F)cc1Cl)c1ccccc1] | 2-(2-chloro-4-fluorophenoxy)-N-hydroxy-2-phenylacetamide | 7-33 | 90% RT: 3.69 min | LRMS (ESI): (calc) 295.6935 (found) 296.01 (MH)+ |
| 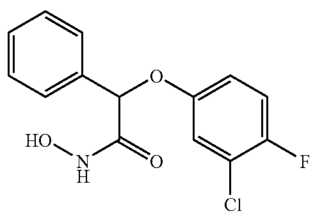 [SMILES: O=C(NO)C(Oc1ccc(F)c(Cl)c1)c1ccccc1] | 2-(3-chloro-4-fluorophenoxy)-N-hydroxy-2-phenylacetamide | 7-34 | 96% RT: 3.73 min | LRMS (ESI): (calc) 295.6935 (found) 296 (MH)+ |
| 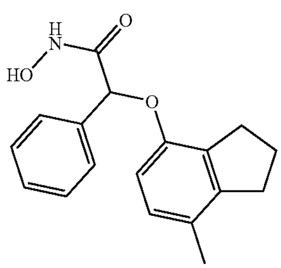 [SMILES: Cc1ccc(OC(C(=O)NO)c2ccccc2)c2c1CCC2] | N-hydroxy-2-(7-methyl-2,3-dihydro-1H-inden-4-yloxy)-2-phenylacetamide | 7-35 | 94% RT: 4.05 min | LRMS (ESI): (calc) 297.3484 (found) 298.1 (MH)+ |
| 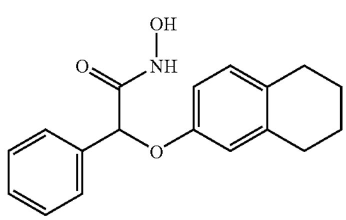 [SMILES: O=C(NO)C(Oc1ccc2c(c1)CCCC2)c1ccccc1] | N-hydroxy-2-phenyl-2-(5,6,7,8-tetrahydronaphthalen-2-yloxy)acetamide | 7-36 | 90% RT: min | 1H NMR (360 MHz, DMSO-d6) d ppm 11.15 (1H, s), 9.08 (1H, s), 7.60 (2H, d, J = 7.27 Hz), 7.38-7.49 (3H, m), 7.01 (1H, d, J = 8.17 Hz), 6.73-6.81 (2H, m), 5.63 (1H, s), 2.70 (4H, d, J = 12.26 Hz), 1.76 (4H, br. s.) |
| 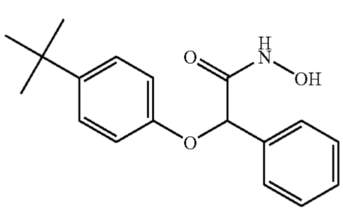 [SMILES: CC(C)(C)c1ccc(OC(C(=O)NO)c2ccccc2)cc1] | 2-(4-tert-butylphenoxy)-N-hydroxy-2-phenylacetamide | 7-37 | 93% RT: 4.16 min | LRMS (ESI): (calc) 299.3642 (found) 300.09 (MH)+ |

-continued

| Structure | Name | Cpd No. | HPLC | MS |
|---|---|---|---|---|
| 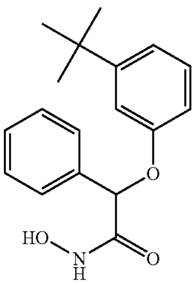 [SMILES: CC(C)(C)c1cccc(OC(C(=O)NO)c2ccccc2)c1] | 2-(3-tert-butylphenoxy)-N-hydroxy-2-phenylacetamide | 7-38 | 91% RT: 4.12 min | LRMS (ESI): (calc) 299.3642 (found) 300.09 (MH)+ |
| 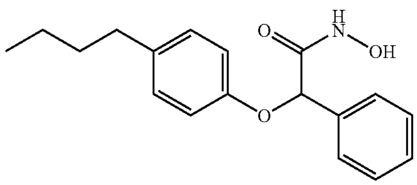 [SMILES: CCCCc1ccc(OC(C(=O)NO)c2ccccc2)cc1] | 2-(4-butylphenoxy)-N-hydroxy-2-phenylacetamide | 7-39 | 94% RT: 4.29 min | LRMS (ESI): (calc) 299.3642 (found) 300.13 (MH)+ |
| 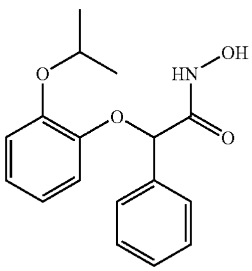 [SMILES: CC(C)Oc1ccccc1OC(C(=O)NO)c1ccccc1] | N-hydroxy-2-(2-isopropoxyphenoxy)-2-phenylacetamide | 7-40 | 91% RT: 3.78 min | LRMS (ESI): (calc) 301.3371 (found) 302.11 (MH)+ |
| 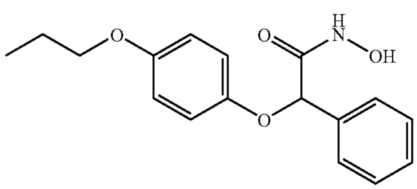 [SMILES: CCCOc1ccc(OC(C(=O)NO)c2ccccc2)cc1] | N-hydroxy-2-phenyl-2-(4-propoxyphenoxy)acetamide | 7-41 | 96% RT: 3.85 min | LRMS (ESI): (calc) 301.3371 (found) 302.11 (MH)+ |
| 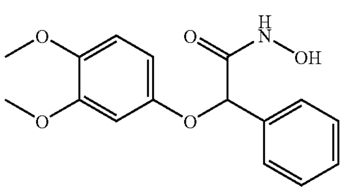 [SMILES: COc1ccc(OC(C(=O)NO)c2ccccc2)cc1OC] | 2-(3,4-dimethoxyphenoxy)-N-hydroxy-2-phenylacetamide | 7-42 | 95% RT: 3.21 min | LRMS (ESI): (calc) 303.3099 (found) 304.13 (MH)+ |
| 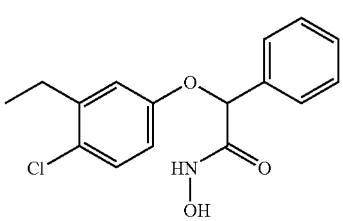 [SMILES: CCc1cc(OC(C(=O)NO)c2ccccc2)ccc1Cl] | 2-(4-chloro-3-ethylphenoxy)-N-hydroxy-2-phenylacetamide | 7-43 | 99% RT: 4.07 min | LRMS (ESI): (calc) 305.7561 (found) 306.03 (MH)+ 1H NMR (360 MHz, DMSO-d6) d ppm 11.13 (1H, s), 9.04 (1H, s), 7.53 (2H, d, J = 6.36 Hz), 7.23-7.46 (4H, m), 6.99 (1H, d, J = 3.18 Hz), 6.81 (1H, dd, J = 9.08, 3.18 Hz), 5.63 (1H, s), 2.62 (2H, q, J = 7.42 Hz), 1.14 (3H, t, J = 7.49 Hz) |
| 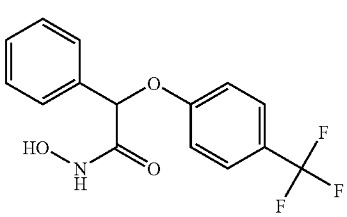 [SMILES: O=C(NO)C(Oc1ccc(C(F)(F)F)cc1)c1ccccc1] | N-hydroxy-2-phenyl-2-(4-(trifluoromethyl)phenoxy)acetamide | 7-44 | 94% RT: 3.83 min | LRMS (ESI): (calc) 311.2559 (found) 312.06 (MH)+ 1H NMR (250 MHz, DMSO-d6) d ppm 11.20 (1H, s), 9.08 (1H, s), 7.65 (2H, d, J = 8.68 Hz), 7.53 (2H, d, J = 6.24 Hz), 7.30-7.43 (3H, m), 7.14 (2H, d, J = 8.53 Hz), 5.77 (1H, s) |

-continued

| Structure | Name | Cpd No. | HPLC | MS |
|---|---|---|---|---|
| 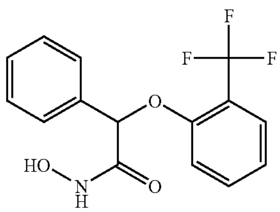 [SMILES: O=C(NO)C(Oc1ccccc1C(F)(F)F)c1ccccc1] | N-hydroxy-2-phenyl-2-(2-trifluoromethyl)phenoxy)acetamide | 7-45 | 91% RT: 3.79 min | LRMS (ESI): (calc) 311.2559 (found) 312.07 (MH)+ |
| 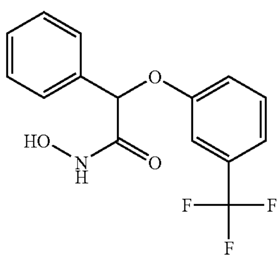 [SMILES: O=C(NO)C(Oc1cccc(C(F)(F)F)c1)c1ccccc1] | N-hydroxy-2-phenyl-2-(3-trifluoromethyl)phenoxy)acetamide | 7-46 | 92% RT: 3.82 min | LRMS (ESI): (calc) 311.2559 (found) 312.07 (MH)+ 1H NMR (360 MHz, DMSO-d6) d ppm 11.22 (1H, br. s.), 9.10 (1H, br. s.), 7.51-7.59 (3H, m), 7.38-7.45 (4H, m), 7.28-7.38 (2H, m), 5.82 (1H, s) |
| 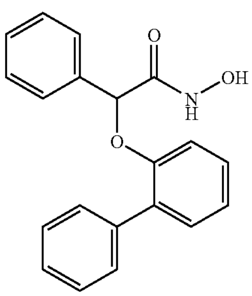 [SMILES: O=C(NO)C(Oc1ccccc1-c1ccccc1)c1ccccc1] | 2-(biphenyl-2-yloxy)-N-hydroxy-2-phenylacetamilde | 7-47 | 97% RT: 4.05 min | LRMS (ESI): (calc) 319.3539 (found) 320.09 (MH)+ 1H NMR (360 MHz, DMSO-d6) d ppm 11.08 (1H, br. s.), 9.10 (1H, br. s.), 7.65-7.78 (2H, m), 7.38-7.51 (4H, m), 7.26-7.38 (6H, m), 7.00-7.12 (2H, m), 5.62 (1H, s) |
| 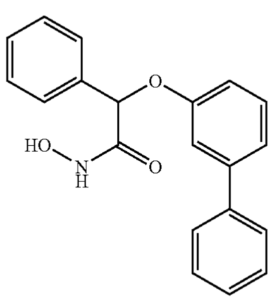 [SMILES: O=C(NO)C(Oc1cccc(-c2ccccc2)c1)c1ccccc1] | 2-(biphenyl-3-yloxy)-N-hydroxy-2-phenylacetamide | 7-48 | 90% RT: 4.05 min | LRMS (ESI): (calc) 319.3539 (found) 320.13 (MH)+ |
| 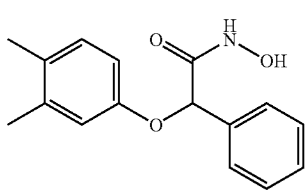 [SMILES: Cc1ccc(OC(C(=O)NO)c2ccccc2)cc1C] | 2-(3,4-dimethylphenoxy)-N-hydroxy-2-phenylacetamide | 7-49 | 90% RT: 3.76 min | LRMS (ESI): (calc) 271.3111 (found) 272.05 (MH)+ |
| 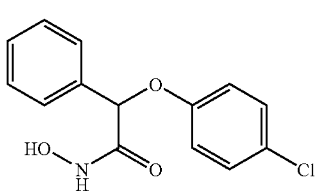 [SMILES: O=C(NO)C(Oc1ccc(Cl)cc1)c1ccccc1] | 2-(4-chlorophenoxy)-N-hydroxy-2-phenylacetamide | 7-50 | 95% RT: 3.68 min | LRMS (ESI): (calc) 277.703 (found) 278.03 (MH)+ |

-continued

| Structure | Name | Cpd No. | HPLC | MS |
|---|---|---|---|---|
| 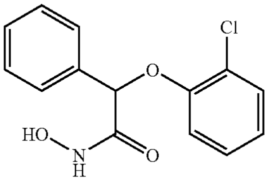 | 2-(2-chlorophenoxy)-N-hydroxy-2-phenylacetamide | 7-51 | 95% RT: 3.61 min | LRMS (ESI): (calc) 277.703 (found) 278.03 (MH)+ |
| 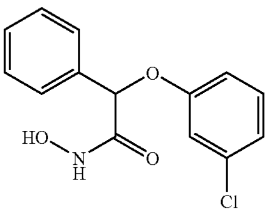 [SMILES: O=C(NO)C(Oc1cccc(Cl)c1)c1ccccc1] | 2-(3-chlorophenoxy)-N-hydroxy-2-phenylacetamide | 7-52 | 94% RT: 3.68 min | LRMS (ESI): (calc) 277.703 (found) 277.99 (MH)+ |
| 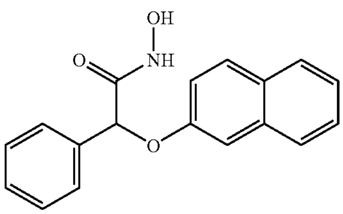 [SMILES: O=C(NO)C(Oc1ccc2ccccc2c1)c1ccccc1] | N-hydroxy-2-(naphthalen-2-yloxy)-2-phenylacetamide | 7-53 | 95% RT: 3.81 min | LRMS (ESI): (calc) 293.3166 (found) 294.09 (MH)+ |
| 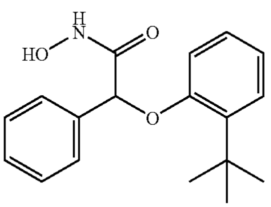 [SMILES: CC(C)(C)c1ccccc1OC(C(=O)NO)c1ccccc1] | 2-(2-tert-butylphenoxy)-N-hydroxy-2-phenylacetamide | 7-54 | 92% RT: 4.16 min | LRMS (ESI): (calc) 299.3642 (found) 300.15 (MH)+ 1H NMR (360 MHz, DMSO-d6) d ppm 11.24 (1H, br. s.), 9.16 (1H, br. s.), 7.65 (2H, d, J = 7.27 Hz), 7.35-7.49 (3H, m), 7.28 (1H, d, J = 7.72 Hz), 7.16 (1H, t, J = 7.72 Hz), 6.82-6.94 (2H, m), 5.68 (1H, s), 1.43 (9H, s) |
| 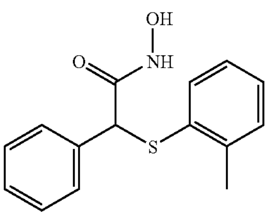 | N-hydroxy-2-phenyl-2-(o-tolylthio)acetamide | 7-55 | 92% RT: 3.67 min | LRMS (ESI): (calc) 273.3501 (found) 274.03 (MH)+ |
| 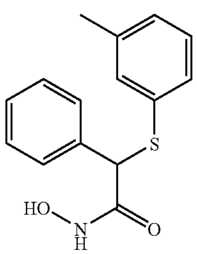 | N-hydroxy-2-phenyl-2-(m-tolylthio)acetamide | 7-56 | 93% RT: 3.7 min | LRMS (ESI): (calc) 273.3501 (found) 274.06 (MH)+ |
| 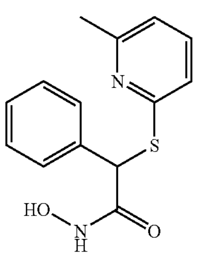 | N-hydroxy-2-(6-methylpyridin-2-ylthio)-2-phenylacetamide | 7-57 | 100% RT: 3.31 min | LRMS (ESI): (calc) 274.3382 (found) 275.01 (MH)+ |

-continued

| Structure | Name | Cpd No. | HPLC | MS |
|---|---|---|---|---|
| | 2-(2-fluorophenylthio)-N-hydroxy-2-phenylacetamide | 7-58 | 97% RT: 3.51 min | LRMS (ESI): (calc) 277.314 (found) 278.03 (MH)+ |
| | 2-(3-fluorophenylthio)-N-hydroxy-2-phenylacetamide | 7-59 | 94% RT: 3.59 min | LRMS (ESI): (calc) 277.314 (found) 278.03 (MH)+ |
| | 2-(2,6-dimethylphenylthio)-N-hydroxy-2-phenylacetamide | 7-60 | 92% RT: 3.88 min | LRMS (ESI): (calc) 287.3767 (found) 288.06 (MH)+ |
| | 2-(3,4-dimethylphenylthio)-N-hydroxy-2-phenylacetamide | 7-61 | 93% RT: 3.87 min | LRMS (ESI): (calc) 287.3767 (found) 288.06 (MH)+ |
| | 2-(3,5-dimethylphenylthio)-N-hydroxy-2-phenylacetamide | 7-62 | 92% RT: 3.91 min | LRMS (ESI): (calc) 287.3767 (found) 288.06 (MH)+ |
| | N-hydroxy-2-(2-methoxyphenylthio)-2-phenylacetamide | 7-63 | 96% RT: 3.47 min | LRMS (ESI): (calc) 289.3495 (found) 290.01 (MH)+ |
| | N-hydroxy-2-(4-methoxyphenylthio)-2-phenylacetamide | 7-64 | 97% RT: 3.52 min | LRMS (ESI): (calc) 289.3495 (found) 290.02 (MH)+ |

| Structure | Name | Cpd No. | HPLC | MS |
| --- | --- | --- | --- | --- |
|  | N-hydroxy-2-(3-methoxyphenylthio)-2-phenylacetamide | 7-65 | 93% RT: 3.56 min | LRMS (ESI): (calc) 289.3495 (found) 290.01 (MH)+ |
| 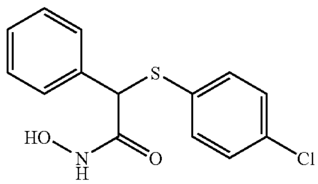 | 2-(4-chlorophenylthio)-N-hydroxy-2-phenylacetamide | 7-66 | 94% RT: 3.79 min | LRMS (ESI): (calc) 293.7686 (found) 293.98 (MH)+ |
| 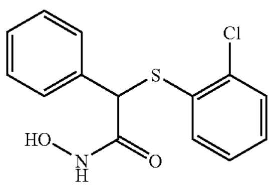 | 2-(2-chlorophenylthio)-N-hydroxy-2-phenylacetamide | 7-67 | 86% RT: 3.68 min | LRMS (ESI): (calc) 293.7686 (found) 293.98 (MH)+ |
| 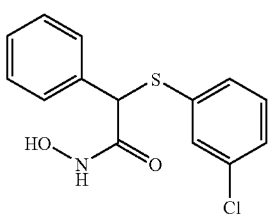 | 2-(3-chlorophenylthio)-N-hydroxy-2-phenylacetamide | 7-68 | 89% RT: 3.79 min | LRMS (ESI): (calc) 293.7686 (found) 293.98 (MH)+ |
|  | N-hydroxy-2-(2-isopropylphenylthio)-2-phenylacetamide | 7-69 | 100% RT: 4.06 min | LRMS (ESI): (calc) 301.4033 (found) 302.05 (MH)+ 1H NMR (360 MHz, DMSO-d6) d ppm 10.90 (1H, br. s.), 9.04-9.07 (1H, m), 7.39-7.45 (2H, m), 7.18-7.34 (6H, m), 7.07-7.13 (1H, m), 4.73 (1H, s), 3.35-3.44 (1H, m), 1.14 (3H, d, J = 6.81 Hz), 1.01 (3H, d, J = 6.81 Hz) |
| 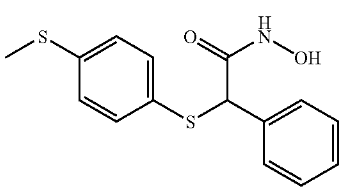 | N-hydroxy-2-(4-methylthio)phenylthio)-2-phenylacetamide | 7-70 | 87% RT: 3.76 min | LRMS (ESI): (calc) 305.4151 (found) 306.02 (MH)+ |
| 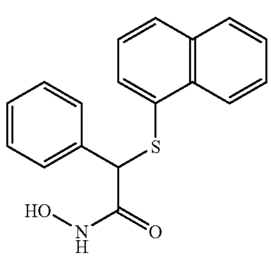 [SMILES: O=C(NO)C(Sc1cccc2ccccc12)c1ccccc1] | N-hydroxy-2-naphthalen-1-ylthio)-2-phenylacetamide | 7-71 | 100% RT: 3.94 min | LRMS (ESI): (calc) 309.3822 (found) 310.05 (MH)+ 1H NMR (360 MHz, DMSO-d6) d ppm 10.90 (1H, br. s.), 9.08 (1H, br. s.), 8.33 (1H, d, J = 8.17 Hz), 7.92-7.99 (1H, m), 7.87 (1H, d, J = 8.17 Hz), 7.54-7.66 (2H, m), 7.37-7.54 (4H, m), 7.22-7.36 (3H, m), 4.87 (1H, s) |

-continued

| Structure | Name | Cpd No. | HPLC | MS |
|---|---|---|---|---|
| 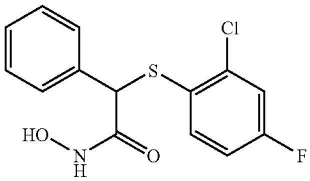 | 2-(2-chloro-4-fluorophenylthio)-N-hydroxy-2-phenylacetamide | 7-72 | 90% RT: 3.77 min | LRMS (ESI): (calc) 311.759 (found) 312 (MH)+ |
| 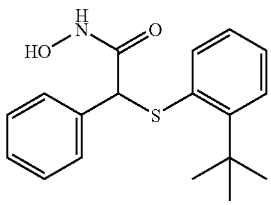 [SMILES: CC(C)(C)c1ccccc1SC(C(=O)NO)c1ccccc1] | 2-(2-tert-butylphenylthio)-N-hydroxy-2-phenylacetamide | 7-73 | 100% RT: 4.19 min | LRMS (ESI): (calc) 315.4298 (found) 316.1 (MH)+ |
| 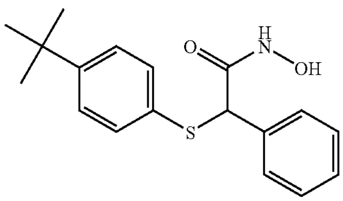 | 2-(4-tert butylphenylthio)-N-hydroxy-2-phenylacetamide | 7-74 | 90% RT: 4.27 min | LRMS (ESI): (calc) 315.4298 (found) 316.1 (MH)+ |
| 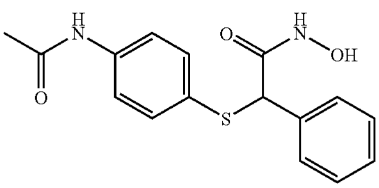 [SMILES: CC(=O)Nc1ccc(SC(C(=O)NO)c2ccccc2)cc1] | 2-(4-acetamidophenylthio)-N-hydroxy-2-phenylacetamide | 7-75 | 96% RT: 3.08 min | LRMS (ESI): (calc) 316.3748 (found) 317.05 (MH)+ 1H NMR (360 MHz, DMSO-d6) d ppm 10.87 (1H, br. s.), 10.01 (1H, br. s.), 9.05 (1H, br. s.), 7.47-7.52 (2H, m), 7.40-7.46 (2H, m), 7.20-7.34 (5H, m), 4.72-4.78 (1H, m), 2.02 (3H, s) |
| 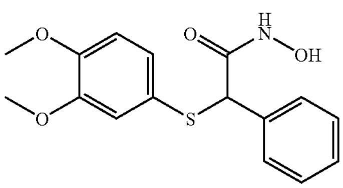 | 2-(3,4-dimethoxyphenylthio)-N-hydroxy-2-phenylacetamide | 7-76 | 94% RT: 3.38 min | LRMS (ESI): (calc) 319.3755 (found) 320.07 (MH)+ |
| 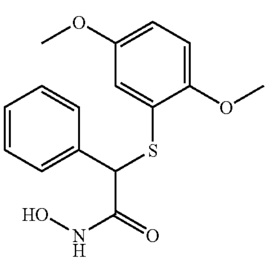 [SMILES: COc1ccc(OC)c(SC(C(=O)NO)c2ccccc2)c1] | 2-(2,5-dimethoxyphenylthio)-N-hydroxy-2-phenylacetamide | 7-78 | 92% RT: 3.51 min | LRMS (ESI): (calc) 319.3755 (found) 320.07 (MH)+ |
| 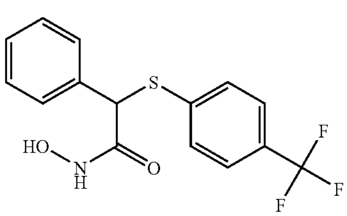 | N-hydroxy-2-phenyl-2-(4-(trifluoromethyl)phenylthio)acetamide | 7-79 | 95% RT: 3.94 min | LRMS (ESI): (calc) 327.3215 (found) 328.07 (MH)+ |

-continued

| Structure | Name | Cpd No. | HPLC | MS |
|---|---|---|---|---|
| 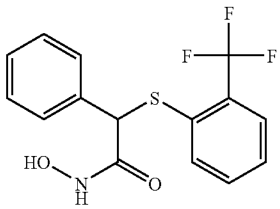 | N-hydroxy-2-phenyl-2-(2-(trifluoromethyl)phenylthio)acetamide | 7-80 | 93% RT: 3.82 min | LRMS (ESI): (calc) 327.3215 (found) 328.07 (MH)+ |
| 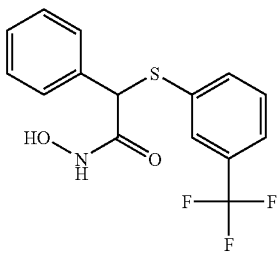 | N-hydroxy-2-phenyl-2-(3-(trifluoromethyl)phenylthio acetamide | 7-81 | 94% RT: 3.93 min | LRMS (ESI): (calc) 327.3215 (found) 328.04 (MH)+ |
| 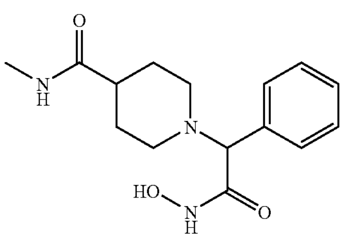 [SMILES: CNC(=O)C1CCN(C(C(=O)NO)c2ccccc2)CC1] | 1-(2-hydroxyamino)-2-oxo-1-phenylethyl)-N-methylpiperidine-4-carboxamide | 7-82 | 98.41% RT: 1.07 min | LRMS (ESI): (calc) 291.3456 (found) 292.15 (MH)+ 1H NMR (250 MHz, DMSO-d6) d ppm 11.09 (1H, br. s.), 9.04 (1H, br. s.) 7.79 (1H, d, J = 4.42 Hz), 7.20-7.62 (5H, m), 3.95 (1H, br. s.), 2.87-3.15 (1H, m), 2.59-2.77 (1H, m), 2.54 (3H, d, J = 4.57 Hz), 1.89-2.40 (3H, m), 1.36-1.89 (4H, m) |
| 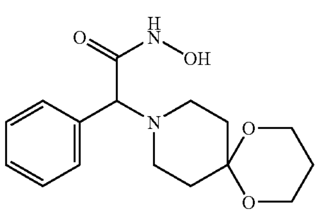 [SMILES: O=C(NO)C(c1ccccc1)N1CCC2(CC1)OCCCO2] | N-hydroxy-2-phenyl-2-(1,5-dioxa-9-azaspiro[5.5]undecan-9-yl)acetamide | 7-83 | 87.56% RT: 1.99 min | LRMS (ESI): (calc) 306.3569 (found) 307.15 (MH)+ $^1$H NMR (250 MHz, DMSO-$d_6$) d ppm 10.84 (1H, br. s.), 8.92 (1H, br. s.) 7.13-7.58 (5H, m), 3.60-3.95 (5H, m), 2.14-2.45 (4H, m), 1.67-1.97 (4H, m), 1.44-1.65 (2H, m) |
| 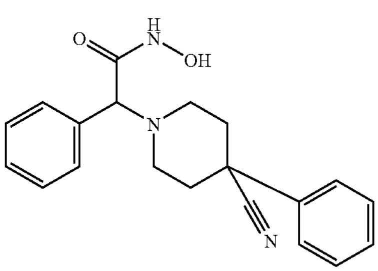 [SMILES: N#CC1(c2ccccc2)CCN(C(C(=O)NO)c2ccccc2)CC1] | 2-(4-cyano-4-phenylpiperidin-1-yl)-N-hydroxy-2-phenylacetamide | 7-22 | 100% RT: 3 min | LRMS (ESI): (calc) 335.3996 (found) 336.14 (MH)+ |
| 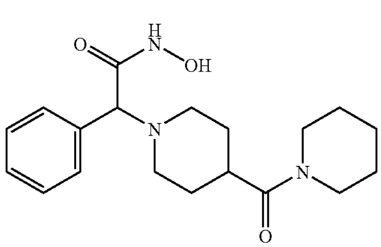 [SMILES: O=C(NO)C(c1ccccc1)N1CCC(C(=O)N2CCCCC2)CC1] | N-hydroxy-2-phenyl-2-(4-(piperidine-1-carbonyl)piperidin-1-yl)acetamide | 7-84 | 88.5% RT: 2.4 min | LRMS (ESI): (calc) 345.436 (found) 346.22 (MH)+ |

| Structure | Name | Cpd No. | HPLC | MS |
|---|---|---|---|---|
| 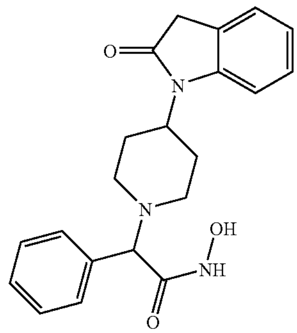 [SMILES: O=C(NO)C(c1ccccc1)N1CCC(N2C(=O)Cc3ccccc32)CC1] | N-hydroxy-2-(4-(2-oxoindolin-1-yl)piperidin-1-yl)-2-phenylacetamide | 7-85 | 92.16% RT: 2.71 min | LRMS (ESI): (calc) 365.4256 (found) 366.13 (MH)+ |
| 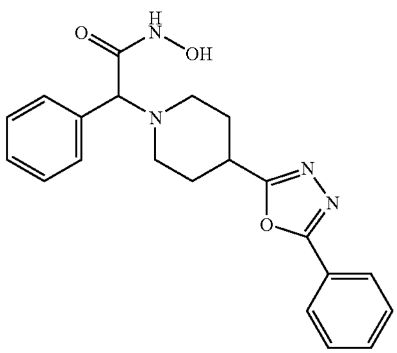 [SMILES: O=C(NO)C(c1ccccc1)N1CCC(c2nnc(-c3ccccc3)o2)CC1] | N-hydroxy-2-phenyl-2-(4-(5-phenyl-1,3,4-oxadiazol-2-yl)piperidin-1-yl)acetamide | 7-86 | 86.72% RT: 2.74 min | LRMS (ESI): (calc) 378.4244 (found) 379.17 (MH)+ 1H NMR (250 MHz, DMSO-d6) d ppm 10.86 (1H, br. s.), 8.92 (1H, br. s.), 7.88-8.09 (2H, m), 7.51-7.70 (3H, m), 7.40-7.50 (2H, m), 7.21-7.39 (3H, m), 3.70 (1H, s), 2.98-3.14 (1H, m), 2.83-2.98 (1H, m), 2.59-2.74 (1H, m), 2.15-2.32 (1H, m), 1.67-2.14 (5H, m) |
| 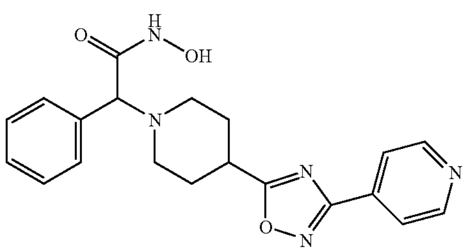 [SMILES: O=C(NO)C(c1ccccc1)N1CCC(c2nc(-c3ccncc3)no2)CC1] | N-hydroxy-2-phenyl-2-(4-(3-(pyridin-4-yl)-1,2,4-oxadiazol-5-yl)piperidin-1-yl)acetamide | 7-87 | 88.54% RT: 2.36 min | LRMS (ESI): (calc) 379.4124 (found) 380.14 (MH)+ |
| 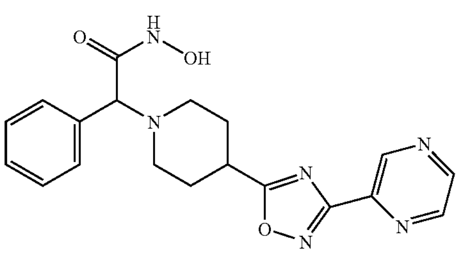 [SMILES: O=C(NO)C(c1ccccc1)N1CCC(c2nc(-c3cnccn3)no2)CC1] | N-hydroxy-2-phenyl-2-(4-(3-pyrazin-2-yl)-1,2,4-oxadiazol-5-yl)piperidin-1-yl)acetamide | 7-88 | 86.96% RT: 2.36 min | LRMS (ESI): (calc) 380.4005 (found) 381.12 (MH)+ 1H NMR (250 MHz, DMSO-d6) d ppm 10.90 (1H, br. s.), 9.23 (1H, d, J = 1.37 Hz), 8.88-9.11 (1H, m), 8.74-9.11 (2H, m), 7.40-7.59 (3H, m), 7.19-7.42 (2H, m), 3.66-3.86 (1H, m), 3.07-3.27 (1H, m), 2.84-3.03 (1H, m), 2.60-2.79 (1H, m), 1.67-2.39 (6H, m) |
| 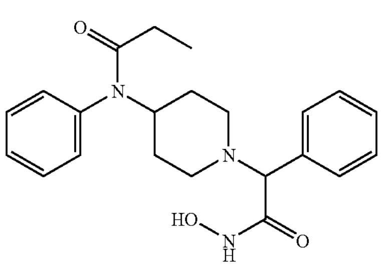 [SMILES: CCC(=O)N(c1ccccc1)C1CCN(C(C(=O)NO)c2ccccc2)CC1] | N-(1-(2-hydroxyamino)-2-oxo-1-phenylethyl)piperidin-4-yl)-N-phenylpropionamide | 7-89 | 97.35% RT: 2.79 min | LRMS (ESI): (calc) 381.4681 (found) 382.19 (MH)+ 1H NMR (250 MHz, DMSO-d6) d ppm 10.03-11.33 (1H, m), 8.18-9.50 (1H, m), 7.37-7.55 (3H, m), 7.10-7.37 (7H, m), 4.44 (1H, t, J = 11.95 Hz), 3.56 (1H, s), 2.79-3.03 (1H, m), 2.52-2.61 (1H, m), 1.97-2.17 (1H, m), 1.51-1.88 (5H, m), 1.00-1.40 (2H, m), 0.86 (3H, t, J = 7.39 Hz) |

-continued

| Structure | Name | Cpd No. | HPLC | MS |
|---|---|---|---|---|
|  | N-hydroxy-2-phenyl-2-(4-(3-(thiophen-2-yl)-1,2,4-oxadiazol-5-yl)piperidin-1-yl)acetamide | 7-90 | 98.42% RT: 2.89 min | LRMS (ESI): (calc) 384.4521 (found) 385.09 (MH)+ |
| 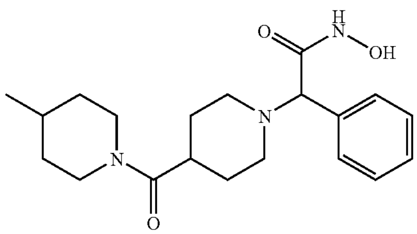 [SMILES: CC1CCN(C(=O)C2CCN(C(C(=O)NO)c3ccccc3)CC2)CC1] | N-hydroxy-2-(4-(4-methylpiperidine-1-carbonyl)piperidin-1-yl)-2-phenylacetamide | 7-91 | 97.92% RT: 2.65 min | LRMS (ESI): (calc) 359.4626 (found) 360.2 (MH)+ |
|  | N-hydroxy-2-(1-methyl-1H-imidazol-2-ylthio)-2-phenylacetamide | 7-92 | 85% RT: 1.83 min | LRMS (ESI): (calc) 263.3155 (found) 363.99 (MH)+ 1H NMR (360 MHz, DMSO-d6) d ppm 11.00 (1H, s), 9.10 (1H, s), 7.22-7.40 (5H, m), 7.19 (1H, d, J = 1.36 Hz), 6.97 (1H, d, J = 0.91 Hz,), 4.98 (1H, s), 3.36 (3H, s) |
| 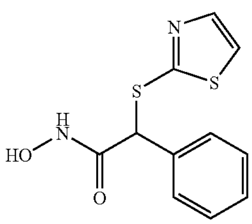 [SMILES: O=C(NO)C(Sc1nccs1)c1ccccc1] | N-hydroxy-2-phenyl-2-(thiazol-2-ylthio)acetamide | 7-93 | 99% RT: 3.09 min | LRMS (ESI): (calc) 266.3393 (found) 266.94 (MH)+ |
| 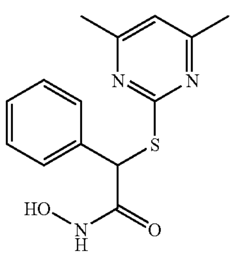 [SMILES: Cc1cc(C)nc(SC(C(=O)NO)c2ccccc2)n1] | 2-(4,6-dimethylpyrimidin-2-ylthio)-N-hydroxy-2-phenylacetamide | 7-94 | 96% RT: 3.22 min | LRMS (ESI): (calc) 389.3528 (found) 290.07 (MH)+ |
| 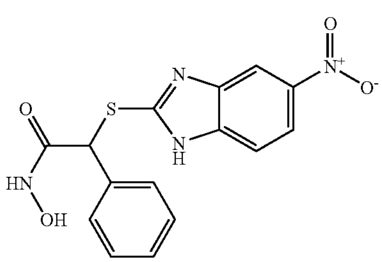 [SMILES: O=C(NO)C(Sc1nc2cc([N+](=O)[O-])ccc2[nH]1)c1ccccc1] | N-hydroxy-2-(5-nitro-1H-benzo[d]imidazol-2-ylthio)-2-phenylacetamide | 7-95 | 96% RT: 3.4 min | LRMS (ESI): (calc) 344.3452 (found) 345.02 (MH)+ |

-continued

| Structure | Name | Cpd No. | HPLC | MS |
|---|---|---|---|---|
| 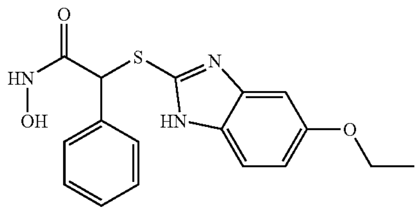 [SMILES: CCOc1ccc2[nH]c(SC(C(=O)NO)c3ccccc3)nc2c1] | 2-(5-ethoxy-1H-benzo[d]imidazol-2-ylthio)-N-hydroxy-2-phenylacetamide | 7-96 | 92% RT: 3.06 min | LRMS (ESI): (calc) 343.4002 (found) 344.11 (MH)+ |

TABLE VIII

Compounds prepared according general Schemes above

| Cpd # | Name | Characterization |
|---|---|---|
| 8-1 | N-hydroxy-2-(3-(4-methylpentyloxy)phenyl)-2-phenylacetamide | LRMS (ESI): (calc.) 327.4174, (found) 328 [M + H], HPLC (215 nM): 100%, RT 4.54 min. |
| 8-2 | N-hydroxy-2-phenyl-2-(3-(pyrrolidin-1-yl)phenyl)acetamide | LRMS (ESI): (calc.) 296.3636, (found) 297 [M + H], HPLC (215 nM): 92%, RT 3.59 min. |
| 8-3 | 2-(3-(butylamino)phenyl)-N-hydroxy-2-phenylacetamide | LRMS (ESI): (calc.) 298.37948, (found) 299 [M + H], HPLC (215 nM): 90% , RT 3.14 min. |
| 8-4 | 2-(3-(tert-butylamino)phenyl)-N-hydroxy-2-phenylacetamide | LRMS (ESI): (calc.) 298.37948, (found) 299 [M + H], HPLC (215 nM): 89% RT 2.53 min. |
| 8-5 | N-hydroxy-2-(3-(2-methoxyethylamino)phenyl)-2-phenylacetamide | LRMS (ESI): (calc.) 300.3523, (found) 301 [M + H], HPLC (215 nM): 96%, RT 2.93 min. |
| 8-6 | N-hydroxy-2-phenyl-2-(3-(piperidin-1-yl)phenyl)acetamide | LRMS (ESI): (calc.) 310.39018, (found) 311 [M + H], HPLC (215 nM): 96%, RT 2.52 min. |
| 8-7 | 2-(3-(cyclopentylamino)phenyl)-N-hydroxy-2-phenylacetamide | LRMS (ESI): (calc.) 310.39018, (found) 311 [M + H], HPLC (215 nM): 94%, RT 3 min. 1H NMR (250 MHz, MeOD) d ppm 7.16-7.46 (5H, m), 6.95-7.14 (1H, m), 6.43-6.72 (3H, m), 4.69 (1H, s), 3.56-3.82 (1H, m), 1.83-2.05 (2H, m), 1.53-1.79 (4H, m), 1.37-1.52 (2H, m) |
| 8-8 | 2-(3-(ethyl(propyl)amino)phenyl)-N-hydroxy-2-phenylacetamide | LRMS (ESI): (calc.) 312.40606, (found) 313 [M + H], HPLC (215 nM): 92%, RT 2.68 min. 1H NMR (250 MHz, MeOD) d ppm 7.20-7.42 (5H, m), 6.98-7.20 (1H, m), 6.50-6.77 (3H, m), 4.71 (1H, s), 3.33-3.43 (2H, m), 3.15-3.26 (2H, m), 1.46-1.66 (2H, m), 1.08 (3H, t), 0.89 (3H, t) |
| 8-9 | N-hydroxy-2-(3-(3-methoxypropylamino)phenyl)-2-phenylacetamide | LRMS (ESI): (calc.) 314.37888, (found) 315 [M + H], HPLC (215 nM): 91%, RT 2.84 min. |
| 8-10 | N-hydroxy-2-(3-(2-(methylthio)ethylamino)phenyl)-2-phenylacetamide | LRMS (ESI): (calc.) 316.4179, (found) 317 [M + H], HPLC (215 nM): 100%, RT 3.41 min. |
| 8-11 | 2-(3-(furan-2-ylmethylamino)phenyl)-N-hydroxy-2-phenylacetamide | LRMS (ESI): (calc.) 322.35782, (found) 323 [M + H], HPLC (215 nM): 89%, RT 3.53 min. |
| 8-12 | 2-(3-(cyclohexylamino)phenyl)-N-hydroxy-2-phenylacetamide | LRMS (ESI): (calc.) 324.41676, (found) 325 [M + H], HPLC (215 nM): 92%, RT 3.04 min. |
| 8-13 | N-hydroxy-2-(3-(4-methylpiperazin-1-yl)phenyl)-2-phenylacetamide | LRMS (ESI): (calc.) 325.40482, (found) 326 [M + H], HPLC (215 nM): 92%, RT 2.43 min. |
| 8-14 | N-hydroxy-2-phenyl-2-(3-(tetrahydro-2H-pyran-4-ylamino)phenyl)acetamide | LRMS (ESI): (calc.) 326.38958, (found) 327 [M + H], HPLC (215 nM): 90%, RT 2.77 min. |
| 8-15 | N-hydroxy-2-phenyl-2-(3-((tetrahydrofuran-2-yl)methylamino)phenyl)acetamide | LRMS (ESI): (calc.) 326.38958, (found) 327 [M + H], HPLC (215 nM): 100%, RT 3.23 min. |
| 8-16 | N-hydroxy-2-phenyl-2-(3-thiomorpholino)phenyl)acetamide | LRMS (ESI): (calc.) 328.4286, (found) 329 [M + H], HPLC (215 nM): 96%, RT 3.46 min. |
| 8-17 | 2-(3-(2-(1H-pyrrol-1-yl)ethylamino)phenyl)-N-hydroxy-2-phenylacetamide | LRMS (ESI): (calc.) 335.39964, (found) 336 [M + H], HPLC (215 nM): 89%, RT 3.68 min. |
| 8-18 | N-hydroxy-2-phenyl-2-(3-(thiophen-2-ylmethylamino)phenyl)acetamide | LRMS (ESI): (calc.) 338.42342, (found) 339 [M + H], HPLC (215 nM): 93%, RT 3.71 min. |
| 8-19 | 2-(3-(cyclohexyl(methyl)amino)phenyl)- | LRMS (ESI): (calc.) 338.44334, (found) 339 [M + H], HPLC (215 nM): 93%, RT 2.86 min. |

TABLE VIII-continued

Compounds prepared according general Schemes above

| Cpd # | Name | Characterization |
|---|---|---|
| 8-20 | N-hydroxy-2-phenylacetamide N-hydroxy-2-phenyl-2-(3-(2-(pyrrolidin-1-yl)ethylamino)phenyl)acetamide | LRMS (ESI): (calc.) 339.4314, (found) 340 [M + H], HPLC (215 nM): 99%, RT 2.53 min. |
| 8-21 | 2-(3-(4-ethylpiperazin-1-yl)phenyl)-N-hydroxy-2-phenylacetamide | LRMS (ESI): (calc.) 339.4314, (found) 340 [M + H], HPLC (215 nM): 88%, RT 2.51 min. |
| 8-22 | 2-(3-(3-(dimethylamino)pyrrolidin-1-yl)phenyl)-N-hydroxy-2-phenylacetamide | LRMS (ESI): (calc.) 339.4314, (found) 340 [M + H], HPLC (215 nM): 85%, RT 2.59 min. |
| 8-23 | N-hydroxy-2-(3-(4-(hydroxymethyl)piperidin-1-yl)phenyl)-2-phenylacetamide | LRMS (ESI): (calc.) 340.41616, (found) 341 [M + H], HPLC (215 nM): 95%, RT 2.36 min. 1H NMR (250 MHz, MeOD) d ppm 7.12-7.38 (6H, m), 6.95-7.04 (1H, m), 6.85-6.94 (1H, m), 6.79 (1H, d, J = 7.31 Hz), 4.73 (1H, s), 3.52-3.73 (2H, m), 3.43 (2H, d, J = 6.40 Hz), 2.58-2.73 (2H, m), 1.74-1.88 (2H, m), 1.48-1.69 (1H, m), 1.23-1.39 (2H, m) |
| 8-24 | 2-(3-(2,6-dimethylmorpholino)phenyl)-N-hydroxy-2-phenylacetamide | LRMS (ESI): (calc.) 340.41616, (found) 341 [M + H], HPLC (215 nM): 92%, RT 3.55 min. |
| 8-25 | N-hydroxy-2-(3-(isoindolin-2-yl)phenyl)-2-phenylacetamide | LRMS (ESI): (calc.) 344.4064, (found) 345 [M + H], HPLC (215 nM): 93%, RT 4.23 min. |
| 8-26 | 2-(3-(benzyl(methyl)amino)phenyl)-N-hydroxy-2-phenylacetamide | LRMS (ESI): (calc.) 346.42228, (found) 347 [M + H], HPLC (215 nM): 91%, RT 3.88 min. |
| 8-27 | N-hydroxy-2-phenyl-2-(3-(2-(pyridin-2-yl)ethylamino)phenyl)acetamide | LRMS (ESI): (calc.) 347.41034, (found) 348 [M + H], HPLC (215 nM): 94%, RT 2.56 min. 1H NMR (250 MHz, MeOD) d ppm 8.43 (1H, d, J = 5.18 Hz), 7.66-7.76 (1H, m), 7.19-7.35 (7H, m), 7.00-7.09 (1H, m), 6.49-6.65 (3H, m), 4.69 (1H, s), 3.40 (2H, t, J = 7.16 Hz), 3.00 (2H, t, J = 7.16 Hz) |
| 8-28 | N-hydroxy-2-(3-(methyl(pyridin-3-ylmethyl)amino)phenyl)-2-phenylacetamide | LRMS (ESI): (calc.) 347.41034, (found) 348 [M + H], HPLC (215 nM): 94%, RT 2.71 min. |
| 8-29 | N-hydroxy-2-phenyl-2-(3-(2-(pyridin-3-yl)ethylamino)phenyl)acetamide | LRMS (ESI): (calc.) 347.41034, (found) 348 [M + H], HPLC (215 nM): 87%, RT 2.58 min. |
| 8-30 | N-hydroxy-2-phenyl-2-(3-(2-(pyridin-4-yl)ethylamino)phenyl)acetamide | LRMS (ESI): (calc.) 347.41034, (found) 348 [M + H], HPLC (215 nM): 99%, RT 2.55 min. |
| 8-31 | N-hydroxy-2-(3-(4-methoxyphenylamino)phenyl)-2-phenylacetamide | LRMS (ESI): (calc.) 348.3951, (found) 349 [M + H], HPLC (215 nM): 93%, RT 3.82 min. |
| 8-32 | 2-(3-(3-(1H-imidazol-1-yl)propylamino)phenyl)-N-hydroxy-2-phenylacetamide | LRMS (ESI): (calc.) 350.41428, (found) 351 [M + H], HPLC (215 nM): 98%, RT 2.47 min. |
| 8-33 | N-hydroxy-2-phenyl-2-(3-(2-(thiophen-2-yl)ethylamino)phenyl)acetamide | LRMS (ESI): (calc.) 352.45, (found) 353 [M + H], HPLC (215 nM): 92%, RT 3.85 min. |
| 8-34 | 2-(3-(3-acetamidopyrrolidin-1-yl)phenyl)-N-hydroxy-2-phenylacetamide | LRMS (ESI): (calc.) 353.41492, (found) 354 [M + H], HPLC (215 nM): 97%, RT 3.19 min. 1H NMR (250 MHz, MeOD) d ppm 7.17-7.37 (5H, m), 7.04-7.16 (1H, m), 6.52-6.66 (2H, m), 6.40-6.51 (1H, m), 4.72 (1H, s), 4.29-4.52 (1H, m), 3.36-3.55 (2H, m), 3.18-3.28 (1H, m), 3.03-3.14 (1H, m), 2.14-2.31 (1H, m), 1.83-2.04 (4H, m) |
| 8-35 | N-hydroxy-2-phenyl-2-(3-(2-(piperidin-1-yl)ethylamino)phenyl)acetamide | LRMS (ESI): (calc.) 353.45798, (found) 354 [M + H], HPLC (215 nM): 98%, RT 2.6 min. |
| 8-36 | 2-(3-(3,4-dihydroisoquinolin-2(1H)-yl)phenyl)-N-hydroxy-2-phenylacetamide | LRMS (ESI): (calc.) 358.43298, (found) 359 [M + H], HPLC (215 nM): 95%, RT 3.98 min. |
| 8-37 | N-hydroxy-2-(3-(methyl(2-(pyridin-2-yl)ethyl)amino)phenyl)-2-phenylacetamide | LRMS (ESI): (calc.) 361.43692, (found) 362 [M + H], HPLC (215 nM): 92%, RT 2.72 min. |
| 8-38 | N-hydroxy-2-(3-(2-phenoxyethylamino)phenyl)-2-phenylacetamide | LRMS (ESI): (calc.) 362.42168, (found) 363 [M + H], HPLC (215 nM): 89%, RT 3.9 min. |
| 8-39 | 2-(3-(4-chlorobenzylamino)phenyl)-N-hydroxy-2-phenylacetamide | LRMS (ESI): (calc.) 366.84076, (found) 367 [M + H], HPLC (215 nM): 87%, RT 4.05 min. |

TABLE VIII-continued

Compounds prepared according general Schemes above

| Cpd # | Name | Characterization |
|---|---|---|
| 8-40 | 2-(3-(4-acetyl-1,4-diazepan-1-yl)phenyl)-N-hydroxy-2-phenylacetamide | LRMS (ESI): (calc.) 367.4415, (found) 368 [M + H], HPLC (215 nM): 95%, RT 3.21 min. |
| 8-41 | N-hydroxy-2-(3-(3-(2-oxopyrrolidin-1-yl)propylamino)phenyl)-2-phenylacetamide | LRMS (ESI): (calc.) 367.4415, (found) 368 [M + H], HPLC (215 nM): 94%, RT 2.82 min. |
| 8-42 | 2-(3-(4-butylpiperazin-1-yl)phenyl)-N-hydroxy-2-phenylacetamide | LRMS (ESI): (calc.) 367.48456, (found) 368 [M + H], HPLC (215 nM): 94%, RT 2.75 min. |
| 8-43 | N-hydroxy-2-(3-(4-(2-methoxyethyl)piperazin-1-yl)phenyl)-2-phenylacetamide | LRMS (ESI): (calc.) 369.45738, (found) 370 [M + H], HPLC (215 nM): 93%, RT 2.56 min. |
| 8-44 | N-hydroxy-2-(3-(3-morpholinopropylamino)phenyl)-2-phenylacetamide | LRMS (ESI): (calc.) 369.45738, (found) 370 [M + H], HPLC (215 nM): 93%, RT 2.44 min. |
| 8-45 | N-hydroxy-2-phenyl-2-(3-(4-(trifluoromethyl)piperidin-1-yl)phenyl)acetamide | LRMS (ESI): (calc.) 378.3881496, (found) 379 [M + H], HPLC (215 nM): 93%, RT 3.84 min. |
| 8-46 | N-hydroxy-2-phenyl-2-(3-(4-(pyridin-4-yl)piperazin-1-yl)phenyl)acetamide | LRMS (ESI): (calc.) 388.46226, (found) 389 [M + H], HPLC (215 nM): 97%, RT 2.76 min. |
| 8-47 | N-hydroxy-2-phenyl-2-(3-(4-(pyridin-2-yl)piperazin-1-yl)phenyl)acetamide | LRMS (ESI): (calc.) 388.46226, (found) 389 [M + H], HPLC (215 nM): 92%, RT 2.78 min. |
| 8-48 | N-hydroxy-2-phenyl-2-(3-(4-(pyrazin-2-yl)piperazin-1-yl)phenyl)acetamide | LRMS (ESI): (calc.) 389.45032, (found) 390 [M + H], HPLC (215 nM): 88%, RT 3.48 min. |
| 8-49 | 2-(3-(1,4'-bipiperidin-1'-yl)phenyl)-N-hydroxy-2-phenylacetamide | LRMS (ESI): (calc.) 393.52184, (found) 394 [M + H], HPLC (215 nM): 87%, RT 2.65 min. |
| 8-50 | 2-(3-(4-benzylpiperazin-1-yl)phenyl)-N-hydroxy-2-phenylacetamide | LRMS (ESI): (calc.) 401.50078, (found) 402 [M + H], HPLC (215 nM): 86%, RT 2.87 min. |
| 8-51 | N-hydroxy-2-(3-(4-(4-methoxyphenyl)piperazin-1-yl)phenyl)-2-phenylacetamide | LRMS (ESI): (calc.) 417.50018, (found) 418 [M + H], HPLC (215 nM): 100%, RT 3.45 min. |
| 8-52 | N-hydroxy-2-(3-(4-(2-morpholinoethyl)piperazin-1-yl)phenyl)-2-phenylacetamide | LRMS (ESI): (calc.) 424.53588, (found) 425 [M + H], HPLC (215 nM): 95%, RT 2.33 min. |
| 8-53 | 2-(4-(allylamino)phenyl)-N-hydroxy-2-phenylacetamide | LRMS (ESI): (calc.) 282.3, (found) 283 [M + H], HPLC (215 nM): 96%, RT 3.02 min |
| 8-54 | 2-(4-(2,5-dihydro-1H-pyrrol-1-yl)phenyl)-N-hydroxy-2-phenylacetamide | LRMS (ESI): (calc.) 294.34772, (found) 295 [M + H], HPLC (215 nM): 94%, RT 3.78 min. |
| 8-55 | 2-(4-(butylamino)phenyl)-N-hydroxy-2-phenylacetamide | LRMS (ESI): (calc.) 298.37948, (found) 299 [M + H], HPLC (215 nM): 93%, RT 3.04 min. |
| 8-56 | 2-(4-(tert-butylamino)phenyl)-N-hydroxy-2-phenylacetamide | LRMS (ESI): (calc.) 298.37948, (found) 299 [M + H], HPLC (215 nM): 97%, RT 2.47 min. 1H NMR (250 MHz, MeOD) d ppm 7.22-7.37 (5H, m), 7.18 (2H, d, J = 8.22 Hz), 6.91 (2H, d, J = 8.53 Hz), 4.71 (1H, s), 1.28 (9H, s) |
| 8-57 | N-hydroxy-2-(4-(2-methoxyethylamino)phenyl)-2-phenylacetamide | LRMS (ESI): (calc.) 300.3523, (found) 301 [M + H], HPLC (215 nM): 97%, RT 2.84 min. |
| 8-58 | 2-(4-(cyclopentylamino)phenyl)-N-hydroxy-2-phenylacetamide | LRMS (ESI): (calc.) 310.39018, (found) 311 [M + H], HPLC (215 nM): 96%, RT 2.9 min. |
| 8-59 | N-hydroxy-2-(4-(pentan-3-ylamino)phenyl)-2-phenylacetamide | LRMS (ESI): (calc.) 312.40606, (found) 313 [M + H], HPLC (215 nM): 96%, RT 3.35 min. |
| 8-60 | 2-(4-(ethyl(propyl)amino)phenyl)-N-hydroxy-2-phenylacetamide | LRMS (ESI): (calc.) 312.40606, (found) 313 [M + H], HPLC (215 nM): 97%, RT 2.63 min. |
| 8-61 | N-hydroxy-2-(4-(3-methoxypropylamino)phenyl)-2-phenylacetamide | LRMS (ESI): (calc.) 314.37888, (found) 315 [M + H], HPLC (215 nM): 94%, RT 2.75 min. |
| 8-62 | N-hydroxy-2-(4-(2-(methylthio)ethylamino)phenyl)-2-phenylacetamide | LRMS (ESI): (calc.) 316.4179, (found) 317 [M + H], HPLC (215 nM): 100%, RT 3.34 min. |

TABLE VIII-continued

Compounds prepared according general Schemes above

| Cpd # | Name | Characterization |
|---|---|---|
| 8-63 | N-hydroxy-2-(4-(methylamino)phenyl)-2-phenylacetamide | LRMS (ESI): (calc.) 256.29974, (found) 257 [M + H], HPLC (215 nM): 98%, RT 2.27 min. |
| 8-64 | 2-(4-(furan-2-ylmethylamino)phenyl)-N-hydroxy-2-phenylacetamide | LRMS (ESI): (calc.) 322.35782, (found) 323 [M + H], HPLC (215 nM): 94%, RT 3.51 min. |
| 8-65 | N-hydroxy-2-(4-(4-methylpiperidin-1-yl)phenyl)-2-phenylacetamide | LRMS (ESI): (calc.) 324.41676, (found) 325 [M + H], HPLC (215 nM): 88%, RT 2.75 min. |
| 8-66 | 2-(4-(azepan-1-yl)phenyl)-N-hydroxy-2-phenylacetamide | LRMS (ESI): (calc.) 324.41676, (found) 325 [M + H], HPLC (215 nM): 96%, RT 3.78 min. |
| 8-67 | 2-(4-(cyclohexylamino)phenyl)-N-hydroxy-2-phenylacetamide | LRMS (ESI): (calc.) 324.41676, (found) 325 [M + H], HPLC (215 nM): 95%, RT 2.98 min. |
| 8-68 | N-hydroxy-2-(4-(4-methylpiperazin-1-yl)phenyl)-2-phenylacetamide | LRMS (ESI): (calc.) 325.40482, (found) 326 [M + H], HPLC (215 nM): 96%, RT 2.36 min. |
| 8-69 | N-hydroxy-2-phenyl-2-(4-(tetrahydro-2H-pyran-4-ylamino)phenyl)acetamide | LRMS (ESI): (calc.) 326.38958, (found) 327 [M + H], HPLC (215 nM): 96%, RT 2.66 min. |
| 8-70 | N-hydroxy-2-phenyl-2-(4-((tetrahydrofuran-2-yl)methylamino)phenyl)acetamide | LRMS (ESI): (calc.) 326.38958, (found) 327 [M + H], HPLC (215 nM): 96%, RT 3.15 min. |
| 8-71 | N-hydroxy-2-(4-(4-hydroxypiperidin-1-yl)phenyl)-2-phenylacetamide | LRMS (ESI): (calc.) 326.38958, (found) 327 [M + H], HPLC (215 nM): 100%, RT 2.27 min. |
| 8-72 | 2-(4-(2-(1H-pyrrol-1-yl)ethylamino)phenyl)-N-hydroxy-2-phenylacetamide | LRMS (ESI): (calc.) 335.39964, (found) 336 [M + H], HPLC (215 nM): 94%, RT 3.65 min. |
| 8-73 | N-hydroxy-2-phenyl-2-(4-(thiophen-2-ylmethylamino)phenyl)acetamide | LRMS (ESI): (calc.) 338.42342, (found) 339 [M + H], HPLC (215 nM): 94%, RT 3.7 min. 1H NMR (250 MHz, MeOD) d ppm 7.15-7.33 (6H, m), 7.05 (2H, m), 6.95-7.01 (1H, m), 6.87-6.94 (1H, m), 6.62 (2H, m), 4.65 (1H, s), 4.45 (2H, s) |
| 8-74 | 2-(4-(cyclohexyl(methyl)amino)phenyl)-N-hydroxy-2-phenylacetamide | LRMS (ESI): (calc.) 338.44334, (found) 339 [M + H], HPLC (215 nM): 96%, RT 2.86 min. |
| 8-75 | 2-(4-((cyclopropylmethyl)(propyl)amino)phenyl)-N-hydroxy-2-phenylacetamide | LRMS (ESI): (calc.) 338.44334, (found) 339 [M + H], HPLC (215 nM): 97%, RT 2.87 min. |
| 8-76 | N-hydroxy-2-(4-(4-methyl-1,4-diazepan-1-yl)phenyl)-2-phenylacetamide | LRMS (ESI): (calc.) 339.4314, (found) 340 [M + H], HPLC (215 nM): 87%, RT 2.53 min. |
| 8-77 | 2-(4-(4-ethylpiperazin-1-yl)phenyl)-N-hydroxy-2-phenylacetamide | LRMS (ESI): (calc.) 339.4314, (found) 340 [M + H], HPLC (215 nM): 97%, RT 2.42 min. |
| 8-78 | 2-(4-(3-(dimethylamino)pyrrolidin-1-yl)phenyl)-N-hydroxy-2-phenylacetamide | LRMS (ESI): (calc.) 339.4314, (found) 340 [M + H], HPLC (215 nM): 89%, RT 2.52 min. |
| 8-79 | 2-(4-(2,6-dimethylmorpholino)phenyl)-N-hydroxy-2-phenylacetamide | LRMS (ESI): (calc.) 340.41616, (found) 341 [M + H], HPLC (215 nM): 92%, RT 3.52 min. |
| 8-80 | 2-(4-(benzyl(methyl)amino)phenyl)-N-hydroxy-2-phenylacetamide | LRMS (ESI): (calc.) 346.42228, (found) 347 [M + H], HPLC (215 nM): 95%, RT 3.95 min. |
| 8-81 | 2-(4-ethylphenylamino)phenyl)-N-hydroxy-2-phenylacetamide | LRMS (ESI): (calc.) 346.42228, (found) 347 [M + H], HPLC (215 nM): 94%, RT 4.26 min. |
| 8-82 | N-hydroxy-2-phenyl-2-(4-(2-(pyridin-2-yl)ethylamino)phenyl)acetamide | LRMS (ESI): (calc.) 347.41034, (found) 348 [M + H], HPLC (215 nM): 94%, RT 2.51 min. |
| 8-83 | N-hydroxy-2-(4-(methyl(pyridin-3-ylmethyl)amino)phenyl)-2-phenylacetamide | LRMS (ESI): (calc.) 347.41034, (found) 348 [M + H], HPLC (215 nM): 98%, RT 2.71 min. |
| 8-84 | N-hydroxy-2-phenyl-2-(4-(2-(pyridin-3-yl)ethylamino)phenyl)acetamide | LRMS (ESI): (calc.) 347.41034, (found) 348 [M + H], HPLC (215 nM): 95%, RT 2.5 min. |
| 8-85 | N-hydroxy-2-phenyl-2-(4-(2-(pyridin-4-yl)ethylamino)phenyl)acetamide | LRMS (ESI): (calc.) 347.41034, (found) 348 [M + H], HPLC (215 nM): 96%, RT 2.49 min. 1H NMR (250 MHz, MeOD) d ppm 8.30-8.46 (2H, m), 7.18-7.37 (7H, m), 7.09 (2H, |

TABLE VIII-continued

Compounds prepared according general Schemes above

| Cpd # | Name | Characterization |
|---|---|---|
|  |  | m, J = 8.53 Hz), 6.59 (2H, m, J = 8.53 Hz), 4.65 (1H, s), 3.36-3.42 (2H, m), 2.91 (2H, t, J = 7.01 Hz) |
| 8-86 | N-hydroxy-2-(4-(4-methoxyphenylamino)phenyl)-2-phenylacetamide | LRMS (ESI): (calc.) 348.3951, (found) 349 [M + H], HPLC (215 nM): 91%, RT 3.8 min. |
| 8-87 | 2-(4-(3-fluorobenzylamino)phenyl)-N-hydroxy-2-phenylacetamide | LRMS (ESI): (calc.) 350.3861632, (found) 351 [M + H], HPLC (215 nM): 93%, RT 3.88 min. |
| 8-88 | 2-(4-(3-fluorobenzylamino)phenyl)-N-hydroxy-2-phenylacetamide | LRMS (ESI): (calc.) 350.3861632, (found) 351 [M + H], HPLC (215 nM): 93%, RT 3.87 min. |
| 8-89 | 2-(4-(3-(1H-imidazol-1-yl)propylamino)phenyl)-N-hydroxy-2-phenylacetamide | LRMS (ESI): (calc.) 350.41428, (found) 351 [M + H], HPLC (215 nM): 98%, RT 2.39 min. 1H NMR (250 MHz, MeOD) d ppm 7.84 (1H, br. s.), 7.15-7.46 (6H, m), 6.90-7.15 (3H, m), 6.56 (2H, d, J = 8.53 Hz), 4.65 (1H, s), 4.17 (2H, t, J = 7.01 Hz), 3.05 (2H, t, J = 6.55 Hz), 1.85-2.18 (2H, m) |
| 8-90 | N-hydroxy-2-phenyl-2-(4-(2-(thiophen-2-yl)ethylamino)phenyl)acetamide | LRMS (ESI): (calc.) 352.45, (found) 353 [M + H], HPLC (215 nM): 94%, RT 3.81 min. |
| 8-91 | 2-(4-(diisobutylamino)phenyl)-N-hydroxy-2-phenylacetamide | LRMS (ESI): (calc.) 354.4858, (found) 355 [M + H], HPLC (215 nM): 97%, RT 4.72 min. |
| 8-92 | N-hydroxy-2-(4-(2-morpholinoethylamino)phenyl)-2-phenylacetamide | LRMS (ESI): (calc.) 355.4308, (found) 356 [M + H], HPLC (215 nM): 94%, RT 2.36 min. 1H NMR (250 MHz, MeOD) d ppm 7.11-7.34 (5H, m), 7.03 (2H, m, J = 8.22 Hz), 6.55 (2H, m, J = 8.53 Hz), 4.59 (1H, s), 3.59-3.70 (4H, m), 3.16 (2H, t, J = 6.55 Hz), 2.53 (2H, t, J = 6.55 Hz), 2.36-2.49 (4H, m) |
| 8-93 | 2-(4-(3,4-dihydroisoquinolin-2(1H)-yl)phenyl)-N-hydroxy-2-phenylacetamide | LRMS (ESI): (calc.) 358.43298, (found) 359 [M + H], HPLC (215 nM): 98%, RT 3.98 min. 1H NMR (250 MHz, MeOD) d ppm 7.27-7.36 (4H, m), 7.18-7.27 (3H, m), 7.09-7.18 (4H, m), 6.89-7.04 (2H, m), 4.71 (1H, s), 4.34 (2H, s), 3.52 (2H, t, J = 5.94 Hz), 2.95 (2H, t, J = 5.79 Hz) |
| 8-94 | N-hydroxy-2-(4-(methyl(2-(pyridin-2-yl)ethyl)amino)phenyl)-2-phenylacetamide | LRMS (ESI): (calc.) 361.43692, (found) 362 [M + H], HPLC (215 nM): 95%, RT 2.69 min. |
| 8-95 | N-hydroxy-2-(4-(2-phenoxyethylamino)phenyl)-2-phenylacetamide | LRMS (ESI): (calc.) 362.42168, (found) 363 [M + H], HPLC (215 nM): 92%, RT 3.86 min. |
| 8-96 | N-hydroxy-2-(4-(4-methoxybenzylamino)phenyl)-2-phenylacetamide | LRMS (ESI): (calc.) 362.42168, (found) 363 [M + H], HPLC (215 nM): 93%, RT 3.61 min. |
| 8-97 | 2-(4-(4-chlorobenzylamino)phenyl)-N-hydroxy-2-phenylacetamide | LRMS (ESI): (calc.) 366.84076, (found) 367 [M + H], HPLC (215 nM): 93%, RT 4.06 min. |
| 8-98 | 2-(4-(4-acetyl-1,4-diazepan-1-yl)phenyl)-N-hydroxy-2-phenylacetamide | LRMS (ESI): (calc.) 367.4415, (found) 368 [M + H], HPLC (215 nM): 93%, RT 3.16 min. |
| 8-99 | N-hydroxy-2-(4-(3-(2-oxopyrrolidin-1-yl)propylamino)phenyl)-2-phenylacetamide | LRMS (ESI): (calc.) 367.4415, (found) 368 [M + H], HPLC (215 nM): 98%, RT 2.74 min. |
| 8-100 | 2-(4-(4-butylpiperazin-1-yl)phenyl)-N-hydroxy-2-phenylacetamide | LRMS (ESI): (calc.) 367.48456, (found) 368 [M + H], HPLC (215 nM): 90%, RT 2.72 min. |
| 8-101 | N-hydroxy-2-(4-(4-(2-methoxyethyl)piperazin-1-yl)phenyl)-2-phenylacetamide | LRMS (ESI): (calc.) 369.45738, (found) 370 [M + H], HPLC (215 nM): 96%, RT 2.49 min. |
| 8-102 | N-hydroxy-2-(4-(3-morpholinopropylamino)phenyl)-2-phenylacetamide | LRMS (ESI): (calc.) 369.45738, (found) 370 [M + H], HPLC (215 nM): 98%, RT 2.33 min. |
| 8-103 | N-hydroxy-2-phenyl-2-(4-(4-(trifluoromethyl)piperidin-1-yl)phenyl)acetamide | LRMS (ESI): (calc.) 378.3881496, (found) 379 [M + H], HPLC (215 nM): 95%, RT 3.8 min. 1H NMR (250 MHz, MeOD) d ppm 7.13-7.40 (7H, m), 6.97 (2H, d, J = 8.83 Hz), 4.71 (1H, s), 3.62-3.85 (2H, m), 2.60-2.88 (2H, m), 2.16-2.47 (1H, m), 1.88-2.07 (2H, m), 1.57-1.86 (2H, m) |
| 8-104 | N-hydroxy-2-phenyl-2-(4-(4-phenylpiperidin-1-yl)phenyl)acetamide | LRMS (ESI): (calc.) 386.48614, (found) 387 [M + H], HPLC (215 nM): 100%, RT 3.45 min. |
| 8-105 | N-hydroxy-2-phenyl-2-(4-(4-(pyrazin-2-yl)piperazin-1-yl)phenyl)acetamide | LRMS (ESI): (calc.) 389.45032, (found) 390 [M + H], HPLC (215 nM): 96%, RT 3.44 min. |

TABLE VIII-continued

Compounds prepared according general Schemes above

| Cpd # | Name | Characterization |
|---|---|---|
| 8-106 | 2-(4-(1,4'-bipiperidin-1'-yl)phenyl)-N-hydroxy-2-phenylacetamide | LRMS (ESI) (calc.) 393.52184, (found) 394 [M + H], HPLC (215 nM): 89%, RT 2.61 min. |
| 8-107 | 2-(4-(benzyl(2-(dimethylamino)ethyl)amino)phenyl)-N-hydroxy-2-phenylacetamide | LRMS (ESI) (calc.) 403.51666, (found) 404 [M + H], HPLC (215 nM): 91%, RT 3.01 min. |
| 8-108 | N-hydroxy-2-(4-(4-(4-methoxyphenyl)piperazin-1-yl)phenyl)-2-phenylacetamide | LRMS (ESI): (calc.) 417.50018, (found) 418 [M + H], HPLC (215 nM): 100%, RT 3.43 min. |
| 8-109 | N-hydroxy-2-(4-(4-(2-morpholinoethyl)piperazin-1-yl)phenyl)-2-phenylacetamide | LRMS (ESI): (calc.) 424.53588, (found) 425 [M + H], HPLC (215 nM): 97%, RT 2.26 min. |
| 8-110 | N-(4-(2-(hydroxyamino)-2-oxo-1-phenylethyl)phenyl)cyclopentaneanecarboxamide | LRMS (ESI): (calc.) 338.40028, (found) 339 [M + H], HPLC (215 nM): 96%, RT 3.54 min. |
| 8-111 | 2-(4-(2-cyclopentylacetamido)phenyl)-N-hydroxy-2-phenylacetamide | LRMS (ESI): (calc.) 352.42686, (found) 353 [M + H], HPLC (215 nM): 89%, RT 3.71 min. |
| 8-112 | N-(4-(2-(hydroxyamino)-2-oxo-1-phenylethyl)phenyl)-2,3-dimethylbenzamide | LRMS (ESI): (calc.) 374.43238, (found) 375 [M + H], HPLC (215 nM): 98%, RT 3.74 min. |
| 8-113 | 2-(3-(allylamino)phenyl)-N-hydroxy-2-phenylacetamide | LRMS (ESI): (calc.) 282.33702, (found) 283 [M + H], HPLC (215 nM): 100%, RT 3.11 min. |
| 8-114 | 2-(4-(3,4-dimethoxybenzylamino)phenyl)-N-hydroxy-2-phenylacetamide | LRMS (ESI): (calc.) 392.44766, (found) 393 [M + H], HPLC (215 nM): 100%, RT 3.39 min. |
| 8-115 | 2-(4-(2,4-dichlorobenzylamino)phenyl)-N-hydroxy-2-phenylacetamide | LRMS (ESI): (calc.) 401.28582, (found) 401 [M + H], HPLC (215 nM): 91%, RT 4.4 min. |
| 8-116 | 2-(3-(cyclopropylethynyl)phenyl)-N-hydroxy-2-phenylacetamide | LRMS (ESI): (calc.) 291.34378, (found) 292 [M + H], HPLC (215 nM): 91%, RT 3.98 min. |
| 8-117 | N-hydroxy-2-(3-(pent-1-ynyl)phenyl)-2-phenylacetamide | LRMS (ESI): (calc.) 293.35966, (found) 294 [M + H], HPLC (215 nM): 93%, RT 4.18 min. |
| 8-118 | N-hydroxy-2-(3-(pent-1-ynyl)phenyl)-2-phenylacetamide | LRMS (ESI): (calc.) 293.35966, (found) 296 [M + H], HPLC (215 nM): 100%, RT 4.33 min. |
| 8-119 | N-hydroxy-2-(3-(3-methoxyprop-1-ynyl)phenyl)-2-phenylacetamide | LRMS (ESI): (calc.) 295.33248, (found) 296 [M + H], HPLC (215 nM): 100%, RT 3.6 min. |
| 8-120 | 2-(3-(hex-1-ynyl)phenyl)-N-hydroxy-2-phenylacetamide | LRMS (ESI): (calc.) 307.38624, (found) 308 [M + H], HPLC (215 nM): 93%, RT 4.41 min. |
| 8-121 | N-hydroxy-2-(3-(4-methylpent-1-ynyl)phenyl)-2-phenylacetamide | LRMS (ESI): (calc.) 307.38624, (found) 308 [M + H], HPLC (215 nM): 91%, RT 4.38 min. |
| 8-122 | 2-(3-(3,3-dimethylbut-1-ynyl)phenyl)-N-hydroxy-2-phenylacetamide | LRMS (ESI): (calc.) 307.38624, (found) 308 [M + H], HPLC (215 nM): 93%, RT 4.34 min. |
| 8-123 | N-hydroxy-2-phenyl-2-(3-(pyridin-2-ylethynyl)phenyl)acetamide | LRMS (ESI): (calc.) 328.36394, (found) 329 [M + H], HPLC (215 nM): 85%, RT 3.55 min. |
| 8-124 | 2-(3-(cyclohexylethynyl)phenyl)-N-hydroxy-2-phenylacetamide | LRMS (ESI): (calc.) 333.42352, (found) 334 [M + H], HPLC (215 nM): 94%, RT 4.67 min. |
| 8-125 | 2-(3-(cyclohexylethynyl)phenyl)-N-hydroxy-2-phenylacetamide | LRMS (ESI): (calc.) 333.42352, (found) 334 [M + H], HPLC (215 nM): 94%, RT 4.67 min. |
| 8-126 | N-hydroxy-2-(3-(oct-1-ynyl)phenyl)-2-phenylacetamide | LRMS (ESI): (calc.) 335.4394, (found) 336 [M + H], HPLC (215 nM): 93%, RT 4.89 min. |
| 8-127 | 2-(3-(3-tert-butoxyprop-1-ynyl)phenyl)-N-hydroxy-2-phenylacetamide | LRMS (ESI): (calc.) 337.41222, (found) 675 [2M + H], HPLC (215 nM): 91%, RT 4.09 min. |
| 8-128 | 2-(3-(3-cyclohexylprop-1-ynyl)phenyl)-N-hydroxy-2-phenylacetamide | LRMS (ESI): (calc.) 347.4501, (found) 348 [M + H], HPLC (215 nM): 92%, RT 4.89 min. |

TABLE VIII-continued

Compounds prepared according general Schemes above

| Cpd # | Name | Characterization |
|---|---|---|
| 8-129 | N-hydroxy-2-phenyl-2-(3-(4-phenylbut-1-ynyl)phenyl)acetamide | LRMS (ESI): (calc.) 355.42904, (found) 356 [M + H], HPLC (215 nM): 89%, RT 4.44 min. |
| 8-130 | 2-(3-((4-ethylphenyl)ethynyl)phenyl)-N-hydroxy-2-phenylacetamide | LRMS (ESI): (calc.) 355.42904, (found) 356 [M + H], HPLC (215 nM): 89%, RT 4.75 min. |
| 8-131 | N-hydroxy-2-(3-((4-methoxyphenyl)ethynyl)phenyl)-2-phenylacetamide | LRMS (ESI): (calc.) 357.40186, (found) 358 [M + H], HPLC (215 nM): 100%, RT 4.29 min. 1H NMR (250 MHz, MeOD) d ppm 7.17-7.50 (11H, m), 6.92 (2H, d, J = 9.14 Hz), 4.79 (1H, s), 3.81 (3H, s) |
| 8-132 | N-hydroxy-2-(3-((3-methoxyphenyl)ethynyl)phenyl)-2-phenylacetamide | LRMS (ESI): (calc.) 357.40186, (found) 358 [M + H], HPLC (215 nM): 90%, RT 4.33 min. |
| 8-133 | 2-(3-((2,4-difluorophenyl)ethynyl)phenyl)-N-hydroxy-2-phenylacetamide | LRMS (ESI): (calc.) 363.3568064, (found) 364 [M + H], HPLC (215 nM): 90%, RT 4.37 min. |
| 8-134 | N-hydroxy-2-phenyl-2-(3-((4-propoxyphenyl)ethynyl)phenyl)acetamide | LRMS (ESI): (calc.) 385.45502, (found) 386 [M + H], HPLC (215 nM): 94%, RT 4.77 min. |
| 8-135 | N-hydroxy-2-phenyl-2-(3-((2-(trifluoromethyl)phenyl)ethynyl)phenyl)acetamide | LRMS (ESI): (calc.) 395.3738496, (found) 396 [M + H], HPLC (215 nM): 93%, RT 4.5 min. |
| 8-136 | N-hydroxy-2-phenyl-2-(3-((3-(trifluoromethyl)phenyl)ethynyl)phenyl)acetamide | LRMS (ESI): (calc.) 395.3738496, (found) 396 [M + H], HPLC (215 nM): 100%, RT 4.66 min. |
| 8-138 | 2-(4-(cyclopropylethynyl)phenyl)-N-hydroxy-2-phenylacetamide | LRMS (ESI): (calc.) 291.34378, (found) 292 [M + H], HPLC (215 nM): 90%, RT 3.99 min. |
| 8-140 | (E)—N-hydroxy-2-(4-(pent-1-enyl)phenyl)-2-phenylacetamide | LRMS (ESI): (calc.) 295.38, (found) 296 [M + H], HPLC (215 nM): 100%, RT 4.37 min. 1H NMR (250 MHz, MeOD) d ppm 7.00-7.42 (9H, m), 5.98-6.46 (2H, m), 4.75 (1H, s), 2.17 (2H, q), 1.35-1.62 (2H, m), 0.95 (3H, t, J = 7.46 Hz) |
| 8-141 | N-hydroxy-2-(4-(3-methoxyprop-1-ynyl)phenyl)-2-phenylacetamide | LRMS (ESI): (calc.) 295.33248, (found) 296 [M + H], HPLC (215 nM): 89%, RT 3.6 min. |
| 8-142 | 2-(4-(hex-1-ynyl)phenyl)-N-hydroxy-2-phenylacetamide | LRMS (ESI): (calc.) 307.38624, (found) 308 [M + H], HPLC (215 nM): 90%, RT 4.43 min. |
| 8-143 | N-hydroxy-2-(4-(4-methylpent-1-ynyl)phenyl)-2-phenylacetamide | LRMS (ESI): (calc.) 307.38624, (found) 308 [M + H], HPLC (215 nM): 92%, RT 4.41 min. |
| 8-144 | 2-(4-(3,3-dimethylbut-1-ynyl)phenyl)-N-hydroxy-2-phenylacetamide | LRMS (ESI): (calc.) 307.38624, (found) 308 [M + H], HPLC (215 nM): 90%, RT 4.37 min. |
| 8-145 | 2-(4-(cyclopentylethynyl)phenyl)-N-hydroxy-2-phenylacetamide | LRMS (ESI): (calc.) 319.39694, (found) 320 [M + H], HPLC (215 nM): 100%, RT 4.48 min. |
| 8-146 | N-hydroxy-2-phenyl-2-(4-(pyridin-2-ylethynyl)phenyl)acetamide | LRMS (ESI): (calc.) 328.36394, (found) 329 [M + H], HPLC (215 nM): 100%, RT 3.52 min. |
| 8-147 | 2-(4-(cyclohexylethynyl)phenyl)-N-hydroxy-2-phenylacetamide | LRMS (ESI): (calc.) 333.42352, (found) 334 [M + H], HPLC (215 nM): 95%, RT 4.7 min. 1H NMR (250 MHz, MeOD) d ppm 7.11-7.36 (9H, m), 4.74 (1H, s), 2.39-2.65 (1H, m), 1.62-1.92 (4H, m), 1.22-1.58 (6H, m) |
| 8-148 | 2-(4-(cyclohexylethynyl)phenyl)-N-hydroxy-2-phenylacetamide | LRMS (ESI): (calc.), (found) [M + H], HPLC (215 nM): %, RT min. |
| 8-149 | N-hydroxy-2-(4-(oct-1-ynyl)phenyl)-2-phenylacetamide | LRMS (ESI): (calc.) 335.4394, (found) 336 [M + H], HPLC (215 nM): 94%, RT 4.9 min. |
| 8-150 | 2-(4-(3-(diethylamino)prop-1-ynyl)phenyl)-N-hydroxy-2-phenylacetamide | LRMS (ESI): (calc.) 336.42746, (found) 337 [M + H], HPLC (215 nM): 90%, RT 2.67 min. 1H NMR (250 MHz, MeOD) d ppm 7.10-7.42 (9H, m), 4.75 (1H, s), 3.64 (2H, s), 2.66 (4H, q, J = 7.11 Hz), 1.10 (6H, t, J = 7.16 Hz) |
| 8-151 | 2-(4-(3-tert-butoxyprop-1-ynyl)phenyl)-N-hydroxy-2-phenylacetamide | LRMS (ESI): (calc.) 337.41222, (found) 338 [M + H], HPLC (215 nM): 100%, RT 4.09 min. |
| 8-152 | N-hydroxy-2-phenyl-2-(4-(p-tolylethynyl)phenyl)acetamide | LRMS (ESI): (calc.) 341.40246, (found) 342 [M + H], HPLC (215 nM): 100%, RT 4.54 min. 1H NMR (250 MHz, MeOD) d ppm 7.23-7.48 (11H, m), 7.17 (2H, d, J = 7.61 Hz), 4.79 (1H, s), 2.34 (3H, s) |
| 8-153 | 2-(4-((2-fluorophenyl)ethynyl)phenyl)-N-hydroxy-2-phenylacetamide | LRMS (ESI): (calc.) 345.3663432, (found) 346 [M + H], HPLC (215 nM): 88%, RT 4.3 min. |

TABLE VIII-continued

Compounds prepared according general Schemes above

| Cpd # | Name | Characterization |
|---|---|---|
| 8-154 | 2-(4-(3-cyclohexylprop-1-ynyl)phenyl)-N-hydroxy-2-phenylacetamide | LRMS (ESI): (calc.) 347.4501, (found) 348 [M + H], HPLC (215 nM): 94%, RT 4.92 min. |
| 8-155 | N-hydroxy-2-phenyl-2-(4-(4-phenylbut-1-ynyl)phenyl)acetamide | LRMS (ESI): (calc.) 355.42904, (found) 356 [M + H], HPLC (215 nM): 94%, RT 4.46 min. |
| 8-156 | 2-(4-((4-ethylphenyl)ethynyl)phenyl)-N-hydroxy-2-phenylacetamide | LRMS (ESI): (calc.) 355.42904, (found) 356 [M + H], HPLC (215 nM): 94%, RT 4.74 min. |
| 8-157 | N-hydroxy-2-(4-((4-methoxyphenyl)ethynyl)phenyl)-2-phenylacetamide | LRMS (ESI): (calc.) 357.40186, (found) 358 [M + H], HPLC (215 nM): 89%, RT 4.29 min. |
| 8-158 | N-hydroxy-2-(4-((3-methoxyphenyl)ethynyl)phenyl)-2-phenylacetamide | LRMS (ESI): (calc.) 357.40186, (found) 358 [M + H], HPLC (215 nM): 91%, RT 4.33 min. |
| 8-159 | 2-(4-((2-chlorophenyl)ethynyl)phenyl)-N-hydroxy-2-phenylacetamide | LRMS (ESI): (calc.) 361.82094, (found) 362 [M + H], HPLC (215 nM): 88%, RT 4.48 min. |
| 8-160 | 2-(4-((4-chlorophenyl)ethynyl)phenyl)-N-hydroxy-2-phenylacetamide | LRMS (ESI): (calc.) 361.82094, (found) 362 [M + H], HPLC (215 nM): 86%, RT 4.62 min. |
| 8-161 | 2-(4-((2,4-difluorophenyl)ethynyl)phenyl)-N-hydroxy-2-phenylacetamide | LRMS (ESI): (calc.) 363.3568064, (found) 364 [M + H], HPLC (215 nM): 94%, RT 4.38 min. |
| 8-162 | N-hydroxy-2-phenyl-2-(4-((4-(trifluoromethyl)phenyl)ethynyl)phenyl)acetamide | LRMS (ESI): (calc.) 395.3738496, (found) 396 [M + H], HPLC (215 nM): 94%, RT 4.67 min. 1H NMR (250 MHz, MeOD) d ppm 7.68 (4H, s), 7.46-7.55 (2H, m), 7.25-7.41 (7H, m), 4.81 (1H, s) |
| 8-163 | N-hydroxy-2-phenyl-2-(4-((2-(trifluoromethyl)phenyl)ethynyl)phenyl)acetamide | LRMS (ESI): (calc.) 395.3738496, (found) 396 [M + H], HPLC (215 nM): 90%, RT 4.52 min. |
| 8-164 | N-hydroxy-2-phenyl-2-(4-((3-(trifluoromethyl)phenyl)ethynyl)phenyl)acetamide | LRMS (ESI): (calc.) 395.3738496, (found) 396 [M + H], HPLC (215 nM): 94%, RT 4.67 min. |
| 8-166 | 2-(4'-(ethylsulfonyl)biphenyl-3-yl)-N-hydroxy-2-phenylacetamide | LRMS (ESI): (calc.) 395.47144, (found) 396 [M + H], HPLC (215 nM): 93%, RT 3.66 min. 1H NMR (250 MHz, MeOD) d ppm 7.91 (2H, m, J = 8.53 Hz), 7.78 (2H, m, J = 8.22 Hz), 7.65 (1H, s), 7.50-7.59 (1H, m), 7.17-7.46 (7H, m), 4.87 (1H, s-masked by H2O), 3.19 (2H, q, J = 7.31 Hz), 1.19 (3H, t, J = 7.46 Hz) |
| 8-167 | N-hydroxy-2-(4'-(N-methylsulfamoyl)biphenyl-3-yl)-2-phenylacetamide | LRMS (ESI): (calc.) 396.4595, (found) 397 [M + H], HPLC (215 nM): 92%, RT 3.55 min. |
| 8-168 | N-hydroxy-2-(3'-(methylsulfonamido)biphenyl-3-yl)-2-phenylacetamide | LRMS (ESI): (calc.) 396.4595, (found) 397 [M + H], HPLC (215 nM): 100%, RT 4.33 min. |
| 8-169 | N-hydroxy-2-(4'-(methylsulfonamido)biphenyl-3-yl)-2-phenylacetamide | LRMS (ESI): (calc.) 396.4595, (found) 397 [M + H], HPLC (215 nM): 100%, RT 3.55 min. |
| 8-170 | 2-(3'-chloro-4'-(trifluoromethyl)biphenyl-3-yl)-N-hydroxy-2-phenylacetamide | LRMS (ESI): (calc.) 405.7975096, (found) 406 [M + H], HPLC (215 nM): 93%, RT 4.57 min. |
| 8-171 | N-hydroxy-2-phenyl-2-m-tolylacetamide | LRMS (ESI): (calc.) 241.2851, (found) 242 [M + H], HPLC (215 nM): 93%, RT 3.54 min. |
| 8-172 | 2-(3-butylphenyl)-N-hydroxy-2-phenylacetamide | LRMS (ESI): (calc.) 283.36484, (found) 284 [M + H], HPLC (215 nM): 94%, RT 4.2 min. |
| 8-173 | N-hydroxy-2-(3-isobutylphenyl)-2-phenylacetamide | LRMS (ESI): (calc.) 283.36484, (found) 284 [M + H], HPLC (215 nM): 88%, RT 4.17 min. |
| 8-174 | 2-(3-cyclopentylphenyl)-N-hydroxy-2-phenylacetamide | LRMS (ESI): (calc.) 295.37554, (found) 296 [M + H], HPLC (215 nM): 94%, RT 4.22 min. |
| 8-175 | N-hydroxy-2-phenyl-2-(3-(pyridin-3-yl)phenyl)acetamide | LRMS (ESI): (calc.) 304.34254, (found) 305 [M + H], HPLC (215 nM): 97%, RT 2.65 min. |
| 8-176 | N-hydroxy-2-phenyl-2-(3-(pyrimidin-5-yl)phenyl)acetamide | LRMS (ESI): (calc.) 305.3306, (found) 306 [M + H], HPLC (215 nM): 93%, RT 3.13 min. |
| 8-177 | N-hydroxy-2-phenyl-2-(3-(thiophen-3-yl)phenyl)acetamide | LRMS (ESI): (calc.) 309.3822, (found) 310 [M + H], HPLC (215 nM): 91%, RT 3.9 min. |
| 8-178 | 2-(3-hexylphenyl)-N-hydroxy-2-phenylacetamide | LRMS (ESI): (calc.) 311.418, (found) 312 [M + H], HPLC (215 nM): 92%, RT 4.67 min. |

TABLE VIII-continued

Compounds prepared according general Schemes above

| Cpd # | Name | Characterization |
|---|---|---|
| 8-180 | N-hydroxy-2-(4'-methylbiphenyl-3-yl)-2-phenylacetamide | LRMS (ESI): (calc.) 317.38106, (found) 318 [M + H], HPLC (215 nM): 93%, RT 4.22 min. 1H NMR (250 MHz, MeOD) d ppm 7.57 (1H, s), 7.41-7.52 (3H, m), 7.13-7.41 (9H, m), 4.85 (1H, s), 2.35 (3H, s) |
| 8-181 | N-hydroxy-2-(3'-methylbiphenyl-3-yl)-2-phenylacetamide | LRMS (ESI): (calc.) 317.38106, (found) 318 [M + H], HPLC (215 nM): 87%, RT 4.21 min. |
| 8-182 | N-hydroxy-2-(2'-methylbiphenyl-3-yl)-2-phenylacetamide | LRMS (ESI): (calc.) 317.38106, (found) 318 [M + H], HPLC (215 nM): 93%, RT 4.17 min. |
| 8-183 | 2-(4'-fluorobiphenyl-3-yl)-N-hydroxy-2-phenylacetamide | LRMS (ESI): (calc.) 321.3449432, (found) 322 [M + H], HPLC (215 nM): 92%, RT 4.06 min. |
| 8-184 | 2-(3'-fluorobiphenyl-3-yl)-N-hydroxy-2-phenylacetamide | LRMS (ESI): (calc.) 321.3449432, (found) 322 [M + H], HPLC (215 nM): 93%, RT 4.06 min. |
| 8-185 | 2-(2'-fluorobiphenyl-3-yl)-N-hydroxy-2-phenylacetamide | LRMS (ESI): (calc.) 321.3449432, (found) 322 [M + H], HPLC (215 nM): 92%, RT 4.01 min. |
| 8-186 | 2-(3-(2-fluoropyridin-3-yl)phenyl)-N-hydroxy-2-phenylacetamide | LRMS (ESI): (calc.) 322.3330032, (found) 323 [M + H], HPLC (215 nM): 100%, RT 3.6 min. |
| 8-187 | 2-(3-(6-fluoropyridin-3-yl)phenyl)-N-hydroxy-2-phenylacetamide | LRMS (ESI): (calc.) 322.3330032, (found) 361 [M + H], HPLC (215 nM): 93%, RT 3.37 min. |
| 8-188 | 2-(3-(3,5-dimethylisoxazol-4-yl)phenyl)-N-hydroxy-2-phenylacetamide | LRMS (ESI): (calc.) 322.35782, (found) 323 [M + H], HPLC (215 nM): 92%, RT 3.58 min. |
| 8-189 | N-hydroxy-2-(3-(4-methylthiophen-3-yl)phenyl)-2-phenylacetamide | LRMS (ESI): (calc.) 323.40878, (found) 324 [M + H], HPLC (215 nM): 90%, RT 4.08 min. |
| 8-190 | 2-(2'-cyanobiphenyl-3-yl)-N-hydroxy-2-phenylacetamide | LRMS (ESI): (calc.) 328.36394, (found) 329 [M + H], HPLC (215 nM): 100%, RT 3.77 min. |
| 8-191 | (E)—N-hydroxy-2-phenyl-2-(3-styrylphenyl)acetamide | LRMS (ESI): (calc.) 329.39176, (found) 330 [M + H], HPLC (215 nM): 92%, RT 4.26 min. |
| 8-193 | N-hydroxy-2-(4'-methoxybiphenyl-3-yl)-2-phenylacetamide | LRMS (ESI): (calc.) 333.38046, (found) 334 [M + H], HPLC (215 nM): 91%, RT 3.98 min. |
| 8-194 | N-hydroxy-2-(3'-methoxybiphenyl-3-yl)-2-phenylacetamide | LRMS (ESI): (calc.) 333.38046, (found) 334 [M + H], HPLC (215 nM): 92%, RT 4 min. |
| 8-195 | N-hydroxy-2-(2'-methoxybiphenyl-3-yl)-2-phenylacetamide | LRMS (ESI): (calc.) 333.38046, (found) 334 [M + H], HPLC (215 nM): 93%, RT 3.99 min. |
| 8-196 | N-hydroxy-2-(4'-(hydroxymethyl)biphenyl-3-yl)-2-phenylacetamide | LRMS (ESI): (calc.) 333.38046, (found) 334 [M + H], HPLC (215 nM): 91%, RT 3.45 min. |
| 8-197 | N-hydroxy-2-(3'-(hydroxymethyl)biphenyl-3-yl)-2-phenylacetamide | LRMS (ESI): (calc.) 333.38046, (found) 334 [M + H], HPLC (215 nM): 90%, RT 3.49 min. |
| 8-198 | N-hydroxy-2-(3-(6-methoxypyridin-3-yl)phenyl)-2-phenylacetamide | LRMS (ESI): (calc.) 334.36852, (found) 335 [M + H], HPLC (215 nM): 94%, RT 3.7 min. |
| 8-199 | 2-(4'-fluoro-2'-methylbiphenyl-3-yl)-N-hydroxy-2-phenylacetamide | LRMS (ESI): (calc.) 335.3715232, (found) 336 [M + H], HPLC (215 nM): 92%, RT 4.22 min. |
| 8-200 | 2-(3'-chlorobiphenyl-3-yl)-N-hydroxy-2-phenylacetamide | LRMS (ESI): (calc.) 337.79954, (found) 338 [M + H], HPLC (215 nM): 93%, RT 4.27 min. |
| 8-201 | 2-(3-(6-chloropyridin-3-yl)phenyl)-N-hydroxy-2-phenylacetamide | LRMS (ESI): (calc.) 338.7876, (found) 339 [M + H], HPLC (215 nM): 100%, RT 3.76 min. |
| 8-203 | 2-(2',5'-difluorobiphenyl-3-yl)-N-hydroxy-2-phenylacetamide | LRMS (ESI): (calc.) 339.3354064, (found) 340 [M + H], HPLC (215 nM): 91%, RT 4.06 min. |
| 8-204 | 2-(2',4'-difluorobiphenyl-3-yl)-N-hydroxy-2-phenylacetamide | LRMS (ESI): (calc.) 339.3354064, (found) 340 [M + H], HPLC (215 nM): 93%, RT 4.09 min. |
| 8-205 | 2-(3',4'-difluorobiphenyl-3-yl)-N-hydroxy-2-phenylacetamide | LRMS (ESI): (calc.) 339.3354064, (found) 340 [M + H], HPLC (215 nM): 94%, RT 4.14 min. |
| 8-206 | 2-(3-(5-chlorothiophen-2-yl)phenyl)-N-hydroxy-2-phenylacetamide | LRMS (ESI): (calc.) 343.82726, (found) 344 [M + H], HPLC (215 nM): 94%, RT 4.31 min. 1H NMR (250 MHz, MeOD) d ppm 7.52-7.58 (1H, m), 7.42-7.50 (1H, m), 7.24-7.40 (7H, m), 7.17 (1H, d, J = 3.65 Hz), 6.95 (1H, d, J = 3.96 Hz), 4.82 (1H, s) |
| 8-207 | N-hydroxy-2-(4'-isopropylbiphenyl-3-yl)-2-phenylacetamide | LRMS (ESI): (calc.) 345.43422, (found) 346 [M + H], HPLC (215 nM): 92%, RT 4.6 min. |

TABLE VIII-continued

Compounds prepared according general Schemes above

| Cpd # | Name | Characterization |
|---|---|---|
| 8-208 | N-hydroxy-2-phenyl-2-(4'-propylbiphenyl-3-yl)acetamide | LRMS (ESI): (calc.) 345.43422, (found) 346 [M + H], HPLC (215 nM): 91%, RT 4.65 min. |
| 8-210 | 2-(3'-(dimethylamino)biphenyl-3-yl)-N-hydroxy-2-phenylacetamide | LRMS (ESI): (calc.) 346.42228, (found) 347 [M + H], HPLC (215 nM): 90%, RT 3.35 min. |
| 8-212 | 2-(3-(benzo[d][1,3]dioxol-5-yl)phenyl)-N-hydroxy-2-phenylacetamide | LRMS (ESI): (calc.) 347.36398, (found) 348 [M + H], HPLC (215 nM): 91%, RT 3.94 min. |
| 8-213 | 2-(2'-ethoxybiphenyl-3-yl)-N-hydroxy-2-phenylacetamide | LRMS (ESI): (calc.) 347.40704, (found) 348 [M + H], HPLC (215 nM): 92%, RT 4.18 min. |
| 8-214 | 2-(3'-ethoxybiphenyl-3-yl)-N-hydroxy-2-phenylacetamide | LRMS (ESI): (calc.) 347.40704, (found) 348 [M + H], HPLC (215 nM): 100%, RT 4.22 min. |
| 8-215 | 2-(4'-ethoxybiphenyl-3-yl)-N-hydroxy-2-phenylacetamide | LRMS (ESI): (calc.) 347.40704, (found) 348 [M + H], HPLC (215 nM): 100%, RT 4.21 min. |
| 8-216 | N-hydroxy-2-(4'-(methoxymethyl)biphenyl-3-yl)-2-phenylacetamide | LRMS (ESI): (calc.) 347.40704, (found) 348 [M + H], HPLC (215 nM): 94%, RT 3.55 min. |
| 8-217 | N-hydroxy-2-(4'-(methylthio)biphenyl-3-yl)-2-phenylacetamide | LRMS (ESI): (calc.) 349.44606, (found) 350 [M + H], HPLC (215 nM): 100%, RT 4.23 min. 1H NMR (250 MHz, MeOD) d ppm 7.56-7.63 (1H, m), 7.44-7.55 (3H, m), 7.19-7.42 (9H, m), 4.85 (1H, s), 2.48 (3H, s) |
| 8-218 | N-hydroxy-2-(3'-(methylthio)biphenyl-3-yl)-2-phenylacetamide | LRMS (ESI): (calc.) 349.44606, (found) 350 [M + H], HPLC (215 nM): 100%, RT 4.23 min. |
| 8-220 | 2-(5'-fluoro-2'-methoxybiphenyl-3-yl)-N-hydroxy-2-phenylacetamide | LRMS (ESI): (calc.) 351.3709232, (found) 352 [M + H], HPLC (215 nM): 93%, RT 4.05 min. |
| 8-221 | 2-(3'-fluoro-4'-methoxybiphenyl-3-yl)-N-hydroxy-2-phenylacetamide | LRMS (ESI): (calc.) 351.3709232, (found) 352 [M + H], HPLC (215 nM): 93%, RT 4.01 min. |
| 8-222 | 2-(3'-chloro-4'-methylbiphenyl-3-yl)-N-hydroxy-2-phenylacetamide | LRMS (ESI): (calc.) 351.82612, (found) 352 [M + H], HPLC (215 nM): 100%, RT 4.09 min. |
| 8-223 | N-hydroxy-2-phenyl-2-(3-(quinolin-8-yl)phenyl)acetamide | LRMS (ESI): (calc.) 354.40122, (found) 355 [M + H], HPLC (215 nM): 89%, RT 3.36 min. |
| 8-224 | N-hydroxy-2-(3-(isoquinolin-5-yl)phenyl)-2-phenylacetamide | LRMS (ESI): (calc.) 354.40122, (found) 355 [M + H], HPLC (215 nM): 90%, RT 2.95 min. |
| 8-226 | N-hydroxy-2-phenyl-2-(3-(quinolin-3-yl)phenyl)acetamide | LRMS (ESI): (calc.) 354.40122, (found) 355 [M + H], HPLC (215 nM): 100%, RT 3.4 min. |
| 8-228 | 2-(3'-chloro-4'-fluorobiphenyl-3-yl)-N-hydroxy-2-phenylacetamide | LRMS (ESI): (calc.) 355.7900032, (found) 356 [M + H], HPLC (215 nM): 92%, RT 4.31 min. |
| 8-229 | 2-(4'-chloro-3'-fluorobiphenyl-3-yl)-N-hydroxy-2-phenylacetamide | LRMS (ESI): (calc.) 355.7900032, (found) 356 [M + H], HPLC (215 nM): 93%, RT 4.33 min. |
| 8-231 | 2-(4'-chloro-2'-fluorobiphenyl-3-yl)-N-hydroxy-2-phenylacetamide | LRMS (ESI): (calc.) 355.7900032, (found) 356 [M + H], HPLC (215 nM): 100%, RT 4.33 min. |
| 8-232 | N-hydroxy-2-(3-(1-methyl-1H-indol-5-yl)phenyl)-2-phenylacetamide | LRMS (ESI): (calc.) 356.4171, (found) 357 [M + H], HPLC (215 nM): 91%, RT 3.53 min. |
| 8-233 | 2-(3-(benzo[b]thiophen-2-yl)phenyl)-N-hydroxy-2-phenylacetamide | LRMS (ESI): (calc.) 359.44088, (found) 360 [M + H], HPLC (215 nM): 92%, RT 4.4 min. |
| 8-234 | 2-(3-(benzo[b]thiophen-3-yl)phenyl)-N-hydroxy-2-phenylacetamide | LRMS (ESI): (calc.) 359.44088, (found) 360 [M + H], HPLC (215 nM): 100%, RT 4.35 min. |
| 8-235 | 2-(3'-acetamidobiphenyl-3-yl)-N-hydroxy-2-phenylacetamide | LRMS (ESI): (calc.) 360.4058, (found) 361 [M + H], HPLC (215 nM): 90%, RT 3.5 min. |
| 8-236 | 3'-(2-(hydroxyamino)-2-oxo-1-phenylethyl)-N-methylbiphenyl-4-carboxamide | LRMS (ESI): (calc.) 360.4058, (found) 361 [M + H], HPLC (215 nM): 93%, RT 3.37 min. |
| 8-237 | 2-(3-(2,3-dihydrobenzo[b][1,4]dioxin-6-yl)phenyl)-N-hydroxy-2-phenylacetamide | LRMS (ESI): (calc.) 361.39056, (found) 362 [M + H], HPLC (215 nM): 89%, RT 3.93 min. |
| 8-239 | N-hydroxy-2-(4'-isopropoxybiphenyl-3-yl)-2 phenylacetamide | LRMS (ESI): (calc.) 361.43362, (found) 362 [M + H], HPLC (215 nM): 92%, RT 4.36 min. |

TABLE VIII-continued

Compounds prepared according general Schemes above

| Cpd # | Name | Characterization |
|---|---|---|
| 8-241 | N-hydroxy-2-(4'-(3-hydroxypropyl)biphenyl-3-yl)-2-phenylacetamide | LRMS (ESI): (calc.) 361.43362, (found) 362 [M + H], HPLC (215 nM): 91%, RT 4.06 min. |
| 8-242 | 2-(4'-acetamidobiphenyl-3-yl)-N-hydroxy-2-phenylacetamide | LRMS (ESI): (calc.) 360.4058, (found) 361 [M + H], HPLC (215 nM): 87%, RT 3.46 min. |
| 8-243 | (E)-2-(3-(4-chlorostyryl)phenyl)-N-hydroxy-2-phenylacetamide | LRMS (ESI): (calc.) 363.83682, (found) 364 [M + H], HPLC (215 nM): 89%, RT 4.55 min. |
| 8-245 | N-hydroxy-2-(3-(4-methylnaphthalen-1-yl)phenyl)-2-phenylacetamide | LRMS (ESI): (calc.) 367.43974, (found) 368 [M + H], HPLC (215 nM): 88%, RT 4.56 min. |
| 8-247 | 2-(5'-chloro-2'-methoxybiphenyl-3-yl)-N-hydroxy-2-phenylacetamide | LRMS (ESI): (calc.) 367.82552, (found) 368 [M + H], HPLC (215 nM): 90%, RT 4.25 min. |
| 8-248 | 2-(3'-chloro-4'-methoxybiphenyl-3-yl)-N-hydroxy-2-phenylacetamide | LRMS (ESI): (calc.) 367.82552, (found) 368 [M + H], HPLC (215 nM): 100%, RT 4.18 min. |
| 8-249 | 2-(2',5'-difluoro-4'-methoxybiphenyl-3-yl)-N-hydroxy-2-phenylacetamide | LRMS (ESI): (calc.) 369.3613864, (found) 370 [M + H], HPLC (215 nM): 100%, RT 4.08 min. |
| 8-251 | 2-(4'-(2-cyanopropan-2-yl)biphenyl-3-yl)-N-hydroxy-2-phenylacetamide | LRMS (ESI): (calc.) 370.44368, (found) 371 [M + H], HPLC (215 nM): 100%, RT 4.12 min. |
| 8-252 | N-hydroxy-2-phenyl-2-(3'-(trifluoromethyl)biphenyl-3-yl)acetamide | LRMS (ESI): (calc.) 371.3524496, (found) 372 [M + H], HPLC (215 nM): 94%, RT 4.35 min.<br>1H NMR (250 MHz, MeOD) d ppm 7.73-7.88 (2H, m), 7.57-7.68 (3H, m), 7.54 (1H, d, J = 7.61 Hz), 7.17-7.47 (7H, m), 4.89 (1H, s-masked by H2O) |
| 8-253 | N-hydroxy-2-phenyl-2-(4'-(trifluoromethyl)biphenyl-3-yl)acetamide | LRMS (ESI): (calc.) 371.3524496, (found) 372 [M + H], HPLC (215 nM): 94%, RT 4.37 min. |
| 8-254 | 2-(4'-(acetamidomethyl)biphenyl-3-yl)-N-hydroxy-2-phenylacetamide | LRMS (ESI): (calc.) 374.43238, (found) 375 [M + H], HPLC (215 nM): 93%, RT 4.79 min. |
| 8-255 | 3'-(2-(hydroxyamino)-2-oxo-1-phenylethyl)-N,N-dimethylbiphenyl-3-carboxamide | LRMS (ESI): (calc.) 374.43238, (found) 375 [M + H], HPLC (215 nM): 91%, RT 3.53 min. |
| 8-256 | 2-(3'-(acetamidomethyl)biphenyl-3-yl)-N-hydroxy-2-phenylacetamide | LRMS (ESI): (calc.) 374.43238, (found) 375 [M + H], HPLC (215 nM): 93%, RT 3.68 min. |
| 8-257 | methyl 3'-(2-(hydroxyamino)-2-oxo-1-phenylethyl)biphenyl-4-ylcarbamate | LRMS (ESI): (calc.) 376.4052, (found) 377 [M + H], HPLC (215 nM): 88%, RT 3.72 min. |
| 8-258 | N-hydroxy-2-(4'-(isopropylthio)biphenyl-3-yl)-2-phenylacetamide | LRMS (ESI): (calc.) 377.49922, (found) 378 [M + H], HPLC (215 nM): 87%, RT 4.62 min. |
| 8-259 | N-cyclopropyl-3'-(2-(hydroxyamino)-2-oxo-1-phenylethyl)biphenyl-4-carboxamide | LRMS (ESI): (calc.) 386.44308, (found) 387 [M + H], HPLC (215 nM): 94%, RT 3.55 min. |
| 8-260 | N-hydroxy-2-phenyl-2-(2'-(trifluoromethoxy)biphenyl-3-yl)acetamide | LRMS (ESI): (calc.) 387.3518496, (found) 388 [M + H], HPLC (215 nM): 92%, RT 4.29 min. |
| 8-261 | N-hydroxy-2-phenyl-2-(4'-(trifluoromethoxy)biphenyl-3-yl)acetamide | LRMS (ESI): (calc.) 387.3518496, (found) 388 [M + H], HPLC (215 nM): 93%, RT 4.44 min. |
| 8-262 | N-hydroxy-2-phenyl-2-(3'-(trifluoromethoxy)biphenyl-3-yl)acetamide | LRMS (ESI): (calc.) 387.3518496, (found) 388 [M + H], HPLC (215 nM): 91%, RT 4.42 min. |
| 8-263 | N-hydroxy-2-(4'-morpholinobiphenyl-3-yl)-2-phenylacetamide | LRMS (ESI): (calc.) 388.45896, (found) 389 [M + H], HPLC (215 nM): 90%, RT 4.08 min. |
| 8-264 | N-hydroxy-2-phenyl-2-p-tolylacetamide | LRMS (ESI): (calc.) 241.2851, (found) 242 [M + H], HPLC (215 nM): 95%, RT 3.55 min. 1H NMR (250 MHz, MeOD) d ppm 7.01-7.38 (9H, m), 4.74 (1H, s), 2.30 (3H, s) |
| 8-265 | 2-(4-ethylphenyl)-N-hydroxy-2-phenylacetamide | LRMS (ESI): (calc.) 255.31168, (found) 256 [M + H], HPLC (215 nM): 95%, RT 3.78 min. |
| 8-266 | 2-(4-butylphenyl)-N-hydroxy-2-phenylacetamide | LRMS (ESI): (calc.) 283.36484, (found) 284 [M + H], HPLC (215 nM): 93%, RT 4.25 min. |

TABLE VIII-continued

Compounds prepared according general Schemes above

| Cpd # | Name | Characterization |
|---|---|---|
| 8-267 | N-hydroxy-2-(4-isobutylphenyl)-2-phenylacetamide | LRMS (ESI): (calc.) 283.36484, (found) 284 [M + H], HPLC (215 nM): 92%, RT 4.21 min. |
| 8-268 | 2-(4-cyclopentylphenyl)-N-hydroxy-2-phenylacetamide | LRMS (ESI): (calc.) 295.37554, (found) 296 [M + H], HPLC (215 nM): 92%, RT 4.27 min. |
| 8-269 | 2-(4-hexylphenyl)-N-hydroxy-2-phenylacetamide | LRMS (ESI): (calc.) 311.418, (found) 312 [M + H], HPLC (215 nM): 94%, RT 4.78 min, 1H NMR (250 MHz, MeOD) d ppm 7.16-7.36 (7H, m), 7.11 (2H, d), 4.75 (1H, s), 2.34-2.71 (2H, m), 1.47-1.70 (2H, m), 1.15-1.43 (6H, m), 0.89 (3H, t) |
| 8-270 | N-hydroxy-2-(4'-methylbiphenyl-4-yl)-2-phenylacetamide | LRMS (ESI): (calc.) 317.38106, (found) 318 [M + H], HPLC (215 nM): 89%, RT 4.24 min. |
| 8-271 | N-hydroxy-2-(2'-methylbiphenyl-4-yl)-2-phenylacetamide | LRMS (ESI): (calc.) 317.38106, (found) 318 [M + H], HPLC (215 nM): 100%, RT 4.19 min. |
| 8-272 | 2-(3'-fluorobiphenyl-4-yl)-N-hydroxy-2-phenylacetamide | LRMS (ESI): (calc.) 321.3449432, (found) 322 [M + H], HPLC (215 nM): 90%, RT 4.08 min. |
| 8-273 | 2-(2'-fluorobiphenyl-4-yl)-N-hydroxy-2-phenylacetamide | LRMS (ESI): (calc.) 321.3449432, (found) 322 [M + H], HPLC (215 nM): 87%, RT 4.04 min. |
| 8-274 | 2-(4-(2-fluoropyridin-3-yl)phenyl)-N-hydroxy-2-phenylacetamide | LRMS (ESI): (calc.) 322.3330032, (found) 323 [M + H], HPLC (215 nM): 100%, RT 3.55 min. |
| 8-275 | 2-(4-(6-fluoropyridin-3-yl)phenyl)-N-hydroxy-2-phenylacetamide | LRMS (ESI): (calc.) 322.3330032, (found) 323 [M + H], HPLC (215 nM): 100%, RT 3.61 min. |
| 8-276 | 2-(4-(3,5-dimethylisoxazol-4-yl)phenyl)-N-hydroxy-2-phenylacetamide | LRMS (ESI): (calc.) 322.35782, (found) 323 [M + H], HPLC (215 nM): 100%, RT 3.55 min. |
| 8-277 | N-hydroxy-2-(4-(4-methylthiophen-3-yl)phenyl)-2-phenylacetamide | LRMS (ESI): (calc.) 323.40878, (found) 324 [M + H], HPLC (215 nM): 90%, RT 4.1 min. |
| 8-278 | 2-(2'-cyanobiphenyl-4-yl)-N-hydroxy-2-phenylacetamide | LRMS (ESI): (calc.) 328.36394, (found) 329 [M + H], HPLC (215 nM): 88%, RT 3.81 min. |
| 8-279 | N-hydroxy-2-(3'-methoxybiphenyl-4-yl)-2-phenylacetamide | LRMS (ESI): (calc.) 333.38046, (found) 334 [M + H], HPLC (215 nM): 92%, RT 4.02 min. |
| 8-280 | N-hydroxy-2-(2'-methoxybiphenyl-4-yl)-2-phenylacetamide | LRMS (ESI): (calc.) 333.38046, (found) 334 [M + H], HPLC (215 nM): 95%, RT 4.02 min. 1H NMR (250 MHz, MeOD) d ppm 7.16-7.50 (11H, m), 6.83-7.10 (2H, m), 4.82 (1H, s), 3.75 (3H, s) |
| 8-281 | N-hydroxy-2-(3'-(hydroxymethyl)biphenyl-4-yl)-2-phenylacetamide | LRMS (ESI): (calc.) 333.38046, (found) 334 [M + H], HPLC (215 nM): 88%, RT 3.46 min. |
| 8-282 | N-hydroxy-2-(4-(6-methoxypyridin-3-yl)phenyl)-2-phenylacetamide | LRMS (ESI): (calc.) 334.36852, (found) 335 [M + H], HPLC (215 nM): 86%, RT 3.72 min. |
| 8-283 | 2-(4'-fluoro-2'-methylbiphenyl-4-yl)-N-hydroxy-2-phenylacetamide | LRMS (ESI): (calc.) 335.3715232, (found) 336 [M + H], HPLC (215 nM): 91%, RT 4.24 min. |
| 8-284 | 2-(3'-chlorobiphenyl-4-yl)-N-hydroxy-2-phenylacetamide | LRMS (ESI): (calc.) 337.79954, (found) 338 [M + H], HPLC (215 nM): 93%, RT 4.29 min. |
| 8-285 | 2-(4-(6-chloropyridin-3-yl)phenyl)-N-hydroxy-2-phenylacetamide | LRMS (ESI): (calc.) 338.7876, (found) 339 [M + H], HPLC (215 nM): 90%, RT 3.76 min. |
| 8-286 | 2-(2',5'-difluorobiphenyl-4-yl)-N-hydroxy-2-phenylacetamide | LRMS (ESI): (calc.) 339.3354064, (found) 340 [M + H], HPLC (215 nM): 89%, RT 4.1 min, 1H NMR (250 MHz, MeOD) d ppm 7.05-7.53 (12H, m), 4.85 (1H, s) |
| 8-287 | 2-(2',4'-difluorobiphenyl-4-yl)-N-hydroxy-2-phenylacetamide | LRMS (ESI): (calc.) 339.3354064, (found) 340 [M + H], HPLC (215 nM): 89%, RT 4.12 min. |
| 8-288 | 2-(4-(5-chlorothiophen-2-yl)phenyl)-N-hydroxy-2-phenylacetamide | LRMS (ESI): (calc.) 343.82726, (found) 344 [M + H], HPLC (215 nM): 98%, RT 4.37 min. |
| 8-289 | N-hydroxy-2-(4'-isopropylbiphenyl-4-yl)-2-phenylacetamide | LRMS (ESI): (calc.) 345.43422, (found) 346 [M + H], HPLC (215 nM): 100%, RT 4.64 min. |
| 8-290 | N-hydroxy-2-phenyl-2-(4'-propylbiphenyl-4-yl)acetamide | LRMS (ESI): (calc.) 345.43422, (found) 346 [M + H], HPLC (215 nM): 93%, RT 4.69 min. |
| 8-291 | 2-(3'-(dimethylamino)biphenyl-4-yl)-N-hydroxy-2-phenylacetamide | LRMS (ESI): (calc.) 346.42228, (found) 347 [M + H], HPLC (215 nM): 100%, RT 3.36 min. |

TABLE VIII-continued

Compounds prepared according general Schemes above

| Cpd # | Name | Characterization |
|---|---|---|
| 8-292 | 2-(4-(benzo[d][1,3]dioxol-5-yl)phenyl)-N-hydroxy-2-phenylacetamide | LRMS (ESI): (calc.) 347.36398, (found) 348 [M + H], HPLC (215 nM): 88%, RT 3.94 min. |
| 8-293 | (E)-2-(4-(4-fluorostyryl)phenyl)-N-hydroxy-2-phenylacetamide | LRMS (ESI): (calc.) 347.3822232, (found) 348 [M + H], HPLC (215 nM): 96%, RT 4.33 min. |
| 8-294 | 2-(2'-ethoxybiphenyl-4-yl)-N-hydroxy-2-phenylacetamide | LRMS (ESI): (calc.) 347.40704, (found) 348 [M + H], HPLC (215 nM): 91%, RT 4.21 min. |
| 8-295 | 2-(3'-ethoxybiphenyl-4-yl)-N-hydroxy-2-phenylacetamide | LRMS (ESI): (calc.) 347.40704, (found) 348 [M + H], HPLC (215 nM): 100%, RT 4.24 min. |
| 8-296 | 2-(4'-ethoxybiphenyl-4-yl)-N-hydroxy-2-phenylacetamide | LRMS (ESI): (calc.) 347.40704, (found) 348 [M + H], HPLC (215 nM): 94%, RT 4.21 min. |
| 8-297 | N-hydroxy-2-(4'-(methoxymethyl)biphenyl-4-yl)-2-phenylacetamide | LRMS (ESI): (calc.) 347.40704, (found) 348 [M + H], HPLC (215 nM): 92%, RT 3.94 min. |
| 8-298 | N-hydroxy-2-(3'-(methylthio)biphenyl-4-yl)-2-phenylacetamide | LRMS (ESI): (calc.) 349.44606, (found) 350 [M + H], HPLC (215 nM): 100%, RT 4.26 min. |
| 8-299 | 2-(5'-fluoro-2'-methoxybiphenyl-4-yl)-N-hydroxy-2-phenylacetamide | LRMS (ESI): (calc.) 351.3709232, (found) 352 [M + H], HPLC (215 nM): 94%, RT 4.08 min. 1H NMR (250 MHz, MeOD) d ppm 7.16-7.49 (9H, m), 6.87-7.07 (3H, m), 4.80 (1H, s), 3.70 (3H, s) |
| 8-300 | 2-(3'-fluoro-4'-methoxybiphenyl-4-yl)-N-hydroxy-2-phenylacetamide | LRMS (ESI): (calc.) 351.3709232, (found) 352 [M + H], HPLC (215 nM): 100%, RT 4.02 min. 1H NMR (250 MHz, MeOD) d ppm 7.46-7.61 (2H, m), 7.20-7.45 (9H, m), 7.00-7.20 (1H, m), 4.81 (1H, s), 3.88 (3H, s) |
| 8-301 | 2-(3'-chloro-4'-methylbiphenyl-4-yl)-N-hydroxy-2-phenylacetamide | LRMS (ESI): (calc.) 351.82612, (found) 352 [M + H], HPLC (215 nM): 92%, RT 4.52 min. |
| 8-302 | N-hydroxy-2-phenyl-2-(4-(quinolin-8-yl)phenyl)acetamide | LRMS (ESI): (calc.) 354.40122, (found) 355 [M + H], HPLC (215 nM): 100%, RT 3.44 min. |
| 8-303 | N-hydroxy-2-(4-(isoquinolin-5-yl)phenyl)-2-phenylacetamide | LRMS (ESI): (calc.) 354.40122, (found) 355 [M + H], HPLC (215 nM): 86%, RT 2.93 min. |
| 8-304 | 2-(3'-chloro-4'-fluorobiphenyl-4-yl)-N-hydroxy-2-phenylacetamide | LRMS (ESI): (calc.) 355.7900032, (found) 356 [M + H], HPLC (215 nM): 87%, RT 4.33 min. |
| 8-305 | 2-(4'-chloro-3'-fluorobiphenyl-4-yl)-N-hydroxy-2-phenylacetamide | LRMS (ESI): (calc.) 355.7900032, (found) 356 [M + H], HPLC (215 nM): 95%, RT 4.36 min. |
| 8-306 | 2-(4'-chloro-2'-fluorobiphenyl-4-yl)-N-hydroxy-2-phenylacetamide | LRMS (ESI): (calc.) 355.7900032, (found) 356 [M + H], HPLC (215 nM): 93%, RT 4.36 min. |
| 8-307 | N-hydroxy-2-(4-(1-methyl-1H-indol-5-yl)phenyl)-2-phenylacetamide | LRMS (ESI): (calc.) 356.4171, (found) 357 [M + H], HPLC (215 nM): 100%, RT 4.13 min. |
| 8-308 | 2-(4-(benzo[b]thiophen-2-yl)phenyl)-N-hydroxy-2-phenylacetamide | LRMS (ESI): (calc.) 359.44088, (found) 360 [M + H], HPLC (215 nM): 98%, RT 4.46 min. |
| 8-309 | 2-(4-(benzo[b]thiophen-3-yl)phenyl)-N-hydroxy-2-phenylacetamide | LRMS (ESI): (calc.) 359.44088, (found) 360 [M + H], HPLC (215 nM): 93%, RT 4.38 min. |
| 8-310 | 2-(3'-acetamidobiphenyl-4-yl)-N-hydroxy-2-phenylacetamide | LRMS (ESI): (calc.) 360.4058, (found) 361 [M + H], HPLC (215 nM): 92%, RT 3.48 min. |
| 8-311 | 2-(4-(2,3-dihydrobenzo[b][1,4]dioxin-6-yl)phenyl)-N-hydroxy-2-phenylacetamide | LRMS (ESI): (calc.) 361.39056, (found) 362 [M + H], HPLC (215 nM): 89%, RT 3.93 min. |
| 8-312 | N-hydroxy-2-(4'-isopropoxybiphenyl-4-yl)-2-phenylacetamide | LRMS (ESI): (calc.) 361.43362, (found) 362 [M + H], HPLC (215 nM): 96%, RT 4.39 min. |
| 8-313 | N-hydroxy-2-(4'-(3-hydroxypropyl)biphenyl-4-yl)-2-phenylacetamide | LRMS (ESI): (calc.) 361.43362, (found) 362 [M + H], HPLC (215 nM): 91%, RT 3.66 min. 1H NMR (250 MHz, MeOD) d ppm 7.43-7.64 (4H, m), 7.08-7.42 (9H, m), 4.83 (1H, br. s.), 3.58 (2H, t, J = 6.09 Hz), 2.70 (2H, t, J = 7.31 Hz), 1.68-1.98 (2H, m) |
| 8-314 | 2-(4'-ethoxy-3'-fluorobiphenyl-4-yl)-N-hydroxy-2-phenylacetamide | LRMS (ESI): (calc.) 365.3975032, (found) 366 [M + H], HPLC (215 nM): 100%, RT 4.23 min. |
| 8-315 | N-hydroxy-2-(4-(4-methylnaphthalen-1-yl)phenyl)-2-phenylacetamide | LRMS (ESI): (calc.) 367.43974, (found) 368 [M + H], HPLC (215 nM): 91%, RT 4.61 min. |

TABLE VIII-continued

Compounds prepared according general Schemes above

| Cpd # | Name | Characterization |
|---|---|---|
| 8-316 | 2-(5'-chloro-2'-methoxybiphenyl-4-yl)-N-hydroxy-2-phenylacetamide | LRMS (ESI): (calc.) 367.82552, (found) 368 [M + H], HPLC (215 nM): 91%, RT 4.29 min. |
| 8-317 | 2-(3'-chloro-4'-methoxybiphenyl-4-yl)-N-hydroxy-2-phenylacetamide | LRMS (ESI): (calc.) 367.82552, (found) 368 [M + H], HPLC (215 nM): 92%, RT 4.17 min. |
| 8-318 | 2-(2',5'-difluoro-4'-methoxybiphenyl-4-yl)-N-hydroxy-2-phenylacetamide | LRMS (ESI): (calc.) 369.3613864, (found) 370 [M + H], HPLC (215 nM): 87%, RT 4.08 min. |
| 8-319 | N-hydroxy-2-(4-(6-hydroxynaphthalen-2-yl)phenyl)-2-phenylacetamide | LRMS (ESI): (calc.) 369.41256, (found) 370 [M + H], HPLC (215 nM): 92%, RT 3.76 min. |
| 8-320 | 2-(4'-(2-cyanopropan-2-yl)biphenyl-4-yl)-N-hydroxy-2-phenylacetamide | LRMS (ESI): (calc.) 370.44368, (found) 371 [M + H], HPLC (215 nM): 100%, RT 4.1 min. |
| 8-321 | N-hydroxy-2-phenyl-2-(3'-(trifluoromethyl)biphenyl-4-yl)acetamide | LRMS (ESI): (calc.) 371.3524496, (found) 372 [M + H], HPLC (215 nM): 91%, RT 4.36 min. |
| 8-322 | N-hydroxy-2-phenyl-2-(4'-(trifluoromethyl)biphenyl-4-yl)acetamide | LRMS (ESI): (calc.) 371.3524496, (found) 372 [M + H], HPLC (215 nM): 92%, RT 4.4 min. |
| 8-323 | 2-(4'-(acetamidomethyl)biphenyl-4-yl)-N-hydroxy-2-phenylacetamide | LRMS (ESI): (calc.) 374.43238, (found) 375 [M + H], HPLC (215 nM): 95%, RT 3.36 min. |
| 8-324 | 4'-(2-(hydroxyamino)-2-oxo-1-phenylethyl)-N,N-dimethylbiphenyl-3-carboxamide | LRMS (ESI): (calc.) 374.43238, (found) 375 [M + H], HPLC (215 nM): 90%, RT 3.5 min. |
| 8-325 | 2-(3'-(acetamidomethyl)biphenyl-4-yl)-N-hydroxy-2-phenylacetamide | LRMS (ESI): (calc.) 374.43238, (found) 375 [M + H], HPLC (215 nM): 97%, RT 3.4 min. |
| 8-326 | methyl 4'-(2-(hydroxyamino)-2-oxo-1-phenylethyl)biphenyl-4-ylcarbamate | LRMS (ESI): (calc.) 376.4052, (found) 377 [M + H], HPLC (215 nM): 94%, RT 3.69 min. |
| 8-327 | N-hydroxy-2-(4'-(isopropylthio)biphenyl-4-yl)-2-phenylacetamide | LRMS (ESI): (calc.) 377.49922, (found) 378 [M + H], HPLC (215 nM): 98%, RT 4.66 min. |
| 8-328 | N-hydroxy-2-(3'-(methylsulfonyl)biphenyl-4-yl)-2-phenylacetamide | LRMS (ESI): (calc.) 381.44486, (found) 382 [M + H], HPLC (215 nM): 93%, RT 3.53 min. |
| 8-329 | N-cyclopropyl-4'-(2-(hydroxyamino)-2-oxo-1-phenylethyl)biphenyl-4-carboxamide | LRMS (ESI): (calc.) 386.44308, (found) 387 [M + H], HPLC (215 nM): 86%, RT 3.53 min. |
| 8-330 | N-hydroxy-2-phenyl-2-(2'-(trifluoromethoxy)biphenyl-4-yl)acetamide | LRMS (ESI): (calc.) 387.3518496, (found) 388 [M + H], HPLC (215 nM): 92%, RT 4.32 min. |
| 8-331 | N-hydroxy-2-phenyl-2-(4'-(trifluoromethoxy)biphenyl-4-yl)acetamide | LRMS (ESI): (calc.) 387.3518496, (found) 388 [M + H], HPLC (215 nM): 94%, RT 4.46 min. 1H NMR (250 MHz, MeOD) d ppm 7.69 (2H, d, J = 8.83 Hz), 7.58 (2H, d), 7.19-7.47 (9H, m), 4.84 (1H, s) |
| 8-332 | N-hydroxy-2-phenyl-2-(3'-(trifluoromethoxy)biphenyl-4-yl)acetamide | LRMS (ESI): (calc.) 387.3518496, (found) 388 [M + H], HPLC (215 nM): 92%, RT 4.46 min. |
| 8-333 | N-hydroxy-2-(4'-(N-methylsulfamoyl)biphenyl-4-yl)-2-phenylacetamide | LRMS (ESI): (calc.) 396.4595, (found) 397 [M + H], HPLC (215 nM): 94%, RT 3.52 min. 1H NMR (250 MHz, MeOD) d ppm 7.70-8.02 (4H, m), 7.60 (2H, d, J = 7.01 Hz), 7.03-7.50 (7H, m), 4.87 (1H, s), 2.52 (3H, s) |
| 8-334 | N-hydroxy-2-(3'-(methylsulfonamido)biphenyl-4-yl)-2-phenylacetamide | LRMS (ESI): (calc.) 396.4595, (found) 397 [M + H], HPLC (215 nM): 93%, RT 3.54 min. |
| 8-335 | N-hydroxy-2-(4'-(methylsulfonamido)biphenyl-4-yl)-2-phenylacetamide | LRMS (ESI): (calc.) 396.4595, (found) 397 [M + H], HPLC (215 nM): 90%, RT 3.48 min. |
| 8-336 | 2-(3'-chloro-4'-(trifluoromethyl)biphenyl-4-yl)-N-hydroxy-2-phenylacetamide | LRMS (ESI): (calc.) 405.7975096, (found) 406 [M + H], HPLC (215 nM): 94%, RT 4.6 min. |
| 8-337 | N-hydroxy-2-phenyl-2-(4-propionylpiperazin-1-yl)acetamide | LRMS (ESI): (calc.) 291.34554, (found) 292.11 [M + H], HPLC (215 nM): 98%, RT 2.05 min. |

TABLE VIII-continued

Compounds prepared according general Schemes above

| Cpd # | Name | Characterization |
|---|---|---|
| 8-338 | 2-(4-(cyclopropanecarbonyl)-1,4-diazepan-1-yl)-N-hydroxy-2-phenylacetamide | LRMS (ESI): (calc.) 317.38282, (found) 318.18 [M + H], HPLC (215 nM): 98.14%, RT 2.03 min. |
| 8-339 | 2-(4-(cyclopropanecarbonyl)piperazin-1-yl)-N-hydroxy-2-phenylacetamide | LRMS (ESI): (calc.) 303.35624, (found) 304.13 [M + H], HPLC (215 nM): 93.9%, RT 2.16 min. |
| 8-340 | N-hydroxy-2-(4-isobutyryl-1,4-diazepan-1-yl)-2-phenylacetamide | LRMS (ESI): (calc.) 319.3987, (found) 320.2 [M + H], HPLC (215 nM): 87.81%, RT 2.17 min. |
| 8-341 | N-hydroxy-2-(4-isobutyrylpiperazin-1-yl)-2-phenylacetamide | LRMS (ESI): (calc.) 305.37212, (found) 306.14 [M + H], HPLC (215 nM): 100%, RT 2.32 min. |
| 8-342 | N-hydroxy-2-(4-(3-methylbut-2-enoyl)-1,4-diazepan-1-yl)-2-phenylacetamide | LRMS (ESI): calc. 331.4094, (found) 332.17 [M + H], HPLC (215 nM): 95.55%, RT 2.32 min. |
| 8-343 | N-hydroxy-2-(4-(3-methylbut-2-enoyl)piperazin-1-yl)-2-phenylacetamide | LRMS (ESI): (calc.) 317.38282, (found) 318.18 [M + H], HPLC (215 nM): 94%, RT 2.46 min. 1H NMR (250 MHz, DMSO-d6) d ppm 10.85 (1H, s), 8.92 (1H, s), 7.23-7.48 (5H, m), 5.86 (1H, s), 3.67 (1H, s), 3.39-3.54 (4H, m), 2.15-2.40 (4H, m), 1.74-1.83 (6H, m) |
| 8-344 | 2-(4-(cyclobutanecarbonyl)piperazin-1-yl)-N-hydroxy-2-phenylacetamide | LRMS (ESI): (calc.) 317.38282, (found) 318.12 [M + H], HPLC (215 nM): 91.6%, RT 2.48 min. |
| 8-345 | N-hydroxy-2-(4-(3-methylbutanoyl)-1,4-diazepan-1-yl)-2-phenylacetamide | LRMS (ESI): (calc.) 333.42528, (found) 334.18 [M + H], HPLC (215 nM): 89.3%, RT 2.43 min. |
| 8-346 | N-hydroxy-2-(4-(3-methylbutanoyl)piperazin-1-yl)-2-phenylacetamide | LRMS (ESI): (calc.) 319.3987, (found) 320.19 [M + H], HPLC (215 nM): 98.07%, RT 2.6 min. |
| 8-347 | N-hydroxy-2-(4-(2-methylbutanoyl)-1,4-diazepan-1-yl)-2-phenylacetamide | LRMS (ESI): (calc.) 333.42528, (found) 334.2 [M + H], HPLC (215 nM): 89.12%, RT 2.41 min. |
| 8-348 | N-hydroxy-2-(4-(2-methylbutanoyl)piperazin-1-yl)-2-phenylacetamide | LRMS (ESI): (calc.) 319.3987, (found) 320.13 [M + H], HPLC (215 nM): 90%, RT 2.58 min. |
| 8-349 | 2-(4-(furan-3-carbonyl)-1,4-diazepan-1-yl)-N-hydroxy-2-phenylacetamide | LRMS (ESI): (calc.) 343.37704, (found) 344.14 [M + H], HPLC (215 nM): 92.62%, RT 2.18 min. |
| 8-350 | 2-(4-(furan-3-carbonyl)piperazin-1-yl)-N-hydroxy-2-phenylacetamide | LRMS (ESI): (calc.) 329.35046, (found) 330.14 [M + H], HPLC (215 nM): 100%, RT 2.39 min. |
| 8-351 | 2-(4-(cyclopentanecarbonyl)-1,4-diazepan-1-yl)-N-hydroxy-2-phenylacetamide | LRMS (ESI): (calc.) 345.43598, (found) 346.31 [M + H], HPLC (215 nM): 93.61%, RT 2.47 min. |
| 8-352 | 2-(4-(cyclopentanecarbonyl)piperazin-1-yl)-N-hydroxy-2-phenylacetamide | LRMS (ESI): (calc.) 331.4094, (found) 332.17 [M + H], HPLC (215 nM): 96%, RT 2.67 min. |
| 8-353 | N-hydroxy-2-phenyl-2-(4-(pyrrolidine-1-carbonyl)-1,4-diazepan-1-yl)acetamide | LRMS (ESI): (calc.) 346.42404, (found) 347.233 [M + H], HPLC (215 nM): 88.42%, RT 2.3 min. |
| 8-354 | N-hydroxy-2-phenyl-2-(4-(pyrrolidine-1-carbonyl)piperazin-1-yl)acetamide | LRMS (ESI): (calc.) 332.39746, (found) 333.15 [M + H], HPLC (215 nM): 97%, RT 2.3 min. |
| 8-355 | 2-(4-(3,3-dimethylbutanoyl)-1,4-diazepan-1-yl)-N-hydroxy-2-phenylacetamide | LRMS (ESI): (calc.) 347.45186, (found) 348.23 [M + H], HPLC (215 nM): 94.68%, RT 2.63 min. |
| 8-356 | 2-(4-(3,3-dimethylbutanoyl)piperazin-1-yl)-N-hydroxy-2-phenylacetamide | LRMS (ESI): (calc.) 333.42528, (found) 334.18 [M + H], HPLC (215 nM): 92.28%, RT 2.78 min. |
| 8-357 | 2-(4-(2-ethylbutanoyl)-1,4-diazepan-1-yl)-N-hydroxy-2-phenylacetamide | LRMS (ESI): (calc.) 347.45186, (found) 348.23 [M + H], HPLC (215 nM): 92.9%, RT 2.62 min. |
| 8-358 | 2-(4-(2-ethylbutanoyl)piperazin-1-yl)-N-hydroxy-2-phenylacetamide | LRMS (ESI): (calc.) 333.42528, (found) 334.18 [M + H], HPLC (215 nM): 95%, RT 2.81 min. 1H NMR (250 MHz, DMSO-d6) d ppm 10.83 (1H, s), 8.91 (1H, s), 7.18-7.56 (5H, m), 3.63 (1H, s), 3.50 (4H, br. s.), 2.27 (4H, br. s.), 1.19-1.57 (5H, m), 0.74 (6H, t, J = 7.23 Hz) |

TABLE VIII-continued

Compounds prepared according general Schemes above

| Cpd # | Name | Characterization |
|---|---|---|
| 8-359 | N-hydroxy-2-(4-((R)-2-methylpentanoyl)-1,4-diazepan-1-yl)-2-phenylacetamide | LRMS (ESI): (calc.) 347.45186, (found) 348.29 [M + H], HPLC (215 nM): 88.26%, RT 2.62 min. |
| 8-360 | N-hydroxy-2-(4-(2-methylpentanoyl)piperazin-1-yl)-2-phenylacetamide | LRMS (ESI): (calc.) 333.42528, (found) 334.18 [M + H], HPLC (215 nM): 95.97%, RT 2.84 min. |
| 8-361 | 2-(4-benzoyl-1,4-diazepan-1-yl)-N-hydroxy-2-phenylacetamide | LRMS (ESI): (calc.) 353.41492, (found) 354.16 [M + H], HPLC (215 nM): 100%, RT 2.45 min. |
| 8-362 | 2-(4-benzoylpiperazin-1-yl)-N-hydroxy-2-phenylacetamide | LRMS (ESI): (calc.) 339.38834, (found) 340.17 [M + H], HPLC (215 nM): 95.84%, RT 2.68 min. |
| 8-363 | 2-(4-(2-chlorobutanoyl)piperazin-1-yl)-N-hydroxy-2-phenylacetamide | LRMS (ESI): (calc.) 339.81718, (found) 340.11 [M + H], HPLC (215 nM): 94.83%, RT 2.79 min. 1H NMR (250 MHz, DMSO-d6) d ppm 10.87 (1H, s), 8.94 (1H, s), 7.24-7.49 (5H, m), 4.82 (1H, t, J = 6.70 Hz), 3.64-3.74 (1H, m), 3.43-3.63 (4H, m), 2.24-2.42 (4H, m), 1.68-2.00 (2H, m), 0.91 (3H, t, J = 7.23 Hz) |
| 8-364 | N-hydroxy-2-(4-(5-methylisoxazole-3-carbonyl)-1,4-diazepan-1-yl)-2-phenylacetamide | LRMS (ESI): (calc.) 358.39168, (found) 359.2 [M + H], HPLC (215 nM): 88.3%, RT 2.36 min. |
| 8-365 | N-hydroxy-2-(4-(5-methylisoxazole-3-carbonyl)piperazin-1-yl)-2-phenylacetamide | LRMS (ESI): (calc.) 344.3651, (found) 345.23 [M + H], HPLC (215 nM): 100%, RT 2.6 min. |
| 8-366 | N-hydroxy-2-phenyl-2-(4-(thiophene-3-carbonyl)piperazin-1-yl)acetamide | LRMS (ESI): (calc.) 345.41606, (found) 346.09 [M + H], HPLC (215 nM): 97.07%, RT 2.58 min. |
| 8-367 | N-hydroxy-2-phenyl-2-(4-(thiophene-2-carbonyl)-1,4-diazepan-1-yl)acetamide | LRMS (ESI): (calc.) 359.44264, (found) 360.14 [M + H], HPLC (215 nM): 92.58%, RT 2.39 min. |
| 8-368 | N-hydroxy-2-phenyl-2-(4-(thiophene-2-carbonyl)piperazin-1-yl)acetamide | LRMS (ESI): (calc.) 345.41606, (found) 346.09 [M + H], HPLC (215 nM): 100%, RT 2.63 min. |
| 8-369 | 2-(4-(2-cyclopentylacetyl)-1,4-diazepan-1-yl)-N-hydroxy-2-phenylacetamide | LRMS (ESI): (calc.) 359.46256, (found) 360.22 [M + H], HPLC (215 nM): 89.58%, RT 2.74 min. |
| 8-370 | 2-(4-(2-cyclopentylacetyl)piperazin-1-yl)-N-hydroxy-2-phenylacetamide | LRMS (ESI): (calc.) 345.43598, (found) 346.16 [M + H], HPLC (215 nM): 100%, RT 2.92 min. 1H NMR (250 MHz, DMSO-d6) d ppm 10.86 (1H, s), 8.93 (1H, s), 7.22-7.50 (5H, m), 3.65 (1H, s), 3.38-3.54 (4H, m), 2.28 (6H, d, J = 7.01 Hz), 2.00-2.16 (1H, m), 1.64-1.79 (2H, m), 1.37-1.62 (4H, m), 0.99-1.18 (2H, m) |
| 8-371 | 2-(4-(cyclohexanecarbonyl)-1,4-diazepan-1-yl)-N-hydroxy-2-phenylacetamide | LRMS (ESI): (calc.) 359.46256, (found) 360.2 [M + H], HPLC (215 nM): 100%, RT 2.68 min. |
| 8-372 | N-hydroxy-2-phenyl-2-(4-(tetrahydro-2H-pyran-4-carbonyl)-1,4-diazepan-1-yl)acetamide | LRMS (ESI): (calc.) 361.43538, (found) 362.16 [M + H], HPLC (215 nM): 100%, RT 2.02 min. 1H NMR (250 MHz, DMSO-d6) d ppm 10.81 (1H, br. s.), 8.93 (1H, br. s.), 7.17-7.53 (5H, m), 3.90-4.16 (1H, m), 3.75-3.90 (2H, m), 3.37-3.67 (6H, m), 3.22-3.31 (1H, m), 2.53-2.90 (4H, m), 1.42-1.84 (6H, m) |
| 8-373 | N-hydroxy-2-phenyl-2-(4-(tetrahydro-2H-pyran-4-carbonyl)piperazin-1-yl)acetamide | LRMS (ESI): (calc.) 347.4088, (found) 348.17 [M + H], HPLC (215 nM): 100%, RT 2.16 min. |
| 8-374 | N-hydroxy-2-(4-(morpholine-4-carbonyl)piperazin-1-yl)-2-phenylacetamide | LRMS (ESI): (calc.) 348.39686, (found) 349.26 [M + H], HPLC (215 nM): 98%, RT 2.04 min. |
| 8-375 | N-hydroxy-2-(4-(4-methylbenzoyl)piperazin-1-yl)-2-phenylacetamide | LRMS (ESI): (calc.) 353.41492, (found) 354.16 [M + H], HPLC (215 nM): 100%, RT 2.91 min. |
| 8-376 | 2-(4-(3-chloro-2,2-dimethylpropanoyl)piperazin-1-yl)-N-hydroxy-2-phenylacetamide | LRMS (ESI): (calc.) 353.84376, (found) 354 [M + H], HPLC (215 nM): 89%, RT 2.72 min. |
| 8-377 | phenyl 4-(2-(hydroxyamino)-2-oxo-1-phenylethyl)-1,4-diazepane-1-carboxylate | LRMS (ESI): (calc.) 369.41432, (found) 370 [M + H], HPLC (215 nM): 92%, RT 2.76 min. |
| 8-378 | 2-(4-(2-fluorobenzoyl)-1,4-diazepan-1-yl)-N-hydroxy-2-phenylacetamide | LRMS (ESI): (calc.) 371.4053832, (found) 372.17 [M + H], HPLC (215 nM): 88.83%, RT 2.52 min. |

TABLE VIII-continued

Compounds prepared according general Schemes above

| Cpd # | Name | Characterization |
|---|---|---|
| 8-379 | 2-(4-(2-fluorobenzoyl)piperazin-1-yl)-N-hydroxy-2-phenylacetamide | LRMS (ESI) (calc.) 357.3788032, (found) 358.13 [M + H], HPLC (215 nM): 100%, RT 2.78 min. |
| 8-380 | 2-(4-(4-fluorobenzoyl)-1,4-diazepan-1-yl)-N-hydroxy-2-phenylacetamide | LRMS (ESI): (calc.) 371.4053832, (found) 372.17 [M + H], HPLC (215 nM): 91.3%, RT 2.56 min. |
| 8-381 | 2-(4-(4-fluorobenzoyl)piperazin-1-yl)-N-hydroxy-2-phenylacetamide | LRMS (ESI): (calc.) 357.3788032, (found) 358.14 [M + H], HPLC (215 nM): 91.7%, RT 2.79 min. |
| 8-382 | 2-(4-(3-fluorobenzoyl)-1,4-diazepan-1-yl)-N-hydroxy-2-phenylacetamide | LRMS (ESI): (calc.) 371.4053832, (found) 372.17 [M + H], HPLC (215 nM): 89.97%, RT 2.55 min. |
| 8-383 | 2-(4-(3-fluorobenzoyl)piperazin-1-yl)-N-hydroxy-2-phenylacetamide | LRMS (ESI): (calc.) 357.3788032, (found) 358.13 [M + H], HPLC (215 nM): 100%, RT 2.82 min. |
| 8-384 | 2-(4-(2,5-dimethylfuran-3-carbonyl)-1,4-diazepan-1-yl)-N-hydroxy-2-phenylacetamide | LRMS (ESI): (calc.) 371.4302, (found) 372.19 [M + H], HPLC (215 nM): 93.24%, RT 2.61 min. |
| 8-385 | 2-(4-(2,5-dimethylfuran-3-carbonyl)piperazin-1-yl)-N-hydroxy-2-phenylacetamide | LRMS (ESI): (calc.) 357.40362, (found) 358.13 [M + H], HPLC (215 nM): 94.92%, RT 2.83 min. |
| 8-386 | 2-(4-(1,3-dimethyl-1H-pyrazole-5-carbonyl)-1,4-diazepan-1-yl)-N-hydroxy-2-phenylacetamide | LRMS (ESI): (calc.) 371.4335, (found) 372.23 [M + H], HPLC (215 nM): 90.69%, RT 2.3 min. |
| 8-387 | 2-(4-(1,3-dimethyl-1H-pyrazole-5-carbonyl)piperazin-1-yl)-N-hydroxy-2-phenylacetamide | LRMS (ESI): (calc.) 357.40692, (found) 358.14 [M + H], HPLC (215 nM): 88.07%, RT 2.54 min. |
| 8-388 | N-hydroxy-2-phenyl-2-(4-(2-(thiophen-2-yl)acetyl)-1,4-diazepan-1-yl)acetamide | LRMS (ESI): (calc.) 373.46922, (found) 374.14 [M + H], HPLC (215 nM): 93.44%, RT 2.5 min. |
| 8-389 | N-hydroxy-2-phenyl-2-(4-(2-(thiophen-2-yl)acetyl)piperazin-1-yl)acetamide | LRMS (ESI): (calc.) 359.44264, (found) 360.08 [M + H], HPLC (215 nM): 100%, RT 2.71 min. |
| 8-390 | N-hydroxy-2-(4-(3-methylthiophene-2-carbonyl)-1,4-diazepan-1-yl)-2-phenylacetamide | LRMS (ESI): (calc.) 373.46922, (found) 374.13 [M + H], HPLC (215 nM): 86.94%, RT 2.56 min. |
| 8-391 | N-hydroxy-2-(4-(3-methylthiophene-2-carbonyl)piperazin-1-yl)-2-phenylacetamide | LRMS (ESI): (calc.) 359.44264, (found) 360.14 [M + H], HPLC (215 nM): 93.51%, RT 2.84 min. |
| 8-392 | 2-(4-(3-cyclopentylpropanoyl)-1,4-diazepan-1-yl)-N-hydroxy-2-phenylacetamide | LRMS (ESI): (calc.) 373.48914, (found) 374.25 [M + H], HPLC (215 nM): 92%, RT 2.97 min. |
| 8-393 | 2-(4-(3-cyclopentylpropanoyl)piperazin-1-yl)-N-hydroxy-2-phenylacetamide | LRMS (ESI): (calc.) 359.46256, (found) 360.2 [M + H], HPLC (215 nM): 96.18%, RT 3.19 min. |
| 8-394 | 2-(4-(3,4-dimethylbenzoyl)-1,4-diazepan-1-yl)-N-hydroxy-2-phenylacetamide | LRMS (ESI): (calc.) 381.46808, (found) 382.23 [M + H], HPLC (215 nM): 92.92%, RT 2.85 min. |
| 8-395 | 2-(4-(3,4-dimethylbenzoyl)piperazin-1-yl)-N-hydroxy-2-phenylacetamide | LRMS (ESI): (calc.) 367.4415, (found) 368 [M + H], HPLC (215 nM): 92%, RT 3.1 min. |
| 8-396 | 2-(4-(2,3-dimethylbenzoyl)piperazin-1-yl)-N-hydroxy-2-phenylacetamide | LRMS (ESI): (calc.) 367.4415, (found) 368.14 [M + H], HPLC (215 nM): 92.79%, RT 3.06 min. |
| 8-397 | 2-(4-(4-ethylbenzoyl)-1,4-diazepan-1-yl)-N-hydroxy-2-phenylacetamide | LRMS (ESI): (calc.) 381.46808, (found) 382.25 [M + H], HPLC (215 nM): 93.16%, RT 2.87 min. |
| 8-398 | 2-(4-(4-ethylbenzoyl)piperazin-1-yl)-N-hydroxy-2-phenylacetamide | LRMS (ESI): (calc.) 367.4415, (found) 368 [M + H], HPLC (215 nM): 95%, RT 3.14 min. |

TABLE VIII-continued

Compounds prepared according general Schemes above

| Cpd # | Name | Characterization |
|---|---|---|
| 8-399 | N-hydroxy-2-(4-(2-phenoxyacetyl)-1,4-diazepan-1-yl)-2-phenylacetamide | LRMS (ESI): (calc.) 383.4409, (found) 384.2 [M + H], HPLC (215 nM): 100%, RT 2.62 min. |
| 8-400 | N-hydroxy-2-(4-(2-phenoxyacetyl)piperazin-1-yl)-2-phenylacetamide | LRMS (ESI): (calc.) 369.41432, (found) 370 [M + H], HPLC (215 nM): 88%, RT 2.68 min. |
| 8-401 | N-hydroxy-2-(4-(4-methoxybenzoyl)-1,4-diazepan-1-yl)-2-phenylacetamide | LRMS (ESI): (calc.) 383.4409, (found) 384.2 [M + H], HPLC (215 nM): 91.2%, RT 2.57 min. |
| 8-402 | N-hydroxy-2-(4-(4-methoxybenzoyl)piperazin-1-yl)-2-phenylacetamide | LRMS (ESI): (calc.) 369.41432, (found) 370.16 [M + H], HPLC (215 nM): 100%, RT 2.74 min. |
| 8-403 | N-hydroxy-2-(4-(3-methoxybenzoyl)piperazin-1-yl)-2-phenylacetamide | LRMS (ESI): (calc.) 369.41432, (found) 370.16 [M + H], HPLC (215 nM): 94.88%, RT 2.81 min. |
| 8-404 | 2-(4-(2-(4-fluorophenyl)acetyl)-1,4-diazepan-1-yl)-N-hydroxy-2-phenylacetamide | LRMS (ESI): (calc.) 385.4319632, (found) 386.22 [M + H], HPLC (215 nM): 96.3%, RT 2.68 min. |
| 8-405 | 2-(4-(2-(4-fluorophenyl)acetyl)piperazin-1-yl)-N-hydroxy-2-phenylacetamide | LRMS (ESI): (calc.) 371.4053832, (found) 372.13 [M + H], HPLC (215 nM): 95%, RT 2.88 min. |
| 8-406 | 2-(4-(5-fluoro-2-methylbenzoyl)-1,4-diazepan-1-yl)-N-hydroxy-2-phenylacetamide | LRMS (ESI): (calc.) 385.4319632, (found) 386.22 [M + H], HPLC (215 nM): 90.26%, RT 2.73 min. |
| 8-407 | 2-(4-(5-fluoro-2-methylbenzoyl)piperazin-1-yl)-N-hydroxy-2-phenylacetamide | LRMS (ESI): (calc.) 371.4053832, (found) 372.15 [M + H], HPLC (215 nM): 92.01%, RT 3.01 min. |
| 8-408 | 2-(4-(3-fluoro-4-methylbenzoyl)-1,4-diazepan-1-yl)-N-hydroxy-2-phenylacetamide | LRMS (ESI): (calc.) 385.4319632, (found) 386.16 [M + H], HPLC (215 nM): 90.65%, RT 2.78 min. |
| 8-409 | 2-(4-(3-fluoro-4-methylbenzoyl)piperazin-1-yl)-N-hydroxy-2-phenylacetamide | LRMS (ESI): (calc.) 371.4053832, (found) 372.17 [M + H], HPLC (215 nM): 88.85%, RT 3.05 min. |
| 8-410 | 2-(4-(4-fluoro-3-methylbenzoyl)-1,4-diazepan-1-yl)-N-hydroxy-2-phenylacetamide | LRMS (ESI): (calc.) 385.4319632, (found) 386.22 [M + H], HPLC (215 nM): 98%, RT 2.77 min. |
| 8-411 | 2-(4-(4-fluoro-3-methylbenzoyl)piperazin-1-yl)-N-hydroxy-2-phenylacetamide | LRMS (ESI): (calc.) 371.4053832, (found) 372.17 [M + H], HPLC (215 nM): 92.1%, RT 3.04 min. 1H NMR (250 MHz, DMSO-d6) d ppm 10.87 (1H, s), 8.92 (1H, s), 7.08-7.50 (8H, m), 3.69 (1H, s), 3.37-3.66 (4H, m), 2.27-2.45 (4H, m), 2.24 (3H, s) |
| 8-412 | 2-(4-(3-cyclohexylpropanoyl)-1,4-diazepan-1-yl)-N-hydroxy-2-phenylacetamide | LRMS (ESI): (calc.) 387.51572, (found) 388.3 [M + H], HPLC (215 nM): 95.55%, RT 3.13 min. |
| 8-413 | 2-(4-(3-cyclohexylpropanoyl)piperazin-1-yl)-N-hydroxy-2-phenylacetamide | LRMS (ESI): (calc.) 373.48914, (found) 374.2 [M + H], HPLC (215 nM): 100%, RT 3.38 min. |
| 8-414 | 2-(4-(2-chlorobenzoyl)piperazin-1-yl)-N-hydroxy-2-phenylacetamide | LRMS (ESI): (calc.) 373.8334, (found) 374.13 [M + H], HPLC (215 nM): 94.15%, RT 2.92 min. |
| 8-415 | 2-(4-(3-chlorobenzoyl)-1,4-diazepan-1-yl)-N-hydroxy-2-phenylacetamide | LRMS (ESI): (calc.) 387.85998, (found) 388.11 [M + H], HPLC (215 nM): 92.78%, RT 2.76 min. |
| 8-416 | 2-(4-(3-chlorobenzoyl)piperazin-1-yl)-N-hydroxy-2-phenylacetamide | LRMS (ESI): (calc.) 373.8334, (found) 374.13 [M + H], HPLC (215 nM): 100%, RT 3.03 min. |
| 8-417 | 2-(4-(4-chlorobenzoyl)piperazin-1-yl)-N-hydroxy-2-phenylacetamide | LRMS (ESI): (calc.) 373.8334, (found) 374.2 [M + H], HPLC (215 nM): 86.95%, RT 3.03 min. |
| 8-418 | 2-(4-(6-chloronicotinoyl)piperazin-1-yl)-N-hydroxy-2-phenylacetamide | LRMS (ESI): (calc.) 374.82146, (found) 375.15 [M + H], HPLC (215 nM): 100%, RT 2.64 min. |

TABLE VIII-continued

Compounds prepared according general Schemes above

| Cpd # | Name | Characterization |
|---|---|---|
| 8-419 | 2-(4-(2-chloroisonicotinoyl)-1,4-diazepan-1-yl)-N-hydroxy-2-phenylacetamide | LRMS (ESI): (calc.) 388.84804, (found) 389.13 [M + H], HPLC (215 nM): 100%, RT 2.4 min. |
| 8-420 | 2-(4-(2-chloroisonicotinoyl)piperazin-1-yl)-N-hydroxy-2-phenylacetamide | LRMS (ESI): (calc.) 374.82146, (found) 375.14 [M + H], HPLC (215 nM): 100%, RT 2.65 min. |
| 8-421 | 2-(4-(3,4-difluorobenzoyl)piperazin-1-yl)-N-hydroxy-2-phenylacetamide | LRMS (ESI): (calc.) 375.3692664, (found) 376.14 [M + H], HPLC (215 nM): 100%, RT 2.95 min. |
| 8-422 | 2-(4-(3,5-difluorobenzoyl)-1,4-diazepan-1-yl)-N-hydroxy-2-phenylacetamide | LRMS (ESI): (calc.) 389.3958464, (found) 390.19 [M + H], HPLC (215 nM): 91.53%, RT 2.67 min. |
| 8-423 | 2-(4-(3,5-difluorobenzoyl)piperazin-1-yl)-N-hydroxy-2-phenylacetamide | LRMS (ESI): (calc.) 375.3692664, (found) 376.21 [M + H], HPLC (215 nM): 92%, RT 2.95 min. |
| 8-424 | 2-(4-(2,2-dimethylbutanoyl)-1,4-diazepan-1-yl)-N-hydroxy-2-phenylacetamide | LRMS (ESI): (calc.) 347.45186, (found) 348.23 [M + H], HPLC (215 nM): 90.73%, RT 2.58 min. |
| 8-425 | 2-(4-(2,2-dimethylbutanoyl)piperazin-1-yl)-N-hydroxy-2-phenylacetamide | LRMS (ESI): (calc.) 333.42528, (found) 334.18 [M + H], HPLC (215 nM): 100%, RT 2.77 min. |
| 8-426 | 2-(4-(2,5-difluorobenzoyl)piperazin-1-yl)-N-hydroxy-2-phenylacetamide | LRMS (ESI): (calc.) 375.3692664, (found) 376.21 [M + H], HPLC (215 nM): 100%, RT 2.89 min. |
| 8-427 | 2-(4-(5-chloro-1-methyl-1H-pyrazole-4-carbonyl)-1,4-diazepan-1-yl)-N-hydroxy-2-phenylacetamide | LRMS (ESI): (calc.) 391.85198, (found) 392.14 [M + H], HPLC (215 nM): 98.36%, RT 2.2 min. |
| 8-428 | 2-(4-(5-chloro-1-methyl-1H-pyrazole-4-carbonyl)piperazin-1-yl)-N-hydroxy-2-phenylacetamide | LRMS (ESI): (calc.) 377.8254, (found) 378.09 [M + H], HPLC (215 nM): 91.73%, RT 2.42 min. |
| 8-429 | N-hydroxy-2-phenyl-2-(4-(2-phenylbutanoyl)piperazin-1-yl)acetamide | LRMS (ESI): (calc.) 381.46808, (found) 382 [M + H], HPLC (215 nM): 91%, RT 3.18 min. |
| 8-430 | N-hydroxy-2-phenyl-2-(4-(4-propylbenzoyl)piperazin-1-yl)acetamide | LRMS (ESI): (calc.) 381.46808, (found) 382.19 [M + H], HPLC (215 nM): 92.69%, RT 3.37 min. |
| 8-431 | 2-(4-(4-(dimethylamino)benzoyl)-1,4-diazepan-1-yl)-N-hydroxy-2-phenylacetamide | LRMS (ESI): (calc.) 396.48272, (found) 397.24 [M + H], HPLC (215 nM): 100%, RT 2.58 min 1H NMR (250 MHz, DMSO-d6) d ppm 10.83 (1H, br. s.), 8.94 (1H, br. s.), 7.17-7.53 (7H, m), 6.69 (2H, d, J = 8.98 Hz), 4.02 (1H, br. s.), 3.42-3.70 (4H, m), 2.93 (6H, s), 2.55-2.84 (4H, m), 1.50-1.89 (2H, m) |
| 8-432 | 2-(4-(4-(dimethylamino)benzoyl)piperazin-1-yl)-N-hydroxy-2-phenylacetamide | LRMS (ESI): (calc.) 382.45614, (found) 383.26 [M + H], HPLC (215 nM): 100%, RT 2.75 min. 1H NMR (250 MHz, DMSO-d6) d ppm 10.86 (1H, s), 8.93 (1H, s), 7.15-7.56 (7H, m), 6.61-6.76 (2H, m), 3.64-3.74 (1H, m), 3.50 (4H, br. s.), 2.93 (6H, s), 2.34 (4H, br. s.) |
| 8-433 | 2-(4-(benzo[d][1,3]dioxole-5-carbonyl)-1,4-diazepan-1-yl)-N-hydroxy-2-phenylacetamide | LRMS (ESI): (calc.) 397.42442, (found) 398.19 [M + H], HPLC (215 nM): 91%, RT 2.49 min. |
| 8-434 | 2-(4-(benzo[d][1,3]dioxole-5-carbonyl)piperazin-1-yl)-N-hydroxy-2-phenylacetamide | LRMS (ESI): (calc.) 383.39784, (found) 384.14 [M + H], HPLC (215 nM): 90.71%, RT 2.7 min. |
| 8-435 | N-hydroxy-2-(4-(2-(4-methoxyphenyl)acetyl)piperazin-1-yl)-2-phenylacetamide | LRMS (ESI): (calc.) 383.4409, (found) 384.2 [M + H], HPLC (215 nM): 93.41%, RT 2.82 min. |
| 8-436 | N-hydroxy-2-(4-(2-(3-methoxyphenyl)acetyl)piperazin-1-yl)-2-phenylacetamide | LRMS (ESI): (calc.) 383.4409, (found) 384.14 [M + H], HPLC (215 nM): 100%, RT 2.85 min. |
| 8-437 | N-hydroxy-2-(4-(2-phenoxypropanoyl)piperazin-1-yl)-2-phenylacetamide | LRMS (ESI): (calc.) 383.4409, (found) 384 [M + H], HPLC (215 nM): 87%, RT 3.02 min. 1H NMR (250 MHz, DMSO-d6) d ppm 10.85 (1H, s), 8.92 (1H, br. s.), 7.16-7.51 (7H, m), 6.87-6.97 (1H, m), 6.76-6.86 (2H, m), 5.08-5.29 (1H, m), 3.66 (1H, s), 3.38-3.64 (4H, m), 2.19-2.39 (4H, m), 1.39 (3H, d, J = 6.09 Hz) |
| 8-438 | 2-(4-(2-(benzyloxy)acetyl)-1,4-diazepan-1-yl)-N-hydroxy-2-phenylacetamide | LRMS (ESI): (calc.) 397.46748, (found) 398 [M + H], HPLC (215 nM): 91%, RT 2.67 min. |

TABLE VIII-continued

Compounds prepared according general Schemes above

| Cpd # | Name | Characterization |
|---|---|---|
| 8-439 | 2-(4-(2-(benzyloxy)acetyl)piperazin-1-yl)-N-hydroxy-2-phenylacetamide | LRMS (ESI) (calc.) 383.4409, (found) 384 [M + H], HPLC (215 nM): 86%, RT 2.68 min. |
| 8-440 | 2-(4-(4-ethoxybenzoyl)-1,4-diazepan-1-yl)-N-hydroxy-2-phenylacetamide | LRMS (ESI): (calc.) 397.46748, (found) 398.24 [M + H], HPLC (215 nM): 89.56%, RT 2.75 min. 1H NMR (250 MHz, DMSO-d6) d ppm 10.82 (1H, s), 8.92 (1H, s), 7.14-7.54 (7H, m), 6.94 (2H, d, J = 8.53 Hz), 3.91-4.18 (3H, m), 3.39-3.87 (4H, m), 2.55-2.84 (4H, m), 1.48-1.90 (2H, m), 1.33 (3H, t, J = 7.01 Hz) |
| 8-441 | 2-(4-(4-ethoxybenzoyl)piperazin-1-yl)-N-hydroxy-2-phenylacetamide | LRMS (ESI): (calc.) 383.4409, (found) 384.14 [M + H], HPLC (215 nM): 100%, RT 2.96 min. |
| 8-442 | 2-(4-(2-ethoxybenzoyl)-1,4-diazepan-1-yl)-N-hydroxy-2-phenylacetamide | LRMS (ESI): (calc.) 397.46748, (found) 398.19 [M + H], HPLC (215 nM): 92.85%, RT 2.7 min. |
| 8-443 | 2-(4-(2-ethoxybenzoyl)piperazin-1-yl)-N-hydroxy-2-phenylacetamide | LRMS (ESI): (calc.) 383.4409, (found) 384.2 [M + H], HPLC (215 nM): 90.1%, RT 2.94 min. |
| 8-444 | N-hydroxy-2-(4-(2-nitrobenzoyl)piperazin-1-yl)-2-phenylacetamide | LRMS (ESI): (calc.) 384.3859, (found) 385.22 [M + H], HPLC (215 nM): 93%, RT 2.76 min. |
| 8-445 | N-hydroxy-2-(4-(3-nitrobenzoyl)piperazin-1-yl)-2-phenylacetamide | LRMS (ESI): (calc.) 384.3859, (found) 385.22 [M + H], HPLC (215 nM): 100%, RT 2.84 min. |
| 8-446 | N-hydroxy-2-phenyl-2-(4-(2-(phenylthio)acetyl)-1,4-diazepan-1-yl)acetamide | LRMS (ESI): (calc.) 399.5065, (found) 400.2 [M + H], HPLC (215 nM): 91.41%, RT 2.8 min. |
| 8-447 | N-hydroxy-2-phenyl-2-(4-(2-(phenylthio)acetyl)piperazin-1-yl)acetamide | LRMS (ESI): (calc.) 385.47992, (found) 386.1 [M + H], HPLC (215 nM): 100%, RT 3.03 min. |
| 8-448 | 2-(4-(3-fluoro-4-methoxybenzoyl)-1,4-diazepan-1-yl)-N-hydroxy-2-phenylacetamide | LRMS (ESI): (calc.) 401.4313632, (found) 402.16 [M + H], HPLC (215 nM): 95.14%, RT 2.62 min. |
| 8-449 | 2-(4-(3-fluoro-4-methoxybenzoyl)piperazin-1-yl)-N-hydroxy-2-phenylacetamide | LRMS (ESI): (calc.) 387.4047832, (found) 388.17 [M + H], HPLC (215 nM): 94.68%, RT 2.84 min. 1H NMR (250 MHz, DMSO-d6) d ppm 10.86 (1H, s), 8.91 (1H, s), 7.05-7.50 (8H, m), 3.85 (3H, s), 3.68 (1H, s), 3.47 (4H, br. s.), 2.34 (4H, br. s.) |
| 8-450 | 2-(4-(2-(4-chlorophenyl)acetyl)piperazin-1-yl)-N-hydroxy-2-phenylacetamide | LRMS (ESI): (calc.) 387.85998, (found) 388.11 [M + H], HPLC (215 nM): 98%, RT 3.11 min. |
| 8-451 | 2-(4-(1-naphthoyl)piperazin-1-yl)-N-hydroxy-2-phenylacetamide | LRMS (ESI): (calc.) 389.44702, (found) 390.15 [M + H], HPLC (215 nM): 93%, RT 3.15 min. |
| 8-452 | 2-(4-(2-chloro-4-fluorobenzoyl)piperazin-1-yl)-N-hydroxy-2-phenylacetamide | LRMS (ESI): (calc.) 391.8238632, (found) 392.08 [M + H], HPLC (215 nM): 100%, RT 3.05 min. |
| 8-453 | N-hydroxy-2-phenyl-2-(4-(2,4,5-trifluorobenzoyl)-1,4-diazepan-1-yl)acetamide | LRMS (ESI): (calc.) 407.3863096, (found) 408.23 [M + H], HPLC (215 nM): 90.04%, RT 2.73 min. |
| 8-454 | N-hydroxy-2-phenyl-2-(4-(2,4,5-trifluorobenzoyl)piperazin-1-yl)acetamide | LRMS (ESI): (calc.) 393.3597296, (found) 394.22 [M + H], HPLC (215 nM): 92.34%, RT 3.02 min. |
| 8-455 | N-hydroxy-2-(4-(3-methylbenzofuran-2-carbonyl)-1,4-diazepan-1-yl)-2-phenylacetamide | LRMS (ESI): (calc.) 407.4623, (found) 408.2 [M + H], HPLC (215 nM): 92.86%, RT 2.98 min. |
| 8-456 | N-hydroxy-2-(4-(3-methylbenzofuran-2-carbonyl)piperazin-1-yl)-2-phenylacetamide | LRMS (ESI): (calc.) 393.43572, (found) 394.16 [M + H], HPLC (215 nM): 100%, RT 3.3 min. |
| 8-457 | 2-(4-(chroman-3-carbonyl)piperazin-1-yl)-N-hydroxy-2-phenylacetamide | LRMS (ESI): (calc.) 395.4516, (found) 396.17 [M + H], HPLC (215 nM): 94.69%, RT 3.11 min. |
| 8-458 | 2-(4-(benzo[b]thiophene-2-carbonyl)piperazin-1-yl)-N-hydroxy-2-phenylacetamide | LRMS (ESI): (calc.) 395.47474, (found) 396.17 [M + H], HPLC (215 nM): 100%, RT 3.22 min. |
| 8-459 | 2-(4-(benzo[b]thiophene-3-carbonyl)-1,4-diazepan-1-yl)- | LRMS (ESI): (calc.) 409.50132, (found) 410.15 [M + H], HPLC (215 nM): 88.32%, RT 2.88 min. |

TABLE VIII-continued

Compounds prepared according general Schemes above

| Cpd # | Name | Characterization |
|---|---|---|
| | N-hydroxy-2-phenylacetamide | |
| 8-460 | 2-(4-(4-tert-butylbenzoyl)-1,4-diazepan-1-yl)-N-hydroxy-2-phenylacetamide | LRMS (ESI): (calc.) 409.52124, (found) 410.23 [M + H], HPLC (215 nM): 100%, RT 3.17 min. |
| 8-461 | 2-(4-(4-tert-butylbenzoyl)piperazin-1-yl)-N-hydroxy-2-phenylacetamide | LRMS (ESI): (calc.) 395.49466, (found) 396.24 [M + H], HPLC (215 nM): 92.48%, RT 3.46 min. 1H NMR (250 MHz, DMSO-d6) d ppm 10.86 (1H, br. s.), 8.92 (1H, br. s.), 7.22-7.48 (9H, m), 3.67-3.73 (1H, m), 3.35-3.66 (4H, m), 2.24-2.45 (4H, m), 1.28 (9H, s) |
| 8-462 | 2-(4-(2,3-dihydrobenzo[b][1,4]dioxine-2-carbonyl)-1,4-diazepan-1-yl)-N-hydroxy-2-phenylacetamide | LRMS (ESI): (calc.) 411.451, (found) 412.18 [M + H], HPLC (215 nM): 93.42%, RT 2.81 min. |
| 8-463 | 2-(4-(2,6-dimethoxybenzoyl)piperazin-1-yl)-N-hydroxy-2-phenylacetamide | LRMS (ESI): (calc.) 399.4403, (found) 400.14 [M + H], HPLC (215 nM): 100%, RT 2.75 min. 1H NMR (250 MHz, DMSO-d6) d ppm 10.87 (1H, br. s.), 8.94 (1H, br. s.), 7.18-7.54 (6H, m), 6.66 (2H, d, J = 8.38 Hz), 3.71 (7H, d, J = 3.81 Hz), 3.47-3.66 (2H, m), 3.00-3.17 (2H, m), 2.09-2.45 (4H, m) |
| 8-464 | 2-(4-(3,5-dimethoxybenzoyl)-1,4-diazepan-1-yl)-N-hydroxy-2-phenylacetamide | LRMS (ESI): (calc.) 413.46688, (found) 414.23 [M + H], HPLC (215 nM): 89.57%, RT 2.7 min. |
| 8-465 | 2-(4-(3,5-dimethoxybenzoyl)piperazin-1-yl)-N-hydroxy-2-phenylacetamide | LRMS (ESI): (calc.) 399.4403, (found) 400.14 [M + H], HPLC (215 nM): 97.52%, RT 2.93 min. 1H NMR (250 MHz, DMSO-d6) d ppm 10.86 (1H, br. s.), 8.92 (1H, br. s.), 7.22-7.48 (5H, m), 6.53 (1H, d, J = 2.28 Hz), 6.46 (2H, d, J = 2.28 Hz), 3.74 (6H, s), 3.70 (1H, br. s.), 3.37-3.67 (4H, m), 2.19-2.45 (4H, m) |
| 8-466 | 2-(4-(2-(4-chlorophenoxy)acetyl)piperazin-1-yl)-N-hydroxy-2-phenylacetamide | LRMS (ESI): (calc.) 403.85938, (found) 404.17 [M + H], HPLC (215 nM): 100%, RT 3.15 min. |
| 8-467 | 2-(4-(2-chloro-6-methoxyisonicotinoyl)-1,4-diazepan-1-yl)-N-hydroxy-2-phenylacetamide | LRMS (ESI): (calc.) 418.87402, (found) 419.12 [M + H], HPLC (215 nM): 96.46%, RT 2.83 min. |
| 8-468 | 2-(4-(6-chloro-2-fluoro-3-methylbenzoyl)piperazin-1-yl)-N-hydroxy-2-phenylacetamide | LRMS (ESI): (calc.) 405.8504432, (found) 406.12 [M + H], HPLC (215 nM): 91%, RT 3.25 min. |
| 8-469 | N-hydroxy-2-phenyl-2-(4-(4-(trifluoromethyl)benzoyl)piperazin-1-yl)acetamide | LRMS (ESI): (calc.) 407.3863096, (found) 408.14 [M + H], HPLC (215 nM): 100%, RT 3.25 min. |
| 8-470 | N-hydroxy-2-phenyl-2-(4-(3-(trifluoromethyl)benzoyl)-1,4-diazepan-1-yl)acetamide | LRMS (ESI): (calc.) 421.4128896, (found) 422.18 [M + H], HPLC (215 nM): 100%, RT 2.92 min. |
| 8-471 | N-hydroxy-2-phenyl-2-(4-(3-(trifluoromethyl)benzoyl)piperazin-1-yl)acetamide | LRMS (ESI): (calc.) 407.3863096, (found) 408.14 [M + H], HPLC (215 nM): 91%, RT 3.22 min. |
| 8-472 | 2-(4-(3,4-dichlorobenzoyl)-1,4-diazepan-1-yl)-N-hydroxy-2-phenylacetamide | LRMS (ESI): (calc.) 422.30504, (found) 422.12 [M + H], HPLC (215 nM): 92.3%, RT 3.02 min. |
| 8-473 | 2-(4-(3,4-dichlorobenzoyl)piperazin-1-yl)-N-hydroxy-2-phenylacetamide | LRMS (ESI): (calc.) 408.27846, (found) 408.13 [M + H], HPLC (215 nM): 98%, RT 3.28 min. |
| 8-474 | N-hydroxy-2-(4-(4-methyl-3,4-dihydro-2H-benzo[b][1,4]oxazine-7-carbonyl)-1,4-diazepan-1-yl)-2-phenylacetamide | LRMS (ESI): (calc.) 424.49282, (found) 425.21 [M + H], HPLC (215 nM): 91.98%, RT 2.66 min. |
| 8-475 | N-hydroxy-2-(4-(4-methyl-3,4-dihydro-2H-benzo[b][1,4]oxazine-7-carbonyl)piperazin-1-yl)-2-phenylacetamide | LRMS (ESI): (calc.) 410.46624, (found) 411.19 [M + H], HPLC (215 nM): 90.31%, RT 2.83 min. |
| 8-476 | 2-(4-(4-butoxybenzoyl)piperazin-1-yl)-N-hydroxy-2-phenylacetamide | LRMS (ESI): (calc.) 411.49406, (found) 412.17 [M + H], HPLC (215 nM): 100%, RT 3.46 min. |
| 8-477 | 2-(4-(2-(3,4-dimethoxyphenyl)acetyl)piperazin-1-yl)-N-hydroxy-2-phenylacetamide | LRMS (ESI): (calc.) 413.46688, (found) 414.19 [M + H], HPLC (215 nM): 100%, RT 2.69 min. |

TABLE VIII-continued

Compounds prepared according general Schemes above

| Cpd # | Name | Characterization |
|---|---|---|
| 8-478 | N-hydroxy-2-(4-(5-methyl-3-phenylisoxazole-4-carbonyl)-1,4-diazepan-1-yl)-2-phenylacetamide | LRMS (ESI): (calc.) 434.48764, (found) 435.22 [M + H], HPLC (215 nM): 93.4%, RT 2.88 min. |
| 8-479 | N-hydroxy-2-(4-(5-methyl-3-phenylisoxazole-4-carbonyl)piperazin-1-yl)-2-phenylacetamide | LRMS (ESI): (calc.) 420.46106, (found) 421.18 [M + H], HPLC (215 nM): 92.58%, RT 3.16 min. |
| 8-480 | N-hydroxy-2-phenyl-2-(4-(4-(thiophen-2-yl)benzoyl)-1,4-diazepan-1-yl)acetamide | LRMS (ESI): (calc.) 435.5386, (found) 436.16 [M + H], HPLC (215 nM): 86.15%, RT 3.1 min. |
| 8-481 | N-hydroxy-2-phenyl-2-(4-(4-(trifluoromethoxy)benzoyl)-1,4-diazepan-1-yl)acetamide | LRMS (ESI): (calc.) 437.4122896, (found) 438.18 [M + H], HPLC (215 nM): 89.54%, RT 3.02 min. |
| 8-482 | N-hydroxy-2-phenyl-2-(4-(4-(trifluoromethoxy)benzoyl)piperazin-1-yl)acetamide | LRMS (ESI): (calc.) 423.3857096, (found) 424.14 [M + H], HPLC (215 nM): 87.48%, RT 3.31 min. 1H NMR (250 MHz, DMSO-d6) d ppm 10.87 (1H, br. s.), 8.92 (1H, br. s.), 7.23-7.58 (9H, m), 3.37-3.76 (5H, m), 2.26-2.44 (4H, m) |
| 8-483 | N-hydroxy-2-phenyl-2-(4-(3-(trifluoromethoxy)benzoyl)-1,4-diazepan-1-yl)acetamide | LRMS (ESI): (calc.) 437.4122896, (found) 438.18 [M + H], HPLC (215 nM): 90.38%, RT 3.01 min. |
| 8-484 | N-hydroxy-2-phenyl-2-(4-(3-(trifluoromethoxy)benzoyl)piperazin-1-yl)acetamide | LRMS (ESI): (calc.) 423.3857096, (found) 424.14 [M + H], HPLC (215 nM): 100%, RT 3.31 min. |
| 8-485 | 2-(4-(2-fluoro-4-(trifluoromethyl)benzoyl)piperazin-1-yl)-N-hydroxy-2-phenylacetamide | LRMS (ESI): (calc.) 425.3767728, (found) 426.15 [M + H], HPLC (215 nM): 100%, RT 3.4 min. |
| 8-486 | 2-(4-(4-fluoro-2-(trifluoromethyl)benzoyl)piperazin-1-yl)-N-hydroxy-2-phenylacetamide | LRMS (ESI): (calc.) 425.3767728, (found) 426.09 [M + H], HPLC (215 nM): 100%, RT 3.22 min. |
| 8-487 | 2-(4-(2-(4-tert-butylphenoxy)acetyl)-1,4-diazepan-1-yl)-N-hydroxy-2-phenylacetamide | LRMS (ESI): (calc.) 439.54722, (found) 440.26 [M + H], HPLC (215 nM): 91.53%, RT 3.32 min. 1H NMR (250 MHz, DMSO-d6) d ppm 10.73-10.91 (1H, m), 8.86-9.00 (1H, m), 7.19-7.50 (7H, m), 6.74-6.88 (2H, m), 4.65-4.85 (2H, m), 3.94-4.11 (1H, m), 3.39-3.60 (4H, m), 2.53-2.82 (4H, m), 1.57-1.84 (2H, m), 1.24 (9H, s) |
| 8-488 | 2-(4-(2-(4-tert-butylphenoxy)acetyl)piperazin-1-yl)-N-hydroxy-2-phenylacetamide | LRMS (ESI): (calc.) 425.52064, (found) 426 [M + H], HPLC (215 nM): 92%, RT 3.62 min. |
| 8-489 | N-hydroxy-2-(4-(4-methoxy-3-(trifluoromethyl)benzoyl)piperazin-1-yl)-2-phenylacetamide | LRMS (ESI): (calc.) 437.4122896, (found) 438 [M + H], HPLC (215 nM): 98%, RT 3.23 min. |
| 8-490 | N-hydroxy-2-phenyl-2-(4-(4-(trifluoromethylthio)benzoyl)-1,4-diazepan-1-yl)acetamide | LRMS (ESI): (calc.) 453.4778896, (found) 454.17 [M + H], HPLC (215 nM): 89.54%, RT 3.18 min. |
| 8-491 | N-hydroxy-2-phenyl-2-(4-(4-(trifluoromethylthio)benzoyl)piperazin-1-yl)acetamide | LRMS (ESI): (calc.) 439.4513096, (found) 440.13 [M + H], HPLC (215 nM): 96.3%, RT 3.5 min. |
| 8-492 | 2-(4-(3-(2-chlorophenyl)-5-methylisoxazole-4-carbonyl)-1,4-diazepan-1-yl)-N-hydroxy-2-phenylacetamide | LRMS (ESI): (calc.) 468.9327, (found) 469.16 [M + H], HPLC (215 nM): 95.62%, RT 2.91 min. |
| 8-493 | 2-(4-(3-(2-chlorophenyl)-5-methylisoxazole-4-carbonyl)piperazin-1-yl)-N-hydroxy-2-phenylacetamide | LRMS (ESI): (calc.) 454.90612, (found) 455.12 [M + H], HPLC (215 nM): 93.38%, RT 3.25 min. |
| 8-494 | N-ethyl-4-(2-(hydroxyamino)-2-oxo-1-phenylethyl)piperazine-1-carboxamide | LRMS (ESI): (calc.) 306.36018, (found) 307 [M + H], HPLC (215 nM): 95%, RT 1.81 min. 1H NMR (500 MHz, DMSO-d6) d ppm 10.84 (1H, br. s.), 8.90 (1H, br. s.), 7.39-7.47 (2H, m), 7.24-7.38 (3H, m), 6.42 (1H, br. s.), 3.62 (1H, br. s.), 3.18-3.29 (4H, m), 2.97-3.07 (2H, m), 2.17-2.34 (4H, m), 0.98 (3H, t, J = 7.09 Hz) |
| 8-495 | 4-(2-(hydroxyamino)-2-oxo-1-phenylethyl)-N-propyl-1,4-diazepane-1-carboxamide | LRMS (ESI): (calc.) 334.41334, (found) 335 [M + H], HPLC (215 nM): 96.01%, RT 2.13 min. |
| 8-496 | 4-(2-(hydroxyamino)-2-oxo-1-phenylethyl)-N-propylpiperazine-1-carboxamide | LRMS (ESI): (calc.) 320.38676, (found) 321 [M + H], HPLC (215 nM): 98.02%, RT 2.12 min. |
| 8-497 | N-butyl-4-(2-(hydroxyamino)-2-oxo-1- | LRMS (ESI): (calc.) 348.43992, (found) 349 [M + H], HPLC (215 nM): 96.24%, RT 2.42 min. |

TABLE VIII-continued

Compounds prepared according general Schemes above

| Cpd # | Name | Characterization |
|---|---|---|
| | phenylethyl)-1,4-diazepane-1-carboxamide | |
| 8-498 | N-butyl-4-(2-(hydroxyamino)-2-oxo-1-phenylethyl)piperazine-1-carboxamide | LRMS (ESI): (calc.) 334.41334, (found) 335 [M + H], HPLC (215 nM): 95.33%, RT 2.42 min. |
| 8-499 | N-tert-butyl-4-(2-(hydroxyamino)-2-oxo-1-phenylethyl)-1,4-diazepane-1-carboxamide | LRMS (ESI): (calc.) 348.43992, (found) 349 [M + H], HPLC (215 nM): 96.57%, RT 2.4 min. |
| 8-500 | N-tert-butyl-4-(2-(hydroxyamino)-2-oxo-1-phenylethyl)piperazine-1-carboxamide | LRMS (ESI): (calc.) 334.41334, (found) 335 [M + H], HPLC (215 nM): 95.98%, RT 2.39 min. |
| 8-501 | N-cyclopentyl-4-(2-(hydroxyamino)-2-oxo-1-phenylethyl)-1,4-diazepane-1-carboxamide | LRMS (ESI): (calc.) 360.45062, (found) 361 [M + H], HPLC (215 nM): 93.81%, RT 2.42 min. |
| 8-502 | N-cyclopentyl-4-(2-(hydroxyamino)-2-oxo-1-phenylethyl)piperazine-1-carboxamide | LRMS (ESI): (calc.) 346.42404, (found) 347 [M + H], HPLC (215 nM): 95.31%, RT 2.45 min. |
| 8-503 | 4-(2-(hydroxyamino)-2-oxo-1-phenylethyl)-N-phenylpiperazine-1-carboxamide | LRMS (ESI): (calc.) 354.40298, (found) 355 [M + H], HPLC (215 nM): 95.56%, RT 2.53 min. |
| 8-504 | N-(furan-2-ylmethyl)-4-(2-(hydroxyamino)-2-oxo-1-phenylethyl)-1,4-diazepane-1-carboxamide | LRMS (ESI): (calc.) 372.41826, (found) 373 [M + H], HPLC (215 nM): 88.08%, RT 2.21 min. |
| 8-505 | N-(furan-2-ylmethyl)-4-(2-(hydroxyamino)-2-oxo-1-phenylethyl)piperazine-1-carboxamide | LRMS (ESI): (calc.) 358.39168, (found) 359 [M + H], HPLC (215 nM): 91.94%, RT 2.26 min. |
| 8-506 | 4-(2-(hydroxyamino)-2-oxo-1-phenylethyl)-N-(thiophen-2-yl)piperazine-1-carboxamide | LRMS (ESI): (calc.) 360.4307, (found) 361 [M + H], HPLC (215 nM): 91.46%, RT 2.5 min. |
| 8-507 | N-cyclohexyl-4-(2-(hydroxyamino)-2-oxo-1-phenylethyl)-1,4-diazepane-1-carboxamide | LRMS (ESI): (calc.) 374.4772, (found) 375 [M + H], HPLC (215 nM): 94.74%, RT 2.63 min. |
| 8-508 | N-cyclohexyl-4-(2-(hydroxyamino)-2-oxo-1-phenylethyl)piperazine-1-carboxamide | LRMS (ESI): (calc.) 360.45062, (found) 361 [M + H], HPLC (215 nM): 93.38%, RT 2.65 min. |
| 8-509 | N-benzyl-4-(2-(hydroxyamino)-2-oxo-1-phenylethyl)-1,4-diazepane-1-carboxamide | LRMS (ESI): (calc.) 382.45614, (found) 383 [M + H], HPLC (215 nM): 92.94%, RT 2.49 min. |
| 8-510 | N-benzyl-4-(2-(hydroxyamino)-2-oxo-1-phenylethyl)piperazine-1-carboxamide | LRMS (ESI): (calc.) 368.42956, (found) 369 [M + H], HPLC (215 nM): 100%, RT 2.56 min. |
| 8-511 | 4-(2-(hydroxyamino)-2-oxo-1-phenylethyl)-N-m-tolyl-1,4-diazepane-1-carboxamide | LRMS (ESI): (calc.) 382.45614, (found) 383 [M + H], HPLC (215 nM): 92.76%, RT 2.63 min. |
| 8-512 | 4-(2-(hydroxyamino)-2-oxo-1-phenylethyl)-N-m-tolylpiperazine-1-carboxamide | LRMS (ESI): (calc.) 368.42956, (found) 369 [M + H], HPLC (215 nM): 90.38%, RT 2.74 min. |
| 8-513 | 4-(2-(hydroxyamino)-2-oxo-1-phenylethyl)-N-p-tolyl-1,4-diazepane-1-carboxamide | LRMS (ESI): (calc.) 382.45614, (found) 383 [M + H], HPLC (215 nM): 93.39%, RT 2.62 min. |
| 8-514 | 4-(2-(hydroxyamino)-2-oxo-1-phenylethyl)-N-p-tolylpiperazine-1-carboxamide | LRMS (ESI): (calc.) 368.42956, (found) 369 [M + H], HPLC (215 nM): 93.87%, RT 2.69 min. |
| 8-515 | N-(4-fluorophenyl)-4-(2-(hydroxyamino)-2-oxo-1-phenylethyl)-1,4-diazepane-1-carboxamide | LRMS (ESI): (calc.) 386.4200232, (found) 387 [M + H], HPLC (215 nM): 96.14%, RT 2.52 min. |
| 8-516 | N-(4-fluorophenyl)-4-(2-(hydroxyamino)-2-oxo-1-phenylethyl)piperazine-1-carboxamide | LRMS (ESI): (calc.) 372.3934432, (found) 373 [M + H], HPLC (215 nM): 95.93%, RT 2.62 min. |

TABLE VIII-continued

Compounds prepared according general Schemes above

| Cpd # | Name | Characterization |
|---|---|---|
| 8-517 | N-(2-fluorophenyl)-4-(2-(hydroxyamino)-2-oxo-1-phenylethyl)-1,4-diazepane-1-carboxamide | LRMS (ESI) (calc.) 386.4200232, (found) 387 [M + H], HPLC (215 nM): 87.5%, RT 2.4 min. |
| 8-518 | N-(2-fluorophenyl)-4-(2-(hydroxyamino)-2-oxo-1-phenylethyl)piperazine-1-carboxamide | LRMS (ESI): (calc.) 372.3934432, (found) 373 [M + H], HPLC (215 nM): 93.26%, RT 2.54 min. |
| 8-519 | N-(3,5-dimethylisoxazol-4-yl)-4-(2-(hydroxyamino)-2-oxo-1-phenylethyl)-1,4-diazepane-1-carboxamide | LRMS (ESI): (calc.) 387.4329, (found) 388 [M + H], HPLC (215 nM): 99%, RT 2.05 min. 1H NMR (500 MHz, DMSO-d6) d ppm 10.82 (1H, br. s.), 8.93 (1H, br. s.), 7.69 (1H, br. s.), 7.14-7.56 (5H, m), 4.05 (1H, br. s.), 3.39-3.59 (4H, m), 2.56-2.84 (4H, m), 2.22 (3H, s), 2.05 (3H, s), 1.61-1.81 (2H, m) |
| 8-520 | N-benzoyl-4-(2-(hydroxyamino)-2-oxo-1-phenylethyl)-1,4-diazepane-1-carboxamide | LRMS (ESI): (calc.) 396.43966, (found) 397 [M + H], HPLC (215 nM): 87.37%, RT 2.45 min. |
| 8-521 | N-benzoyl-4-(2-(hydroxyamino)-2-oxo-1-phenylethyl)piperazine-1-carboxamide | LRMS (ESI): (calc.) 382.41308, (found) 383 [M + H], HPLC (215 nM): 100%, RT 2.58 min. |
| 8-522 | 4-(2-(hydroxyamino)-2-oxo-1-phenylethyl)-N-(2-methylbenzyl)-1,4-diazepane-1-carboxamide | LRMS (ESI): (calc.) 396.48272, (found) 397 [M + H], HPLC (215 nM): 92.8%, RT 2.67 min. |
| 8-523 | 4-(2-(hydroxyamino)-2-oxo-1-phenylethyl)-N-(2-methylbenzyl)piperazine-1-carboxamide | LRMS (ESI): (calc.) 382.45614, (found) 383 [M + H], HPLC (215 nM): 90.93%, RT 2.74 min. |
| 8-524 | N-(2,6-dimethylphenyl)-4-(2-(hydroxyamino)-2-oxo-1-phenylethyl)-1,4-diazepane-1-carboxamide | LRMS (ESI): (calc.) 396.48272, (found) 397 [M + H], HPLC (215 nM): 92.19%, RT 2.54 min. |
| 8-525 | N-(2,5-dimethylphenyl)-4-(2-(hydroxyamino)-2-oxo-1-phenylethyl)-1,4-diazepane-1-carboxamide | LRMS (ESI): (calc.) 396.48272, (found) 397 [M + H], HPLC (215 nM): 92%, RT 2.77 min. |
| 8-526 | N-(2,5-dimethylphenyl)-4-(2-(hydroxyamino)-2-oxo-1-phenylethyl)piperazine-1-carboxamide | LRMS (ESI): (calc.) 382.45614, (found) 383 [M + H], HPLC (215 nM): 92%, RT 2.83 min. |
| 8-527 | 4-(2-(hydroxyamino)-2-oxo-1-phenylethyl)-N-phenethyl-1,4-diazepane-1-carboxamide | LRMS (ESI): (calc.) 396.48272, (found) 397 [M + H], HPLC (215 nM): 90.59%, RT 2.65 min. |
| 8-528 | 4-(2-(hydroxyamino)-2-oxo-1-phenylethyl)-N-phenethylpiperazine-1-carboxamide | LRMS (ESI): (calc.) 382.45614, (found) 383 [M + H], HPLC (215 nM): 91.65%, RT 2.7 min. |
| 8-529 | N-(2-ethylphenyl)-4-(2-(hydroxyamino)-2-oxo-1-phenylethyl)piperazine-1-carboxamide | LRMS (ESI): (calc.) 382.45614, (found) 383 [M + H], HPLC (215 nM): 92.9%, RT 2.76 min. |
| 8-530 | N-(4-ethylphenyl)-4-(2-(hydroxyamino)-2-oxo-1-phenylethyl)-1,4-diazepane-1-carboxamide | LRMS (ESI): (calc.) 396.48272, (found) 397 [M + H], HPLC (215 nM): 87.65%, RT 2.83 min. |
| 8-531 | N-(4-ethylphenyl)-4-(2-(hydroxyamino)-2-oxo-1-phenylethyl)piperazine-1-carboxamide | LRMS (ESI): (calc.) 382.45614, (found) 383 [M + H], HPLC (215 nM): 92.16%, RT 2.96 min. |
| 8-532 | N-(2,3-dimethylphenyl)-4-(2-(hydroxyamino)-2-oxo-1-phenylethyl)-1,4-diazepane-1-carboxamide | LRMS (ESI): (calc.) 396.48272, (found) 397 [M + H], HPLC (215 nM): 93.58%, RT 2.63 min. |
| 8-533 | N-(2,3-dimethylphenyl)-4-(2-(hydroxyamino)-2-oxo-1-phenylethyl)piperazine-1-carboxamide | LRMS (ESI): (calc.) 382.45614, (found) 383 [M + H], HPLC (215 nM): 92.81%, RT 2.74 min. |
| 8-534 | 4-(2-(hydroxyamino)-2-oxo-1-phenylethyl)-N-(4-methoxyphenyl)-1,4-diazepane-1-carboxamide | LRMS (ESI): (calc.) 398.45554, (found) 399 [M + H], HPLC (215 nM): 88.68%, RT 2.44 min. |
| 8-535 | 4-(2-(hydroxyamino)-2-oxo-1-phenylethyl)-N-(4- | LRMS (ESI): (calc.) 384.42896, (found) 385 [M + H], HPLC (215 nM): 93.83%, RT 2.53 min. |

TABLE VIII-continued

Compounds prepared according general Schemes above

| Cpd # | Name | Characterization |
|---|---|---|
| | methoxyphenyl)piperazine-1-carboxamide | |
| 8-536 | 4-(2-(hydroxyamino)-2-oxo-1-phenylethyl)-N-(2-methoxyphenyl)-1,4-diazepane-1-carboxamide | LRMS (ESI): (calc.) 398.45554, (found) 399 [M + H], HPLC (215 nM): 100%, RT 2.6 min. |
| 8-537 | 4-(2-(hydroxyamino)-2-oxo-1-phenylethyl)-N-(2-methoxyphenyl)piperazine-1-carboxamide | LRMS (ESI): (calc.) 384.42896, (found) 385 [M + H], HPLC (215 nM): 100%, RT 2.68 min. |
| 8-538 | N-(5-fluoro-2-methylphenyl)-4-(2-(hydroxyamino)-2-oxo-1-phenylethyl)-1,4-diazepane-1-carboxamide | LRMS (ESI): (calc.) 400.4466032, (found) 401 [M + H], HPLC (215 nM): 86.51%, RT 2.58 min. |
| 8-539 | N-(5-fluoro-2-methylphenyl)-4-(2-(hydroxyamino)-2-oxo-1-phenylethyl)piperazine-1-carboxamide | LRMS (ESI): (calc.) 386.4200232, (found) 387 [M + H], HPLC (215 nM): 91.74%, RT 2.74 min. |
| 8-540 | 4-(2-(hydroxyamino)-2-oxo-1-phenylethyl)-N-(2-(thiophen-2-yl)ethyl)-1,4-diazepane-1-carboxamide | LRMS (ESI): (calc.) 402.51044, (found) 403 [M + H], HPLC (215 nM): 94.49%, RT 2.59 min. |
| 8-541 | 4-(2-(hydroxyamino)-2-oxo-1-phenylethyl)-N-(2-(thiophen-2-yl)ethyl)piperazine-1-carboxamide | LRMS (ESI): (calc.) 388.48386, (found) 389 [M + H], HPLC (215 nM): 90.3%, RT 2.61 min. |
| 8-542 | N-(3-chlorophenyl)-4-(2-(hydroxyamino)-2-oxo-1-phenylethyl)piperazine-1-carboxamide | LRMS (ESI): (calc.) 388.84804, (found) 389 [M + H], HPLC (215 nM): 98%, RT 2.95 min. |
| 8-543 | N-(4-chlorophenyl)-4-(2-(hydroxyamino)-2-oxo-1-phenylethyl)piperazine-1-carboxamide | LRMS (ESI): (calc.) 388.84804, (found) 389 [M + H], HPLC (215 nM): 93.87%, RT 2.9 min. |
| 8-544 | N-(3,4-difluorophenyl)-4-(2-(hydroxyamino)-2-oxo-1-phenylethyl)-1,4-diazepane-1-carboxamide | LRMS (ESI): (calc.) 404.4104864, (found) 405 [M + H], HPLC (215 nM): 94.1%, RT 2.64 min. 1H NMR (500 MHz, DMSO-d6) d ppm 10.81 (1H, br. s.), 8.92 (1H, br. s.), 8.42 (1H, br. s.), 7.56-7.76 (1H, m), 7.38-7.48 (2H, m), 7.21-7.36 (5H, m), 4.02 (1H, br. s.), 3.38-3.61 (4H, m), 2.54-2.78 (4H, m), 1.61-1.83 (2H, m) |
| 8-545 | 4-(2-(hydroxyamino)-2-oxo-1-phenylethyl)-N-(4-isopropylphenyl)-1,4-diazepane-1-carboxamide | LRMS (ESI): (calc.) 410.5093, (found) 411 [M + H], HPLC (215 nM): 87.88%, RT 3.01 min. |
| 8-546 | 4-(2-(hydroxyamino)-2-oxo-1-phenylethyl)-N-(4-isopropylphenyl)piperazine-1-carboxamide | LRMS (ESI): (calc.) 396.48272, (found) 397 [M + H], HPLC (215 nM): 87.12%, RT 3.13 min. |
| 8-547 | 4-(2-(hydroxyamino)-2-oxo-1-phenylethyl)-N-mesityl-1,4-diazepane-1-carboxamide | LRMS (ESI): (calc.) 410.5093, (found) 411 [M + H], HPLC (215 nM): 90.93%, RT 2.74 min. |
| 8-548 | 4-(2-(hydroxyamino)-2-oxo-1-phenylethyl)-N-mesitylpiperazine-1-carboxamide | LRMS (ESI): (calc.) 396.48272, (found) 397 [M + H], HPLC (215 nM): 100%, RT 2.87 min. |
| 8-549 | N-(4-(dimethylamino)phenyl)-4-(2-(hydroxyamino)-2-oxo-1-phenylethyl)-1,4-diazepane-1-carboxamide | LRMS (ESI): (calc.) 411.49736, (found) 206 [M + H], HPLC (215 nM): 90%, RT 0.75 min. 1H NMR (250 MHz, DMSO-d6) d ppm 10.80 (1H, br. s.), 8.91 (1H, br. s.), 7.88 (1H, br. s.), 7.05-7.58 (7H, m), 6.63 (2H, d, J = 9.14 Hz), 4.01 (1H, br. s.), 3.39-3.67 (4H, m), 2.81 (6H, s), 2.56-2.73 (4H, m), 1.52-1.88 (2H, m) |
| 8-550 | N-(4-(dimethylamino)phenyl)-4-(2-(hydroxyamino)-2-oxo-1-phenylethyl)piperazine-1-carboxamide | LRMS (ESI): (calc.) 397.47078, (found) 199 [M + H], HPLC (215 nM): 95%, RT 1.88 min. 1H NMR (500 MHz, DMSO-d6) d ppm 10.86 (1H, br. s.), 8.93 (1H, br. s.), 8.17 (1H, br. s.), 7.40-7.50 (2H, m), 7.26-7.40 (3H, m), 7.20 (2H, m, J = 8.83 Hz), 6.64 (2H, m, J = 8.67 Hz), 3.67 (1H, br. s.), 3.36-3.46 (4H, m), 2.82 (6H, s), 2.25-2.44 (4H, m) |
| 8-551 | N-(benzo[d][1,3]dioxol-5-yl)-4-(2-(hydroxyamino)-2-oxo-1-phenylethyl)-1,4-diazepane-1-carboxamide | LRMS (ESI): (calc.) 412.43906, (found) 413 [M + H], HPLC (215 nM): 87.59%, RT 2.41 min. |
| 8-552 | N-(benzo[d][1,3]dioxol-5-yl)-4-(2-(hydroxyamino)-2-oxo-1-phenylethyl)piperazine-1-carboxamide | LRMS (ESI): (calc.) 398.41248, (found) 399 [M + H], HPLC (215 nM): 100%, RT 2.55 min. |

TABLE VIII-continued

Compounds prepared according general Schemes above

| Cpd # | Name | Characterization |
|---|---|---|
| 8-553 | N-(2-ethoxyphenyl)-4-(2-(hydroxyamino)-2-oxo-1-phenylethyl)-1,4-diazepane-1-carboxamide | HPLC (215 nM): %, RT min. 1H NMR (500 MHz, DMSO-d6) d ppm 10.80 (1H, s), 8.91 (1H, s), 7.81 (1H, dd, J = 7.88, 0.95 Hz), 7.42 (2H, d, J = 7.09 Hz), 7.18-7.36 (4H, m), 6.91-7.00 (2H, m), 6.81-6.90 (1H, m), 3.94-4.08 (3H, m), 3.51-3.59 (2H, m), 3.47 (2H, t, J = 4.97 Hz), 2.61-2.74 (2H, m), 2.58 (2H, t, J = 5.44 Hz), 1.74 (2H, br. s.), 1.31 (3H, t, J = 6.94 Hz) |
| 8-554 | N-(2-ethoxyphenyl)-4-(2-(hydroxyamino)-2-oxo-1-phenylethyl)piperazine-1-carboxamide | LRMS (ESI): (calc.) 398.45554, (found) 399 [M + H], HPLC (215 nM): 96%, RT 2.94 min. |
| 8-555 | 4-(2-(hydroxyamino)-2-oxo-1-phenylethyl)-N-(2-methoxybenzyl)-1,4-diazepane-1-carboxamide | LRMS (ESI): (calc.) 412.48212, (found) 413 [M + H], HPLC (215 nM): 92.82%, RT 2.63 min. |
| 8-556 | 4-(2-(hydroxyamino)-2-oxo-1-phenylethyl)-N-(2-methoxybenzyl)piperazine-1-carboxamide | LRMS (ESI): (calc.) 398.45554, (found) 399 [M + H], HPLC (215 nM): 94.18%, RT 2.7 min. |
| 8-557 | 4-(2-(hydroxyamino)-2-oxo-1-phenylethyl)-N-(4-methoxybenzyl)-1,4-diazepane-1-carboxamide | LRMS (ESI): (calc.) 412.48212, (found) 413 [M + H], HPLC (215 nM): 93.36%, RT 2.55 min. |
| 8-558 | 4-(2-(hydroxyamino)-2-oxo-1-phenylethyl)-N-(4-methoxybenzyl)piperazine-1-carboxamide | LRMS (ESI): (calc.) 398.45554, (found) 399 [M + H], HPLC (215 nM): 98%, RT 2.63 min. |
| 8-559 | 4-(2-(hydroxyamino)-2-oxo-1-phenylethyl)-N-(2-nitrophenyl)-1,4-diazepane-1-carboxamide | LRMS (ESI): (calc.) 413.42712, (found) 414 [M + H], HPLC (215 nM): 89.55%, RT 2.74 min. 1H NMR (500 MHz, DMSO-d6) d ppm 10.81 (1H, br. s.), 9.26 (1H, s), 8.93 (1H, br. s.), 7.99 (1H, dd, J = 8.28, 1.18 Hz), 7.93 (1H, d, J = 8.04 Hz), 7.62-7.70 (1H, m), 7.38-7.48 (2H, m), 7.24-7.37 (3H, m), 7.12-7.22 (1H, m), 4.04 (1H, s), 3.42-3.63 (4H, m), 2.55-2.76 (4H, m), 1.75 (2H, br. s.) |
| 8-560 | 4-(2-(hydroxyamino)-2-oxo-1-phenylethyl)-N-(2-nitrophenyl)piperazine-1-carboxamide | LRMS (ESI): (calc.) 399.40054, (found) 400 [M + H], HPLC (215 nM): 96.73%, RT 2.9 min. 1H NMR (500 MHz, DMSO-d6) d ppm 10.88 (1H, br. s.), 9.24 (1H, s), 8.94 (1H, br. s.), 7.92 (1H, d, J = 8.20 Hz), 7.62 (2H, d, J = 3.94 Hz), 7.43-7.50 (2H, m), 7.26-7.41 (3H, m), 7.13-7.24 (1H, m), 3.70 (1H, br. s.), 3.39-3.54 (4H, m), 2.25-2.43 (4H, m) |
| 8-561 | 4-(2-(hydroxyamino)-2-oxo-1-phenylethyl)-N-(4-(methylthio)phenyl)-1,4-diazepane-1-carboxamide | LRMS (ESI): (calc.) 414.52114, (found) 415 [M + H], HPLC (215 nM): 100%, RT 2.8 min. |
| 8-562 | 4-(2-(hydroxyamino)-2-oxo-1-phenylethyl)-N-(4-(methylthio)phenyl)piperazine-1-carboxamide | LRMS (ESI): (calc.) 400.49456, (found) 401 [M + H], HPLC (215 nM): 97%, RT 2.9 min. |
| 8-563 | N-(4-tert-butylphenyl)-4-(2-(hydroxyamino)-2-oxo-1-phenylethyl)-1,4-diazepane-1-carboxamide | LRMS (ESI): (calc.) 424.53588, (found) 425 [M + H], HPLC (215 nM): 88.34%, RT 3.12 min. |
| 8-564 | N-(4-tert-butylphenyl)-4-(2-(hydroxyamino)-2-oxo-1-phenylethyl)piperazine-1-carboxamide | LRMS (ESI): (calc.) 410.5093, (found) 411 [M + H], HPLC (215 nM): 92.82%, RT 3.27 min. |
| 8-565 | N-(2,4-dimethoxyphenyl)-4-(2-(hydroxyamino)-2-oxo-1-phenylethyl)-1,4-diazepane-1-carboxamide | LRMS (ESI): (calc.) 428.48152, (found) 429 [M + H], HPLC (215 nM): 100%, RT 2.58 min. |
| 8-566 | N-(2,4-dimethoxyphenyl)-4-(2-(hydroxyamino)-2-oxo-1-phenylethyl)piperazine-1-carboxamide | LRMS (ESI): (calc.) 414.45494, (found) 415 [M + H], HPLC (215 nM): 88.52%, RT 2.61 min. |
| 8-567 | N-(3,5-dimethoxyphenyl)-4-(2-(hydroxyamino)-2-oxo-1-phenylethyl)piperazine-1-carboxamide | LRMS (ESI): (calc.) 414.45494, (found) 415 [M + H], HPLC (215 nM): 94%, RT 2.76 min. |
| 8-568 | N-(2,4-dichlorophenyl)-4-(2-(hydroxyamino)-2-oxo-1-phenylethyl)piperazine-1-carboxamide | LRMS (ESI): (calc.) 423.2931, (found) 423 [M + H], HPLC (215 nM): 87%, RT 3.11 min. |
| 8-569 | 4-(2-(hydroxyamino)-2-oxo-1-phenylethyl)-N-(4- | LRMS (ESI): (calc.) 438.4003496, (found) 439 [M + H], HPLC (215 nM): 87.26%, RT 3.16 min. |

TABLE VIII-continued

Compounds prepared according general Schemes above

| Cpd # | Name | Characterization |
|---|---|---|
| | (trifluoromethoxy)phenyl)piperazine-1-carboxamide | |
| 8-570 | N-benzhydryl-4-(2-(hydroxyamino)-2-oxo-1-phenylethyl)piperazine-1-carboxamide | HPLC (215 nM): 93%, RT min. 1H NMR (500 MHz, DMSO-d6) d ppm 10.83 (1H, br. s.), 8.91 (1H, s), 7.43 (2H, d, J = 7.09 Hz), 7.24-7.37 (11H, m), 7.19-7.24 (2H, m), 7.16 (1H, d, J = 8.67 Hz), 6.04 (1H, d, J = 8.67 Hz), 3.64 (1H, s), 3.35-3.41 (4H, m), 2.18-2.32 (4H, m) |
| 8-571 | 4-(2-(hydroxyamino)-2-oxo-1-phenylethyl)-N-(3,4,5-trimethoxybenzyl)piperazine-1-carboxamide | LRMS (ESI): (calc.) 458.5075, (found) 459 [M + H], HPLC (215 nM): 95%, RT 2.57 min. |
| 8-572 | N-hydroxy-2-(4-(methylsulfonyl)piperazin-1-yl)-2-phenylacetamide | LRMS (ESI): (calc.) 313.37266, (found) 314.08 [M + H], HPLC (215 nM): 88.73%, RT 2.22 min. |
| 8-573 | N-hydroxy-2-(4-(methylsulfonyl)-1,4-diazepan-1-yl)-2-phenylacetamide | LRMS (ESI): (calc.) 327.39924, (found) 328.14 [M + H], HPLC (215 nM): 98.28%, RT 1.84 min. 1H NMR (250 MHz, DMSO-d6) d ppm 10.58-11.10 (1H, m), 8.68-9.19 (1H, m), 7.18-7.54 (5H, m), 3.86-4.24 (1H, m), 3.13-3.32 (4H, m), 2.91 (3H, s), 2.66 (4H, m), 1.58-1.83 (2H, m) |
| 8-574 | 2-(4-(ethylsulfonyl)piperazin-1-yl)-N-hydroxy-2-phenylacetamide | LRMS (ESI): (calc.) 327.39924, (found) 328.14 [M + H], HPLC (215 nM): 90.73%, RT 2.43 min. |
| 8-575 | 2-(4-(ethylsulfonyl)-1,4-diazepan-1-yl)-N-hydroxy-2-phenylacetamide | LRMS (ESI): (calc.) 341.42582, (found) 342.15 [M + H], HPLC (215 nM): 98.02%, RT 2.15 min. |
| 8-576 | N-hydroxy-2-phenyl-2-(4-(propylsulfonyl)piperazin-1-yl)acetamide | LRMS (ESI): (calc.) 341.42582, (found) 342.19 [M + H], HPLC (215 nM): 93.75%, RT 2.72 min. |
| 8-577 | N-hydroxy-2-phenyl-2-(4-(propylsulfonyl)-1,4-diazepan-1-yl)acetamide | LRMS (ESI): (calc.) 355.4524, (found) 356.17 [M + H], HPLC (215 nM): 92.22%, RT 2.44 min. |
| 8-578 | 2-(4-(butylsulfonyl)piperazin-1-yl)-N-hydroxy-2-phenylacetamide | LRMS (ESI): (calc.) 355.4524, (found) 356.17 [M + H], HPLC (215 nM): 90.25%, RT 3.02 min. |
| 8-579 | 2-(4-(butylsulfonyl)-1,4-diazepan-1-yl)-N-hydroxy-2-phenylacetamide | LRMS (ESI): (calc.) 369.47898, (found) 370.21 [M + H], HPLC (215 nM): 100%, RT 2.69 min. |
| 8-580 | N-hydroxy-2-phenyl-2-(4-(phenylsulfonyl)-1,4-diazepan-1-yl)acetamide | LRMS (ESI): (calc.) 389.46862, (found) 390.19 [M + H], HPLC (215 nM): 91.46%, RT 2.76 min. |
| 8-581 | N-hydroxy-2-phenyl-2-(4-(thiophen-2-ylsulfonyl)piperazin-1-yl)acetamide | LRMS (ESI): (calc.) 381.46976, (found) 382.13 [M + H], HPLC (215 nM): 95%, RT 3.2 min. |
| 8-582 | N-hydroxy-2-phenyl-2-(4-(thiophen-2-ylsulfonyl)-1,4-diazepan-1-yl)acetamide | LRMS (ESI): (calc.) 395.49634, (found) 396.11 [M + H], HPLC (215 nM): 93.67%, RT 2.72 min. |
| 8-583 | 2-(4-(benzylsulfonyl)piperazin-1-yl)-N-hydroxy-2-phenylacetamide | LRMS (ESI): (calc.) 389.46862, (found) 390.19 [M + H], HPLC (215 nM): 97.8%, RT 3.13 min. |
| 8-584 | 2-(4-(benzylsulfonyl)-1,4-diazepan-1-yl)-N-hydroxy-2-phenylacetamide | LRMS (ESI): (calc.) 403.4952, (found) 404.17 [M + H], HPLC (215 nM): 90.24%, RT 2.8 min. |
| 8-585 | N-hydroxy-2-phenyl-2-(4-(p-tolylsulfonyl)piperazin-1-yl)acetamide | LRMS (ESI): (calc.) 389.46862, (found) 390.22 [M + H], HPLC (215 nM): 90.12%, RT 3.36 min. |
| 8-586 | N-hydroxy-2-phenyl-2-(4-(p-tolylsulfonyl)-1,4-diazepan-1-yl)acetamide | LRMS (ESI): (calc.) 403.4952, (found) 404.17 [M + H], HPLC (215 nM): 92.7%, RT 2.94 min. |
| 8-587 | N-hydroxy-2-phenyl-2-(4-(o-tolylsulfonyl)piperazin-1-yl)acetamide | LRMS (ESI): (calc.) 389.46862, (found) 390.19 [M + H], HPLC (215 nM): 92.43%, RT 3.35 min. 1H NMR (250 MHz, DMSO-d6) d ppm 10.83 (1H, s), 8.90 (1H, s), 7.76 (1H, d, J = 7.92 Hz), 7.53-7.65 (1H, m), 7.21-7.50 (7H, m), 3.69 (1H, s), 3.03 (4H, br. s.), 2.55 (3H, s), 2.26-2.46 (4H, m) |
| 8-588 | N-hydroxy-2-phenyl-2-(4-(o-tolylsulfonyl)-1,4-diazepan-1-yl)acetamide | LRMS (ESI): (calc.) 403.4952, (found) 404.22 [M + H], HPLC (215 nM): 92.91%, RT 2.95 min. |
| 8-589 | N-hydroxy-2-phenyl-2-(4-(m-tolylsulfonyl)piperazin-1-yl)acetamide | LRMS (ESI): (calc.) 389.46862, (found) 390.19 [M + H], HPLC (215 nM): 88.69%, RT 3.42 min. |
| 8-590 | N-hydroxy-2-phenyl-2-(4-(m-tolylsulfonyl)-1,4-diazepan-1-yl)acetamide | LRMS (ESI): (calc.) 403.4952, (found) 404.17 [M + H], HPLC (215 nM): 933%, RT 2.98 min. |
| 8-591 | 2-(4-(3-fluorophenylsulfonyl)piperazin- | LRMS (ESI): (calc.) 393.4325032, (found) 394.16 [M + H], HPLC (215 nM): 100%, RT 3.36 min. |

TABLE VIII-continued

Compounds prepared according general Schemes above

| Cpd # | Name | Characterization |
|---|---|---|
| | 1-yl)-N-hydroxy-2-phenylacetamide | |
| 8-592 | 2-(4-(3-fluorophenylsulfonyl)-1,4-diazepan-1-yl)-N-hydroxy-2-phenylacetamide | LRMS (ESI): (calc.) 407.4590832, (found) 408.17 [M + H], HPLC (215 nM): 89.53%, RT 2.9 min. |
| 8-593 | 2-(4-(2-fluorophenylsulfonyl)piperazin-1-yl)-N-hydroxy-2-phenylacetamide | LRMS (ESI): (calc.) 393.4325032, (found) 394.16 [M + H], HPLC (215 nM): 91.61%, RT 3.26 min. |
| 8-594 | 2-(4-(2-fluorophenylsulfonyl)-1,4-diazepan-1-yl)-N-hydroxy-2-phenylacetamide | LRMS (ESI): (calc.) 407.4590832, (found) 408.15 [M + H], HPLC (215 nM): 90.79%, RT 2.83 min. |
| 8-595 | 2-(4-(1,2-dimethyl-1H-imidazol-4-ylsulfonyl)piperazin-1-yl)-N-hydroxy-2-phenylacetamide | LRMS (ESI): (calc.) 393.46062, (found) 394.16 [M + H], HPLC (215 nM): 92.87%, RT 2.4 min. 1H NMR (250 MHz, DMSO-d6) d ppm 10.83 (1H, s), 8.89 (1H, s), 7.71 (1H, s), 7.19-7.40 (5H, m), 3.55-3.68 (4H, m), 2.96 (4H, br. s.), 2.26-2.44 (7H, m) |
| 8-596 | 2-(4-(1,2-dimethyl-1H-imidazol-4-ylsulfonyl)-1,4-diazepan-1-yl)-N-hydroxy-2-phenylacetamide | LRMS (ESI): (calc.) 407.4872, (found) 408.2 [M + H], HPLC (215 nM): 92.92%, RT 2.21 min. 1H NMR (250 MHz, DMSO-d6) d ppm 10.79 (1H, br. s.), 8.92 (1H, br. s.), 7.67 (1H, s), 7.20-7.46 (5H, m), 4.02 (1H, s), 3.59 (3H, s), 3.06-3.31 (4H, m), 2.54-2.75 (4H, m), 2.30 (3H, s), 1.54-1.79 (2H, m) |
| 8-597 | 2-(4-(3,5-dimethylisoxazol-4-ylsulfonyl)piperazin-1-yl)-N-hydroxy-2-phenylacetamide | LRMS (ESI): (calc.) 394.44538, (found) 395.16 [M + H], HPLC (215 nM): 95.88%, RT 3.23 min. |
| 8-598 | 2-(4-(3,4-dimethylphenylsulfonyl)piperazin-1-yl)-N-hydroxy-2-phenylacetamide | LRMS (ESI): (calc.) 403.4952, (found) 404.26 [M + H], HPLC (215 nM): 87.99%, RT 3.52 min. |
| 8-599 | 2-(4-(3,4-dimethylphenylsulfonyl)-1,4-diazepan-1-yl)-N-hydroxy-2-phenylacetamide | LRMS (ESI): (calc.) 417.52178, (found) 418.22 [M + H], HPLC (215 nM): 90.88%, RT 3.09 min. |
| 8-600 | 2-(4-(2,5-dimethylphenylsulfonyl)piperazin-1-yl)-N-hydroxy-2-phenylacetamide | LRMS (ESI): (calc.) 403.4952, (found) 404.17 [M + H], HPLC (215 nM): 89.93%, RT 3.54 min. |
| 8-601 | 2-(4-(2,5-dimethylphenylsulfonyl)-1,4-diazepan-1-yl)-N-hydroxy-2-phenylacetamide | LRMS (ESI): (calc.) 417.52178, (found) 418.22 [M + H], HPLC (215 nM): 92.34%, RT 3.14 min. |
| 8-602 | 2-(4-(3,5-dimethylphenylsulfonyl)piperazin-1-yl)-N-hydroxy-2-phenylacetamide | LRMS (ESI): (calc.) 403.4952, (found) 404.26 [M + H], HPLC (215 nM): 92.44%, RT 3.57 min. |
| 8-603 | 2-(4-(3,5-dimethylphenylsulfonyl)-1,4-diazepan-1-yl)-N-hydroxy-2-phenylacetamide | LRMS (ESI): (calc.) 417.52178, (found) 418.22 [M + H], HPLC (215 nM): 95.15%, RT 3.13 min. |
| 8-604 | N-hydroxy-2-(4-(4-methoxyphenylsulfonyl)piperazin-1-yl)-2-phenylacetamide | LRMS (ESI): (calc.) 405.46802, (found) 406.19 [M + H], HPLC (215 nM): 91.23%, RT 3.25 min. |
| 8-605 | N-hydroxy-2-(4-(4-methoxyphenylsulfonyl)-1,4-diazepan-1-yl)-2-phenylacetamide | LRMS (ESI): (calc.) 419.4946, (found) 420.19 [M + H], HPLC (215 nM): 90.91%, RT 2.84 min. |
| 8-606 | N-hydroxy-2-(4-(3-methoxyphenylsulfonyl)-1,4-diazepan-1-yl)-2-phenylacetamide | LRMS (ESI): (calc.) 419.4946, (found) 420.17 [M + H], HPLC (215 nM): 90.53%, RT 2.91 min. |
| 8-607 | 2-(4-(4-fluoro-2-methylphenylsulfonyl)piperazin-1-yl)-N-hydroxy-2-phenylacetamide | LRMS (ESI): (calc.) 407.4590832, (found) 408.16 [M + H], HPLC (215 nM): 95.24%, RT 3.46 min. |
| 8-608 | 2-(4-(4-fluoro-2-methylphenylsulfonyl)-1,4-diazepan-1-yl)-N-hydroxy-2-phenylacetamide | LRMS (ESI): (calc.) 421.4856632, (found) 422.18 [M + H], HPLC (215 nM): 88.01%, RT 3.05 min. |
| 8-609 | 2-(4-(4-chlorophenylsulfonyl)piperazin-1-yl)-N-hydroxy-2-phenylacetamide | LRMS (ESI): (calc.) 409.8871, (found) 410.09 [M + H], HPLC (215 nM): 92.86%, RT 3.55 min. |

TABLE VIII-continued

Compounds prepared according general Schemes above

| Cpd # | Name | Characterization |
|---|---|---|
| 8-610 | 2-(4-(4-chlorophenylsulfonyl)-1,4-diazepan-1-yl)-N-hydroxy-2-phenylacetamide | LRMS (ESI): (calc.) 423.91368, (found) 424.14 [M + H], HPLC (215 nM): 88.4%, RT 3.07 min. |
| 8-611 | 2-(4-(2-chlorophenylsulfonyl)piperazin-1-yl)-N-hydroxy-2-phenylacetamide | LRMS (ESI): (calc.) 409.8871, (found) 410.09 [M + H], HPLC (215 nM): 94.27%, RT 3.34 min. |
| 8-612 | 2-(4-(3-chlorophenylsulfonyl)piperazin-1-yl)-N-hydroxy-2-phenylacetamide | LRMS (ESI): (calc.) 409.8871, (found) 410.09 [M + H], HPLC (215 nM): 89.4%, RT 3.57 min. |
| 8-613 | 2-(4-(5-chlorothiophen-2-ylsulfonyl)piperazin-1-yl)-N-hydroxy-2-phenylacetamide | LRMS (ESI): (calc.) 415.91482, (found) 416.07 [M + H], HPLC (215 nM): 96.25%, RT 3.64 min. |
| 8-614 | 2-(4-(5-chlorothiophen-2-ylsulfonyl)-1,4-diazepan-1-yl)-N-hydroxy-2-phenylacetamide | LRMS (ESI): (calc.) 429.9414, (found) 430.12 [M + H], HPLC (215 nM): 94.73%, RT 3.14 min. |
| 8-615 | N-hydroxy-2-(4-(2-methoxy-4-methylphenylsulfonyl)piperazin-1-yl)-2-phenylacetamide | LRMS (ESI): (calc.) 419.4946, (found) 420.17 [M + H], HPLC (215 nM): 87.87%, RT 3.2 min. |
| 8-616 | N-hydroxy-2-(4-(2-methoxy-4-methylphenylsulfonyl)-1,4-diazepan-1-yl)-2-phenylacetamide | LRMS (ESI): (calc.) 433.52118, (found) 434.21 [M + H], HPLC (215 nM): 93.72%, RT 2.91 min. |
| 8-617 | 2-(4-(3-chloro-4-methylphenylsulfonyl)piperazin-1-yl)-N-hydroxy-2-phenylacetamide | LRMS (ESI): (calc.) 423.91368, (found) 424.17 [M + H], HPLC (215 nM): 93.92%, RT 3.73 min. 1H NMR (250 MHz, DMSO-d6) d ppm 10.69-10.93 (1H, m), 8.79-8.98 (1H, m), 7.55-7.74 (3H, m), 7.17-7.41 (5H, m), 3.59-3.77 (1H, m), 2.74-3.03 (4H, m), 2.27-2.46 (7H, m) |
| 8-618 | 2-(4-(3-chloro-4-methylphenylsulfonyl)-1,4-diazepan-1-yl)-N-hydroxy-2-phenylacetamide | LRMS (ESI): (calc.) 437.94026, (found) 438.12 [M + H], HPLC (215 nM): 88.01%, RT 3.25 min. |
| 8-619 | 2-(4-(4-chlorobenzylsulfonyl)piperazin-1-yl)-N-hydroxy-2-phenylacetamide | LRMS (ESI): (calc.) 423.91368, (found) 424.17 [M + H], HPLC (215 nM): 90.85%, RT 3.41 min. |
| 8-620 | 2-(4-(4-chlorobenzylsulfonyl)-1,4-diazepan-1-yl)-N-hydroxy-2-phenylacetamide | LRMS (ESI): (calc.) 437.94026, (found) 438.14 [M + H], HPLC (215 nM): 90.9%, RT 3.08 min. |
| 8-621 | 2-(4-(3-chlorobenzylsulfonyl)piperazin-1-yl)-N-hydroxy-2-phenylacetamide | LRMS (ESI): (calc.) 423.91368, (found) 424.17 [M + H], HPLC (215 nM): 88.33%, RT 3.41 min. |
| 8-622 | N-hydroxy-2-(4-(naphthalen-2-ylsulfonyl)piperazin-1-yl)-2-phenylacetamide | LRMS (ESI): (calc.) 425.50072, (found) 426.19 [M + H], HPLC (215 nM): 90.45%, RT 3.64 min. |
| 8-623 | N-hydroxy-2-(4-(naphthalen-2-ylsulfonyl)-1,4-diazepan-1-yl)-2-phenylacetamide | LRMS (ESI): (calc.) 439.5273, (found) 440.17 [M + H], HPLC (215 nM): 90.78%, RT 3.2 min. 1H NMR (250 MHz, DMSO-d6) d ppm 10.76 (1H, br. s.), 8.90 (1H, br. s.), 8.38-8.52 (1H, m), 8.02-8.25 (3H, m), 7.61-7.86 (3H, m), 7.20-7.38 (5H, m), 3.89-4.10 (1H, m), 3.23-3.31 (4H, m), 2.54-2.69 (4H, m), 1.49-1.83 (2H, m) |
| 8-624 | 2-(4-(4-tert-butylphenylsulfonyl)-1,4-diazepan-1-yl)-N-hydroxy-2-phenylacetamide | LRMS (ESI): (calc.) 445.57494, (found) 446.24 [M + H], HPLC (215 nM): 91.16%, RT 3.45 min. |
| 8-625 | 2-(4-(4-acetamidophenylsulfonyl)piperazin-1-yl)-N-hydroxy-2-phenylacetamide | LRMS (ESI): (calc.) 432.49336, (found) 433.24 [M + H], HPLC (215 nM): 94.38%, RT 2.87 min. |
| 8-626 | 2-(4-(4-acetamidophenylsulfonyl)-1,4-diazepan-1-yl)-N-hydroxy-2-phenylacetamide | LRMS (ESI): (calc.) 446.51994, (found) 447.18 [M + H], HPLC (215 nM): 87.99%, RT 2.58 min. |
| 8-627 | 2-(4-(3,4-dimethoxyphenylsulfonyl)piperazin-1-yl)-N-hydroxy-2-phenylacetamide | LRMS (ESI): (calc.) 435.494, (found) 436.16 [M + H], HPLC (215 nM): 90.85%, RT 3.13 min. |
| 8-628 | 2-(4-(3,4-dimethoxyphenylsulfonyl)- | LRMS (ESI): (calc.) 449.52058, (found) 450.21 [M + H], HPLC (215 nM): 95.23%, RT 2.8 min. |

TABLE VIII-continued

Compounds prepared according general Schemes above

| Cpd # | Name | Characterization |
|---|---|---|
| 8-629 | 1,4-diazepan-1-yl)-N-hydroxy-2-phenylacetamide N-hydroxy-2-phenyl-2-(4-(3-(trifluoromethyl)phenylsulfonyl)piperazin-1-yl)acetamide | LRMS (ESI): (calc.) 443.4400096, (found) 444.16 [M + H], HPLC (215 nM): 93.18%, RT 3.73 min. |
| 8-630 | N-hydroxy-2-phenyl-2-(4-(3-(trifluoromethyl)phenylsulfonyl)-1,4-diazepan-1-yl)acetamide | LRMS (ESI): (calc.) 457.4665896, (found) 458.17 [M + H], HPLC (215 nM): 93.52%, RT 3.24 min. |
| 8-631 | 2-(4-(2,5-dichlorothiophen-3-ylsulfonyl)piperazin-1-yl)-N-hydroxy-2-phenylacetamide | LRMS (ESI): (calc.) 450.35988, (found) 450.05 [M + H], HPLC (215 nM): 92.97% RT 3.78 min. |
| 8-632 | 2-(4-(cyclopropylmethyl)piperazin-1-yl)-N-hydroxy-2-phenylacetamide | LRMS (ESI): (calc.) 289.37272, (found) 290 [M + H], HPLC (215 nM): 91.32%, RT 2.01 min. |
| 8-633 | N-hydroxy-2-(4-isobutylpiperazin-1-yl)-2-phenylacetamide | LRMS (ESI): (calc.) 291.3886, (found) 292 [M + H], HPLC (215 nM): 96.04%, RT 2.18 min. |
| 8-634 | N-hydroxy-2-(4-isopentylpiperazin-1-yl)-2-phenylacetamide | LRMS (ESI): (calc.) 305.41518, (found) 306 [M + H], HPLC (215 nM): 90.43%, RT 2.39 min. 1H NMR (250 MHz, DMSO-d6) d ppm 10.92 (1H, s), 8.95 (1H, br. s.), 7.16-7.53 (5H, m), 3.73 (1H, s), 3.16-3.56 (4H, m), 2.61-3.06 (6H, m), 1.30-1.65 (3H, m), 0.88 (6H, d, J = 6.40 Hz) |
| 8-635 | 2-(4-(2-ethylbutyl)-1,4-diazepan-1-yl)-N-hydroxy-2-phenylacetamide | LRMS (ESI): (calc.) 333.46834, (found) 334 [M + H], HPLC (215 nM): 88.76%, RT 2.68 min. |
| 8-636 | N-hydroxy-2-(4-(2-methylpentyl)-1,4-diazepan-1-yl)-2-phenylacetamide | LRMS (ESI): (calc.) 333.46834, (found) 334 [M + H], HPLC (215 nM): 90%, RT 2.68 min. |
| 8-637 | 2-(4-(3,3-dimethylbutyl)-1,4-diazepan-1-yl)-N-hydroxy-2-phenylacetamide | LRMS (ESI): (calc.) 333.46834, (found) 334 [M + H], HPLC (215 nM): 92.59%, RT 2.72 min. |
| 8-638 | 2-(4-(3,3-dimethylbutyl)piperazin-1-yl)-N-hydroxy-2-phenylacetamide | LRMS (ESI): (calc.) 319.44176, (found) 320 [M + H], HPLC (215 nM): 98.91%, RT 2.57 min. 1H NMR (250 MHz, DMSO-d6) d ppm 10.92 (1H, br. s.), 8.95 (1H, br. s.), 7.15-7.54 (5H, m), 3.71 (1H, br. s.), 3.21-3.55 (4H, m), 2.57-3.04 (6H, m), 1.46 (2H, br. s.), 0.89 (9H, s) |
| 8-639 | N-hydroxy-2-phenyl-2-(4-(pyridin-4-ylmethyl)-1,4-diazepan-1-yl)acetamide | LRMS (ESI): (calc.) 340.41946, (found) 341 [M + H], HPLC (215 nM): 91%, RT 1.3 min. |
| 8-640 | N-hydroxy-2-phenyl-2-(4-(pyridin-4-ylmethyl)piperazin-1-yl)acetamide | LRMS (ESI): (calc.) 326.39288, (found) 327 [M + H], HPLC (215 nM): 96%, RT 1.22 min. |
| 8-641 | N-hydroxy-2-(4-((1-methyl-1H-pyrrol-2-yl)methyl)-1,4-diazepan-1-yl)-2-phenylacetamide | LRMS (ESI): (calc.) 342.43534, (found) 343 [M + H], HPLC (215 nM): 87.99%, RT 2.44 min. |
| 8-642 | N-hydroxy-2-(4-((1-methyl-1H-pyrrol-2-yl)methyl)piperazin-1-yl)-2-phenylacetamide | LRMS (ESI): (calc.) 328.40876, (found) 329 [M + H], HPLC (215 nM): 100%, RT 2.34 min. |
| 8-643 | N-hydroxy-2-(4-((1-methyl-1H-imidazol-2-yl)methyl)-1,4-diazepan-1-yl)-2-phenylacetamide | LRMS (ESI): (calc.) 343.4234, (found) 344 [M + H], HPLC (215 nM): 96%, RT 1.26 min. |
| 8-644 | N-hydroxy-2-(4-((1-methyl-1H-imidazol-2-yl)methyl)piperazin-1-yl)-2-phenylacetamide | LRMS (ESI): (calc.) 329.39682, (found) 330 [M + H], HPLC (215 nM): 97%, RT 1.19 min. |
| 8-645 | 2-(4-(cyclohex-3-enylmethyl)-1,4-diazepan-1-yl)-N-hydroxy-2-phenylacetamide | LRMS (ESI): (calc.) 343.46316, (found) 344 [M + H], HPLC (215 nM): 90.58%, RT 2.62 min. |
| 8-646 | 2-(4-(cyclohexylmethyl)piperazin-1-yl)-N-hydroxy-2-phenylacetamide | LRMS (ESI): (calc.) 331.45246, (found) 332 [M + H], HPLC (215 nM): 95.17%, RT 2.61 min. 1H NMR (250 MHz, DMSO-d6) d ppm 10.84 (1H, br. s.), 8.90 (1H, br. s.), 7.13-7.51 (5H, m), 3.64 (1H, br. s.), 3.11-3.51 (4H, m), 1.96-2.43 (6H, m), 1.33-1.81 (6H, m), 1.08-1.33 (3H, m), 0.54-0.93 (2H, m) |
| 8-647 | N-hydroxy-2-phenyl-2-(4-(thiazol-2-ylmethyl)-1,4-diazepan-1-yl)acetamide | LRMS (ESI): (calc.) 346.44718, (found) 347 [M + H], HPLC (215 nM): 95.64%, RT 2.2 min. |
| 8-648 | N-hydroxy-2-phenyl-2-(4-(thiazol-2- | LRMS (ESI): (calc.) 332.4206, (found) 333 [M + H], HPLC (215 nM): 96.27%, RT 2.07 min. |

TABLE VIII-continued

Compounds prepared according general Schemes above

| Cpd # | Name | Characterization |
|---|---|---|
| | ylmethyl)piperazin-1-yl)acetamide | |
| 8-649 | N-hydroxy-2-(4-(2-methylbenzyl)piperazin-1-yl)-2-phenylacetamide | LRMS (ESI): (calc.) 339.4314, (found) 340 [M + H], HPLC (215 nM): 86.39%, RT 2.55 min. |
| 8-650 | N-hydroxy-2-(4-((6-methylpyridin-2-yl)methyl)-1,4-diazepan-1-yl)-2-phenylacetamide | LRMS (ESI): (calc.) 354.44604, (found) 355 [M + H], HPLC (215 nM): 91%, RT 2.21 min. |
| 8-651 | N-hydroxy-2-(4-(3-hydroxybenzyl)piperazin-1-yl)-2-phenylacetamide | LRMS (ESI): (calc.) 341.40422, (found) 342 [M + H], HPLC (215 nM): 94.05%, RT 2.25 min. |
| 8-652 | 2-(4-(2-fluorobenzyl)-1,4-diazepan-1-yl)-N-hydroxy-2-phenylacetamide | LRMS (ESI): (calc.) 357.4218632, (found) 358 [M + H], HPLC (215 nM): 87.96%, RT 2.53 min. |
| 8-653 | 2-(4-(2-fluorobenzyl)piperazin-1-yl)-N-hydroxy-2-phenylacetamide | LRMS (ESI): (calc.) 343.3952832, (found) 344 [M + H], HPLC (215 nM): 89.36%, RT 2.41 min. |
| 8-654 | 2-(4-(3-fluorobenzyl)piperazin-1-yl)-N-hydroxy-2-phenylacetamide | LRMS (ESI): (calc.) 343.3952832, (found) 344 [M + H], HPLC (215 nM): 86.07%, RT 2.46 min. |
| 8-655 | 2-(4-(2-ethylhexyl)-1,4-diazepan-1-yl)-N-hydroxy-2-phenylacetamide | LRMS (ESI): (calc.) 361.5215, (found) 362 [M + H], HPLC (215 nM): 91.16%, RT 3.12 min. |
| 8-656 | 2-(4-(2-ethylhexyl)piperazin-1-yl)-N-hydroxy-2-phenylacetamide | LRMS (ESI): (calc.) 347.49492, (found) 348 [M + H], HPLC (215 nM): 86.75%, RT 2.94 min. |
| 8-657 | (E)-2-(4-cinnamyl-1,4-diazepan-1-yl)-N-hydroxy-2-phenylacetamide | LRMS (ESI): (calc.) 365.46868, (found) 366 [M + H], HPLC (215 nM): 91.15%, RT 2.87 min. |
| 8-658 | N-hydroxy-2-phenyl-2-(4-(2-phenylpropyl)piperazin-1-yl)acetamide | LRMS (ESI): (calc.) 353.45798, (found) 354 [M + H], HPLC (215 nM): 99.03% RT 2.68 min. |
| 8-659 | 2-(4-(3,5-dimethylbenzyl)-1,4-diazepan-1-yl)-N-hydroxy-2-phenylacetamide | LRMS (ESI): (calc.) 367.48456, (found) 368 [M + H], HPLC (215 nM): 89.26%, RT 2.9 min. |
| 8-660 | 2-(4-(3,5-dimethylbenzyl)piperazin-1-yl)-N-hydroxy-2-phenylacetamide | LRMS (ESI): (calc.) 353.45798, (found) 354 [M + H], HPLC (215 nM): 97.92%, RT 2.87 min. |
| 8-661 | N-hydroxy-2-(4-(2-methoxybenzyl)-1,4-diazepan-1-yl)-2-phenylacetamide | LRMS (ESI): (calc.) 369.45738, (found) 370 [M + H], HPLC (215 nM): 88.35%, RT 2.65 min. |
| 8-662 | N-hydroxy-2-(4-(2-methoxybenzyl)piperazin-1-yl)-2-phenylacetamide | LRMS (ESI): (calc.) 355.4308, (found) 356 [M + H], HPLC (215 nM): 97.75%, RT 2.56 min. |
| 8-663 | 2-(4-(2-chlorobenzyl)-1,4-diazepan-1-yl)-N-hydroxy-2-phenylacetamide | LRMS (ESI): (calc.) 373.87646, (found) 374 [M + H], HPLC (215 nM): 89.17%, RT 2.69 min. |
| 8-664 | 2-(4-(2-chlorobenzyl)piperazin-1-yl)-N-hydroxy-2-phenylacetamide | LRMS (ESI): (calc.) 359.84988, (found) 360 [M + H], HPLC (215 nM): 87.3%, RT 2.55 min. |
| 8-665 | 2-(4-((1H-indol-5-yl)methyl)-1,4-diazepan-1-yl)-N-hydroxy-2-phenylacetamide | LRMS (ESI): (calc.) 378.46744, (found) 379 [M + H], HPLC (215 nM): 88.07%, RT 2.6 min. |
| 8-666 | 2-(4-((1H-indol-5-yl)methyl)piperazin-1-yl)-N-hydroxy-2-phenylacetamide | LRMS (ESI): (calc.) 364.44086, (found) 365 [M + H], HPLC (215 nM): 100%, RT 2.53 min. |
| 8-667 | 2-(4-((2,3-dihydrobenzofuran-5-yl)methyl)piperazin-1-yl)-N-hydroxy-2-phenylacetamide | LRMS (ESI): (calc.) 367.4415, (found) 368 [M + H], HPLC (215 nM): 91.82%, RT 2.51 min. |
| 8-668 | N-hydroxy-2-(4-(4-methoxy-3-methylbenzyl)-1,4-diazepan-1-yl)-2-phenylacetamide | LRMS (ESI): (calc.) 383.48396, (found) 384 [M + H], HPLC (215 nM): 88.45%, RT 2.83 min. |
| 8-669 | N-hydroxy-2-(4-(4-(methylthio)benzyl)piperazin-1-yl)-2-phenylacetamide | LRMS (ESI): (calc.) 371.4964, (found) 372 [M + H], HPLC (215 nM): 88.08%, RT 2.73 min. |
| 8-670 | N-hydroxy-2-phenyl-2-(4-(quinolin-4-ylmethyl)-1,4-diazepan-1-yl)acetamide | LRMS (ESI): (calc.) 390.47814, (found) 196 [M + H], HPLC (215 nM): 93.74%, RT 2.29 min. |

TABLE VIII-continued

Compounds prepared according general Schemes above

| Cpd # | Name | Characterization |
|---|---|---|
| 8-671 | N-hydroxy-2-phenyl-2-(4-(quinolin-4-ylmethyl)piperazin-1-yl)acetamide | LRMS (ESI): (calc.) 376.45156, (found) 189 [M + H], HPLC (215 nM): 89.27%, RT 2.18 min. |
| 8-672 | (E)-N-hydroxy-2-(4-(3-(4-methoxyphenyl)allyl)-1,4-diazepan-1-yl)-2-phenylacetamide | LRMS (ESI): (calc.) 395.49466, (found) 396 [M + H], HPLC (215 nM): 90.72%, RT 2.89 min. |
| 8-673 | (E)-N-hydroxy-2-(4-(3-(2-methoxyphenyl)allyl)piperazin-1-yl)-2-phenylacetamide | LRMS (ESI): (calc.) 381.46808, (found) 382 [M + H], HPLC (215 nM): 90.83%, RT 2.89 min. |
| 8-674 | 2-(4-(4-tert-butylbenzyl)-1,4-diazepan-1-yl)-N-hydroxy-2-phenylacetamide | LRMS (ESI): (calc.) 395.53772, (found) 396 [M + H], HPLC (215 nM): 88.93%, RT 3.2 min. |
| 8-675 | 2-(4-((2,3-dihydrobenzo[b][1,4]dioxin-6-yl)methyl)-1,4-diazepan-1-yl)-N-hydroxy-2-phenylacetamide | LRMS (ESI): (calc.) 397.46748, (found) 398 [M + H], HPLC (215 nM): 90.8%, RT 2.64 min. |
| 8-676 | 2-(4-((2,3-dihydrobenzo[b][1,4]dioxin-6-yl)methyl)piperazin-1-yl)-N-hydroxy-2-phenylacetamide | LRMS (ESI): (calc.) 383.4409, (found) 384 [M + H], HPLC (215 nM): 97.98%, RT 2.59 min. |
| 8-677 | 2-(4-(3,4-dimethoxybenzyl)piperazin-1-yl)-N-hydroxy-2-phenylacetamide | LRMS (ESI): (calc.) 385.45678, (found) 386 [M + H], HPLC (215 nM): 91.98%, RT 2.42 min. |
| 8-678 | N-hydroxy-2-phenyl-2-(4-(3-(trifluoromethyl)benzyl)piperazin-1-yl)acetamide | LRMS (ESI): (calc.) 393.4027896, (found) 394 [M + H], HPLC (215 nM): 87.06%, RT 2.8 min. |
| 8-679 | N-hydroxy-2-phenyl-2-(4-(4-(trifluoromethyl)benzyl)piperazin-1-yl)acetamide | LRMS (ESI): (calc.) 393.4027896, (found) 394 [M + H], HPLC (215 nM): 97.92%, RT 2.82 min. |
| 8-680 | 2-(4-(2,4-dichlorobenzyl)-1,4-diazepan-1-yl)-N-hydroxy-2-phenylacetamide | LRMS (ESI): (calc.) 408.32152, (found) 408 [M + H], HPLC (215 nM): 94.16%, RT 2.94 min. |
| 8-681 | 2-(4-(2,4-dichlorobenzyl)piperazin-1-yl)-N-hydroxy-2-phenylacetamide | LRMS (ESI): (calc.) 394.29494, (found) 394 [M + H], HPLC (215 nM): 88.52%, RT 2.81 min. |
| 8-682 | 2-(4-(biphenyl-4-ylmethyl)-1,4-diazepan-1-yl)-N-hydroxy-2-phenylacetamide | LRMS (ESI): (calc.) 415.52736, (found) 416 [M + H], HPLC (215 nM): 90.33%, RT 3.15 min. |
| 8-683 | N-hydroxy-2-phenyl-2-(4-(4-(pyridin-2-yl)benzyl)-1,4-diazepan-1-yl)acetamide | LRMS (ESI): (calc.) 416.51542, (found) 209 [M + 2H]/2, HPLC (215 nM): 90.84%, RT 2.52 min. 1H NMR (250 MHz, DMSO-d6) d ppm 10.82-11.01 (1H, m), 8.85-9.09 (1H, m), 8.57-8.74 (1H, m), 8.07-8.24 (2H, m), 7.98-8.06 (1H, m), 7.82-7.97 (1H, m), 7.56-7.77 (2H, m), 7.13-7.53 (6H, m), 4.17-4.58 (1H, m), 4.04-4.17 (1H, m), 2.59-3.25 (8H, m), 1.76-2.10 (2H, m) |
| 8-684 | 2-(4-(3-(benzo[d][1,3]dioxol-5-yl)-2-methylpropyl)-1,4-diazepan-1-yl)-N-hydroxy-2-phenylacetamide | LRMS (ESI): (calc.) 425.52064, (found) 426 [M + H], HPLC (215 nM): 85.93%, RT 2.92 min. |
| 8-685 | 2-(4-(3-(benzo[d][1,3]dioxol-5-yl)-2-methylpropyl)piperazin-1-yl)-N-hydroxy-2-phenylacetamide | LRMS (ESI): (calc.) 411.49406, (found) 412 [M + H], HPLC (215 nM): 87.82%, RT 2.82 min. |
| 8-686 | 2-(4-bromophenyl)-N-hydroxy-2-phenylacetamide | LRMS (ESI): (calc.) 306.15458, (found) 306 [M + H], HPLC (215 nM): 95%, RT 3.71 min. |
| 8-687 | 2-(3-bromophenyl)-N-hydroxy-2-phenylacetamide | LRMS (ESI): (calc.) 306.15458, (found) 306 [M + H], HPLC (215 nM): 93%, RT 3.68 min. |
| 8-688 | 4-(2-(hydroxyamino)-2-oxo-1-phenylethyl)-N-((S)-1-phenylethyl)piperazine-1-carboxamide | LRMS (ESI): (calc.) 382.45614, (found) 383 [M + H], HPLC (215 nM): 94.57%, RT 2.7 min. |
| 8-689 | 2-(4-(4-fluorobenzyl)-1,4-diazepan-1-yl)-N-hydroxy-2-phenylacetamide | LRMS (ESI): (calc.) 357.4218632, (found) 358 [M + H], HPLC (215 nM): 91.35%, RT 2.59 min. |
| 8-690 | 2-(4-(4-chlorobenzyl)-1,4-diazepan-1-yl)-N-hydroxy-2-phenylacetamide | LRMS (ESI): (calc.) 373.87646, (found) 374 [M + H], HPLC (215 nM): 88.13%, RT 2.78 min. |

Compositions

In a second aspect, the invention provides compositions comprising a pharmaceutically acceptable carrier, excipient, or diluent, and a compound having the Formula (VI):

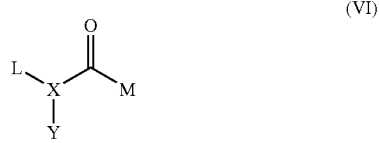

(VI)

or an N-oxide, hydrate, solvate, pharmaceutically acceptable salt, prodrug or complex thereof, or a racemic or scalemic mixture, diastereomer or enantiomer thereof, wherein M is selected from the group consisting of alkyl, —N($R^e$)O$R^s$, —CF$_3$, —C(O)NR$^e$R$^f$, -heteroaryl, —H, —OH, —C(O)OR$^e$, —CH$_2$—SR$^e$, —CH$_2$—S(acetyl) and -heterocycloalkyl;

X is selected from the group consisting of CH, C(OH), C($C_1$-$C_4$alkyl), C(halo), C(aryl), C(heteroaryl), C($R^c$),

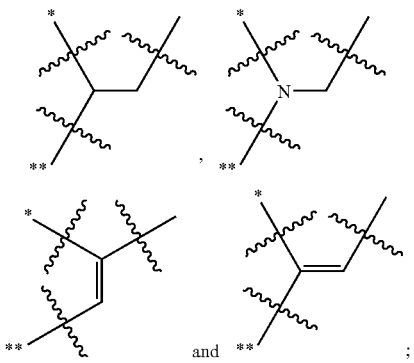

and wherein * represents the point of attachment to group L and ** represents the point of attachment to group Y;

L and Y are independently selected from the group consisting of $C_1$-$C_4$alkyl, heteroalkyl, alkenyl, alkynyl, —NR$^a$R$^b$, —NR$^c$R$^d$, —OR$^e$, —$C_0$-$C_3$alkyl-aryl, —$C_0$-$C_3$alkyl-heteroaryl, —$C_0$-$C_3$alkyl-heterocyclyl, —$C_0$-$C_3$alkyl-cycloalkyl, —$C_2$-$C_4$alkenyl-aryl, —$C_2$-$C_4$alkenyl-heteroaryl, —$C_2$-$C_4$alkenyl-heterocyclyl, —$C_2$-$C_4$alkenyl-cycloalkyl, —$C_2$-$C_4$alkynyl-aryl, —$C_2$-$C_4$alkynyl-heteroaryl, —$C_2$-$C_4$alkynyl-heterocyclyl, —$C_2$-$C_4$alkynyl-cycloalkyl, —O—$C_0$-$C_3$alkyl-aryl, —O—$C_0$-$C_3$alkyl-heteroaryl, —O—$C_0$-$C_3$alkyl-cycloalkyl, —O—$C_0$-$C_3$alkyl-heterocycloalkyl, —C(O)NH—$C_0$-$C_3$alkyl-aryl, —C(O)NH—$C_0$-$C_3$alkyl-heteroaryl, —O—$C_0$-$C_3$alkyl-aryl-aryl, —O—$C_0$-$C_3$alkyl-heteroaryl-aryl, —O—$C_0$-$C_3$alkyl-aryl-heteroaryl, —O—$C_0$-$C_3$alkyl-heteroaryl-heteroaryl, —S(O)$_{0-2}$—$C_0$-$C_3$alkyl-aryl, —S(O)$_{0-2}$—$C_0$-$C_3$alkyl-heteroaryl, —S(O)$_{0-2}$—$C_0$-$C_3$alkyl-aryl-aryl, —S(O)$_{0-2}$—$C_0$-$C_3$alkyl-heteroaryl-aryl, —S(O)$_{0-2}$—$C_0$-$C_3$alkyl-aryl-heteroaryl, —S(O)$_{0-2}$—$C_0$-$C_3$alkyl-heteroaryl-heteroaryl, -aryl-$C_0$-$C_3$alkyl-aryl, -heteroaryl-$C_0$-$C_3$alkyl-aryl, —$C_0$-$C_3$alkyl-aryl-$C_0$-$C_2$alkyl-N($R^e$)—$C_0$-$C_2$alkyl-aryl, —$C_0$-$C_3$alkyl-aryl-$C_0$-$C_2$alkyl-N($R^e$)—$C_0$-$C_2$alkyl-heteroaryl, —$C_0$-$C_3$alkyl-heteroaryl-$C_0$-$C_2$alkyl-N($R^e$)—$C_0$-$C_2$alkyl-aryl, —$C_0$-$C_3$alkyl-heteroaryl-$C_0$-$C_2$alkyl-N($R^e$)—$C_0$-$C_2$alkyl-heteroaryl, —$C_0$-$C_3$alkyl-aryl-$C_0$-$C_2$alkyl-N($R^e$)—S(O)$_2$—$C_0$-$C_2$alkyl-aryl, —$C_0$-$C_3$alkyl-aryl-$C_0$-$C_2$alkyl-N($R^e$)S(O)$_2$—$C_0$-$C_2$alkyl-heteroaryl, —$C_0$-$C_3$alkyl-heteroaryl-$C_0$-$C_2$alkyl-N($R^e$)S(O)$_2$—$C_0$-$C_2$alkyl-aryl, —$C_0$-$C_3$alkyl-heteroaryl-$C_0$-$C_2$alkyl-N($R^e$)—S(O)$_2$—$C_0$-$C_2$alkyl-heteroaryl, —N($R^e$)—S(O)$_2$—N($R^f$)—, —N($R^e$)—C(O)—, —C(O)—N($R^e$)—, —N($R^e$)—C(O)—N($R^f$)—, —N($R^e$)—C(O)—O—, —O—C(O)—N($R^e$), —O—, —N($R^e$)—C(O)—$C_2$-$C_4$alkyl-O—, —O—$C_2$-$C_4$alkyl-N($R^e$)—, -heterocyclyl-$C_0$-$C_3$alkyl-aryl, -cycloalkyl-$C_0$-$C_3$alkyl-aryl, -aryl-$C_0$-$C_3$alkyl-heteroaryl, -heteroaryl-$C_0$-$C_3$alkyl-heteroaryl, -heterocyclyl-$C_0$-$C_3$alkyl-heteroaryl, -cycloalkyl-$C_0$-$C_3$alkyl-heteroaryl, -aryl-$C_0$-$C_3$alkyl-heterocyclyl, -heteroaryl-$C_0$-$C_3$alkyl-heterocyclyl, -heterocyclyl-$C_0$-$C_3$alkyl-heterocyclyl, -cycloalkyl-$C_0$-$C_3$alkyl-heterocyclyl, -heterocyclyl-$C_0$-$C_3$alkyl-O—$C_0$-$C_3$alkyl-aryl, -heterocyclyl-$C_0$-$C_3$alkyl-O—$C_0$-$C_3$alkyl-heteroaryl, -heterocyclyl-$C_0$-$C_3$alkyl-O—C(O)NH—$C_0$-$C_3$alkyl-aryl, -heterocyclyl-$C_0$-$C_3$alkyl-O—C(O)NH—$C_0$-$C_3$alkyl-heteroaryl, -heterocyclyl-$C_0$-$C_3$alkyl-heteroaryl-aryl, -heterocyclyl-$C_0$-$C_3$alkyl-heteroaryl-heteroaryl, -heterocyclyl-$C_0$-$C_3$alkyl-aryl-aryl, -heterocyclyl-$C_0$-$C_3$alkyl-aryl-heteroaryl, -heterocyclyl-$C_0$-$C_3$alkyl-heteroaryl-$C_0$-$C_3$alkyl-aryl, -heterocyclyl-$C_0$-$C_3$alkyl-heteroaryl-$C_0$-$C_3$alkyl-heteroaryl, -heterocyclyl-$C_0$-$C_3$alkyl-aryl-$C_0$-$C_3$alkyl-aryl, -heterocyclyl-$C_0$-$C_3$alkyl-aryl-$C_0$-$C_3$alkyl-heteroaryl, -heterocyclyl-S(O)$_2$—$C_0$-$C_3$alkyl-aryl, -heterocyclyl-S(O)$_2$—$C_0$-$C_3$alkyl-heteroaryl, -heterocyclyl-S(O)$_2$—$C_0$-$C_3$alkyl-alkyl, -heterocyclyl-S(O)$_2$—$C_0$-$C_3$alkyl-cycloalkyl, -heterocyclyl-S(O)$_2$—$C_0$-$C_3$alkyl-heterocyclyl, -heterocyclyl-C(O)—$C_0$-$C_3$alkyl-aryl, -heterocyclyl-C(O)—$C_0$-$C_3$alkyl-heteroaryl, -heterocyclyl-C(O)—$C_0$-$C_3$alkyl-alkyl, -heterocyclyl-C(O)—$C_0$-$C_3$alkyl-cycloalkyl, -heterocyclyl-C(O)—$C_0$-$C_3$alkyl-heterocyclyl, -heterocyclyl-C(O)NH—$C_0$-$C_3$alkyl-aryl, -heterocyclyl-C(O)NH—$C_0$-$C_3$alkyl-heteroaryl, -heterocyclyl-C(O)NH—$C_0$-$C_3$alkyl-alkyl, -heterocyclyl-C(O)NH—$C_0$-$C_3$alkyl-cycloalkyl, -heterocyclyl-C(O)NH—$C_0$-$C_3$alkyl-heterocyclyl, -heterocyclyl-C(O)O—$C_0$-$C_3$alkyl-aryl, -heterocyclyl-C(O)O—$C_0$-$C_3$alkyl-heteroaryl, -heterocyclyl-C(O)O—$C_0$-$C_3$alkyl-alkyl, heterocyclyl-C(O)O—$C_0$-$C_3$alkyl-cycloalkyl, -heterocyclyl-C(O)O—$C_0$-$C_3$alkyl-heterocyclyl, -heterocyclyl-S(O)$_2$—NH—$C_0$-$C_3$alkyl-aryl, -heterocyclyl-S(O)$_2$—NH—$C_0$-$C_3$alkyl-heteroaryl, -heterocyclyl-S(O)$_2$—NH—$C_0$-$C_3$alkyl-alkyl, -heterocyclyl-S(O)$_2$—NH—$C_0$-$C_3$alkyl-cycloalkyl, -heterocyclyl-S(O)$_2$—NH—$C_0$-$C_3$alkyl-heterocyclyl, —$C_0$-$C_3$alkyl-heterocyclyl-$C_2$-$C_4$alkenyl-aryl, —$C_0$-$C_3$alkyl-heterocyclyl-CH(aryl)$_2$, —$C_0$-$C_3$alkyl-heterocyclyl-CH(heteroaryl)$_2$, —$C_0$-$C_3$alkyl-heterocyclyl-CH(aryl)(heteroaryl), —$C_0$-$C_3$alkyl-aryl-$C_0$-$C_3$alkyl-heterocyclyl-$C_0$-$C_3$alkyl-aryl, —$C_0$-$C_3$alkyl-heteroaryl-$C_0$-$C_3$alkyl-heterocyclyl-$C_0$-$C_3$alkyl-aryl, —$C_0$-$C_3$alkyl-aryl-$C_0$-$C_3$alkyl-heterocyclyl-$C_0$-$C_3$alkyl-heteroaryl, —$C_0$-$C_3$alkyl-heteroaryl-$C_0$-$C_3$alkyl-heterocyclyl-$C_0$-$C_3$alkyl-heteroaryl, —$C_0$-$C_3$alkyl-heteroaryl-$C_0$-$C_3$alkyl-heterocyclyl-$C_0$-$C_3$alkyl-heteroaryl, —$C_0$-$C_3$alkyl-aryl-heterocyclyl-S(O)$_2$-aryl, —$C_0$-$C_3$alkyl-heteroaryl-heterocyclyl-S(O)$_2$-aryl, —$C_0$-$C_3$alkyl-aryl-heterocyclyl-S(O)$_2$-heteroaryl, —$C_0$-$C_3$alkyl-heteroaryl-heterocyclyl-S(O)$_2$-heteroaryl, —$C_0$-$C_3$alkyl-aryl-S(O)$_2$-heterocyclyl-aryl, —$C_0$-$C_3$alkyl-heteroaryl-S(O)$_2$-heterocyclyl-aryl, —$C_0$-$C_3$alkyl-aryl-S(O)$_2$-heterocyclyl-heteroaryl, —$C_0$-$C_3$alkyl-heteroaryl-S(O)$_2$-heterocyclyl-heteroaryl, —$C_0$-$C_3$alkyl-aryl-heterocyclyl-C(O)-aryl, —$C_0$-$C_3$alkyl-heteroaryl-heterocyclyl-C(O)-aryl, —$C_0$-$C_3$alkyl-aryl-heterocyclyl-C(O)-heteroaryl, —$C_0$-$C_3$alkyl-heteroaryl-heterocyclyl-C(O)-heteroaryl, —$C_0$-$C_3$alkyl-aryl-C(O)-heterocyclyl-aryl, —$C_0$-$C_3$alkyl-heteroaryl-C(O)-heterocyclyl-aryl, —$C_0$-$C_3$alkyl-aryl-C(O)-heterocyclyl-heteroaryl, —$C_0$-$C_3$alkyl-heteroaryl-C(O)-heterocyclyl-heteroaryl, —$C_0$-$C_3$alkyl-aryl-heterocyclyl-C(O)NR$^e$-aryl, —$C_0$-$C_3$alkyl-heteroaryl-heterocyclyl-C(O)NR$^e$-aryl, —$C_0$-

C₃alkyl-aryl-heterocyclyl-C(O)NRᵉ-heteroaryl, —C₀-C₃alkyl-heteroaryl-heterocyclyl-C(O)NRᵉ-heteroaryl, —C₀-C₃alkyl-aryl-NRᵉC(O)-heterocyclyl-aryl, —C₀-C₃alkyl-heteroaryl-NRᵉC(O)-heterocyclyl-aryl, —C₀-C₃alkyl-aryl-NRᵉC(O)-heterocyclyl-heteroaryl, —C₀-C₃alkyl-heteroaryl-NRᵉC(O)-heterocyclyl-heteroaryl, —C₀-C₃alkyl-aryl-heterocyclyl-C(O)O-aryl, —C₀-C₃alkyl-heteroaryl-heterocyclyl-C(O)O-aryl, —C₀-C₃alkyl-aryl-heterocyclyl-C(O)O-heteroaryl, —C₀-C₃alkyl-heteroaryl-heterocyclyl-C(O)O-heteroaryl, —C₀-C₃alkyl-aryl-OC(O)-heterocyclyl-aryl, —C₀-C₃alkyl-heteroaryl-OC(O)-heterocyclyl-aryl, —C₀-C₃alkyl-aryl-OC(O)-heterocyclyl-heteroaryl, and —C₀-C₃alkyl-heteroaryl-OC(O)-heterocyclyl-heteroaryl, provided that if an L or a Y is bound directly to a nitrogen of X, then the L or Y is not —NRᵃRᵇ, —NRᶜRᵈ, —ORᵉ, —S(O)₀₋₁—C₀-C₃alkyl-aryl, —S(O)₀₋₁—C₀-C₃alkyl-heteroaryl, —S(O)₀₋₁—C₀-C₃alkyl-aryl-aryl, —S(O)₀₋₁—C₀-C₃alkyl-heteroaryl-aryl, —S(O)₀₋₁—C₀-C₃alkyl-aryl-heteroaryl or —S(O)₀₋₁—C₀-C₃alkyl-heteroaryl-heteroaryl, in which each Rᵃ and Rᵇ together with the nitrogen to which they are bound form a 4 to 7 membered heterocyclyl having 1 or 2 annular heteroatoms, or a 5 to 8 membered bridged heterocyclyl having 1 or 2 annular heteroatoms, the heterocyclyl being optionally substituted with 1-3 substituents independently selected from the group consisting of H, OH, oxo (i.e., =O), —N(Rᶜ)(Rᵈ), C₁-C₆alkyl, aryl, heteroaryl, —C₁-C₆alkyl-aryl, —C₁-C₆alkyl-heteroaryl, —C₁-C₃alkoxy-C₁-C₃alkyl, —C₂-C₃alkyl-OH, —C₂-C₃alkyl-O—C₁-C₄alkyl, —C₅-C₆cycloalkyl, -C₀-C₃alkyl-N(H)—C(O)—C₁-C₃alkyl, —C₀₋₃alkyl-N(H)—C(O)-haloalkyl, —C₀-C₃alkyl-NHC(O)O—C₁-C₃alkyl-aryl, —C₀-C₃alkyl-CF₃, —C₀-C₃alkyl-NHC(O)O—C₁-C₃alkyl-heteroaryl and —C₀-C₃alkyl-NH₂, wherein said heterocyclyl is optionally fused to an aryl or heteroaryl;

each Rᶜ and Rᵈ is independently selected from the group consisting of H, —C₁-C₆alkyl, —C₂-C₃alkyl-ORᵉ, aryl, heteroaryl, -heteroaryl-heteroaryl, -heteroaryl-aryl, -aryl-heteroaryl, —C(O)-aryl, —C₁-C₃-alkoxy-C₁-C₃-alkyl, —C₂-C₃alkyl-O—C₁-C₃alkyl, —C₂-C₃alkyl-NRᵉRᶠ, —CH₂—C(CH₃)₂—NRᵉRᶠ, in which each aryl and heteroaryl is optionally substituted with one, two or three substituents independently selected from amino, OCH₃ and OH; or Rᶜ and Y together with the carbon to which they are bound form an optionally substituted 4 to 7 membered ring system having 0-2 annular heteroatoms, each Rᵉ and Rᶠ is independently selected from the group consisting of —H, -alkyl, -aryl, -aryl-aryl, -hetetoaryl, heteroaryl-aryl, heteroaryl-heteroaryl, C(O)-alkyl and —C(O)CF₃; and each Rˢ is independently selected from the group consisting of —H, C₁-C₆alkyl, aryl, heteroaryl, heterocyclyl, cycloalkyl and a protecting group, wherein each cycloalkyl, heterocyclyl, aryl, alkyl and heteroaryl moiety is optionally substituted, and wherein a cycloalkyl, heterocyclyl, aryl, alkyl or heteroaryl moiety in L is optionally connected to a cycloalkyl, heterocyclyl, aryl, alkyl or heteroaryl in Y by a bond or by a bridging substituent, provided that
the compound does not have the formula (C)

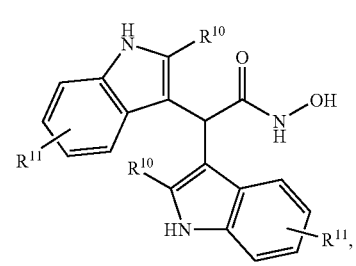

(C)

in which each R¹⁰ is selected from the group consisting of H, OH, —CH₂OH, NH₂, COOH and C₁-C₄alkyl; and each R¹¹ is selected from the group consisting of H, halo, C₁-C₆alkyl, C₁-C₄alkoxy, —OC(O)C₁-C₄alkyl, —NH₂, —NH(C₁-C₄alkyl), —N(C₁-C₄alkyl)₂, —SH, —S—C₁-C₄alkyl, —COOH and —C(O)O—C₁-C₄alkyl; and the compound is not 10,11-dihydro-5H-dibenzo[a,d]cycloheptene-5-hydroxamic acid.

In a preferred embodiment of the second aspect of the invention, M is

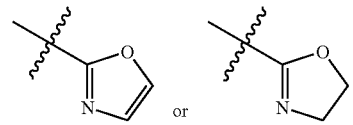

In a preferred embodiment of the second aspect of the invention, M is NHOH.

In another preferred embodiment of the second aspect of the invention, M is —H.

In another preferred embodiment of the second aspect of the invention, X is CH.

In another preferred embodiment of the second aspect of the invention, X is C(OH) or C(halo).

In another preferred embodiment of the second aspect of the invention, X is

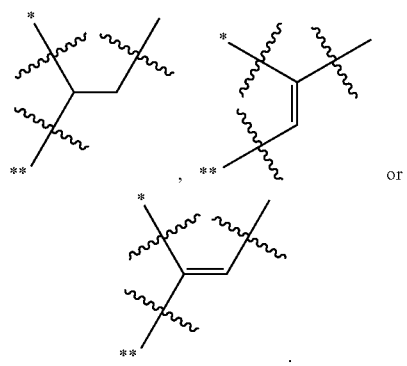

In another preferred embodiment of the second aspect of the invention, X is

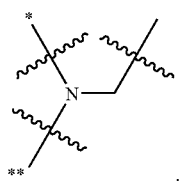

In another preferred embodiment of the second aspect of the invention, L and Y are independently selected from the group consisting of aryl, heteroaryl, alkyl, —O-aryl, —O-cycloalkyl, heterocyclyl, cycloalkyl, —S-aryl, —S-heteroaryl, —C(O)NH-aryl, —S-heteroaryl-aryl, —S-aryl-aryl, -aryl-heterocyclyl, -heteroaryl-heterocyclyl, —$C_1$-$C_3$alkyl-aryl, —S(O)$_2$-aryl, —S(O)$_2$-heteroaryl, —NHS(O)$_2$-aryl, -heterocyclyl-$C_0$-$C_3$alkyl-aryl, -heterocyclyl-$C_0$-$C_3$alkyl-heteroaryl, -heteroaryl-$C_0$-$C_3$alkyl-heteroaryl, heteroaryl-$C_0$-$C_3$alkyl-aryl, -aryl-aryl, -aryl-heteroaryl, -heterocyclyl-O-aryl, -heterocyclyl-O—$C_0$-$C_3$alkyl-aryl, -heterocyclyl-O—$C_0$-$C_3$alkyl-heteroaryl, -heterocyclyl-S(O)$_2$—$C_0$-$C_3$alkyl-aryl and -heterocyclyl-S(O)$_2$—$C_0$-$C_3$alkyl-heteroaryl, wherein each said cycloalkyl, heterocyclyl, aryl, alkyl and heteroaryl moiety of the forgoing L and Y is optionally substituted with a substituent selected from the group consisting of —N($R^e$)C(O)—$C_0$-$C_3$alkyl-aryl, —N($R^e$)C(O)—$C_0$-$C_3$alkyl-heteroaryl, —N($R^e$)C(O)—$C_0$-$C_3$alkyl-heterocyclyl, —N($R^e$)C(O)—$C_0$-$C_3$alkyl-cycloalkyl, —N($R^e$)C(O)—$C_0$-$C_8$alkyl, —N($R^a$)($R^b$), —N($R^c$)($R^d$), —CF$_3$, aryl, heteroaryl, cycloalkyl, heterocyclyl, —$C_1$-$C_3$alkyl-aryl, —$C_1$-$C_3$alkyl-heteroaryl, —$C_1$-$C_3$alkyl-cycloalkyl, —$C_1$-$C_3$alkyl-heterocyclyl, and wherein each cycloalkyl, heterocyclyl, aryl, alkyl and heteroaryl moiety in L is further optionally substituted with halo or —O—$C_1$-$C_3$alkyl.

In another aspect of the second embodiment of the invention, each cycloalkyl and heterocyclyl moiety is optionally gem or spiro substituted with —OH, —CN or -alkyl In another preferred embodiment of the second aspect of the invention, L and Y are independently selected from the group consisting of aromatic polycycle, non-aromatic polycycle, polyheteroaryl, non-aromatic polyheterocyclic and mixed aryl and non-aryl polyheterocycle.

In another preferred embodiment of the second aspect of the invention, L and Y are independently selected from aryl, heteroaryl, O-aryl, heterocyclyl, cycloalkyl, —S-aryl, —S-heteroaryl and —C(O)NH-aryl, —S-heteroaryl-aryl, -aryl-heterocyclyl, -heteroaryl-heterocyclyl, —$C_1$-$C_3$alkyl-aryl, —S(O)$_2$-aryl, —S(O)$_2$-heteroaryl, -heterocyclyl-$C_0$-$C_3$alkyl-aryl, -heteroaryl-$C_0$-$C_3$alkyl-heteroaryl, heteroaryl-$C_0$-$C_3$alkyl-aryl, -aryl-aryl and -heterocyclyl-O-aryl, each of which is optionally substituted.

In another preferred embodiment of the second aspect of the invention, the compound has the Formula (VII):

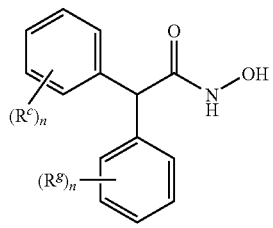

(VII)

wherein
$R^c$ is as described above with respect to Formula (VI);
each n is independently 0-3; and $R^g$ is selected from the group consisting of —$C_0$-$C_3$alkyl-aryl, —$C_0$-$C_3$alkyl-heteroaryl, —$C_0$-$C_3$alkyl -cycloalkyl, —$C_0$-$C_3$alkyl-heterocylyl, —NR$^a$R$^b$, —NR$^c$R$^d$, —OR$^e$ In another preferred embodiment of the second aspect of the invention, the compound has the Formula (VIII):

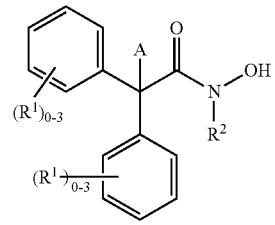

(VIII)

wherein
each $R^1$ is independently alkyl, NO$_2$, halo or alkoxy,
$R^2$ is H or $C_1$-$C_5$alkyl, and
A is H, phenyl or OH.

As described above, a cycloalkyl, heterocyclyl, aryl, alkyl or heteroaryl moiety in L is optionally connected to a cycloalkyl, heterocyclyl, aryl, alkyl or heteroaryl in Y by a bond or by a bridging substituent. Such a bridging substituent preferably has 1-6 atoms along the shortest path between the cycloalkyl, heterocyclyl, aryl, alkyl or heteroaryl moiety in L and the cycloalkyl, heterocyclyl, aryl, alkyl or heteroaryl moiety in Y. For example, another preferred embodiment of the second aspect of the invention, the compound has the Formula (IX):

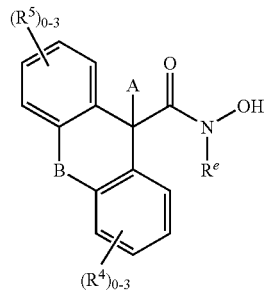

(IX)

wherein
$R^4$ and $R^5$ are independently selected from the group consisting of H, halo, —NH$_2$, —NO$_2$, —$C_0$-$C_4$alkyl-aryl, —$C_0$-$C_4$alkyl-heteroaryl, —$C_0$-$C_4$alkyl-heterocyclyl, —$C_0$-$C_4$alkyl-cycloalkyl, —OMe, alkyl, CN and CF$_3$;
A is H, phenyl or OH; and
B is a bond, —O—, —N($R^6$)—, —S(O)$_{0-2}$—, —CH($R^4$)—, —C($R^5$)($R^4$)—, —C($R^4$)—N($R^c$)—, —N($R^c$)—C($R^4$)—, —C($R^4$)—O—, —O—C($R^4$)—, —S(O)$_{0-2}$—C($R^4$)—, —C($R^4$)—S(O)$_{0-2}$—, —C($R^4$)=C($R^5$)—, —CH($R^4$)—CH($R^5$)—, —C($R^4$)=N($R^6$)—, —C(O)N($R^6$)—, —S(O)$_2$N($R^6$)—, —C($R^5$)($R^4$)—C($R^5$)($R^4$)—, —C($R^5$)(H)—C(H)($R^4$)—, —N(CH$_2$Ph)-, or

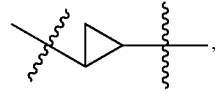

in which $R^6$ is alkyl, cycloalkyl or heterocyclyl.

In another preferred embodiment of the second aspect of the invention, the compound has the Formula (X):

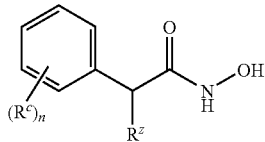

(X)

wherein
n is 0-3;
$R^z$ is selected from the group consisting of

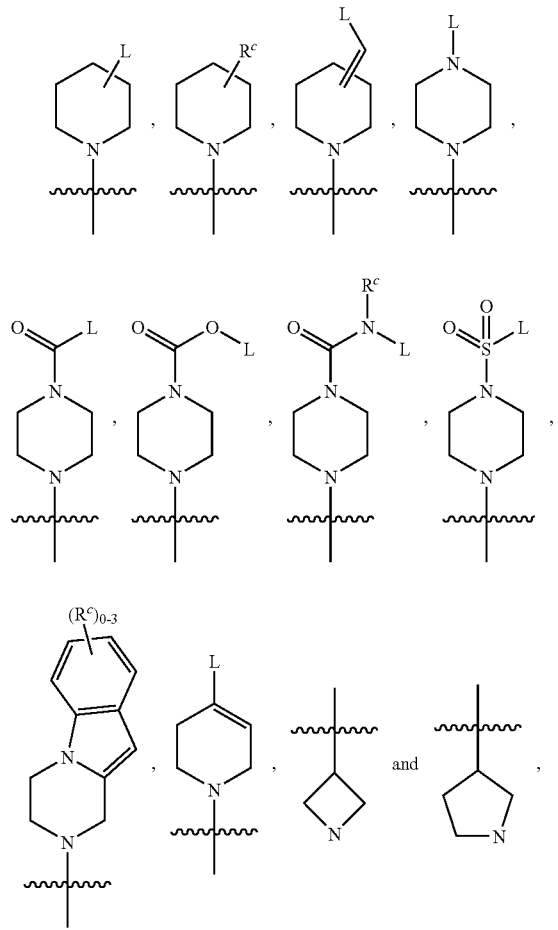

$R^c$ and L are as described above with respect to Formula (VI), wherein when L is bound directly to N or O, it is not —$NR^aR^b$, —$NR^cR^d$, —$OR^e$, —$S(O)_{0-1}$—$C_0$-$C_3$alkyl-aryl, —$S(O)_{0-1}$—$C_0$-$C_3$alkyl-heteroarylaryl, —$S(O)_{0-1}$—$C_0$-$C_3$alkyl-aryl-aryl, —$S(O)_{0-1}$—$C_0$-$C_3$alkyl-heteroaryl-aryl, —$S(O)_{0-1}$—$C_0$-$C_3$alkyl-aryl-heteroaryl or —$S(O)_{0-1}$—$C_0$-$C_3$alkyl-heteroaryl-heteroaryl.

In another preferred embodiment of the second aspect of the invention, the compound has the Formula (XI)

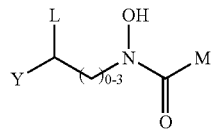

(XI)

wherein
M is H or alkyl; and
L and Y are as defined in Formula (VI).

In another preferred embodiment of the second aspect of the invention, the invention provides compositions comprising a pharmaceutically acceptable carrier, excipient, or diluent, and a compound having the Formula (VI-A):

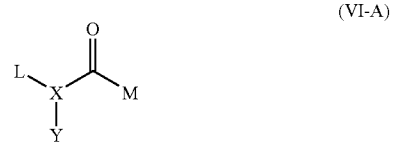

(VI-A)

or an N-oxide, hydrate, solvate, pharmaceutically acceptable salt, prodrug or complex thereof, or a racemic or scalemic mixture, diastereomer or enantiomer thereof, wherein
M, X, Y and L are as defined for Formula (VI), and wherein Y is further selected from the group consisting of —$Z^1$—$Z$—$Z^2$-D, -D, —$Z^1$—$Z^3$—Z-D, —$Z^1$—$Z^3$—$Z^2$—Z-D, —$Z^1$—$Z^2$-D, —$Z^1$—Z—$Z^3$—$Z^2$-D, —Z—$Z^3$—$Z^2$—Z-D, —$Z^1$—Z—$Z^2$, —Z—$Z^3$-D and —$Z^2$—$Z^1$—$Z^2$-D,
wherein
$Z^1$ is selected from the group consisting of chemical bond, alkyl, aryl, heterocyclyl, bridged heterocyclyl, spiro heterocyclyl, cycloalkyl, heteroaryl, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;
Z is selected from the group consisting of chemical bond, —O—, —$S(O)_{0-2}$—, —$N(R^c)C(O)$—, —$C(O)N(R^c)$—$C(O)$—, —$C(O)N(R^c)$—, —$N(R^c)S(O)_2$—, —$N(R^c)$—, —$N(R^c)(C_2$-$C_4$alkyl-$OR^d)$—, —$C(O)$—, —$C(NOR^{21})$—, —CH[C(O)N($R^{21}$)($R^{22}$)]—$C(O)N(R^{22})$—, —CH(N($R^{21}$)($R^{22}$))—$C(O)N(R^{22})$—, —CH[C(O)N($R^e$)($R^f$)]—$C(O)N(R^{22})$—, —$S(O)_2N(R^{21})$—, —$N(R^{21})S(O)_2N(R^{22})$—, —OC(O)—, —C(O)O—, —$N(R^{21})C(NR^{22})$—, —$C(NR^{22})N(R^{21})$—, —$N(R^{21})C(O)N(R^{22})$—, —$N(R^{21})C(O)O$—, —$OC(O)N(R^{21})$—, —$N(R^{21})C(S)$—, —$C(S)N(R^{21})$—, —$N(R^{21})C(S)N(R^{22})$—, —$N(R^{21})C(S)O$—, —$OC(S)N(R^{21})$—, —O—$C_2$-$C_4$alkyl-$N(R^{21})$—, —$N(R^{21})$—$C_2$-$C_4$alkyl-O—, —$N(R^1)$—$C_2$-$C_4$alkyl-$S(O)_{0-2}$—, —N[$C_2$-$C_4$alkyl-N($R^1$)($R^2$)]—, —$N(C_2$-$C_4$alkyl-O-alkyl)-$C_2$-$C_4$alkyl-O—, —O—$C_2$-$C_4$alkyl-N($R^c$)—$C_2$-$C_4$alkyl-O—, —$N(R^c)$—$C_2$-$C_4$alkyl-$N(R^d)$—, —O—$C_1$-$C_4$alkyl-$S(O)_2N(R^{21})$—, —O—$C_1$-$C_4$alkyl-O—, —O—$C_1$-$C_4$alkyl-O—$C_1$-$C_4$alkyl-O—, —$S(O)_2N(R^{12})$—$C_2$-$C_4$alkyl-O—, —O—$C_2$-$C_4$alkyl-$N(R^{21})S(O)_2$—, —$N(R^2)S(O)_2$—$C_1$-$C_4$alkyl-O—, —C(O)—$C_1$-$C_4$alkyl-$N(R^{21})$—, —N(C(O)—$C_1$-$C_4$alkyl)-, —$N(R^{21})$—$C_1$-$C_4$alkyl-C(O)—, —O—$C_1$-$C_4$alkyl-C(O)N($R^{21}$)—, —$C(O)N(R^{21})$—$C_2$-$C_4$alkyl-O—, —C(O)—$C_1$-$C_4$alkyl-O—, —C(O)—$C_1$-$C_4$alkyl-$S(O)_{0-2}$—, —O—$C_2$-$C_4$alkyl-$N(R^{21})C(O)$—, —$N(R^2)C(O)$—$C_1$-$C_4$alkyl-O—, —$N(R^2)C(O)$—$C_1$-$C_4$alkyl-$S(O)_{0-2}$—, —O—$C_1$-$C_4$alkyl-C(O)—, —C(O)—$C_1$-$C_4$alkyl-O—, —N($R^{21}$)—$C_1$-$C_4$alkyl-C(O), —C(O)—$C_1$-$C_4$alkyl-N($R^{21}$)—, —O—$C_1$-$C_4$alkyl-C(S)—, —C(S)—$C_1$-$C_4$alkyl-O—, —N($R^{21}$)—$C_1$-$C_4$alkyl-C(S), —C(S)—$C_1$-$C_4$alkyl-N($R^{21}$)—, —N($R^{21}$)—$C_1$-$C_4$alkyl-C(S)—, —O—$C_1$-$C_4$alkyl-C(S)N($R^{21}$)—, —C(S)N($R^{21}$)—$C_2$-$C_4$alkyl-O—, —O—$C_2$-$C_4$alkyl-N($R^{21}$)C(S)—, —N($R^{21}$)C(O)—$C_1$-$C_4$alkyl-O—, —N($R^{21}$)C(S)—$C_1$-$C_4$alkyl-O—, —N($R^{21}$)—$C_1$-$C_4$alkyl-S(O)$_2$—, —O—$C_1$-$C_4$alkyl-S(O)$_2$ N($R^{21}$)—, —S(O)$_2$N($R^2$)—$C_2$-$C_4$alkyl-O—, —O—$C_2$-$C_4$alkyl-N($R^{21}$)S(O)$_2$—, —N($R^{21}$)S(O)$_2$—$C_1$-$C_4$alkyl-O—, —O—$C_2$-$C_4$alkyl-OC(O)N($R^{21}$)—, —O—$C_2$-$C_4$alkyl-OC(S)N($R^{21}$)—, wherein each alkyl moiety is optionally substituted;

$Z^2$ is selected from the group consisting of a chemical bond, alkyl, alkenyl, alkynyl, alkyl-alkenyl, alkynyl-alkyl and alkyl-alkynyl, wherein each alkyl, alkenyl and alkynyl moiety is optionally substituted;

$Z^3$ is selected from the group consisting of a chemical bond, —$C_1$-$C_5$alkyl-, —$C_0$-$C_5$alkyl-aryl-, —$C_0$-$C_5$alkyl-heterocyclyl-, —$C_0$-$C_5$alkyl-bridged heterocyclyl-, -spiro heterocyclyl-, —$C_0$-$C_5$alkyl-cycloalkyl- and —$C_0$-$C_5$alkyl-heteroaryl-, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;

D is selected from the group consisting of H, aryl, heteroaryl, alkyl, alkenyl, alkynyl, heteroalkyl, cycloalyl, heterocyclyl, bridged heterocyclyl, spiro heterocyclyl, aromatic polycycles, non-aromatic polycycles, polyheteroaryl groups, non-aromatic polyheterocyclic, mixed aryl and non-aryl polyheterocycle, each of which is optionally substituted and each of which is optionally fused to one or more aryl or heteroaryl rings, or one or more saturated or partially unsaturated cycloalkyl or heterocyclyl rings, each of which ring is optionally substituted, wherein each $R^{21}$ and $R^{22}$ is independently selected from the group consisting of —H, -alkyl, -aryl and heteroaryl, wherein each said aryl and heteroaryl moiety is optionally substituted; and L is selected from the group consisting of cycloalkyl, heterocyclyl, aryl and heteroaryl (preferably aryl and heteroaryl), wherein each aryl, heteroaryl, heterocyclyl, cycloalkyl and aryl group is optionally fused to a heterocyclyl, or is optionally substituted with a substituent selected from the group consisting of halo, —O-alkyl, —S-alkyl, —$NO_2$, —N($R^e$)C(O)—$C_0$-$C_3$alkyl-aryl, —N($R^e$)C(O)—$C_0$-$C_3$alkyl-heteroaryl, —N($R^a$)($R^b$), —N($R^c$)($R^d$), —OH, -alkyl, aryl, heteroaryl, —$OCF_3$ and —$CF_3$.

In a preferred embodiment of the second aspect of the invention, each cycloalkyl, heterocyclyl, aryl, alkyl, alkenyl and heteroaryl moiety in Z, $Z_1$, $Z_2$, $Z_3$ and D is optionally substituted with a substituent selected from the group consisting of —N($R^e$)C(O)—$C_1$-$C_6$alkyl, —N($R^e$)C(O)—$C_0$-$C_3$alkyl-aryl, —N($R^e$)C(O)—$C_0$-$C_3$alkyl-heteroaryl, —N($R^e$)C(O)—$C_0$-$C_3$alkyl-heterocyclyl, —N($R^e$)C(O)—$C_0$-$C_3$alkyl-cycloalkyl, —N($R^e$)C(O)—$C_0$-$C_8$alkyl, —N($R^a$)($R^b$), —N($R^c$)($R^d$), —$CF_3$, —O—$CF_3$, —S—$CF_3$, aryl, heteroaryl, cycloalkyl, heterocyclyl, —$C_1$-$C_3$alkyl-aryl, —$C_1$-$C_3$alkyl-heteroaryl, —$C_1$-$C_3$alkyl-cycloalkyl, —$C_1$-$C_3$alkyl-heterocyclyl, halo, alkyl, —O-alkyl, —S(O)$_{0-2}$-alkyl, —$C_0$-$C_3$alkyl-CN, $NO_2$, —C(O)-alkyl and —OH.

In another preferred embodiment of the second aspect of the invention, the invention provides compositions comprising a pharmaceutically acceptable carrier, excipient, or diluent, and a compound having the Formula (XX):

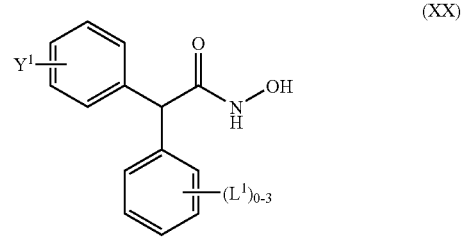

(XX)

or an N-oxide, hydrate, solvate, pharmaceutically acceptable salt, prodrug or complex thereof, or a racemic or scalemic mixture, diastereomer or enantiomer thereof, wherein each $L^1$ is independently selected from the group consisting of H, halo, —O-alkyl, —S-alkyl, —$NO_2$, —N($R^e$)C(O)—$C_0$-$C_3$alkyl-aryl, —N($R^e$)C(O)—$C_0$-$C_3$alkyl-heteroaryl, —N($R^a$)($R^b$), —N($R^c$)($R^d$), —OH, -alkyl, —$OCF_3$, and —$CF_3$; and $Y^1$ is selected from the group consisting of —Z—$Z^2$-D, —$Z^1$—$Z^2$-D, —$CH_2$-D and D.

In another preferred embodiment of the second aspect of the invention, the invention provides compositions comprising a pharmaceutically acceptable carrier, excipient, or diluent, and a compound having the Formula (XX-A):

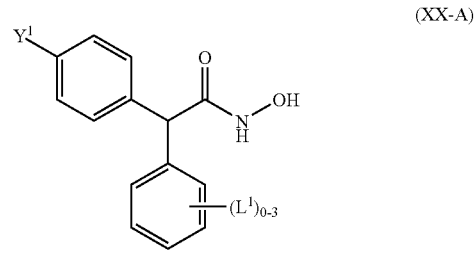

(XX-A)

or an N-oxide, hydrate, solvate, pharmaceutically acceptable salt, prodrug or complex thereof, or a racemic or scalemic mixture, diastereomer or enantiomer thereof, wherein each $L^1$ is independently selected from the group consisting of H, halo, —O—$CH_3$, —$CH_3$ and —OH; and $Y^1$ is selected from the group consisting of —Z—$Z^2$-D, —$Z^1$—$Z^2$-D, —$CH_2$-D and D;

wherein

Z is selected from the group consisting of —O—, —S(O)$_{0-2}$—, —N($R^c$)C(O)—, —C(O)N($R^c$)—, —N($R^c$)S(O)$_2$—, —N($R^c$)—, —S(O)$_2$N($R^{21}$)—, —O—$C_2$-$C_4$alkyl-N($R^{21}$)—, —N($R^{21}$)—$C_2$-$C_4$alkyl-O—, —N($R^c$)—$C_2$-$C_4$alkyl-N($R^d$)—, and —O—$C_1$-$C_4$alkyl-O—;

$Z^1$ is selected from the group consisting of aryl, heterocyclyl, bridged heterocyclyl, spiro heterocyclyl, cycloalkyl and heteroaryl, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;

$Z^2$ is a chemical bond or an optionally substituted alkyl; and

D is selected from the group consisting of H, aryl, heteroaryl, alkyl, cycloalkyl and heterocyclyl, each of which is optionally substituted and each of which is optionally fused to one or more aryl or heteroaryl rings, or one or more saturated or partially unsaturated cycloalkyl or heterocyclyl rings, each of which ring is optionally substituted.

In another preferred embodiment of the second aspect of the invention, the invention provides compositions comprising a pharmaceutically acceptable carrier, excipient, or diluent, and a compound having the Formula (XX):

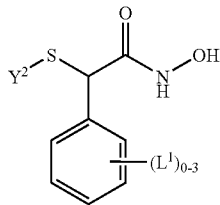

(XXI)

or an N-oxide, hydrate, solvate, pharmaceutically acceptable salt, prodrug or complex thereof, or a racemic or scalemic mixture, diastereomer or enantiomer thereof, wherein each $L^1$ is independently selected from the group consisting of H, halo, —O-alkyl, —S-alkyl, —$NO_2$, —N($R^e$)C(O)—$C_0$-$C_3$alkyl-aryl, —N($R^e$)C(O)—$C_0$-$C_3$alkyl-heteroaryl, —N($R^a$)($R^b$), —N($R^c$)($R^d$), —OH, -alkyl, —$OCF_3$ and —$CF_3$; and $Y^2$ is —$Z^2$—$Z^1$—$Z^2$-D, —$CH_2$-D or D;

wherein $Z^1$ is selected from the group consisting of aryl, heterocyclyl, cycloalkyl and heteroaryl, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;

$Z^2$ is a chemical bond or an optionally substituted alkyl; and

D is selected from the group consisting of H, aryl, heteroaryl, alkyl, cycloalyl and heterocyclyl, each of which is optionally substituted and each of which is optionally fused to one or more aryl or heteroaryl rings, or one or more saturated or partially unsaturated cycloalkyl or heterocyclyl rings, each of which ring is optionally substituted.

In another preferred embodiment of the second aspect of the invention, in Formulae (VI)-(XI) each aryl, heterocyclyl, cycloalkyl and heteroaryl is independently optionally substituted with one, two or three substituents independently selected from the group consisting of H, halo, oxo, OH, $C_1$-$C_3$-hydrocarbyl, $OCH_3$, —CN, —S(O)$_{0-2}$—$C_1$-$C_4$alkyl, —$CF_3$, —$OCF_3$, alkyl, —$NH_2$, —N(alkyl)$_2$, —NH(alkyl), —N(aryl)(alkyl), —N(-alkyl-aryl)(alkyl), —N(heteroaryl)(alkyl), —N(-alkyl-heteroalkylaryl)(alkyl), —NH(aryl), —NH(-alkyl-aryl), —NH(heteroaryl), —NH(-alkyl-heteroalkylaryl), —N(—$C_2$-$C_4$alkyl-O-alkyl)(alkyl), —NH(—$C_2$-$C_4$alkyl-Oalkyl), —$NO_2$, —O—$C_1$-$C_4$alkyl, —$C_0$-$C_4$alkyl-aryl, —$C_0$-$C_4$alkyl-heteroaryl, —$C_0$-$C_4$alkyl-heterocyclyl, —$C_0$-$C_4$alkyl-cycloalkyl, —NHS(O)$_2$-alkyl, —S(O)$_2$NH-alkyl, —$NR^aR^b$, —$NR^cR^d$, —$OR^e$, —$C_2$-$C_4$alkyl-$NR^aR^b$, $C_2$-$C_4$alkyl-$NR^cR^d$, —S(O)$_{0-1}R^e$, —($CR^{32}R^{33}$)$_s$—$NR^{30}R^{31}$ and ($X^{30}$—$Y^{31}$—), in which $R^{30}$ and $R^{31}$ are each independently hydrogen, cyano, oxo, hydroxyl, $C_1$-$C_8$ alkyl, $C_1$-$C_8$heteroalkyl, $C_1$-$C_8$alkenyl, carboxamido-, $C_1$-$C_3$alkyl-carboxamido-, carboxamido-$C_1$-$C_3$alkyl-, amidino-, $C_2$-$C_8$hydroxyalkyl-, $C_1$-$C_3$alkyl-aryl-, aryl-$C_1$-$C_3$ alkyl-, $C_1$-$C_3$alkyl-heteroaryl-, heteroaryl-$C_1$-$C_3$alkyl-, $C_1$-$C_3$alkyl-heterocyclyl-, heterocyclyl-$C_1$-$C_3$alkyl-, $C_1$-$C_3$alkyl-cycloalkyl-, cycloalkyl-$C_1$-$C_3$alkyl-, $C_2$-$C_8$alkoxy-, $C_2$-$C_8$alkoxy-$C_1$-$C_4$alkyl-, $C_1$-$C_8$alkoxy-carbonyl-, aryloxy-carbonyl-, aryl-$C_1$-$C_3$alkoxy-carbonyl-, heteroaryloxy-carbonyl-, heteroaryl-$C_1$-$C_3$alkoxy-carbonyl-, $C_1$-$C_8$acyl, $C_0$-$C_8$alkyl-carbonyl-, aryl-$C_0$-$C_8$alkyl-carbonyl-, heteroaryl-$C_0$-$C_8$alkyl-carbonyl-, cycloalkyl-$C_0$-$C_8$alkyl-carbonyl-, $C_0$-$C_8$alkyl-NH-carbonyl-, aryl-$C_0$-$C_8$alkyl-NH-carbonyl-, heteroaryl-$C_0$-$C_8$alkyl-NH-carbonyl-, cycloalkyl-$C_0$-$C_8$alkyl-NH-carbonyl-, $C_0$-$C_8$alkyl-O-carbonyl-, aryl-$C_0$-$C_8$alkyl-O-carbonyl-, heteroaryl-$C_0$-$C_8$alkyl-O-carbonyl-, cycloalkyl-$C_0$-$C_8$alkyl-O-carbonyl-, $C_1$-$C_8$alkylsulfonyl-, aryl-alkyl-sulfonyl-, aryl-sulfonyl-, heteroaryl-alkyl-sulfonyl-, heteroaryl-sulfonyl-, $C_1$-$C_8$alkyl-NH-sulfonyl-, aryl-alkyl-NH-sulfonyl-, aryl-NH-sulfonyl-, heteroaryl-alkyl-NH-sulfonyl-, heteroaryl-NH-sulfonyl-, aroyl-, aryl-, cycloalkyl-, heterocyclyl-, heteroaryl-, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, or protecting group, each of which is optionally substituted with one or more substituents selected from halo, cyano, oxo, carboxy, formyl, nitro, amino, amidino and guanidino, or $R^{30}$ and $R^{31}$ taken together with the N to which they are attached form a heterocyclyl or heteroaryl, each of which is optionally substituted with from 1 to 3 substituents selected from the group consisting of halo, cyano, oxo, carboxy, formyl, nitro, amino, amidino, guanidino, a protecting group, and ($X^{30}$—$Y^{31}$—), in which $X^{30}$ is selected from the group consisting of $C_1$-$C_8$alkyl-, $C_2$-$C_8$alkenyl-, $C_2$-$C_8$alkynyl-, $C_0$-$C_3$alkyl-$C_2$-$C_8$alkenyl-$C_0$-$C_3$alkyl-, $C_0$-$C_3$alkyl-$C_2$-$C_8$alkynyl-$C_0$-$C_3$alkyl-, $C_0$-$C_3$alkyl-O—$C_0$-$C_3$alkyl-, HO—$C_0$-$C_3$alkyl-, $C_0$-$C_4$alkyl-N($R^{30}$)—$C_0$-$C_3$alkyl-, N($R^{30}$)($R^{31}$)—$C_0$-$C_3$alkyl-, N($R^{30}$)($R^3$)—$C_0$-$C_3$alkenyl-, N($R^{30}$)($R^{31}$)—$C_0$-$C_3$alkynyl-, (N($R^{30}$)($R^{31}$))$_2$—C=N—, $C_0$-$C_3$alkyl-S(O)$_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with from 1 to 3 substituents selected from halo, cyano, oxo, carboxy, formyl, nitro, amino, amidino and guanidino; and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C(N$R^{30}$)—N($R^{31}$)—, —N($R^{30}$)—C(N$R^{31}$)—, —C(N$R^{31}$)—N($R^{30}$), —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —S(O)$_{0-2}$—, —$SO_2$N($R^{31}$)—, —N($R^{31}$)—$SO_2$— and —N($R^{30}$)—$SO_2$N($R^{31}$)—; and $R^{32}$ and $R^{33}$ are independently selected from hydrogen, halo and hydroxyl.

In another embodiment of the second aspect of the invention, the compound is selected from the group consisting of 2-(4-(diethylamino)phenyl)-N-hydroxy-2-phenylacetamide; 2-(4-(dimethylamino)phenyl)-N-hydroxy-2-phenylacetamide; 2-(biphenyl-4-yl)-N-hydroxy-2-phenylacetamide; N-hydroxy-2-phenyl-2-(4-(pyrrolidin-1-yl)phenyl)acetamide and 2-(4'-fluorobiphenyl-4-yl)-N-hydroxy-2-phenylacetamide.

In another embodiment of the second aspect of the invention, the compound is selected from the group consisting of N-hydroxy-2-phenylbutanamide;
N-hydroxy-2-phenoxy-2-phenylacetamide;
N-hydroxy-2-phenyl-2-(4-(piperidin-1-yl)phenyl)acetamide;
2-(4-benzylpiperidin-1-yl)-N-hydroxy-2-phenylacetamide;
2-cyclohexyl-N-hydroxy-2-phenylacetamide;
2-benzyl-N-hydroxy-2-phenylacetamide;
N-hydroxy-2-phenyl-2-(phenylthio)acetamide;
N-hydroxy-2-phenyl-2-(1H-pyrrol-1-yl)acetamide;
N-hydroxy-2-phenyl-2-(4-phenylpiperazin-1-yl)acetamide;
2-(4-benzylpiperazin-1-yl)-N-hydroxy-2-phenylacetamide;
N-hydroxy-2-phenyl-2-(5-(thiophen-2-yl)-1H-benzo[d]imidazol-2-yl)acetamide;
N-hydroxy-2-(isoindolin-2-yl)-2-phenylacetamide;
2-(benzo[d]thiazol-2-yl)-N-hydroxy-2-phenylacetamide;
2-(5-chloro-6-fluoro-1H-benzo[d]imidazol-2-yl)-N-hydroxy-2-phenylacetamide;
N-hydroxy-2-phenyl-2-(4-phenyl-1H-1,2,3-triazol-1-yl)acetamide;
N-hydroxy-2-(4-phenethyl-1H-1,2,3-triazol-1-yl)-2-phenylacetamide;
2-(4-(4-fluorobenzyl)piperidin-1-yl)-N-hydroxy-2-phenylacetamide;
$N^1$-hydroxy-2-phenyl-$N^3$-(3-(trifluoromethyl)phenyl)malonamide;
2-(4-(1H-indol-3-yl)piperidin-1-yl)-N-hydroxy-2-phenylacetamide;
2-(4-benzyl-1H-1,2,3-triazol-1-yl)-N-hydroxy-2-phenylacetamide;
N-hydroxy-2-phenyl-2-(4-(pyrimidin-2-yl)piperazin-1-yl)acetamide;
2-(4-(4-chlorophenyl)pyrimidin-2-ylthio)-N-hydroxy-2-phenylacetamide;
N-hydroxy-2-(5-(2-methoxyphenyl)-1,3,4-thiadiazol-2-yl)-2-phenylacetamide;
2-(4,5-diphenyl-1H-imidazol-2-ylthio)-N-hydroxy-2-phenylacetamide;
N-hydroxy-2-(4-phenoxypiperidin-1-yl)-2-phenylacetamide;
N-hydroxy-2-phenyl-2-(4-phenylpiperidin-1-yl)acetamide and 2-(biphenyl-4-ylthio)-N-hydroxy-2-phenylacetamide.

In another embodiment of the second aspect of the invention, the compound is selected from the group consisting of
2-(N-benzylphenylsulfonamido)-N-hydroxyacetamide;
N-hydroxy-3,3-diphenylpropanamide;
2,2-bis(2,3-dihydrobenzofuran-5-yl)-N-hydroxyacetamide;
N-hydroxy-2,2-diphenylpropanamide;
(E)-N-hydroxy-2,3-diphenylacrylamide;
N-hydroxy-2,2-di(thiophen-2-yl)acetamide and
N-hydroxy-9H-xanthene-9-carboxamide.

In another embodiment of the second aspect of the invention, the compound is selected from the group consisting of
N-hydroxy-2,2-diphenylacetamide;
N-hydroxy-2-phenoxy-2-phenylacetamide;
N-hydroxy-2,2-bis(4-nitrophenyl)acetamide;
N-hydroxy-2-phenyl-2-(piperidin-1-yl)acetamide;
2-(N-benzylphenylsulfonamido)-N-hydroxyacetamide;
N-hydroxy-3,3-diphenylpropanamide;
N-hydroxy-9H-xanthene-9-carboxamide;
2,2-bis(2,3-dihydrobenzofuran-5-yl)-N-hydroxyacetamide;
2-(4-benzylpiperidin-1-yl)-N-hydroxy-2-phenylacetamide;
2-cyclohexyl-N-hydroxy-2-phenylacetamide;
N-hydroxy-2,3-diphenylpropanamide;
N-hydroxy-2-phenyl-2-(phenylthio)acetamide;
N-hydroxy-2-phenyl-2-(1H-pyrrol-1-yl)acetamide;
N-hydroxy-2,2-diphenylpropanamide;
2,2-bis(4-chlorophenyl)-N-hydroxyacetamide;
N-hydroxy-2-phenyl-2-(4-phenylpiperazin-1-yl)acetamide;
2-(4-benzylpiperazin-1-yl)-N-hydroxy-2-phenylacetamide;
2,2-bis(4-fluorophenyl)-N-hydroxyacetamide;
2-(4-(diethylamino)phenyl)-N-hydroxy-2-phenylacetamide;
N-hydroxy-2-phenyl-2-(6-(thiophen-2-yl)-1H-benzo[d]imidazol-2-yl)acetamide;
(E)-N-hydroxy-2,3-diphenylacrylamide;
N-hydroxy-2-(isoindolin-2-yl)-2-phenylacetamide;
N-hydroxy-2,2-di(thiophen-2-yl)acetamide;
2-(benzo[d]thiazol-2-ylthio)-N-hydroxy-2-phenylacetamide;
2-(5-chloro-6-fluoro-1H-benzo[d]imidazol-2-yl)-N-hydroxy-2-phenylacetamide;
N-hydroxy-2-phenyl-2-(4-phenyl-1H-1,2,3-triazol-1-yl)acetamide;
N-hydroxy-2-(4-phenethyl-1H-1,2,3-triazol-1-yl)-2-phenylacetamide;
N,2-dihydroxy-2,2-diphenylacetamide;
2-(4-(dimethylamino)phenyl)-N-hydroxy-2-phenylacetamide;
2-(4-(4-fluorobenzyl)piperidin-1-yl)-N-hydroxy-2-phenylacetamide;
N-hydroxy-2-(4-phenethylpiperidin-1-yl)-2-phenylacetamide;
2-(biphenyl-4-yl)-N-hydroxy-2-phenylacetamide;
$N^1$-hydroxy-2-phenyl-$N^3$-(3-(trifluoromethyl)phenyl)malonamide;
2-(4-(1H-indol-3-yl)piperidin-1-yl)-N-hydroxy-2-phenylacetamide;
2-(4-benzyl-1H-1,2,3-triazol-1-yl)-N-hydroxy-2-phenylacetamide;
N-hydroxy-2-phenyl-2-(4-(pyrimidin-2-yl)piperazin-1-yl)acetamide;
2-(4-(4-chlorophenyl)pyrimidin-2-ylthio)-N-hydroxy-2-phenylacetamide;
N-hydroxy-2-(5-(2-methoxyphenyl)-1,3,4-thiadiazol-2-yl)-2-phenylacetamide;
2-(5-(4-bromophenyl)-1,3,4-thiadiazol-2-yl)-N-hydroxy-2-phenylacetamide;
2-(biphenyl-4-yl)-2-(4-(dimethylamino)phenyl)-N-hydroxyacetamide;
N-hydroxy-2-phenyl-2-(4-(pyrrolidin-1-yl)phenyl)acetamide;
2-(4,5-diphenyl-1H-imidazol-2-ylthio)-N-hydroxy-2-phenylacetamide;
N-hydroxy-2-(4-phenoxypiperidin-1-yl)-2-phenylacetamide;
N-hydroxy-2-phenyl-2-(4-phenylpiperidin-1-yl)acetamide;
2-(4'-fluorobiphenyl-4-yl)-N-hydroxy-2-phenylacetamide and
2-(biphenyl-4-ylthio)-N-hydroxy-2-phenylacetamide.

Compositions of the invention may be formulated by any method known in the art and may be prepared for administration by any route, including, without limitation, parenteral, oral, sublingual, transdermal, topical, intranasal, intratracheal, or intrarectal. In certain preferred embodiments, compositions of the invention are administered intravenously in a hospital setting. In certain other preferred embodiments, administration may preferably be by the oral route. The compositions may be in any form, including but not limited to, liquid solutions or suspensions; for oral administration, formulations may be in the form of tablets or capsules; and for intranasal formulations, in the form of powders, nasal drops or aerosols. The compositions of the invention may be administered systemically or locally.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, or other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

In a preferred embodiment of the second aspect, the composition comprises a compound, N-oxide, hydrate, solvate, pharmaceutically acceptable salt, complex or prodrug of a compound according to the present invention as described herein present in at least about 30% enantiomeric or diastereomeric excess. In certain desirable embodiments of the invention, the compound, N-oxide, hydrates, solvate, pharmaceutically acceptable salt, complex or prodrug is present in at least about 50%, at least about 80%, or even at least about 90% enantiomeric or diastereomeric excess. In certain other desirable embodiments of the invention, the compound, N-oxide, hydrate, solvate, pharmaceutically acceptable salt, complex or prodrug is present in at least about 95%, more preferably at least about 98% and even more preferably at least about 99% enantiomeric or diastereomeric excess. In other embodiments of the invention, a compound, N-oxide, hydrate, solvate, pharmaceutically acceptable salt, complex or prodrug is present as a substantially racemic mixture. In a preferred embodiment, the composition further comprises an additional therapeutic or inhibitory agent.

As used herein, the term "pharmaceutically acceptable salts" is intended to mean salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate). As used herein, the term "salt" is also meant to encompass complexes, such as with an alkaline metal or an alkaline earth metal.

The active compound is included in the pharmaceutically acceptable carrier or diluent in an amount sufficient to deliver an inhibition effective amount without causing serious toxic effects. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

Depending on the particular condition or disease to be treated, an additional HDAC inhibitory agent or an additional therapeutic agent, that could be normally administered to treat that condition or disease may also be present in the compositions of this invention. In other words, compounds of this invention can be administered as the sole pharmaceutical agent or in combination with one or more other additional therapeutic (pharmaceutical) agents where the combination causes no unacceptable adverse effects. As used herein, additional therapeutic agents that are normally administered to treat a particular disease or condition are known as "appropriate for the disease or condition being treated". Administration of such agents may be done sequentially or concurrently. In certain preferred embodiments of the present invention the composition comprises at least one compound according to the present invention and at least one other HDAC inhibitor known in the art or which will be discovered. The active ingredients of such compositions preferably act synergistically to produce a therapeutic effect.

In certain preferred embodiments of the second and third aspects of the invention, the additional agent is an antisense oligonucleotide that inhibits the expression of a histone deacetylase gene. The combined use of a nucleic acid level inhibitor (e.g., antisense oligonucleotide) and a protein level inhibitor (i.e., inhibitor of histone deacetylase enzyme activity) results in an improved inhibitory effect, thereby reducing the amounts of the inhibitors required to obtain a given inhibitory effect as compared to the amounts necessary when either is used individually. The antisense oligonucleotide according to this aspect of the invention is complementary to regions of RNA or double-stranded DNA that encode one or more of, for example, HDAC-1, HDAC-2, HDAC-3, HDAC-4, HDAC-5, HDAC-6, HDAC-7, HDAC-8, HDAC-9, HDAC-10 and HDAC-11 (see e.g., GenBank Accession Number U50079 for HDAC-1, GenBank Accession Number U31814 for HDAC-2, and GenBank Accession Number U75697 for HDAC-3).

Inhibition of Histone Deacetylase

In a third aspect, the present invention provides a method of inhibiting a histone deacetylase selected from the group consisting of HDAC-4, HDAC-5, HDAC-6, HDAC-7, HDAC-8, HDAC-9, HDAC-10 and HDAC-11. One embodiment according to the third aspect comprises contacting the histone deacetylase with an inhibition effective amount of an inhibitor of histone deacetylase having the structure (XII):

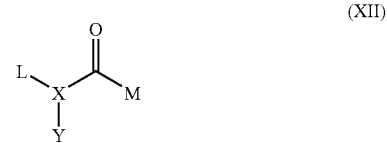

(XII)

or an N-oxide, hydrate, solvate, pharmaceutically acceptable salt, prodrug or complex thereof, or a racemic or scalemic mixture, diastereomer or enantiomer thereof, wherein M is selected from the group consisting of alkyl, —N(R$^e$)OR$^s$, —CF$_3$, —C(O)NR$^e$R$^f$, -heteroaryl, —H, —OH, —C(O)OR$^e$, —CH$_2$—S(acetyl), —CH$_2$—SR$^e$ and -heterocycloalkyl;

X is selected from the group consisting of CH, C(OH), C(C$_1$-C$_4$alkyl), C(halo), C(aryl), C(heteroaryl), C(R$^c$),

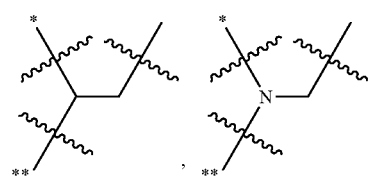

-continued

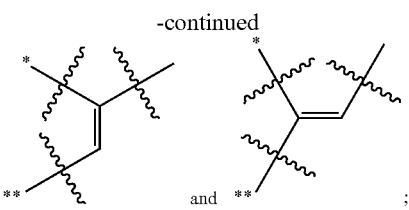

and wherein * represents the point of attachment to group L and ** represents the point of attachment to group Y;

L and Y are independently selected from the group consisting of $C_1$-$C_4$alkyl, heteroalkyl, alkenyl, alkynyl, —$NR^aR^b$, —$NR^cR^d$, —$OR^e$, —$C_0$-$C_3$alkyl-aryl, —$C_0$-$C_3$alkyl-heteroaryl, —$C_0$-$C_3$alkyl-heterocyclyl, —$C_0$-$C_3$alkyl-cycloalkyl, —$C_2$-$C_4$alkenyl-aryl, —$C_2$-$C_4$alkenyl-heteroaryl, —$C_2$-$C_4$alkenyl-heterocyclyl, —$C_2$-$C_4$alkenyl-cycloalkyl, —$C_2$-$C_4$alkynyl-aryl, —$C_2$-$C_4$alkynyl-heteroaryl, —$C_2$-$C_4$alkynyl-heterocyclyl, —$C_2$-$C_4$alkynyl-cycloalkyl, —O—$C_0$-$C_3$alkyl-aryl, —O—$C_0$-$C_3$alkyl-heteroaryl, —O—$C_0$-$C_3$alkyl-cycloalkyl, —O—$C_0$-$C_3$alkyl-heterocycloalkyl, —C(O)NH—$C_0$-$C_3$alkyl-aryl, —C(O)NH—$C_0$-$C_3$alkyl-heteroaryl, —O—$C_0$-$C_3$alkyl-aryl-aryl, —O—$C_0$-$C_3$alkyl-heteroaryl-aryl, —O—$C_0$-$C_3$alkyl-aryl-heteroaryl, —O—$C_0$-$C_3$alkyl-heteroaryl-heteroaryl, —$S(O)_{0-2}$—$C_0$-$C_3$alkyl-aryl, —$S(O)_{0-2}$—$C_0$-$C_3$alkyl-heteroaryl, —$S(O)_{0-2}$—$C_0$-$C_3$alkyl-aryl-aryl, —$S(O)_{0-2}$—$C_0$-$C_3$alkyl-heteroaryl-aryl, —$S(O)_{0-2}$—$C_0$-$C_3$alkyl-aryl-heteroaryl, —$S(O)_{0-2}$—$C_0$-$C_3$alkyl-heteroaryl-heteroaryl, -aryl-$C_0$-$C_3$alkyl-aryl, -heteroaryl-$C_0$-$C_3$alkyl-aryl, —$C_0$-$C_3$alkyl-aryl-$C_0$-$C_2$alkyl-N($R^e$)—$C_0$-$C_2$alkyl-aryl, —$C_0$-$C_3$alkyl-aryl-$C_0$-$C_2$alkyl-N($R^e$)—$C_0$-$C_2$alkyl-heteroaryl, —$C_0$-$C_3$alkyl-heteroaryl-$C_0$-$C_2$alkyl-N($R^e$)—$C_0$-$C_2$alkyl-aryl, —$C_0$-$C_3$alkyl-heteroaryl-$C_0$-$C_2$alkyl-N($R^e$)—$C_0$-$C_2$alkyl-heteroaryl, —$C_0$-$C_3$alkyl-aryl-$C_0$-$C_2$alkyl-N($R^e$)—$S(O)_2$—$C_0$-$C_2$alkyl-aryl, —$C_0$-$C_3$alkyl-aryl-$C_0$-$C_2$alkyl-N($R^e$)$S(O)_2$—$C_0$-$C_2$alkyl-heteroaryl, —$C_0$-$C_3$alkyl-heteroaryl-$C_0$-$C_2$alkyl-N($R^e$)$S(O)_2$—$C_0$-$C_2$alkyl-aryl, —$C_0$-$C_3$alkyl-heteroaryl-$C_0$-$C_2$alkyl-N($R^e$)—$S(O)_2$—$C_0$-$C_2$alkyl-heteroaryl, —N($R^e$)—$S(O)_2$—N($R^f$)—, —N($R^e$)—C(O)—, —C(O)—N($R^e$)—, —N($R^e$) C(O)—N($R^f$)—, —N($R^e$)—C(O)—O—, —O—C(O)—N($R^e$)—, —O—, —N($R^e$)—C(O)—$C_2$-$C_4$alkyl-O—, —O—$C_2$-$C_4$alkyl-N($R^e$)—, -heterocyclyl-$C_0$-$C_3$alkyl-aryl, -cycloalkyl-$C_0$-$C_3$alkyl-aryl, -aryl-$C_0$-$C_3$alkyl-heteroaryl, -heteroaryl-$C_0$-$C_3$alkyl-heteroaryl, -heterocyclyl-$C_0$-$C_3$alkyl-heteroaryl, -cycloalkyl-$C_0$-$C_3$alkyl-heteroaryl, -aryl-$C_0$-$C_3$alkyl-heterocyclyl, -heteroaryl-$C_0$-$C_3$alkyl-heterocyclyl, -heterocyclyl-$C_0$-$C_3$alkyl-heterocyclyl, -cycloalkyl-$C_0$-$C_3$alkyl-heterocyclyl, -heterocyclyl-$C_0$-$C_3$alkyl-O—$C_0$-$C_3$alkyl-aryl, -heterocyclyl-$C_0$-$C_3$alkyl-O—$C_0$-$C_3$alkyl-heteroaryl, -heterocyclyl-$C_0$-$C_3$alkyl-O—C(O)NH—$C_0$-$C_3$alkyl-aryl, heterocyclyl-$C_0$-$C_3$alkyl-O—C(O)NH—$C_0$-$C_3$alkyl-heteroaryl, -heterocyclyl-$C_0$-$C_3$alkyl-heteroaryl-aryl, -heterocyclyl-$C_0$-$C_3$alkyl-heteroaryl-heteroaryl, -heterocyclyl-$C_0$-$C_3$alkyl-aryl-aryl, -heterocyclyl-$C_0$-$C_3$alkyl-aryl-heteroaryl, -heterocyclyl-$C_0$-$C_3$alkyl-heteroaryl-$C_0$-$C_3$alkyl-aryl, -heterocyclyl-$C_0$-$C_3$alkyl-heteroaryl-$C_0$-$C_3$alkyl-heteroaryl, -heterocyclyl-$C_0$-$C_3$alkyl-aryl-$C_0$-$C_3$alkyl-aryl, -heterocyclyl-$C_0$-$C_3$alkyl-aryl-$C_0$-$C_3$alkyl-heteroaryl, -heterocyclyl-$S(O)_2$—$C_0$-$C_3$alkyl-aryl, -heterocyclyl-$S(O)_2$—$C_0$-$C_3$alkyl-heteroaryl, -heterocyclyl-$S(O)_2$—$C_0$-$C_3$alkyl-alkyl, -heterocyclyl-$S(O)_2$—$C_0$-$C_3$alkyl-cycloalkyl, -heterocyclyl-$S(O)_2$—$C_0$-$C_3$alkyl-heterocyclyl, -heterocyclyl-C(O)—$C_0$-$C_3$alkyl-aryl, -heterocyclyl-C(O)—$C_0$-$C_3$alkyl-heteroaryl, -heterocyclyl-C(O)—$C_0$-$C_3$alkyl-alkyl, -heterocyclyl-C(O)—$C_0$-$C_3$alkyl-cycloalkyl, -heterocyclyl-C(O)—$C_0$-$C_3$alkyl-heterocyclyl, -heterocyclyl-C(O)NH—$C_0$-$C_3$alkyl-aryl, -heterocyclyl-C(O)NH—$C_0$-$C_3$alkyl-heteroaryl, -heterocyclyl-C(O)NH—$C_0$-$C_3$alkyl-alkyl, -heterocyclyl-C(O)NH—$C_0$-$C_3$alkyl-cycloalkyl, -heterocyclyl-C(O)NH—$C_0$-$C_3$alkyl-heterocyclyl, -heterocyclyl-C(O)O—$C_0$-$C_3$alkyl-aryl, -heterocyclyl-C(O)O—$C_0$-$C_3$alkyl-heteroaryl, -heterocyclyl-C(O)O—$C_0$-$C_3$alkyl-alkyl, -heterocyclyl-C(O)O—$C_0$-$C_3$alkyl-cycloalkyl, -heterocyclyl-C(O)O—$C_0$-$C_3$alkyl-heterocyclyl, -heterocyclyl-$S(O)_2$—NH—$C_0$-$C_3$alkyl-aryl, -heterocyclyl-$S(O)_2$—NH—$C_0$-$C_3$alkyl-heteroaryl, -heterocyclyl-$S(O)_2$—NH—$C_0$-$C_3$alkyl-alkyl, -heterocyclyl-$S(O)_2$—NH—$C_0$-$C_3$alkyl-cycloalkyl, -heterocyclyl-$S(O)_2$—NH—$C_0$-$C_3$alkyl-heterocyclyl, —$C_0$-$C_3$alkyl-heterocyclyl-$C_2$-$C_4$alkenyl-aryl, —$C_0$-$C_3$alkyl-heterocyclyl-CH(aryl)$_2$, —$C_0$-$C_3$alkyl-heterocyclyl-CH(heteroaryl)$_2$, —$C_0$-$C_3$alkyl-heterocyclyl-CH(aryl)(heteroaryl), —$C_0$-$C_3$alkyl-aryl-$C_0$-$C_3$alkyl-heterocyclyl-$C_0$-$C_3$alkyl-aryl, —$C_0$-$C_3$alkyl-heteroaryl-$C_0$-$C_3$alkyl-heterocyclyl-$C_0$-$C_3$alkyl-aryl, —$C_0$-$C_3$alkyl-aryl-$C_0$-$C_3$alkyl-heterocyclyl-$C_0$-$C_3$alkyl-heteroaryl, —$C_0$-$C_3$alkyl-heteroaryl-$C_0$-$C_3$alkyl-heterocyclyl-$C_0$-$C_3$alkyl-heteroaryl, —$C_0$-$C_3$alkyl-aryl-heterocyclyl-$S(O)_2$-aryl, —$C_0$-$C_3$alkyl-heteroaryl-heterocyclyl-$S(O)_2$-aryl, —$C_0$-$C_3$alkyl-aryl-heterocyclyl-$S(O)_2$-heteroaryl, —$C_0$-$C_3$alkyl-heteroaryl-heterocyclyl-$S(O)_2$-heteroaryl, —$C_0$-$C_3$alkyl-aryl-$S(O)_2$-heterocyclyl-aryl, —$C_0$-$C_3$alkyl-heteroaryl-$S(O)_2$-heterocyclyl-aryl, —$C_0$-$C_3$alkyl-aryl-$S(O)_2$-heterocyclyl-heteroaryl, —$C_0$-$C_3$alkyl-heteroaryl-$S(O)_2$-heterocyclyl-heteroaryl, —$C_0$-$C_3$alkyl-aryl-heterocyclyl-C(O)-aryl, —$C_0$-$C_3$alkyl-heteroaryl-heterocyclyl-C(O)-aryl, —$C_0$-$C_3$alkyl-aryl-heterocyclyl-C(O)-heteroaryl, —$C_0$-$C_3$alkyl-heteroaryl-heterocyclyl-C(O)-heteroaryl, —$C_0$-$C_3$alkyl-aryl-C(O)-heterocyclyl-aryl, —$C_0$-$C_3$alkyl-heteroaryl-C(O)-heterocyclyl-aryl, —$C_0$-$C_3$alkyl-aryl-C(O)-heterocyclyl-heteroaryl, —$C_0$-$C_3$alkyl-heteroaryl-C(O)-heterocyclyl-heteroaryl, —$C_0$-$C_3$alkyl-aryl-heterocyclyl-C(O)$NR^e$-aryl, —$C_0$-$C_3$alkyl-heteroaryl-heterocyclyl-C(O)$NR^e$-aryl, —$C_0$-$C_3$alkyl-aryl-heterocyclyl-C(O)$NR^e$-heteroaryl, —$C_0$-$C_3$alkyl-heteroaryl-heterocyclyl-C(O)$NR^e$-heteroaryl, —$C_0$-$C_3$alkyl-aryl-$NR^e$C(O)-heterocyclyl-aryl, —$C_0$-$C_3$alkyl-heteroaryl-$NR^e$C(O)-heterocyclyl-aryl, —$C_0$-$C_3$alkyl-aryl-$NR^e$C(O)-heterocyclyl-heteroaryl, —$C_0$-$C_3$alkyl-heteroaryl-$NR^e$C(O)-heterocyclyl-heteroaryl, —$C_0$-$C_3$alkyl-aryl-heterocyclyl-C(O)O-aryl, —$C_0$-$C_3$alkyl-heteroaryl-heterocyclyl-C(O)O-aryl, —$C_0$-$C_3$alkyl-aryl-heterocyclyl-C(O)O-heteroaryl, —$C_0$-$C_3$alkyl-heteroaryl-heterocyclyl-C(O)O-heteroaryl, —$C_0$-$C_3$alkyl-aryl-OC(O)-heterocyclyl-aryl, —$C_0$-$C_3$alkyl-heteroaryl-OC(O)-heterocyclyl-aryl, —$C_0$-$C_3$alkyl-aryl-OC(O)-heterocyclyl-heteroaryl, and —$C_0$-$C_3$alkyl-heteroaryl-OC(O)-heterocyclyl-heteroaryl, provided that if an L or a Y is bound directly to a nitrogen of X, then the L or Y is not —$NR^aR^b$, —$NR^cR^d$, —$OR^e$, —$S(O)_{0-1}$—$C_0$-$C_3$alkyl-aryl, —$S(O)_{0-1}$—$C_0$-$C_3$alkyl-heteroaryl, —$S(O)_{0-1}$—$C_0$-$C_3$alkyl-aryl-aryl, —$S(O)_{0-1}$—$C_0$-$C_3$alkyl-heteroaryl-aryl, —$S(O)_{0-1}$—$C_0$-$C_3$alkyl-aryl-heteroaryl or —$S(O)_{0-1}$—$C_0$-$C_3$alkyl-heteroaryl-heteroaryl, in which each $R^a$ and $R^b$ together with the nitrogen to which they are bound form a 4 to 7 membered heterocyclyl having 1 or 2 annular heteroatoms, or a 5 to 8 membered bridged heterocyclyl having 1 or 2 annular heteroatoms, the heterocyclyl being optionally substituted with 1-3 substituents independently selected from the group consisting of H, OH, oxo (i.e., =O), —N($R^c$)($R^d$), $C_1$-$C_6$alkyl, aryl, heteroaryl, —$C_1$-$C_6$alkyl-aryl, —$C_1$-$C_6$alkyl-heteroaryl, —$C_1$-$C_3$alkoxy-$C_1$-

C$_3$alkyl, —C$_2$-C$_3$alkyl-OH, —C$_2$-C$_3$alkyl-O—C$_1$-C$_4$alkyl, —C$_5$-C$_6$cycloalkyl, —C$_0$-C$_3$alkyl-N(H)—C(O)—C$_1$-C$_3$alkyl, —C$_{0-3}$alkyl-N(H)—C(O)-haloalkyl, —C$_0$-C$_3$alkyl-NHC(O)O—C$_1$-C$_3$alkyl-aryl, —C$_0$-C$_3$alkyl-CF$_3$, —C$_0$-C$_3$alkyl-NHC(O)O—C$_1$-C$_3$alkyl-heteroaryl and —C$_0$-C$_3$alkyl-NH$_2$, wherein said heterocyclyl is optionally fused to an aryl or heteroaryl;

each R$^c$ and R$^d$ is independently selected from the group consisting of H, —C$_1$-C$_6$alkyl, —C$_2$-C$_3$alkyl-OR$^e$, aryl, heteroaryl, -heteroaryl-heteroaryl, -heteroaryl-aryl, -aryl-heteroaryl, —C(O)-aryl, —C$_1$-C$_3$-alkoxy-C$_1$-C$_3$-alkyl, —C$_2$-C$_3$alkyl-O—C$_1$-C$_3$alkyl, —C$_2$-C$_3$alkyl-NR$^e$R$^f$, —CH$_2$—C(CH$_3$)$_2$—NR$^e$R$^f$, in which each aryl and heteroaryl is optionally substituted with one, two or three substituents independently selected from amino, OCH$_3$ and OH; or R$^c$ and Y together with the carbon to which they are bound form an optionally substituted 4 to 7 membered ring system having 0-2 annular heteroatoms;

each R$^e$ and R$^f$ is independently selected from the group consisting of —H, -alkyl, -aryl, -aryl-aryl, -hetetoaryl, heteroaryl-aryl, heteroaryl-heteroaryl, C(O)-alkyl and —C(O)CF$_3$; and each R$^s$ is independently selected from the group consisting of —H, C$_1$-C$_6$alkyl, aryl, heteroaryl, heterocyclyl, cycloalkyl and a protecting group wherein each cycloalkyl, heterocyclyl, aryl, alkyl and heteroaryl moiety is optionally substituted, and wherein a cycloalkyl, heterocyclyl, aryl, alkyl or heteroaryl moiety in L is optionally connected to a cycloalkyl, heterocyclyl, aryl, alkyl or heteroaryl in Y by a bond or by a bridging substituent.

In a preferred embodiment of the second aspect of the invention, M is

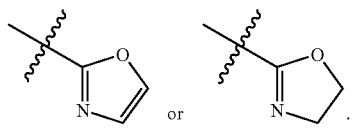 [SMILES: *c1ncco1 ; *C1=NCCO1]

In a preferred embodiment of the third aspect of the invention, M is NHOH.

In another preferred embodiment of the third aspect of the invention, M is —H.

In another preferred embodiment of the third aspect of the invention, X is CH.

In another preferred embodiment of the third aspect of the invention, X is C(OH) or C(halo).

In another preferred embodiment of the third aspect of the invention, X is

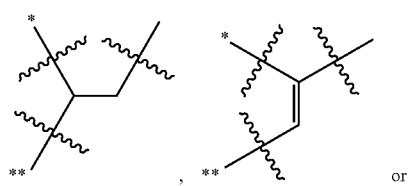

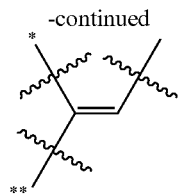

In another preferred embodiment of the third aspect of the invention, X is

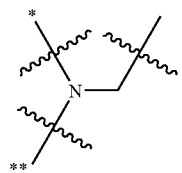

In a preferred embodiment of the third aspect of the invention, L and Y are independently selected from the group consisting of aryl, heteroaryl, alkyl, —O-aryl, —O-cycloalkyl, heterocyclyl, cycloalkyl, —S-aryl, —S-heteroaryl, —C(O)NH-aryl, —S-heteroaryl-aryl, —S-aryl-aryl, -aryl-heterocyclyl, -heteroaryl-heterocyclyl, —C$_1$-C$_3$alkyl-aryl, —S(O)$_2$-aryl, —S(O)$_2$-heteroaryl, —NHS(O)$_2$-aryl, -heterocyclyl-C$_0$-C$_3$alkyl-aryl, -heterocyclyl-C$_0$-C$_3$alkyl-heteroaryl, -heteroaryl-C$_0$-C$_3$alkyl-heteroaryl, heteroaryl-C$_0$-C$_3$alkyl-aryl, -aryl-aryl, -aryl-heteroaryl, -heterocyclyl-O-aryl, -heterocyclyl-O—C$_0$-C$_3$alkyl-aryl, -heterocyclyl-O—C$_0$-C$_3$alkyl-heteroaryl, -heterocyclyl-S(O)$_2$—C$_0$-C$_3$alkyl-aryl and -heterocyclyl-S(O)$_2$—C$_0$-C$_3$alkyl-heteroaryl, wherein each said cycloalkyl, heterocyclyl, aryl, alkyl and heteroaryl moiety of the forgoing L and Y is optionally substituted with a substituent selected from the group consisting of —N(R$^e$)C(O)—C$_0$-C$_3$alkyl-aryl, —N(R$^e$)C(O)—C$_0$-C$_3$alkyl-heteroaryl, —N(R$^e$)C(O)—C$_0$-C$_3$alkyl-heterocyclyl, —N(R$^e$)C(O)—C$_0$-C$_3$alkyl-cycloalkyl, —N(R$^e$)C(O)—C$_0$-C$_8$alkyl, —N(R$^a$)(R$^b$), —N(R$^c$)(R$^d$), —CF$_3$, aryl, heteroaryl, cycloalkyl, heterocyclyl, —C$_1$-C$_3$alkyl-aryl, —C$_1$-C$_3$alkyl-heteroaryl, —C$_1$-C$_3$alkyl-cycloalkyl, —C$_1$-C$_3$alkyl-heterocyclyl, and wherein each cycloalkyl, heterocyclyl, aryl, alkyl and heteroaryl moiety in L is further optionally substituted with halo or —O—C$_1$-C$_3$alkyl.

In another preferred embodiment of the third aspect of the invention, each cycloalkyl and heterocyclyl moiety is optionally gem or spiro substituted with —OH, —CN or -alkyl.

In another preferred embodiment of the third aspect of the invention, L and Y are independently selected from the group consisting of aromatic polycycle, non-aromatic polycycle, polyheteroaryl, non-aromatic polyheterocyclic, and mixed aryl and non-aryl polyheterocycle.

In another preferred embodiment of the third aspect of the invention, L and Y are independently selected from aryl, heteroaryl, O-aryl, heterocyclyl, cycloalkyl, —S-aryl, —S-heteroaryl and —C(O)NH-aryl, —S-heteroaryl-aryl, -aryl-heterocyclyl, -heteroaryl-heterocyclyl, —C$_1$-C$_3$alkyl-aryl, —S(O)$_2$-aryl, —S(O)$_2$-heteroaryl, -heterocyclyl-C$_0$-C$_3$alkyl-aryl, heteroaryl-C$_0$-C$_3$alkyl-heteroaryl, heteroaryl-C$_0$-C$_3$alkyl-aryl, -aryl-aryl and -heterocyclyl-O-aryl, each of which is optionally substituted.

In another preferred embodiment of the third aspect of the invention, the compound has the Formula (XIII):

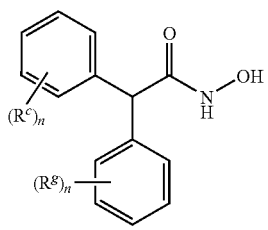

(XIII)

wherein
$R^c$ is as described above with respect to Formula (XII);
each n is independently 0-3; and
$R^g$ is selected from the group consisting of —$C_0$-$C_3$alkyl-aryl, —$C_0$-$C_3$alkyl-heteroaryl, —$C_0$-$C_3$alkyl -cycloalkyl, —$C_0$-$C_3$alkyl-heterocyclyl, —$NR^aR^b$, —$NR^cR^d$, —$OR^e$ In another preferred embodiment of the third aspect of the invention, the compound has the Formula (XIV):

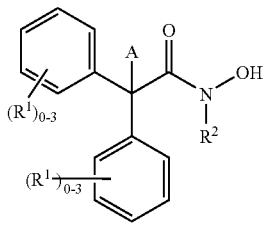

(XIV)

wherein
$R^1$ is alkyl, $NO_2$, halo or alkoxy,
$R^2$ is H or $C_1$-$C_5$alkyl, and
A is H, phenyl or OH.

As described above, a cycloalkyl, heterocyclyl, aryl, alkyl or heteroaryl moiety in L is optionally connected to a cycloalkyl, heterocyclyl, aryl, alkyl or heteroaryl in Y by a bond or by a bridging substituent. Such a bridging substituent desirably has 1-6 atoms along the shortest path between the cycloalkyl, heterocyclyl, aryl, alkyl or heteroaryl moiety in L and the cycloalkyl, heterocyclyl, aryl, alkyl or heteroaryl moiety in Y. For example, in another preferred embodiment of the third aspect of the invention, the compound has the Formula (XV):

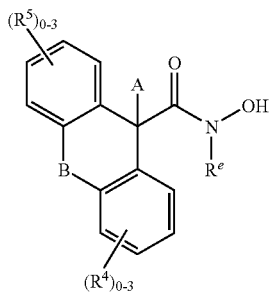

(XV)

wherein
$R^4$ and $R^5$ are independently selected from the group consisting of H, halo, —$NH_2$, —$NO_2$, —$C_0$-$C_4$alkyl-aryl, —$C_0$-$C_4$alkyl-heteroaryl, —$C_0$-$C_4$alkyl-heterocyclyl, —$C_0$-$C_4$alkyl-cycloalkyl, —OMe, alkyl, CN and $CF_3$;

A is H, phenyl or OH; and
B is a bond, —O—, —$N(R^6)$—, —$S(O)_{0-2}$—, —$CH(R^4)$—, —$C(R^5)(R^4)$—, —$C(R^4)$—$N(R^c)$—, —$N(R^c)$—$C(R^4)$—, —$C(R^4)$—O—, —O—$C(R^4)$—, —$S(O)_{0-2}$—$C(R^4)$—, —$C(R^4)$—$S(O)_{0-2}$—, —$C(R^4)$=$C(R^5)$—, —$CH(R^4)$—$CH(R^5)$—, —$C(R^4)$=$N(R^6)$—, —$C(O)N(R^6)$—, —$S(O)_2N(R^6)$—, —$C(R^5)(R^4)$—$C(R^5)(R^4)$—, —$C(R^5)(H)$—$C(H)(R^4)$—, —$N(CH_2Ph)$-, or

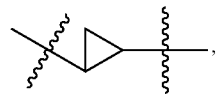

in which $R^6$ is alkyl, cycloalkyl or heterocyclyl.
In another preferred embodiment of the third aspect of the invention, the compound has the Formula (XVI):

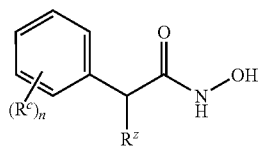

(XVI)

wherein
n is 0-3;
$R^z$ is selected from the group consisting of

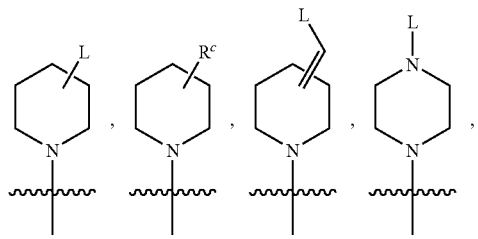

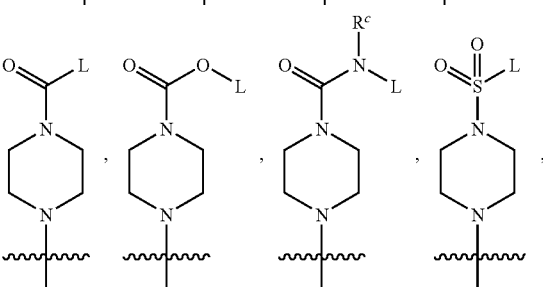

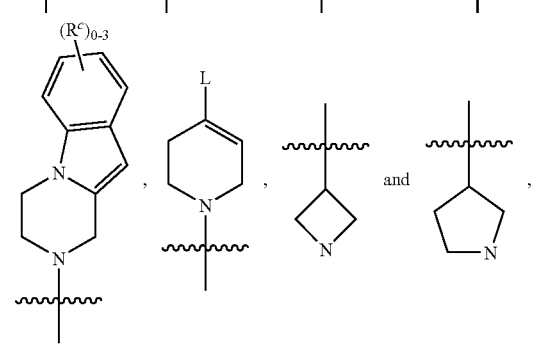

$R^c$ and L are as described above with respect to Formula (XII), wherein when L is bound directly to N or O, it is not —NR$^a$R$^b$, —NR$^c$R$^d$, —OR$^e$, —S(O)$_{0-1}$—C$_0$-C$_3$alkyl-aryl, —S(O)$_{0-1}$—C$_0$-C$_3$alkyl-heteroaryl, —S(O)$_{0-1}$—C$_0$-C$_3$alkyl-aryl-aryl, —S(O)$_{0-1}$—C$_0$-C$_3$alkyl-heteroaryl-aryl, —S(O)$_{0-1}$—C$_0$-C$_3$alkyl-aryl-heteroaryl or —S(O)$_{0-1}$—C$_0$-C$_3$alkyl-heteroaryl-heteroaryl.

In another preferred embodiment of the third aspect of the invention the compound has the Formula (XVII)

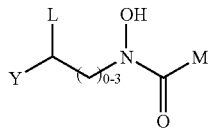

(XVII)

wherein

M is H or alkyl; and

L and Y are as defined in Formula (XII).

In another preferred embodiment of the third aspect of the invention, the compound has the Formula (XII-A):

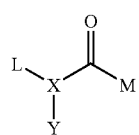

(XII-A)

or an N-oxide, hydrate, solvate, pharmaceutically acceptable salt, prodrug or complex thereof, or a racemic or scalemic mixture, diastereomer or enantiomer thereof, wherein M, X, Y and L are as defined for Formula (XII), and wherein Y is further selected from the group consisting of —Z$^1$—Z—Z$^2$-D, -D, —Z$^1$—Z$^3$—Z-D, —Z$^1$—Z$^3$—Z$^2$—Z-D, —Z$^1$—Z$^2$-D, —Z$^1$—Z—Z$^3$—Z$^2$-D, —Z—Z$^3$—Z$^2$-D, —Z$^1$—Z—Z$^3$-D and —Z$^2$—Z$^1$—Z$^2$-D, wherein Z$^1$ is selected from the group consisting of chemical bond, alkyl, aryl, heterocyclyl, bridged heterocyclyl, spiro heterocyclyl, cycloalkyl, heteroaryl, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;

Z is selected from the group consisting of chemical bond, —O—, —S(O)$_{0-2}$—, —N(R$^c$)C(O)—, —C(O)N(R$^c$)—C(O)—, —C(O)N(R$^c$)—, —N(R$^c$)S(O)$_2$—, —N(R$^c$)—, —N(R$^c$)(C$_2$-C$_4$alkyl-OR$^d$)—, —C(O)—, —C(NOR$^{21}$)—, —CH[C(O)N(R$^2$)(R$^{22}$)]—C(O)N(R$^{22}$)—, —CH(N(R$^{21}$)(R$^{22}$))—C(O)N(R$^{22}$)—, —CH[C(O)N(R$^e$)(R$^f$)]—C(O)N(R$^{22}$)—, —S(O)$_2$N(R$^{21}$)—, —N(R$^{21}$)S(O)$_2$N(R$^{22}$)—, —OC(O)—, —C(O)O—, —N(R$^{21}$)C(NR$^{22}$)—, —C(NR$^{22}$)N(R$^{21}$)—, —N(R$^{21}$)C(O)N(R$^{22}$)—, —N(R$^{21}$)C(O), —OC(O)N(R$^{21}$)—, —N(R$^{21}$)C(S)—, —C(S)N(R$^{21}$)—, —N(R$^{21}$)C(S)N(R$^{22}$)—, —N(R$^{21}$)C(S)O—, —OC(S)N(R$^{21}$)—, —O—C$_2$-C$_4$alkyl-N(R$^{21}$)—, —N(R$^{21}$)—C$_2$-C$_4$alkyl-O—, —N(R$^1$)—C$_2$-C$_4$alkyl-S(O)$_{0-2}$—, —N[C$_2$-C$_4$alkyl-N(R$^1$)(R$^2$)]—, —N(C$_2$-C$_4$alkyl-O-alkyl)-C$_2$-C$_4$alkyl-O—, —O—C$_2$-C$_4$alkyl-N(R$^c$)—, —N(R$^c$)—C$_2$-C$_4$alkyl-O—, —N(R$^c$)—C$_2$-C$_4$alkyl-N(R$^{21}$)—, —O—C$_1$-C$_4$alkyl-S(O)$_2$N(R$^{21}$)—, —O—C$_1$-C$_4$alkyl-O—, —O—C$_1$-C$_4$alkyl-O—C$_1$-C$_4$alkyl-O—, —S(O)$_2$N(R$^{21}$)—C$_2$-C$_4$alkyl-O—, —O—C$_2$-C$_4$alkyl-N(R$^{21}$)S(O)$_2$—, —N(R$^{21}$)S(O)$_2$—C$_1$-C$_4$alkyl-O—, —C(O)—C$_1$-C$_4$alkyl-N(R$^{21}$)—, —N(C(O)—C$_1$-C$_4$alkyl)-, —N(R$^{21}$)—C$_1$-C$_4$alkyl-C(O)—, —O—C$_1$-C$_4$alkyl-C(O)N(R$^{21}$)—, —C(O)N(R$^{21}$)—C$_2$-C$_4$alkyl-O—, —C(O)—C$_1$-C$_4$alkyl-O—, —C(O)—C$_1$-C$_4$alkyl-S(O)$_{0-2}$—, —O—C$_2$-C$_4$alkyl-N(R$^{21}$)C(O)—, —N(R$^{21}$)C(O)—C$_1$-C$_4$alkyl-O—, —N(R$^{21}$)C(O)—C$_1$-C$_4$alkyl-S(O)$_{0-2}$—, —O—C$_1$-C$_4$alkyl-C(O)—, —C(O)—C$_1$-C$_4$alkyl-O—, —N(R$^{21}$)—C$_1$-C$_4$alkyl-C(O), —C(O)—C$_1$-C$_4$alkyl-N(R$^{21}$)—, —O—C$_1$-C$_4$alkyl-C(S)—, —C(S)—C$_1$-C$_4$alkyl-O—, —N(R$^{21}$)—C$_1$-C$_4$alkyl-C(S), —C(S)—C$_1$-C$_4$alkyl-N(R$^{21}$)—, —N(R$^{21}$)—C$_1$-C$_4$alkyl-C(S)—, —O—C$_1$-C$_4$alkyl-C(S)N(R$^{21}$)—, —C(S)N(R$^{21}$)—C$_2$-C$_4$alkyl-O—, —O—C$_2$-C$_4$alkyl-N(R$^{21}$)C(S)—, —N(R$^{21}$)C(O)—C$_1$-C$_4$alkyl-O—, —N(R$^{21}$)C(S)—C$_1$-C$_4$alkyl-O—, —N(R$^{21}$)—C$_1$-C$_4$alkyl-S(O)$_2$—, —O—C$_1$-C$_4$alkyl-S(O)$_2$N(R$^{21}$)—, —S(O)$_2$N(R$^{21}$)—C$_2$-C$_4$alkyl-O—, —O—C$_2$-C$_4$alkyl-N(R$^{21}$)S(O)$_2$—, —N(R$^{21}$)S(O)$_2$—C$_1$-C$_4$alkyl-O—, —O—C$_2$-C$_4$alkyl-OC(O)N(R$^{21}$)—, —O—C$_2$-C$_4$alkyl-OC(S)N(R$^{21}$)—, wherein each alkyl moiety is optionally substituted;

Z$^2$ is selected from the group consisting of a chemical bond, alkyl, alkenyl, alkynyl, alkyl-alkenyl, alkynyl-alkyl and alkyl-alkynyl, wherein each alkyl, alkenyl and alkynyl moiety is optionally substituted;

Z$^3$ is selected from the group consisting of a chemical bond, —C$_1$-C$_5$alkyl-, —C$_0$-C$_5$alkyl-aryl-, —C$_0$-C$_5$alkyl-heterocyclyl-, —C$_0$-C$_5$alkyl-bridged heterocyclyl-, -spiro heterocyclyl-, —C$_0$-C$_5$alkyl-cycloalkyl- and —C$_0$-C$_5$alkyl-heteroaryl-, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;

D is selected from the group consisting of H, aryl, heteroaryl, alkyl, alkenyl, alkynyl, heteroalkyl, cycloalyl, heterocyclyl, bridged heterocyclyl, spiro heterocyclyl, aromatic polycycles, non-aromatic polycycles, polyheteroaryl groups, non-aromatic polyheterocyclic, mixed aryl and non-aryl polyheterocycle, each of which is optionally substituted and each of which is optionally fused to one or more aryl or heteroaryl rings, or one or more saturated or partially unsaturated cycloalkyl or heterocyclyl rings, each of which ring is optionally substituted, wherein each R$^{21}$ and R$^{22}$ is independently selected from the group consisting of —H, -alkyl, -aryl and heteroaryl, wherein each said aryl and heteroaryl moiety is optionally substituted; and L is selected from the group consisting of cycloalkyl, heterocyclyl, aryl and heteroaryl (preferably aryl and heteroaryl), wherein each aryl, heteroaryl, heterocyclyl, cycloalkyl and aryl group is optionally fused to a heterocyclyl, or is optionally substituted with a substituent selected from the group consisting of halo, —O-alkyl, —S-alkyl, —NO$_2$, —N(R$^e$)C(O)—C$_0$-C$_3$alkyl-aryl, —N(R$^e$)C(O)—C$_0$-C$_3$alkyl-heteroaryl, —N(R$^a$)(R$^b$), —N(R$^c$)(R$^d$), —OH, -alkyl, aryl, heteroaryl, —OCF$_3$ and —CF$_3$.

In a preferred embodiment of the second aspect of the invention, each cycloalkyl, heterocyclyl, aryl, alkyl, alkenyl and heteroaryl moiety in Z, Z$_1$, Z$_2$, Z$_3$ and D is optionally substituted with a substituent selected from the group consisting of —N(R$^e$)C(O)—C$_1$-C$_6$alkyl, —N(R$^e$)C(O)—C$_0$-C$_3$alkyl-aryl, —N(R$^e$)C(O)—C$_0$-C$_3$alkyl-heteroaryl, —N(R$^e$)C(O)—C$_0$-C$_3$alkyl-heterocyclyl, —N(R$^e$)C(O)—C$_0$-C$_3$alkyl-cycloalkyl, —N(R$^e$)C(O)—C$_0$-C$_8$alkyl, —N(R$^a$)(R$^b$), —N(R$^c$)(R$^d$), —CF$_3$, —O—CF$_3$, —S—CF$_3$, aryl, heteroaryl, cycloalkyl, heterocyclyl, —C$_1$-C$_3$alkyl-aryl, —C$_1$-C$_3$alkyl-heteroaryl, —C$_1$-C$_3$alkyl-cycloalkyl, —C$_1$-

$C_3$alkyl-heterocyclyl, halo, alkyl, —O-alkyl, —S(O)$_{0-2}$-alkyl, —C$_0$-C$_3$alkyl-CN, NO$_2$, —C(O)-alkyl and —OH.

In another preferred embodiment of the third aspect of the invention, the compound has the Formula (XX):

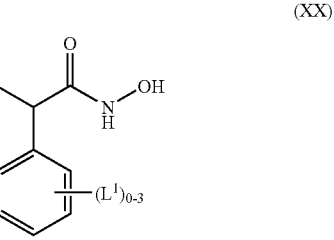

(XX)

or an N-oxide, hydrate, solvate, pharmaceutically acceptable salt, prodrug or complex thereof, or a racemic or scalemic mixture, diastereomer or enantiomer thereof, wherein each L$^1$ is independently selected from the group consisting of H, halo, —O-alkyl, —S-alkyl, —NO$_2$, —N(R$^e$)C(O)—C$_0$-C$_3$alkyl-aryl, —N(R$^e$)C(O)—C$_0$-C$_3$alkyl-heteroaryl, —N(R$^a$)(R$^b$), —N(R$^c$)(R$^d$), —OH, -alkyl, —OCF$_3$, and —CF$_3$; and Y$^1$ is selected from the group consisting of —Z—Z$^2$-D, —Z$^1$—Z$^2$-D, —CH$_2$-D and D.

In another preferred embodiment of the third aspect of the invention, the compound has the Formula (XX-A):

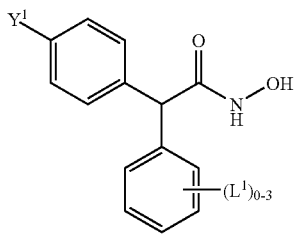

(XX-A)

or an N-oxide, hydrate, solvate, pharmaceutically acceptable salt, prodrug or complex thereof, or a racemic or scalemic mixture, diastereomer or enantiomer thereof, wherein each L$^1$ is independently selected from the group consisting of H, halo, —O—CH$_3$, —CH$_3$ and —OH; and Y$^1$ is selected from the group consisting of —Z—Z$^2$-D, —Z$^1$—Z$^2$-D, —CH$_2$-D and D;

wherein

Z is selected from the group consisting of —O—, —S(O)$_{0-2}$—, —N(R$^c$)C(O)—, —C(O)N(R$^c$)—, —N(R$^e$)S(O)$_2$—, —N(R$^c$)—, —S(O)$_2$N(R$^{21}$)—, —O—C$_2$-C$_4$alkyl-N(R$^{21}$)—, —N(R$^{21}$)—C$_2$-C$_4$alkyl-O—, —N(R$^e$)—C$_2$-C$_4$alkyl-N(R$^d$)—, and —O—C$_1$-C$_4$alkyl-O—;

Z$^1$ is selected from the group consisting of aryl, heterocyclyl, bridged heterocyclyl, spiro heterocyclyl, cycloalkyl and heteroaryl, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;

Z$^2$ is a chemical bond or an optionally substituted alkyl; and

D is selected from the group consisting of H, aryl, heteroaryl, alkyl, cycloalyl and heterocyclyl, each of which is optionally substituted and each of which is optionally fused to one or more aryl or heteroaryl rings, or one or more saturated or partially unsaturated cycloalkyl or heterocyclyl rings, each of which ring is optionally substituted.

In another preferred embodiment of the third aspect of the invention, the compound has the Formula (XX):

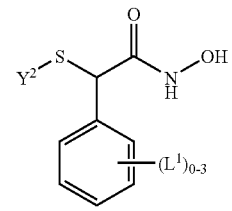

(XXI)

or an N-oxide, hydrate, solvate, pharmaceutically acceptable salt, prodrug or complex thereof, or a racemic or scalemic mixture, diastereomer or enantiomer thereof, wherein each L$^1$ is independently selected from the group consisting of H, halo, —O-alkyl, —S-alkyl, —NO$_2$, —N(R$^e$)C(O)—C$_0$-C$_3$alkyl-aryl, —N(R$^e$)C(O)—C$_0$-C$_3$alkyl-heteroaryl, —N(R$^a$)(R$^b$), —N(R$^c$)(R$^d$), —OH, -alkyl, —OCF$_3$ and —CF$_3$; and Y$^2$ is —Z$^2$—Z$^1$—Z$^2$-D, —CH$_2$-D or D;

wherein

Z$^1$ is selected from the group consisting of aryl, heterocyclyl, cycloalkyl and heteroaryl, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;

Z$^2$ is a chemical bond or an optionally substituted alkyl; and

D is selected from the group consisting of H, aryl, heteroaryl, alkyl, cycloalyl and heterocyclyl, each of which is optionally substituted and each of which is optionally fused to one or more aryl or heteroaryl rings, or one or more saturated or partially unsaturated cycloalkyl or heterocyclyl rings, each of which ring is optionally substituted.

Another preferred embodiment of the third aspect of the invention, in Formulae (XII)-(XVII) each aryl, heterocyclyl, cycloalkyl and heteroaryl is independently optionally substituted with one, two or three substituents independently selected from the group consisting of H, halo, =O, OH, C$_1$-C$_3$-hydrocarbyl, OCH$_3$, —CN, —S(O)$_{0-2}$—C$_1$-C$_4$alkyl, —CF$_3$, —OCF$_3$, alkyl, —NH$_2$, —N(alkyl)$_2$, —NH(alkyl), —N(aryl)(alkyl), —N(-alkyl-aryl)(alkyl), —N(heteroaryl)(alkyl), —N(-alkyl-heteroalkylaryl)(alkyl), —NH(aryl), —NH(-alkyl-aryl), —NH(heteroaryl), —NH(-alkyl-heteroalkylaryl), —N(—C$_2$-C$_4$alkyl-O-alkyl)(alkyl), —NH(—C$_2$-C$_4$alkyl-Oalkyl), —NO$_2$, —O—C$_1$-C$_4$alkyl, —C$_0$-C$_4$alkyl-aryl, —C$_0$-C$_4$alkyl-heteroaryl, —C$_0$-C$_4$alkyl-heterocyclyl, —C$_0$-C$_4$alkyl-cycloalkyl, —NHS(O)$_2$-alkyl, —S(O)$_2$NH-alkyl, —NR$^a$R$^b$, —NR$^c$R$^d$, —OR$^e$, —C$_2$-C$_4$alkyl-NR$^a$R$^b$, C$_2$-C$_4$alkyl-NR$^c$R$^d$, —S(O)$_{0-1}$R$^e$, —(CR$^{32}$R$^{33}$)$_s$—NR$^{30}$R$^{31}$, and (X$^{30}$—Y$^{31}$—), in which R$^{30}$ and R$^{31}$ are each independently hydrogen, cyano, oxo, hydroxyl, C$_1$-C$_8$ alkyl, C$_1$-C$_8$heteroalkyl, C$_1$-C$_8$alkenyl, carboxamido-, C$_1$-C$_3$alkyl-carboxamido-, carboxamido-C$_1$-C$_3$alkyl-, amidino-, C$_2$-C$_8$hydroxyalkyl-, C$_1$-C$_3$alkyl-aryl-, aryl-C$_1$-C$_3$ alkyl-, C$_1$-C$_3$alkyl-heteroaryl-, heteroaryl-C$_1$-C$_3$alkyl-, C$_1$-C$_3$alkyl-heterocyclyl-, heterocyclyl-C$_1$-

$C_3$alkyl-, $C_1$-$C_3$alkyl-cycloalkyl-, cycloalkyl-$C_1$-$C_3$alkyl-, $C_2$-$C_8$alkoxy-, $C_2$-$C_8$alkoxy-$C_1$-$C_4$alkyl-, $C_1$-$C_8$alkoxy-carbonyl-, aryloxy-carbonyl-, aryl-$C_1$-$C_3$alkoxy-carbonyl-, heteroaryloxy-carbonyl-, heteroaryl-$C_1$-$C_3$alkoxy-carbonyl-, $C_1$-$C_8$acyl, $C_0$-$C_8$alkyl-carbonyl-, aryl-$C_0$-$C_8$alkyl-carbonyl-, heteroaryl-$C_0$-$C_8$alkyl-carbonyl-, cycloalkyl-$C_0$-$C_8$alkyl-carbonyl-, $C_0$-$C_8$alkyl-NH-carbonyl-, aryl-$C_0$-$C_8$alkyl-NH-carbonyl-, heteroaryl-$C_0$-$C_8$alkyl-NH-carbonyl-, cycloalkyl-$C_0$-$C_8$alkyl-NH-carbonyl-, $C_0$-$C_8$alkyl-O-carbonyl-, aryl-$C_0$-$C_8$alkyl-O-carbonyl-, heteroaryl-$C_0$-$C_8$alkyl-O-carbonyl-, cycloalkyl-$C_0$-$C_8$alkyl-O-carbonyl-, $C_1$-$C_8$alkylsulfonyl-, aryl-alkyl-sulfonyl-, aryl-sulfonyl-, heteroaryl-alkyl-sulfonyl-, heteroaryl-sulfonyl-, $C_1$-$C_8$alkyl-NH-sulfonyl-, aryl-alkyl-NH-sulfonyl-, aryl-NH-sulfonyl-, heteroaryl-alkyl-NH-sulfonyl-, heteroaryl-NH-sulfonyl, aroyl-, aryl-, cycloalkyl-, heterocyclyl-, heteroaryl-, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, or protecting group, each of which is optionally substituted with one or more substituents selected from halo, cyano, oxo, carboxy, formyl, nitro, amino, amidino and guanidino, or $R^{30}$ and $R^{31}$ taken together with the N to which they are attached form a heterocyclyl or heteroaryl, each of which is optionally substituted with from 1 to 3 substituents selected from the group consisting of halo, cyano, oxo, carboxy, formyl, nitro, amino, amidino, guanidino, a protecting group, and ($X^{30}$—$Y^{31}$—), in which $X^{30}$ is selected from the group consisting of $C_1$-$C_8$alkyl-, $C_2$-$C_8$alkenyl-, $C_2$-$C_8$alkynyl-, $C_0$-$C_3$alkyl-$C_2$-$C_8$alkenyl-$C_0$-$C_3$alkyl-, $C_0$-$C_3$alkyl-$C_2$-$C_8$alkynyl-$C_0$-$C_3$alkyl-, $C_0$-$C_3$alkyl-O—$C_0$-$C_3$alkyl-, HO—$C_0$-$C_3$alkyl-, CO—$C_4$alkyl-N($R^{30}$)—$C_0$-$C_3$alkyl-, N($R^{30}$)($R^{31}$)—$C_0$-$C_3$alkyl-, N($R^{30}$)($R^3$)—$C_0$-$C_3$alkenyl-, N($R^{30}$)($R^3$)—$C_0$-$C_3$alkynyl-, (N($R^{30}$)($R^{31}$))$_2$—C=N—, $C_0$-$C_3$alkyl-S(O)$_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with from 1 to 3 substituents selected from halo, cyano, oxo, carboxy, formyl, nitro, amino, amidino and guanidino; and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{31}$)—, —N($R^{30}$)—C(O)—N($R^{31}$)—, —N($R^{30}$)—C(NR$^{30}$)—N($R^{31}$)—, —N($R^{30}$)—C(NR$^{31}$)—, —C(N$^{31}$)—N($R^{30}$), —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —S(O)$_{0-2}$—, —SO$_2$N($R^{31}$)—, —N($R^{31}$)—SO$_2$— and —N($R^{30}$)—SO$_2$N($R^{31}$)—; and $R^{32}$ and $R^{33}$ are independently selected from hydrogen, halo and hydroxyl.

In another embodiment of the third aspect of the invention, the compound is selected from the group consisting of
N-hydroxy-2,2-bis(4-nitrophenyl)acetamide;
2-(4-(diethylamino)phenyl)-N-hydroxy-2-phenylacetamide;
2-(4-(dimethylamino)phenyl)-N-hydroxy-2-phenylacetamide;
2-(biphenyl-4-yl)-N-hydroxy-2-phenylacetamide;
N-hydroxy-2-phenyl-2-(4-(pyrrolidin-1-yl)phenyl)acetamide and
2-(4'-fluorobiphenyl-4-yl)-N-hydroxy-2-phenylacetamide.

In another embodiment of the third aspect of the invention, the compound is selected from the group consisting of
N-hydroxy-2-phenylbutanamide;
N-hydroxy-2-phenoxy-2-phenylacetamide;
N-hydroxy-2-phenyl-2-(4-(piperidin-1-yl)phenyl)acetamide;
2-(4-benzylpiperidin-1-yl)-N-hydroxy-2-phenylacetamide;
2-cyclohexyl-N-hydroxy-2-phenylacetamide;
2-benzyl-N-hydroxy-2-phenylacetamide;
N-hydroxy-2-phenyl-2-(phenylthio)acetamide;
N-hydroxy-2-phenyl-2-(1H-pyrrol-1-yl)acetamide;
N-hydroxy-2-phenyl-2-(4-phenylpiperazin-1-yl)acetamide;
2-(4-benzylpiperazin-1-yl)-N-hydroxy-2-phenylacetamide;
N-hydroxy-2-phenyl-2-(5-(thiophen-2-yl)-1H-benzo[d]imidazol-2-yl)acetamide;
N-hydroxy-2-(isoindolin-2-yl)-2-phenylacetamide;
2-(benzo[d]thiazol-2-yl)-N-hydroxy-2-phenylacetamide;
2-(5-chloro-6-fluoro-1H-benzo[d]imidazol-2-yl)-N-hydroxy-2-phenylacetamide;
N-hydroxy-2-phenyl-2-(4-phenyl-1H-1,2,3-triazol-1-yl)acetamide;
N-hydroxy-2-(4-phenethyl-1H-1,2,3-triazol-1-yl)-2-phenylacetamide;
2-(4-(4-fluorobenzyl)piperidin-1-yl)-N-hydroxy-2-phenylacetamide;
$N^1$-hydroxy-2-phenyl-$N^3$-(3-(trifluoromethyl)phenyl)malonamide;
2-(4-(1H-indol-3-yl)piperidin-1-yl)-N-hydroxy-2-phenylacetamide;
2-(4-benzyl-1H-1,2,3-triazol-1-yl)-N-hydroxy-2-phenylacetamide;
N-hydroxy-2-phenyl-2-(4-(pyrimidin-2-yl)piperazin-1-yl)acetamide;
2-(4-(4-chlorophenyl)pyrimidin-2-ylthio)-N-hydroxy-2-phenylacetamide;
N-hydroxy-2-(5-(2-methoxyphenyl)-1,3,4-thiadiazol-2-yl)-2-phenylacetamide;
2-(4,5-diphenyl-1H-imidazol-2-ylthio)-N-hydroxy-2-phenylacetamide;
N-hydroxy-2-(4-phenoxypiperidin-1-yl)-2-phenylacetamide;
N-hydroxy-2-phenyl-2-(4-phenylpiperidin-1-yl)acetamide and
2-(biphenyl-4-ylthio)-N-hydroxy-2-phenylacetamide.

In another embodiment of the third aspect of the invention, the compound is selected from the group consisting of
2-(N-benzylphenylsulfonamido)-N-hydroxyacetamide;
N-hydroxy-3,3-diphenylpropanamide;
2,2-bis(2,3-dihydrobenzofuran-5-yl)-N-hydroxyacetamide;
N-hydroxy-2,2-diphenylpropanamide;
(E)-N-hydroxy-2,3-diphenylacrylamide;
N-hydroxy-2,2-di(thiophen-2-yl)acetamide and
N-hydroxy-9H-xanthene-9-carboxamide.

In another embodiment of the third aspect of the invention, the compound is selected from the group consisting of
N-hydroxy-2,2-diphenylacetamide;
N-hydroxy-2-phenoxy-2-phenylacetamide;
N-hydroxy-2,2-bis(4-nitrophenyl)acetamide;
N-hydroxy-2-phenyl-2-(piperidin-1-yl)acetamide;
2-(N-benzylphenylsulfonamido)-N-hydroxyacetamide;
N-hydroxy-3,3-diphenylpropanamide;
N-hydroxy-9H-xanthene-9-carboxamide;
2,2-bis(2,3-dihydrobenzofuran-5-yl)-N-hydroxyacetamide;
2-(4-benzylpiperidin-1-yl)-N-hydroxy-2-phenylacetamide;
2-cyclohexyl-N-hydroxy-2-phenylacetamide;
N-hydroxy-2,3-diphenylpropanamide;
N-hydroxy-2-phenyl-2-(phenylthio)acetamide;
N-hydroxy-2-phenyl-2-(1H-pyrrol-1-yl)acetamide;
N-hydroxy-2,2-diphenylpropanamide;

2,2-bis(4-chlorophenyl)-N-hydroxyacetamide;
N-hydroxy-2-phenyl-2-(4-phenylpiperazin-1-yl)acetamide;
2-(4-benzylpiperazin-1-yl)-N-hydroxy-2-phenylacetamide;
2,2-bis(4-fluorophenyl)-N-hydroxyacetamide;
2-(4-(diethylamino)phenyl)-N-hydroxy-2-phenylacetamide;
N-hydroxy-2-phenyl-2-(6-(thiophen-2-yl)-1H-benzo[d]imidazol-2-yl)acetamide;
(E)-N-hydroxy-2,3-diphenylacrylamide;
N-hydroxy-2-(isoindolin-2-yl)-2-phenylacetamide;
N-hydroxy-2,2-di(thiophen-2-yl)acetamide;
2-(benzo[d]thiazol-2-ylthio)-N-hydroxy-2-phenylacetamide;
2-(5-chloro-6-fluoro-1H-benzo[d]imidazol-2-yl)-N-hydroxy-2-phenylacetamide;
N-hydroxy-2-phenyl-2-(4-phenyl-1H-1,2,3-triazol-1-yl)acetamide;
N-hydroxy-2-(4-phenethyl-1H-1,2,3-triazol-1-yl)-2-phenylacetamide;
N,2-dihydroxy-2,2-diphenylacetamide;
2-(4-(dimethylamino)phenyl)-N-hydroxy-2-phenylacetamide;
2-(4-(4-fluorobenzyl)piperidin-1-yl)-N-hydroxy-2-phenylacetamide;
N-hydroxy-2-(4-phenethylpiperidin-1-yl)-2-phenylacetamide;
2-(biphenyl-4-yl)-N-hydroxy-2-phenylacetamide;
$N^1$-hydroxy-2-phenyl-$N^3$-(3-(trifluoromethyl)phenyl)malonamide;
2-(4-(1H-indol-3-yl)piperidin-1-yl)-N-hydroxy-2-phenylacetamide;
2-(4-benzyl-1H-1,2,3-triazol-1-yl)-N-hydroxy-2-phenylacetamide;
N-hydroxy-2-phenyl-2-(4-(pyrimidin-2-yl)piperazin-1-yl)acetamide;
2-(4-(4-chlorophenyl)pyrimidin-2-ylthio)-N-hydroxy-2-phenylacetamide;
N-hydroxy-2-(5-(2-methoxyphenyl)-1,3,4-thiadiazol-2-yl)-2-phenylacetamide;
2-(5-(4-bromophenyl)-1,3,4-thiadiazol-2-yl)-N-hydroxy-2-phenylacetamide;
2-(biphenyl-4-yl)-2-(4-(dimethylamino)phenyl)-N-hydroxyacetamide;
N-hydroxy-2-phenyl-2-(4-(pyrrolidin-1-yl)phenyl)acetamide;
2-(4,5-diphenyl-1H-imidazol-2-ylthio)-N-hydroxy-2-phenylacetamide;
N-hydroxy-2-(4-phenoxypiperidin-1-yl)-2-phenylacetamide;
N-hydroxy-2-phenyl-2-(4-phenylpiperidin-1-yl)acetamide;
2-(4'-fluorobiphenyl-4-yl)-N-hydroxy-2-phenylacetamide and
2-(biphenyl-4-ylthio)-N-hydroxy-2-phenylacetamide.

In one embodiment of the third aspect, the contacting is performed in a cell.

In another embodiment of the third aspect, the invention provides a method of inhibiting a histone deacetylase selected from the group consisting of HDAC-4, HDAC-5, HDAC-6, HDAC-7, HDAC-8, HDAC-9, HDAC-10 and HDAC-11 preferably in a cell, comprising contacting the histone deacetylase (or the cell) with a histone deacetylase inhibiting amount of a composition comprising a compound according to any of Formulae (VI)-(XI), (VI-A), (XX), (XX-A) and (XXI), or a preferred embodiment thereof, or an N-oxide, hydrate, solvate, pharmaceutically-acceptable salt, prodrug or complex thereof, or a racemic or scalemic mixture, diasteromer or enantiomer thereof, and a pharmaceutically-acceptable carrier as described herein.

In another embodiment of the third aspect, the invention provides a method of inhibiting a histone deacetylase selected from the group consisting of HDAC-4, HDAC-5, HDAC-6, HDAC-7, HDAC-8, HDAC-9, HDAC10 and HDAC-11, preferably in a cell, comprising contacting the histone deacetylase (or the cell in which inhibition of histone deacetylase is desired) with a histone deacetylase inhibiting amount of a compound according to any of Formulae (XII)-(XVII), (XII-A), (XX), (XX-A) and (XXI) or a preferred embodiment thereof, or an N-oxide, hydrate, solvate, pharmaceutically-acceptable salt, prodrug or complex thereof, or a racemic or scalemic mixture, diasteromer or enantiomer thereof, optionally in a composition with a pharmaceutically-acceptable carrier, as described herein.

Because compounds of the invention inhibit histone deacetylase, they are useful research tools for in vitro study histone deacetylases and their role in biological processes.

Measurement of the enzymatic activity of a histone deacetylase can be achieved using known methodologies. For Example, Yoshida et al., J. Biol. Chem., 265: 17174-17179 (1990), describes the assessment of histone deacetylase enzymatic activity by the detection of acetylated histones in trichostatin A treated cells. Taunton et al., Science, 272: 408-411 (1996), similarly describes methods to measure histone deacetylase enzymatic activity using endogenous and recombinant HDAC-1.

In another embodiment of the third aspect of the invention, a cell in which inhibition of histone deacetylase is desired is contacted with the compound, N-oxide, hydrate, solvate, pharmaceutically acceptable salt, prodrug, complex, racemic or scalemic mixture, diasteromer or enantiomer as described above. Desirably, the cell is in a mammal, preferably a human.

The compounds of the present invention are preferably selective for inhibiting class II histone deacetylase. In another preferred embodiment the compounds of the present invention are selective HDAC-4, HDAC-5 and/or HDAC-7 inhibitors, and may additionally be active against HDAC-11. A subset of the compounds of the present invention preferably has selective inhibitory activity against HDAC-8. Another subset of the compounds of the present invention preferably has selective inhibitory activity against HDAC-11. Another subset of the compounds of the present invention preferably has selective inhibitory activity against HDAC-4, HDAC-5, HDAC-6 HDAC-7, HDAC-8 and/or HDAC-11.

In certain preferred embodiments of the third aspect of the invention, the method further comprises contacting a histone deacetylase enzyme or a cell expressing histone deacetylase activity with an additional inhibitory agent. The combined use of separate agents results in an improved inhibitory effect, thereby reducing the amounts of individual inhibitors required to obtain a given inhibitory effect as compared to the amounts necessary when either is used alone. Administration of such separate agents may be done sequentially or concurrently. When co-administered, the separate agents preferably act synergistically to produce a therapeutic effect.

In certain preferred embodiments of the third aspect of the invention, the method further comprises contacting a histone deacetylase enzyme or a cell expressing histone deacetylase activity with an antisense oligonucleotide that inhibits the expression of a histone deacetylase gene. The combined use of a nucleic acid level inhibitor (e.g., antisense oligonucleotide) and a protein level inhibitor (i.e., inhibitor of histone deacetylase enzyme activity) results in an improved inhibitory effect, thereby reducing the amounts of the inhibitors required to obtain a given inhibitory effect as compared to the amounts necessary when either is used individually.

The exact nucleotide sequence and chemical structure of an antisense oligonucleotide utilized in the invention can be varied, so long as the oligonucleotide retains its ability to inhibit expression of the gene of interest. This is readily determined by testing whether the particular antisense oligonucleotide is active. Useful assays for this purpose include quantitating the mRNA encoding a product of the gene, a Western blotting analysis assay for the product of the gene, an activity assay for an enzymatically active gene product, or a soft agar growth assay, or a reporter gene construct assay, or an in vivo tumor growth assay, all of which are known in the art, or are as described in detail in this specification or in, for example, Ramchandani et al. (1997) Proc. Natl. Acad. Sci. USA 94: 684-689.

Particularly preferred oligonucleotides have nucleotide sequences of from about 13 to about 35 nucleotides. Yet additional particularly preferred oligonucleotides have nucleotide sequences of from about 15 to about 26 nucleotides.

In a preferred embodiment of the third aspect of the invention, the invention provides a method of treating a patient having a disease or condition ameliorated by modulating HDAC activity comprising administering to the patient a treatment effective amount of a compound according to any of Formulae (I)-(V), (XII)-(XVII), (XII-A), (XX), (XX-A) and (XXI) or a preferred embodiment thereof, or an N-oxide, hydrate, solvate, pharmaceutically-acceptable salt, prodrug or complex thereof, or a racemic or scalemic mixture, diasteromer or enantiomer thereof, or a composition comprising a compound according to any of Formulae (VI)-(XI), (VI-A), (XX), (XX-A) and (XXI), or a preferred embodiment thereof, or an N-oxide, hydrate, solvate, pharmaceutically-acceptable salt, prodrug or complex thereof, or a racemic or scalemic mixture, diasteromer or enantiomer thereof, with a pharmaceutically-acceptable carrier.

In a preferred embodiment of the third aspect of the invention, the disease or condition ameliorated by modulating HDAC activity is selected from the group consisting of a cell proliferative disease (such as cancer), diabetes, inflammation, cardiac disease, stroke, epilepsy, depression, immunological disease and viral or fungal infection.

In a preferred embodiment of any of the first, second and third aspects of the invention, the compound is selected from the group consisting of
2-(biphenyl-4-yl)-N-hydroxy-2-phenylacetamide,
2-(4'-fluorobiphenyl-4-yl)-N-hydroxy-2-phenylacetamide,
N-hydroxy-2-(4'-methoxybiphenyl-4-yl)-2-phenylacetamide,
N-hydroxy-2-phenyl-2-(4-(pyridin-4-yl)phenyl)acetamide,
N-hydroxy-2-phenyl-2-(4-(pyridin-3-yl)phenyl)acetamide,
2-(4'-(dimethylamino)biphenyl-4-yl)-N-hydroxy-2-phenylacetamide,
N-hydroxy-2-phenyl-2-(4-(pyrimidin-5-yl)phenyl)acetamide and N-hydroxy-2-(4'-morpholinobiphenyl-4-yl)-2-phenylacetamide.

In a preferred embodiment of any of the first, second and third aspects of the invention, the compound is selected from the group consisting of
2-(4-(diethylamino)phenyl)-N-hydroxy-2-phenylacetamide,
2-(4-(dimethylamino)phenyl)-N-hydroxy-2-phenylacetamide,
N-hydroxy-2-phenyl-2-(4-(pyrrolidin-1-yl)phenyl)acetamide,
N-hydroxy-2-(4-morpholinophenyl)-2-phenylacetamide,
2-(4-fluorophenyl)-N-hydroxy-2-(4-morpholinophenyl)acetamide,
2-(3-fluorophenyl)-N-hydroxy-2-(4-morpholinophenyl)acetamide,
2-(3-fluorophenyl)-N-hydroxy-2-(4-(pyrrolidin-1-yl)phenyl)acetamide and
2-(4-(diethylamino)phenyl)-2-(3-fluorophenyl)-N-hydroxyacetamide.

In another preferred embodiment of any of the first, second and third aspects of the invention, the compound is selected from the group consisting of
2-(4-(benzyloxy)phenyl)-N-hydroxy-2-phenylacetamide,
N-hydroxy-2-(4-(2-morpholinoethoxy)phenyl)-2-phenylacetamide,
N-hydroxy-2-(4-(2-morpholinoethoxy)phenyl)-2-phenylacetamide,
N-hydroxy-2-phenyl-2-(4-(2-(pyrrolidin-1-yl)ethoxy)phenyl)acetamide,
N-hydroxy-2-(4-(1-methylpiperidin-4-yloxy)phenyl)-2-phenylacetamide,
2-(4-(1-benzylpiperidin-4-yloxy)phenyl)-N-hydroxy-2-phenylacetamide,
N-hydroxy-2-(4-morpholinophenyl)-2-m-tolylacetamide,
2-(4-(1-(cyclopropylmethyl)piperidin-4-yloxy)phenyl)-N-hydroxy-2-phenylacetamide,
N-hydroxy-2-(4-morpholinophenyl)-2-o-tolylacetamide and
N-hydroxy-2-(4-(2-morpholino-2-oxoethoxy)phenyl)-2-phenylacetamide.

In another preferred embodiment of any of the first, second and third aspects of the invention, the compound is selected from the group consisting of
2-(4-(4-chlorophenyl)pyrimidin-2-ylthio)-N-hydroxy-2-phenylacetamide,
2-(biphenyl-4-ylthio)-N-hydroxy-2-phenylacetamide and
N-hydroxy-2-(naphthalen-2-ylthio)-2-phenylacetamide.

In another preferred embodiment of any of the first, second and third aspects of the invention, the compound is selected from the group consisting of
2-(4'-(dimethylamino)biphenyl-4-yl)-N-hydroxy-2-phenylacetamide,
2-(4-(benzyloxy)phenyl)-N-hydroxy-2-phenylacetamide,
2-(4-(4-benzylpiperidin-1-yl)phenyl)-N-hydroxy-2-phenylacetamide,
N-hydroxy-2-phenyl-2-(4-propylphenyl)acetamide,
2-(3-(4-fluorobenzyloxy)phenyl)-N-hydroxy-2-phenylacetamide,
N-hydroxy-2-(4-(2-morpholino-2-oxoethoxy)phenyl)-2-phenylacetamide,
N-hydroxy-2-(4-phenethoxyphenyl)-2-phenylacetamide,
N-hydroxy-2-(4-(3-methoxybenzyloxy)phenyl)-2-phenylacetamide,
2-(4-(4-fluorobenzylamino)phenyl)-N-hydroxy-2-phenylacetamide,
N-(4-(2-(hydroxyamino)-2-oxo-1-phenylethyl)phenyl)-3-methylbutanamide,
N-(4-(2-(hydroxyamino)-2-oxo-1-phenylethyl)phenyl)benzamide,
N-(4-(2-(hydroxyamino)-2-oxo-1-phenylethyl)phenyl)cyclohexanecarboxamide,
4-fluoro-N-(4-(2-(hydroxyamino)-2-oxo-1-phenylethyl)phenyl)benzamide,
N-(4-(2-(hydroxyamino)-2-oxo-1-phenylethyl)phenyl)-2,5-dimethylfuran-3-carboxamide,
N-(4-(2-(hydroxyamino)-2-oxo-1-phenylethyl)phenyl)-3-methylthiophene-2-carboxamide,
N-hydroxy-2-(4-(2-phenoxyacetamido)phenyl)-2-phenylacetamide,
N-(3-(2-(hydroxyamino)-2-oxo-1-phenylethyl)phenyl)-4-methoxybenzamide,
3-cyclohexyl-N-(4-(2-(hydroxyamino)-2-oxo-1-phenylethyl)phenyl)propanamide, 3-chloro-N-(4-(2-(hydroxyamino)-2-oxo-1-phenylethyl)phenyl)benzamide,
2-chloro-N-(4-(2-(hydroxyamino)-2-oxo-1-phenylethyl)phenyl)isonicotinamide,
N-(4-(2-(hydroxyamino)-2-oxo-1-phenylethyl)phenyl)benzo[d][1,3]dioxole-5-carboxamide,
N-(3-(2-(hydroxyamino)-2-oxo-1-phenylethyl)phenyl)benzo[d][1,3]dioxole-5-carboxamide,
N-hydroxy-2-(4-(isopentylamino)phenyl)-2-phenylacetamide,
2-(4-(benzylamino)phenyl)-N-hydroxy-2-phenylacetamide,
N-hydroxy-2-phenyl-2-(4-(pyridin-4-ylmethylamino)phenyl)acetamide,
N-hydroxy-2-phenyl-2-(3-(pyridin-4-ylmethylamino)phenyl)acetamide,
2-(4-(cyclohexylmethylamino)phenyl)-N-hydroxy-2-phenylacetamide,
N-hydroxy-2-(4-(3-methoxybenzylamino)phenyl)-2-phenylacetamide,
N-hydroxy-2-(3-(3-methoxybenzylamino)phenyl)-2-phenylacetamide,
N-hydroxy-2-phenyl-2-(4-(propylsulfonamido)phenyl)acetamide,
N-hydroxy-2-phenyl-2-(4-(phenylsulfonamido)phenyl)acetamide,
2-(4-(4-chlorophenylsulfonamido)phenyl)-N-hydroxy-2-phenylacetamide,
N-hydroxy-2-phenyl-2-(3-(pyridin-3-ylethynyl)phenyl)acetamide,
N-hydroxy-2-phenyl-2-(4-(phenylethynyl)phenyl)acetamide,
N-hydroxy-2-phenyl-2-(3-propylphenyl)acetamide,
2-(4'-(dimethylamino)biphenyl-3-yl)-N-hydroxy-2-phenylacetamide,
2-(3',4'-dimethoxybiphenyl-3-yl)-N-hydroxy-2-phenylacetamide,
N-hydroxy-2-phenyl-2-(2'-(trifluoromethyl)biphenyl-3-yl)acetamide,
3'-(2-(hydroxyamino)-2-oxo-1-phenylethyl)-N,N-dimethylbiphenyl-4-carboxamide,
N-hydroxy-2-(4'-(methylsulfonyl)biphenyl-3-yl)-2-phenylacetamide,
2-(4'-ethylbiphenyl-4-yl)-N-hydroxy-2-phenylacetamide,
2-(4'-chlorobiphenyl-4-yl)-N-hydroxy-2-phenylacetamide,
2-(4-(2,3-dihydrobenzofuran-5-yl)phenyl)-N-hydroxy-2-phenylacetamide,
2-(3',4'-dimethoxybiphenyl-4-yl)-N-hydroxy-2-phenylacetamide,
2-(4'-(ethylthio)biphenyl-4-yl)-N-hydroxy-2-phenylacetamide,
4'-(2-(hydroxyamino)-2-oxo-1-phenylethyl)-N,N-dimethylbiphenyl-4-carboxamide,
2-(3-(benzo[d][1,3]dioxol-5-ylmethylbenzo[d][1,3]dioxol-5-ylmethoxy)phenyl)-N-hydroxy-2-phenylacetamide,
(E)-2-(3-(cinnamyloxy)phenyl)-N-hydroxy-2-phenylacetamide,
2-(3-(3-chlorobenzyloxy)phenyl)-N-hydroxy-2-phenylacetamide,
2-(4-(benzo[d][1,3]dioxol-5-ylmethylbenzo[d][1,3]dioxol-5-ylmethoxy)phenyl)-N-hydroxy-2-phenylacetamide,
2-(3-(3-(dimethylamino)propoxy)phenyl)-N-hydroxy-2-phenylacetamide,
2-(3-(3-(dimethylamino)-2-methylpropoxy)phenyl)-N-hydroxy-2-phenylacetamide,
N-hydroxy-2-(3-(2-(1-methylpyrrolidin-2-yl)ethoxy)phenyl)-2-phenylacetamide,
2-(4-ethoxyphenyl)-N-hydroxy-2-phenylacetamide,
N-hydroxy-2-phenyl-2-(4-(prop-2-ynyloxy)phenyl)acetamide,
2-(4-(allyloxy)phenyl)-N-hydroxy-2-phenylacetamide,
N-hydroxy-2-(4-isopropoxyphenyl)-2-phenylacetamide,
2-(4-(but-3-enyloxy)phenyl)-N-hydroxy-2-phenylacetamide,
N-hydroxy-2-(4-(2-methoxyethoxy)phenyl)-2-phenylacetamide,
2-(4-((3,5-dimethylisoxazol-4-yl)methoxy)phenyl)-N-hydroxy-2-phenylacetamide,
N-hydroxy-2-(4-(3-methylbut-2-enyloxy)phenyl)-2-phenylacetamide,
2-(4-(2-ethylbutoxy)phenyl)-N-hydroxy-2-phenylacetamide,
N-hydroxy-2-phenyl-2-(4-(1-phenylethoxy)phenyl)acetamide,
2-(4-(2-fluorobenzyloxy)phenyl)-N-hydroxy-2-phenylacetamide,
2-(4-(2-cyanobenzyloxy)phenyl)-N-hydroxy-2-phenylacetamide,
N-hydroxy-2-(4-(2-phenoxyethoxy)phenyl)-2-phenylacetamide,
2-(4-(2-chlorobenzyloxy)phenyl)-N-hydroxy-2-phenylacetamide,
2-(4-(2,4-difluorobenzyloxy)phenyl)-N-hydroxy-2-phenylacetamide,
2-(4-(2-(benzyloxy)ethoxy)phenyl)-N-hydroxy-2-phenylacetamide,
2-(4-(2-(4-fluorophenoxy)ethoxy)phenyl)-N-hydroxy-2-phenylacetamide,
N-hydroxy-2-phenyl-2-(4-(phenylamino)phenyl)acetamide,
N-hydroxy-2-phenyl-2-(4-(pyridin-2-ylmethylamino)phenyl)acetamide,
2-(4-(4-acetylpiperazin-1-yl)phenyl)-N-hydroxy-2-phenylacetamide,
2-(4-(4-(4-fluorophenyl)piperazin-1-yl)phenyl)-N-hydroxy-2-phenylacetamide,
N-hydroxy-2-(4-(2-(2-methoxyethoxy)ethoxy)phenyl)-2-phenylacetamide,
2-(4-(4-chlorobenzylamino)phenyl)-N-hydroxy-2-phenylacetamide,
N-(4-(2-(hydroxyamino)-2-oxo-1-phenylethyl)phenyl)propionamide,
N-(4-(2-(hydroxyamino)-2-oxo-1-phenylethyl)phenyl)cyclopropanecarboxamide,
N-(4-(2-(hydroxyamino)-2-oxo-1-phenylethyl)phenyl)butyramide,
N-(4-(2-(hydroxyamino)-2-oxo-1-phenylethyl)phenyl)isobutyramide,
N-hydroxy-2-(4-(2-methoxyacetamido)phenyl)-2-phenylacetamide,
N-(4-(2-(hydroxyamino)-2-oxo-1-phenylethyl)phenyl)-2-methylbutanamide,
N-(3-(2-(hydroxyamino)-2-oxo-1-phenylethyl)phenyl)-2-methylbutanamide,
N-(4-(2-(hydroxyamino)-2-oxo-1-phenylethyl)phenyl)pivalamide,
N-(3-(2-(hydroxyamino)-2-oxo-1-phenylethyl)phenyl)pivalamide,
N-(4-(2-(hydroxyamino)-2-oxo-1-phenylethyl)phenyl)furan-2-carboxamide,
N-(4-(2-(hydroxyamino)-2-oxo-1-phenylethyl)phenyl)furan-3-carboxamide,
N-(4-(2-(hydroxyamino)-2-oxo-1-phenylethyl)phenyl)-3,3-dimethylbutanamide,
2-ethyl-N-(4-(2-(hydroxyamino)-2-oxo-1-phenylethyl)phenyl)butanamide, N-(4-(2-(hydroxyamino)-2-oxo-1-phenylethyl)phenyl)-2,2-dimethylbutanamide,
N-(4-(2-(hydroxyamino)-2-oxo-1-phenylethyl)phenyl)-2-methylpentanamide,
N-(4-(2-(hydroxyamino)-2-oxo-1-phenylethyl)phenyl)isonicotinamide,
N-(4-(2-(hydroxyamino)-2-oxo-1-phenylethyl)phenyl)-5-methylisoxazole-3-carboxamide,
N-(4-(2-(hydroxyamino)-2-oxo-1-phenylethyl)phenyl)thiophene-2-carboxamide,
N-(4-(2-(hydroxyamino)-2-oxo-1-phenylethyl)phenyl)tetrahydro-2H-pyran-4-carboxamide,
N-(4-(2-(hydroxyamino)-2-oxo-1-phenylethyl)phenyl)-4-methylbenzamide,
N-(4-(2-(hydroxyamino)-2-oxo-1-phenylethyl)phenyl)-2-methylbenzamide,
N-(4-(2-(hydroxyamino)-2-oxo-1-phenylethyl)phenyl)-3-methylbenzamide,
5-chloro-N-(4-(2-(hydroxyamino)-2-oxo-1-phenylethyl)phenyl)pentanamide,
2-fluoro-N-(4-(2-(hydroxyamino)-2-oxo-1-phenylethyl)phenyl)benzamide,
3-fluoro-N-(4-(2-(hydroxyamino)-2-oxo-1-phenylethyl)phenyl)benzamide,
N-(4-(2-(hydroxyamino)-2-oxo-1-phenylethyl)phenyl)-1,3-dimethyl-1H-pyrazole-5-carboxamide,
3-cyclopentyl-N-(4-(2-(hydroxyamino)-2-oxo-1-phenylethyl)phenyl)propanamide,
N-(4-(2-(hydroxyamino)-2-oxo-1-phenylethyl)phenyl)cinnamamide,
N-(4-(2-(hydroxyamino)-2-oxo-1-phenylethyl)phenyl)-3-phenylpropanamide,
N-(4-(2-(hydroxyamino)-2-oxo-1-phenylethyl)phenyl)-3,4-dimethylbenzamide,
4-ethyl-N-(4-(2-(hydroxyamino)-2-oxo-1-phenylethyl)phenyl)benzamide,
2-(4-(2-(4-fluorophenyl)acetamido)phenyl)-N-hydroxy-2-phenylacetamide,
5-fluoro-N-(4-(2-(hydroxyamino)-2-oxo-1-phenylethyl)phenyl)-2-methylbenzamide,
3-fluoro-N-(4-(2-(hydroxyamino)-2-oxo-1-phenylethyl)phenyl)-4-methylbenzamide,
4-fluoro-N-(4-(2-(hydroxyamino)-2-oxo-1-phenylethyl)phenyl)-3-methylbenzamide,
4-chloro-N-(4-(2-(hydroxyamino)-2-oxo-1-phenylethyl)phenyl)benzamide,
3,4-difluoro-N-(4-(2-(hydroxyamino)-2-oxo-1-phenylethyl)phenyl)benzamide,
3,5-difluoro-N-(4-(2-(hydroxyamino)-2-oxo-1-phenylethyl)phenyl)benzamide,
2,5-difluoro-N-(4-(2-(hydroxyamino)-2-oxo-1-phenylethyl)phenyl)benzamide,
5-chloro-N-(4-(2-(hydroxyamino)-2-oxo-1-phenylethyl)phenyl)-1-methyl-1H-pyrazole-4-carboxamide,
N-(4-(2-(hydroxyamino)-2-oxo-1-phenylethyl)phenyl)-2-phenylbutanamide,
N-(4-(2-(hydroxyamino)-2-oxo-1-phenylethyl)phenyl)-4-propylbenzamide,
4-(dimethylamino)-N-(4-(2-(hydroxyamino)-2-oxo-1-phenylethyl)phenyl)benzamide,
N-hydroxy-2-(4-(2-(4-methoxyphenyl)acetamido)phenyl)-2-phenylacetamide,
N-hydroxy-2-(4-(2-(3-methoxyphenyl)acetamido)phenyl)-2-phenylacetamide,
N-(4-(2-(hydroxyamino)-2-oxo-1-phenylethyl)phenyl)-2-phenoxypropanamide,
2-(4-(2-(benzyloxy)acetamido)phenyl)-N-hydroxy-2-phenylacetamide,
4-ethoxy-N-(4-(2-(hydroxyamino)-2-oxo-1-phenylethyl)phenyl)benzamide,
N-(4-(2-(hydroxyamino)-2-oxo-1-phenylethyl)phenyl)-2-nitrobenzamide,
N-(4-(2-(hydroxyamino)-2-oxo-1-phenylethyl)phenyl)-3-nitrobenzamide,
N-hydroxy-2-phenyl-2-(4-(2-(phenylthio)acetamido)phenyl)acetamide,
3-fluoro-N-(4-(2-(hydroxyamino)-2-oxo-1-phenylethyl)phenyl)-4-methoxybenzamide,
2-(4-(2-(4-chlorophenyl)acetamido)phenyl)-N-hydroxy-2-phenylacetamide,
1-acetyl-N-(4-(2-(hydroxyamino)-2-oxo-1-phenylethyl)phenyl)piperidine-4-carboxamide,
N-(4-(2-(hydroxyamino)-2-oxo-1-phenylethyl)phenyl)-1-naphthamide,
2,4,5-trifluoro-N-(4-(2-(hydroxyamino)-2-oxo-1-phenylethyl)phenyl)benzamide,
N-(4-(2-(hydroxyamino)-2-oxo-1-phenylethyl)phenyl)-3-methylbenzofuran-2-carboxamide,
4-tert-butyl-N-(4-(2-(hydroxyamino)-2-oxo-1-phenylethyl)phenyl)benzamide,
N-(4-(2-(hydroxyamino)-2-oxo-1-phenylethyl)phenyl)-2,3-dihydrobenzo[b][1,4]dioxine-2-carboxamide,
N-(4-(2-(hydroxyamino)-2-oxo-1-phenylethyl)phenyl)-2,6-dimethoxybenzamide,
N-(4-(2-(hydroxyamino)-2-oxo-1-phenylethyl)phenyl)-3,5-dimethoxybenzamide,
2-(4-(2-(4-chlorophenoxy)acetamido)phenyl)-N-hydroxy-2-phenylacetamide,
6-chloro-2-fluoro-N-(4-(2-(hydroxyamino)-2-oxo-1-phenylethyl)phenyl)-3-methylbenzamide,
N-(4-(2-(hydroxyamino)-2-oxo-1-phenylethyl)phenyl)-4-(trifluoromethyl)benzamide,
N-(4-(2-(hydroxyamino)-2-oxo-1-phenylethyl)phenyl)-3-(trifluoromethyl)benzamide,
3,4-dichloro-N-(4-(2-(hydroxyamino)-2-oxo-1-phenylethyl)phenyl)benzamide,
3,5-dichloro-N-(4-(2-(hydroxyamino)-2-oxo-1-phenylethyl)phenyl)benzamide,
N-(4-(2-(hydroxyamino)-2-oxo-1-phenylethyl)phenyl)-4-methyl-3,4-dihydro-2H-benzo[b][1,4]oxazine-7-carboxamide,
4-butoxy-N-(4-(2-(hydroxyamino)-2-oxo-1-phenylethyl)phenyl)benzamide,
2-(4-(2-(3,4-dimethoxyphenyl)acetamido)phenyl)-N-hydroxy-2-phenylacetamide,
N-(4-(2-(hydroxyamino)-2-oxo-1-phenylethyl)phenyl)-5-methyl-3-phenylisoxazole-4-carboxamide,
N-(4-(2-(hydroxyamino)-2-oxo-1-phenylethyl)phenyl)-4-(trifluoromethoxy)benzamide,
N-(4-(2-(hydroxyamino)-2-oxo-1-phenylethyl)phenyl)-3-(trifluoromethoxy)benzamide,
2-fluoro-N-(4-(2-(hydroxyamino)-2-oxo-1-phenylethyl)phenyl)-4-(trifluoromethyl)benzamide,
4-fluoro-N-(4-(2-(hydroxyamino)-2-oxo-1-phenylethyl)phenyl)-2-(trifluoromethyl)benzamide,
2-(4-(2-(4-tert-butylphenoxy)acetamido)phenyl)-N-hydroxy-2-phenylacetamide,
N-(4-(2-(hydroxyamino)-2-oxo-1-phenylethyl)phenyl)-4-methoxy-3-(trifluoromethyl)benzamide,
N-(4-(2-(hydroxyamino)-2-oxo-1-phenylethyl)phenyl)-5-nitrobenzo[b]thiophene-2-carboxamide,
2-(4-(cyclopropylmethylamino)phenyl)-N-hydroxy-2-phenylacetamide, N-hydroxy-2-(4-(isobutylamino)phenyl)-2-phenylacetamide,
N-hydroxy-2-(4-(3-methylbut-2-enylamino)phenyl)-2-phenylacetamide,
N-hydroxy-2-(4-(neopentylamino)phenyl)-2-phenylacetamide,
N-hydroxy-2-(4-(2-methylbutylamino)phenyl)-2-phenylacetamide,
2-(4-(cyclopentylmethylamino)phenyl)-N-hydroxy-2-phenylacetamide,
2-(4-(2-ethylbutylamino)phenyl)-N-hydroxy-2-phenylacetamide,
N-hydroxy-2-(4-(2-methylpentylamino)phenyl)-2-phenylacetamide,
2-(4-(3,3-dimethylbutylamino)phenyl)-N-hydroxy-2-phenylacetamide,
N-hydroxy-2-phenyl-2-(4-(pyridin-3-ylmethylamino)phenyl)acetamide,
N-hydroxy-2-(4-((1-methyl-1H-imidazol-2-yl)methylamino)phenyl)-2-phenylacetamide,
2-(4-(cyclohex-3-enylmethylamino)phenyl)-N-hydroxy-2-phenylacetamide,
N-hydroxy-2-phenyl-2-(4-(thiazol-2-ylmethylamino)phenyl)acetamide,
N-hydroxy-2-phenyl-2-(3-(thiazol-2-ylmethylamino)phenyl)acetamide,
N-hydroxy-2-(4-(2-methylbenzylamino)phenyl)-2-phenylacetamide,
N-hydroxy-2-(4-(3-methylbenzylamino)phenyl)-2-phenylacetamide,
N-hydroxy-2-(4-((6-methylpyridin-2-yl)methylamino)phenyl)-2-phenylacetamide,
N-hydroxy-2-(4-(3-hydroxybenzylamino)phenyl)-2-phenylacetamide,
2-(4-(2-fluorobenzylamino)phenyl)-N-hydroxy-2-phenylacetamide,
(E)-N-hydroxy-2-phenyl-2-(4-(3-(pyridin-3-yl)allylamino)phenyl)acetamide,
N-hydroxy-2-phenyl-2-(4-(2-phenylpropylamino)phenyl)acetamide,
2-(4-(3,5-dimethylbenzylamino)phenyl)-N-hydroxy-2-phenylacetamide,
2-(4-((1H-indol-5-yl)methylamino)phenyl)-N-hydroxy-2-phenylacetamide,
2-(3-((1H-indol-5-yl)methylamino)phenyl)-N-hydroxy-2-phenylacetamide,
2-(4-(benzo[d][1,3]dioxol-5-ylmethylamino)phenyl)-N-hydroxy-2-phenylacetamide,
2-(3-(benzo[d][1,3]dioxol-5-ylmethylamino)phenyl)-N-hydroxy-2-phenylacetamide,
N-hydroxy-2-(4-(4-methoxy-3-methylbenzylamino)phenyl)-2-phenylacetamide,
N-hydroxy-2-(4-(4-(methylthio)benzylamino)phenyl)-2-phenylacetamide,
(E)-N-hydroxy-2-(4-(3-(4-methoxyphenyl)allylamino)phenyl)-2-phenylacetamide,
(E)-N-hydroxy-2-(4-(3-(2-methoxyphenyl)allylamino)phenyl)-2-phenylacetamide,
2-(4-(4-tert-butylbenzylamino)phenyl)-N-hydroxy-2-phenylacetamide,
2-(4-((2,3-dihydrobenzo[b][1,4]dioxin-6-yl)methylamino)phenyl)-N-hydroxy-2-phenylacetamide,
N-hydroxy-2-phenyl-2-(4-(3-(trifluoromethyl)benzylamino)phenyl)acetamide,
N-hydroxy-2-phenyl-2-(3-(3-(trifluoromethyl)benzylamino)phenyl)acetamide,
N-hydroxy-2-phenyl-2-(4-(4-(trifluoromethyl)benzylamino)phenyl)acetamide,
2-(4-(biphenyl-4-ylmethylamino)phenyl)-N-hydroxy-2-phenylacetamide,
N-hydroxy-2-(4-(methylsulfonamido)phenyl)-2-phenylacetamide,
2-(4-(ethylsulfonamido)phenyl)-N-hydroxy-2-phenylacetamide,
N-hydroxy-2-(4-(1-methylethylsulfonamido)phenyl)-2-phenylacetamide,
2-(4-(butylsulfonamido)phenyl)-N-hydroxy-2-phenylacetamide,
2-(4-(3-chloropropylsulfonamido)phenyl)-N-hydroxy-2-phenylacetamide,
N-hydroxy-2-phenyl-2-(4-(2,2,2-trifluoroethylsulfonamido)phenyl)acetamide,
N-hydroxy-2-phenyl-2-(4-(phenylmethylsulfonamido)phenyl)acetamide,
N-hydroxy-2-(4-(4-methylphenylsulfonamido)phenyl)-2-phenylacetamide,
N-hydroxy-2-(4-(2-methylphenylsulfonamido)phenyl)-2-phenylacetamide,
2-(4-(4-fluorophenylsulfonamido)phenyl)-N-hydroxy-2-phenylacetamide,
2-(4-(3-fluorophenylsulfonamido)phenyl)-N-hydroxy-2-phenylacetamide,
2-(4-(2-fluorophenylsulfonamido)phenyl)-N-hydroxy-2-phenylacetamide,
2-(4-(1,2-dimethyl-1H-imidazole-4-sulfonamido)phenyl)-N-hydroxy-2-phenylacetamide,
2-(4-(3,5-dimethylisoxazole-4-sulfonamido)phenyl)-N-hydroxy-2-phenylacetamide,
2-(4-(3,4-dimethylphenylsulfonamido)phenyl)-N-hydroxy-2-phenylacetamide,
2-(4-(2,5-dimethylphenylsulfonamido)phenyl)-N-hydroxy-2-phenylacetamide,
2-(4-(4-ethylphenylsulfonamido)phenyl)-N-hydroxy-2-phenylacetamide,
2-(4-(3,5-dimethylphenylsulfonamido)phenyl)-N-hydroxy-2-phenylacetamide,
N-hydroxy-2-(4-(3-methoxyphenylsulfonamido)phenyl)-2-phenylacetamide,
2-(4-(4-fluoro-2-methylphenylsulfonamido)phenyl)-N-hydroxy-2-phenylacetamide,
2-(4-(2-chlorophenylsulfonamido)phenyl)-N-hydroxy-2-phenylacetamide,
2-(4-(3-chlorophenylsulfonamido)phenyl)-N-hydroxy-2-phenylacetamide,
2-(4-(2,6-difluorophenylsulfonamido)phenyl)-N-hydroxy-2-phenylacetamide,
2-(4-(2,4-difluorophenylsulfonamido)phenyl)-N-hydroxy-2-phenylacetamide,
2-(4-(5-chlorothiophene-2-sulfonamido)phenyl)-N-hydroxy-2-phenylacetamide,
N-hydroxy-2-(4-(2-methoxy-4-methylphenylsulfonamido)phenyl)-2-phenylacetamide,
N-hydroxy-2-(4-(2-nitrophenylsulfonamido)phenyl)-2-phenylacetamide,
2-(4-(3-chloro-4-methylphenylsulfonamido)phenyl)-N-hydroxy-2-phenylacetamide,
N-hydroxy-2-(4-(naphthalene-1-sulfonamido)phenyl)-2-phenylacetamide,
N-hydroxy-2-(4-(naphthalene-2-sulfonamido)phenyl)-2-phenylacetamide,
2-(4-(4-tert-butylphenylsulfonamido)phenyl)-N-hydroxy-2-phenylacetamide, N-hydroxy-2-(4-((2-nitrophenyl)methylsulfonamido)phenyl)-2-phenylacetamide, 2-(4-(3,4-dimethoxyphenylsulfonamido)phenyl)-N-hydroxy-2-phenylacetamide, 2-(3-(3,4-dimethoxyphenylsulfonamido)phenyl)-N-hydroxy-2-phenylacetamide, N-hydroxy-2-phenyl-2-(4-(3-(trifluoromethyl)phenylsulfonamido)phenyl)acetamide, 2-(4-(2,5-dichlorothiophene-3-sulfonamido)phenyl)-N-hydroxy-2-phenylacetamide, 2-(4-(4,5-dichlorothiophene-2-sulfonamido)phenyl)-N-hydroxy-2-phenylacetamide, (E)-2-(4-(cinnamylamino)phenyl)-N-hydroxy-2-phenylacetamide and 2-(4-(benzo[c][1,2,5]thiadiazole-5-sulfonamido)phenyl)-N-hydroxy-2-phenylacetamide.

The following examples are intended to further illustrate certain preferred embodiments of the invention, and are not intended to limit the scope of the invention.

ASSAY EXAMPLES

Assay Example 1

Inhibition of Histone Deacetylase Enzymatic Activity

Inhibition of HDAC-1, 2, 3, 6 and 8

The following protocol is used to assay the compounds of the invention. In the assay, the buffer used is 25 mM HEPES, pH 8.0, 137 mM NaCl, 2.7 mM KCl, 1 mM $MgCl_2$ and the substrate is Boc-Lys(Ac)-AMC in a 50 mM stock solution in DMSO. The enzyme stock solution is 4.08 μg/mL in buffer.

The compounds are pre-incubated (2 μL in DMSO diluted to 13 μL in buffer for transfer to assay plate) with enzyme (20 μL of 4.08 μg/mL) for 10 minutes at room temperature (35 μL pre-incubation volume). The mixture is pre-incubated for 5 minutes at room temperature. The reaction is started by bringing the temperature to 37° C. and adding 15 μL substrate. Total reaction volume is 50 μL. The reaction is stopped after 20 minutes by addition of 50 μL developer, prepared as directed by Biomol (FLUOR DE LYS™ developer, Cat. # KI-105). A plate is incubated in the dark for 10 minutes at room temperature before reading ($\lambda_{Ex}$=360 nm, $\lambda_{Em}$=470 nm, Cutoff filter at 435 nm).

Inhibition of Class II HDAC and HDAC-11

A 30 mM stock of Boc-Lys(trifluoroacetyl)-AMC substrate is prepared in DMSO. 2 μL test compound in DMSO is diluted to 50 μL in buffer (25 mM HEPES, pH 8.0, 137 mM NaCl, 2.7 mM KCl, 1 mM $MgCl_2$, 0.1% BSA) and pre-incubated with HDAC enzyme (30 μL of a final enzyme concentration of 0.1-0.2 nM) for 10 minutes at room temperature. Reaction is started by adding 18 μL Boc-Lys(trifluoroacetyl)-AMC substrate and incubating at 37° C. for 20-30 minutes. The reaction is stopped by adding 50 μL trypsin (1 mg/mL) and a known HDAC inhibitor. The plate is then incubated in the dark for 20 minutes at room temperature and read with Ex=360 nm, Em=470 nm, cutoff filter at 435 nm.

All compounds exemplified have an $IC_{50}$ value less than or equal to 15 μM against one or more of HDAC-4, HDAC-5, HDAC-6, HDAC-7, HDAC-8, HDAC-9, HDAC-10 and HDAC-11.

Table 3 shows selected examples. In Table 3, A≤1 uM and 1 uM<C<15 uM.

TABLE 3

| Cpd number | HDAC IC50(uM) | Cpd number | HDAC IC50(uM) | Cpd number | HDAC IC50(uM) |
|---|---|---|---|---|---|
| 1-1 | A | 1-3 | A | 1-5 | C |
| 1-2 | A | 1-4 | A | 1-6 | A |
| 1-7 | A | 5-15 | A | 5-69 | A |
| 1-8 | A | 5-16 | C | 5-70 | A |
| 1-9 | A | 5-17 | A | 5-71 | C |
| 1-10 | A | 5-18 | A | 5-72 | A |
| 1-11 | C | 5-19 | C | 5-73 | A |
| 1-12 | A | 5-20 | A | 5-74 | A |
| 1-13 | C | 6-45 | A | 5-75 | A |
| 1-14 | A | 5-21 | A | 5-76 | A |
| 1-15 | A | 5-22 | A | 5-77 | A |
| 1-16 | A | 5-23 | A | 5-78 | A |
| 1-17 | C | 5-24 | A | 5-79 | A |
| 1-18 | A | 5-25 | A | 5-80 | A |
| 1-19 | A | 5-26 | A | 5-81 | A |
| 1-20 | A | '5-27 | A | 5-82 | A |
| 1-21 | A | 5-28 | A | 5-83 | A |
| 1-22 | C | 5-29 | A | 5-84 | A |
| 1-23 | C | 5-30 | A | 5-85 | A |
| 1-24 | A | 5-31 | C | 5-86 | A |
| 1-25 | C | 5-32 | C | 5-87 | C |
| 1-26 | A | 5-33 | A | 5-88 | A |
| 1-27 | C | 5-34 | A | 5-89 | A |
| 1-28 | A | 5-35 | A | 5-90 | A |
| 1-29 | A | 5-36 | A | 5-91 | A |
| 1-30 | A | 5-37 | A | 5-92 | A |
| 1-31 | A | 5-38 | A | 5-93 | A |
| 1-32 | A | 5-39 | C | 5-94 | A |
| 1-33 | A | 5-40 | A | 5-95 | A |
| 1-34 | A | 5-41 | A | 5-96 | A |
| 1-35 | A | 5-42 | C | 5-97 | A |
| 1-36 | A | 5-43 | A | 5-98 | C |
| 1-37 | A | 5-44 | A | 5-99 | A |
| 1-38 | A | 5-45 | A | 5-100 | A |
| 1-39 | A | 5-46 | A | 5-101 | A |
| 1-40 | A | 5-47 | A | 5-102 | A |
| 1-41 | A | 5-48 | A | 5-103 | C |
| 1-42 | C | 5-49 | A | 5-104 | A |
| 1-43 | A | 5-50 | A | 5-105 | A |
| 1-44 | A | 5-51 | A | 5-106 | A |
| 1-45 | A | 5-52 | A | 5-107 | A |
| 1-46 | A | 5-53 | A | 5-108 | A |
| 1-47 | A | 5-54 | C | 5-109 | A |
| 5-1 | A | 5-55 | A | 5-110 | A |
| 5-2 | A | 5-56 | A | 5-111 | A |
| 5-3 | A | 5-57 | C | 5-112 | A |
| 5-4 | A | 5-58 | A | 5-113 | A |
| 5-5 | A | 5-59 | A | 5-113b | C |
| 5-6 | C | 5-60 | C | 5-114 | C |
| 5-7 | A | 5-61 | C | 5-115 | C |
| 5-8 | A | 5-62 | A | 5-116 | A |
| 5-9 | A | 5-63 | A | 5-117 | C |
| 5-10 | A | 5-64 | A | 5-118 | A |
| 5-11 | A | 5-65 | A | 5-119 | C |
| 5-12 | A | 5-66 | A | 5-120 | C |
| 5-13 | A | 5-67 | A | 5-121 | C |
| 5-14 | C | 5-68 | A | 5-122 | A |
| 5-123 | A | 2-54 | C | 2-109 | A |
| 5-125 | A | 2-55 | A | 2-110 | A |
| 5-126 | C | 2-56 | C | 2-111 | A |
| 5-127 | C | 2-57 | A | 2-112 | A |
| 5-128 | C | 2-58 | C | 2-113 | A |
| 5-129 | C | 2-59 | A | 2-114 | A |
| 6-16 | A | 2-60 | A | 2-115 | A |
| 5-130 | A | 2-61 | A | 2-116 | A |
| 6-17 | A | 2-62 | A | 2-117 | A |
| 6-18 | C | 2-63 | A | 6-23 | A |
| 5-131 | A | 2-64 | C | 6-24 | C |
| 5-132 | A | 2-65 | A | 6-25 | A |
| 6-19 | A | 2-66 | C | 3-5 | A |
| 6-20 | C | 2-67 | A | 3-6 | A |
| 2-5 | C | 2-68 | A | 3-7 | A |
| 2-6 | A | 2-69 | A | 3-8 | C |
| 2-7 | C | 2-70 | A | 3-9 | A |
| 2-8 | A | 2-71 | A | 3-10 | A |
| 2-9 |  | 2-72 |  | 3-11 | A |
| 2-10 | C | 2-73 | C | 3-12 | A |

TABLE 3-continued

| Cpd number | HDAC IC50(uM) | Cpd number | HDAC IC50(uM) | Cpd number | HDAC IC50(uM) |
|---|---|---|---|---|---|
| 2-11 | A | 2-74 | A | 3-13 | A |
| 2-12 | A | 2-75 | A | 3-14 | C |
| 2-13 | A | 2-76 | A | 3-15 | A |
| 2-14 | A | 2-77 | A | 3-16 | A |
| 2-15 | C | 2-78 | A | 3-17 | A |
| 2-16 | C | 2-79 | C | 3-18 | C |
| 2-21 | C | 2-80 | A | 3-19 | A |
| 2-22 | C | 2-81 | A | 3-20 | A |
| 2-23 | C | 2-82 | A | 3-21 | C |
| 2-24 | C | 2-83 | C | 3-22 | A |
| 2-27 | C | 2-84 | A | 3-24 | C |
| 2-28 | C | 2-85 | A | 3-25 | C |
| 2-29 | C | 2-86 | A | 3-26 | C |
| 2-31 | C | 2-87 | C | 3-27 | C |
| 2-34 | C | 2-88 | A | 3-29 | C |
| 2-36 | C | 2-89 | C | 3-30 | C |
| 2-37 | C | 2-90 | A | 3-31 | C |
| 2-38 | A | 2-91 | C | 3-32 | C |
| 2-39 | C | 2-92 | A | 3-33 | C |
| 2-40 | C | 2-93 | C | 3-34 | A |
| 2-41 | C | 2-94 | C | 3-35 | A |
| 2-42 | C | 2-95 | A | 3-36 | A |
| 2-43 | A | 2-96 | A | 3-42 | A |
| 2-44 | A | 2-97 | A | 3-43 | A |
| 2-45 | C | 2-98 | A | 3-44 | A |
| 2-46 | C | 2-99 | A | 3-45 | A |
| 2-47 | C | 2-100 | C | 3-46 | A |
| 2-48 | C | 2-101 | A | 3-47 | A |
| 2-49 | A | 2-102 | A | 3-49 | A |
| 6-21 | C | 2-103 | A | 3-50 | A |
| 6-22 | A | 2-104 | A | 3-51 | A |
| 2-50 | A | 2-105 | A | 3-52 | A |
| 2-51 | A | 2-106 | A | 3-53 | A |
| 2-52 | C | 2-107 | A | 3-54 | C |
| 2-53 | A | 2-108 | A | 3-55 | A |
| 3-56 | A | 3-78 | C | 6-40 | A |
| 3-57 | A | 3-79 | A | 6-42 | C |
| 3-58 | A | 3-80 | A | 6-43 | A |
| 3-59 | A | 3-81 | A | 7-1 | C |
| 3-60 | A | 3-82 | A | 7-2 | C |
| 3-61 | A | 3-83 | A | 7-5 | C |
| 3-62 | A | 3-84 | A | 7-11 | C |
| 3-64 | A | 3-85 | A | 7-17 | C |
| 3-65 | A | 3-86 | A | 7-18 | C |
| 3-66 | A | 3-87 | C | 7-20 | C |
| 3-67 | A | 3-88 | C | 7-31 | A |
| 3-68 | A | 3-89 | A | 7-33 | C |
| 3-69 | A | 3-90 | A | 7-34 | c |
| 3-70 | A | 6-26 | C | 7-35 | C |
| 3-71 | A | 6-27 | C | 7-36 | C |
| 3-72 | C | 6-29 | C | 7-37 | C |
| 3-73 | C | 6-37 | A | 7-41 | C |
| 3-74 | A | 6-38 | C | 7-42 | C |
| 3-75 | A | 6-39 | A | 7-44 | C |
| 3-76 | A | 6-46 | A |  |  |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound, N oxide, pharmaceutically acceptable salt, a racemic or scalemic mixture, or diastereomer or enantiomer thereof according of the Formula (II):

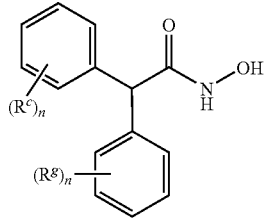

(II)

wherein
each n is independently 0-3; and
$R^g$ is independently selected from the group consisting of $-C_0$-$C_3$alkyl-aryl, -$C_0$-$C_3$alkyl-heteroaryl, $-C_0$-$C_3$alkyl-cycloalkyl, and $-C_0$-$C_3$alkyl-heterocylyl; and
each $R^c$ is selected from the group consisting of H, $-C_1$-$C_6$alkyl, $-C_2$-$C_3$alkyl-$OR^e$, heteroaryl, -heteroaryl-heteroaryl, -heteroaryl-aryl, -aryl-heteroaryl, $-C(O)$-aryl, $-C_1$-$C_3$-alkoxy-$C_1$-$C_3$-alkyl, $-C_2$-$C_3$alkyl-$O-C_1$-$C_3$alkyl, $-C_2$-$C_3$alkyl-$NR^eR^f$, and $-CH_2-C(CH_3)_2-NR^eR^f$, in which each aryl and heteroaryl is optionally substituted with one, two or three substituents independently selected from amino, $OCH_3$ and OH;
wherein each $R^e$ and $R^f$ is independently selected from the group consisting of $-H$, -alkyl, -aryl, -aryl-aryl, -hetetoaryl, heteroaryl-aryl, heteroaryl-heteroaryl, $-C(O)$-alkyl, and $-C(O)CF_3$; and
wherein each cycloalkyl, heterocyclyl, aryl, alkyl and heteroaryl moiety is optionally substituted unless expressly stated otherwise,
the heterocyclyl substituents are selected from hydroxyl, halogen, cyano, nitro, alkyl, cycloalkyl, alkenyl, cycloalkenyl, alkynyl, heterocycle, aryl, $-OR^u$, $-SR^u$, $-S(=O)R^y$, $-S(=O)_2R^y$, $-P(=O)_2R^y$, $-S(=O)_2OR^y$, $-P(=O)_2OR^y$, $-NR^vR^w$, $-NR^vS(=O)_2R^y$, $-NR^vP(=O)_2R^y$, $-S(=O)_2NR^vR^w$, $-P(=O)_2NR^vR^w$, $-C(=O)OR^y$, $-C(=O)R^u$, $-C(=O)NR^vR^w$, $-OC(=O)R^u$, $-OC(=O)NR^vR^w$, $-NR^vC(=O)OR^y$, $-NR^xC(=O)NR^vR^w$, $-NR^xS(=O)_2NR^vR^w$, $-NR^xP(=O)_2NR^vR^w$, $-NR^vC(=O)R^u$, or $-NR^vP(=O)_2R^y$, wherein $R^u$ is hydrogen, alkyl, cycloalkyl, alkenyl, cycloalkenyl, alkynyl, heterocycle, or aryl; $R^v$, $R^w$ and $R^x$ are independently hydrogen, alkyl, cycloalkyl, heterocycle or aryl, or said $R^v$ and $R^w$ together with the N to which they are bonded optionally form a heterocycle; and $R^y$ is alkyl, cycloalkyl, alkenyl, cycloalkenyl, alkynyl, heterocycle or aryl,
the aryl substituents are selected from hydroxyl, cyano, nitro, cycloalkyl, alkenyl, cycloalkenyl, alkynyl, heterocycle, aryl, $-OR^u$, $-SR^u$, $-S(=O)R^y$, $-S(=O)_2R^y$, $-P(=O)_2R^y$, $-S(=O)_2OR^y$, $-P(=O)_2OR^y$, $-NR^vR^w$, $-NR^vS(=O)_2R^y$, $-NR^vP(=O)_2R^y$, $-S(=O)_2NR^vR^w$, $-P(=O)_2NR^vR^w$, $-C(=O)OR^y$, $-C(=O)R^u$, $-C(=O)NR^vR^w$, $-OC(=O)R^u$, $-OC(=O)NR^vR^w$, $-NR^vC(=O)OR^y$, $-NR^xC(=O)NR^vR^w$, $-NR^xS(=O)_2N R^vR^w$, $-NR^xP(=O)_2NR^vR^w$, $-NR^vC(=O)R^u$ or $-NR^vP(=O)_2 R^y$, wherein $R^u$ is hydrogen, alkyl, cycloalkyl, alkenyl, cycloalkenyl, heterocycle or aryl; $R^v$, $R^w$ and $R^x$ are independently hydrogen, alkyl, cycloalkyl, heterocycle or aryl, or said $R^v$ and $R^w$ together with the N to which they are bonded optionally form a heterocycle; and $R^y$ is alkyl, cycloalkyl, alkenyl, cycloalkenyl, alkynyl, heterocycle or aryl;

provided the compound does not have the formula (B)

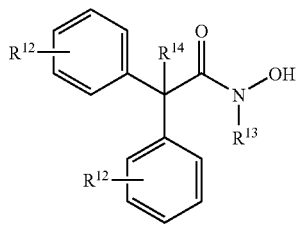
(B)

in which
each $R^{12}$ is independently H, alkyl, halo or alkoxy;
$R^{13}$ is hydrogen; and
$R^{14}$ is H.

2. A compound, N oxide, pharmaceutically acceptable salt, a racemic or scalemic mixture, or diastereomer or enantiomer thereof of Formula XX:

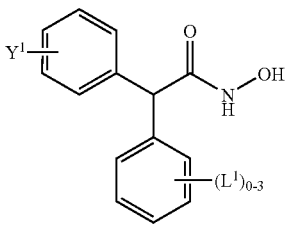
(XX)

wherein
each $L^1$ is independently selected from the group consisting of H, halo, —O-alkyl, —S-alkyl, —NO$_2$, —N(R$^e$)C(O)—C$_0$-C$_3$alkyl-aryl, —N(R$^e$)C(O)—C$_0$-C$_3$alkyl-heteroaryl, —N(R$^a$)(R$^b$), —N(R$^c$)(R$^d$), —OH, -alkyl, —OCF$_3$, and —CF$_3$; and
$Y^1$ is selected from the group consisting of —Z—Z$^2$-D, wherein
Z is selected from the group consisting of —O—, —N(R$^c$)C(O)—, —C(O)N(R$^c$)—C(O)—, —C(O)N(R$^c$)—, —N(R$^c$)—, —N(R$^c$)(C$_2$-C$_4$alkyl-OR$^d$)—, —C(O)—, —C(NOR$^{21}$)—, —CH[C(O)N(R$^{21}$)(R$^{22}$)]-C(O)N(R$^{22}$)—, —CH(N(R$^{21}$)(R$^{22}$))—C(O)N(R$^{22}$)—, —CH[C(O)N(R$^c$)(R$^f$)]—C(O)N(R$^{22}$)—, —S(O)$_2$N(R$^{21}$)—, —N(R$^{21}$)S(O)$_2$N(R$^{22}$)—, —OC(O)—, —C(O)O—, —N(R$^{21}$)C(NR$^{22}$)—, —C(NR$^{22}$)N(R$^{21}$)—, —N(R$^{21}$)C(O)N(R$^{22}$)—, —N(R$^{21}$)C(O)O—, —OC(O)N(R$^{21}$)—, —N(R$^{21}$)C(S)—, —C(S)N(R$^{21}$)—, —N(R$^{21}$)C(S)N(R$^{22}$)—, —N(R$^{21}$)C(S)O—, —OC(S)N(R$^{21}$)—, —O—C$_2$-C$_4$alkyl-N(R$^{21}$)—, —N(R$^{21}$)—C$_2$-C$_4$alkyl-O—, —N(C$_2$-C$_4$alkyl-O-alkyl)-C$_2$-C$_4$alkyl-O—, —O—C$_2$-C$_4$alkyl-N(R$^c$)—, —N(R$^{21}$)—C$_2$-C$_4$alkyl-O—, —N(R$^c$)—C$_2$-C$_4$alkyl-N(R$^d$)—, —O—C$_1$-C$_4$alkyl-S(O)$_2$N(R$^{21}$)—, —O—C$_1$-C$_4$alkyl-O—, —O—C$_1$-C$_4$alkyl-O—C$_1$-C$_4$alkyl-O—, —S(O)$_2$N(R$^{21}$)—C$_2$-C$_4$alkyl-O—, —O—C$_2$-C$_4$alkyl-N(R$^{21}$)S(O)$_2$—, —N(R$^{21}$)S(O)$_2$—C$_1$-C$_4$alkyl-O—, —C(O)—C$_1$-C$_4$alkyl-N(R$^{21}$)—, —N(C(O)—C$_1$-C$_4$alkyl)-, —N(R$^{21}$)—C$_1$-C$_4$alkyl-C(O)—, —O—C$_1$-C$_4$alkyl-C(O)N(R$^{21}$)—, —C(O)N(R$^{21}$)—C$_2$-C$_4$alkyl-O—, —C(O)—C$_1$-C$_4$alkyl-O—, —C(O)—C$_1$-C$_4$alkyl-S(O)$_{0-2}$—, —O—C$_2$-C$_4$alkyl-N(R$^{21}$)C(O)—, —N(R$^{21}$)C(O)—C$_1$-C$_4$alkyl-O—, —N(R$^{21}$)C(O)—C$_1$-C$_4$alkyl-S(O)$_{0-2}$—, —O—C$_1$-C$_4$alkyl-C(O)—, —C(O)—C$_1$-C$_4$alkyl-O—, —N(R$^{21}$)—C$_1$-C$_4$alkyl-C(O), —C(O)—C$_1$-C$_4$alkyl-N(R$^{21}$)—, —O—C$_1$-C$_4$alkyl-C(S)—, —C(S)—C$_1$-C$_4$alkyl-O—, —N(R$^{21}$)—C$_1$-C$_4$alkyl-C(S), —C(S)—C$_1$-C$_4$alkyl-N(R$^{21}$)—, —N(R$^{21}$)—C$_1$-C$_4$alkyl-C(S)—, —O—C$_1$-C$_4$alkyl-C(S)N(R$^{21}$)—, —C(S)N(R$^{21}$)—C$_2$-C$_4$alkyl-O—, —O—C$_2$-C$_4$alkyl-N(R$^{21}$)C(S)—, —N(R$^{21}$)C(O)—C$_1$-C$_4$alkyl-O—, —N(R$^{21}$)C(S)—C$_1$-C$_4$alkyl-O—, —N(R$^{21}$)—C$_1$-C$_4$alkyl-S(O)$_2$—, —O—C$_1$-C$_4$alkyl-S(O)$_2$N(R$^{21}$)—, —S(O)$_2$N(R$^{21}$)—C$_2$-C$_4$alkyl-O—, —O—C$_2$-C$_4$alkyl-N(R$^{21}$)S(O)$_2$—, —N(R$^{21}$)S(O)$_2$—C$_1$-C$_4$alkyl-O—, —O—C$_2$-C$_4$alkyl-OC(O)N(R$^{21}$)—, and —O—C$_2$-C$_4$alkyl-OC(S)N(R$^{21}$)—, wherein each alkyl moiety is optionally substituted;

$Z^2$ is selected from the group consisting of a alkyl, alkenyl, alkynyl, alkyl-alkenyl, alkynyl-alkyl, and alkyl-alkynyl, wherein each alkyl, alkenyl and alkynyl moiety is optionally substituted;

D is selected from the group consisting of H, aryl, heteroaryl, alkyl, alkenyl, alkynyl, heteroalkyl, cycloalkyl, heterocyclyl, bridged heterocyclyl, spiro heterocyclyl, aromatic polycycles, non-aromatic polycycles, polyheteroaryl groups, non-aromatic polyheterocyclic, mixed aryl, and non-aryl polyheterocycle, each of which is optionally substituted and each of which is optionally fused to one or more aryl or heteroaryl rings, or one or more saturated or partially unsaturated cycloalkyl or heterocyclyl rings, each of which ring is optionally substituted, wherein each $R^{21}$ and $R^{22}$ is independently selected from the group consisting of —H, -alkyl, -aryl and heteroaryl, wherein each said aryl and heteroaryl moiety is optionally substituted;

in which
each $R^a$ and $R^b$ together with the nitrogen to which they are bound form a 4 to 7 membered heterocyclyl having 1 or 2 annular heteroatoms, or a 5 to 8 membered bridged heterocyclyl having 1 or 2 annular heteroatoms, the heterocyclyl being optionally substituted with 1-3 substituents independently selected from the group consisting of H, OH, oxo, N(R$^c$)(R$^d$), C$_1$-C$_6$alkyl, aryl, heteroaryl, —C$_1$-C$_6$alkyl-aryl, —C$_1$-C$_6$alkyl-heteroaryl, —C$_1$-C$_3$alkoxy-C$_1$-C$_3$alkyl, —C$_2$-C$_3$alkyl-O—H, —C$_2$-C$_3$alkyl-O—C$_1$-C$_4$alkyl, —C$_5$-C$_6$cycloalkyl, —C$_0$-C$_3$alkyl-N(H)—C(O)—C$_1$-C$_3$alkyl, —C$_{0-3}$alkyl-N(H)—C(O)-haloalkyl, —C$_0$-C$_3$alkyl-NHC(O)O—C$_1$-C$_3$alkyl-aryl, —C$_0$-C$_3$alkyl-CF$_3$, —C$_0$-C$_3$alkyl-NHC(O)O—C$_1$-C$_3$alkyl-heteroaryl, and —C$_0$-C$_3$alkyl-NH$_2$, wherein said heterocyclyl is optionally fused to an aryl or heteroaryl;

each $R^c$ is selected from the group consisting of H, —C$_1$-C$_6$alkyl, —C$_2$-C$_3$alkyl-OR$^e$, heteroaryl, -heteroaryl-heteroaryl, -heteroaryl-aryl, -aryl-heteroaryl, —C(O)-aryl, —C$_1$-C$_3$-alkoxy-C$_1$-C$_3$-alkyl, —C$_{1-2}$—C$_3$alkyl-O—C$_1$-C$_3$alkyl, —C$_2$-C$_3$alkyl-NR$^e$R$^f$, —CH$_2$—C(CH$_3$)$_2$—NR$^e$R$^f$, in which each aryl and heteroaryl is optionally substituted with one, two or three substituents independently selected from amino, OCH$_3$ and OH;

each $R^d$ is independently selected from the group consisting of H, —C$_1$-C$_6$alkyl, —C$_2$-C$_3$alkyl, aryl, heteroaryl, -heteroaryl-heteroaryl, -heteroaryl-aryl, -aryl-heteroaryl, —C(O)-aryl, —C$_1$-C$_3$-alkoxy-C$_1$-

$C_3$-alkyl, —$C_2$-$C_3$alkyl-O—$C_1$-$C_3$alkyl, —$C_2$-$C_3$alkyl-NR$^e$R$^f$, and —CH$_2$—C(CH$_3$)$_2$—NR$^e$R$^f$, in which each aryl and heteroaryl is optionally substituted with one, two or three substituents independently selected from amino, OCH$_3$ and OH; or each R$^e$ and R$^f$ is independently selected from the group consisting of —H, -alkyl, -aryl, -aryl-aryl, -hetetoaryl, heteroaryl-aryl, heteroaryl-heteroaryl, —C(O)-alkyl, and —C(O)CF$_3$; and wherein each cycloalkyl, heterocyclyl, aryl, alkyl and heteroaryl moiety is optionally substituted unless expressly stated otherwise, the heterocyclyl substituents are selected from hydroxyl, halogen, cyano, nitro, alkyl, cycloalkyl, alkenyl, cycloalkenyl, alkynyl, heterocycle, aryl, —OR$^o$, —SR$^u$, —S(=O)R$^y$, —S(=O)$_2$R$^y$, —P(=O)$_2$R$^y$, —S(=O)$_2$OR$^y$, —P(=O)$_2$OR$^y$, —NR$^v$R$^w$, —NR$^v$S(=O)$_2$R$^y$, —NR$^v$P(=O)$_2$R$^y$, —S(=O)$_2$NR$^v$R$^w$, —P(=O)$_2$NR$^v$R$^w$, —C(=O)OR$^y$, —C(=O)R$^u$, —C(=O)NR$^v$R$^w$, —OC(=O)R$^u$, —OC(=O)NR$^v$R$^w$, —NR$^x$C(=O)OR$^y$, —NR$^x$C(=O)NR$^v$R$^w$, —NR$^x$S(=O)$_2$NR$^v$R$^w$, —N R$^x$P(=O)$_2$NR$^v$R$^w$, —NR$^x$C(=O)R$^u$ or —NR$^v$P(=O)$_2$R$^y$, wherein R$^u$ is hydrogen, alkyl, cycloalkyl, alkenyl, cycloalkenyl, alkynyl, heterocycle or aryl; R$^v$, R$^w$ and R$^x$ are independently hydrogen, alkyl, cycloalkyl, heterocycle or aryl, or said R$^v$ and R$^w$ together with the N to which they are bonded optionally form a heterocycle; and R$^y$ is alkyl, cycloalkyl, alkenyl, cycloalkenyl, alkynyl, heterocycle or aryl, the aryl substituents are selected from hydroxyl, cyano, nitro, cycloalkyl, alkenyl, cycloalkenyl, alkynyl, heterocycle, aryl, —OR$^u$, —SR$^u$, —S(=O)R$^y$, —S(=O)$_2$R$^y$, —P(=O)$_2$R$^y$, —S(=O)$_2$OR$^y$, —P(=O)$_2$OR$^y$, —NR$^v$R$^w$, —NR$^v$S(=O)$_2$R$^y$, —NR$^v$P(=O)$_2$R$^y$, —S(=O)$_2$NR$^v$R$^w$, —P(=O)$_2$NR$^v$R$^w$, —C(=O)OR$^y$, —C(=O)R$^u$, —C(=O)NR$^v$R$^w$, —OC(=O)R$^u$, —OC(=O)NR$^v$R$^w$, —NR$^x$C(=O)OR$^y$, —NR$^x$C(=O)NR$^v$R$^w$,—NR$^x$S(=O)$_2$NR$^v$R$^w$, —NR$^x$P(=O)$_2$NR$^v$R$^w$, —NR$^x$C(=O)R$^u$ or —NR$^v$P(=O)$_2$R$^y$, wherein R$^u$ is hydrogen, alkyl, cycloalkyl, alkenyl, cycloalkenyl, heterocycle or aryl; R$^v$, R$^w$ and R$^x$ are independently hydrogen, alkyl, cycloalkyl, heterocycle or aryl, or said R$^v$ and R$^w$ together with the N to which they are bonded optionally form a heterocycle; and R$^y$ is alkyl, cycloalkyl, alkenyl, cycloalkenyl, alkynyl, heterocycle or aryl;

provided the compound does not have the formula (B)

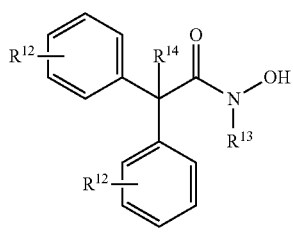

(B)

in which
each R$^{12}$ is independently H, alkyl, halo or alkoxy;
R$^{13}$ is hydrogen; and
R$^{14}$ is H.

3. The compound, N oxide, pharmaceutically acceptable salt, a racemic or scalemic mixture, or diastereomer or enantiomer thereof according to claim 2, wherein the compound has Formula XX-A:

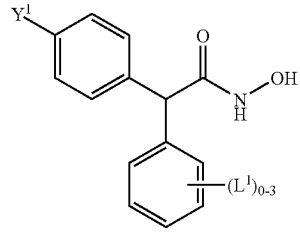

(XX-A)

wherein
each L$^1$ is independently selected from the group consisting of H, —O—CH$_3$, —CH$_3$ and —OH; and
Y$^1$ is selected from the group consisting of —Z—Z$^2$-D;
wherein
Z is selected from the group consisting of —O—, —N(R$^c$)C(O)—, —C(O)N(R$^c$)—, —N(R$^c$)—, —S(O)$_2$N(R$^{21}$)—, —O—C$_2$-C$_4$alkyl-N(R$^{21}$)—, —N(R$^{21}$)—C$_2$-C$_4$alkyl-O—, —N(R$^c$)—C$_2$-C$_4$alkyl-N(R$^d$)—, and —O—C$_1$-C$_4$alkyl-O—;
Z$^2$ is an optionally substituted alkyl; and
D is selected from the group consisting of H, aryl, heteroaryl, alkyl, cycloalkyl and heterocyclyl, each of which is optionally substituted and each of which is optionally fused to one or more aryl or heteroaryl rings, or one or more saturated or partially unsaturated cycloalkyl or heterocyclyl rings, each of which ring is optionally substituted.

4. A pharmaceutical composition comprising a pharmaceutically acceptable carrier, excipient, or diluent, and a compound according to claim 1.

5. A compound selected from the group consisting of
2-(4-(benzyloxy)phenyl)-N-hydroxy-2-phenylacetamide,
N-hydroxy-2-(4-(2-morpholinoethoxy)phenyl)-2-phenylacetamide,
N-hydroxy-2-phenyl-2-(4-(2-(pyrrolidin-1-yl)ethoxy)phenyl)acetamide,
N-hydroxy-2-(4-morpholinophenyl)-2-m-tolylacetamide,
N-hydroxy-2-(4-morpholinophenyl)-2-o-tolylacetamide,
N-hydroxy-2-(4-(2-morpholino-2-oxoethoxy)phenyl)-2-phenylacetamide,
2-(4-(diethylamino)phenyl)-N-hydroxy-2-phenylacetamide,
2-(4-(dimethylamino)phenyl)-N-hydroxy-2-phenylacetamide,
2-(biphenyl-4-yl)-N-hydroxy-2-phenylacetamide,
N-hydroxy-2-phenyl-2-(4-(pyrrolidin-1-yl)phenyl)acetamide,
2-(4-(4-cyclopentylpiperazin-1-yl)phenyl)-N-hydroxy-2-phenylacetamide,
2-(4'-(dimethylamino)biphenyl-4-yl)-N-hydroxy-2-phenylacetamide,
2-(4-(diethylamino)phenyl)-2-(3-fluorophenyl)-N-hydroxyacetamide,
N-hydroxy-2-(4-(2-phenoxyethoxy)phenyl)-2-phenylacetamide,
N-(4-(2-(hydroxyamino)-2-oxo-1-phenylethyl)phenyl)-4-methylbenzamide; and
2-(4-(diethylamino)phenyl)-N-hydroxy-2-(3-methoxyphenyl)acetamide;
or an N-oxide, or pharmaceutically acceptable salt thereof, racemic or scalemic mixture thereof, or a diastereomer or enantiomer thereof.

* * * * *